United States Patent
Obrecht et al.

(10) Patent No.: US 9,695,191 B2
(45) Date of Patent: *Jul. 4, 2017

(54) CONFORMATIONALLY CONSTRAINED, FULLY SYNTHETIC MACROCYCLIC COMPOUNDS

(75) Inventors: Daniel Obrecht, Bättwil (CH); Philipp Ermert, Allschwil (CH); Said Oumouch, Mulhouse (FR); Franck Lach, Les Grandes Loges (FR); Anatol Luther, Binzen (DE); Karsten Marx, Basel (CH); Kerstin Möhle, Wettswil (CH)

(73) Assignee: POLYPHOR AG, Allschwil (CH)

( * ) Notice: Subject to any disclaimer, the term of this patent is extended or adjusted under 35 U.S.C. 154(b) by 1052 days.

This patent is subject to a terminal disclaimer.

(21) Appl. No.: 13/388,891

(22) PCT Filed: Aug. 5, 2009

(86) PCT No.: PCT/EP2009/060168
§ 371 (c)(1),
(2), (4) Date: Mar. 30, 2012

(87) PCT Pub. No.: WO2011/015241
PCT Pub. Date: Feb. 10, 2011

(65) Prior Publication Data
US 2012/0202821 A1     Aug. 9, 2012

(51) Int. Cl.
| | |
|---|---|
| *C07D 273/02* | (2006.01) |
| *A61K 31/407* | (2006.01) |
| *C07D 273/00* | (2006.01) |
| *A61K 31/4985* | (2006.01) |
| *A61K 31/437* | (2006.01) |
| *C07D 498/04* | (2006.01) |
| *C07D 497/18* | (2006.01) |
| *C07D 498/18* | (2006.01) |

(52) U.S. Cl.
CPC .......... *C07D 498/04* (2013.01); *A61K 31/407* (2013.01); *A61K 31/437* (2013.01); *A61K 31/4985* (2013.01); *C07D 497/18* (2013.01); *C07D 498/18* (2013.01)

(58) Field of Classification Search
USPC .......................... 514/250, 411, 286; 540/455
See application file for complete search history.

(56) References Cited

U.S. PATENT DOCUMENTS

2012/0270881 A1 * 10/2012 Obrecht ............... C07D 497/18
514/250

FOREIGN PATENT DOCUMENTS

WO    WO 01/77113 A2 * 10/2001 ........... C07D 498/00

OTHER PUBLICATIONS

Chen et al., Syntheses of Novel 4-tert-Alkyl Ether Proline-Based 16- and 17-Membered Macrocyclic Compounds, 2002, J. Org. Chem., 67, 2730-2733.*
Arasappan et al., Novel Dipeptide Macrocycles from 4-Oxo, -Thio, and -Amino-Substituted Proline Derivatives, 2002, J. Org. Chem, 67, 3923-3926.*
Chen et al., Novel Potent Hepatitis C Virus NS3 Serine Protease Inhibitors Derived from Proline-Based Macrocycles, J. Med. Chem., 2006, 49, 995-1005.*

* cited by examiner

*Primary Examiner* — Kristin Vajda
(74) *Attorney, Agent, or Firm* — Birch, Stewart, Kolasch & Birch, LLP

(57) ABSTRACT

Conformationally restricted, spatially defined 12-30 membered macrocyclic ring systems of type (I) are constituted by three distinct building blocks: an aromatic template a, a conformation modulator b and a spacer moiety c as detailed in the description and the claims. Macrocycles of type (I) are readily manufactured by parallel synthesis or combinatorial chemistry. They are designed to interact with specific biological targets. In particular, they show agonistic or antagonistic activity on the motilin receptor (MR receptor), on the serotonin receptor of subtype 5-$HT_{2B}$ (5-$HT_{2B}$ receptor), and on the prostaglandin F2•receptor (FP receptor). They are thus potentially useful for the treatment of hypomotility disorders of the gastrointestinal tract such as diabetic gastroparesis and constipation type irritable bowl syndrome; of CNS related diseases like migraine, schizophrenia, psychosis or depression; of ocular hypertension such as associated with glaucoma and preterm labour.

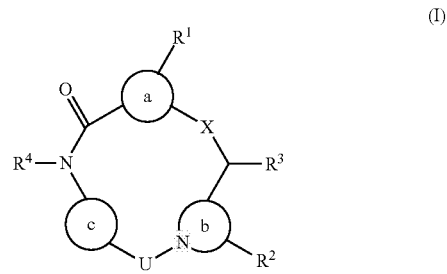

13 Claims, No Drawings

CONFORMATIONALLY CONSTRAINED, FULLY SYNTHETIC MACROCYCLIC COMPOUNDS

Macrocyclic natural and synthetic products have played a crucial role in the development of new drugs, especially as anti-infectives (see Review: F. von Nussbaum, M. Brands, B. Hinzen, S. Weigand, D. Häbich, *Angew. Chem. Int. Ed. Engl.* 2006, 45, 5072-5129; D. Obrecht, J. A. Robinson, F. Bernardini, C. Bisang, S. J. DeMarco, K. Moehle, F. O. Gombert, *Curr. Med. Chem.* 2009, 16, 42-65), as anti-cancer drugs and in other therapeutic areas (C. E. Ballard, H. Yu, B. Wang, *Curr. Med. Chem.* 2002, 9, 471-498; F. Sarabia, S. Chammaa, A. S. Ruiz, L. M. Ortiz, F. J. Herrera, *Curr. Med. Chem.* 2004, 11, 1309-1332). They often display remarkable biological activities, and many macrocycles or their derivatives have been successfully developed into drugs (L. A. Wessjohann, E. Ruijter, D. Garcia-Rivera, W. Brandt, *Mol. Divers.* 2005, 9, 171-186; D. J. Newman, G. M. Gragg, K. M. Snader, *J. Nat. Prod.* 2003, 66, 1022-1037). The chemical diversity of macrocyclic natural products is immense and provides a tremendous source of inspiration for drug design.

Macrocyclic natural and synthetic products generally exhibit semi-rigid backbone conformations placing appended substituents in well-defined positions in space. Certain ring sizes are preferred (L. A. Wessjohann, E. Ruijter, D. Garcia-Rivera, W. Brandt, *Mol. Divers.* 2005, 9, 171-186), e.g. 16-membered rings are frequently found in oxygen-containing macrocycles, such as polyketides (M. Q. Zhang, B. Wilkinson, *Curr. Opin. Biotechnol.* 2007, 18, 478-488). It is hypothesized that the semi-rigid scaffolds may possess some of the favorable binding properties of rigid molecules (entropy), yet still retaining enough flexibility to adapt suitable conformations in the binding event (induced fit).

Macrocyclic natural and synthetic products are generally classified according to the chemical nature of the backbone, e.g. cyclic peptides (Y. Hamady, T. Shioiri, *Chem. Rev.* 2005, 105, 4441-4482; N.-H. Tan, J. Zhou, *Chem. Rev.* 2006, 106, 840-895); cyclic depsipeptides (F. Sarabia, S. Chammaa, A. S. Ruiz, L. M. Ortiz, F. J. Herrera, *Curr. Med. Chem.* 2004, 11, 1309-1332); macrocyclic lactones (macrolactones) and macrolides; macrocyclic lactams, macrocyclic amines, macrocyclic ethers, macrocyclic ureas and urethanes, and others. The conformational, physico-chemical, pharmacological and pharmacodynamic properties of macrocyclic natural and synthetic compounds depend largely on the ring size, the chemical nature of the backbone, and of appended groups (L. A. Wessjohann, E. Ruijter, D. Garcia-Rivera, W. Brandt, *Mol. Divers.* 2005, 9, 171-186). By modifying these three parameters nature has generated a virtually unlimited repertoire of molecular diversity. Despite their undisputed interesting biological properties, natural products show some limitations for drug development, such as:

- High structural complexity
- Metabolic instability
- Low oral bioavailability
- Low membrane permeability; intracellular targets not amenable
- Low tissue penetration
- Short half-life
- Chemical synthesis often very complex and lengthy
- Often accessible only by fermentation or recombinant methods
- High production costs
- Complex QC and development processes.

Broadly speaking, the present invention describes novel, fully synthetic, macrocyclic natural product-like molecules of type I, which can be synthesized e.g. by connecting suitably protected building blocks A, B, and C in a modular fashion to a linear precursor followed by subsequent cyclization (Scheme 1).

Scheme 1: Summary of the invention

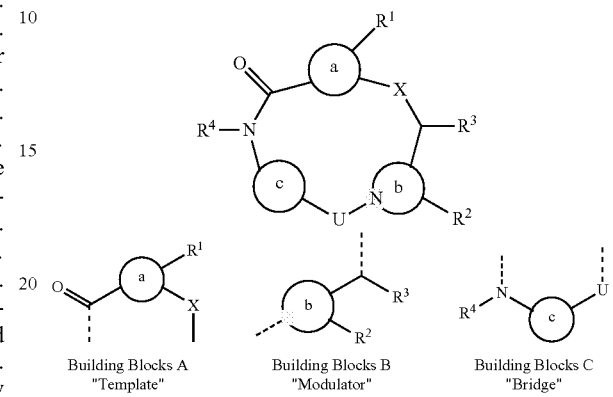

Building Blocks A "Template"   Building Blocks B "Modulator"   Building Blocks C "Bridge"

Building blocks A serve as conformation-inducing templates and are based on appropriately substituted ($R^1$) and protected phenolic or thiophenolic aromatic carboxylic acids.

Building blocks B are appropriately substituted ($R^2$, $R^3$) and protected tertiary amino alcohols, preferably derived from an amino acid such as substituted proline, substituted pipecolic acid or substituted piperazine-2-carboxylic acid. Building blocks B are linked to building block A via an ether (X=O) or thioether (X=S) bond and to building block C via a secondary or tertiary amide bond. The sulfur atom of a thioether linkage can easily and selectively be oxidized to the corresponding sulfoxide (S=O) or sulfone (S(=O)$_2$) which forms part of the invention. Importantly, the amide bond between modulator B and spacer C can also be part of an extended connector moiety U. For example in the case of a standard amide bond, U corresponds to a carbonyl group (—C(=O)—). If U is defined as a carbamoyl moiety (—NR$^4$—C(=O)—) the functional connection between B and C corresponds to a urea moiety. Similarly a carboxyl group (—O—C(=O)—) as U describes a carbamate linkage between B and C. In addition, U can represent an oxalyl group (—C(=O)—C(=O)—) or the corresponding acetal) (—C(—OR$^{20}$)$_2$—C(=O)—).

Importantly, in the case that $R^2$ of building block B constitutes an amine substituent, an alternative incorporation into the macrocyclic ring via the exocyclic amine functionality is possible:

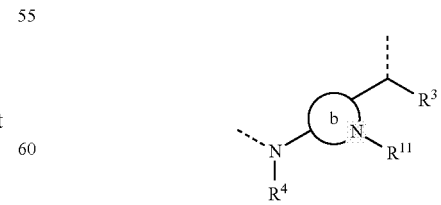

This alternative binding mode is also part of the invention.

Building blocks B serve as a conformational modulator by influencing the conformation of the macrocycle through cis/trans-isomerization of the amide bond.

In molecules of type I the building blocks A and B are connected via the bridges C; the structural element C is linked to A by a secondary or tertiary amide bond. The bridge C can be constituted by one to three appropriately and independently substituted ($R^4$-$R^{10}$; $R^{14-17}$) subunits c1-c3 derived from suitably substituted and protected precursors, most often from, but not limited to, appropriately substituted and protected amino acid derivatives or suitably substituted and protected amine derivatives.

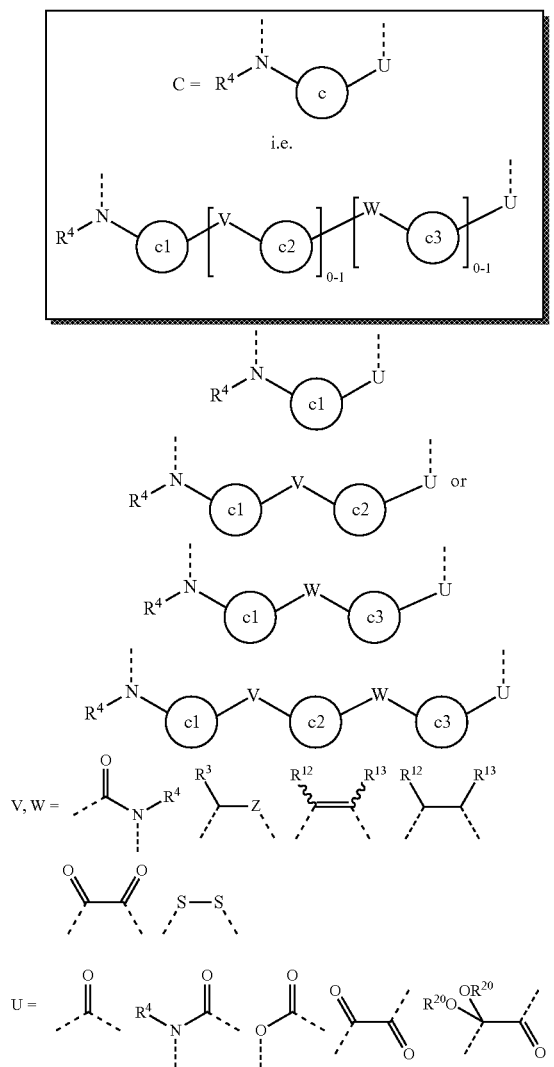

These subunits c1-c3 are in turn independently connected to each other by an amide bond (—C(=O)NR$^4$—), a methylene-heteroatom linkage (—CHR$^3$—Z—), an alkene [1,2]diyl moiety (—CHR$^{12}$=CHR$^{13}$—), introduced by olefin metathesis, an alkane[1,2]diyl spacer (—CHR$^{12}$—CHR$^{13}$—), accessible from the metathesis product by hydrogenation, an oxalyl group (—C(=O)—C(=O)—) or a disulfide bridge (—S—S—).

The spatial orientation of the substituents $R^1$-$R^{13}$ in compounds of type I is modulated by the ring size and the stereochemical connectivity within building blocks A, B and C. Both, the macrocyclic backbone and the substituents $R^1$-$R^{13}$ can contribute to the biological activity of compounds of type I.

The backbone of the compounds of type I is composed of an aromatic ether/thioether linkage and one or more tertiary amide bonds; in some cases an aliphatic ether linkage, an ethylidene or an ethylene moiety may also be part of the backbone as defined above. Ether linkages in macrocyclic molecules have been shown to be beneficial by favorably influencing physico-chemical and pharmacological properties, such as e.g. solubility in water, metabolic stability towards proteolytic degradation, cell permeability and oral absorption (K. X. Chen et al., *J. Med. Chem.* 2006, 49, 995-1005). In addition, tertiary amide containing macrocycles show increased proteolytic stability, cell permeability and oral bioavailability compared to the parent molecules with secondary amide bonds (E. Biron, J. Chatterjee, O. Ovadia, D. Langenegger, J. Brueggen, D. Hoyer, H. A. Schmid, R. Jelinek, C. Gilon, A. Hoffmann, H. Kessler, *Angew. Chem. Int. Ed.* 2008, 47, 1-6; J. Chatterjee, O. Ovadia, G. Zahn, L. Marinelli, A. Hoffmann, C. Gilon, H. Kessler, *J. Med. Chem.* 2007, 50, 5878-5881). For example, the cyclic undecapeptide cyclosporin A (INN: Ciclosporin), which is used as immunosuppressant in organ transplants, contains seven N-methylated amino acids and possesses good oral bioavailability when formulated appropriately (P. R. Beauchesne, N. S. C. Chung, K. M. Wasan, *Drug Develop. Ind. Pharm.* 2007, 33, 211-220). Peptidyl cis/trans isomerization of proline and pipecolic acid containing polypeptides and proteins is a well known process in protein folding events. In vivo, this process can be mediated by peptidyl prolyl cis/trans isomerases such as the cyclophilins, the FK506-binding proteins and the parvulins (A. Bell, P. Monaghan, A. P. Page, *Int. J. Parasitol.* 2006, 36, 261-276). Besides their role in protein folding and in the immune system, peptidyl prolyl cis/trans isomerases have been implicated in cell cycle control (P. E. Shaw, *EMBO Reports* 2002, 3, 521-526) and therefore constitute interesting pharmaceutical targets. FK506 and cyclosporin A which bind to the FK506-binding protein and cyclophilins, respectively, are both macrocyclic natural products, with the former one containing a pipecolic acid residue.

For many existing and emerging biological targets it is difficult to find classical small molecule hits as starting points for drug development (J. A. Robinson, S. DeMarco, F. Gombert, K. Moehle, D. Obrecht, *Drug Disc. Today* 2008, 13, 944-951). Many of these extra- and intracellular "difficult targets" involve protein-protein interactions, such as receptor tyrosine kinases, growth factor receptors, transcriptional activators/transcription factors, chaperones, and others. For several of them macrocyclic natural and synthetic compounds have been described as good starting points for drug discovery programs (e.g. D. Obrecht, J. A. Robinson, F. Bernardini, C. Bisang, S. J. DeMarco, K. Moehle, F. O. Gombert, *Curr. Med. Chem.* 2009, 16, 42-65).

The novel and fully synthetic macrocyclic compounds of type I described in this invention combine unique features of macrocyclic natural products with beneficial physico-chemical and pharmacological properties of traditional small molecules, like:

Natural product-like structural complexity
Good solubility
High metabolic stability
Improved oral bioavailability
Improved membrane permeability
Extra- and intracellular targets amenable
Improved tissue penetration
Small molecule-like pharmacokinetics
Modular chemical synthesis
Synthesis process amenable to parallelization Reasonable production costs Small molecule-like QC and development processes More particularly, the present invention provides macrocyclic compounds of the general formula I (Figure 2), which are comprised of building blocks of general formulae A, B and C as depicted in Scheme 2 below.

Scheme 2: Compounds of type I and building blocks A, B and C

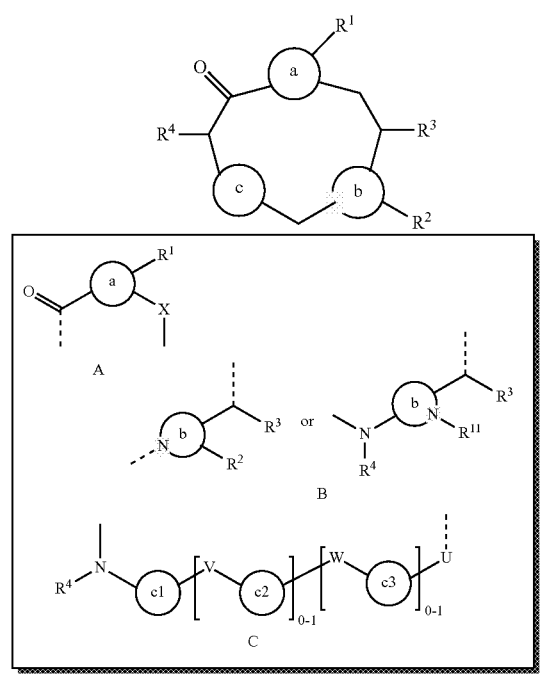

With respect to the building blocks A, B and C, the encircled moieties, i.e. a in A, b in B and c1-c3 in C, shall represent their most basic skeletons appropriately and independently substituted as is detailed later on. The basic skeletons of a and b correspond to the ring systems depicted in Table 1 and Table 2.

TABLE 1

Ring Systems a1-a25 of Building Blocks A

| | |
|---|---|
|  | a1 |
|  | a2 |
|  | a3 |
|  | a4 |

TABLE 1-continued

Ring Systems a1-a25 of Building Blocks A

| | |
|---|---|
| 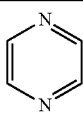 | a5 |
| 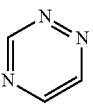 | a6 |
| 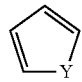 | a7 |
| 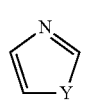 | a8 |
| 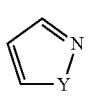 | a9 |
| 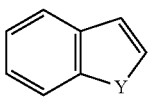 | a10 |
| 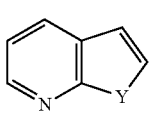 | a11 |
| 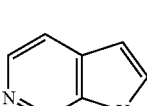 | a12 |
| 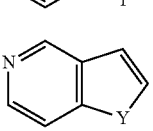 | a13 |
| 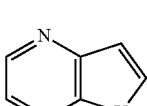 | a14 |
| 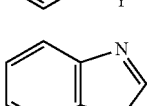 | a15 |
| 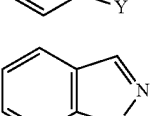 | a16 |
| 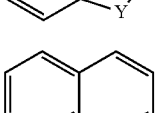 | a17 |
| 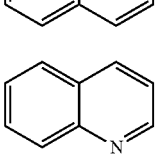 | a18 |

TABLE 1-continued

Ring Systems a1-a25 of Building Blocks A

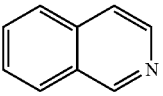 a19

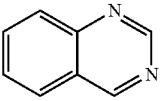 a20

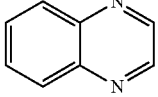 a21

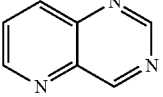 a22

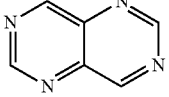 a23

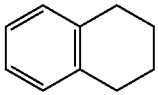 a24

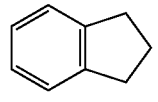 a25

TABLE 2

Ring Systems b1-b11 of Building Blocks B

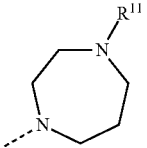 b1

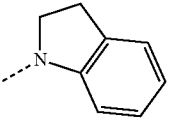 b2

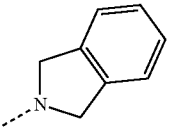 b3

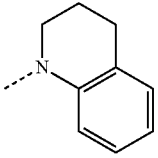 b4

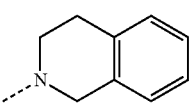 b5

 b6

TABLE 2-continued

Ring Systems b1-b11 of Building Blocks B

 b7

 b8

 b9

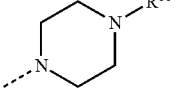 b10

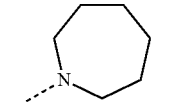 b11

Depending on the substitution pattern of skeletons b alternative binding modes are feasible. For skeletons b3 and b4 such incorporation via the exocyclic nitrogen atom is represented by the following two structures, which form part of the invention:

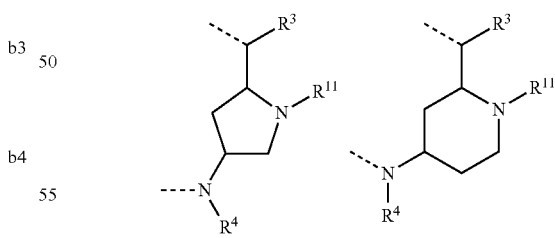

The encircled parts of the bridge subunits c1-c3 represent optionally substituted groups. Definitions of c1-c3 are exemplified in Table 3, each reading from the N-terminus to the C-terminus of the linker C. In the simplest case the linker C is constituted by one subunit c1, i.e. c1-1 to c1-6. For the embodiments consisting of two or three subunits all possible combinations of the subunits c1-c3 and the connectivities U, V and W are part of the invention.

TABLE 3

Scope of Subunits c1-c3 of the Linker Group C

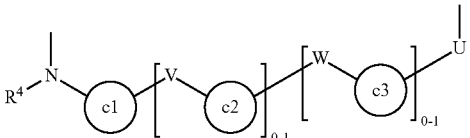

U = 

V, W = 

The substituents directly attached to the basic skeletons containing building block A, B and C, i.e. $R^1$-$R^{17}$, are defined as follows:

$R^1$: H; F; Cl; Br; I; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl;

—$(CR^{18}R^{19})_qOR^{20}$; —$(CR^{18}R^{19})_qSR^{20}$; —$(CR^{18}R^{19})_qNR^4R^{11}$;

—$(CR^{18}R^{19})_qOCONR^4R^{11}$; —$(CR^{18}R^{19})_qOCOOR^{21}$;

—$(CR^{18}R^{19})_qNR^4COOR^{21}$;

—$(CR^{18}R^{19})_qNR^4COR^{22}$; —$(CR^{18}R^{19})_qNR^4CONR^4R^{11}$;

—$(CR^{18}R^{19})_qNR^4SO_2R^{23}$;

—$(CR^{18}R^{19})_qNR^4SO_2NR^4R^{11}$; —$(CR^{18}R^{19})_qCOOR^{21}$;

—$(CR^{18}R^{19})_qCONR^4R^{11}$;

—$(CR^{18}R^{19})_qSO_2NR^4R^{11}$; —$(CR^{18}R^{19})_qOPO(OR^{21})_2$;

—$(CR^{18}R^{19})_qPO(OR^{21})_2$;

—$(CR^{18}R^{19})_qCOR^{22}$; —$(CR^{18}R^{19})_qSO_2R^{23}$; —$(CR^{18}R^{19})_qOSO_3R^{21}$; —$(CR^{18}R^{19})_qR^{24}$;

—$(CR^{18}R^{19})_qR^{25}$; or —$(CR^{18}R^{19})_qR^{26}$.

$R^2$: H; $CF_3$; alkyl; alkenyl; cycloalkyl; heterocycloalkyl; aryl; heteroaryl; arylalkyl; heteroarylalkyl; —$(CR^{18}R^{19})_qOR^{20}$; —$(CR^{18}R^{19})_qSR^{20}$; —$(CR^{18}R^{19})_qNR^4R^{11}$; —$(CR^{18}R^{19})_qOCONR^4R^{11}$; —$(CR^{18}R^{19})_qOCOOR^{21}$; —$(CR^{18}R^{19})_qNR^4COOR^{21}$; —$(CR^{18}R^{19})_qNR^4COR^{22}$; —$(CR^{18}R^{19})_qNR^4CONR^4R^{11}$; —$(CR^{18}R^{19})_qNR^4SO_2R^{23}$; —$(CR^{18}R^{19})_qNR^4SO_2NR^4R^{11}$; —$(CR^{18}R^{19})_qCOOR^{21}$; —$(CR^{18}R^{19})_qCONR^4R^{11}$; —$(CR^{18}R^{19})_qSO_2NR^4R^{11}$; —$(CR^{18}R^{19})_qPO(OR^{21})_2$; —$(CR^{18}R^{19})_qCOR^{22}$; —$(CR^{18}R^{19})_qSO_2R^{23}$; —$(CR^{18}R^{19})_qR^{24}$; —$(CR^{18}R^{19})_qR^{25}$; or —$(CR^{18}R^{19})_qR^{26}$.

$R^3$: H; $CF_3$; alkyl; cycloalkyl; heterocycloalkyl; aryl; heteroaryl; arylalkyl; heteroarylalkyl.

$R^4$: H; alkyl; alkenyl; cycloalkyl; heterocycloalkyl; aryl; heteroaryl; arylalkyl; heteroarylalkyl; or a suitable N-protecting group.

$R^5$, $R^7$ and $R^9$ are independently defined as: H; F; $CF_3$; alkyl; alkenyl; cycloalkyl; heterocycloalkyl; aryl; heteroaryl; arylalkyl; heteroarylalkyl; —$(CR^{18}R^{19})_sOR^{20}$; —$(CR^{18}R^{19})_sSR^{20}$; —$(CR^{18}R^{19})_sNR^4R^{11}$; —$(CR^{18}R^{19})_sOCONR^4R^{11}$; —$(CR^{18}R^{19})_sOCOOR^{21}$; —$(CR^{18}R^{19})_sNR^4COOR^{21}$; —$(CR^{18}R^{19})_sNR^4COR^{22}$; —$(CR^{18}R^{19})_sNR^4CONR^4R^{11}$; —$(CR^{18}R^{19})_sNR^4SO_2R^{23}$; —$(CR^{18}R^{19})_sNR^4SO_2NR^4R^{11}$; —$(CR^{18}R^{19})_qCOOR^{21}$; —$(CR^{18}R^{19})_qCONR^4R^{11}$; —$(CR^{18}R^{19})_qSO_2NR^4R^{11}$; —$(CR^{18}R^{19})_qPO(OR^{21})_2$; —$(CR^{18}R^{19})_qCOR^{22}$; —$(CR^{18}R^{19})_qSO_2R^{23}$; —$(CR^{18}R^{19})_qR^{24}$; —$(CR^{18}R^{19})_qR^{25}$; or —$(CR^{18}R^{19})_qR^{26}$.

$R^6$, $R^8$ and $R^{10}$ are independently defined as: H; F; $CF_3$; alkyl; alkenyl; cycloalkyl; heterocycloalkyl; aryl; heteroaryl; arylalkyl; or heteroarylalkyl.

$R^{11}$: H; alkyl; alkenyl; cycloalkyl; heterocycloalkyl; aryl; heteroaryl; arylalkyl; heteroarylalkyl; a suitable protecting group; —$(CR^{18}R^{19})_rOR^{20}$; —$(CR^{18}R^{19})_rSR^{20}$; —$(CR^{18}R^{19})_rNR^4R^{27}$; —$(CR^{18}R^{19})_rOCONR^4R^{27}$; —$(CR^{18}R^{19})_rOR^{21}$; —$(CR^{18}R^{19})_rNR^4COOR^{21}$; —$(CR^{18}R^{19})_rNR^4CONR^4R^{27}$; —$(CR^{18}R^{19})_rNR^4SO_2R^{23}$; —$(CR^{18}R^{19})_rNR^4SO_2NR^4R^{27}$; —$(CR^{18}R^{19})_qCOOR^{21}$; —$(CR^{18}R^{19})_qCONR^4R^{27}$; —$(CR^{18}R^{19})_qCOR^{22}$; —$(CR^{18}R^{19})_qSO_2R^{23}$; —$(CR^{18}R^{19})_qSO_2NR^4R^{27}$; —$(CR^{18}R^{19})_qR^{24}$; —$(CR^{18}R^{19})_sR^{25}$; or —$(CR^{18}R^{19})_qR^{26}$.

$R^{12}$ and $R^{13}$ are independently defined as H; or alkyl.

$R^{14}$ and $R^{16}$ are independently defined as: H; F; $CF_3$; alkyl; alkenyl; cycloalkyl; heterocycloalkyl; aryl; heteroaryl; arylalkyl; heteroarylalkyl; —$(CR^{18}R^{19})_sOR^{20}$; —$(CR^{18}R^{19})_sNR^4R^{11}$; —$(CR^{18}R^{19})_sNR^4COOR^{21}$; —$(CR^{18}R^{19})_sNR^4COR^{22}$; —$(CR^{18}R^{19})_sNR^4CONR^4R^{11}$; —$(CR^{18}R^{19})_sNR^4SO_2R^{23}$; —$(CR^{18}R^{19})_sNR^4SO_2NR^4R^{11}$; —$(CR^{18}R^{19})_qCOOR^{21}$; —$(CR^{18}R^{19})_qCONR^4R^{11}$; —$(CR^{18}R^{19})_qSO_2NR^4R^{11}$; —$(CR^{18}R^{19})_qCOR^{22}$.

$R^{15}$ and $R^{17}$ are independently defined as: H; F; $CF_3$; alkyl; alkenyl; cycloalkyl; heterocycloalkyl; aryl; heteroaryl; arylalkyl; or heteroarylalkyl.

Substituents introduced in the sub-definitions of the radical $R^1$-$R^{17}$ are:

$R^{18}$: H; F; $CF_3$; alkyl; alkenyl; cycloalkyl; heterocycloalkyl; aryl; heteroaryl; arylalkyl; heteroarylalkyl; —$(CR^{29}R^{30})_sOR^{31}$; —$(CR^{29}R^{30})_sSR^{31}$; —$(CR^{29}R^{30})_sNR^{28}R^{31}$; —$(CR^{29}R^{30})_sOCONR^{28}R^{31}$; —$(CR^{29}R^{30})_sOCOOR^{21}$; —$(CR^{29}R^{30})_sNR^{28}COOR^{21}$; —$(CR^{29}R^{30})_sNR^{28}COR^{31}$; —$(CR^{29}R^{30})_sNR^{28}CONR^{28}R^{31}$; —$(CR^{29}R^{30})_sNR^{28}SO_2R^{23}$; —$(CR^{29}R^{30})_sNR^{28}SO_2NR^{28}R^{31}$; —$(CR^{29}R^{30})_qCOOR^{21}$; —$(CR^{29}R^{30})_qCONR^{28}R^{31}$; —$(CR^{29}R^{30})_qSO_2NR^{28}R^{31}$; —$(CR^{29}R^{30})_qPO(OR^{21})_2$; —$(CR^{29}R^{30})_qCOR^{31}$; —$(CR^{29}R^{30})_qSO_2R^{23}$; —$(CR^{29}R^{30})_qR^{24}$; —$(CR^{29}R^{30})_qR^{25}$; or —$(CR^{29}R^{30})_qR^{26}$.

$R^{19}$: H; $CF_3$; alkyl; alkenyl; cycloalkyl; heterocycloalkyl; aryl; heteroaryl; arylalkyl; heteroarylalkyl.

$R^{20}$: H; alkyl; alkenyl; cycloalkyl; heterocycloalkyl; aryl; heteroaryl; arylalkyl; heteroarylalkyl; —$(CR^{29}R^{30})_rOR^{31}$; —$(CR^{29}R^{30})_rSR^{31}$; —$(CR^{29}R^{30})_rNR^{28}R^{31}$; —$(CR^{29}R^{30})_rOCONR^{28}R^{31}$; —$(CR^{29}R^{30})_rNR^{28}COOR^{21}$; —$(CR^{29}R^{30})_rNR^{28}COR^{31}$; —$(CR^{29}R^{30})_rNR^{28}CONR^{28}R^{31}$; —$(CR^{29}R^{30})_rNR^{28}SO_2R^{23}$; —$(CR^{29}R^{30})_rNR^{28}SO_2NR^{28}R^{31}$; —$(CR^{29}R^{30})_qCOOR^{21}$; —$(CR^{29}R^{30})_qCONR^{28}R^{31}$; —$(CR^{29}R^{30})_qSO_2NR^{28}R^{31}$; —$(CR^{29}R^{30})_qCOR^{31}$; —$(CR^{29}R^{30})_qSO_2R^{23}$; —$(CR^{29}R^{30})_qR^{24}$; —$(CR^{29}R^{30})_qR^{25}$; or —$(CR^{29}R^{30})_qR^{26}$.

$R^{21}$: alkyl; alkenyl; cycloalkyl; heterocycloalkyl; aryl; heteroaryl; arylalkyl; heteroarylalkyl; or a suitable O-protecting group.

$R^{22}$: alkyl; alkenyl; cycloalkyl; heterocycloalkyl; aryl; heteroaryl; arylalkyl; heteroarylalkyl; —$(CR^{29}R^{30})_sOR^{31}$; —$(CR^{29}R^{30})_sSR^{31}$; —$(CR^{29}R^{30})_sNR^{28}R^{31}$; —$(CR^{29}R^{30})_sOCONR^{28}R^{31}$; —$(CR^{29}R^{30})_sNR^{28}COOR^{21}$; —$(CR^{29}R^{30})_sNR^{28}COR^{31}$; —$(CR^{29}R^{30})_sNR^{28}CONR^{28}R^{31}$; —$(CR^{29}R^{30})_sNR^{28}SO_2R^{23}$; —$(CR^{29}R^{30})_sNR^{28}SO_2NR^{28}R^{31}$; —$(CR^{29}R^{30})_sCOOR^{21}$; —$(CR^{29}R^{30})_sCONR^{28}R^{31}$; —$(CR^{29}R^{30})_sSO_2NR^{28}R^{31}$; —$(CR^{29}R^{30})_tCOR^{31}$; —$(CR^{29}R^{30})_sSO_2R^{23}$; —$(CR^{29}R^{30})_tR^{24}$; —$(CR^{29}R^{30})_tR^{25}$; or —$(CR^{29}R^{30})_tR^{26}$.

$R^{23}$: H; alkyl; alkenyl; cycloalkyl; heterocycloalkyl; aryl; heteroaryl; arylalkyl; heteroarylalkyl; —$(CR^{32}R^{33})_rR^{24}$.

$R^{24}$: aryl, preferably an optionally substituted phenyl group of type $C_6H_2R^{34}R^{35}R^{31}$; or a heteroaryl group, preferably one of the groups of formulae H1-H34 (Table 4).

TABLE 4

Groups of Formulae H1-H34

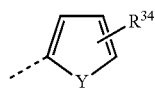

H1

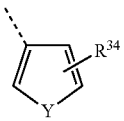

H2

TABLE 4-continued

Groups of Formulae H1-H34

| Structure | Label |
|---|---|
| imidazole-type with N, Y, R³⁴ | H3 |
| isomer with N, Y, R³⁴ | H4 |
| thiazole-type with N, Y, R³⁶ | H5 |
| thiazole-type with N, Y, R³⁶ | H6 |
| thiadiazole N–N, Y, R³⁶ | H7 |
| pyridine with R³⁴ (2-sub) | H8 |
| pyridine with R³⁴ (3-sub) | H9 |
| pyridine with R³⁴ (4-sub) | H10 |
| pyrimidine with R³⁴ | H11 |
| pyrimidine with R³⁶ | H12 |
| pyrimidine with R³⁶ | H13 |
| pyrazine with R³⁴ | H14 |
| triazine with R³⁶ | H15 |
| triazine N–N with R³⁴ | H16 |
| triazine with R³⁶ | H17 |
| triazine with R³⁶ | H18 |
| benzofuran with Y, R³⁴ | H19 |
| benzofuran with Y, R³⁴ | H20 |
| benzofuran with Y, R³⁴ | H21 |
| benzofuran with Y, R³⁴ | H22 |
| benzazole with N, Y, R³⁴ | H23 |
| benzazole with N, Y, R³⁴ | H24 |
| quinoline with R³⁴ | H25 |
| isoquinoline with R³⁴ | H26 |
| naphthyridine with R³⁴ | H27 |
| naphthyridine with R³⁴ | H28 |

TABLE 4-continued
Groups of Formulae H1-H34
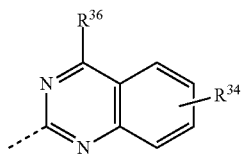 H29
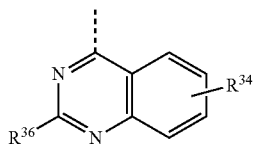 H30
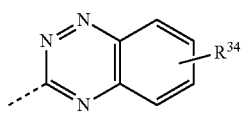 H31
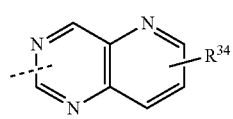 H32
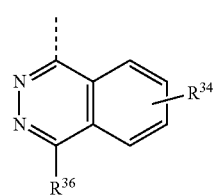 H33
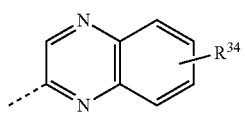 H34
$R^{25}$: One of the groups of formulae H35-H41 as shown in Table 5 below.
TABLE 5
Radicals of formulae H35-H41
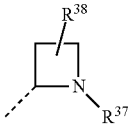 H35
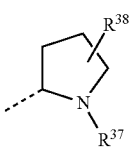 H36
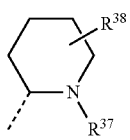 H37
TABLE 5-continued
Radicals of formulae H35-H41
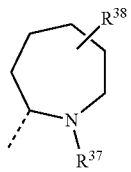 H38
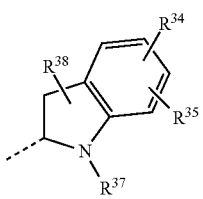 H39
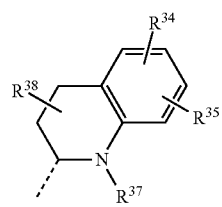 H40
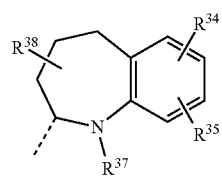 H41
$R^{26}$: One of the groups of formulae H42-H50 as shown in Table 6 below.
TABLE 6
Groups of Formulae H42-H50
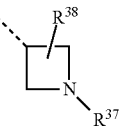 H42
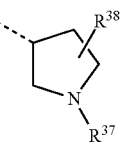 H43
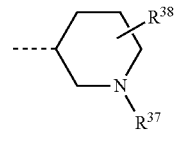 H44
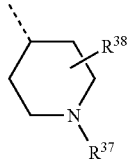 H45

TABLE 6-continued

Groups of Formulae H42-H50

H46: (azepane with $R^{38}$, N-$R^{37}$)

H47: (azocane with $R^{38}$, N-$R^{37}$)

H48: (indoline with $R^{34}$, $R^{35}$, $R^{38}$, N-$R^{37}$)

H49: (tetrahydroquinoline with $R^{34}$, $R^{35}$, $R^{38}$, N-$R^{37}$)

H50: (benzazepine with $R^{34}$, $R^{35}$, $R^{38}$, N-$R^{37}$)

$R^{27}$: H; alkyl; alkenyl; cycloalkyl; heterocycloalkyl; aryl; heteroaryl; arylalkyl; heteroarylalkyl; a suitable protecting group; —$(CR^{29}R^{30})_qR^{24}$.

$R^{28}$: H; alkyl; alkenyl; cycloalkyl; heterocycloalkyl; aryl; heteroaryl; arylalkyl; heteroarylalkyl; a suitable N-protecting group; —$(CR^{32}R^{33})_sOR^{21}$;
—$(CR^{32}R^{33})_sNR^{43}R^{42}$; —$(CR^{32}R^{33})_sNR^{42}CONR^{43}R^{42}$;
—$(CR^{32}R^{33})_sNR^{42}COR^{21}$; —$(CR^{32}R^{33})_sNR^{42}SO_2NR^{21}$;
—$(CR^{32}R^{33})_qCOOR^{21}$;
—$(CR^{32}R^{33})_qCOR^{23}$; —$(CR^{32}R^{33})_qSO_2R^{21}$.

$R^{29}$: H; F; $CF_3$; alkyl; alkenyl; cycloalkyl; heterocycloalkyl; aryl; heteroaryl; arylalkyl; heteroarylalkyl;
—$(CR^{32}R^{33})_sOR^{31}$; —$(CR^{32}R^{33})_sSR^-$; —$(CR^{32}R^{33})_sNR^{28}R^{31}$;
—$(CR^{32}R^{33})_sOCONR^{28}R^{31}$; —$(CR^{32}R^{33})_sOCOOR^{21}$;
—$(CR^{32}R^{33})_sNR^{28}COOR^{21}$;
—$(CR^{32}R^{33})_sNR^{28}COR^{31}$; —$(CR^{32}R^{33})_sNR^{28}CONR^{28}R^{31}$;
—$(CR^{32}R^{33})_sNR^{28}SO_2R^{23}$;
—$(CR^{32}R^{33})_sNR^{28}SO_2NR^{28}R^{31}$; —$(CR^{32}R^{33})_qCOOR^{21}$;
—$(CR^{32}R^{33})_qCONR^{28}R^{31}$;
—$(CR^{32}R^{33})_qSO_2NR^{28}R^{31}$; —$(CR^{32}R^{33})_qPO(OR^{21})_2$;
—$(CR^{32}R^{33})_qCOR^{31}$;
—$(CR^{32}R^{33})_qSO_2R^{23}$; —$(CR^{32}R^{33})_qR^{31}$.

$R^{30}$: H; F; $CF_3$; alkyl; alkenyl; cycloalkyl; heterocycloalkyl; aryl; heteroaryl; arylalkyl; heteroarylalkyl.

$R^{31}$: H; alkyl; alkenyl; cycloalkyl; heterocycloalkyl; aryl; heteroaryl; arylalkyl; heteroarylalkyl; or one of the groups of formulae H51-H55 as shown in Table 7 below.

TABLE 7

Groups of Formulae H51-H55

H51: $-[C(R^{39})(R^{40})]_{0-20}-R^{41}$

H52: $-([C(R^{39})(R^{40})]_q[C(OR^{21})(R^{40})]_s[C(R^{39})(R^{40})]_q)_u-R^{41}$

H53: $-([C(R^{39})(R^{40})]_q[C(NR^{28}R^{43})(R^{40})]_s[C(R^{39})(R^{40})]_q)_u-R^{41}$

H54: $-([C(R^{39})(R^{40})]_q[C(R^{12})=C(R^{13})]_s[C(R^{39})(R^{40})]_q)_u-R^{41}$

H55: $-([C(R^{39})(R^{40})]_s-Q-[C(R^{39})(R^{40})]_s)_u-R^{41}$ $R^{32}$ and $R^{33}$ are independently defined as H; F; $CF_3$; alkyl; alkenyl; cycloalkyl; heterocycloalkyl; aryl; heteroaryl; arylalkyl; heteroarylalkyl.

$R^{34}$ and $R^{35}$ are independently defined as H; F; Cl; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl;
—$(CR^{29}R^{30})_qOR^{31}$; —$(CR^{29}R^{30})_qSR^{31}$; —$(CR^{29}R^{30})_qNR^{28}R^{31}$;
—$(CR^{29}R^{30})_qOCONR^{28}R^{31}$;
—$(CR^{29}R^{30})_qNR^{28}COOR^{21}$; —$(CR^{29}R^{30})_qNR^{28}COR^{31}$;
—$(CR^{29}R^{30})_qNR^{28}CONR^{28}R^{31}$;
—$(CR^{29}R^{30})_qNR^{28}SO_2R^{23}$; —$(CR^{29}R^{30})_qNR^{28}SO_2NR^{28}R^{31}$; —$(CR^{29}R^{30})_qCOOR^{21}$;
—$(CR^{29}R^{30})_qCONR^{28}R^{31}$; —$(CR^{29}R^{30})_qSO_2NR^{28}R^{31}$;
—$(CR^{29}R^{30})_qCOR^{31}$;
—$(CR^{29}R^{30})_qSO_2R^{23}$; or —$(CR^{29}R^{30})_qR^{31}$.

$R^{36}$: H; alkyl; alkenyl; alkynyl; cycloalkyl; heterocycloalkyl; aryl; heteroaryl; arylalkyl; heteroarylalkyl; or —$NR^{28}R^{31}$.

$R^{37}$: H; alkyl; alkenyl; cycloalkyl; heterocycloalkyl; aryl; heteroaryl; arylalkyl; heteroarylalkyl; a suitable N-protecting group; —$(CR^{29}R^{30})_rOR^{21}$;
—$(CR^{29}R^{30})_rSR^{31}$; —$(CR^{29}R^{30})_rNR^{28}R^{31}$; —$(CR^{29}R^{30})_rOCONR^{28}R^{31}$;
—$(CR^{29}R^{30})_rNR^{28}COOR^{21}$; —$(CR^{29}R^{30})_rNR^{28}COR^{31}$;
—$(CR^{29}R^{30})_rNR^{28}CONR^{28}R^{31}$;
—$(CR^{29}R^{30})_rNR^{28}SO_2R^{23}$; —$(CR^{29}R^{30})_r$
$NR^{28}SO_2NR^{28}R^{31}$; —$(CR^{29}R^{30})_rCOOR^{21}$;

—(CR$^{29}$R$^{30}$)$_q$CONR$^{28}$R$^{31}$; —(CR$^{29}$R$^{30}$)$_r$SO$_2$NR$^{28}$R$^{31}$; —(CR$^{29}$R$^{30}$)$_q$COR$^{31}$; —(CR$^{29}$R$^{30}$)$_q$SO$_2$R$^{23}$; or —(CR$^{29}$R$^{30}$)$_q$R$^{31}$.

R$^{38}$: H; alkyl; alkenyl; cycloalkyl; heterocycloalkyl; aryl; heteroaryl; arylalkyl; heteroarylalkyl; —(CR$^{29}$R$^{30}$)$_q$OR$^{31}$; —(CR$^{29}$R$^{30}$)$_q$SR$^{31}$; —(CR$^{29}$R$^{30}$)$_q$NR$^{28}$R$^{31}$; —(CR$^{29}$R$^{30}$)$_q$NR$^{28}$COOR$^{21}$; —(CR$^{29}$R$^{30}$)$_q$NR$^{28}$COR$^{31}$; —(CR$^{29}$R$^{30}$)$_q$NR$^{28}$CONR$^{28}$R$^{31}$; —(CR$^{29}$R$^{30}$)$_q$COOR$^{21}$; —(CR$^{29}$R$^{30}$)$_q$CONR$^{28}$R$^{31}$; —(CR$^{29}$R$^{30}$)$_q$COR$^{31}$; or —(CR$^{29}$R$^{30}$)$_q$R$^{31}$.

R$^{39}$: H; F; CF$_3$; alkyl; alkenyl; cycloalkyl; heterocycloalkyl; aryl; heteroaryl; arylalkyl; heteroarylalkyl; —(CR$^{32}$R$^{33}$)$_u$OR$^{21}$; —(CR$^{32}$R$^{33}$)$_u$NR$^{28}$R$^{43}$; —(CR$^{32}$R$^{33}$)$_t$COOR$^{21}$; or —(CR$^{32}$R$^{33}$)$_t$CONR$^{28}$R$^{43}$.

R$^{40}$: H; F; CF$_3$; alkyl; alkenyl; cycloalkyl; heterocycloalkyl; aryl; heteroaryl; arylalkyl; heteroarylalkyl; —(CR$^{32}$R$^{33}$)$_u$OR$^{21}$; —(CR$^{32}$R$^{33}$)$_u$NR$^{28}$R$^{43}$; —(CR$^{32}$R$^{33}$)$_t$COOR$^{21}$; or —(CR$^{32}$R$^{33}$)$_t$CONR$^{28}$R$^{43}$.

R$^{41}$: H; CF$_3$; alkyl; alkenyl; cycloalkyl; heterocycloalkyl; aryl; heteroaryl; arylalkyl; heteroarylalkyl; —OR$^{21}$; —NR$^{28}$R$^{43}$; —NR$^{28}$COR$^{23}$; —NR$^{28}$COOR$^{21}$; —NR$^{28}$SO$_2$R$^{23}$; —NR$^{28}$CONR$^{28}$R$^{43}$; —COOR$^{21}$; —CONR$^{28}$R$^{43}$; —C(=NR$^{43}$)NR$^{28}$N$^{43}$; —NR$^{28}$C(=NR$^{43}$)NR$^{28}$N$^{43}$; or one of the groups of formulae H56-H110 as shown in Table 8 below.

TABLE 8

| Groups of Formulae H56-H110 | |
|---|---|
| 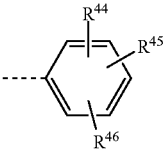 | H56 |
| 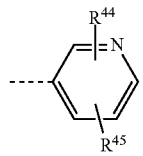 | H57 |
| 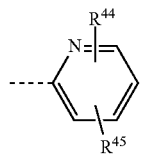 | H58 |
| 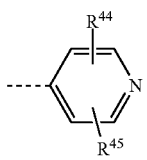 | H59 |
| 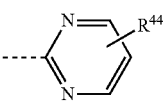 | H60 |

TABLE 8-continued

| Groups of Formulae H56-H110 | |
|---|---|
| 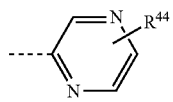 | H61 |
| 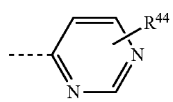 | H62 |
| 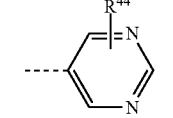 | H63 |
| 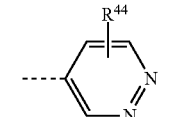 | H64 |
| 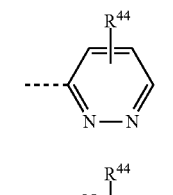 | H65 |
| 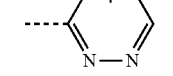 | H66 |
| 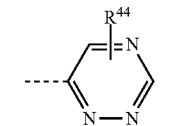 | H67 |
| 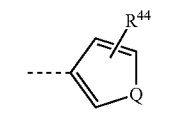 | H68 |
| 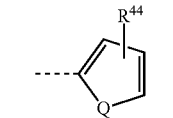 | H69 |
| 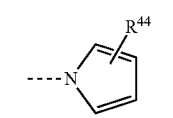 | H70 |
| 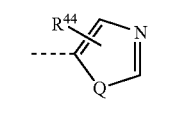 | H71 |
| 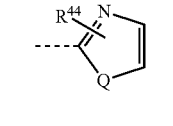 | H72 |

TABLE 8-continued
Groups of Formulae H56-H110
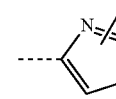 H73
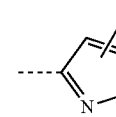 H74
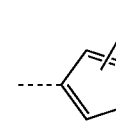 H75
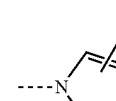 H76
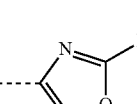 H77
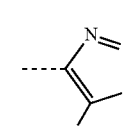 H78
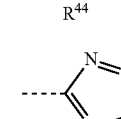 H79
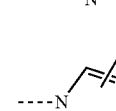 H80
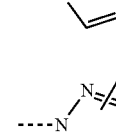 H81
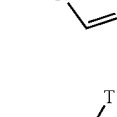 H82
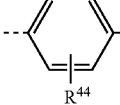 H83
TABLE 8-continued
Groups of Formulae H56-H110
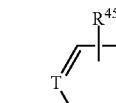 H84
H85
H86
H87
H88
H89
H90
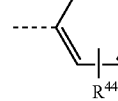 H91

TABLE 8-continued
Groups of Formulae H56-H110
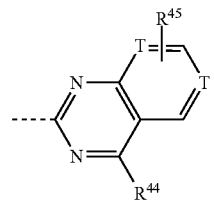 H92
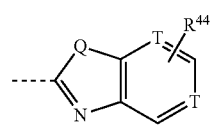 H93
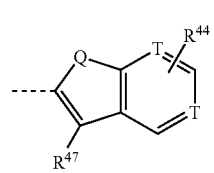 H94
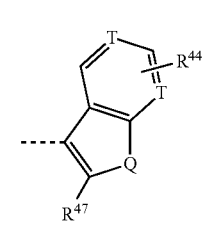 H95
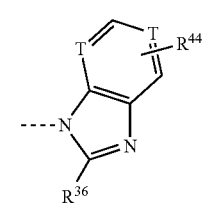 H96
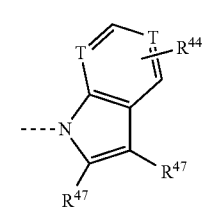 H97
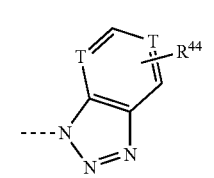 H98
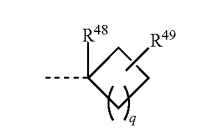 H99
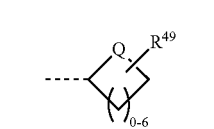 H100
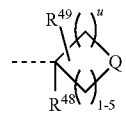 H101
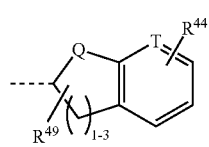 H102
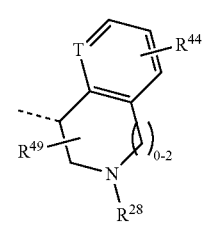 H103
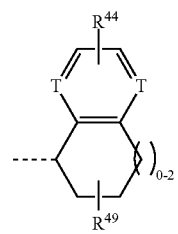 H104
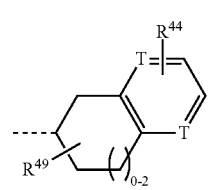 H105
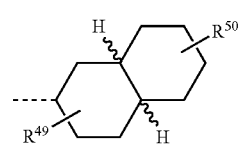 H106
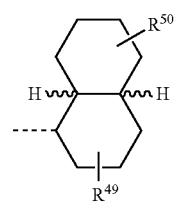 H106
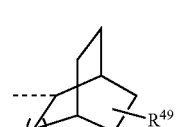 H108
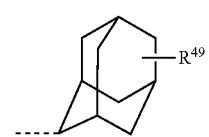 H109

TABLE 8-continued

Groups of Formulae H56-H110

H110

R⁴²: H; alkyl; alkenyl; cycloalkyl; cycloheteroalkyl; aryl; heteroaryl; —(CR²³R³³)ₛOR²¹; —(CR²³R³³)ₛNR²⁸R⁴³; —(CR²³R³³)_q COOR²¹; or —(CR²³R³³)_q CONR²¹R⁴³.

R⁴³: H; alkyl; alkenyl; cycloalkyl; heterocycloalkyl; aryl; heteroaryl; arylalkyl; heteroarylalkyl; or a suitable N-protecting group.

R⁴⁴, R⁴⁵ and R⁴⁶ are independently defined as H; F; CF₃; OCF₃; OCHF₂; NO₂; CN; alkyl; alkenyl; alkynyl; cycloalkyl; heterocycloalkyl; aryl; heteroaryl; arylalkyl; heteroarylalkyl; —OR²³; —NR²⁸R⁴³; —NR²⁸COR²³; —NR²⁸SO₂R²³; —NR²⁸CONR²⁸R⁴³; —COR²³; —SO₂R²³;

R⁴⁷: H; CF₃; alkyl; alkenyl; alkynyl; cycloalkyl; heterocycloalkyl; aryl; heteroaryl; arylalkyl; heteroarylalkyl; —COOR²¹; or —CONR²⁸R⁴³.

R⁴⁸: H; F; CF₃; alkyl; alkenyl; cycloalkyl; cycloheteroalkyl; aryl; heteroaryl; —(CR²³R³³)ₜOR²¹; —(CR²³R³³)ₜNR²⁸R⁴³; —(CR²³R³³)ₜ COOR²¹; —(CR²³R³³)ₜCONR²¹R⁴³

R⁴⁹ and R⁵⁰ are independently defined as H; F; CF₃; alkyl; alkenyl; cycloalkyl; heterocycloalkyl; aryl; heteroaryl; arylalkyl; heteroarylalkyl; —(CR³²R³³)_q OR²¹; —(CR³²R³³)_q NR²⁸R⁴³; —(CR³²R³³)_q COOR²¹; or —(CR³²R³³)_q CONR²⁸R⁴³.

Taken together the following pairs of said substituents can define cyclic structural elements:
Taken together (R⁴ and R¹¹); (R⁴ and R²⁷); (R⁵ and R⁶); (R⁵ and R⁷); (R⁵ and R⁹); (R⁵ and R¹⁴); (R⁵ and R¹⁶); (R⁷ and R⁸); (R⁷ and R⁹); (R⁷ and R¹⁶); (R⁹ and R¹⁰); (R¹⁴ and R¹⁵); (R¹⁶ and R¹⁷); (R¹⁸ and R¹⁹); (R²⁷ and R²⁸); (R²⁸ and R³¹); (R²⁸ and R⁴³); (R²⁹ and R³⁰); (R³² and R³³); (R³⁴ and R³⁵); (R³⁷ and R³⁸); (R³⁹ and R⁴⁰); (R³⁹ and R⁴¹); (R³⁹ and R⁴⁹); (R⁴² and R⁴³); (R⁴⁴ and R⁴⁵); or (R⁴⁴ and R⁴⁶) can form optionally substituted cycloalkyl or heterocycloalkyl moieties.

In addition, the structural elements —NR⁴R¹¹; —NR²⁷R²⁸; —NR²⁸R³¹ or —NR²⁸R⁴³ can form one of the groups of formulae H111-H118 as shown in Table 9 below.

TABLE 9

Heterocyclic Groups Defined by Linking the Residues of the Disubstituted Amino Groups —NR⁴R¹¹; —NR²⁷R²⁸; —NR²⁸R³¹ or —NR²⁸R⁴³.

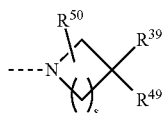
H111

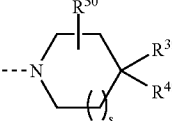
H112

TABLE 9-continued

Heterocyclic Groups Defined by Linking the Residues of the Disubstituted Amino Groups —NR⁴R¹¹; —NR²⁷R²⁸; —NR²⁸R³¹ or —NR²⁸R⁴³.

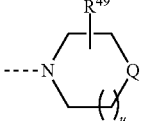
H113

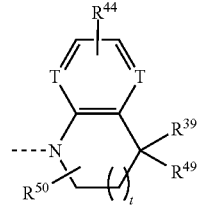
H114

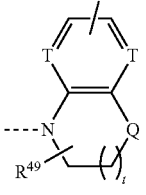
H115

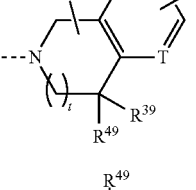
H116

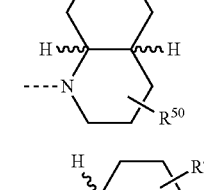
H117

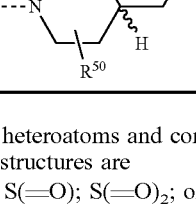
H118

Variable heteroatoms and connector groups in the aforementioned structures are

Z: O; S; S(=O); S(=O)₂; or NR²⁸.
Y: O; S; or NR³⁷.
X: O; S; S(=O); or S(=O)₂.
Q: O; S; or NR²⁸.
U, V and W: As defined in Table 3.
T: CR⁴⁶ or N. In case T occurs several times in the same ring structure each T is defined independently of the other.

And indices are defined as: q=0-4; r=2-4; s=1-4; t=0-2; and u=1-2.

Salts are especially the pharmaceutically acceptable salts of compounds of formula I.

Such salts are formed, for example, as acid addition salts, preferably with organic or inorganic acids, from compounds of type I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

As used in this description, the term "alkyl", taken alone or in combinations (i.a. as part of another group, such as "arylalkyl") designates saturated, straight-chain or branched hydrocarbon radicals having up to 24, preferably up to 12, carbon atoms. In accordance with a preferred embodiment of the present invention "alkyl" is "lower alkyl" which designated alkyl groups having up to 6 carbon atoms.

The term "alkenyl", taken alone or in combinations, designates straight chain or branched hydrocarbon radicals having up to 24, preferably up to 12, carbon atoms and containing at least one or, depending on the chain length, up to four olefinic double bonds. Such alkenyl moieties can exist as E or Z configurations, both of which are part of the invention.

The term "alkynyl", taken alone or in combinations, refers to an aliphatic hydrocarbon chain and includes, but is not limited to, straight and branched chains having 2 to 10 carbon atoms (unless explicitly specified otherwise) and containing at least one triple bond.

The term "cycloalkyl", taken alone or in combinations, refers to a saturated alicyclic moiety having from three to ten carbon atoms.

The term "heterocycloalkyl", taken alone or in combinations, describes a saturated or partially unsaturated heterocyclic moiety having from three to seven ring carbon atoms and one or more ring heteroatoms selected from nitrogen, oxygen and sulphur. This term includes, for example, azetidinyl, pyrrolidinyl, tetrahydrofuranyl, piperidinyl and the like.

The term "aryl", taken alone or in combinations, designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "arylalkyl", as used herein, whether used alone or as part of another group, refers to the group —$R^a$-$R^b$, where $R^a$ is an alkyl group as defined above, substituted by $R^b$, an aryl group, as defined above. Examples of arylalkyl moieties include, but are not limited to, benzyl, 1-phenylethyl, 2-phenylethyl, 3-phenylpropyl, 2-phenylpropyl and the like. Similarly, the term "lower arylalkyl", refers to the above moiety —$R^a$-$R^b$ but wherein $R^a$ is a "lower alkyl" group.

The term "heteroarylalkyl", whether used alone or as part of another group, refers to the group —$R^a$-$R^c$, where $R^a$ is an alkyl group as defined above, substituted by $R^c$, a heteroaryl group, as defined above. Analogously the term "lower heteroarylalkyl", refers to the above moiety —$R^a$-$R^c$ but wherein $R^a$ is a "lower alkyl" group.

The terms "alkoxy" and "aryloxy", taken alone or in combinations, refer to the group —O—$R^a$, wherein $R^a$, is an alkyl group or an aryl group as defined above.

"Amino" designates primary (i.e. —$NH_2$), secondary (i.e. —NRH) and tertiary (i.e. —NRR') amines. Particular secondary and tertiary amines are alkylamines, dialkylamines, arylamines, diarylamines, arylalkylamines and diarylamines wherein the alkyl is as herein defined and optionally substituted.

The term "optionally substituted" is intended to mean that a group, such as but not limited to alkyl, alkenyl, alkynyl, cycloalkyl, aryl, heteroaryl, heterocycloalkyl, alkoxy and aryloxy may be substituted with one or more substituents independently selected from, e.g., halogen (F, Cl, Br, I), cyano (—CN), nitro (—$NO_2$), —$SR^a$, —S(O)$R^a$, —S(O)$_2$$R^a$, —$R^a$, —C(O)$R^a$, —C(O)O$R^a$, —C(O)N$R^b$$R^c$, —C(=N$R^a$)N$R^R$$R^c$, —O$R^a$, —OC(O)$R^a$, —OC(O)O$R^a$, —OC(O)N$R^b$$R^c$, —OS(O)$R^a$, —OS(O)$_2$$R^a$, —OS(O)N$R^b$$R^c$, —OS(O)$_2$N$R^b$$R^c$, —N$R^b$$R^c$, —N$R^a$C(O)$R^b$, —N$R^a$C(O)O$R^b$, —N$R^a$C(O)N$R^b$$R^c$, —N$R^a$ C(=N$R^d$)N$R^b$$R^c$, —N$R^a$S(O)$R^b$, —N$R^a$S(O)$_2$$R^b$, wherein $R^a$, $R^b$, $R^c$, and $R^d$ are each independently, e.g., hydrogen, alkyl, alkenyl, alkynyl, cycloalkyl, aryl, heteroaryl, or heterocycloalkyl as described herein; or $R^b$ and $R^c$ may be taken together with the N atom to which they are attached forming heterocycloalkyl or heteroaryl. These groups in turn can be substituted with any described moiety, including, but not limited to, one or more moieties selected from the group consisting of halogen (fluoro, chloro, bromo, or iodo), hydroxyl, amino, alkylamino (e.g., monoalkylamino, dialkylamino, or trialkylamino), arylamino (e.g., monoarylamino, diarylamino, or triarylamino), hydroxy, carboxy, alkoxy, aryloxy, nitro, cyano, sulfonic acid, sulfate, phosphonic acid, phosphate, or phosphonate.

Said groups, especially but not limited to hydroxy, amino and carboxyl, may be either unprotected or protected, if necessary, as well-known to those skilled in the art. Examples of suitable protecting groups are as detailed in Peter G. M. Wuts, Theodora W. Greene, *Greene's Protective Groups in Organic Synthesis*, John Wiley and Sons, 4th Edition, 2006.

As used herein, all groups that can be substituted in one embodiment are indicated to be "optionally substituted," unless otherwise specified.

As mentioned earlier herein, the term "lower" designates radicals and compounds having up to 6 carbon atoms. Thus, for example, the term "lower alkyl" designates saturated, straight-chain, or branched hydrocarbon radicals having up to 6 carbon atoms, such as methyl, ethyl, n-propyl, isopropyl, n-butyl, s-butyl, isobutyl, t-butyl, and the like. Similarly, the term "lower cycloalkyl" designates saturated cyclic hydrocarbon radicals having up to 6 carbon atoms, such as cyclopropyl, cyclobutyl, cyclopentyl, cyclohexyl and the like.

The present invention includes within its scope so-called "prodrugs" of the compounds of this invention. In general, such prodrugs will be functional derivatives of the compounds, which in vivo are readily convertible into the required compound. Conventional procedures for the selection and preparation of suitable prodrug derivatives are described, for example, in Hans Bundgaard, *Design of Prodrugs*, Elsevier, 1985; and in Valentino J. Stella et al., *Prodrugs: Challenges and Rewards*, Springer, 1st ed., 2007.

Some of the aforementioned substituents can occur several times within the same molecular entity, for example, but not limited to $R^{14}$, $R^{15}$, $R^{16}$, $R^{17}$, $R^{18}$, $R^{19}$, $R^{28}$, $R^{19}$, $R^{30}$, $R^{31}$, $R^{32}$, $R^{33}$, $R^{39}$, $R^{40}$, $R^{41}$, $R^{42}$, $R^{43}$, $R^{44}$, $R^{45}$, $R^{46}$, and $R^{50}$. Each of such multiply occurring substituents shall be selected independently from the other radicals of the same type and within the scope of the definition of the respective group.

All possible stereoisomers, explicitly also including rotamers and atropisomers, of macrocycles of type I are part of this invention.

The general scope of the current invention is defined by groups of selected building blocks A, B and C and the appending substituents as outlined in this section.

Building blocks A1-A626 (Table 10) constitute a subset of possible building blocks based on the ring systems a1-a25 (Table 1). As structural characteristic, groups of type A carry one nucleophilic moiety XH (where X is O or S) and one carboxylic acid C(O)OH functionality. The underlying divalent radicals of type —X-a-CO— are an integral part of macrocyclic backbones of type I, into which they are incorporated by appropriate reactions of the XH and COOH groups of the respective starting materials with suitable reactants.

As mentioned earlier hereinabove, building blocks of type A act as templates and exert an important conformational constraint on products of type I. The structural effects of building blocks of type A depend largely on the relative orientation of the attachment vectors of —X— and —C(O)— and on the spatial distance between these groups. Molecular modeling revealed that the distances (typically between 2.5 and 7.5 Å) and vector arrangements for —X— and —C(O)— in A1-A626 (Table 10) vary considerably, thus strongly influencing the conformations of macrocycles of type I.

The general scope of the current invention is defined by groups of selected building blocks A, B and C and the appending substituents as outlined in this section.

Building blocks A1-A626 (Table 10) constitute a subset of possible building blocks based on the ring systems a1-a25 (Table 1). As structural characteristic, groups of type A carry one nucleophilic moiety XH (where X is O or S) and one carboxylic acid C(O)OH functionality. The underlying divalent radicals of type —X-a-CO— are an integral part of macrocyclic backbones of type I, into which they are incorporated by appropriate reactions of the XH and COOH with suitable reactants.

As mentioned earlier hereinabove, building blocks of type A act as templates and exert an important conformational constraint on products of type I. The structural effects of building blocks of type A depends largely on the relative orientation of the attachment vectors of —X— and —C(O)— and on the spatial distance between these groups. Molecular modeling revealed that the distances (typically between 2.5 and 7.5 Å) and vector arrangements for —X— and —C(O)— in A1-A626 (Table 10) vary considerably, thus strongly influencing the conformations of macrocycles of type I.

TABLE 10

Radicals A1 (a1)-A626 (a25)

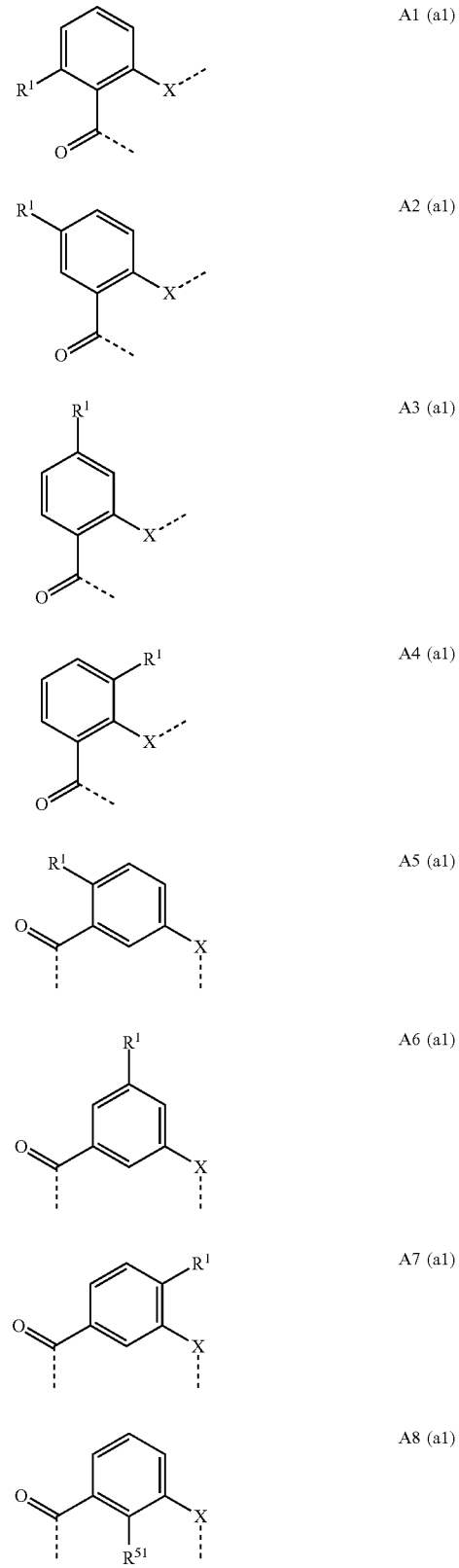

TABLE 10-continued

Radicals A1 (a1)-A626 (a25)

| Structure | Label |
|---|---|
| 2-R¹, 4-X benzoyl | A9 (a1) |
| 3-R¹, 4-X benzoyl | A10 (a1) |
| 3-R³⁴, 2-R¹, 6-X benzoyl | A11 (a1) |
| 4-R³⁴, 2-R¹, 6-X benzoyl | A12 (a1) |
| 4-R³⁴, 2-R¹, 6-X benzoyl (isomer) | A13 (a1) |
| 3-R¹, 2-R³⁴, 6-X benzoyl | A14 (a1) |
| 4-R³⁴, 2-R¹(pos), 6-X benzoyl | A15 (a1) |
| 3-R¹, 4-R³⁴, 2-X benzoyl | A16 (a1) |
| 4-R¹, 2-R³⁴, 6-X benzoyl | A17 (a1) |
| 4-R¹, 2-R³⁴, 6-X (variant) | A18 (a1) |
| 4-R¹, 3-R³⁴, 2-X benzoyl | A19 (a1) |
| 3-R¹, 2-R³⁴, 6-X benzoyl | A20 (a1) |
| 3-R¹, 5-R³⁴, 2-X benzoyl | A21 (a1) |
| 4-R³⁴, 3-R¹, 2-X benzoyl | A22 (a1) |
| 6-R³⁴, 3-X, 2-R⁵¹ benzoyl | A23 (a1) |

(Structures shown: substituted benzoyl radicals A9–A23 with positions of R¹, R³⁴, R⁵¹, and X as depicted.)

TABLE 10-continued
Radicals A1 (a1)-A626 (a25)
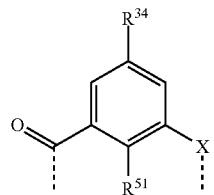 A24 (a1)
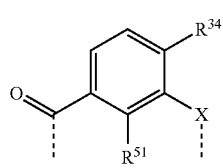 A25 (a1)
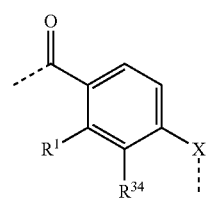 A26 (a1)
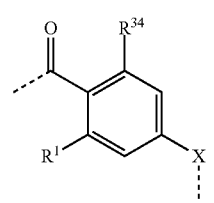 A27 (a1)
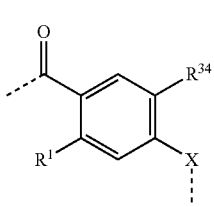 A28 (a1)
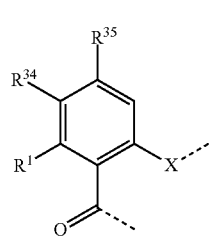 A29 (a1)
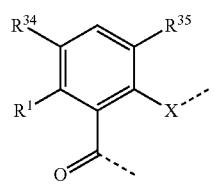 A30 (a1)
TABLE 10-continued
Radicals A1 (a1)-A626 (a25)
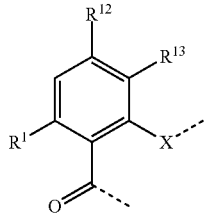 A31 (a1)
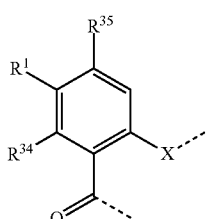 A32 (a1)
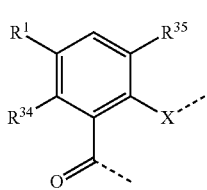 A33 (a1)
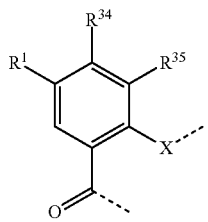 A34 (a1)
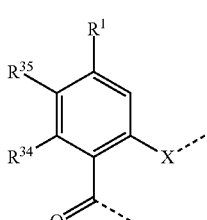 A35 (a1)
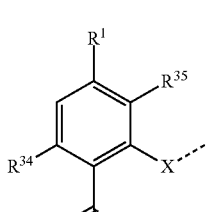 A36 (a1)
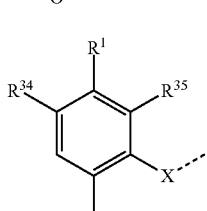 A37 (a1)

TABLE 10-continued
Radicals A1 (a1)-A626 (a25)
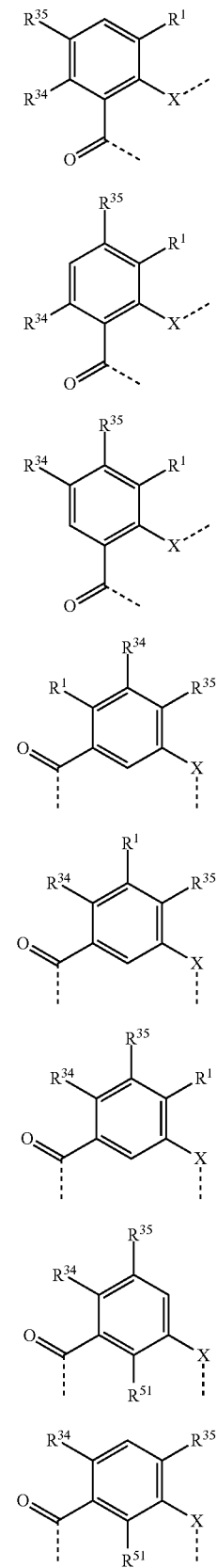
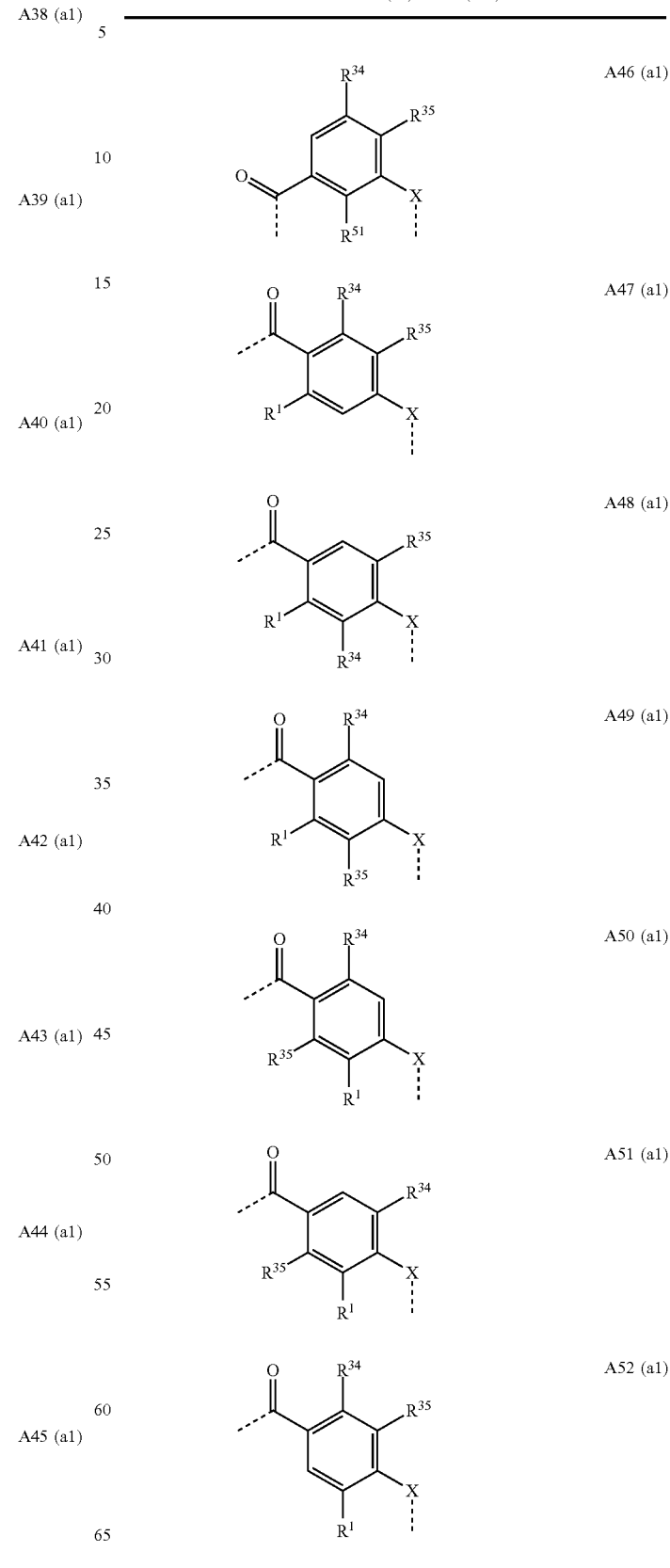

TABLE 10-continued

Radicals A1 (a1)–A626 (a25)

| Structure | Label |
|---|---|
| (benzene with R35, R34, R52, R1, X, C=O) | A53 (a1) |
| (benzene with R35, R1, R52, R34, X, C=O) | A54 (a1) |
| (benzene with R1, R35, R52, R34, X, C=O) | A55 (a1) |
| (benzene with R52, R35, R1, R34, X, C=O) | A56 (a1) |
| (benzene with R35, R34, R52, R51, X, C=O) | A57 (a1) |
| (benzene with R34, R35, R1, R52, C=O) | A58 (a1) |
| (benzene with R34, R35, R52, R1, X, C=O) | A59 (a1) |
| (pyridine with R1, X, C=O) | A60 (a2) |
| (pyridine with R1, X, C=O) | A61 (a2) |
| (pyridine with R1, X, C=O) | A62 (a2) |
| (pyridine with R1, X, C=O) | A63 (a2) |
| (pyridine with R1, X, C=O) | A64 (a2) |
| (pyridine with R1, X, C=O) | A65 (a2) |
| (pyridine with R1, X, C=O) | A66 (a2) |
| (pyridine with R1, X, C=O) | A67 (a2) |

TABLE 10-continued
Radicals A1 (a1)-A626 (a25)
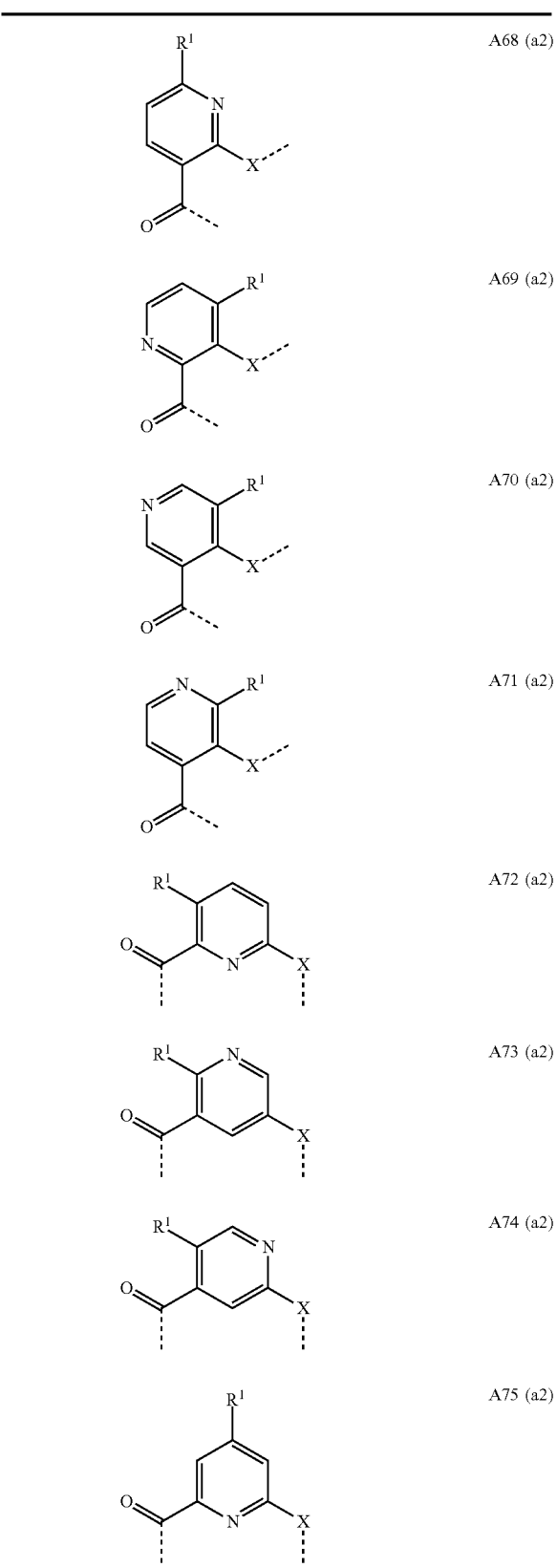
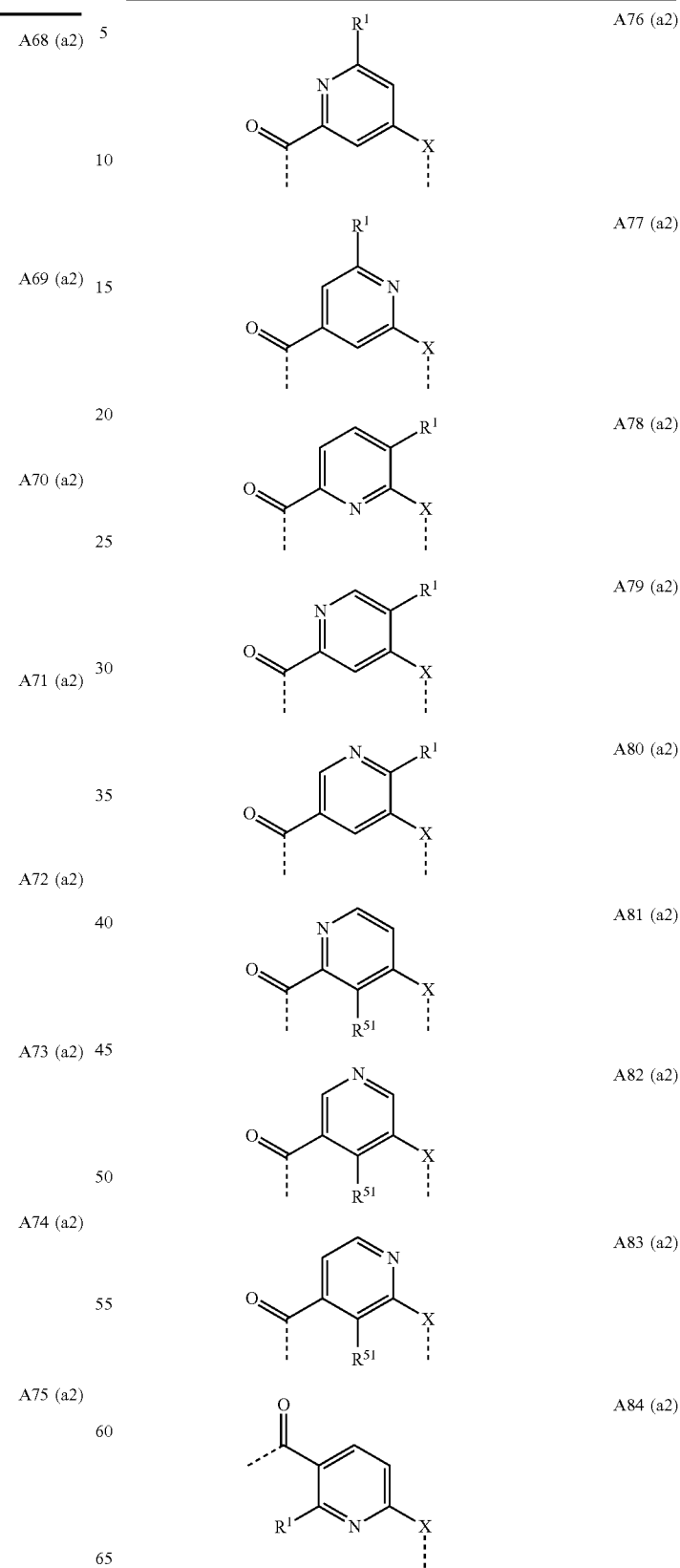

TABLE 10-continued

Radicals A1 (a1)-A626 (a25)

| Structure | Label |
|---|---|
| (pyridine with C=O, R¹, X) | A85 (a2) |
| (pyridine with C=O, R¹, X) | A86 (a2) |
| (pyridine with C=O, R¹, X) | A87 (a2) |
| (pyridine with C=O, R¹, X) | A88 (a2) |
| (pyridine with C=O, R¹, X) | A89 (a2) |
| (pyridine with R³⁶, R¹, X, C=O) | A90 (a2) |
| (pyridine with R³⁴, R¹, X, C=O) | A91 (a2) |
| (pyridine with R³⁶, R¹, X, C=O) | A92 (a2) |
| (pyridine with R³⁶, R¹, X, C=O) | A93 (a2) |
| (pyridine with R³⁴, R¹, X, C=O) | A94 (a2) |
| (pyridine with R³⁶, R¹, X, C=O) | A95 (a2) |
| (pyridine with R³⁴, R¹, X, C=O) | A96 (a2) |
| (pyridine with R¹, R³⁶, X, C=O) | A97 (a2) |
| (pyridine with R¹, R³⁴, X, C=O) | A98 (a2) |
| (pyridine with R¹, R³⁶, X, C=O) | A99 (a2) |
| (pyridine with R¹, R³⁶, X, C=O) | A100 (a2) |

TABLE 10-continued

Radicals A1 (a1)-A626 (a25)

A101 (a2), A102 (a2), A103 (a2), A104 (a2), A105 (a2), A106 (a2), A107 (a2), A108 (a2), A109 (a2), A110 (a2), A111 (a2), A112 (a2), A113 (a2), A114 (a2), A115 (a2)

TABLE 10-continued
Radicals A1 (a1)-A626 (a25)
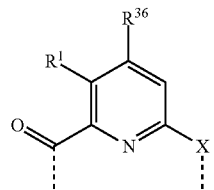 A116 (a2)
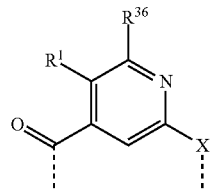 A117 (a2)
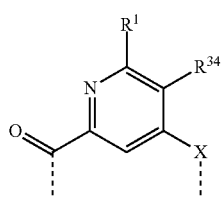 A118 (a2)
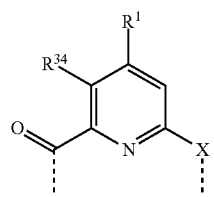 A119 (a2)
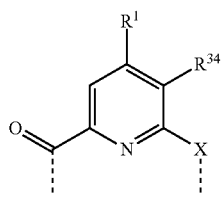 A120 (a2)
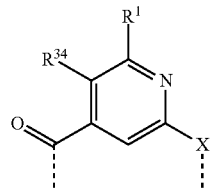 A121 (a2)
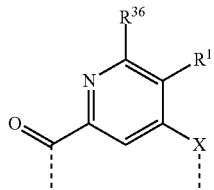 A122 (a2)
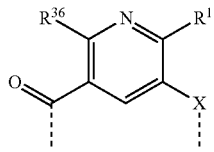 A123 (a2)
TABLE 10-continued
Radicals A1 (a1)-A626 (a25)
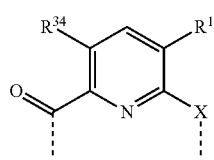 A124 (a2)
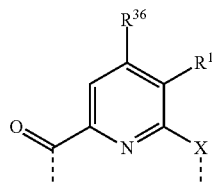 A125 (a2)
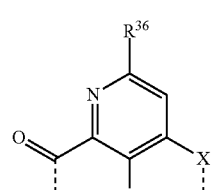 A126 (a2)
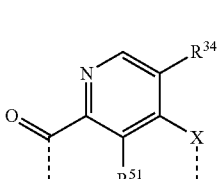 A127 (a2)
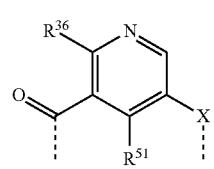 A128 (a2)
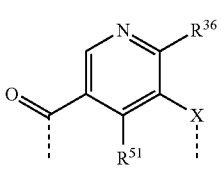 A129 (a2)
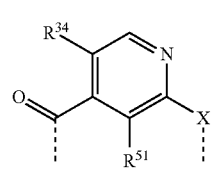 A130 (a2)
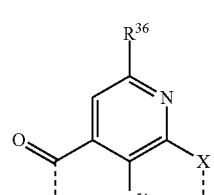 A131 (a2)

TABLE 10-continued

Radicals A1 (a1)-A626 (a25)

A132 (a2), A133 (a2), A134 (a2), A135 (a2), A136 (a2), A137 (a2), A138 (a2), A139 (a2), A140 (a2), A141 (a2), A142 (a2), A143 (a2), A144 (a3), A145 (a3), A146 (a3), A147 (a3)

TABLE 10-continued
Radicals A1 (a1)-A626 (a25)
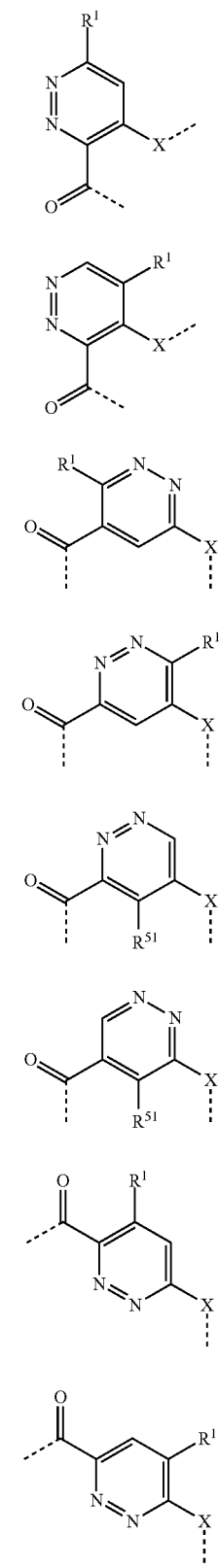
A148 (a3)
A149 (a3)
A150 (a3)
A151 (a3)
A152 (a3)
A153 (a3)
A154 (a3)
A155 (a3)
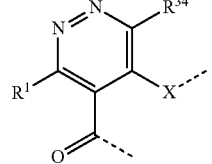 A156 (a3)
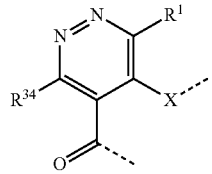 A157 (a3)
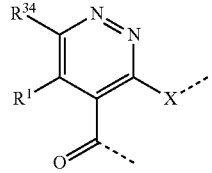 A158 (a3)
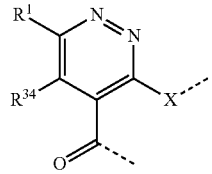 A159 (a3)
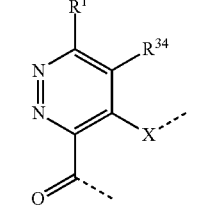 A160 (a3)
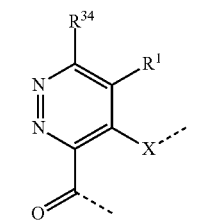 A161 (a3)
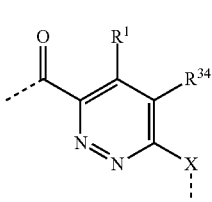 A162 (a3)
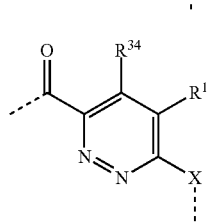 A163 (a3)

TABLE 10-continued
Radicals A1 (a1)-A626 (a25)
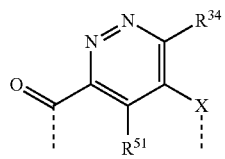 A164 (a3)
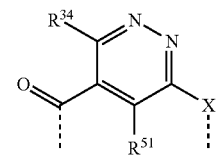 A165 (a3)
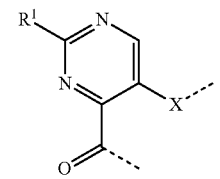 A166 (a4)
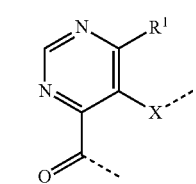 A167 (a4)
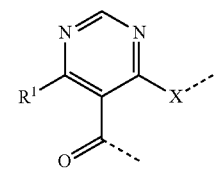 A168 (a4)
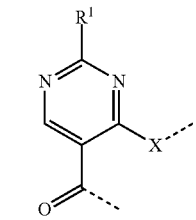 A169 (a4)
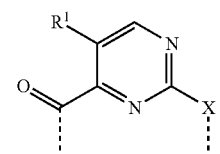 A170 (a4)
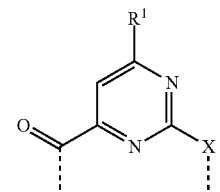 A171 (a4)
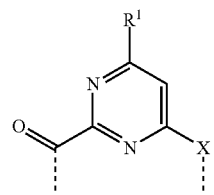 A172 (a4)
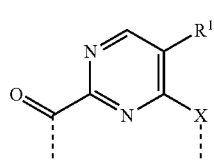 A173 (a4)
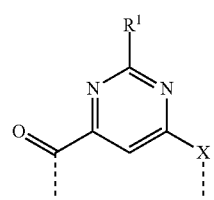 A174 (a4)
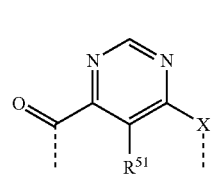 A175 (a4)
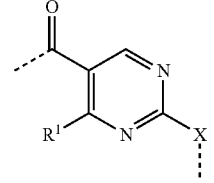 A176 (a4)
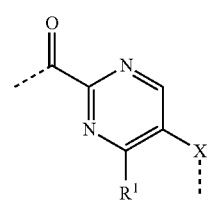 A177 (a4)
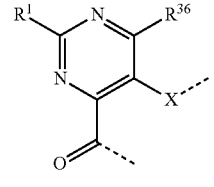 A178 (a4)
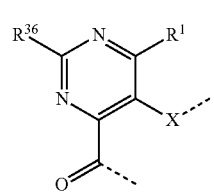 A179 (a4)

TABLE 10-continued

Radicals A1 (a1)-A626 (a25)

A180 (a4)
A181 (a4)
A182 (a4)
A183 (a4)
A184 (a4)
A185 (a4)
A186 (a4)
A187 (a4)
A188 (a4)
A189 (a5)
A190 (a5)
A191 (a5)
A192 (a5)
A193 (a5)
A194 (a5)

TABLE 10-continued

Radicals A1 (a1)-A626 (a25)

| Structure | Label |
|---|---|
| (pyrazine with R¹, R³⁴, X, C=O) | A195 (a5) |
| (pyrazine with R¹, R³⁴, X, C=O) | A196 (a5) |
| (pyrazine with R¹, R³⁴, X, C=O) | A197 (a5) |
| (pyrazine with R³⁴, R¹, X, C=O) | A198 (a5) |
| (pyrazine with R³⁴, R¹, X, C=O) | A199 (a5) |
| (pyrazine with R¹, R³⁴, X, C=O) | A200 (a5) |
| (triazine with R¹, X, C=O) | A201 (a6) |
| (triazine with R¹, X, C=O) | A202 (a6) |
| (triazine with R¹, X, C=O) | A203 (a6) |
| (triazine with R¹, X, C=O) | A204 (a6) |
| (triazine with R¹, X, C=O) | A205 (a6) |
| (triazine with R¹, X, C=O) | A206 (a6) |
| (furan/thiophene Y with R¹, X, C=O) | A207 (a7) |
| (furan/thiophene Y with R¹, X, C=O) | A208 (a7) |
| (furan/thiophene Y with R¹, X, C=O) | A209 (a7) |
| (furan/thiophene Y with R¹, X, C=O) | A210 (a7) |

TABLE 10-continued
Radicals A1 (a1)-A626 (a25)
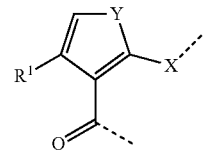 A211 (a7)
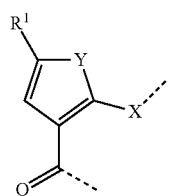 A212 (a7)
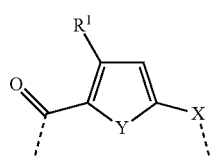 A213 (a7)
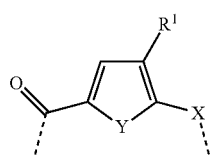 A214 (a7)
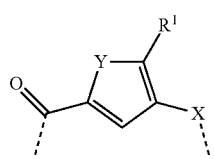 A215 (a7)
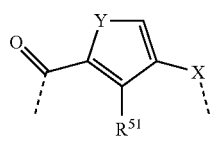 A216 (a7)
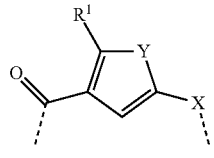 A217 (a7)
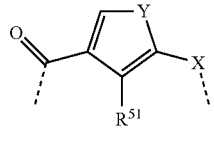 A218 (a7)
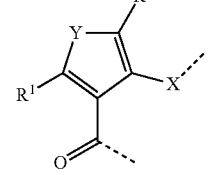 A219 (a7)
TABLE 10-continued
Radicals A1 (a1)-A626 (a25)
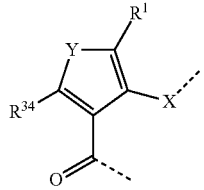 A220 (a7)
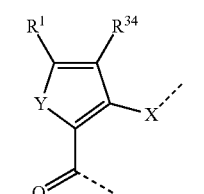 A221 (a7)
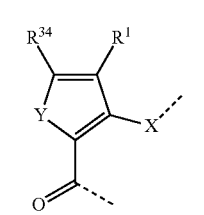 A222 (a7)
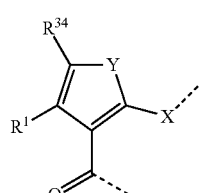 A223 (a7)
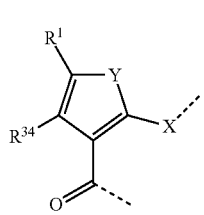 A224 (a7)
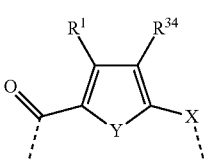 A225 (a7)
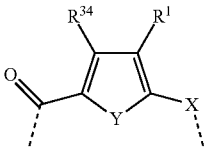 A226 (a7)
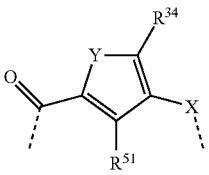 A227 (a7)

TABLE 10-continued
Radicals A1 (a1)-A626 (a25)
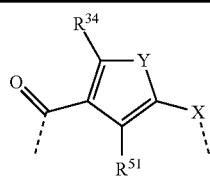 A228 (a7)
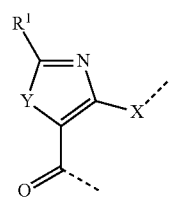 A229 (a8)
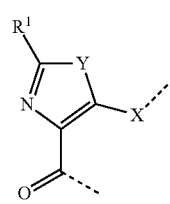 A230 (a8)
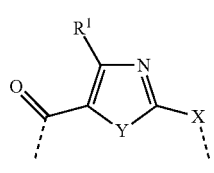 A231 (a8)
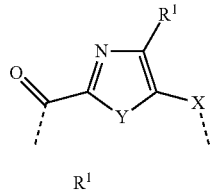 A232 (a8)
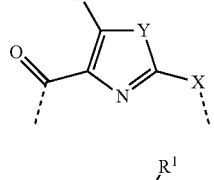 A233 (a8)
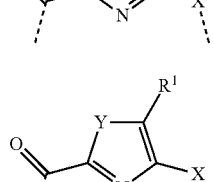 A234 (a8)
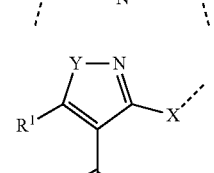 A235 (a9)
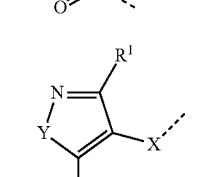 A236 (a9)
TABLE 10-continued
Radicals A1 (a1)-A626 (a25)
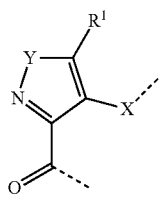 A237 (a9)
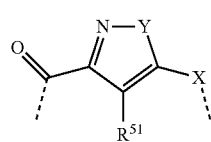 A238 (a9)
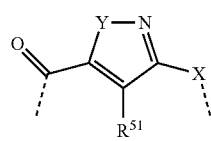 A239 (a9)
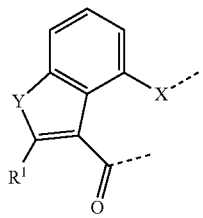 A240 (a10)
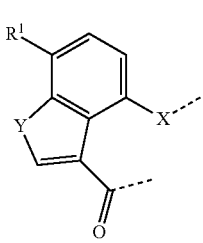 A241 (a10)
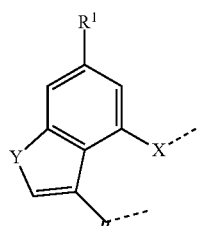 A242 (a10)
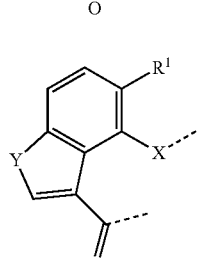 A243 (a10)

TABLE 10-continued
Radicals A1 (a1)-A626 (a25)
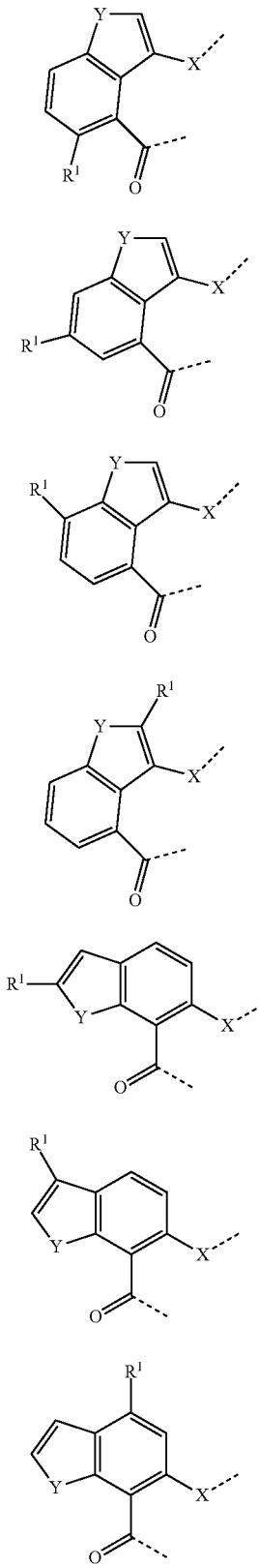
A244 (a10)
A245 (a10)
A246 (a10)
A247 (a10)
A248 (a10)
A249 (a10)
A250 (a10)
TABLE 10-continued
Radicals A1 (a1)-A626 (a25)
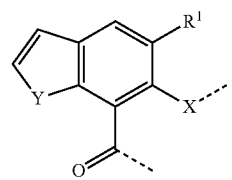
A251 (a10)
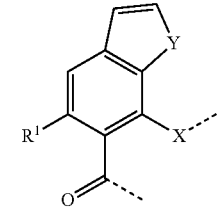
A252 (a10)
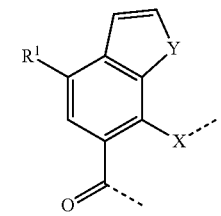
A253 (a10)
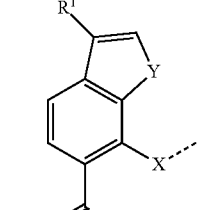
A254 (a10)
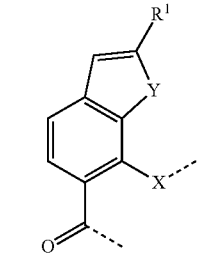
A255 (a10)
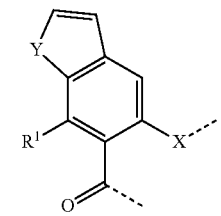
A256 (a10)

TABLE 10-continued

Radicals A1 (a1)-A626 (a25)

A257 (a10)

A258 (a10)

A259 (a10)

A260 (a10)

A261 (a10)

A262 (a10)

A263 (a10)

A264 (a10)

A265 (a10)

A266 (a10)

A267 (a10)

A268 (a10)

A269 (a10)

TABLE 10-continued
Radicals A1 (a1)-A626 (a25)
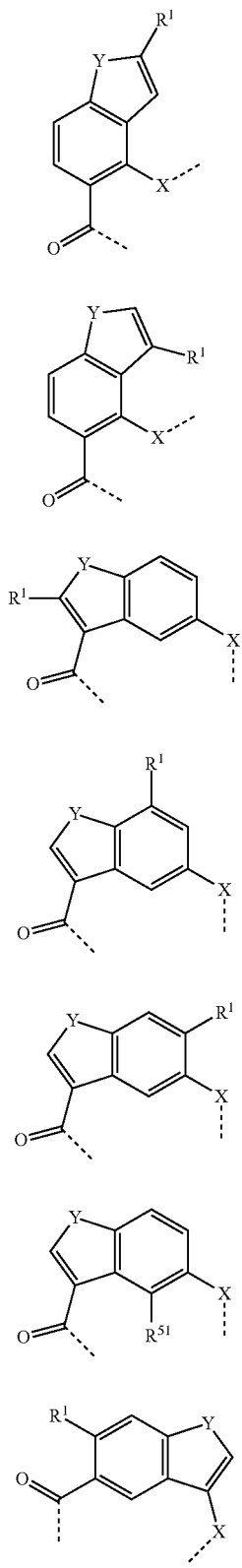
A270 (a10)
A271 (a10)
A272 (a10)
A273 (a10)
A274 (a10)
A275 (a10)
A276 (a10)
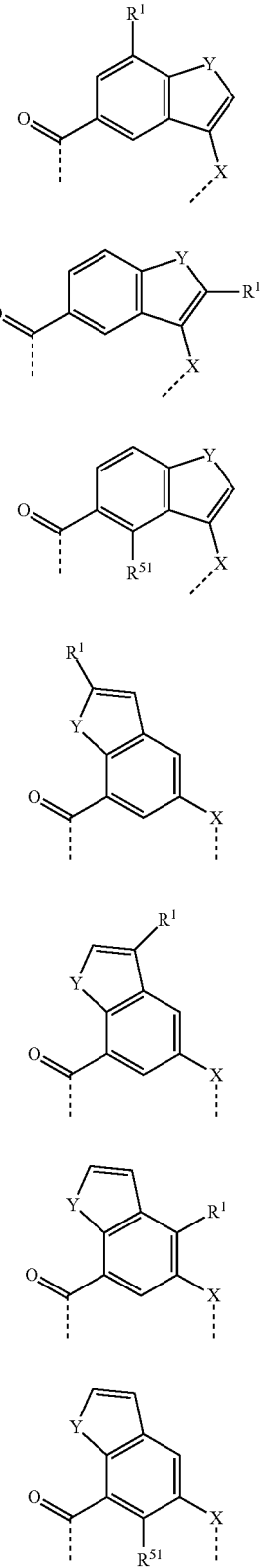
A277 (a10)
A278 (a10)
A279 (a10)
A280 (a10)
A281 (a10)
A282 (a10)
A283 (a10)

TABLE 10-continued
Radicals A1 (a1)-A626 (a25)
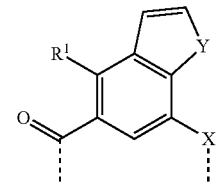 A284 (a10)
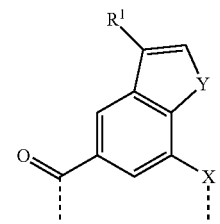 A285 (a10)
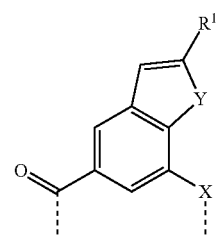 A286 (a10)
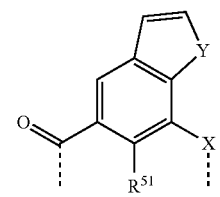 A287 (a10)
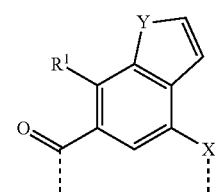 A288 (a10)
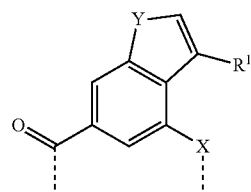 A280 (a10)
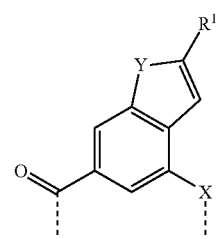 A290 (a10)
TABLE 10-continued
Radicals A1 (a1)-A626 (a25)
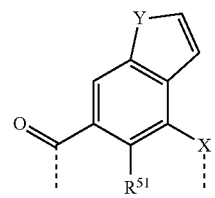 A291 (a10)
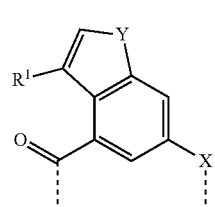 A292 (a10)
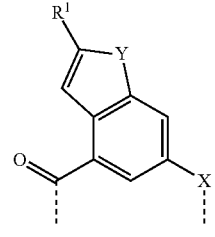 A293 (a10)
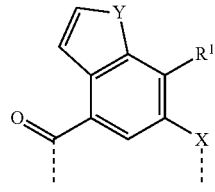 A294 (a10)
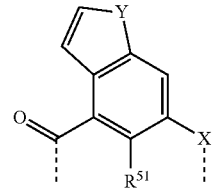 A295 (a10)
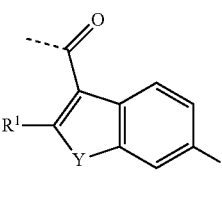 A296 (a10)
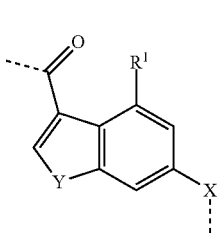 A297 (a10)

TABLE 10-continued
Radicals A1 (a1)-A626 (a25)
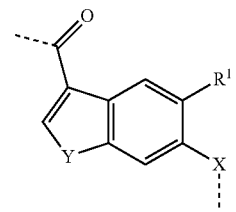 A298 (a10)
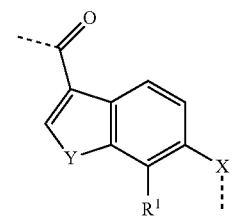 A299 (a10)
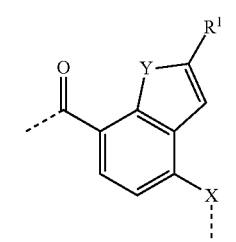 A300 (a10)
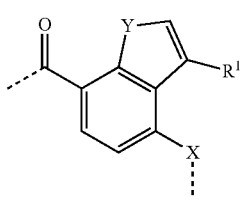 A301 (a10)
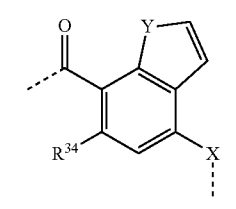 A302 (a10)
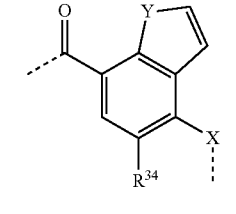 A303 (a10)
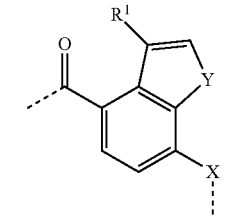 A304 (a10)
TABLE 10-continued
Radicals A1 (a1)-A626 (a25)
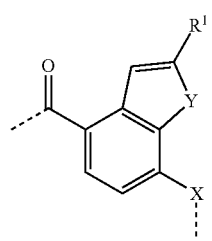 A305 (a10)
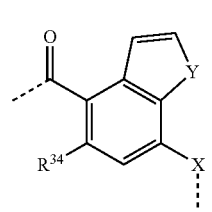 A306 (a10)
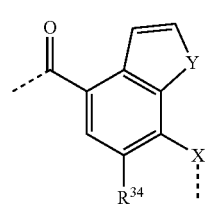 A307 (a10)
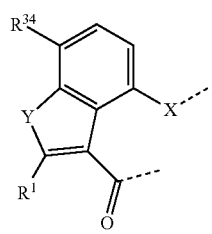 A308 (a10)
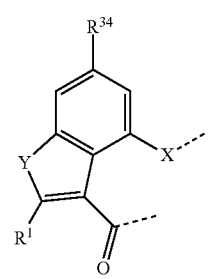 A309 (a10)
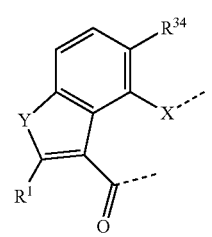 A310 (a10)

TABLE 10-continued
Radicals A1 (a1)-A626 (a25)
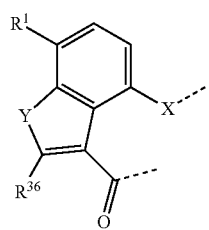 A311 (a10)
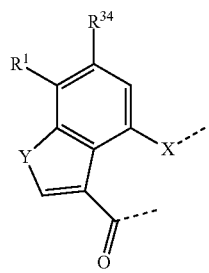 A312 (a10)
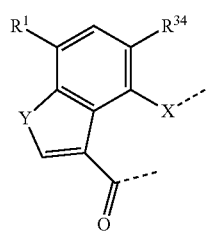 A313 (a10)
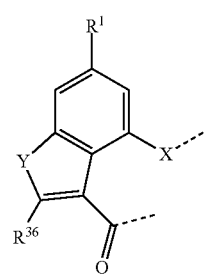 A314 (a10)
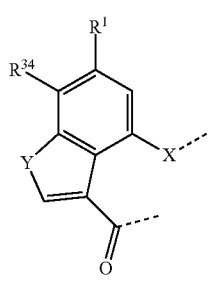 A315 (a10)
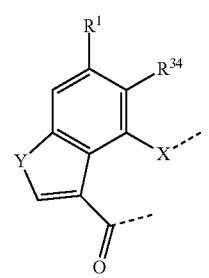 A316 (a10)
TABLE 10-continued
Radicals A1 (a1)-A626 (a25)
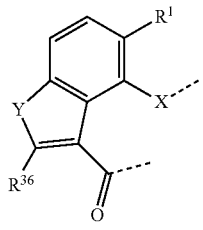 A317 (a10)
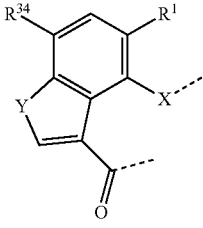 A318 (a10)
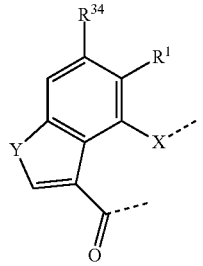 A319 (a10)
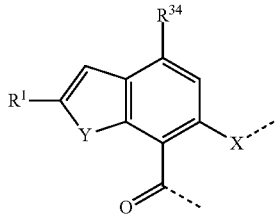 A320 (a10)
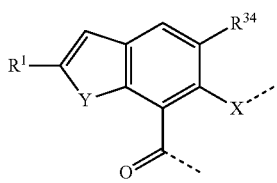 A321 (a10)
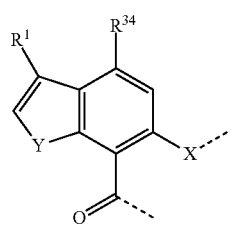 A322 (a10)
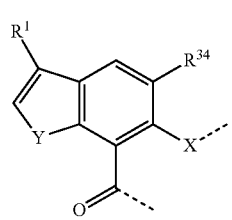 A323 (a10)

TABLE 10-continued
Radicals A1 (a1)-A626 (a25)
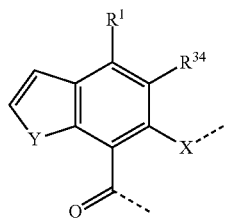 A324 (a10)
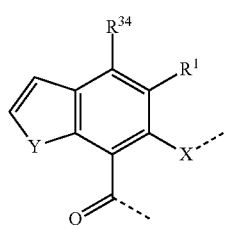 A325 (a10)
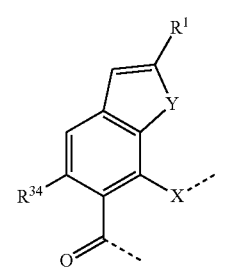 A326 (a10)
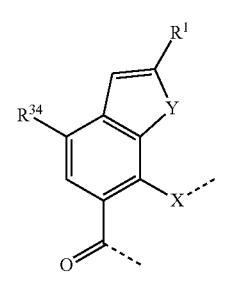 A327 (a10)
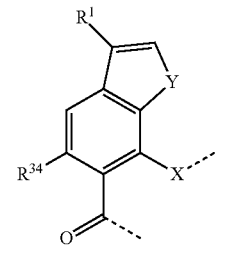 A328 (a10)
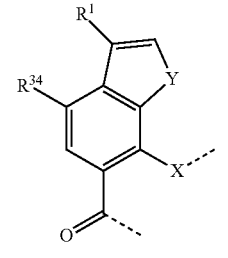 A329 (a10)
TABLE 10-continued
Radicals A1 (a1)-A626 (a25)
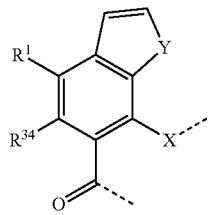 A330 (a10)
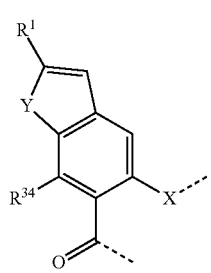 A331 (a10)
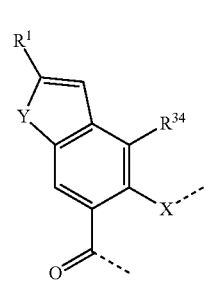 A332 (a10)
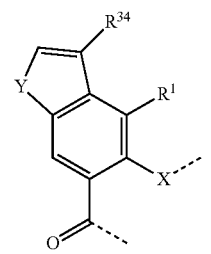 A333 (a10)
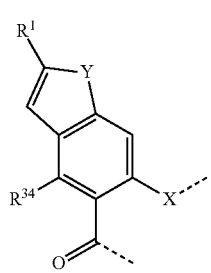 A334 (a10)
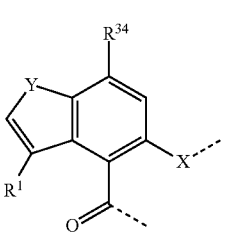 A335 (a10)

TABLE 10-continued
Radicals A1 (a1)-A626 (a25)
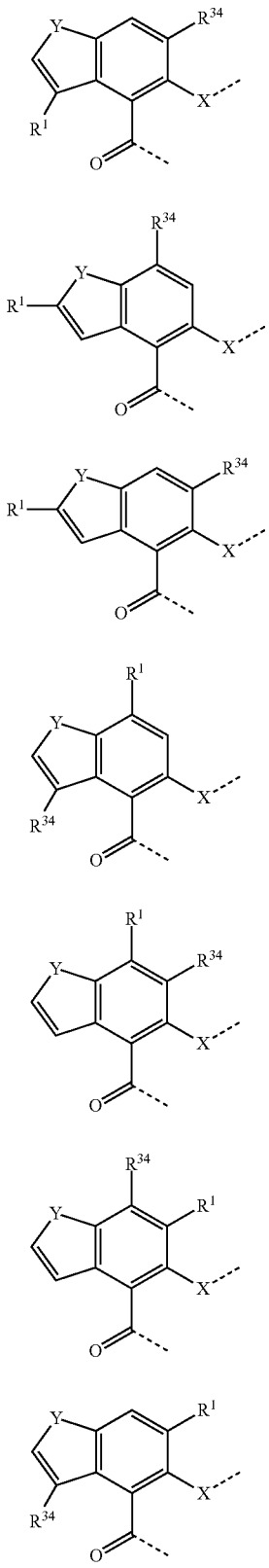
A336 (a10)
A337 (a10)
A338 (a10)
A339 (a10)
A340 (a10)
A341 (a10)
A342 (a10)
TABLE 10-continued
Radicals A1 (a1)-A626 (a25)
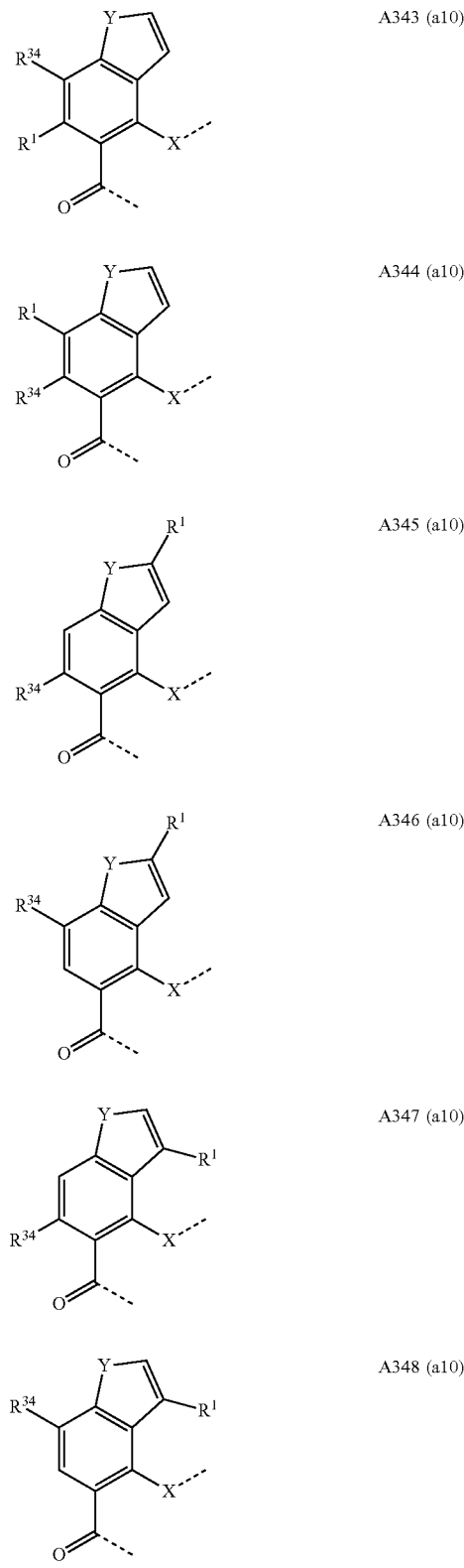
A343 (a10)
A344 (a10)
A345 (a10)
A346 (a10)
A347 (a10)
A348 (a10)

TABLE 10-continued
Radicals A1 (a1)-A626 (a25)
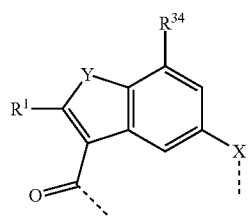 A349 (a10)
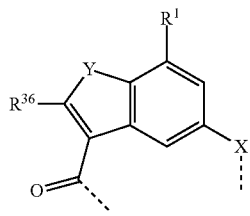 A350 (a10)
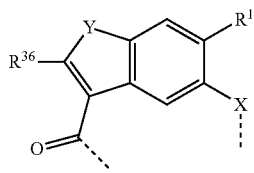 A351 (a10)
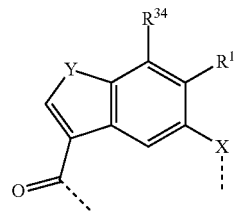 A352 (a10)
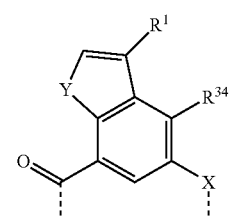 A353 (a10)
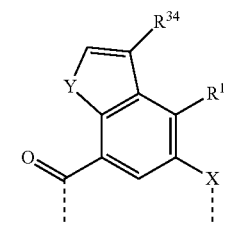 A354 (a10)
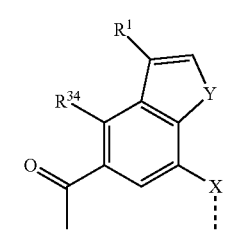 A355 (a10)
TABLE 10-continued
Radicals A1 (a1)-A626 (a25)
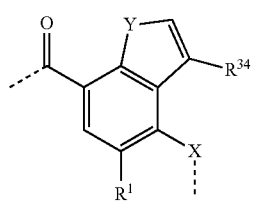 A356 (a10)
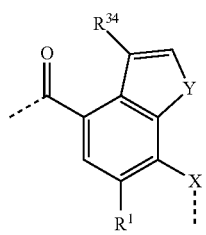 A357 (a10)
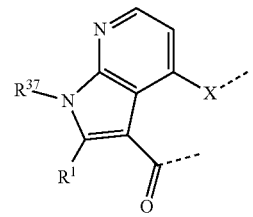 A358 (a11)
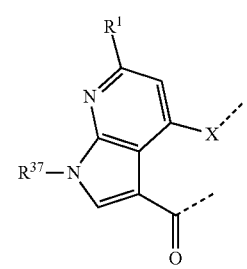 A359 (a11)
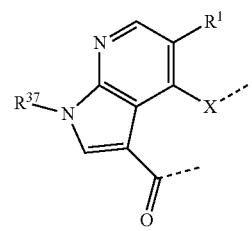 A360 (a11)
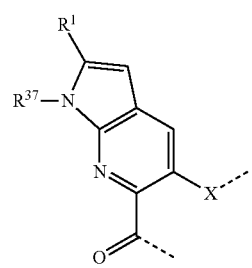 A361 (a11)

TABLE 10-continued
Radicals A1 (a1)-A626 (a25)
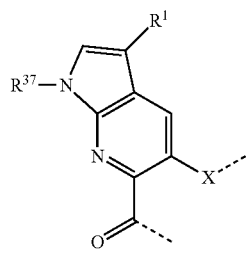 A362 (a11)
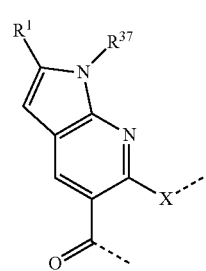 A363 (a11)
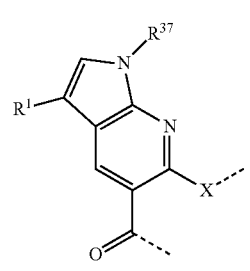 A364 (a11)
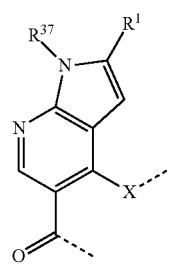 A365 (a11)
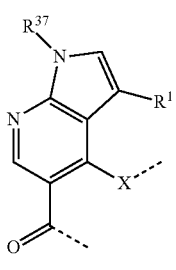 A366 (a11)
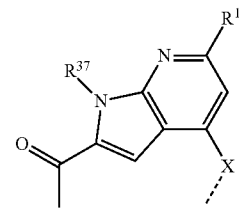 A367 (a11)
TABLE 10-continued
Radicals A1 (a1)-A626 (a25)
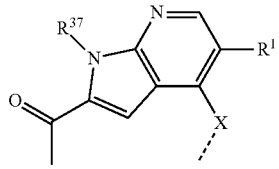 A368 (a11)
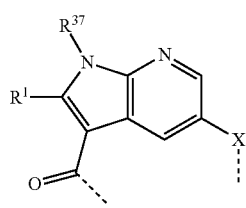 A369 (a11)
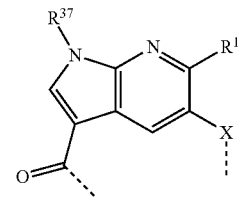 A370 (a11)
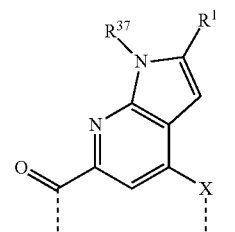 A371 (a11)
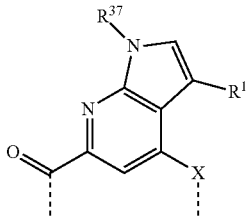 A372 (a11)
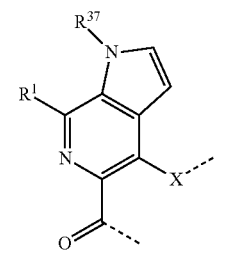 A373 (a12)
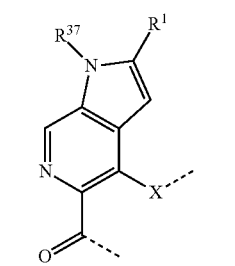 A374 (a12)

TABLE 10-continued

Radicals A1 (a1)-A626 (a25)

A375 (a12)
A376 (a12)
A377 (a12)
A378 (a12)
A379 (a12)
A380 (a12)
A381 (a12)
A382 (a12)
A383 (a12)
A384 (a12)
A385 (a12)
A386 (a13)
A387 (a13)
A388 (a13)

TABLE 10-continued

Radicals A1 (a1)-A626 (a25)

A389 (a13)

A390 (a13)

A391 (a13)

A392 (a13)

A393 (a13)

A394 (a13)

A395 (a13)

A396 (a13)

A397 (a13)

A398 (a13)

A399 (a14)

A400 (a14)

A401 (a14)

TABLE 10-continued

Radicals A1 (a1)-A626 (a25)

A402 (a14)

A403 (a14)

A404 (a14)

A405 (a14)

A406 (a14)

A407 (a14)

A408 (a14)

A409 (a14)

A410 (a14)

A411 (a14)

A412 (a14)

A413 (a14)

A414 (a15)

TABLE 10-continued
Radicals A1 (a1)-A626 (a25)
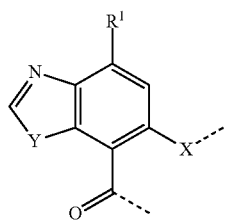 A415 (a15)
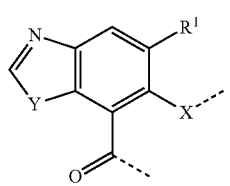 A416 (a15)
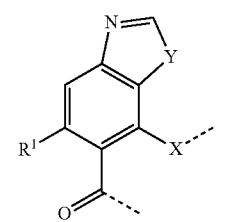 A417 (a15)
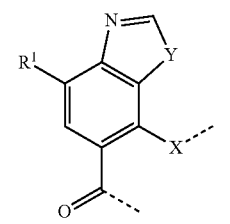 A418 (a15)
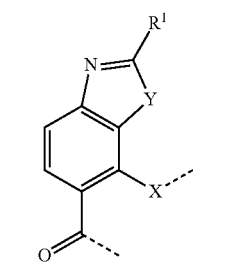 A419 (a15)
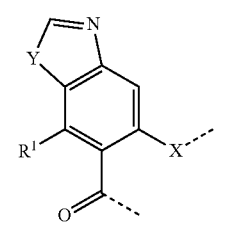 A420 (a15)
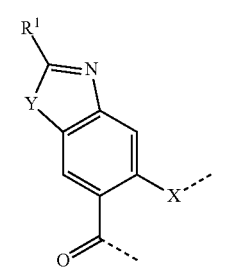 A421 (a15)
TABLE 10-continued
Radicals A1 (a1)-A626 (a25)
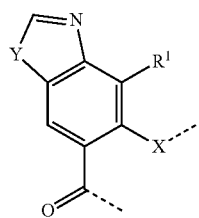 A422 (a15)
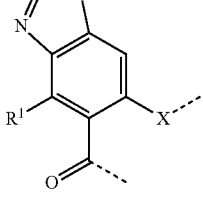 A423 (a15)
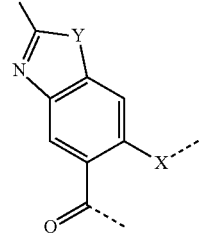 A424 (a15)
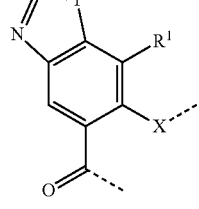 A425 (a15)
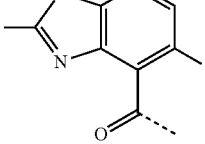 A426 (a15)
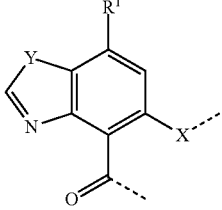 A427 (a15)
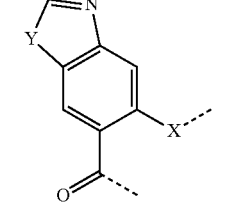 A428 (a15)

TABLE 10-continued
Radicals A1 (a1)-A626 (a25)
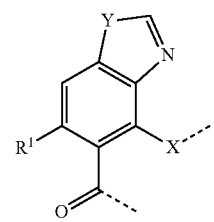 A429 (a15)
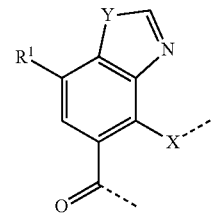 A430 (a15)
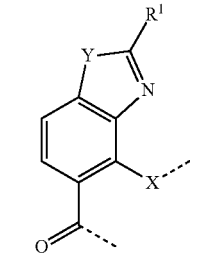 A431 (a15)
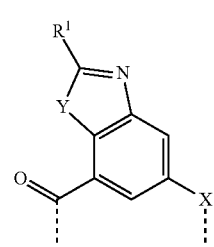 A432 (a15)
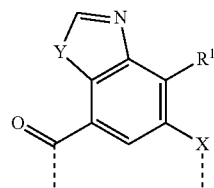 A433 (a15)
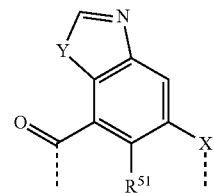 A434 (a15)
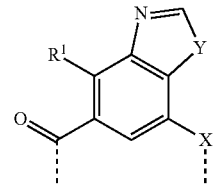 A435 (a15)
TABLE 10-continued
Radicals A1 (a1)-A626 (a25)
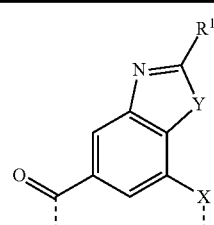 A436 (a15)
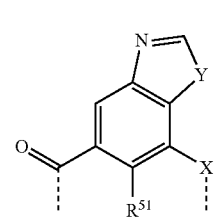 A437 (a15)
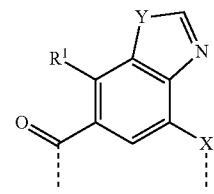 A438 (a15)
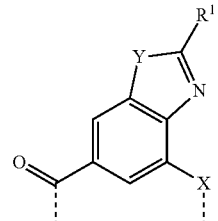 A439 (a15)
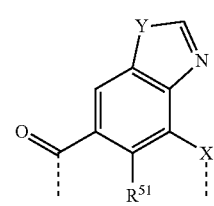 A440 (a15)
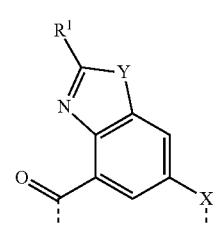 A441 (a15)
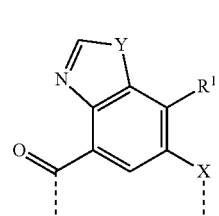 A442 (a15)

TABLE 10-continued
Radicals A1 (a1)-A626 (a25)
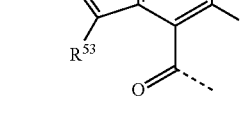 A443 (a15)
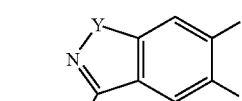 A444 (a15)
A445 (a15)
A446 (a15)
A447 (a15)
A448 (a15)
A449 (a15)
A450 (a16)
A451 (a16)
A452 (a16)
A453 (a16)
A454 (a16)
A455 (a16)
A456 (a16)

TABLE 10-continued
Radicals A1 (a1)-A626 (a25)
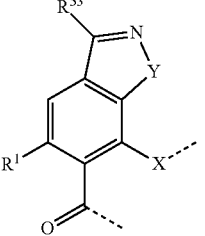 A457 (a16)
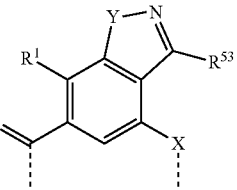 A458 (a16)
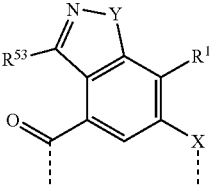 A459 (a16)
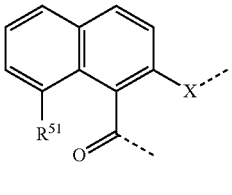 A460 (a17)
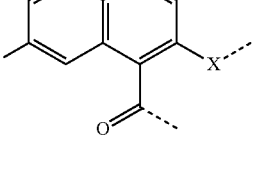 A461 (a17)
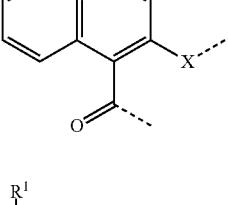 A462 (a17)
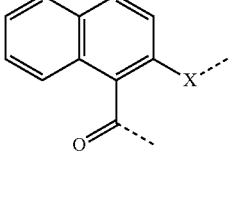 A463 (a17)
TABLE 10-continued
Radicals A1 (a1)-A626 (a25)
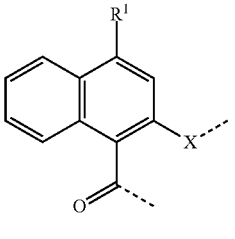 A464 (a17)
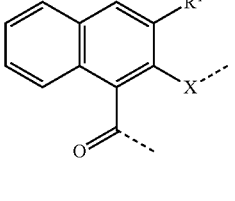 A465 (a17)
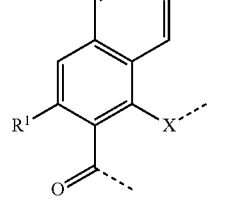 A466 (a17)
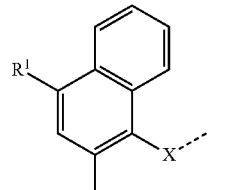 A467 (a17)
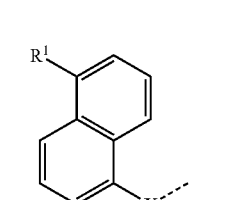 A468 (a17)
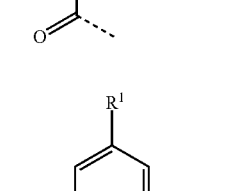 A469 (a17)

TABLE 10-continued
Radicals A1 (a1)-A626 (a25)
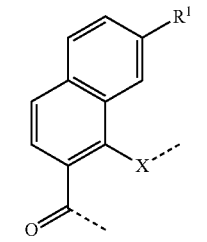 A470 (a17)
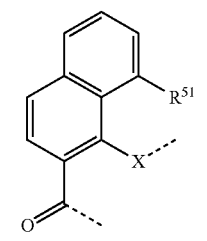 A471 (a17)
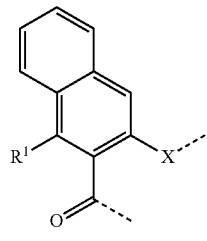 A472 (a17)
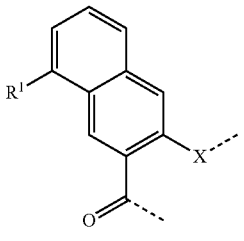 A473 (a17)
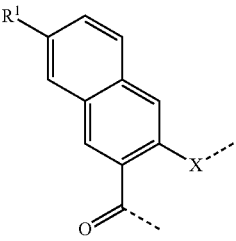 A474 (a17)
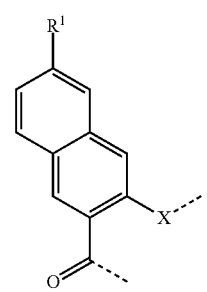 A475 (a17)
TABLE 10-continued
Radicals A1 (a1)-A626 (a25)
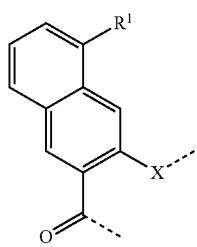 A476 (a17)
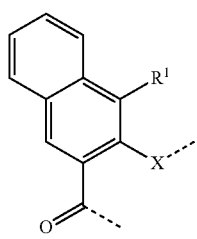 A477 (a17)
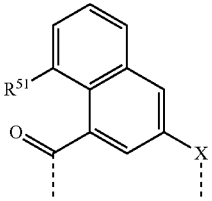 A478 (a17)
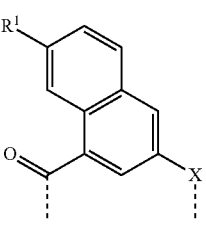 A479 (a17)
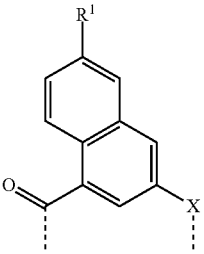 A480 (a17)
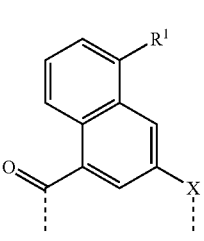 A481 (a17)

TABLE 10-continued
Radicals A1 (a1)-A626 (a25)
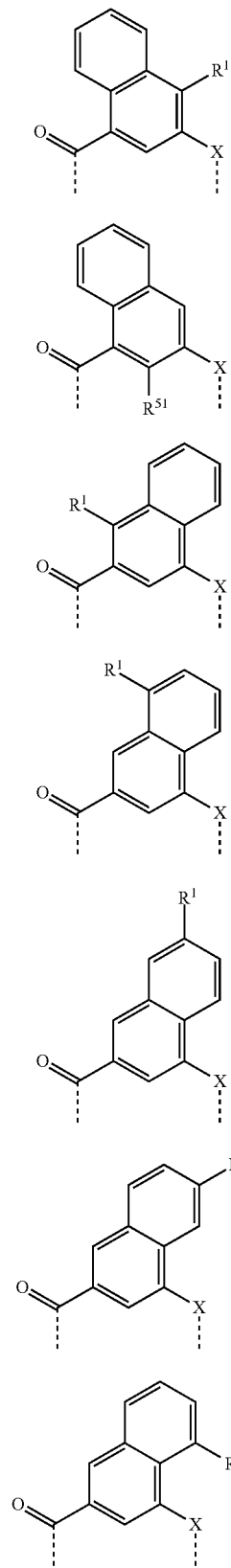
A482 (a17)
A483 (a17)
A484 (a17)
A485 (a17)
A486 (a17)
A487 (a17)
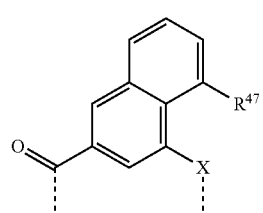
A488 (a17)
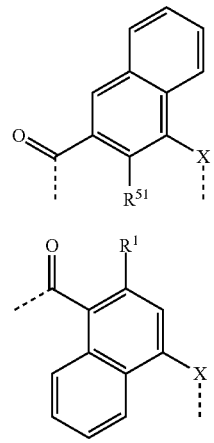
A489 (a17)
A490 (a17)
A491 (a17)
A492 (a17)
A493 (a17)
A494 (a17)
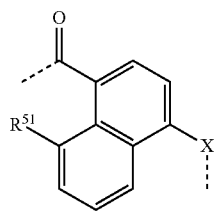
A495 (a17)

TABLE 10-continued

Radicals A1 (a1)-A626 (a25)

A496 (a17), A497 (a17), A498 (a17), A499 (a17), A500 (a17), A501 (a17), A502 (a17), A503 (a17), A504 (a17), A505 (a17), A506 (a17), A507 (a17)

TABLE 10-continued
Radicals A1 (a1)-A626 (a25)
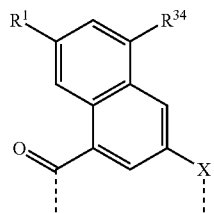 A508 (a17)
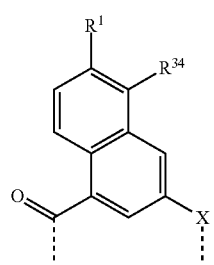 A509 (a17)
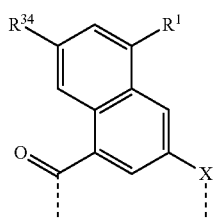 A510 (a17)
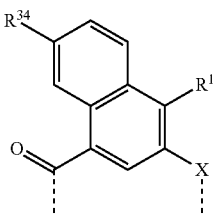 A511 (a17)
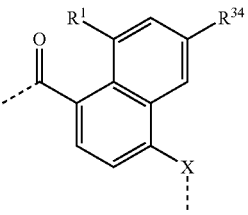 A512 (a17)
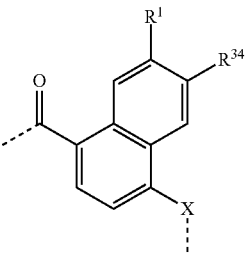 A513 (a17)
TABLE 10-continued
Radicals A1 (a1)-A626 (a25)
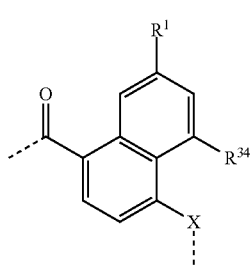 A514 (a17)
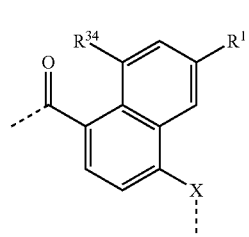 A515 (a17)
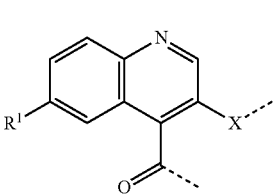 A516 (a18)
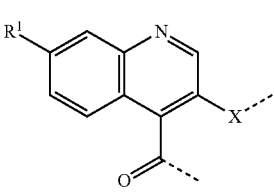 A517 (a18)
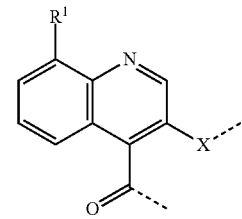 A518 (a18)
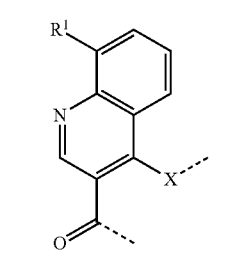 A519 (a18)

TABLE 10-continued

Radicals A1 (a1)-A626 (a25)

A520 (a18), A521 (a18), A522 (a18), A523 (a18), A524 (a18), A525 (a18), A526 (a18), A527 (a18), A528 (a18), A529 (a18), A530 (a18), A531 (a18), A532 (a18)

TABLE 10-continued
Radicals A1 (a1)-A626 (a25)
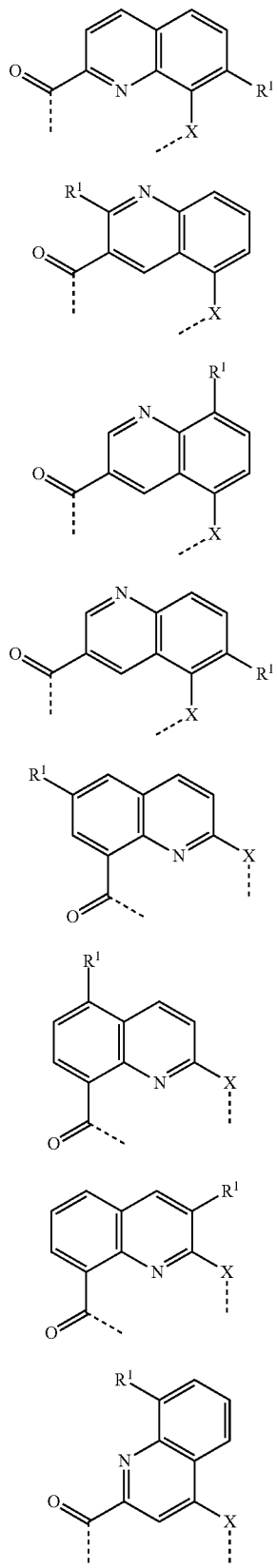
A533 (a18)
A534 (a18)
A535 (a18)
A536 (a18)
A537 (a18)
A538 (a18)
A539 (a18)
A540 (a18)
TABLE 10-continued
Radicals A1 (a1)-A626 (a25)
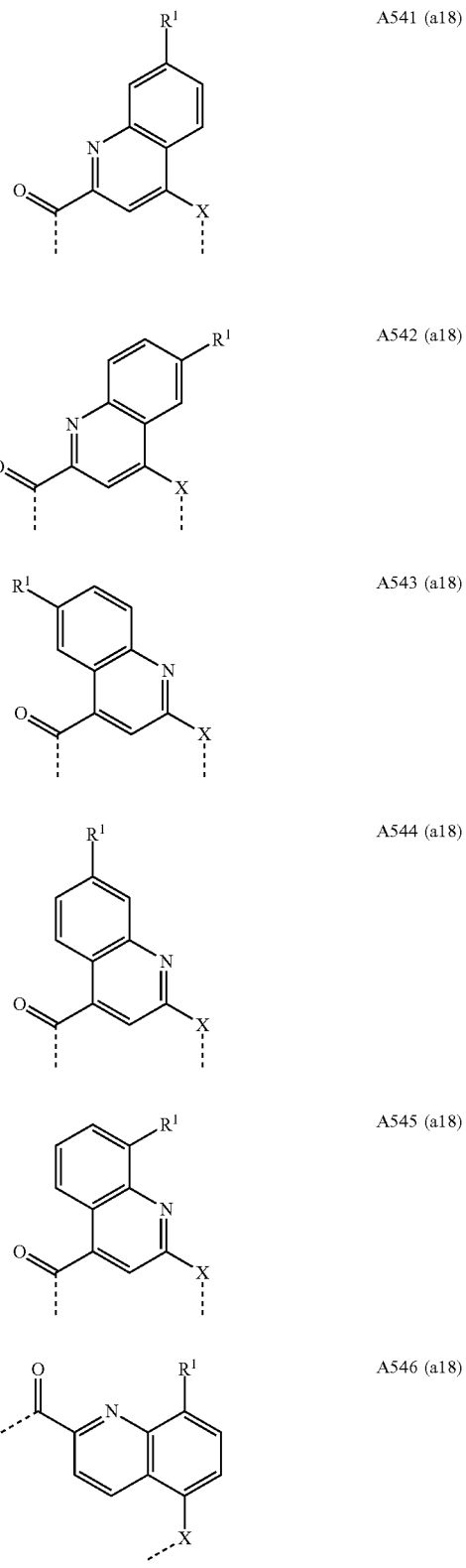
A541 (a18)
A542 (a18)
A543 (a18)
A544 (a18)
A545 (a18)
A546 (a18)

TABLE 10-continued
Radicals A1 (a1)-A626 (a25)
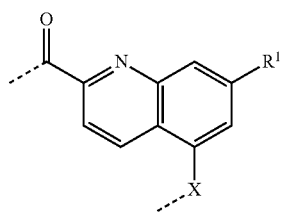 A547 (a18)
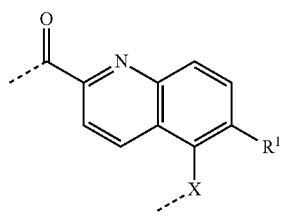 A548 (a18)
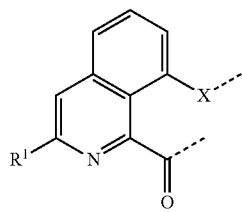 A549 (a19)
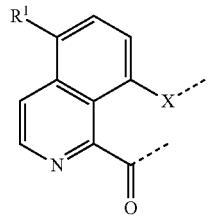 A550 (a19)
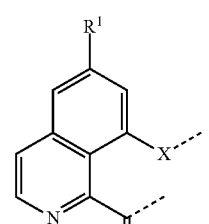 A551 (a19)
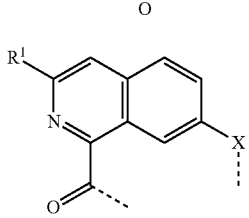 A552 (a19)
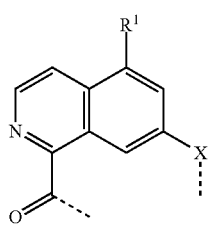 A553 (a19)
TABLE 10-continued
Radicals A1 (a1)-A626 (a25)
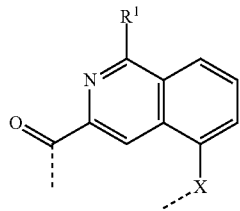 A554 (a19)
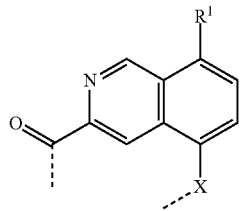 A555 (a19)
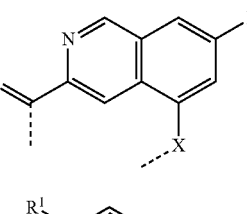 A556 (a19)
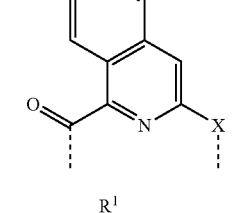 A557 (a19)
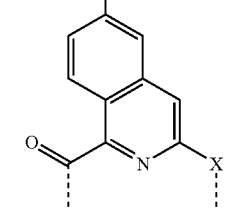 A558 (a19)
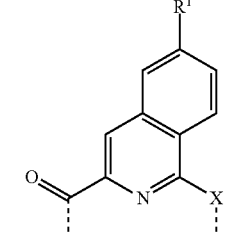 A559 (a19)
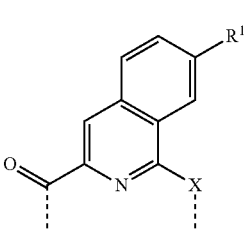 A560 (a19)

TABLE 10-continued
Radicals A1 (a1)-A626 (a25)
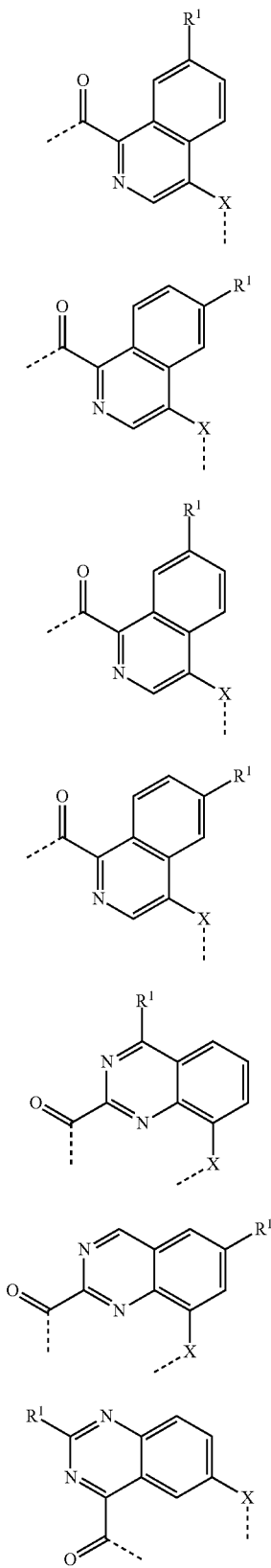
A561 (a19)
A562 (a19)
A563 (a19)
A564 (a19)
A565 (a20)
A566 (a20)
A567 (a20)
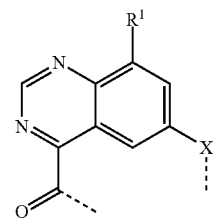
A568 (a20)
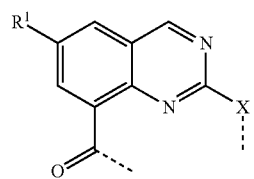
A569 (a20)
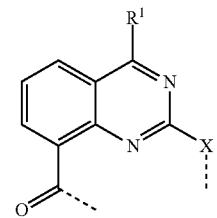
A570 (a20)
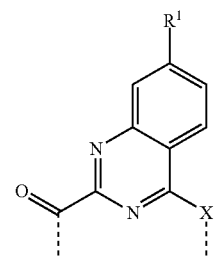
A571 (a20)
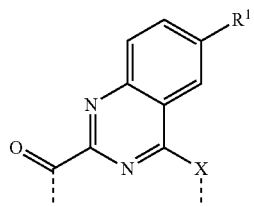
A572 (a20)
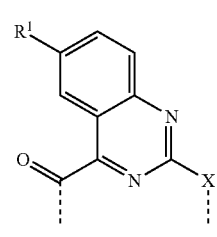
A573 (a20)
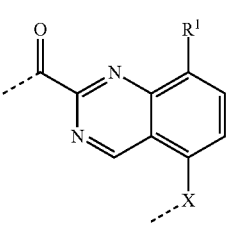
A574 (a20)

TABLE 10-continued

Radicals A1 (a1)-A626 (a25)

A575 (a20)

A576 (a20)

A577 (a20)

A578 (a21)

A579 (a21)

A580 (a21)

A581 (a21)

A582 (a21)

A583 (a21)

A584 (a21)

A585 (a21)

A586 (a21)

A587 (a21)

A588 (a22)

TABLE 10-continued
Radicals A1 (a1)-A626 (a25)
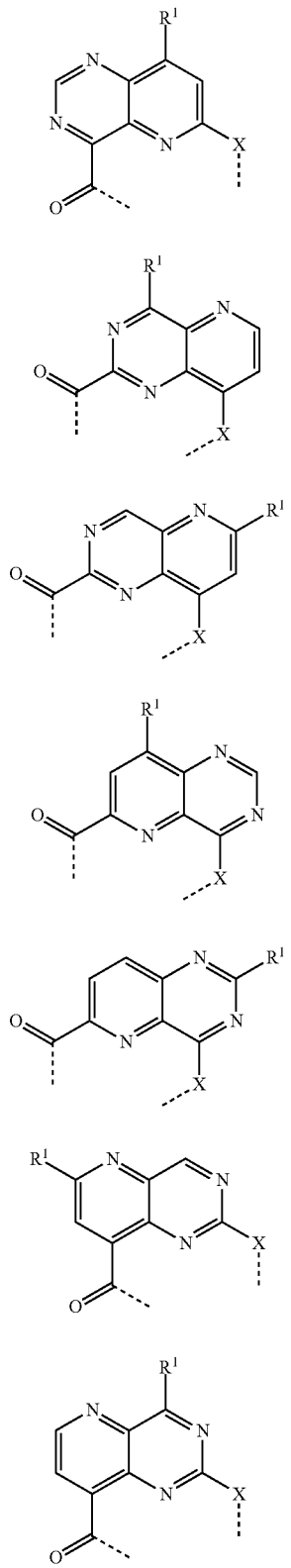
A589 (a22)
A590 (a22)
A591 (a22)
A592 (a22)
A593 (a22)
A594 (a22)
A595 (a22)
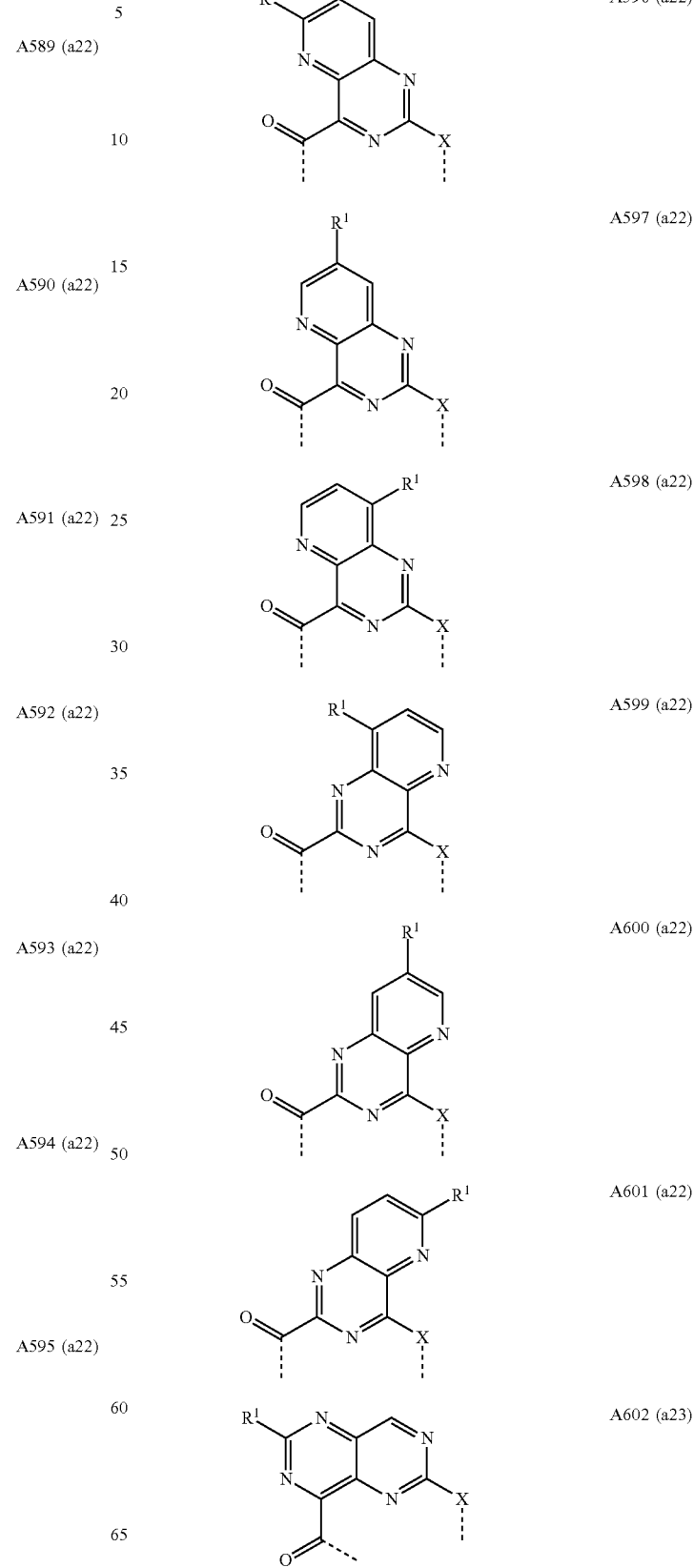
A596 (a22)
A597 (a22)
A598 (a22)
A599 (a22)
A600 (a22)
A601 (a22)
A602 (a23)

TABLE 10-continued
Radicals A1 (a1)-A626 (a25)
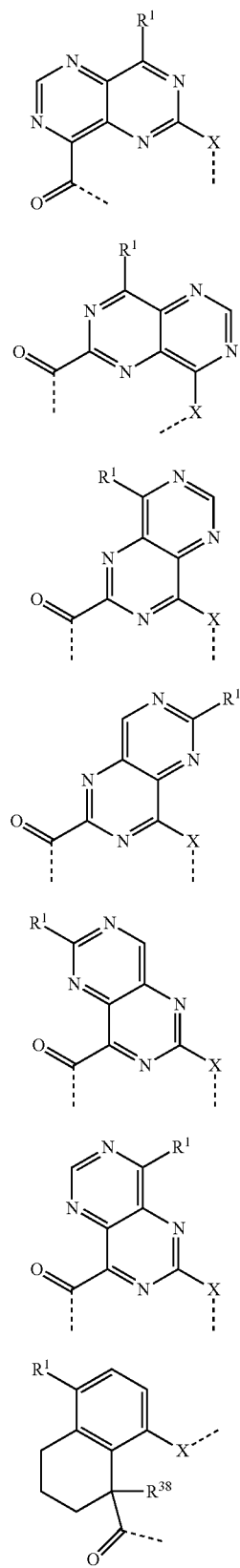
A603 (a23)
A604 (a23)
A605 (a23)
A606 (a23)
A607 (a23)
A608 (a23)
A609 (a24)
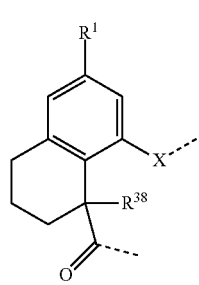
A610 (a24)
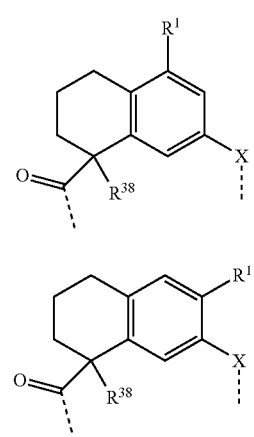
A611 (a24)
A612 (a24)
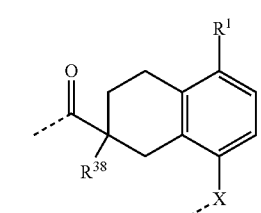
A613 (a24)
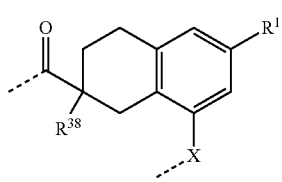
A614 (a24)
A615 (a24)
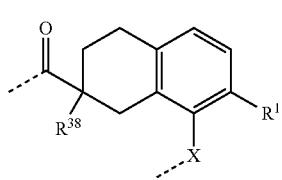
A616 (a24)

TABLE 10-continued

Radicals A1 (a1)-A626 (a25)

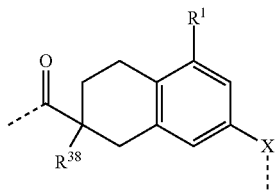 A617 (a24)

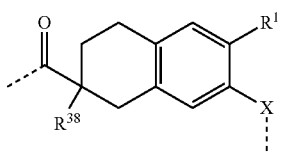 A618 (a24)

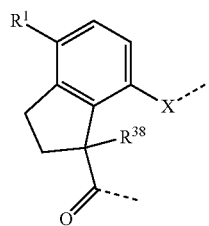 A619 (a25)

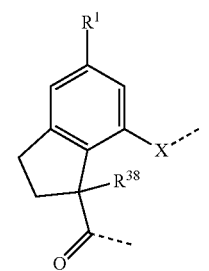 A620 (a25)

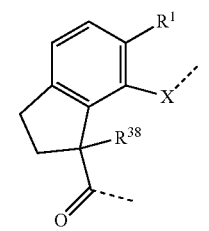 A621 (a25)

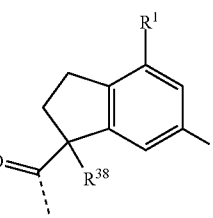 A622 (a25)

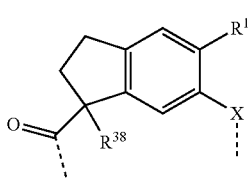 A623 (a25)

TABLE 10-continued

Radicals A1 (a1)-A626 (a25)

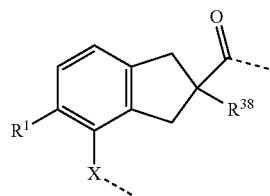 A624 (a25)

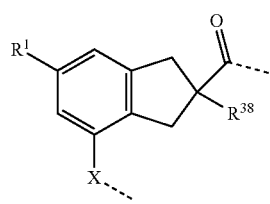 A625 (a25)

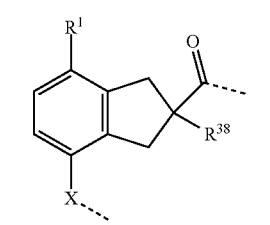 A626 (a25)

Divalent building blocks B1-B21 (Table 11, hereinbelow) constitute a subset of possible building blocks based on the ring systems b1-b11 (Table 2, above). They are based on optionally substituted cyclic secondary amines carrying a moiety of type —CHR$^3$-LG, wherein LG is a suitable leaving group (e.g., but not limited to, —OH forming a suitable LG in situ during Mitsunobu reactions, or halogens like —Br or —I amenable to S$_N$ reactions) that can be replaced by the nucleophilic groups of building blocks A thus forming an ether (—O—) or a thioether (—S—) linkage between building blocks of type A and B. In most products of type I, the secondary amine nitrogen of building block B forms a tertiary amide linkage with the carboxyl group of building blocks of type C. In case a suitable exocyclic amine functionality is present, it can be, instead of the ring-nitrogen, involved in the formation of a secondary or preferably tertiary amide bond to C. Such an alternative binding mode is realized with, but not limited to, B10.

By virtue of inducing peptidyl cis-trans isomerization or stabilizing cis amide bonds, building blocks of type B can function as conformational modulators in products of type I.

TABLE 11

Radicals B1-B21

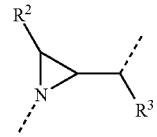 B1 (b1)

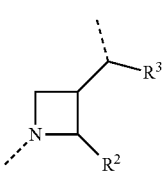 B2 (b2)

TABLE 11-continued
Radicals B1-B21
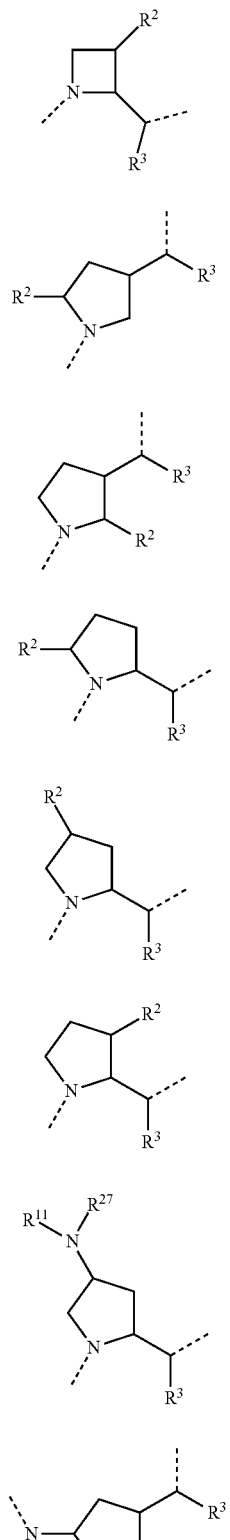
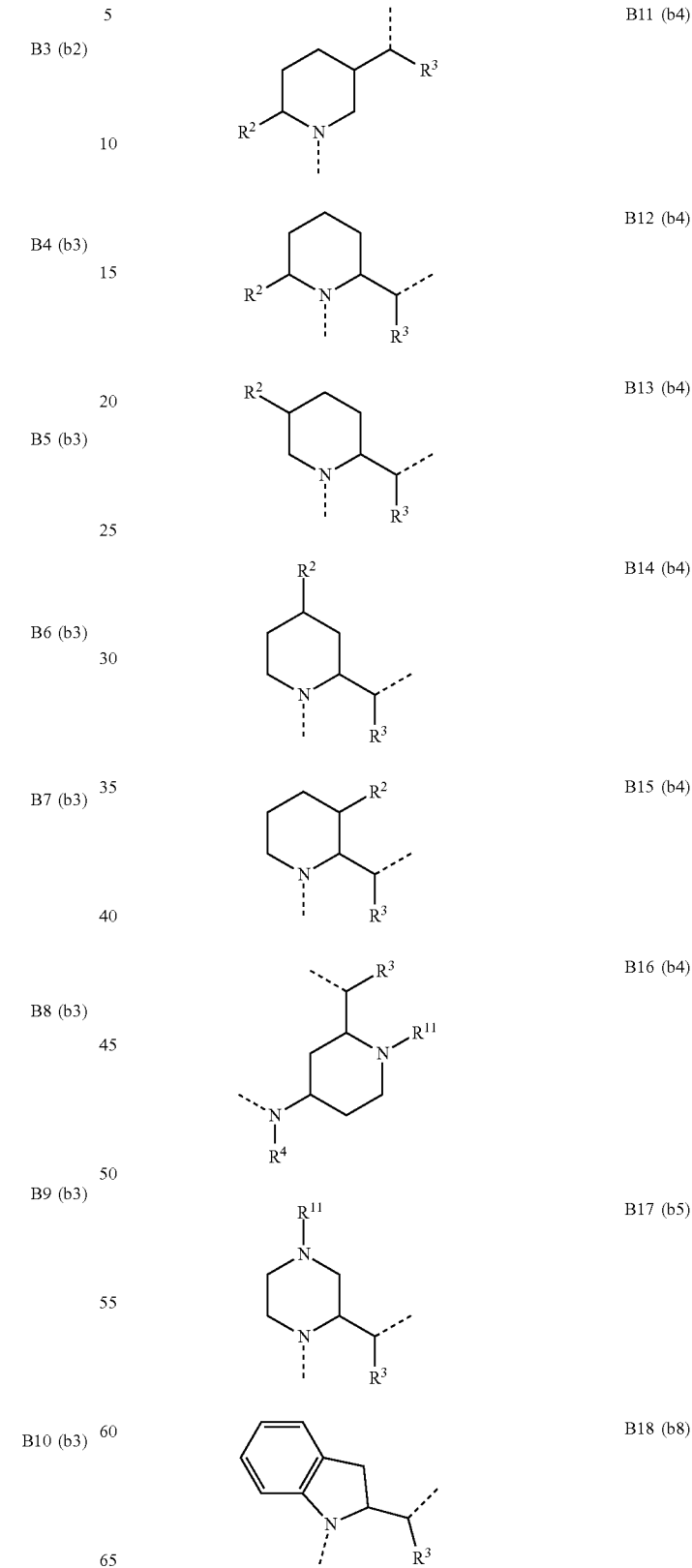

TABLE 11-continued

Radicals B1-B21

B19 (b10) [structure: tetrahydroquinoline with CH(R³) substituent]

B20 (b11) [structure: tetrahydroisoquinoline with CH(R³) substituent at position 1]

B21 (b11) [structure: tetrahydroisoquinoline with CH(R³) substituent at position 3]

The divalent moiety C may consist of an ensemble of one to three subunits c1-c3, each derived from suitably protected and functionalized amine or amino acid derivatives. As a consequence the C moiety directly influences the ring size of the resulting macrocycle and can be regarded as spacer or linker. This linker ensemble C is joined to building block A via its N-terminus and to building block B via its C-terminus to form a macrocyclic ring of type I. According to its definition the connections within the linker ensemble, i.e. V or W, can be accomplished by amide bonds ($-NR^4-C(=O)-$), an alkene[1,2]diyl ($-CHR^{12}=CHR^{13}-$), an alkane[1,2]diyl ($-CHR^{12}-CHR^{13}-$), or methylene-heteroatom moiety ($-CHR^3-Z-$), an oxalyl unit ($-C(=O)-C(=O)-$) or a disulfide bridge ($-S-S-$). With respect to the macrocyclic backbone of I it follows that the linker C contributes at least one amide bonds.

Suitable linker C can be represented by, but are not limited to, the moieties shown in Table 12. For example C1 represents a linker moiety constituted of one to three α-amino acid derivatives connected along their main chains, while $C_7$-$C_{10}$ are equivalent to dipeptide moieties of β-amino acids. The simplest embodiments in which at least one connection between the subunits is realized by a non-amidic group are C2-C5. Finally C58-C101 shall depict situations in which a longer (>3 C-atoms) side chain connection of a suitable diamine or diacid is involved in an amide bond.

TABLE 12

Representative Embodiments of Linker C

C1 [structure]

C2 [structure]

C3 [structure]

C4 [structure]

C5 [structure]

C6 [structure]

TABLE 12-continued

Representative Embodiments of Linker C

[Chemical structures C7 through C17 showing linker embodiments]

C7, C8, C9, C10, C11, C12, C13, C14, C15, C16, C17

TABLE 12-continued

Representative Embodiments of Linker C

| Structure | Label |
|---|---|
| Chemical structure with $R^4, R^{14}, R^5, R^{12}, R^7, R^{16}$ groups | C18 |
| Chemical structure with $R^4, R^5, R^{14}, R^{14}, R^4, R^7, R^{16}$ groups | C19 |
| Chemical structure with $R^4, R^5, R^{14}, R^{14}, R^4, R^{16}, R^7, R^{16}$ groups | C20 |
| Chemical structure with $R^4, R^5, R^{14}, R^{14}, R^4, R^{16}, R^7$ groups | C21 |
| Chemical structure with $R^4, R^{14}, R^5, R^{14}, R^4, R^7, R^{16}$ groups | C22 |
| Chemical structure with $R^4, R^{14}, R^5, R^{14}, R^4, R^{16}, R^7, R^{16}$ groups | C23 |
| Chemical structure with $R^4, R^{14}, R^5, R^{14}, R^4, R^{16}, R^7$ groups | C24 |
| Chemical structure with $R^4, R^{14}, R^{14}, R^5, R^4, R^7, R^{16}$ groups | C25 |
| Chemical structure with $R^4, R^{14}, R^{14}, R^5, R^4, R^{16}, R^7, R^{16}$ groups | C26 |
| Chemical structure with $R^4, R^{14}, R^{14}, R^5, R^4, R^{16}, R^7$ groups | C27 |
| Chemical structure with $R^4, R^5, R^{14}, R^{14}, R^3, R^7, R^{16}$ groups | C28 |

TABLE 12-continued

Representative Embodiments of Linker C

[Structures C29 through C40 depicting chemical linker formulas with R-group substituents, N, C, Z, and U atoms.]

TABLE 12-continued

Representative Embodiments of Linker C

| Structure | Label |
|---|---|
| Chemical structure with R⁴, R¹⁴, R⁵, R¹⁴, R¹², R¹⁶, R⁷, R¹⁶ substituents | C41 |
| Chemical structure C42 | C42 |
| Chemical structure C43 | C43 |
| Chemical structure C44 | C44 |
| Chemical structure C45 | C45 |
| Chemical structure C46 | C46 |
| Chemical structure C47 | C47 |
| Chemical structure C48 | C48 |
| Chemical structure C49 | C49 |
| Chemical structure C50 | C50 |
| Chemical structure C51 | C51 |
| Chemical structure C52 | C52 |

TABLE 12-continued
Representative Embodiments of Linker C
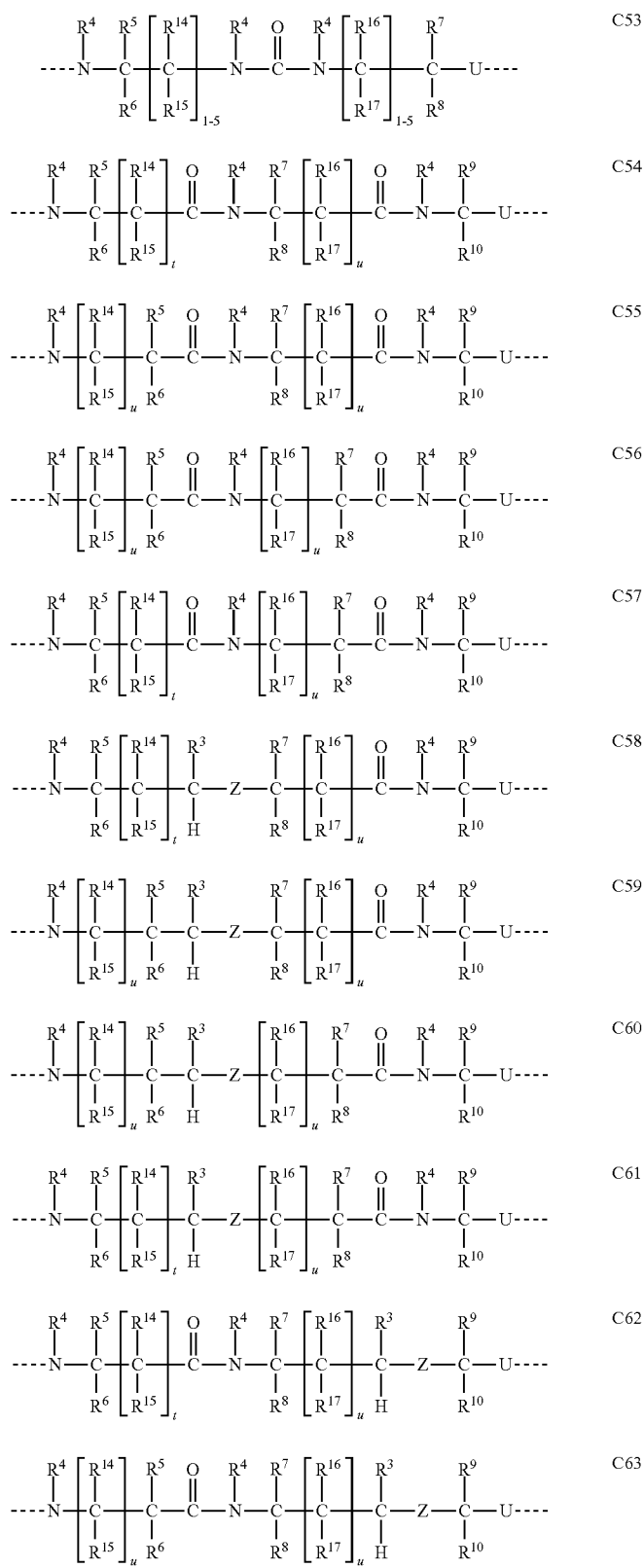

TABLE 12-continued

Representative Embodiments of Linker C (Chemical structures C64–C74 depicting representative embodiments of Linker C, containing substituents $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, along with N, C, Z, U atoms/groups and bracketed repeat units with subscripts $t$ and $u$.)

TABLE 12-continued

Representative Embodiments of Linker C

[Structures C75 through C85 depicting representative embodiments of Linker C, containing variable substituents R³–R¹⁷, Z, U, and repeat indices t and u.]

TABLE 12-continued

Representative Embodiments of Linker C

| Structure | Label |
|---|---|
| Chemical structure with R groups | C86 |
| Chemical structure with R groups | C87 |
| Chemical structure with R groups | C88 |
| Chemical structure with R groups | C89 |
| Chemical structure with R groups | C90 |
| Chemical structure with R groups | C91 |
| Chemical structure with R groups | C92 |
| Chemical structure with R groups | C93 |
| Chemical structure with R groups | C94 |
| Chemical structure with R groups | C95 |
| Chemical structure with R groups | C96 |

TABLE 12-continued

Representative Embodiments of Linker C

C97

C98

C99

C100

C101

According to the preceding explanations, products of type I contain at least two amide bonds. As mentioned in the introduction, tertiary amide containing products generally show various ratios of cis and trans amide bond conformations in solution; this preference is in contrast to secondary amides that generally adopt trans conformations only. The occurrence of cis and/or trans conformations in macrocyclic natural products containing tertiary amides is well documented. In some cases a rapid equilibration between the cis and trans amide bonds, the so-called "peptidyl cis/trans isomerization", is observed; whereas in other cases discrete cis and trans tertiary amide bonds are detected as two stable conformers in solution at room temperature.

All possible stereoisomers, including atropisomers, and distinct conformers or rotamers of macrocycles of type I are part of this invention.

Within the general scope of building blocks A preferred radicals are:

Within the general scope of building blocks A preferred radicals are A1(a1); A2(a1); A3(a1); A4(a1); A5(a1); A6(a1); A7(a1); A9(a1); A10(a1); A73(a2); A170(a4); A209 (a7); A240(a10); A272(a10); A532(a18); A609(a24); A612 (a24) and A614(a24) (Table 13).

TABLE 13

Preferred Building Blocks of Type A

A1 (a1)

TABLE 13-continued

Preferred Building Blocks of Type A

A2 (a1)

A3 (a1)

A4 (a1)

A5 (a1)

TABLE 13-continued
Preferred Building Blocks of Type A
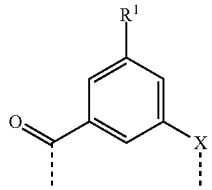
A6 (a1)
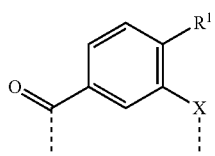
A7 (a1)
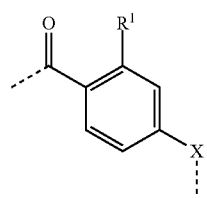
A9 (a1)
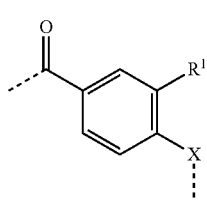
A10 (a1)
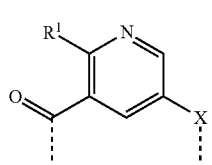
A73 (a2)
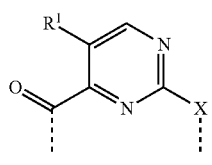
A170 (a4)
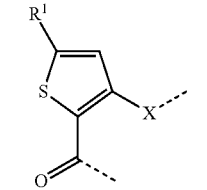
A209 (a7)
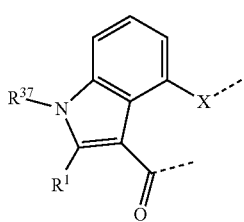
A240 (a10)
TABLE 13-continued
Preferred Building Blocks of Type A
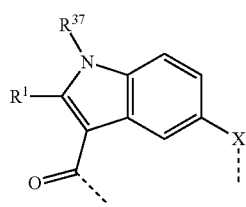
A272 (a10)
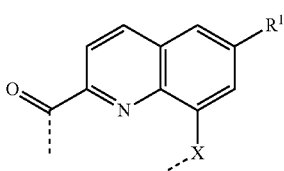
A532 (a18)
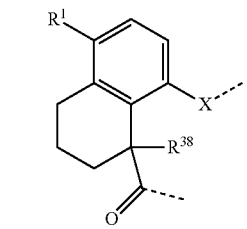
A609 (a24)
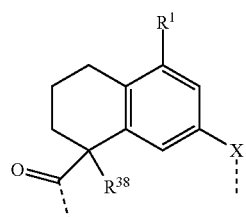
A612 (a24)
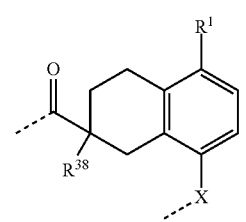
A614 (a24)
Preferred building blocks of type B are B4 (b3); B5 (b3); B6 (b3); B7 (b3); B8 (b3); B9 (b3); B10 (b3); B12 (b4); B13 (b4); B14 (b4); B15 (b4); B16 (b4) and B17 (b5) (Table 14).
TABLE 14
Preferred Building Blocks of Type B
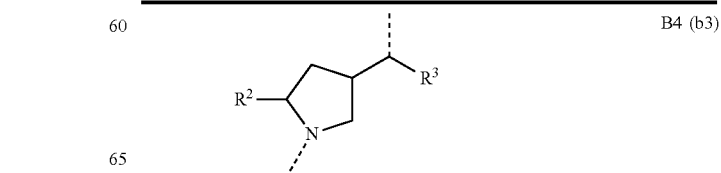
B4 (b3)

TABLE 14-continued

Preferred Building Blocks of Type B (structures B5 (b3), B6 (b3), B7 (b3), B8 (b3), B9 (b3), B10 (b3), B12 (b4), B13 (b4), B14 (b4), B15 (b4), B16 (b4), B17 (b5))

Preferred embodiments of linker C are shown in Table 15.

TABLE 15

Preferred Linker of type C (structures C1, C2, C3, C4, C5, C6)

TABLE 15-continued
Preferred Linker of type C
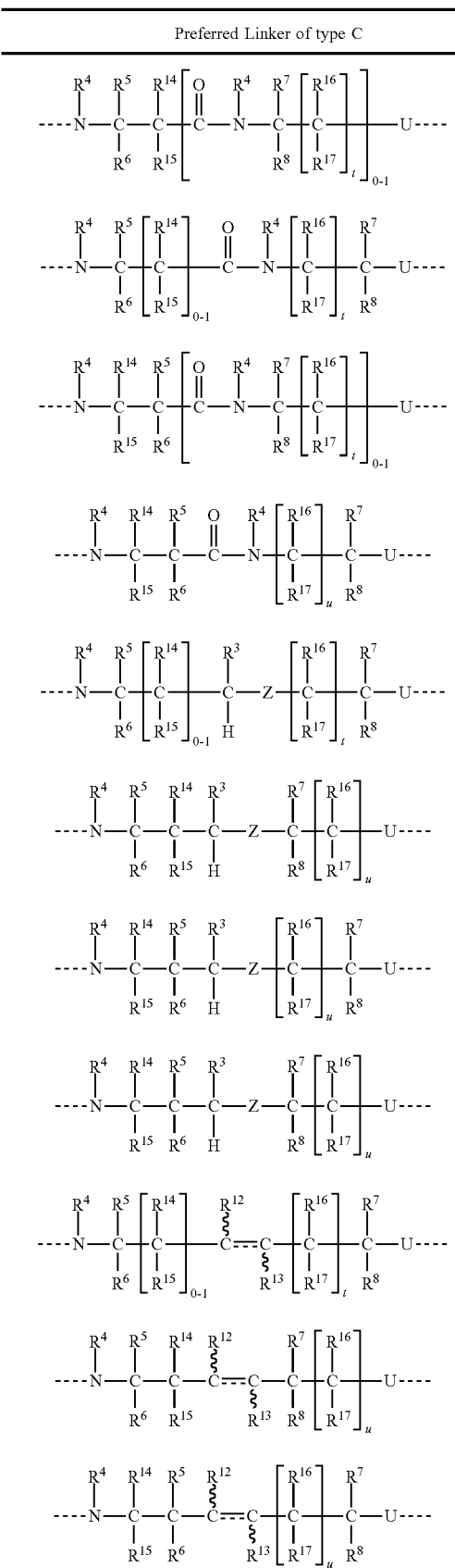
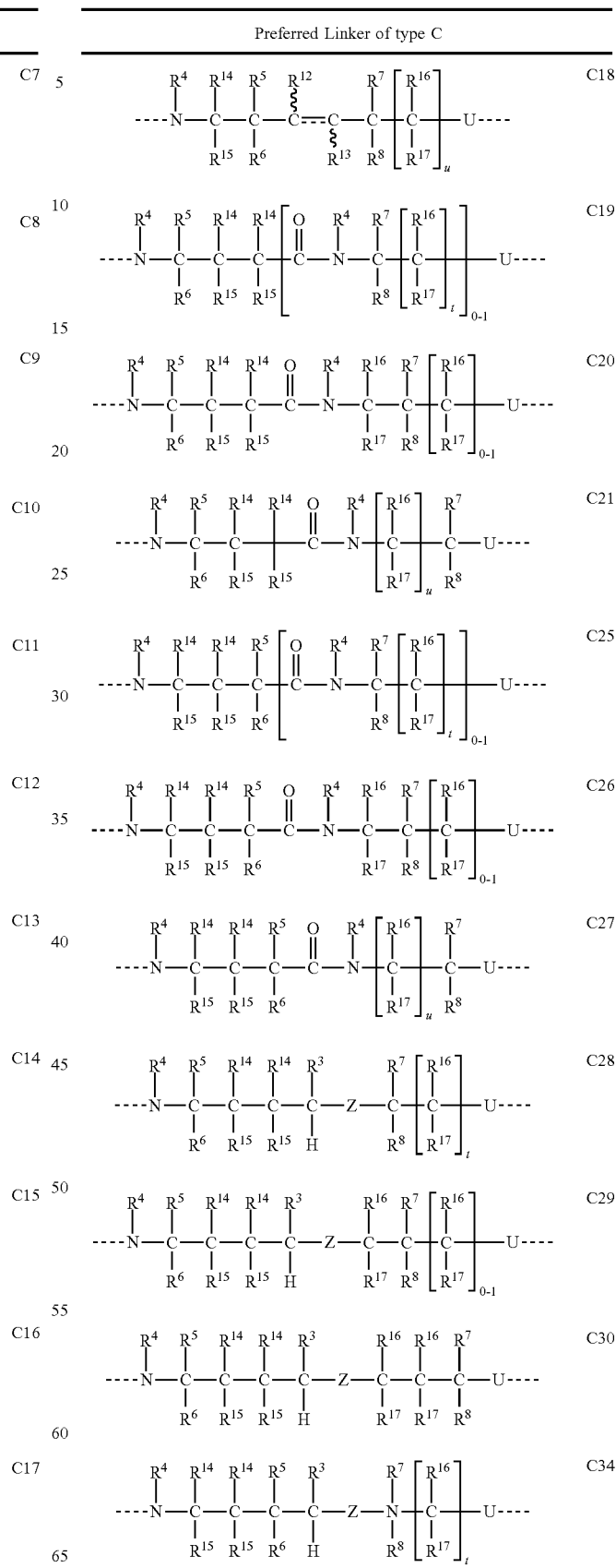

TABLE 15-continued

Preferred Linker of type C (Structural formulas C35–C61 not transcribed.)

TABLE 15-continued

Preferred Linker of type C (Structural formulas C62–C89 depicting linker structures, not transcribed as text.)

TABLE 15-continued

Preferred Linker of type C

C90: structure with $R^4, R^5, [R^{14}]_{1-5}, R^6, R^{15}, R^4, O, R^7, [R^{16}]_t, R^8, R^{17}, O, R^4, R^9, [R^{10}]_{0-1}$ — N—C—C—N—C—C—C—N—C—U C91: structure $R^4, [R^{14}]_{1-5}, R^{15}, R^5, R^6, R^4, O, R^7, [R^{16}]_t, R^8, R^{17}, O, R^4, R^9, [R^{10}]_{0-1}$ — N—C—C—N—C—C—C—N—C—U C92: structure $R^4, [R^{14}]_{1-5}, R^{15}, R^5, R^6, R^4, O, [R^{16}]_t, R^7, R^{17}, R^8, O, R^4, R^9, [R^{10}]_{0-1}$ — N—C—C—N—C—C—C—N—C—U C93: structure $R^4, R^5, [R^{14}]_{1-5}, R^6, R^{15}, R^4, O, [R^{16}]_t, R^7, R^{17}, R^8, O, R^4, R^9, [R^{10}]_{0-1}$ — N—C—C—N—C—C—C—N—C—U The preferred substituents of the preferred building blocks A, B and C are defined as:

$R^1$: H; F; Cl; Br; I; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl;
—$(CR^{18}R^{19})_qOR^{20}$; —$(CR^{18}R^{19})_qNR^4R^{11}$; —$(CR^{18}R^{19})_qNR^4COOR^{21}$;
—$(CR^{18}R^{19})_qNR^4COR^{22}$; —$(CR^{18}R^{19})_qNR^4CONR^4R^{11}$; —$(CR^{18}R^{19})_qNR^4SO_2R^{23}$;
—$(CR^{18}R^{19})_qNR^4SO_2NR^4R^{11}$; —$(CR^{18}R^{19})_qCOOR^{21}$; —$(CR^{18}R^{19})_qCONR^4R^{11}$;
—$(CR^{18}R^{19})_qSO_2NR^4R^{11}$; —$(CR^{18}R^{19})_qPO(OR^{21})_2$; —$(CR^{18}R^{19})_qCOR^{22}$;
—$(CR^{18}R^{19})_qSO_2R^{23}$; —$(CR^{18}R^{19})_qOSO_3R^{21}$;
—$(CR^{18}R^{19})_qR^{24}$; —$(CR^{18}R^{19})_qR^{25}$; or
—$(CR^{18}R^{19})_qR^{26}$.

$R^2$: H; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_qOR^{20}$; —$(CR^{18}R^{19})_qNR^4R^{11}$; —$(CR^{18}R^{19})_qNR^4COOR^{21}$;
—$(CR^{18}R^{19})_qNR^4COR^{22}$; —$(CR^{18}R^{19})_qNR^4CONR^4R^{11}$; —$(CR^{18}R^{19})_qNR^4SO_2R^{23}$;
—$(CR^{18}R^{19})_qNR^4SO_2NR^4R^{11}$;
—$(CR^{18}R^{19})_qCOOR^{21}$; —$(CR^{18}R^{19})_qCONR^4R^{11}$;
—$(CR^{18}R^{19})_qSO_2NR^4R^{11}$;
—$(CR^{18}R^{19})_qPO(OR^{21})_2$; —$(CR^{18}R^{19})_qCOR^{22}$;
—$(CR^{18}R^{19})_qSO_2R^{23}$;
—$(CR^{18}R^{19})_qR^{24}$; —$(CR^{18}R^{19})_qR^{25}$; or —$(CR^{18}R^{19})_qR^{26}$.

$R^3$: Defined as above.

$R^4$: H; lower alkyl; lower alkenyl; lower cycloalkyl; lower heterocycloalkyl; or a suitable N-protecting group.

$R^5$, $R^7$ and $R^9$ are independently defined as: H; F; $CF_3$; lower alkyl; lower alkenyl; lower cycloalkyl; lower heterocycloalkyl; aryl; heteroaryl; lower arylalkyl; lower heteroarylalkyl;
$(CR^{18}R^{19})_sOR^{20}$; —$(CR^{18}R^{19})_sNR^4R^{11}$; —$(CR^{18}R^{19})_sNR^4COOR^{21}$;
—$(CR^{18}R^{19})_sNR^4COR^{22}$; —$(CR^{18}R^{19})_sNR^4CONR^4R^{11}$; —$(CR^{18}R^{19})_sNR^4SO_2R^{23}$;
—$(CR^{18}R^{19})_sNR^4SO_2NR^4R^{11}$; —$(CR^{18}R^{19})_qCOOR^{21}$; —$(CR^{18}R^{19})_qCONR^4R^{11}$;
—$(CR^{18}R^{19})_qSO_2NR^4R^{11}$; —$(CR^{18}R^{19})_qPO(OR^{21})_2$; —$(CR^{18}R^{19})_qCOR^{22}$;
—$(CR^{18}R^{19})_qSO_2R^{23}$; —$(CR^{18}R^{19})_qR^{24}$; —$(CR^{18}R^{19})_qR^{25}$; or —$(CR^{18}R^{19})_qR^{26}$.

$R^6$, $R^8$ and $R^{10}$ are independently defined as: H; $CF_3$; or lower alkyl.

$R^{11}$: H; lower alkyl; lower alkenyl; lower cycloalkyl; lower heterocycloalkyl; aryl; heteroaryl; lower arylalkyl; lower heteroarylalkyl; a suitable protecting group;
—$(CR^{18}R^{19})_rOR^{20}$; —$(CR^{18}R^{19})_rNR^4R^{27}$; —$(CR^{18}R^{19})_rNR^4COOR^{21}$;
—$(CR^{18}R^{19})_rNR^4CONR^4R^{27}$; —$(CR^{18}R^{19})_rNR^4SO_2R^{23}$;
—$(CR^{18}R^{19})_rNR^4SO_2NR^4R^{27}$;
—$(CR^{18}R^{19})_qCOOR^{21}$;
—$(CR^{18}R^{19})_qCONR^4R^{27}$; —$(CR^{18}R^{19})_qCOR^{22}$;
—$(CR^{18}R^{19})_qSO_2R^{23}$;
—$(CR^{18}R^{19})_qSO_2NR^4R^{27}$; —$(CR^{18}R^{19})_qR^{24}$;
—$(CR^{18}R^{19})_sR^{25}$; or —$(CR^{18}R^{19})_qR^{26}$.

$R^{12}$ and $R^{13}$ are independently defined as H; or lower alkyl.

$R^{14}$ and $R^{16}$ are independently defined as: H; F; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_sOR^{20}$; —$(CR^{18}R^{19})_sNR^4R^{11}$; —$(CR^{18}R^{19})_sNR^4COOR^{21}$;
—$(CR^{18}R^{19})_sNR^4COR^{22}$; —$(CR^{18}R^{19})_sNR^4CONR^4R^{11}$;
—$(CR^{18}R^{19})_sNR^4SO_2R^{23}$;
—$(CR^{18}R^{19})_qCOOR^{21}$; —$(CR^{18}R^{19})_qCONR^4R^{11}$;
—$(CR^{18}R^{19})_qCOR^{22}$.

$R^{15}$ and $R^{17}$ are independently defined as: H; $CF_3$; lower alkyl.

$R^{18}$: H; F; $CF_3$; lower alkyl; lower alkenyl; lower cycloalkyl; lower heterocycloalkyl; aryl; heteroaryl; lower arylalkyl; lower heteroarylalkyl;
—$(CR^{29}R^{30})_sOR^{31}$; —$(CR^{29}R^{30})_sNR^{28}R^{31}$; —$(CR^{29}R^{30})_sNR^{28}COOR^{21}$;
—$(CR^{29}R^{30})_sNR^{28}COR^{31}$; —$(CR^{29}R^{30})_sNR^{28}CONR^{28}R^{31}$;
—$(CR^{29}R^{30})_sNR^{28}SO_2R^{23}$;
—$(CR^{29}R^{30})_sNR^{28}SO_2NR^{28}R^{31}$;
—$(CR^{29}R^{30})_qCOOR^{21}$; —$(CR^{29}R^{30})_qCONR^{28}R^{31}$;
—$(CR^{29}R^{30})_qSO_2NR^{28}R^{31}$;
—$(CR^{29}R^{30})_qPO(OR^{21})_2$; $(CR^{29}R^{30})_qCOR^{31}$;
—$(CR^{29}R^{30})_q SO_2R^{23}$;
—$(CR^{29}R^{30})_qR^{24}$; —$(CR^{29}R^{30})_qR^{25}$; or —$(CR^{29}R^{30})_qR^{26}$.

$R^{19}$: H; $CF_3$; or lower alkyl.

$R^{20}$: H; lower alkyl; lower alkenyl; lower cycloalkyl; lower heterocycloalkyl; aryl; heteroaryl; lower arylalkyl; lower heteroarylalkyl;
—$(CR^{29}R^{30})_rOR^{31}$; —$(CR^{29}R^{30})_rNR^{28}R^{31}$; —$(CR^{29}R^{30})_rNR^{28}COOR^{21}$;
—$(CR^{29}R^{30})_rNR^{28}COR^{31}$; —$(CR^{29}R^{30})_rNR^{28}CONR^{28}R^{31}$;
—$(CR^{29}R^{30})_rNR^{28}SO_2R^{23}$;
—$(CR^{29}R^{30})_qCOOR^{21}$; —$(CR^{29}R^{30})_qCONR^{28}R^{31}$;
—$(CR^{29}R^{30})_qSO_2NR^{28}R^{31}$;
—$(CR^{29}R^{30})_qCOR^{31}$; —$(CR^{29}R^{30})_qSO_2R^{23}$; —$(CR^{29}R^{30})_qR^{24}$; —$(CR^{29}R^{30})_qR^{25}$; or
—$(CR^{29}R^{30})_qR^{26}$.

$R^{21}$ and $R^{23}$: Defined as above.

$R^{22}$: lower alkyl; lower alkenyl; lower cycloalkyl; lower heterocycloalkyl; aryl; heteroaryl; lower arylalkyl; lower heteroarylalkyl;
—$(CR^{29}R^{30})_sOR^{31}$; —$(CR^{29}R^{30})_sNR^{28}R^{31}$; —$(CR^{29}R^{30})_sNR^{28}COOR^{21}$;
—$(CR^{29}R^{30})_sNR^{28}COR^{31}$; —$(CR^{29}R^{30})_sNR^{28}CONR^{28}R^{31}$;
—$(CR^{29}R^{30})_sNR^{28}SO_2$—$R^{23}$;

—(CR$^{29}$R$^{30}$)$_s$COOR$^{21}$; —(CR$^{29}$R$^{30}$)$_s$CONR$^{28}$R$^{31}$; —(CR$^{29}$R$^{30}$)$_s$SO$_2$NR$^{28}$R$^{31}$; —(CR$^{29}$R$^{30}$)$_s$COR$^{31}$; —(CR$^{29}$R$^{30}$)$_s$SO$_2$R$^{23}$; —(CR$^{29}$R$^{30}$)$_t$R$^{24}$; —(CR$^{29}$R$^{30}$)$_t$R$^{25}$; or —(CR$^{18}$R$^{19}$)$_t$R$^{26}$.

R$^{24}$, R$^{25}$ and R$^{26}$: Defined as above.

R$^{27}$ and R$^{28}$: Defined as above.

R$^{29}$: H; F; CF$_3$; lower alkyl; lower alkenyl; lower cycloalkyl; lower heterocycloalkyl; aryl; heteroaryl; lower arylalkyl; lower heteroarylalkyl; —(CR$^{32}$R$^{33}$)$_s$OR$^{31}$; —(CR$^{32}$R$^{33}$)$_s$NR$^{28}$R$^{31}$; —(CR$^{32}$R$^{33}$)$_s$NR$^{28}$COOR$^{21}$;

—(CR$^{32}$R$^{33}$)$_s$NR$^{28}$COR$^{31}$; —(CR$^{32}$R$^{33}$)$_s$NR$^{28}$CONR$^{28}$R$^{31}$; —(CR$^{32}$R$^{33}$)$_s$NR$^{28}$SO$_2$R$^{23}$;
—(CR$^{32}$R$^{33}$)$_q$COOR$^{21}$; —(CR$^{32}$R$^{33}$)$_q$CONR$^{28}$R$^{31}$; —(CR$^{32}$R$^{33}$)$_q$SO$_2$NR$^{28}$R$^{31}$;
—(CR$^{32}$R$^{33}$)$_q$PO(OR$^{21}$)$_2$; —(CR$^{32}$R$^{33}$)$_q$COR$^{31}$; —(CR$^{32}$R$^{33}$)$_q$SO$_2$R$^{23}$; —(CR$^{32}$R$^{33}$)$_q$R$^{31}$.

R$^{30}$ and R$^{33}$: H; CF$_3$; lower alkyl.

R$^{31}$ and R$^{32}$: Defined as above.

R$^{34}$ and R$^{35}$ are independently defined as H; F; Cl; CF$_3$; OCF$_3$; OCHF$_2$; NO$_2$; CN; lower alkyl; lower alkenyl; lower alkynyl; lower cycloalkyl; lower heterocycloalkyl; aryl; heteroaryl; lower arylalkyl; lower heteroarylalkyl; —(CR$^{29}$R$^{30}$)$_q$OR$^{31}$; —(CR$^{29}$R$^{30}$)$_q$NR$^{28}$R$^{31}$;
—(CR$^{29}$R$^{30}$)$_q$NR$^{28}$COOR$^{21}$; —(CR$^{29}$R$^{30}$)$_q$NR$^{28}$COR$^{31}$; —(CR$^{29}$R$^{30}$)$_q$NR$^{28}$CONR$^{28}$R$^{31}$;
—(CR$^{29}$R$^{30}$)$_q$NR$^{28}$SO$_2$R$^{23}$; —(CR$^{29}$R$^{30}$)$_q$COOR$^{21}$; —(CR$^{29}$R$^{30}$)$_q$CONR$^{28}$R$^{31}$; —(CR$^{29}$R$^{30}$)$_q$SO$_2$NR$^{28}$R$^{31}$; —(CR$^{29}$R$^{30}$)$_q$COR$^{31}$;
—(CR$^{29}$R$^{30}$)$_q$SO$_2$R$^{23}$; or —(CR$^{29}$R$^{30}$)$_q$R$^{31}$.

R$^{36}$: Defined as above.

R$^{37}$: H; lower alkyl; lower alkenyl; lower cycloalkyl; lower heterocycloalkyl; aryl; heteroaryl; lower arylalkyl; lower heteroarylalkyl; a suitable N-protecting group; —(CR$^{29}$R$^{30}$)$_r$OR$^{31}$; —(CR$^{29}$R$^{30}$)$_r$NR$^{28}$R$^{31}$;
—(CR$^{29}$R$^{30}$)$_r$NR$^{28}$COOR$^{21}$; —(CR$^{29}$R$^{30}$)$_r$NR$^{28}$COR$^{31}$; —(CR$^{29}$R$^{30}$)$_r$NR$^{28}$CONR$^{28}$R$^{31}$;
—(CR$^{29}$R$^{30}$)$_r$NR$^{28}$SO$_2$R$^{23}$; —(CR$^{29}$R$^{30}$)$_q$COOR$^{21}$; —(CR$^{29}$R$^{30}$)$_q$CONR$^{28}$R$^{31}$; —(CR$^{29}$R$^{30}$)$_r$SO$_2$NR$^{28}$R$^{31}$; —(CR$^{29}$R$^{30}$)$_q$COR$^{31}$;
—(CR$^{29}$R$^{30}$)$_s$SO$_2$R$^{23}$; or —(CR$^{29}$R$^{30}$)$_q$R$^{31}$.

R$^{38}$: H; lower alkyl; lower alkenyl; lower cycloalkyl; lower heterocycloalkyl; aryl; heteroaryl; lower arylalkyl; lower heteroarylalkyl; —(CR$^{29}$R$^{30}$)$_q$OR$^{31}$; —(CR$^{29}$R$^{30}$)$_q$NR$^{28}$R$^{31}$; —(CR$^{29}$R$^{30}$)$_q$NR$^{28}$COOR$^{21}$;
—(CR$^{29}$R$^{30}$)$_q$NR$^{28}$COR$^{31}$; —(CR$^{29}$R$^{30}$)$_q$NR$^{28}$CONR$^{28}$R$^{31}$; —(CR$^{29}$R$^{30}$)$_q$COOR$^{21}$;
—(CR$^{29}$R$^{30}$)$_q$CONR$^{28}$R$^{31}$; —(CR$^{29}$R$^{30}$)$_q$COR$^{31}$; or —(CR$^{29}$R$^{30}$)$_q$R$^{31}$.

R$^{39}$; R$^{10}$; R$^{41}$; R$^{42}$; R$^{43}$; R$^{44}$; R$^{45}$; R$^{46}$; R$^{47}$; R$^{48}$; R$^{49}$ and R$^{50}$: Defined as above.

In the aforementioned preferred structures the variable heteroatom Z and the connector U are defined as:

Z: O; S(=O); or S(=O)$_2$.

U: —C(=O)—; —NR$^4$—C(=O)—; —C(=O)—C(=O)—;
or —C(—OR$^{20}$)$_2$—C(=O)—.

Defined as above are:
Substituents that can be pairwise taken together and form optionally substituted cycloalkyl or heterocycloalkyl moieties.
Structural elements that can form one of the groups of formulae H111-H118 (Table 9).

Variable heteroatoms Q, T, X and Y.

Indices q-u.

The above preferred structures include all possible stereoisomers, explicitly also including rotamers and atropisomers, of macrocycles of type I.

Particularly preferred among the building blocks of type A are A1(a1); A2(a1); A3(a1); A4(a1); A5(a1); A6(a1); A7(a1); A9(a1); A10(a1); A73(a2); A170(a4); A209(a7); A240(a10); A272(a10); A532(a18); A614(a24). For most of these building blocks, oxygen is the preferred nucleophilic moiety. However in the case of A170 it consists of a sulfur atom; and in the case of the three building blocks A5-A7, both oxygen and sulfur derivatives are part of the invention (Table 16).

TABLE 16

Particularly Preferred Building Blocks of Type A

TABLE 16-continued
Particularly Preferred Building Blocks of Type A
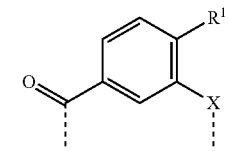 A7 (a1)
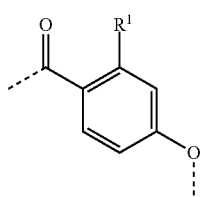 A9 (a1)
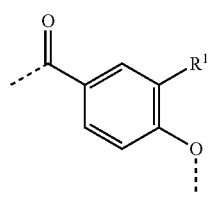 A10 (a1)
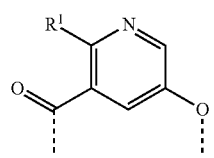 A73 (a2)
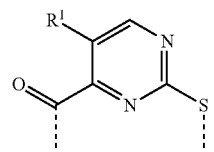 A170 (a4)
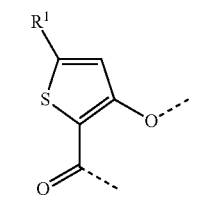 A209 (a7)
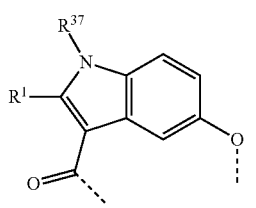 A272 (a10)
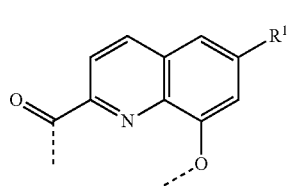 A532 (a18)
TABLE 16-continued
Particularly Preferred Building Blocks of Type A
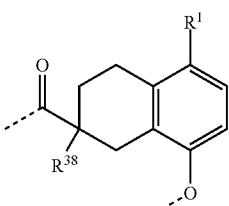 A614 (a24)
Among the building blocks of type B particularly preferred are B7, B8, B9 and B-17 as shown in Table 17.
TABLE 17
Particularly Preferred Building Blocks of Type B
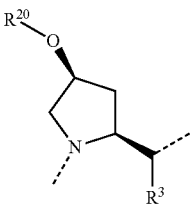 B7-1
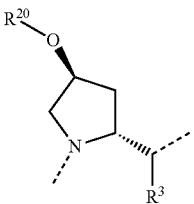 B7-2
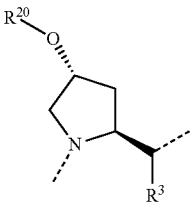 B7-3
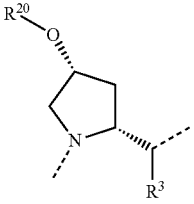 B7-4
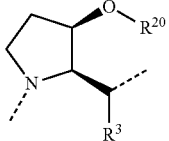 B8-1
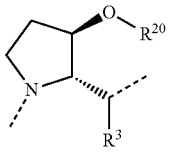 B8-2

TABLE 17-continued
Particularly Preferred Building Blocks of Type B
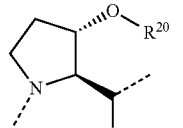 B8-3
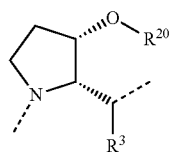 B8-4
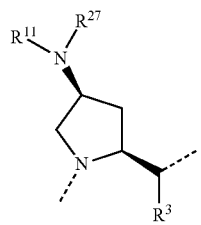 B9-1
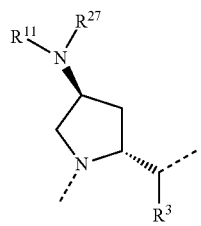 B9-2
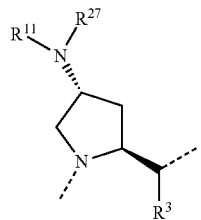 B9-3
TABLE 17-continued
Particularly Preferred Building Blocks of Type B
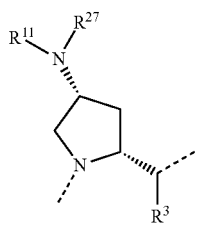 B9-4
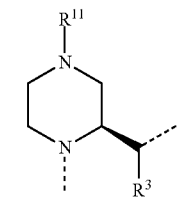 B17-1
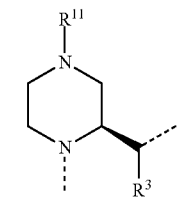 B17-2
Particularly preferred embodiments of the linker C are listed in Table 18.
TABLE 18
Particularly Preferred Embodiments of Linker C
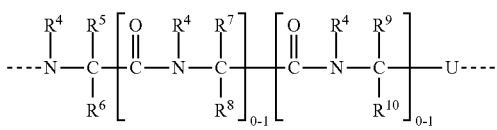 C1
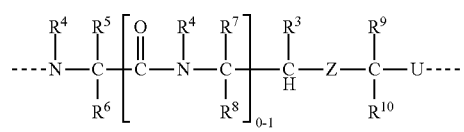 C2
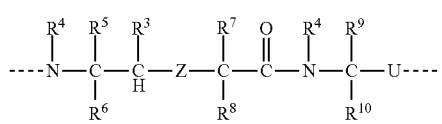 C3

TABLE 18-continued
Particularly Preferred Embodiments of Linker C
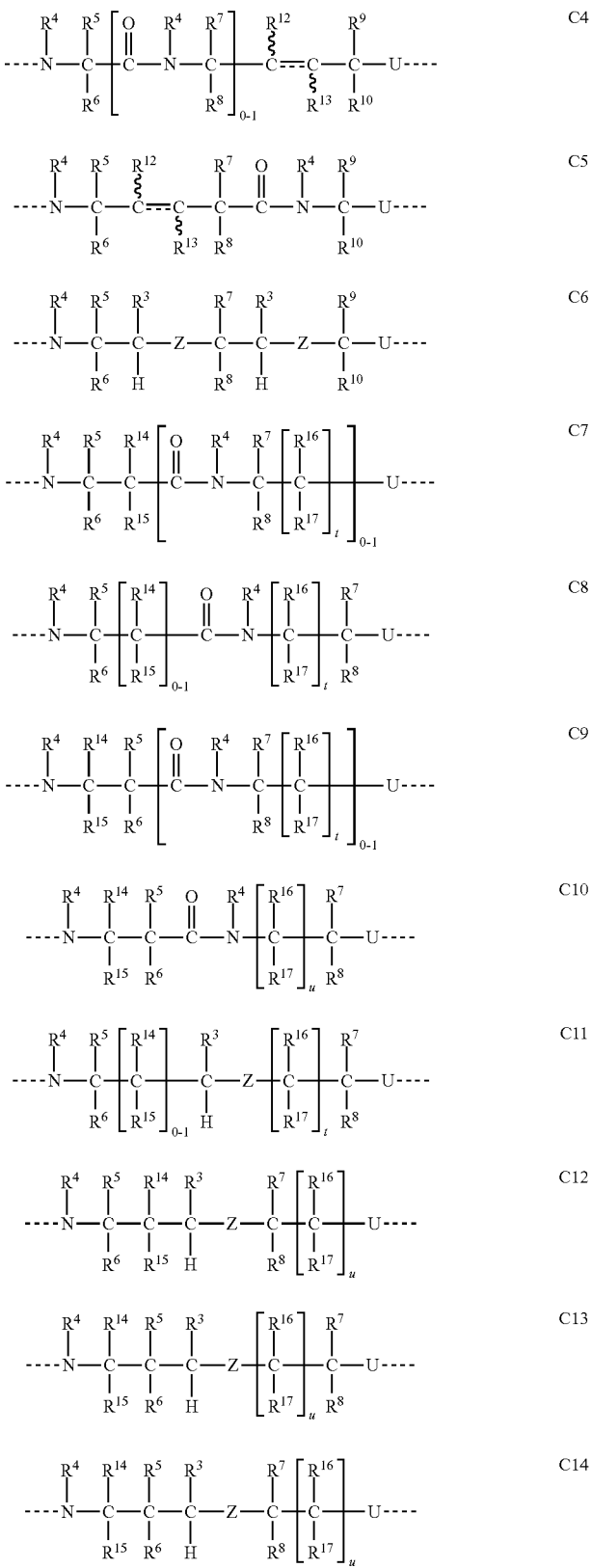
C4
C5
C6
C7
C8
C9
C10
C11
C12
C13
C14

TABLE 18-continued
Particularly Preferred Embodiments of Linker C
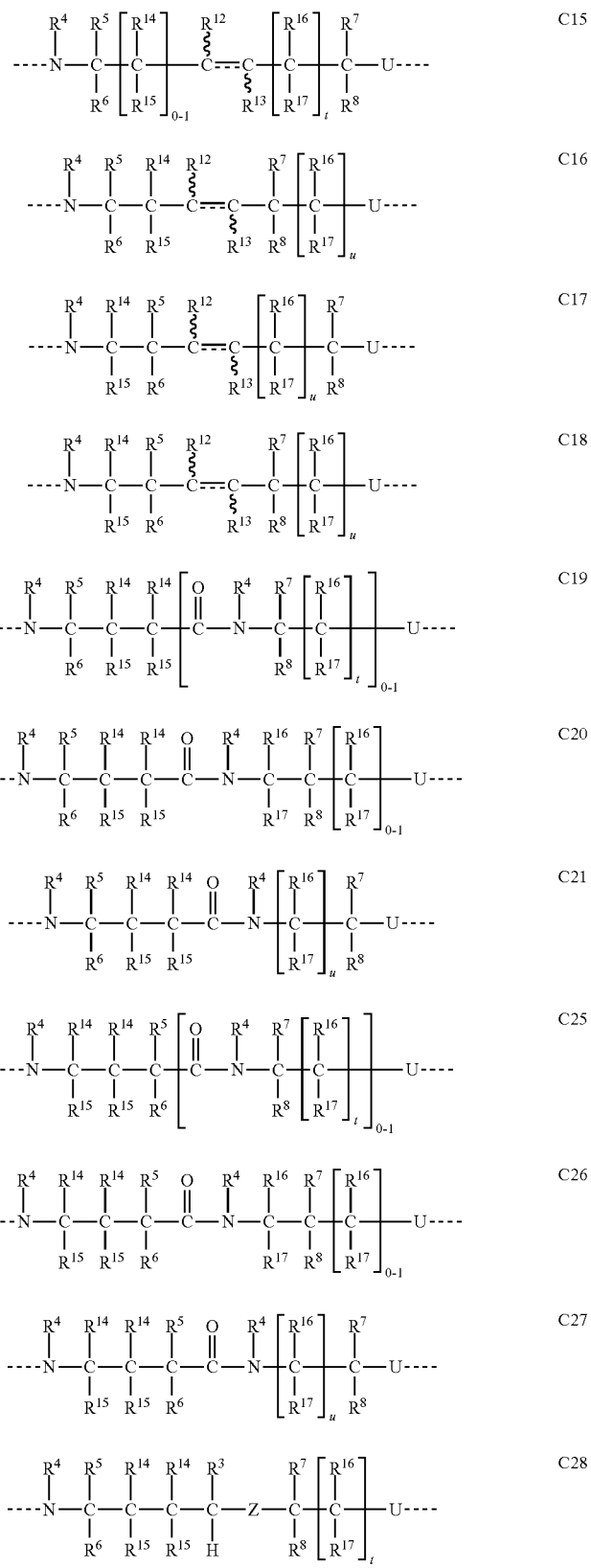

TABLE 18-continued

Particularly Preferred Embodiments of Linker C (Structural formulas for linkers C29, C30, C34, C35, C36, C37, C38, C39, C43, C44, C45, and C46 are shown.)

TABLE 18-continued

Particularly Preferred Embodiments of Linker C

C47

C48

C49

C54

C55

C56

C57

C58

C59

C60

C61

TABLE 18-continued

Particularly Preferred Embodiments of Linker C

| Structure | Label |
|---|---|
| (chemical structure) | C62 |
| (chemical structure) | C63 |
| (chemical structure) | C64 |
| (chemical structure) | C65 |
| (chemical structure) | C70 |
| (chemical structure) | C71 |
| (chemical structure) | C72 |
| (chemical structure) | C73 |
| (chemical structure) | C74 |
| (chemical structure) | C75 |
| (chemical structure) | C76 |
| (chemical structure) | C77 |

TABLE 18-continued

Particularly Preferred Embodiments of Linker C

[Structure C90: —N(R⁴)(R⁵)—C(R⁶)—[C(R¹⁴)(R¹⁵)]₁₋₅—N(R⁴)—C(=O)—C(R⁷)(R⁸)—[C(R¹⁶)(R¹⁷)]ₜ—C(=O)—N(R⁴)—[C(R⁹)(R¹⁰)]₀₋₁—U—]

[Structure C91: —N(R⁴)—[C(R¹⁴)(R¹⁵)]₁₋₅—C(R⁵)(R⁶)—N(R⁴)—C(=O)—C(R⁷)(R⁸)—[C(R¹⁶)(R¹⁷)]ₜ—C(=O)—N(R⁴)—[C(R⁹)(R¹⁰)]₀₋₁—U—]

[Structure C92: —N(R⁴)—[C(R¹⁴)(R¹⁵)]₁₋₅—C(R⁵)(R⁶)—N(R⁴)—C(R⁷)(=O)—[C(R¹⁶)(R⁸)(R¹⁷)]ₜ—C(=O)—N(R⁴)—[C(R⁹)(R¹⁰)]₀₋₁—U—]

[Structure C93: —N(R⁴)(R⁵)—C(R⁶)—[C(R¹⁴)(R¹⁵)]₁₋₅—N(R⁴)—C(=O)—C(R⁷)(R⁸)—[C(R¹⁶)(R¹⁷)]ₜ—C(=O)—N(R⁴)—[C(R⁹)(R¹⁰)]₀₋₁—U—]

The particularly preferred substituents on the particularly preferred building blocks A, B and C are defined as:

$R^1$: H; F; Cl; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl;
—$(CR^{18}R^{19})_q OR^{20}$; —$(CR^{18}R^{19})_q NR^4 R^{11}$; —$(CR^{18}R^{19})_q NR^4 COR^{22}$;
—$(CR^{18}R^{19})_q NR^4 CONR^4 R^{11}$; —$(CR^{18}R^{19})_q NR^4 SO_2 R^{23}$;
—$(CR^{18}R^{19})_q NR^4 SO_2 NR^4 R^{11}$;
—$(CR^{18}R^{19})_q COOR^{21}$; —$(CR^{18}R^{19})_q CONR^4 R^{11}$;
—$(CR^{18}R^{19})_q SO_2 NR^4 R^{11}$;
—$(CR^{18}R^{19})_q COR^{22}$; —$(CR^{18}R^{19})_q SO_2 R^{23}$; —$(CR^{18}R^{19})_q R^{24}$; —$(CR^{18}R^{19})_q R^{25}$; or
—$(CR^{18}R^{19})_q R^{26}$.

$R^2$: H; $CF_3$; lower alkyl; lower alkenyl; lower cycloalkyl; lower heterocycloalkyl; aryl; heteroaryl; lower arylalkyl; lower heteroarylalkyl; —$(CR^{18}R^{19})_q OR^{20}$; —$(CR^{18}R^{19})_q NR^4 R^{11}$; —$(CR^{18}R^{19})_q NR^4 COR^{22}$;
—$(CR^{18}R^{19})_q NR^4 CONR^4 R^{11}$; —$(CR^{18}R^{19})_q NR^4 SO_2 R^{23}$;
—$(CR^{18}R^{19})_q NR^4 SO_2 NR^4 R^{11}$;
—$(CR^{18}R^{19})_q COOR^{21}$; —$(CR^{18}R^{19})_q CONR^4 R^{11}$;
—$(CR^{18}R^{19})_q SO_2 NR^4 R^{11}$;
—$(CR^{18}R^{19})_q COR^{22}$; —$(CR^{18}R^{19})_q SO_2 R^{23}$; —$(CR^{18}R^{19})_q R^{24}$; —$(CR^{18}R^{19})_q R^{25}$; or
—$(CR^{18}R^{19})_q R^{26}$.

$R^3$: Defined as earlier hereinabove.

$R^4$: H; lower alkyl; lower alkenyl; or a suitable N-protecting group.

$R^5$, $R^7$ and $R^9$ are independently defined as: H; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_q OR^{20}$; —$(CR^{18}R^{19})_s NR^4 R^{11}$; —$(CR^{18}R^{19})_s NR^4 COR^{22}$;
—$(CR^{18}R^{19})_s NR^4 CONR^4 R^{11}$; —$(CR^{18}R^{19})_s NR^4 SO_2 R^{23}$;
—$(CR^{18}R^{19})_q COOR^{21}$;
—$(CR^{18}R^{19})_q CONR^4 R^{11}$;
—$(CR^{18}R^{19})_q SO_2 NR^4 R^{11}$; —$(CR^{18}R^{19})_q COR^{22}$;
—$(CR^{18}R^{19})_q SO_2 R^{23}$;
—$(CR^{18}R^{19})_q R^{24}$; —$(CR^{18}R^{19})_q R^{25}$; or —$(CR^{18}R^{19})_q R^{26}$.

$R^6$, $R^8$ and $R^{10}$ are independently defined as: H; $CF_3$; or $CH_3$.

$R^{11}$; H; lower alkyl; lower alkenyl; lower cycloalkyl; lower heterocycloalkyl; aryl; heteroaryl; lower arylalkyl; lower heteroarylalkyl; a suitable protecting group;
—$(CR^{18}R^{19})_q OR^{20}$; —$(CR^{18}R^{19})_r NR^4 R^{27}$;
—$(CR^{18}R^{19})_r NR^4 CONR^4 R^{27}$;
—$(CR^{18}R^{19})_r NR^4 SO_2 R^{23}$; —$(CR^{18}R^{19})_q COOR^{21}$;
—$(CR^{18}R^{19})_c$—$CONR^4 R^{27}$; —$(CR^{18}R^{19})_q COR^{22}$;
—$(CR^{18}R^{19})_q R^{24}$; —$(CR^{18}R^{19})_3 R^{25}$; or —$(CR^{18}R^{19})_q R^{26}$.

$R^{12}$ and $R^{13}$ are independently defined as H; or lower alkyl.

$R^{14}$ and $R^{16}$ are independently defined as: H; F; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_3 OR^{20}$; —$(CR^{18}R^{19})_s NR^4 R^{11}$; —$(CR^{18}R^{19})_s NR^4 COR^{22}$;
—$(CR^{18-19})_q COOR^{21}$; —$(CR^{18}R^{19})_q CONR^4 R^{11}$.

$R^{15}$ and $R^{17}$ are independently defined as: H; $CF_3$; or $CH_3$.

$R^{18}$: H; F; $CF_3$; lower alkyl; lower alkenyl; lower cycloalkyl; lower heterocycloalkyl; aryl; heteroaryl; lower arylalkyl; lower heteroarylalkyl;
—$(CR^{29}R^{30})_s OR^{31}$; —$(CR^{29}R^{30})_s NR^{28} R^{31}$;
—$(CR^{29}R^{30})_s NR^{28} COR^{31}$; —$(CR^{29}R^{30})_s NR^{28} CONR^{28} R^{31}$;
—$(CR^{29}R^{30})_s NR^{28} SO_2 R^{23}$;
—$(CR^{29}R^{30})_q COOR^{21}$; —$(CR^{29}R^{30})_q CONR^{28} R^{31}$;
—$(CR^{29}R^{30})_q SO_2 NR^{28} R^{31}$;
—$(CR^{29}R^{30})_q COR^{31}$; —$(CR^{29}R^{30})_q SO_2 R^{23}$; —$(CR^{29}R^{30})_q R^{24}$; —$(CR^{29}R^{30})_q R^{25}$; or
—$(CR^{29}R^{30})_q R^{26}$.

$R^{19}$: H; $CF_3$; or $CH_3$.

$R^{20}$: H; lower alkyl; lower alkenyl; lower cycloalkyl; lower heterocycloalkyl; aryl; heteroaryl; lower arylalkyl; lower heteroarylalkyl; —

$-(CR^{29}R^{30})_rOR^{31}$; $-(CR^{29}R^{30})_rNR^{28}R^{31}$; $-(CR^{29}R^{30})_r NR^{28}COR^{31}$;
$-(CR^{29}R^{30})_rNR^{28}CONR^{28}R^{31}$; $-(CR^{29}R^{30})_r NR^{28}SO_2R^{23}$; $-(CR^{29}R^{30})_qCOOR^{21}$;
$-(CR^{29}R^{30})_qCONR^{28}R^{31}$; $-(CR^{29}R^{30})_qSO_2NR^{28}R^{31}$; $-(CR^{29}R^{30})_qCOR^{31}$;
$-(CR^{29}R^{30})_qSO_2R^{23}$; $-(CR^{29}R^{30})_qR^{24}$; $-(CR^{29}R^{30})_q R^{25}$; or $-(CR^{29}R^{30})_qR^{26}$.

$R^{21}$ and $R^{23}$: Defined as above $R^{22}$: lower alkyl; lower alkenyl; lower cycloalkyl; lower heterocycloalkyl; aryl; heteroaryl; lower arylalkyl; lower heteroarylalkyl; $-(CR^{29}R^{30})_sOR^{31}$; $-(CR^{29}R^{30})_sNR^{28}R^{31}$; $-(CR^{29}R^{30})_s NR^{28}COR^{31}$; $-(CR^{29}R^{30})_sNR^{28}CONR^{28}R^{31}$; $-(CR^{29}R^{30})_sNR^{28}SO_2R^{23}$; $-(CR^{29}R^{30})_sCOOR^{21}$;
$-(CR^{29}R^{30})_sCONR^{28}R^{31}$; $-(CR^{29}R^{30})_sSO_2NR^{28}R^{31}$; $-(CR^{29}R^{30})_tCOR^{31}$;
$-(CR^{29}R^{30})_sSO_2R^{23}$; $-(CR^{29}R^{30})_tR^{24}$; $-(CR^{29}R^{30})_tR^{25}$; or $-(CR^{29}R^{30})_tR^{26}$.

$R^{24}$, $R^{25}$ and $R^{26}$: Defined as above.

$R^{27}$ and $R^{28}$: Defined as above.

$R^{29}$: H; F; $CF_3$; lower alkyl; lower alkenyl; lower cycloalkyl; lower heterocycloalkyl; aryl; heteroaryl; lower arylalkyl; lower heteroarylalkyl;
$-(CR^{32}R^{33})_sOR^{31}$; $-(CR^{32}R^{33})_sNR^{28}R^{31}$;
$-(CR^{32}R^{33})_sNR^{28}COR^{31}$; $-(CR^{32}R^{33})_sNR^{28}CONR^{28}R^{31}$;
$-(CR^{32}R^{33})_sCOOR^{21}$; $-(CR^{32}R^{33})_qCONR^{28}R^{31}$;
$-(CR^{32}R^{33})_qCOR^{31}$; $-(CR^{32}R^{33})_qR^{31}$.

$R^{30}$ and $R^{33}$: H; $CF_3$; or $CH_3$.

$R^{31}$ and $R^{32}$: Defined as above $R^{34}$ and $R^{35}$ are independently defined as H; F; Cl; $CF_3$; $OCF_3$; $OCHF_2$; lower alkyl; lower alkenyl; lower alkynyl; lower cycloalkyl; lower heterocycloalkyl; aryl; heteroaryl; lower arylalkyl; lower heteroarylalkyl;
$-(CR^{29}R^{30})_qOR^{31}$; $-(CR^{29}R^{30})_qNR^{28}R^{31}$;
$-(CR^{29}R^{30})_qNR^{28}COR^{31}$; $-(CR^{29}R^{30})_q NR^{28}CONR^{28}R^{31}$; $-(CR^{29}R^{30})_qNR^{28}SO_2R^{23}$;
$-(CR^{29}R^{30})_qCOOR^{21}$;
$-(CR^{29}R^{30})_qCONR^{28}R^{31}$; $-(CR^{29}R^{30})_qSO_2NR^{28}R^{31}$; $-(CR^{29}R^{30})_qCOR^{31}$;
$-(CR^{29}R^{30})_qSO_2R^{23}$; or $-(CR^{29}R^{30})_qR^{31}$.

$R^{36}$: Defined as in Part 3 "General Scope of the Invention".

$R^{37}$: H; lower alkyl; lower alkenyl; lower cycloalkyl; lower heterocycloalkyl; aryl; heteroaryl; lower arylalkyl; lower heteroarylalkyl; a suitable N-protecting group; $-(CR^{29}R^{30})_rOR^{31}$; $-(CR^{29}R^{30})_rNR^{28}R^{31}$;
$-(CR^{29}R^{30})_rNR^{28}COOR^{21}$; $-(CR^{29}R^{30})_rNR^{28}COR^{31}$;
$-(CR^{29}R^{30})_rNR^{28}CONR^{28}R^{31}$;
$-(CR^{29}R^{30})_qCOOR^{21}$; $-(CR^{29}R^{30})_qCONR^{28}R^{31}$;
$-(CR^{29}R^{30})_qCOR^{31}$;
or $-(CR^{29}R^{30})_qR^{31}$.

$R^{38}$: H; lower alkyl; lower alkenyl; lower cycloalkyl; lower heterocycloalkyl; aryl; heteroaryl; lower arylalkyl; lower heteroarylalkyl;
$-(CR^{29}R^{30})_qOR^{31}$; $-(CR^{29}R^{30})_qNR^{28}R^{31}$; $-(CR^{29}R^{30})_q NR^{28}COR^{31}$;
$-(CR^{29}R^{30})_qNR^{28}CONR^{28}R^{31}$;
$-(CR^{29}R^{30})_qCOOR^{21}$; $-(CR^{29}R^{30})_qCONR^{28}R^{31}$;
$-(CR^{29}R^{30})_qCOR^{31}$;
or $-(CR^{29}R^{30})_qR^{31}$.

$R^{39}$; $R^{40}$; $R^{41}$; $R^{42}$; $R^{43}$; $R^{44}$; $R^{45}$; $R^{46}$; $R^{47}$; $R^{48}$; $R^{49}$ and $R^{50}$: Defined as above.

In the aforementioned structures the variable heteroatom Z and the connector U are defined as:

Z: O; or $S(=O)_2$.

U: $-C(=O)-$; $-NR^4-C(=O)-$; or $-C(=O)-C(=O)-$.

Defined as above are:

Substituents that can be pairwise taken together and form optionally substituted cycloalkyl or heterocycloalkyl moieties.

Structural elements that can form one of the groups of formulae H111-H118 (Table 9).

Variable heteroatoms Q, T, X and Y.

Indices q-u.

The above particularly preferred structures include all possible stereoisomers, exlicity also rotamers and atropisomers, of macrocycles of type I.

Examples of, but not limited to, readily accessible substances that define possible subunits of the linker C are listed in Table 19.

TABLE 19

Substances Representing Subunits of Particularly Preferred Linkers C

| Code | Chemical Name |
|---|---|
| Ala | L-Alanine |
| DAla | D-Alanine |
| Arg | L-Arginine |
| DArg | D-Arginine |
| Asn | L-Asparagine |
| DAsn | D-Asparagine |
| Asp | L-Aspartic acid |
| DAsp | D-Aspartic acid |
| Cys | L-Cysteine |
| DCys | D-Cysteine |
| Glu | L-Glutamic acid |
| DGlu | D-Glutamic acid |
| Gln | L-Glutamine |
| DGln | D-Glutamine |
| Gly | Glycine |
| His | L-Histidine |
| DHis | D-Histidine |
| Ile | L-Isoleucine |
| DIle | D-Isoleucine |
| Leu | L-Leucine |
| DLeu | D-Leucine |
| Lys | L-Lysine |

TABLE 19-continued

Substances Representing Subunits of Particularly Preferred Linkers C

| Code | Chemical Name |
| --- | --- |
| $^D$Lys | D-Lysine |
| Met | L-Methionine |
| $^D$Met | D-Methionine |
| Phe | L-Phenylalanine |
| $^D$Phe | D-Phenylalanine |
| Pro | L-Proline |
| $^D$Pro | D-Proline |
| Ser | L-Serine |
| $^D$Ser | D-Serine |
| Thr | L-Threonine |
| $^D$Thr | D-Threonine |
| Trp | L-Tryptophan |
| $^D$Trp | D-Tryptophan |
| Tyr | L-Tyrosine |
| $^D$Tyr | D-Tyrosine |
| Val | L-Valine |
| $^D$Val | D-Valine |
| Apa | 3-Amino-propanoic acid |
| H-$\beta^3$-HAla-OH | (3S)-3-Amino-butyric acid |
| H-$\beta^3$-HVal-OH | (3R)-3-Amino-4-methyl-valeric acid |
| H-$\beta^3$-HIle-OH | (3R,4S)-3-Amino-4-methyl-hexanoic acid |
| H-$\beta^3$-HLeu-OH | (3S)-3-Amino-5-methyl-hexanoic acid |
| H-$\beta^3$-HMet-OH | (3S)-3-Amino-5-methylthio pentanoic acid |
| H-$\beta^3$-HTyr-OH | (3S)-3-Amino-4-(4'-hydroxyphenyl)-butyric acid |
| H-$\beta^3$-HHis-OH | (3S)-3-Amino-4-(imidazole-4'-yl)-butyric acid |
| H-$\beta^3$-HPhe-OH | (3S)-3-Amino-4-phenyl butyric acid |
| H-$\beta^3$-HTrp-OH | (3S)-3-Amino-4-(indol-3'-yl)-butyric acid |
| H-$\beta^3$-HSer-OH | (3R)-3-Amino-4-hydroxy-butyric acid |
| H-$\beta^3$-HAsp-OH | 3-Amino-pentanedioic acid |
| H-$\beta^3$-HGlu-OH | (3S)-3-Amino-hexanedioic acid |
| H-$\beta^3$-HLys-OH | (3S)-3,7-Diamino-heptanoic acid |
| H-$\beta^3$-HArg-OH | (3S)-3-Amino-6-guanidino-hexanoic-acid |
| H-$\beta^3$-HCys-OH | (3R)-3-Amino-4-mercapto-butyric acid |
| H-$\beta^3$-HAsn-OH | (3S)-3-Amino-4-carbamoyl-butyric acid |
| H-$\beta^3$-HGln-OH | (3S)-3-Amino-5-carbamoyl-pentanoic acid |
| H-$\beta^3$-HThr-OH | (3R,4R)-3-Amino-4-hydroxy-pentanoic acid |
| Gaba | 4-Amino-butyric acid |
| H-$\gamma^4$-DiHAla-OH | (4S)-4-Amino-pentanoic acid |
| H-$\gamma^4$-DiHVal-OH | (4R)-4-Amino-5-methyl-hexanoic acid |
| H-$\gamma^4$-DiHIle-OH | (4R,5S)-4-Amino-5-methyl-heptanoic acid |
| H-$\gamma^4$-DiHLeu-OH | (4R)-4-Amino-6-methyl-heptanoic acid |
| H-$\gamma^4$-DiHMet-OH | (4R)-4-Amino-6-methylthio-hexanoic acid |
| H-$\gamma^4$-DiHTyr-OH | (4R)-4-Amino-5-(4'-hydroxyphenyl)-pentanoic acid |
| H-$\gamma^4$-DiHHis-OH | (4R)-4-Amino-5-(imidazole-4'-yl)-pentanoic acid |
| H-$\gamma^4$-DiHPhe-OH | (4R)-4-Amino-5-phenyl-pentanoic acid |
| H-$\gamma^4$-DiHTrp-OH | (4R)-4-Amino-5-(indol-3'-yl)-pentanoic acid |
| H-$\gamma^4$-DiHSer-OH | (4R)-4-Amino-5-hydroxy-pentanoic acid |
| H-$\gamma^4$-DiHAsp-OH | (4R)-4-Amino-hexanedioic acid |
| H-$\gamma^4$-DiHGlu-OH | 4-Amino-heptanedioic acid |
| H-$\gamma^4$-DiHLys-OH | (4S)-4,8-Diamino-octanoic acid |
| H-$\gamma^4$-DiHArg-OH | (4S)-4-Amino-7-guanidino-heptanoic-acid |
| H-$\gamma^4$-DiHCys-OH | (4R)-4-Amino-5-mercapto-pentanoic acid |
| H-$\gamma^4$-DiHAsn-OH | (4R)-4-Amino-5-carbamoyl-pentanoic acid |
| H-$\gamma^4$-DiHGln-OH | (3S)-3-Amino-5-carbamoyl-hexanoic acid |
| H-$\gamma^4$-DiHThr-OH | (4R,5R)-4-Amino-5-hydroxy-hexanoic acid |
| Cit | L-Citrulline |
| $^D$Cit | D-Citrulline |
| Orn | L-Ornithine |
| $^D$Orn | D-Ornithine |
| tBuA | L-t-Butylalanine |
| $^D$tBuA | D-t-Butylalanine |
| Sar | Sarcosine |
| Pen | L-Penicillamine |
| $^D$Pen | D-Penicillamine |
| tBuG | L-tert.-Butylglycine |
| $^D$tBuG | D-tert.-Butylglycine |
| 4AmPhe | L-para-Aminophenylalanine |
| $^D$4AmPhe | D-para-Aminophenylalanine |
| 3AmPhe | L-meta-Aminophenylalanine |
| $^D$3AmPne | D-meta-Aminophenylalanine |

TABLE 19-continued

Substances Representing Subunits of Particularly Preferred Linkers C

| Code | Chemical Name |
|---|---|
| 2AmPhe | L-ortho-Aminophenylalanine |
| $^D$2AmPhe | D-ortho-Aminophenylalanine |
| Phe(mC(NH$_2$)=NH) | L-meta-Amidinophenylalanine |
| $^D$Phe(mC(NH$_2$)=NH) | D-meta-Amidinophenylalanine |
| Phe(pC(NH$_2$)=NH) | L-para-Amidinophenylalanine |
| $^D$Phe(pC(NH$_2$)=NH) | D-para-Amidinophenylalanine |
| Phe(mNHC(NH$_2$)=NH) | L-meta-Guanidinophenylalanine |
| $^D$Phe(mNHC(NH$_2$)=NH) | D-meta-Guanidinophenylalanine |
| Phe(pNHC(NH$_2$)=NH) | L-para-Guanidinophenylalanine |
| $^D$Phe(pNHC(NH$_2$)=NH) | D-para-Guanidinophenylalanine |
| 2Pal | (2S)-2-Amino-3-(pyridine-2'-yl)-propionic acid |
| $^D$2Pal | (2R)-2-Amino-3-(pyridine-2'-yl)-propionic acid |
| 4Pal | (2S)-2-Amino-3-(pyridine-4'-yl)-propionic acid |
| $^D$4Pal | (2R)-2-Amino-3-(pyridine-4'-yl)-propionic acid |
| Phg | L-Phenylglycine |
| $^D$Phg | D-Phenylglycine |
| Cha | L-Cyclohexylalanine |
| $^D$Cha | D-Cyclohexylalanine |
| C$_4$al | L-3-Cyclobutylalanine |
| $^D$C$_4$al | D-3-Cyclobutylalanine |
| C$_5$al | L-3-Cyclopentylalanine |
| $^D$C$_5$al | D-3-Cyclopentylalanine |
| Nle | L-Norleucine |
| $^D$Nle | D-Norleucine |
| 2-Nal | L-2-Naphthylalanine |
| $^D$2Nal | D-2-Naphthylalanine |
| 1-Nal | L-1-Naphthylalanine |
| $^D$1Nal | D-1-Naphthylalanine |
| 4ClPhe | L-4-Chlorophenylalanine |
| $^D$4ClPhe | D-4-Chlorophenylalanine |
| 3ClPhe | L-3-Chlorophenylalanine |
| $^D$3ClPhe | D-3-Chlorophenylalanine |
| 2ClPhe | L-2-Chlorophenylalanine |
| $^D$2ClPhe | D-2-Chlorophenylalanine |
| 3,4Cl$_2$Phe | L-3,4-Dichlorophenylalanine |
| $^D$3,4Cl$_2$Phe | D-3,4-Dichlorophenylalanine |
| 4FPhe | L-4-Fluorophenylalanine |
| $^D$4FPhe | D-4-Fluorophenylalanine |
| 3FPhe | L-3-Fluorophenylalanine |
| $^D$3FPhe | D-3-Fluorophenylalanine |
| 2FPhe | L-2-Fluorophenylalanine |
| $^D$2FPhe | D-2-Fluorophenylalanine |
| Thi | L-β-2-Thienylalanine |
| $^D$Thi | D-β-2-Thienylalanine |
| Tza | L-2-Thiazolylalanine |
| $^D$Tza | D-2-Thiazolylalanine |
| Mso | L-Methionine sulfoxide |
| $^D$Mso | D-Methionine sulfoxide |
| AcLys | N-Acetyllysine |
| $^D$AcLys | N-Acetyl-D-lysine |
| Dap | 2,3-Diaminopropionic acid |
| $^D$Dap | D-2,3-Diaminopropionic acid |
| Dab | 2,4-Diaminobutyric acid |
| $^D$Dab | (2R)-2,4-Diaminobutyric acid |
| Dbu | (2S)-2,3-Diamino-butyric acid |
| $^D$Dbu | (2R)-2,3-Diamino-butyric acid |
| Abu | γ-Aminobutyric acid (GABA) |
| Aha | ε-Aminohexanoic acid |
| Aib | α-Aminoisobutyric acid |
| Cyp | 1-Amino cyclopentane carboxylic acid |
| Y(Bzl) | L-O-Benzyltyrosine |
| $^D$Y(Bzl) | D-O-Benzyltyrosine |
| H(Bzl) | (3S)-2-Amino-3-(1'-benzylimidazole-4'-yl)-propionic acid |
| $^D$H(Bzl) | (3R)-2-Amino-3-(1'-benzylimidazole-4'-yl)-propionic acid |
| Bip | L-(4-phenyl)phenylalanine |
| $^D$Bip | D-(4-phenyl)phenylalanine |
| S(Bzl) | L-O-Benzylserine |
| $^D$S(Bzl) | D-O-Benzylserine |
| T(Bzl) | L-O-Benzylthreonine |

TABLE 19-continued

Substances Representing Subunits of Particularly Preferred Linkers C

| Code | Chemical Name |
|---|---|
| $^D$T(Bzl) | D-O-Benzylthreonine |
| alloT | (2S,3S)-2-Amino-3-hydroxy-butyric acid |
| $^D$alloT | (2R,3S)-2-Amino-3-hydroxy-butyric acid |
| Leu3OH | (2S,3R)-2-Amino-3-hydroxy-4-methyl-pentanoic acid |
| $^D$Leu3OH | (2R,3R)-2-Amino-3-hydroxy-4-methyl-pentanoic acid |
| hAla | L-Homo-alanine |
| $^D$hAla | D-Homo-alanine |
| hArg | L-Homo-arginine |
| $^D$hArg | D-Homo-arginine |
| hCys | L-Homo-cysteine |
| $^D$hCys | D-Homo-cysteine |
| hGlu | L-Homo-glutamic acid |
| $^D$hGlu | D-glutamic acid |
| hGln | L-Homo-glutamine |
| $^D$hGln | D-Homo-glutamine |
| hHis | L-Homo-histidine |
| $^D$hHis | D-Homo-histidine |
| hIle | L-Homo-isoleucine |
| $^D$hIle | D-Homo-isoleucine |
| hLeu | L-Homo-leucine |
| $^D$hLeu | D-Homo-leucine |
| hNle | L-Homo-norleucine |
| $^D$hNle | D-Homo-norleucine |
| hLys | L-Homo-lysine |
| $^D$hLys | D-Homo-lysine |
| hMet | L-Homo-Methionine |
| $^D$hMet | D-Homo-Methionine |
| hPhe | L-Homo-phenylalanine |
| $^D$hPhe | D-Homo-phenylalanine |
| hSer | L-Homo-serine |
| $^D$hSer | D-Homo-serine |
| hThr | L-Homo-threonine |
| $^D$hThr | D-Homo-threonine |
| hTrp | L-Homo-tryptophan |
| $^D$hTrp | D-Homo-tryptophan |
| hTyr | L-Homo-tyrosine |
| $^D$hTyr | D-Homo-tyrosine |
| hVal | L-Homo-valine |
| $^D$hVal | D-Homo-valine |
| hCha | L-Homo-cyclohexylalanine |
| $^D$hCha | D-Homo-cyclohexylalanine |
| Bpa | L-4-Benzoylphenylalanine |
| $^D$Bpa | D-4-Benzoylphenylalanine |
| OctG | L-Octylglycine |
| $^D$OctG | D-Octylglycine |
| Tic | (3S)-1,2,3,4-Tetrahydroisoquinoline-3-carboxylic acid |
| $^D$Tic | (3R)-1,2,3,4-Tetrahydroisoquinoline-3-carboxylic acid |
| Tiq | (1S)-1,2,3,4-Tetrahydroisoquinoline-1-carboxylic acid |
| $^D$Tiq | (1R)-1,2,3,4-Tetrahydroisoquinoline-1-carboxylic acid |
| Oic | (2S,3aS,7aS)-1-Octahydro-1H-indole-2-carboxylic acid |
| $^D$Oic | (2R,3aS,7aS)-1-Octahydro-1H-indole-2-carboxylic acid |
| 4AmPyrr1 | (2S,4S)-4-Amino-pyrrolidine-2-carboxylic acid |
| $^D$4AmPyrr1 | (2R,4S)-4-Amino-pyrrolidine-2-carboxylic acid |
| 4AmPyrr2 | (2S,4R)-4-Amino-pyrrolidine-2-carboxylic acid |
| $^D$4AmPyrr2 | (2R,4R)-4-Amino-pyrrolidine-2-carboxylic acid |
| 4PhePyrr1 | (2S,4R)-4-Phenyl-pyrrolidine-2-carboxylic acid |
| $^D$4PhePyrr1 | (2R,4R)-4-Phenyl-pyrrolidine-2-carboxylic acid |
| 4PhePyrr2 | (2S,4S)-4-Phenyl-pyrrolidine-2-carboxylic acid |
| $^D$4PhePyrr2 | (2R,4S)-4-Phenyl-pyrrolidine-2-carboxylic acid |

TABLE 19-continued

Substances Representing Subunits of Particularly Preferred Linkers C

| Code | Chemical Name |
|---|---|
| 5PhePyrr1 | (2S,5R)-5-Phenyl-pyrrolidine-2-carboxylic acid |
| $^D$5PhePyrr1 | (2R,5R)-5-Phenyl-pyrrolidine-2-carboxylic acid |
| 5PhePyrr2 | (2S,5S)-5-Phenyl-pyrrolidine-2-carboxylic acid |
| $^D$5PhePyrr2 | (2R,5S)-5-Phenyl-pyrrolidine-2-carboxylic acid |
| 4Hyp1 | (4S)-L-Hydroxyproline |
| $^D$4Hyp1 | (4S)-D-Hydroxyproline |
| 4Hyp2 | (4R)-L-Hydroxyproline |
| $^D$4Hyp2 | (4R)-D-Hydroxyproline |
| 4Mp1 | (4S)-L-Mercaptoproline |
| $^D$4Mp1 | (4S)-D-Mercaptoproline |
| 4Mp2 | (4R)-L-Mercaptoproline |
| $^D$4Mp2 | (4R)-D-Mercaptoproline |
| Pip | L-Pipecolic acid |
| $^D$Pip | D-Pipecolic acid |
| H-$\beta^3$-HCit-OH | (3S)-3-Amino-6-carbamidyl-hexanoic acid |
| H-$\beta^3$-HOrn-OH | (3S)-3,6-Diamino-hexanoic acid |
| H-$\beta^3$-HtBuA-OH | (3S)-3-Amino-5,5-dimethyl-hexanoic acid |
| H-$\beta^3$-HSar-OH | N-Methyl-3-amino-propionic acid |
| H-$\beta^3$-HPen-OH | (3R)-3-Amino-4-methyl-4-mercapto-pentanoic acid |
| H-$\beta^3$-HtBuG-OH | (3R)-3-Amino-4,4-dimethyl-pentanoic acid |
| H-$\beta^3$-H4AmPhe-OH | (3S)-3-Amino-4-(4'-aminophenyl)-butyric acid |
| H-$\beta^3$-H3AmPhe-OH | (3S)-3-Amino-4-(3'-aminophenyl)-butyric acid |
| H-$\beta^3$-H2AmPhe-OH | (3S)-3-Amino-4-(2'-aminophenyl)-butyric acid |
| H-$\beta^3$-HPhe(mC(NH$_2$)=NH)—OH | (3S)-3-Amino-4-(3'-amidinophenyl)-butyric acid |
| H-$\beta^3$-HPhe(pC(NH$_2$)=NH)—OH | (3S)-3-Amino-4-(4'-amidinophenyl)-butyric acid |
| H-$\beta^3$-HPhe(mNHC(NH$_2$)=NH)—OH | (3S)-3-Amino-4-(3'-guanidinophenyl)-butyric acid |
| H-$\beta^3$-HPhe(pNHC(NH$_2$)=NH)—OH | (3S)-3-Amino-4-(4'-guanidino-phenyl)-butyric acid |
| H-$\beta^3$-H2Pal-OH | (3S)-3-Amino-4-(pyridine-2'-yl)-butyric acid |
| H-$\beta^3$-H4Pal-OH | (3S)-3-Amino-4-(pyridine-4'-yl)-butyric acid |
| H-$\beta^3$-HPhg-OH | (3R)-3-Amino-3-phenyl-propionic acid |
| H-$\beta^3$-HCha-OH | (3S)-3-Amino-4-cyclohexyl-butyric acid |
| H-$\beta^3$-HC$_4$al-OH | (3S)-3-Amino-4-cyclobutyl-butyric acid |
| H-$\beta^3$-HC$_5$al-OH | (3S)-3-Amino-4-cyclopentyl-butyric acid |
| H-$\beta^3$-HNle-OH | (3S)-3-Amino-heptanoic acid |
| H-$\beta^3$-H2Nal-OH | (3S)-3-Amino-4-(2'-naphthyl)-butyric acid |
| H-$\beta^3$-H1Nal-OH | (3S)-3-Amino-4-(1'-naphthyl)-butyric acid |
| H-$\beta^3$-H4ClPhe-OH | (3S)-3-Amino-4-(4'-chlorophenyl)-butyric acid |
| H-$\beta^3$-H3ClPhe-OH | (3S)-3-Amino-4-(3'-chlorophenyl)-butyric acid |
| H-$\beta^3$-H2ClPhe-OH | (3S)-3-Amino-4-(2'-chlorophenyl)-butyric acid |
| H-$\beta^3$-H3,4Cl$_2$Phe-OH | (3S)-3-Amino-4-(3',4'-dichlorophenyl)-butyric acid |
| H-$\beta^3$-H4FPhe-OH | (3S)-3-Amino-4-(4'-fluorophenyl)-butyric acid |
| H-$\beta^3$-H3FPhe-OH | (3S)-3-Amino-4-(3'-fluorophenyl)-butyric acid |
| H-$\beta^3$-H2FPhe-OH | (3S)-3-Amino-4-(2'-fluorophenyl)-butyric acid |
| H-$\beta^3$-HThi-OH | (3R)-3-Amino-4-(2'-thienyl)-butyric acid |
| H-$\beta^3$-HTza-OH | (3R)-3-Amino-4-(2'-thiazolyl)-butyric acid |
| H-$\beta^3$-HMso-OH | (3R)-3-Amino-4-methylsulfoxyl-butyric acid |
| H-$\beta^3$-HAcLys-OH | (3S)-7-Acetylamino-3-amino-heptanoic acid |
| H-$\beta^3$-HDpr-OH | (3R)-3,4-diamino-butyric acid |
| H-$\beta^3$-HA$_2$Bu—OH | (3S)-3,5-Diamino-pentanoic acid |
| H-$\beta^3$-HDbu-OH | (3R)-3,4-Diamino-pentanoic acid |
| H-$\beta^3$-HAib-OH | Amino-dimethyl acetic acid |
| H-$\beta^3$-HCyp-OH | 1-Amino-cyclopentane-1-yl-acetic acid |

TABLE 19-continued

Substances Representing Subunits of Particularly Preferred Linkers C

| Code | Chemical Name |
|---|---|
| H-β³-HY(Bzl)-OH | (3S)-3-Amino-4-(4'-benzyloxyphenyl)-butyric acid |
| H-β³-HH(Bzl)-OH | (3S)-3-Amino-4-(1'-benzylimidazole-4'-yl)-butyric acid |
| H-β³-HBip-OH | (3S)-3-Amino-4-biphenylyl-butyric acid |
| H-β³-HS(Bzl)-OH | (3S)-3-Amino-4-(benzyloxy)-butyric acid |
| H-β³-HT(Bzl)-OH | (3R,4R)-3-Amino-4-benzyloxy-pentanoic acid |
| H-β³-HalloT-OH | (3R,4S)-3-Amino-4-hydroxy-pentanoic acid |
| H-β³-HLeu3OH—OH | (3R,4R)-3-Amino-4-hydroxy-5-methyl-hexanoic acid |
| H-β³-HhAla-OH | (3S)-3-Amino-pentanoic acid |
| H-β³-HhArg-OH | (3S)-3-Amino-7-guanidino-heptanoic acid |
| H-β³-HhCys-OH | (3R)-Amino-5-mercapto-pentanoic acid |
| H-β³-HhGlu-OH | (3S)-3-Amino-heptanedioic acid |
| H-β³-HhGln-OH | (3S)-3-Amino-6-carbamoyl hexanoic acid |
| H-β³-HhHis-OH | (3S)-3-Amino-5-(imidazole-4'-yl)-pentanoic acid |
| H-β³-HhIle-OH | (3S,5S)-3-Amino-5-methyl-heptanoic acid |
| H-β³-HhLeu-OH | (3S)-3-Amino-6-methyl-heptanoic acid |
| H-β³-HhNle-OH | (3S)-3-Amino-octanoic acid |
| H-β³-DiAoc-OH | (3S)-3,8-Diamino-octanoic acid |
| H-β³-HhMet-OH | (3S)-3-Amino-6-methylthio-hexanoic acid |
| H-β³-HhPe-OH | (3S)-3-Amino-5-phenyl-pentanoic acid |
| H-β³-HhSer-OH | (3S)-3-Amino-5-hydroxy-pentanoic acid |
| H-β³-HhThr-OH | (3S,5R)-3-Amino-5-hydroxy-hexanoic acid |
| H-β³-HhTrp-OH | (3S)-3-Amino-5-(indol-3'-yl)-pentanoic acid |
| H-β³-HhThr-OH | (3S)-3-Amino-5-(4'-hydroxyphenyl)-pentanoic acid |
| H-β³-HhCha-OH | (3S)-3-Amino-5-cyclohexyl-pentanoic acid |
| H-β³-HBpa-OH | (3S)-3-Amino-4-(4'-benzoylphenyl)-butyric acid |
| H-β³-HOctG-OH | (3S)-3-Amino-undecanoic acid |
| H-β³-HNle-OH | (3S)-3-Amino-heptanoic acid |
| H-β³-HTic-OH | (3S)-1,2,3,4-Tetrahydroisoquinoline-3-yl-acetic acid |
| H-β³-HTiq-OH | (1S)-1,2,3,4-Tetrahydroisoquinoline-1-acetic acid |
| H-β³-HOic-OH | (2S,3aS,7aS)-1-Octahydro-1H-indole-2-yl-acetic acid |
| H-β³-H4AmPyrr1-OH | (2S,4S)-4-Amino-pyrrolidine-2-acetic acid |
| H-β³-H4AmPyrr2-OH | (2S,4R)-4-Amino-pyrrolidine-2-acetic acid |
| H-β³-H4PhePyrr1-OH | (2S,4R)-4-Phenyl-pyrrolidine-2-acetic acid |
| H-β³-H4PhePyrr2-OH | (2S,4S)-4-Phenyl-pyrrolidine-2-acetic acid |
| H-β³-H5PhePyrr1-OH | (2S,5R)-5-Phenyl-pyrrolidine-2-acetic acid |
| H-β³-H5PhePyrr2-OH | (2S,5S)-5-Phenyl-pyrrolidine-2-acetic acid |
| H-β³-H4Hyp1-OH | (2S,4S)-4-Hydroxy-pyrrolidine-2-acetic acid |
| H-β³-H4Hyp2-OH | (2S,4R)-4-Hydroxy-pyrrolidine-2-acetic acid |
| H-β³-H4Mp1-OH | (2R,4S)-4-Mercapto-pyrrolidine-2-acetic acid |
| H-β³-H4Mp2-OH | (2R,4R)-4-Mercapto-pyrrolidine-2-acetic acid |
| H-β³-HPip-OH | (2S)-piperidine-2-acetic acid |
| H-β³-HPro-OH | (2S)-pyrrolidine-2-acetic acid |
| H-β³-H$^D$Pro-OH | (2R)-pyrrolidine-2-acetic acid |
| Ahb | 4-Amino-2-hydroxy butyric acid |
| H-γ⁴-DiHCit-OH | (4S)-4-Amino-7-carbamidyl-heptanoic acid |
| H-γ⁴-DiHOrn-OH | (4S)-4,7-Diamino-heptanoic acid |
| H-γ⁴-DiHtBuA-OH | (4R)-4-Amino-6,6-dimethyl-heptanoic acid |
| H-γ⁴-DiHSar-OH | N-Methyl-4-amino-butyric acid |
| H-γ⁴-DiHPen-OH | (4R)-4-Amino-5-methyl-5-mercapto-hexanoic acid |
| H-γ⁴-DiHtBuG-OH | (4R)-4-Amino-5,5-dimethyl-hexanoic acid |
| H-γ⁴-DiH4AmPhe-OH | (4R)-4-Amino-5-(4'-aminophenyl)-pentanoic acid |

TABLE 19-continued

Substances Representing Subunits of Particularly Preferred Linkers C

| Code | Chemical Name |
| --- | --- |
| H-γ$^4$-DiH3AmPhe-OH | (4R)-4-Amino-5-(3'-aminophenyl)-pentanoic acid |
| H-γ$^4$-DiH2AmPhe-OH | (4R)-4-Amino-5-(2'-aminophenyl)-pentanoic acid |
| H-γ$^4$-DiHPhe(mC(NH$_2$)=NH)—OH | (4R)-4-Amino-5-(3'-amidinophenyl)-pentanoic acid |
| H-γ$^4$-DiHPhe(pC(NH$_2$)=NH)—OH | (4R)-4-Amino-5-(4'-amidinophenyl)-pentanoic acid |
| H-γ$^4$-DiHPhe(mNHC(NH$_2$)=NH)—OH | (4R)-4-Amino-5-(3'-guanidino-phenyl)-pentanoic acid |
| H-γ$^4$-DiHPhe(pNHC(NH$_2$)=NH)—OH | (4R)-4-Amino-5-(4'-guanidino-phenyl)-pentanoic acid |
| H-γ$^4$-DiH2Pal-OH | (4R)-4-Amino-5-(pyridine-4'-yl)-pentanoic acid |
| H-γ$^4$-DiH4Pal-OH | (4R)-4-Amino-5-(pyridine-4'-yl)-pentanoic acid |
| H-γ$^4$-DiHPhg-OH | (4R)-4-Amino-4-phenyl-butyric acid |
| H-γ$^4$-DiHCha-OH | (4R)-4-Amino-5-cyclohexyl-pentanoic acid |
| H-γ$^4$-DiHC$_4$al-OH | (4R)-4-Amino-5-cyclobutyl-pentanoic acid |
| H-γ$^4$-DiHC$_5$al-OH | (4R)-4-Amino-5-cyclopentyl-pentanoic acid |
| H-γ$^4$-DiHNle-OH | (4S)-4-Amino-octanoic acid |
| H-γ$^4$-DiH2Nal-OH | (4S)-4-Amino-5-(2'-naphthyl)-pentanoic acid |
| H-γ$^4$-DiH1Nal-OH | (4S)-4-Amino-5-(1'-naphthyl)-pentanoic acid |
| H-γ$^4$-DiH4ClPhe-OH | (4R)-4-Amino-5-(4'-chlorophenyl)-pentanoic acid |
| H-γ$^4$-DiH3ClPhe-OH | (4R)-4-Amino-5-(3'-chlorophenyl)-pentanoic acid |
| H-γ$^4$-DiH2ClPhe-OH | (4R)-4-Amino-5-(2'-chlorophenyl)-pentanoic acid |
| H-γ$^4$-DiH3,4Cl$_2$Phe-OH | (4R)-4-Amino-5-(3',4'-dichloro-phenyl)-pentanoic acid |
| H-γ$^4$-DiH4FPhe-OH | (4R)-4-Amino-5-(4'-fluorophenyl)-pentanoic acid |
| H-γ$^4$-DiH3FPhe-OH | (4R)-4-Amino-5-(3'-fluorophenyl)-pentanoic acid |
| H-γ$^4$-DiH2FPhe-OH | (4R)-4-Amino-5-(2'-fluorophenyl)-pentanoic acid |
| H-γ$^4$-DiHThi-OH | (4R)-4-Amino-5-(2'-thienyl)-pentanoic acid |
| H-γ$^4$-DiHTza-OH | (4R)-4-Amino-5-(2'-thiazolyl)-pentanoic acid |
| H-γ$^4$-DiHMso-OH | (4R)-4-Amino-5-methylsulfoxyl-pentanoic acid |
| H-γ$^4$-DiHAcLys-OH | (4S)-8-Acetylamino-4-amino-ocatanoic acid |
| H-γ$^4$-DiHDpr-OH | (4R)-4,5-diamino-pentanoic acid |
| H-γ$^4$-DiHA$_2$Bu—OH | (4R)-4,5-Diamino-hexanoic acid |
| H-γ$^4$-DiHDbu-OH | (4R)-4,5-Diamion-hexanoic acid |
| H-γ$^4$-DiHAib-OH | 3-Amino-3,3-dimethyl propionic acid |
| H-γ$^4$-DiHCyp-OH | (1'-Amino-cyclopentane-1'-yl)-3-propionic acid |
| H-γ$^4$-DiHY(Bzl)-OH | (4R)-4-Amino-5-(4'-benzyloxyphenyl)-pentanoic acid |
| H-γ$^4$-DiHH(Bzl)-OH | (4R)-4-Amino-5-(1'-benzylimidazole-4'-yl)-pentanoic acid |
| H-γ$^4$-DiHBip-OH | (4R)-4-Amino-5-biphenylyl-pentanoic acid |
| H-γ$^4$-DiHS(Bzl)-OH | (4S)-4-Amino-5-(benzyloxy)-pentanoic acid |
| H-γ$^4$-DiHT(Bzl)-OH | (4R,5R)-4-Amino-5-benzyloxy-hexanoic acid |
| H-γ$^4$-DiHalloT-OH | (4R,5S)-4-Amino-5-hydroxy-hexanoic acid |
| H-γ$^4$-DiHLeu3OH—OH | (4R,5R)-4-Amino-5-hydroxy-6-methyl-heptanoic acid |
| H-γ$^4$-DiHhAla-OH | (4S)-4-Amino-hexanoic acid |
| H-γ$^4$-DiHhArg-OH | (4S)-4-Amino-8-guanidino-octanoic acid |
| H-γ$^4$-DiHhCys-OH | (4R)-Amino-6-mercapto-hexanoic acid |
| H-γ$^4$-DiHhGlu-OH | (4S)-4-Amino-ocatanedioic acid |
| H-γ$^4$-DiHhGln-OH | (4S)-4-Amino-7-carbamoyl-heptanoic acid |
| H-γ$^4$-DiHhHis-OH | (4S)-4-Amino-6-(imidazole-4'-yl)-hexanoic acid |
| H-γ$^4$-DiHhIle-OH | (4S,6S)-4-Amino-6-methyl-octanoic acid |
| H-γ$^4$-DiHhLeu-OH | (4S)-4-Amino-7-methyl-ocatanoic acid |
| H-γ$^4$-DiHhNle-OH | (4S)-4-Amino-nonanoic acid |
| H-γ$^4$-DiHhLys-OH | (4S)-4,9-Diamino-nonanoic acid |
| H-γ$^4$-DiHhMet-OH | (4R)-4-Amino-7-methylthioheptanoic acid |

TABLE 19-continued

Substances Representing Subunits of Particularly Preferred Linkers C

| Code | Chemical Name |
|---|---|
| H-γ$^4$-DiHhPhe-OH | (4S)-4-Amino-6-phenyl-hexanoic acid |
| H-γ$^4$-DiHhSer-OH | (4R)-4-Amino-6-hydroxy-hexanoic acid |
| H-γ$^4$-DiHhThr-OH | (4R,6R)-4-Amino-6-hydroxy-heptanoic acid |
| H-γ$^4$-DiHhTrp-OH | (4S)-4-Amino-6-(indol-3'-yl)-hexanoicacid |
| H-γ$^4$-DiHhTyr-OH | (4S)-4-Amino-6-(4'-hydroxyphenyl)-hexanoic acid |
| H-γ$^4$-DiHhCha-OH | (4R)-4-Amino-5-cyclohexyl-pentanoic acid |
| H-γ$^4$-DihBpa-OH | (4R)-4-Amino-5-(4'-benzoylphenyl)-pentanoic acid |
| H-γ$^4$-DiHOctG-OH | (4S)-4-Amino-dodecanoic acid |
| H-γ$^4$-DiHNle-OH | (4S)-4-Amino-octanoic acid |
| H-γ$^4$-DiHTic-OH | (3R)-1',2',3',4'-Tetrahydroisoquinoline-3'-yl-3-propionic acid |
| H-γ$^4$-DiHTiq-OH | (1'R)-1',2',3',4'-Tetrahydroisoquinoline-1'-yl-3-propionic acid |
| H-γ$^4$-DiHOic-OH | (2'S,3'aS,7'aS)-1'-Octahydro-1H-indole-2'-yl-3-propionic acid |
| H-γ$^4$-DiH4AmPyrr1-OH | (2'R,4'S)-4'-Amino-pyrrolidine-2'-yl-3-propionic acid |
| H-γ$^4$-DiH4AmPyrr2-OH | (2'R,4'R)-4'-Amino-pyrrolidine-2'-yl-3-propionic acid |
| H-γ$^4$-DiH4PhePyrr1-OH | (2'R,4'R)-4'-Phenyl-pyrrolidine-2'-yl-3-propionic acid |
| H-γ$^4$-DiH4PhePyrr2-OH | (2'R,4'S)-4'-Phenyl-pyrrolidine-2'-yl-3-propionic acid |
| H-γ$^4$-DiH5PhePyrr1-OH | (2'S,5'R)-5'-Phenyl-pyrrolidine-2'-yl-3-propionic acid |
| H-γ$^4$-DiH5PhePyrr2-OH | (2'S,5'S)-5'-Phenyl-pyrrolidine-2'-yl-3-propionic acid |
| H-γ$^4$-DiH4Hyp1-OH | (2'R,4'S)-4'-Hydroxy-pyrrolidine-2'-yl-2-propionic acid |
| H-γ$^4$-DiH4Hyp2-OH | (2'R,4'R)-4'-Hydroxy-pyrrolidine-2'-yl-3-propionic acid |
| H-γ$^4$-DiH4Mp1-OH | (2'R,4'S)-4'-Mercapto-pyrrolidine-2'-yl-3-propionic acid |
| H-γ$^4$-DiH4Mp2-OH | (2'R,4'R)-4'-Mercapto-pyrrolidine-2'-yl-3-propionic acid |
| H-γ$^4$-DiHPip-OH | (2'S)-Piperidine-2'-yl-3-propionic acid |
| H-γ$^4$-DiHPro-OH | (2'S)-Pyrrolidine-2'-yl-3-propionic acid |
| (AEt)G | N-(2-Aminoethyl)glycine |
| (APr)G | N-(3-Amino-n-propyl)glycine |
| (ABu)G | N-(4-Amino-n-butyl)glycine |
| (APe)G | N-(5-Amino-n-pentyl)glycine |
| (GuEt)G | N-(2-Guanidinoethyl)glycine |
| (GuPr)G | N-(3-Guanidino-n-propyl)glycine |
| (GuBu)G | N-(4-Guanidino-n-butyl)glycine |
| (GuPe)G | N-(5-Guanidino-n-pentyl)glycine |
| (PEG$_3$-NH$_2$)G | N—[H$_2$N—(CH$_2$)$_3$—(OCH$_2$—CH$_2$)$_2$—O(CH$_2$)$_3$] glycine |
| (Me)G | N-Methylglycine |
| (Et)G | N-Ethylglycine |
| (Bu)G | N-Butylglycine |
| (Pe)G | N-Pentylglycine |
| (Ip)G | N-Isopropylglycine |
| (2MePr)G | N-(2-Methylpropyl)glycine |
| (3MeBu)G | N-(3-Methylbutyl)glycine |
| (1MePr)G | (1S)-N-(1-Methylpropyl)glycine |
| (2MeBu)G | (2S)-N-(2-Methylbutyl)glycine |
| (MthEt)G | N-(Methylthioethyl)glycine |
| (MthPr)G | N-(Methylthiopropyl)glycine |
| (Ben)G | N-(Benzyl)glycine |
| (PhEt)G | N-(2-Phenylethyl)glycine |
| (HphMe)G | N-([4'-hydroxyphenyl]methyl)glycine |
| (HphEt)G | N-(2-[4'-hydroxyphenyl]ethyl)glycine |
| (ImMe)G | N-(Imidazol-5-yl-methyl)glycine |
| (ImEt)G | N-(2-(Imidazol-5'-yl)ethyl)glycine |
| (InMe)G | N-(Indol-2-yl-methyl)glycine |
| (InEt)G | N-(2-(Indol-2'-yl)ethyl)glycine |
| (CboMe)G | N-(Carboxymethyl)glycine |
| (CboEt)G | N-(2-Carboxyethyl)glycine |
| (CboPr)G | N-(3-Carboxypropyl)glycine |
| (CbaMe)G | N-(Carbamoylmethyl)glycine |
| (CbaEt)G | N-(2-Carbamoylethyl)glycine |
| (CbaPr)G | N-(3-Carbamoylpropyl)glycine |
| (HyEt)G | N-(2-Hydroxyethyl)glycine |
| (HyPr)G | (2R)-N-(2-Hydroxypropyl)glycine |

TABLE 19-continued

Substances Representing Subunits of Particularly Preferred Linkers C

| Code | Chemical Name |
|---|---|
| (Mcet)G | N-(2-Mercaptoethyl)glycine |
| NMeAla | L-N-Methylalanine |
| NMe$^D$Ala | D-N-Methylalanine |
| NMeVal | L-N-Methylvaline |
| NMe$^D$Val | D-N-Methylvaline |
| NMeIle | L-N-Methylisoleucine |
| NMe$^D$Ile | D-N-Methylisoleucine |
| NMeLeu | L-N-Methylleucine |
| NMe$^D$Leu | D-N-Methylleucine |
| NMeNle | L-N-Methylnorleucine |
| NMe$^D$Nle | D-N-Methylnorleucine |
| NMeMet | L-N-Methylmethionine |
| NMe$^D$Met | D-N-Methylmethionine |
| NMeTyr | L-N-Methyltyrosine |
| NMe$^D$Tyr | D-N-Methyltyrosine |
| NMeHis | L-N-Methylhistidine |
| NMe$^D$His | D-N-Methylhistidine |
| NMePhe | L-N-Methylphenylalanine |
| NMe$^D$Phe | D-N-Methylphenylalanine |
| NMeTrp | L-N-Methyltryptophane |
| NMe$^D$Trp | D-N-Methyltryptophane |
| NMeSer | L-N-Methylserine |
| NMe$^D$Ser | D-N-Methylserine |
| NMeAsp | L-N-Methylaspartic acid |
| NMe$^D$Asp | D-N-Methylaspartic acid |
| NMeGlu | L-N-Methylglutamic acid |
| NMe$^D$Glu | D-N-Methylglutamic acid |
| NMeLys | L-N-Methyllysine |
| NMe$^D$Lys | D-N-Methyllysine |
| NMeArg | L-N-Methylarginine |
| NMe$^D$Arg | D-N-Methylarginine |
| NMeDab | L-N-Methyl-2,4-diamino butyric acid |
| NMe$^D$Dab | D-N-Methyl-2,4-diamino butyric acid |
| NMeCys | L-N-Methylcysteine |
| NMe$^D$Cys | D-N-Methylcysteine |
| NMeAsn | L-N-Methylasparagine |
| NMe$^D$Asn | D-N-Methylasparagine |
| NMeGln | L-N-Methylglutamine |
| NMe$^D$Gln | D-N-Methylglutamine |
| NMeThr | L-N-Methylthreonine |
| NMe$^D$Thr | D-N-Methylthreonine |

Particularly preferred macrocyclic compounds of formula I are the examples: Ex.9, Ex.11, Ex.12, Ex.16, Ex.30, Ex.49, Ex.184, Ex.200, and Ex.213.

Synthesis of the Building Blocks

Building blocks C used in the synthesis of the macrocyclic compounds of the invention are detailed to the level of fully-defined structures shown in Table 19, above and are easily available. Possible synthetic approaches to the modulator building blocks B and, especially, the production of the template building blocks A are described in some detail hereinbelow.

Synthesis of the Template Building Blocks A

General Transformations

Building blocks of type A are based on readily available substances carrying a carboxylic acid group and either a phenolic (Ar/Hetar-OH) or a thiophenolic moiety (Ar/Hetar-SH). The —COOH group may be attached to the same ring as the —OH/—SH group or to an annelated ring which in turn may be aromatic or partially unsaturated.

In general phenol derivatives are more abundantly described in the literature than the corresponding thiophenols. However, transformations of phenols into thiophenols are well established. Therefore the phenolic systems can be regarded as precursors towards their thio-analogs. Alternatively thiophenols might be derived from the corresponding aryl halides or diazonium salts.

Selected examples of general scope for the transformations Ar/Hetar-X→Ar/Hetar-SH(X=OH, F, Cl, Br, I, N$_2^+$) are introduced below:

T-I) A sequence of broad applicability is the transformation of a phenol into a thiocarbamate with N,N-dimethylthiocarbamoyl chloride, followed by Newman-Kwart rearrangement and subsequent hydrolysis (A. Gallardo-Godoy et al., *J. Med. Chem.* 2005, 48, 2407-2419; P. Beaulieu et al., *Biorg. Med. Chem. Lett.* 2006, 16, 4987-4993; H. Sugiyama et al., *Chem. Pharm. Bull.* 2007, 55, 613-624; S. Lin et al., *Org. Prep. Proced. Int.* 2000; 547-556).

T-II) The direct transformation of an —OH adjacent to a pyridinic nitrogen (equivalent to the pyridone tautomer) can be accomplished by heating with P$_2$S$_5$ (K. Hirai et al., *Heterocycles* 1994, 38, 277-280).

T-III) As an alternative to phenols, halogen-substituted (esp. with F or Cl) aromatic ring systems might serve as precursors. In case the halogen is in a position activated by an electron withdrawing group in ortho- or para-position the —SH moiety or a protected analog can be introduced under mild conditions by nucleophilic aromatic substitution reactions (S$_N$Ar) (G. J. Atwell et al., *J. Med. Chem.* 1994, 37, 371-380). Especially in the field of heterocyclic compounds, where the electron withdrawing effect is exerted by pyridine-like nitrogen atoms, this type of substitution is often utilized (S. McCombie et al., *Heterocycles*, 1993, 35, 93-97).

T-IV) Similarly, in Sandmeyer-type reactions a diazonium group ($-N_2^+$) is replaced (C. Mukherjee, E. Biehl, *Heterocycles* 2004, 63, 2309-2318).

T-V) In non-activated positions the substitution of halogen atoms (esp. Br or I) can be accomplished via the corresponding organolithium or Grignard reagents (J. L. Kice, A. G. Kutateladze, *J. Org. Chem.* 1993, 58, 917-923; P. C. Kearney et al., *J. Am. Chem. Soc.* 1993, 115, 9907-9919; K.-Y. Jen, M. P. Cava, *Tetrahedron Lett.* 1982, 23, 2001-2004). Alternatively, transition metal-catalyzed transformations are feasible for this type of reaction, e.g. Cu-catalyzed substitution with benzothioic S-acid (N. Sawada et al., *Tetrahedron Lett.* 2006, 47, 6595-6597), or Pd-catalyzed substitution with KS-Si(i-Pr)$_3$ followed by desilylation of the thus introduced —SSi(i-Pr)$_3$ group (A. M. Rane et al., *Tetrahedron Lett.* 1994, 35, 3225-3226).

The hydroxyl group attached to the aromatic ring (Ar—OH or Hetar-OH) in turn, if not part of a commercially available substance, can be introduced by various methods:

H-I) Analogously to T-III) the hydroxy group or a surrogate can be introduced by an $S_NAr$ reaction of halogen atoms, esp. Cl or F, ortho or para to an electron withdrawing substituent (W. Cantrell, *Tetrahedron Lett.* 2006, 47, 4249-4251) or to a pyridinic nitrogen atom (S. D. Taylor et al., *J. Org. Chem.* 2006, 71, 9420-9430).

H-II) Sandmeyer-type hydroxylations of aromatic amines via intermediate diazonium salts (P. Madsen et al., *J. Med. Chem.* 2002, 45, 5755-5775).

H-III) The substitution of halogen atoms (esp. Br and I), not activated for an $S_NAr$, can be achieved by transition metal-catalyzed C—O-couplings; predominant are Pd-catalysts (K. W. Anderson et al., *J. Am. Chem. Soc.* 2006, 128, 10694-10695; B. J. Gallon et al., *Angew. Chem., Int. Ed.* 2007, 46, 7251-7254), but also others, like Cu-catalysts (J. E. Ellis, S. R. Lenger, *Synth. Commun.* 1998, 28, 1517-1524), find application.

H-IV) Of broad scope is also a two-step process which first transforms halogen atoms (Cl, Br and I) into a boronate and then oxidatively cleaves the carbon-boron bond to the phenol (J. R. Vyvyan et al., *J. Org. Chem.* 2004, 69, 2461-2468).

The carboxylic acid groups of template building blocks A, if not already present in a commercial available building block, can be introduced by standard procedures:

C-I) The oxidation of functional groups like hydroxymethyl (—CH$_2$—OH) or aldehyde (—C(=O)H) can be achieved under mild conditions (G. V. M. Sharma et al., *Synth. Commun.* 2000, 30, 397-406; C. Wiles et al., *Tetrahedron Lett.* 2006, 47, 5261-5264). Also methyl groups on benzene rings can be oxidized; however, as harsh reaction conditions are usually required, its applicability is limited. In contrast, the relative acidic methyl groups ortho or para to a pyridine nitrogen can be oxidized under milder conditions; making this the method of choice for many pyridine ring analogs (T. R. Kelly, F. Lang, *J. Org. Chem.* 1996, 61, 4623-4633).

C-II) Halogen atoms can easily be replaced by a carboxyl group or surrogates thereof, e.g. by halogen metal exchange and subsequent carboxylation of the intermediate Grignard or organolithium species (C. G. Screttas, B. R. Steele, *J. Org. Chem.* 1989, 54, 1013-1017), or by utilizing Mander's reagent (methyl cyanoformate) (A. Lepretre et al., *Tetrahedron* 2000, 56, 265-274).

C-III) In the case that acidified ring positions are to be carboxylated, a viable method is deprotonation with a strong base (usually tert-butyl lithium) followed by carboxylation of the intermediate organolithium species in analogy to C-II).

C-IV) Hydrolysis of ester, amide or nitrile groups. The CN group in turn can easily be introduced by treating organic halides with CuCN (Rosenmund-von Braun reaction: C. F. Koelsch, A. G. Whitney, *J. Org. Chem.,* 1941, 6, 795-803).

Applied to commercially available starting materials these general transformations offer a tool box for accessing templates A. Further literature example are cited within the category of each embodiment below.

A1-A59 Phenyl Derivatives

A plethora of hydroxy benzoic acids with diverse substitution patterns are commercially available and can be directly incorporated as template A into the macrocyclic backbone. In several other cases the presence of an optional substituent provides a suitable functionality that can be further extended into more complex high variation substituents by standard methods of organic synthesis and parallel/combinatorial chemistry.

Even not so common tetrasubstituted hydroxy benzoic acids (A53-A59) can be built up by procedures in accordance with the general methods mentioned above, for example by carboxylation of pentasubstituted phenol derivatives (K. Sung, R. J. Lagow, *J. Mater. Chem.* 1996, 6, 917-918; E. Marzi, M. Schlosser, *Tetrahedron* 2005, 61, 3393-3402; K. C. Nicolaou et al., *Angew. Chem., Int. Ed.* 1999, 38, 3334-3339). Alternative approaches to tetrasubstituted hydroxy benzoic acids involve, for example, the oxidation of benzaldehydes followed by the introduction of substituents into remaining free positions, also feasible to build up polysubstituted benzoic acids from less substituted ones (K. C. Nicolaou et al., *Chem. Eur. J.* 2000, 6, 3095-3115).

A60-A143 Pyridine Derivatives

As in the case of the above class of compounds also for pyridine derivatives a very large number of substances are commercially available which can be incorporated into the macrocycle directly, or can easily be transformed into suitable hydroxyl pyridine carboxylic acids by the general methods mentioned above: selected literature examples can be cited for transformations of type C-III (M. Shimano et al. *Tetrahedron Lett.* 1998, 39; 4363-4366; ibid., Tetrahedron 1998, 54, 12745-12774); for H-II (L. Carpino et al., *J. Org. Chem.* 2004, 69; 54-61); and for C-I (T. R. Kelly, F. Lang, *Tetrahedron Lett.* 1995, 36, 5319-5322), or for C-IV (J. L. LaMattina, R. L. Taylor, *J. Org. Chem.* 1981, 46, 4179-4182).

A144-A165 Pyridazine Derivatives

In analogy to general transformations which are readily available, suitably substituted methylpyridazines can be oxidized to the corresponding 3- or 4-carboxylic acids with dichromate (M. Morishita et al., *Chem. Pharm. Bull.* 1994, 42, 371-372; M. Winn et al., *J. Med. Chem.* 1993, 36, 2676-2688). Of similarly broad scope is the hydrolysis of the corresponding nitriles under chemical conditions (hydroxide; G. Heinisch, D. Lassnigg, *Arch. Pharm.* (Weinheim, Ger.) 1987, 320, 1222-1226) or under enzymatic conditions (nitrilase from *Rhodococcus* sp.; N. Klempier et al., *Tetrahedron Lett.* 1991, 32, 341-344). One possibility to construct the heterocyclic pyridazine core from non-cyclic precursors starts with β-ketoesters which can be subjected to a Staudinger reaction followed by aza-Wittig-cyclization of the intermediate azides (S. V. Galiullina et al., *Russ. J. Org. Chem.* 2007, 43, 607-614; M. Guillaume et al., *Synthesis*

1995, 8, 920-922) or directly cyclocondensed with monohydrazone (E. E. Schweizer, K.-J. Lee, *J. Org. Chem.* 1982, 47, 2768-2773).

A166-A189 Pyrimidine Derivatives

Similarly as with the pyridine derivatives, a large number of suitable building blocks are commercially available and can be directly incorporated into the macrocycle, or they can easily be transformed into the target compounds by the standard procedures mentioned above, including selected examples for transformations of type C-I (Y. Honma et al., *Chem. Pharm. Bull.* 1982, 30, 4314-4324); and C-IV (I. V. Oleinik, O. A. Zagulyaeva, Chem. Heterocycl. Compd. 1993, 29, 427-431). In addition, the pyrimidine core can easily be constructed by cyclocondensation of oxalylic compounds with malonamidine derivative (G. A. Howard et al., *J. Chem. Soc.* 1944, 476-477) or of malonates with amidine derivatives (M. Otsuka et al., *Chem. Pharm. Bull.* 1985, 33, 515-519).

A190-A200 Pyrazine Derivatives

Pyrazine carboxylic acids are easily obtained by cyclocondensation of $\alpha,\beta$-diaminopropionic acid with $\alpha,\beta$-dicarbonyl derivatives (J. Bostroem et al., *Bioorg. Med. Chem.* 2007, 15, 4077-4084). Standard protocol examples are for C-I (J. R. Young et al., *Bioorg. Med. Chem. Lett.* 2000, 10, 1723-1728); for C-111 (N. Ple et al., *Tetrahedron* 1998, 54, 9701-9710); and for H-II (A. P. Krapcho et al., *J. Heterocycl. Chem.* 1997, 34, 27-32). Highly chemoselective oxidations of type C-I can be achived by biotransformations with *Pseudomonas putida* (A. Kiener, *Ang. Chem.* 1992, 104, 748-749).

A201-A206 Triazine Derivatives

A possible route to suitably substituted precursors of difunctional triazines is the cyclocondensation of amidrazones with $\alpha,\beta$-diketones or $\alpha,\beta$-diketoesters (M. Sagi et al., *Heterocycles* 1990, 30, 1009-1021). Also $\alpha,\gamma$-diketoesters are described as suitable starting materials, in this case, however, a multi step reaction sequence being required that proceeds via intermediate 4-nitrosopyrazoles (R. Fusco, S. Rossi, Tetrahedron 1958, 3, 209-224).

A207-A228 Furan, Thiophene and Pyrrole Derivatives

The furans A207 and A208 can be synthesized from suitably substituted 2-formyl- or 2-acetyl-3-oxo-butanoates by bromination followed by cyclization (A. Becker, *Helv. Chim. Acta* 1949, 32, 1114-1122; R. Richter, *Helv. Chim. Acta* 1949, 32, 1123-1136). The thiophenes A207 and A208 can be prepared from (substituted) 3-methoxycarbonyl-tetrahydrothiophene-4-one by oxidation (M. R. Banks et al., *J. Chem. Res*. (M) 1984, 369-389) or by condensation with aldehydes followed by isomerization (R. Jaunin, *Helv. Chim. Acta* 1980, 63, 1542-1553). The pyrroles A207 and A208 (X=O) can be obtained from N-protected, suitably substituted 3-amino-acrylates by reaction with (substituted) 2-chloroacetyl chlorides followed by base-induced cyclization (E. Benary, R. Konrad, *Chem. Ber.* 1923, 56, 44-52). The thioanalogues (X=S) can be synthesized from 3-methoxycarbonyl-furan by dibromination/methanolysis, subsequent reaction with 3-mercapto-propionate and amines, followed by acid-induced cyclization and S-deprotection (F. Eiden, U. Grusdt, *Arch. Pharm.* 1989, 322, 807-810).

The furans A209 and A210 (X=O) are accessible from (substituted) acetyl(methoxycarbonyl)methylene]-triphenylphosphorane by reaction with aldehydes followed by ozonolysis and acid-induced isomerization (H. H. Wasserman, G. M. Lee, *Tetrahedron Lett.* 1994, 35, 9783-9786). The thiophenes A209 and A210 can be prepared from 2-mercaptoacetate and (substituted) acetylene carboxylates (H. Fiesselmann, G. Pfeiffer, *Chem. Ber.* 1954, 87, 848-856) or from acetyl acetates and 2-mercaptoacetate followed by base-induced cyclization (H. Fiesselmann, F. Thoma, *Chem. Ber.* 1956, 89, 1907-1912).

The pyrroles A209 and A210 can be obtained by condensation of beta-alanine ethyl ester and (substituted) 2,3-dioxo-pent-4-enoic esters (H. H. Wasserman et al., *Tetrahedron Lett.* 1989, 30, 1721-1724) or by reaction of suitably substituted 3-oxo-propanoates with glycine esters (A. Treibs, A. Ohorodnik, *Liebigs Ann. Chem.* 1958, 611, 139-149). The thioanalogues (X=S) can be synthesized from (substituted) pyrrolidine-2-carboxylates by subsequent reaction with bistosylsulfur diimide and trimethylphosphite followed by demethylation (J. Häusler, *Monatsh. Chem.* 1986, 117, 269-274).

The furans of type A211 and A212 can be synthesized from diazomalonates and suitably substituted alkynes in a two-step-procedure catalyzed by rhodium(II)-acetate (P. Müller, C. Gränicher, *Helv. Chim. Acta* 1993, 76, 521-534). The thioanalogues (X=S) can be obtained from suitably substituted oxazoles by deprotonation and reaction with dimethyl disulfide, then bromination, lithiation and carboxylation followed by demethylation (S. M. Nolan, T. Cohen, *J. Org. Chem.* 1981, 46, 2473-2476). The thiophenes A211 and A212 are accessible from (substituted) thiophenes by 5-alkylation and/or 3-carboxylation by deprotonation or lithiation (J. Sicé, *J. Am. Chem. Soc.* 1953, 75, 3697-3700). The thioanalogues (X=S) can be obtained from (substituted) 2-trimethylsilyloxy-cyclopropanecarboxylates by reaction with carbon disulfide (C. Brückner, H.-U. Reissig, *Liebigs Ann. Chem.* 1988, 465-470).

The pyrroles A211 and A212 can be prepared from suitably substituted 2-chloroethylidene-malonates by substitution with sodium azide followed by cyclization in the presence of triphenylphosphine (F.-P. Montforts et al., *Liebigs Ann. Chem.* 1990, 1037-1043). The thioanalogues (X=S) can be obtained from suitably substituted 2-oxoethyl-malonates by reaction with isothiocyanates followed by acid-induced cyclization and decarboxylation (J. Fuentes et al., *Tetrahedron: Asymm.* 1998, 9, 2517-2532).

Furans of type A213 and A214 are accessible either by 5-lithiation/carboxylation of (substituted) O-protected 2-hydroxy-furans or by 5-bromination of furan-2-carboxylates followed by substitution with methylate and demethylation (D. G. Manly, E. D. Amstutz, *J. Org. Chem.* 1956, 21, 516-519). The thioanalogues (X=S) can be obtained from (substituted) 1,1-bis(methylthio)prop-1-en-3-one and bromoacetate followed by demethylation (A. Datta et al., *Tetrahedron* 1989, 45, 7631-7641). The thiophenes A213 and A214 can be prepared analogously as for the compounds A211 and A212 (J. Sicé, *J. Am. Chem. Soc.* 1953, 75, 3697-3700). The thioanalogues of thiophenes A213 and A214 (X=S) can be synthesized from suitably substituted 2-chloro-thiophenes by 5-carboxylation and subsequent substitution with sodium hydrogensulfide (K. Clarke et al., *J. Chem. Soc., Perkin Trans.* 11980, 1029-1037). The pyrrols A213 and A214 can be obtained from suitably substituted, N-protected glutamate, which is transformed into the didehydro derivative and cyclized in the presence of LiCuMe$_2$ (M. M. Paz., F. J. Sardina, *J. Org. Chem.* 1993, 58, 6990-6995). The thiophenes A215 and A216 (X=S) can be synthesized from (substituted) 3-bromo-thiophenes by a sequence of 3-lithiation/sulfanylation, 2-bromination, 4-lithiation/carboxylation, 2-debromination and 3-demethylation (E. C. Taylor, D. E. Vogel, *J. Org. Chem.* 1985, 50, 1002-1004). The pyrroles A215 and A216 can be prepared from aminooxoacetate and oxalyl chloride, alcoholysis of the isocyanate, reaction with (3-bromoacetonyl)triphenylphosphonium bromide and N-deprotection (J. P. Bazureau et al., *Tetrahedron Lett.* 1988, 29, 1921-1922), or from (substituted) N-Pfp-protected 3-oxo-prolinates by subsequent reaction with base and acid (F.-A. Marcotte, W. D. Lubell, *Org. Lett.* 2002, 4, 2601-2603). The thioanalogues (X=S) can be obtained from suitably substituted pyrrole-2-carboxylates by subsequent reaction with dicyanodisulfane and zinc/acetic acid (A. Berlin et al., *J. Chem. Soc, Perkin Trans. 2* 1990, 5, 699-704).

The furans A217 and A218 may be obtained from (substituted) acetylene carboxylates by reaction with suitably substituted ethoxyvinylidene-tetracarbonyl-ferrocene complexes followed by O-deprotection (Atiq-ur-Rehman et al., *J. Am. Chem. Soc.* 1993, 115, 9848-9849). The thioanalogues (X=S) can be synthesized from suitably substituted furan-3-carboxylates by subsequent 5-bromination, reaction with dimethyl disulfide and S-deprotection (G. Majetich et al., *Tetrahedron Lett.* 1994, 35, 4887-4890). The thiophenes A217 and A218 should be accessible from (substituted) formylsuccinates by cyclization in the presence of methanol, hydrogen chloride and hydrogen sulfide, followed by demethylation (S. Mitra et al., *J. Chem. Soc.* 1939, 1116-1117); or from (substituted) 2,4-dibromothiophene by subsequent reaction with methanol, butyllithium and carbon dioxide followed by demethylation (D. Spinelli et al., *J. Chem. Res. (M)* 1993, 8, 1873-1890). The pyrroles A217 and A218 (keto-tautomer) can be obtained from suitably substituted aminomethylene succinates by base-induced cyclization (C. A. Grob, P. Ankli, *Helv. Chim. Acta* 1949, 32, 2023-2038). The thioanalogues (X=S) can be synthesized from (substituted) dimethyl(trimethylsilyl)methyl-carbonimidodithioate and (substituted) acetylene carboxylates in the presence of silver fluoride (A. Padwa et al., *J. Org. Chem.* 1987, 52, 1027-1035).

A229-A234 Oxazole, Thiazole and Imidazole Derivatives

The oxazoles of type A229 can be obtained by reaction of acetyl isocyanates and diazoacetate followed by cyclization (O. Tsuge et al., *Tetrahedron* 1973, 29, 1983-1990), whereas the thiazoles A229 can be synthesized from bromomalonates and thioamides (F. A. J. Kerdesky et al., *J. Med. Chem.* 1991, 34, 2158-2165). The imidazoles A229 are accessible by reaction of aminomalonate with substituted acetimidates (M. S. Poonian, E. F. Nowoswiat, *J. Org. Chem.* 1980, 45, 203-208).

The oxazoles and thiazoles of type A230 are accessible by cyclizing monoethyl acetamidomalonate in the presence of trifluoroacetic anhydride (to the oxazoles; J. Morgan et al., *J. Chem. Soc., Perkin Trans. 1* 1997, 5, 613-620), or in the presence of phosphorus pentasulfide (to the thiazoles; A. G. Long, A. Tulley, *J. Chem. Soc.* 1964, 1190-1192). The thiazoles A230 (with X=S) can be synthesized either from N-thioacetyl-glycine by PCl$_3$-mediated cyclization followed by subsequent reaction with the Vilsmeyer reagent and hydrosulfide and oxidation of the intermediate aldehyde (to give 2-substituted 5-mercapto-thiazoles; I. Y. Kvitko et al., *Chem. Heterocycl. Comp.* 1980, 16, 28-31) or from (substituted) 3-bromo-2-oxo-propionic acid by reaction with thiourea, 2-deamination via diazotation, 5-bromination, substitution and deprotection (to give 2-unsubstituted 5-mercapto-thiazoles; B. Blank et al., *J. Med. Chem.* 1977, 20, 572-576). The imidazoles A230 (X=O) can be obtained from aminomalonate by reaction with trimethylorthoformiate followed by cyclization in the presence of ammonia or amines (R. S. Hosmane, B. B. Lim, *Tetrahedron Lett.* 1985, 26, 1915-1918) or, for (X=S) by subsequent reaction of 2-amino-2-cyano-acetate with (substituted) trimethylorthoformiate and hydrogen sulfide A. K. Sen, A. K. Mukhopadhyay, *Indian J. Chem. B.* 1981, 20, 275-278).

The oxazoles A231 (X=S) should be obtainable starting from hydroxyacetaldehyde dimer and potassium thiocyanate followed by S-methylation, lithiation/acylation with chloroformiate and demethylation (C. M. Shafer, T. F. Molinski, *J. Org. Chem.* 1998, 63, 551-555). The corresponding thiazoles A231 (X=S) may be synthesized from suitably substituted beta-ketoesters by subsequent reaction with [hydroxy(tosyloxy)iodo]benzene and ammonium dithiocarbamate (P.-F. Zhang, Z.-C. Chen, *Synth. Comm.* 2001, 31, 415-420). The imidazoles A231 (X=S) can be prepared from N-protected glycine by subsequent reaction with formic acid, methyl formiate and potassium thiocyanate (G. van Lommen et al., *Bioorg. Med. Chem. Lett.* 2005, 15, 497-500), or by C-alkylation of N-protected glycine with suitably substituted chloroacetates followed by reaction with potassium thiocyanate (J. Singh et al., *Tetrahedron Lett.* 1993, 34, 211-214). Oxazoles of type A232 can be prepared from suitably substituted diazoacetates by rhodium-catalyzed reaction with cyanoformiate (G. Shi et al., *J. Fluorine Chem.* 1991, 52, 149-157). Oxazoles of type A233 can be obtained by heating suitably substituted acetylene carboxylates with diazoacetate followed by demethylation (R. Huisgen, H. Blaschke, *Chem. Ber.* 1965, 98, 2985-2997). The S-analogues of oxazoles A233 (X=S) are accessible from N-(bismethylthio)glycine esters by reaction with DMF-acetals followed by acid-induced cyclization and demethylation (R. Gompper, U. Heinemann, *Angew. Chem.* 1981, 93, 297-298). The thiazoles A233 (X=O) can be prepared from suitably substituted cysteine ethyl ester by reaction with diphosgene followed by bromination/elimination (G. Serra et al., *Heterocycles* 1995, 41, 2701-2711).

The oxazoles A234 (X=O) can be prepared from suitably substituted hydroxyacetonitriles and oxalyl chloride followed by methanolysis of the intermediate and demethylation (K. van Aken, G. Hoornaert, *J. Chem. Soc., Chem. Comm.* 1992, 12, 895-896). The thiazoles A234 (X=O) are accessible from suitably substituted 2-mercaptoacetate and cyanoformiate (G. Satzinger, *Liebigs Ann. Chem.* 1978, 473-511). The corresponding thioanalogues (X=S) can be prepared from (substituted) S-methyl 3-oxopropanedithioates and glycine esters followed by cyclization induced by thionyl chloride and demethylation (A. Rahman et al., *Synthesis* 1984, 250-252).

A235-A239 Isoxazole, Isothiazole and Pyrazole Derivatives

Isoxazoles A235 can be synthesized from (2-methoxymethylene)-malonate substituted in 2-position by reaction with hydroxylamine followed by aqueous HCl (K. Bowden et al., *J. Chem. Soc. C* 1968, 172-185). The corresponding pyrazoles A235 can be prepared similarly but with hydrazine instead of hydroxylamine (T. M. Willson et al., *Bioorg. Med. Chem. Lett.* 1996, 6, 1047-1050).

The isothiazoles A236 can be obtained from suitably substituted O-toluenesulfonyloxyiminoacetates by reaction with thioglycolates (B. Rezessy et al., *Tetrahedron Lett.* 1992, 33, 6523-6526). The corresponding pyrazoles A236 can be prepared either from suitably substituted 2-oxopropionates by reaction with ethyl hydrazinoacetate followed by methoxide-mediated cyclization (R. N. Comber et al., *Carbohyd. Res.* 1992, 216, 441-452) or from substituted 3-oxopropionates by 2-diazotation followed by cyclization in the presence of sodium hydride (F. J. L. Herrera, C. U. Baelo, *Carbohyd. Res.* 1985, 143, 161-174). The isoxazoles A237 are accessible by reaction of 4-chloro-3-oxo-butanoates substituted in 4-position with isopentylnitrite (G. Hesse, G. Krehbiel, *Chem. Ber.* 1955, 88, 130-133). The pyrazoles A237 can be obtained from suitably substituted malonates by reaction with diazoacetate (A. Bertho, H. Nüssel, *Liebigs Ann. Chem.* 1927, 457, 278-307). The pyrazoles of type A238 (keto-isomers) can be synthesized from suitably substituted ketosuccinic acids by reaction with hydrazines in the presence of acetic acid (K. J. Duffy et al., *J. Med. Chem.* 2001, 44, 3730-3745).

Isoxazoles of type A239 can be obtained from 3-substituted 2-bromomaleic acids by esterification followed by reaction with hydroxyurea (C. Bennouna et al., *Bull. Soc. Chim. Fr.* 1980, 2, 478-480). The isothiazoles A239 can be prepared from 3-substituted 2-aminofurmaramides by subsequent reaction with hydrogen sulfide and bromine followed by hydrolysis of the formed amides (J. Lykkeberg, P. Krogsgaard-Larsen, *Acta Chem. Scand. B* 1976, 30, 781-785). The corresponding pyrazoles are accessible from (substituted) maleates by reaction with hydrazines followed by oxidation to give the pyrazole ring (G. P. Lahm et al., *Bioorg. Med. Chem. Lett.* 2007, 17, 6274-6279).

A240-A357 Benzofurane, Benzothiophene and Indole Derivatives

The benzothiophenes A240 can be prepared in a multistep sequence starting from suitably substituted 2-hydroxy-benzaldehydes, which are transformed into the 3-isopropoxy-2,3-dihydrobenzothiophen-2-ones and then further on functionalized in 2-position and carboxylated in 3-position (A. V. Kalinin et al., *J. Org. Chem.* 2003, 68, 5992-5999).

A possible route to benzofuranes of type A241-A243 involves condensation of suitably substituted cyclohexane-1,3-diones and 3-bromo-2-oxo-propionic acid followed by Pd-catalyzed dehydrogenation (G. Kneen, P. J. Maddocks, *Synth. Comm.* 1986, 16, 1635-1640). The indoles A244-A247 can be obtained from suitably substituted 2-bromo-3-nitro-benzoates by a Stille coupling to the corresponding 1-ethoxy-styrene followed by a Pd-catalyzed reductive cyclization in the presence of CO and subsequent deprotection of the alcohol and acid (R. W. Clawson et al., *Tetrahedron* 2006, 62, 10829-10834).

The benzofuranes of type A248-A251 can be synthesized from suitably substituted 2,6-dihydroxy-benzoates by reaction with 2-chloroketones (F. H. Curd, A. Robertson, *J. Chem. Soc.* 1933, 714-720) or with chloroacetonitrile in the presence of Lewis acids and HCl followed by acetylation and reductive deoxygenation in 3-position (W. Gruber, K. Horvath, *Mh. Chem.* 1950, 81, 828-836). The corresponding indoles A250 and A251 should accessible from 6-hydroxy-3-methyl-2-nitro-benzoic acid, which is reacted with dimethylformamide followed by hydrogenation of the nitro group, cyclization, diazotation of the amine and hydroxylation (H. D. Hollis Showalter et al., *J. Org. Chem.* 1996, 61, 1155-1158). The benzothiophenes A250 and A251 could be obtained from suitably substituted 2-(thiophen-3-yl-)acetaldehydes by reaction with propargyl alcohol followed by iodo-cyclization, oxidation of the alcohol to the acid and transformation of the 6-iodo-compound into the alcohol (J. P. Waldo et al., *J. Org. Chem.* 2008, 73, 6679-6685).

The benzothiophenes of type A252-A255 are accessible from suitably substituted methyl 3-methyl-thiophene-2-carboxylate, which is first transformed into the 3-toluenesulfinylmethyl compound and then further reacted with suitably substituted acrylates in the presence of base to give the methyl esters of A252-A255 (J. W. Terpstra, A. M. van Leusen, *J. Org. Chem.* 1986, 51, 230-238). Indoles A252-A255 can be synthesized from methyl 2-methoxy-4-methyl-benzoates, which are subsequently brominated in 5-position, nitrated in 3-position, then reacted with dimethylformamide and reduced with Ra/Ni and hydrazine, which triggers a cyclization to the 7-methoxy-6-methoxycarbonyl-indoles. These intermediates can then be deprotected to the indoles A252-A255 (P. L. Beaulieu et al., *Bioorg. Med. Chem. Lett.* 2006, 16, 4987-4993).

Possible precursors for benzofuranes A256-A259 and A264-A267 are suitably substituted 2,4-dihydroxy-benzoates which are subjected to alkylation in 4-position with bromoacetaldehyde diethyl acetal followed by cyclization mediated by Amberlyst A15 (M. Dixit et al., *Synlett* 2006, 10, 1497-1502). Indoles of type A256-A259 (TMS-protected in 4-position, if there is no other substituent) and A264-A267 can be obtained from suitably substituted 5-hydroxy-indoles by formation of the diethyl carbamate followed by anionic Fries rearrangement to the diethyl amide, which is subsequently hydrolyzed with aqueous sodium hydroxide or perchloric acid (E. J. Griffen et al., *J. Org. Chem.* 1995, 60, 1484-1485). The benzothiophenes of type A260 and A263 should accessible from 4,6-dibromo-benzene-1,3-carbaldehyde (substituted in 2- or 5-position) by subsequent substitution of the bromides with methoxide and with 2-mercaptoacetate followed by cyclization, decarboxylation, demethylation and oxidation of the aldehyde to the acid (A. E. Jakobs et al., *Tetrahedron* 1994, 50, 9315-9324).

Benzofuranes of type A268-A271 can be synthesized from the corresponding 4-hydroxy-benzofuranes by carboxylation with carbon dioxide in the presence of methoxide (T. Reichstein, R. Hirt, *Helv. Chim. Acta* 1933, 16, 121-129) or from suitably substituted 5-carbomethoxy-6-hydroxy-salicylaldehydes by reaction with bromoacetates followed by saponification and cyclization in the presence of acetic anhydride (R. T. Foster, A. Robertson, *J. Chem. Soc.* 1948, 115-116). The preparation of the corresponding benzothiophenes A268-A271 should be possible from suitably substituted 4-oxo-tetrahydrobenzothiophene by acylation with dimethyl carbonate followed by aromatization with DDQ (P. P. Yadav et al., *Bioorg. Med. Chem.* 2005, 13, 1497-1505). The indoles A268-A271 can be prepared similarly from the 4-oxo-tetrahydroindoles, or alternatively from suitably substituted N-protected 4-amino-salicylic acid via Claisen rearrangement of the O-allyl ether followed by cleavage of the double bond and cyclization (T. Kakigami et al., *Chem. Pharm. Bull.* 1988, 46, 42-52). Benzofuranes of type A273-A275 can be obtained from 4-O-protected 4-hydroxy-salicylaldehydes by reaction with ethyl diazoacetate in the presence of tetrafluoroboric acid followed by dehydration and deprotection (M. E. Dudley et al., *Synthesis* 2006, 1711-1714). The benzothiophenes A272-A275 are accessible from 5-bromo-benzothiophene (which, in turn, can be prepared from suitably substituted 4-bromo-thiophenols and bromoacetaldehyde diethyl acetal) by Friedel-Crafts acylation, conversion of the methyl ketone into the carboxylate, substitution of the bromide with methoxide and demethylation (S. Mitsumori et al., *J. Med. Chem.* 2003, 46, 2446-2455). The synthesis of corresponding indoles A272-A275 should be possible by the reaction of suitably substituted para-benzoquinones with substituted 2-aminoacrylates in a Nenitzescu reaction (E. A. Steck et al., *J. Org. Chem.* 1959, 24, 1750-1752) Benzofuranes of type A276-A279 can be obtained from the 3-acetyl-4-hydroxy-benzoates by bromination of the methyl ketone followed by base-induced cyclization to the keto-tautomer of A276-A279 (G. Doria et al., *Farmaco* 1980, 35, 674-680). The synthesis of 2-substituted benzofuranes A278 can be achieved by alkylation or acylation. The corresponding benzothiophenes A276-A279 may be prepared from suitably substituted 4-fluorobenzoates and thioglycolate by $AlCl_3$-induced intramolecular Fridel-Crafts acylation of the intermediate 4-alkoxycarbonyl-phenylsulfanyl acetates (D. L. Gernert et al., *Bioorg. Med. Chem. Lett.* 2004, 14, 2759-2764).

The benzofuranes and benzothiophenes of type A284-A287 can be synthesized from suitably substituted 3-furaldehydes or 3-formyl-thiophenes by condensation with diethyl succinate followed by cyclization in the presence of acetic anhydride and then base (D. Simoni et al., *J. Med. Chem.* 2006, 49, 3143-3152). The indoles of type A284 and A287 are accessible from 3-methoxy-4-amino-benzoates by subsequent 5-iodination, Sonogashira coupling with TMS-acetylene and CuI-mediated cyclization followed by demethylation (J. Ezquerra et al., *J. Org. Chem.* 1996, 61, 5804-5812). Benzofuranes and benzothiophenes of type A288-A291 can be obtained from suitably substituted 2-furaldehydes similarly as described for A284-A287 (D. Simoni et al., *J. Med. Chem.* 2006, 49, 3143-3152). The indoles A288-A291 can be synthesized similarly from pyrrole-2-carbaldehydes and diethyl succinate followed by base-induced cyclization (C. Fuganti, S. Serra, *J. Chem. Res.* (M) 1998, 10, 2769-2782).

The indoles of type A292-A295 can be prepared from N-protected ethyl furo[3,2-b]pyrrole-5-carboxylates by decarboxylation with copper chromite in quinoline followed by Diels-Alder reaction with ethyl propiolate and subsequent deprotection (A. Krutosikova, M. Hanes, *Collect. Czech. Chem. Comm.* 1992, 57, 1487-1494).

Benzofuranes of type A296-A299 can be obtained from suitably substituted (p-acetoxyphenoxy)acetyl chlorides by reaction with cyanide followed by cyclization with 1,3-dihydroxy-benzene mediated by zinc(II)-chloride and hydrogen chloride (L. Crombie et al., *J. Chem. Soc., Perkin Trans.* 1 1987, 2783-2786). The corresponding benzothiophenes A296-A299 can be synthesized from suitably substituted 3-bromothiophenols similarly to the synthesis of A272-A275 (S. Mitsumori et al., *J. Med. Chem.* 2003, 46, 2446-2455). The access of the indoles A296-A299 can be achieved either from O-protected 6-hydroxyindoles by acylation in 3-position with trichloroacetyl chloride and methanolysis followed by deprotection (M. Fedouloff et al., *Bioorg. Med. Chem.* 2001, 9, 2119-2128) or by acylation of suitably substituted indoles in 3-position followed by 6-hydroxylation via a Friedel-Crafts acylation/Baeyer-Villiger oxidation sequence (S, Nakatsuka et al., *Heterocycles* 1987, 26, 1471-1474).

The benzofuranes A300-A303 can be obtained from suitably substituted 3-acetyl-furanes by transformation into the silylenol ether followed by Diels-Alder reaction, elimination and dehydrogenation (A. Benitez et al., *J. Org. Chem.* 1996, 61, 1487-1492).

The benzofuranes A304-A307 can be synthesized either from substituted 2-allyl-3-allyloxy-4-methoxy-benzaldehydes by isomerization/metathesis followed by oxidation of the aldehyde and demethylation (W. A. L. van Otterlo et al., *Tetrahedron* 2005, 61, 7746-7755) or from substituted 2-hydroxy-3-methoxy-6-bromo-benzaldehydes by reduction of the alcohol, formation of the phosphonium salt and cyclization in the presence of an acid chloride followed by lithiation/carboxylation and demethylation (K. Hagihara et al., *Bioorg. Med. Chem. Lett.* 2007, 17, 1616-1621). The corresponding benzothiophenes A304-A307 are accessible from suitably substituted methyl thiophene-2-carboxylates by transformation into the 1-(2'-thienyl)-1,4-dioxobutanes followed by $BF_3$-mediated cyclization, 4-carbonylation by Vilsmeyer-Haack reaction, oxidation of the aldehyde and demethylation (S. S. Samanta et al., *J. Chem. Soc., Perkin Trans.* 1 1997, 3673-3678).

The indoles A304-A307 can be obtained either by Diels-Alder reaction of the silylenolate of N-protected 2-acetylpyrrole with propiolate followed by air oxidation (M. Ohno et al., *Heterocycles* 1991, 32, 1199-1202) or from suitably substituted 4-benzyloxy-2-methyl-3-nitro-benzoates (prepared from the 3-methylphenols in a multistep sequence) by subsequent reaction with dimethylformamide and zinc/acetic acid followed by deprotection (M. Tanaka et al., *Eur. J. Med. Chem.* 1996, 31, 187-198).

A358-A372 Pyrrolo[2,3-b]Pyridine Derivatives

The pyrrolopyridines A365 and A366 can be synthesized from 7-azaindole, which is first transformed into N-protected 4-chloro-7-azaindole via the pyridyl-N-oxide (X. Wang et al., *J. Org. Chem.* 2006, 71, 4021-4023), followed by 5-lithiation and carboxylation, hydrolysis of the chloride and of the ester and N-deprotection (A. L'Heureux et al., *Tetrahedron Lett.* 2004, 45, 2317-2320). The pyrrolopyridines of type A367 and A368 can be obtained from suitably substituted 4-chloro-3-formyl-pyridines by reaction with azidoacetate followed by a Hemetsberger-Knittel reaction (P. J. Roy et al., *Synthesis* 2005, 2751-2757). The pyrrolopyridines of type A369 and A370 may be accessible from the corresponding substituted 5-chloro-pyrrolopyridine by formylation in a Duff reaction, oxidation to the acid and hydrolysis of the chloride (R. H. Bahekar et al., *Bioorg. Med. Chem.* 2007, 15, 6782-6795) The synthesis of pyrrolopyridines A371 and A372 may be possible from 4-chloro-7-azaindole by pyridyl-N-oxidation and -methylation followed by substitution with cyanide and hydrolysis of the nitrile and chloride (T. Storz et al., *Synthesis* 2008, 201-214).

A373-A385 Pyrrolo[2,3-c]pyridine Derivatives

The pyrrolopyridine A379 might be obtained from suitably substituted 4-iodo-3-nitro-pyridines by a Sonogashira coupling, ethanolysis of the alkyne, reduction of the nitro group and $TiCl_4$-mediated cyclization (T. Sakamoto et al., *Chem. Pharm. Bull.* 1986, 34, 2362-2368). The pyrrolopyridines of type A382 and A383 can be prepared from 2-methoxy-4-iodo-5-aminopyridines by Sonogashira coupling with TMS-acetylene, CuI-mediated cyclization, formylation (and oxidation) in 3-position and demethylation (D. Mazeas et al., *Heterocycles* 1999, 50, 1065-1080).

Pyrrolopyridines of type A384 and A385 are accessible from suitably substituted 4-methoxy-pyrrole-2-carbaldehyde by reductive amination with 3,3-diethoxy-2-amino-propionate, $TiCl_4$-mediated cyclization and demethylation (S. K. Singh et al., *Heterocycles* 1997, 44, 379-392).

A386-A398 Pyrrolo[3,2-c]pyridine Derivatives

The pyrrolopyridines A387 and A388 could be accessible starting from suitably substituted N-alkylated 2-formyl-pyrroles via the 2-pyrrylacryl azides, which are then cyclized to the pyrrolopyridinones. These intermediates are then transformed into the 3-carboxy compounds via the corresponding aldehydes (J. S. New et al., *J. Med. Chem.* 1989, 32, 1147-1156). The pyrrolopyridines of type A389 and A390 can be obtained from suitably substituted 2-methoxy-3-formyl-pyridines by reaction with azidoacetate followed by a Hemetsberger-Knittel reaction, similarly to the synthesis of A367 and A368 (P. J. Roy et al., *Synthesis* 2005, 2751-2757).

A399-A413 Pyrrolo[3,2-b]pyridine Derivatives

Pyrrolopyridines of type A406 and A407 can be obtained from substituted 2-(6-methoxy-3-nitro-2-pyridyl)-acetates by Knoevenagel reaction with formaldehyde followed by Pd-catalyzed cyclization in the presence of hydrogen and CO (B. C. G. Soederberg et al., *Synthesis* 2008, 6, 903-912).

Pyrrolopyridines A410 and A413 can be synthesized from suitably substituted 2-chloro-3-nicotinonitriles by Sonogashira coupling with TMS-acetylene followed by ethanolysis of the alkyne and degradation of the nitrile and finally acid-induced cyclization (T. Sakamoto et al., *Chem. Pharm. Bull.* 1986, 34, 2362-2368). Alternatively, the synthesis of A410 and A413 can be achieved by reaction of suitably substituted 3-nitro-pyridines with vinylmagnesium bromide (Z. Zhang et al., *J. Org. Chem.* 2002, 67, 2345-2347). The pyrrolopyridines A408 and A412 can be obtained from 2-alkynyl-3-amino-pyridines by CuI-catalyzed cyclization (A. M. Palmer et al., *Bioorg. Med. Chem.* 2008, 16, 1511-1530).

A414-A449 Benzoxazole, Benzothiazole and Benzoimidazole Derivatives

Benzoxazoles A415 and A416 can be prepared starting from N-acylated 3-chloro-4-anisidines via benzyne-formation and carboxylation (D. R. Reavill, S. K. Richardson, *Synth. Comm.* 1990, 20, 1423-1436). The corresponding benzimidazoles A415 and A416 are accessible from of 2-amino-3-halo-benzoates by acylation of the amine, nitration in 6-position, alkylation of the amide and cyclization under reductive conditions (K. Kubo et al., *J. Med. Chem.* 1993, 36, 1772-1784).

Benzimidazoles of type A417-A419 can be obtained from 4-acetamido-2-methoxy-benzoates by subsequent chlorination in 5-position and nitration in 3-position, followed by reductive cyclization of the obtained 3-nitro-4-amino-benzoates in the presence of carboxylic acids or formic acid (S. Bolgunas et al., *J. Med. Chem.* 2006, 49, 4762-4766). This reductive cyclization procedure might also be applicable to the synthesis of other benzimidazoles. Benzimidazoles A420-A422 are accessible from the corresponding 5-methoxy-6-methyl-benzimidazoles by demethylation and oxidation of the methyl group to the carboxylate (B. D. Palmer et al., *J. Med. Chem.* 1999, 42, 2373-2382). Benzoxazoles of type A423-A425 can be obtained by condensation of substituted 4-methylene-2-oxazolin-5-ones and 4-triphenylphosphoranylidene-3-oxobutanoates followed by iodine-mediated aromatization (F. Clericl et al., *Tetrahedron* 1991, 47, 8907-8916). The synthesis of the corresponding benzimidazoles A423-A425 should be possible starting from 4-amino-2-hydroxy-5-nitrobenzoates via acylation, then reduction of the nitro group and cyclization, as is described for the 2-chloro-benzoates (A. Tanaka et al., *Chem. Pharm. Bull.* 1994, 42, 560-569). Benzoxazoles of type A426-A428 can be synthesized starting from 2,5-dihydroxybenzoate, which is aminated in 6-position in a multistep sequence, then acylated and cyclized (D. Diez-Martin et al., *Tetrahedron* 1992, 48, 7899-7939).

The benzimidazoles A429-A431 should be accessible from O-protected 3,4-diamino-2-hydroxy-benzoates, which are mono-acylated and then cyclized under acidic conditions (Y. Hirokawa et al., *Chem. Pharm. Bull.* 2002, 50, 941-959; A. Viger, P. B. Dervan, *Bioorg. Med. Chem.* 2006, 14, 8539-8549). Benzothiazoles of type A438-A440 can be synthesized by heating suitably substituted 4-amino-3-methoxy-benzoates with potassium thiocyanate in the presence of copper(II)-sulfate and subsequent 2-desamination and 3-demethylation (I. A. Ismail et al., *J. Org. Chem.* 1980, 45, 2243-2246). Benzimidazoles A441-A443 can be prepared by a multi-step sequence from 8-aminoquinolines via the corresponding 5,6-dihydro-4H-imidazoquinolines (R. C. Elderfield, F. J. Kreysa, *J. Am. Chem. Soc.* 1948, 70, 44-48). Benzimidazoles A444 and A447 can be obtained by reaction of suitably substituted 3-amino-4-methoxy-benzoates with nitriles followed by NaOCl-induced cyclization and subsequent deprotection (J. Reagn et al., *Bioorg. Med. Chem. Lett.* 1998, 8, 2737-2742).

A450-A459 Benzoisoxazole, Benzoisothiazole and Indazole Derivatives

Benzoisoxazoles of type A456 and A459 can be synthesized starting from 2,6-dihydroxy-3-formyl-4-methyl-benzoates by reaction with hydroxylamine followed by thermal cyclization (D. H. R. Barton et al., *J. Chem. Soc. C* 1971, 2166-2174). The application of this method to the synthesis of the other benzisoxazoles (A450-A455, A457 and A458) should be possible. The preparation of indazoles A457 has been described by reaction of 3-amino-2-methoxy-4-methylbenzoate with isoamylnitrite followed by demethylation (S. Bolgunas et al., *J. Med. Chem.* 2006, 49, 4762-4766); the application to other indazoles (A450-A456 and A458) appears feasible.

A460-A515 Naphthalene Derivatives

A relatively large number of suitably substituted naphthalene derivatives is commercially available. In addition, naphthalenes of type A460-A465 and A496-A499 can be obtained from the corresponding 2-hydroxy-naphthalenes via lithiation and carboxylation (K. Takahashi et al., *Tetrahedron* 1994, 50, 1327-1340). Alternatively, the demethylation of 2-methoxynaphthalene carboxylic acids has been described (Y. Gao et al., *J. Med. Chem.* 2001, 44, 2869-2878). Higher substituted compounds can be prepared in a multistep sequence from suitably substituted 2-bromotoluenes via 2-tetralone-1-carboxylates analogously to the method described by F. C. Goerth et al., *Eur. J. Org. Chem.* 2000, 2605-2612.

Naphthalenes of type A478-A483 and A508-A511 can be prepared either by demethylation of the 3-methoxynaphthalene-1-carboxylates (R. E. Royer et al., *J. Med. Chem.* 1995, 38, 2427-2432) or by diazotation and subsequent hydrolysis of the corresponding 3-aminonaphthalene-1-carboxylates (K. J. Duffy et al., *J. Med. Chem.* 2001, 44, 3730-3745).

The naphthalenes of type A484-A489 and A504-A507 can be easily built up by a condensation reaction with succinic esters, starting either from suitably substituted benzaldehydes (A. M. El-Abbady et al., *J. Org. Chem.* 1961, 26, 4871-4873; M. Kitamura et al., *Angew. Chem. Int. Ed.* 1999, 38, 1229-1232) or from benzophenones (F. G. Baddar et al., *J. Chem. Soc.* 1955, 1714-1718), depending on the substitution pattern in the desired product.

Naphthalene derivatives of type A490-A495 and A512-A515 can be obtained from 2-methoxynaphthalenes by bromination in 4-position, lithiation of the bromide followed by carboxylation and demethylation (J. A. O'Meara et al., *J. Med. Chem.* 2005, 48, 5580-5588) or from 2-chloro-naphthalene by reaction with phthalic anhydride followed by KOH-induced cleavage (G. Heller, *Chem. Ber.* 1912, 45, 674-679).

A516-A548 Quinoline Derivatives

The synthesis of quinolines of type A516-A518 can be accomplished by reaction of suitably substituted isatins with substituted phenacylbromides (H. John, *J. Prakt. Chem.* 1932, 133, 259-272; E. J. Cragoe et al., *J. Org. Chem.* 1953, 18, 552-560).

Quinolines of type A522-A524 are easily accessible from suitably substituted 2-amino-benzaldehydes via a modified Friedländer synthesis (D. L. Boger, J.-H. Chen, *J. Org. Chem.* 1995, 60, 7369-7371). Similarly, quinoline derivatives A527-A529 can be obtained from 2-aminobenzaldehydes by condensation with malonic acid (J. Troeger, C. Cohaus, *J. Prakt. Chem.* 1927, 117, 97-116).

Quinolines A525 can be synthesized from the corresponding 2-cyanoquinoline-1-oxides by rearrangement (C. Kaneko, S. Yamada, *Chem. Pharm. Bull.* 1967, 15, 663-669). The quinolines A526 (with a substitution in 4-position)

are in principle accessible from substituted 2-aminoacetophenones (with the substitution on the acetyl moiety) by reaction with 3-chloro-3-oxopropionate and subsequent base-induced cyclization (A. Capelli et al., *Bioorg. Med. Chem.* 2002, 10, 779-802).

Quinolines of type A530-A533 can be built up starting from 2-anisidines by reaction with 2-oxosuccinic esters followed by thermal cyclization, demethylation and removal of the 4-hydroxy group via hydrogenation of the corresponding chloride (L. Musajo, M. Minchilli, *Chem. Ber.* 1941, 74, 1839-1843). For the synthesis of quinolines of type A543-A545 the condensation of suitably substituted isatins with malonic acid has been described (e.g. W. Borsche, W. Jacobs, *Chem. Ber.* 1914, 47, 354-363; J. A. Aeschlimann, *J. Chem. Soc.* 1926, 2902-2911).

A549-A564 Isoquinoline Derivatives

Isoquinolines of type A549-A553 with the carboxylate in the 1-position can be prepared from suitably substituted benzaldehydes, which are transformed into the aminoethanes followed by reaction with oxalic ester aldehyde or acid chloride, cyclization, oxidative aromatization and finally saponification (M. Keizo et al., *Chem. Pharm. Bull.* 1982, 30, 4170-4174; S, Naoki et al., *Chem. Pharm. Bull.* 1989, 37, 1493-1499).

Isoquinoline-3-carboxylates (A554-A556) are accessible from hydroxylated phenylalanines via a Bischler-Napieralski reaction followed by oxidative aromatization, or alternatively from suitably substituted 2-methyl benzaldehydes, which are reacted with methyl azidoacetate and then cyclized under thermal conditions followed by aromatization (Y. Fukuda et al., *J. Med. Chem.* 1999, 42, 1448-1458; T. R. Burke et al., *Heterocycles* 1992, 34, 757-764).

Compounds of type A557 and A558 can be built up by reaction between suitably substituted 2-aminobenzoic acids and 5-chloro-3-carboxy-1,2,4-pyrazines in the presence of amylnitrite followed by hydrolysis (A. M. d'A. Rocha Gonsalves, T. M. V. D. Pinho e Melo, *Tetrahedron* 1992, 48, 6821-6826), whereas isoquinolines A559 and A560 can be prepared by reaction of 2-formylbenzoic acids with 2-thioxothiazolidin-4-one followed by cyclization and transformation of the isothiochromenone into the isoquinoline with ethanolic ammonia (D. J. Dijksman, G. T. Newbold, *J. Chem. Soc.* 1951, 1213-1217).

The access to isoquinolines A561 and A562 might be possible by transformation of suitably substituted isquinolines into the corresponding Reissert compounds, nitration in 4-position and hydrolysis of the nitrile (M. Sugiura et al., *Chem. Pharm. Bull.* 1992, 40, 2262-2266) followed by hydrogenation of the nitro group, diazotation of the amine and transformation into the hydroxyl group.

Isoquinolines of type A563 and A564 are accessible from suitably substituted (2-methoxycarbonyl-phenyl-)acetic acids via reaction with methyl formate followed by cyclization of the formed enol and amination of the isochromenone (H. E. Ungnade et al., *J. Org. Chem.* 1945, 10, 533-536).

A565-A577 Quinazoline Derivatives

The most general routes to quinazolines use appropriately substituted phenyl derivatives onto which the pyrimido ring is cyclized, e.g. the cyclocondensation of 2-amino benzamides with oxalates (M. Suesse et al., *Helv. Chim. Acta* 1986, 69, 1017-1024), of ortho-carbonyl substituted phenyl oxalamic acid esters with ammonium formate (S. Ferrini et al., *Org. Lett.* 2007, 9, 69-72), or of 2-amino benzonitriles with carbonylformimidate or chloroformamidine (A. McKillop et al., *Tetrahedron Lett.* 1982, 23, 3357-3360; N. Harris et al., *J. Med. Chem.* 1990, 33, 434-444), or of ortho-oxalyl anilides with ammonia (M. T. Bogert, F. P. Nabenhauer, *J. Am. Chem. Soc.* 1924, 46, 1702-1707).

A578-A587 Quinoxaline Derivatives

The synthesis of quinoxalines of types A578-581 via their 2-carbaldehydes is well-described (E. Lippmann et al., *Zeitschr. Chem.* 1990, 30, 251-252). The other representatives of these groups A582-587 are available by cyclocondensation of β-dicarbonyl derivatives or β-keto-esters with appropriately substituted ortho-phenylendiamines (S. Grivas et al., *Acta Chem. Scand.* 1993, 47, 521-528; A. Zychilinski, I. Ugi, *Heterocycles* 1998, 49, 29-32; D. Zhou et al., *Bioorg. Med. Chem.* 2008, 16, 6707-6723). Unique to the quinoxaline is the possibility to introduce a carboxyl group in the 2-position by enzyme catalyst biotransformation applying *Arthrobacter nicotianae* (T. Yoshida et al., *Biosci. Biotech. Biochem.* 2002, 66, 2388-2394).

A588-A601 Pyrido[5,4-d]pyrimidine Derivatives

The bicyclic core can be accessed by annelating suitably substituted pyridines by cyclocondensation reactions. Feasible starting materials include pyridine-2,3-dicarboxylic acids (A. Tikad et al., *Synlett* 2006, 12, 1938-1942), 3-aminopyridine-2-carboxylates (M. Hayakawa et al., *Bioorg. Med. Chem.* 2006, 14, 6847-6858) or 3-aminopyridine-2-nitriles (J. B. Smaill et al., *J. Med. Chem.* 2009, 43, 1380-1397).

A602-A608 Pyrimido[5,4-d]pyrimidine Derivatives

Access to the pyrimidopyrimidine group of templates might be achieved via the literature-known 4,6-dichloro derivative (G. Rewcastle et al., *J. Med. Chem.* 1997, 40; 12, 1820-1826) or the corresponding 2,4,6,8-tetrachloro derivative (J. Northen et al., *J. Chem. Soc., Perkin Trans.* 1, 2002, 108-115) using the general methods described above and separation of the expected isomeric mixtures.

A609-A618 Tetraline Derivatives

A large number of reaction sequences that lead to tetraline derivatives involve an intramolceular Friedel-Crafts acylation as a key step, and the prerequisite cyclization precusors can be elaborated from phenylacetonitriles, 2-phenyl malonates (R. S, Natekar, S. D. Samant, *Indian J. Chem., Sect. B: Org. Chem. Incl. Med. Chem.* 2002, 41, 187-190; L. Gong, H. Parnes, *J. Labelled Compd. Radiopharm.* 1996, 38, 425-434). Alternatively, the intramolecular cyclization can be achieved by a Buchner Reaction (A. Cheung et al., *Bioorg. Med. Chem. Lett.* 2003, 13, 133-138). Subsequently, the carbonyl groups of the thus obtained 1- or 2-tetralones can easily be converted into carboxyl moieties (M. Meyer et al., *J. Med. Chem.* 1997, 40, 104-1062; F. Berardi et al., *J. Med. Chem.* 2004, 47, 2308-2317).

A619-A626 Indane Derivatives

Indane derivatives of types A619-A623 with a carboxyl group in the 1-position are accessible from appropriately substituted and easily available 3-cyano-indenes by hydrogenation to the indane core followed by hydrolysis to the carboxylic acid moiety (T. McLean et al. *J. Med. Chem.* 2006, 49, 4269-4274). Also indan-1-ones can be transferred into indane-1-carboxylic acids, for example via oxiranes (D.-I. Kato et al., *J. Org. Chem.* 2003, 68, 7234-7242), or in a Corey-Seebach-type reaction via 1,3-dithianes (Y.-P. Pang et al., *J. Org. Chem.* 1991, 56, 4499-4508).

Indane derivatives of types A624-A626 with a carboxyl group in 2-position can be obtained from readily accessible, suitably substituted indan-1-ones by treatment of the corresponding enolate with a dimethyl carbonate, hydrogenation of the carbonyl group and hydrolysis of the introduced ester group (T. Tanaka et al., *Chem. Pharm. Bull.* 1994, 42, 1756-1759; U. Hacksell et al. *J. Med. Chem.* 1981, 24, 429-434). Alternatively the indane ring system can be built up starting from ortho-xylenes by NBS bromination of both methyl residues, alkylation-spirocyclization with the enolate of barbituric acid and finally decarboxylative ring cleavage to indane-2-carboxylic acids (G. A. Kraus et al., *J. Org. Chem.* 2002, 67, 5857-5859).

Synthesis of Building Blocks for the Modulators B

The Modulator moieties B of the macrocycle I are derived from appropriately substituted aminoalcohols, wherein the amino and alcohol group, which contribute to the ring connectivity, are separated from by 2-4 C-atoms.

If not already present in a commercial building block, the substituent $R^3$ can be introduced by standard nucleophilic addition of organo metallic reagents to carbonyl or carboxyl derivatives. For B18-B21, carrying no additional C-substituent on their ring system, such precursors are commercially available. Similarly, in the case of B9, B10, B16 and B17 the diversification of the substituent pattern can be easily achieved by standard transformations of the commercial analogs with free amine functionalities (i.e. —$NH_2$→$NR^{11}R^{27}$ in the case of B9 and —NH→—$NR^{11}$ for B10, B16 and B17).

B1 Aziridine Derivatives

Usually, the access to hydroxymethyl aziridines relies on reaction sequences involving the construction of the aziridine ring. The starting materials with the broadest applicability are β-ketoesters: Transformation into the β-hyroxy-imino analog, intramolecular cyclisation to the aziridine ring and reduction of the ester to the alcohol group leads to building blocks of type B1 (e.g. T. Sakai et al., *J. Org. Chem.* 2005, 70, 1369-1375). An alternative approach uses α,β-dihaloester which are converted into substances of type B1 via aziridination with ammonia and reduction of the ester group (P. Davoli et al., *Tetrahedron* 2001, 57, 1801-1812).

B2-B3 Azetidine Derivatives

The standard approaches to hydroxymethyl azetidines comprises subjecting easily accessible O-protected glycidols to, successively, an epoxide-ring opening with azide, transformation of the OH group of the thus obtained alcohol into a suitable leaving group (e.g. tosylate or sulfate), reduction of the azide to an amine and concomitant intramolceular cyclization (F. Hosono et al., *Tetrahedron* 1994, 50, 13335-13346; D.-G. Liu, G.-Q. Lin, *Tetrahedron Lett.* 1999, 40, 337-340).

B4-B8 Pyrrolidine Derivatives and B11-B15 Piperidine Derivatives

The synthetic approaches to the pyrrolidine and piperidine classes of building blocks B rely on the same strategies and are therefore discussed together. Intramolecular cyclization reactions are the predominant routes applicable to a broad number of diversely substituted substrates: Amines carrying a residue with a leaving group in the ω-position lead directly to the desired saturated ring systems by an intramoleular nulceophilic substitution (G. Ceulemans et al., *Tetrahedron* 1997, 53, 14957-14974; S. H. Kang, D. H. Ryu, *Tetrahedron Lett.* 1997, 38, 607-610; J. L. Ruano et al., *Synthesis* 2006, 687-691). Also N-haloamines can be directly transformed to the desired compounds by the Hofmann-Löffler-Freytag reaction (M. E. Wolff, *Chem. Rev.* 1963, 63, 55-64). Alternatively amines carrying two substituents, each with an alkene or alkyne bond, can be subjected to a ring closing metathesis (RCM) reaction (Y. Coquerel, J. Rodriguez, *Eur. J. Org. Chem.* 2008, 1125-1132) and subsequent reduction of the thus obtained partially unsaturated ring to the saturated heterocycle.

Also the reduction of the corresponding aromatic five- and six-membered heterocycles to their saturated analogs is described in the literature. However, due to the large number of commercially available pyridines this approach is mainly applied to the synthesis of the piperidine system (J. Bolos et al., *J. Heterocycl. Chem.* 1994, 31, 1493-1496; A. Solladie-Cavallo et al., *Tetrahedron Lett.* 2003, 44, 8501-8504; R. Naef et al., *J. Agric. Food Chem.* 2005, 53, 9161-9164).

Procedures for the synthesis of libraries of macrocyclic compounds of general structure I are described below but it will immediately apparent to those skilled in the art how these procedures have to be modified if it is intended to synthesize one single macrocyclic compound of formula I.

The macrocyclic compounds of the invention are obtained by cyclization of suitable linear precursors which are derived from optionally substituted hydroxyaryl, hydroxyheteroaryl, mercaptoaryl, or mercaptoheteroaryl carboxylic acids A ("template", a), substituted amino alcohols B ("modulator", b) and one to three building blocks of type C forming the "bridge", c.

Variable substituents are introduced by pre- or postcyclative derivatization of one or more orthogonally protected attachment points (e.g. amino groups, carboxyl groups, hydroxyl groups) on building blocks B and C, and optionally A. Variable R-groups may also be introduced as side chain motifs in building blocks C.

The macrocyclic products of the invention can be prepared either in solution or on a solid support.

In accordance with the present invention, the ring closure reaction is, in principle, possible between any of the building blocks.

Macrocycles of general structure I with building block c forming the bridge c are obtained by either
a) macrolactamisation between c and B; or
b) macrolactamisation between A and c; or
c) aryl- or thioaryl ether formation between A and B; or, alternatively,
d) Ring closure metathesis reaction within building blocks of type C is also possible.

Macrocycles of structure I with orthogonally protected exocyclic functional groups (attachment points for derivatization) are prepared in solution by a process which comprises:

$a^1$) condensation of an appropriately protected hydroxy- or mercapto-aryl/heteroaryl carboxylic acid PG-A-OH and a suitably C-terminal- and appropriately side-chain-protected building block H-c1-OPG to form PG-A-c1-OPG;

$b^1$) if required release of the aryl/heteroaryl (phenolic) OH group or mercapto group, respectively;

$c^1$) aryl/heteroaryl ether or thioether formation with a suitably N-protected amino alcohol HO—B-PG leading to the fully protected linear cyclization precursor PG-B-A-c1-OPG;

$d^1$) cleavage of the "main chain" protective groups (PG) affording the free amino acid H—B-A-c1-OH (still carrying appropriately protected side chain functional groups); followed by either $e^1$) intramolecular amide coupling affording protected macrocycles of general formula I (yielding cyclo-(B-A-c1) still carrying orthogonally protected side chain functional groups); or $f^1$) N-reprotection of the product obtained in step $d^1$);

$g^1$) coupling of a suitably C-protected amino acid H-c2-OPG;

$h^1$) cleavage of the "main chain" protective groups affording the free amino acid H—B-A-c1-c2-OH (still carrying appropriately protected side chain functional groups);

$i^1$) intramolecular amide coupling affording the protected macrocycles of general formula I (yielding cyclo-(B-A-c1-c2); still carrying orthogonally protected side chain functional groups); or j¹) N-protection of the product obtained in step d¹);

k¹) coupling of a suitably C-protected amino acid H-c2-OPG l¹) cleavage of the C-terminal protective group or cleavage of N- and C-terminal main chain protective groups and reprotection of the N-terminus;

m¹) coupling of a suitably C-protected amino acid H-c3-OPG;

n¹) release of the "main chain" protective groups affording the free amino acid H—B-A-c1-c2-c3-OH (still carrying protected side chain functional groups); and o¹) intramolecular amide coupling affording the protected macrocycles of general formula I (yielding cyclo-(B-A-c1-c2-c3), still carrying protected side chain functional groups).

The appropriately protected, preferably acyloxy- or acylmercapto-, most preferably acetyloxy- or acetylmercapto-substituted aryl/heteroaryl carboxylic acid (PG¹-A-OH) is converted into the corresponding acid chloride and condensed with a suitably protected amino acid ester H-c1-OPG² in the presence of an auxiliary base (e.g i-Pr$_2$NEt, Et$_3$N, pyridine, collidine) and in solvents like CH$_2$Cl$_2$, CHCl$_3$, THF to afford after deacylation (preferably by aminolysis) the hydroxyl or mercapto aryl/heteroaryl amide H-A-c1-OPG².

The aminolysis is advantageously carried out with a dialkylaminoalkyl amine in solvents like THF at 0-25° C. Acyl amine side products formed in the course of the reaction can thus be removed by extraction with acidic aqueous solutions.

Alternatively, the acyloxy or acylmercapto aryl/heteroaryl carboxylic acid (PG¹-A-OH) can be coupled in the presence of a coupling reagent (such as benzotriazol derivatives like HBTU, HCTU, PyBOP, or their aza analogs such as HATU, or carbodiimides such as EDC) to the amino acid ester H-c1-OPG² to afford, after deacylation, the phenol or thiophenol H-A-c1-OPG².

The phenol H-A-c1-OPG² can also be directly obtained from the hydroxyaryl/heteroaryl carboxylic acid H-A-OH and the amino acid ester H-c1-OPG² in the presence of a coupling reagent.

Alkylation of the phenol or thiophenol H-A-C$_1$—OPG² with a suitably N-protected amino alcohol HO—B-PG³ to give the ether or thioether PG³-B-A-c1-OPG² is achieved using azodicarboxylic acid derivatives such as DEAD, DIAD or ADDP in the presence of trialkyl or triaryl phosphines in solvents like benzene, toluene, CH$_2$Cl$_2$, CHCl$_3$ or THF at 0° C. to room temperature. As a variation, the reaction can be induced with CMBP in toluene at temperatures ranging from 20-110° C.

As an alternative, the alcohol HO—B-PG³ can be converted into a corresponding sulfonates (such as for example the mesylate, tosylate, triflate) or a corresponding halide (such as chloride, bromide and iodide) and subsequently be treated with the phenol or thiophenol H-A-c1-OPG² in the presence of an auxiliary base such as for example NaH or K$_2$CO$_3$ in solvents like DMF, DMSO, NMP, HMPA, THF, to give the ether or thioether PG³-B-A-c1-OPG².

Simultaneous or stepwise cleavage of the main chain protective groups provides the linear amino acid cyclization precursor H-B-A-c1-OH. Alloc (for PG³) and allylester groups (for PG²) are preferred as protecting groups and best cleaved simultaneously mediated by palladium catalysts, e.g. Pd(PPh$_3$)$_4$, in the presence of 1,3-dimethyl barbituric acid in solvents like CH$_2$Cl$_2$ or EtOAc or mixtures thereof.

Macrolactamization occurs upon treatment of the cyclization precursor H—B-A-c1-OH—if required in the presence of an auxiliary base such as i-Pr$_2$NEt—with coupling reagents like T3P or FDPP in solvents like CH$_2$Cl$_2$ or DMF under high dilution conditions and at temperatures ranging from 20 to 100° C. to yield cyclo-(B-A-c1).

For examples of macrolactamizations mediated by FDPP see J. Dudash, J. Jiang, S. C. Mayer, M. M. Joullié, Synth. Commun. 1993, 23 (3), 349-356; R. Samy, H. Y. Kim, M. Brady, and P. L. Toogood, J. Org. Chem. 1999, 64, 2711-2728.

It is well known that many other coupling reagents have been used in such head to tail cyclizations to prepare macrolactams, and such other coupling reagents might, alternatively, be engaged in the above mentioned reactions. Examples include benzotriazole derivatives such as HBTU, HCTU, PyBOP and their aza analogs such as HATU, as well as DPPA, and carbodiimides like EDC, DIPCDI; for examples see P. Li, P. P. Roller, Current Topics in Mecicinal Chemistry 2002, 2, 325-341; D. L. Boger, S. Miyazaki, S. H. Kim, J. H. Wu, S. L. Castle, O. Loiseleur, and Q. Jin, J. Am. Chem. Soc. 1999, 121, 10004-10011).

Another option to obtain macrolactams comprises the intramolecular reaction of an active ester with an in situ released amino group (carbamate deprotection, azide reduction) as demonstrated for example in the synthesis of peptide alkaloids and vancomycin model systems (U. Schmidt, A. Lieberknecht, H. Griesser, J. Talbiersky, J. Org. Chem. 1982, 47, 3261-3264; K. C. Nicolaou, J. M. Ramanjulu, S, Natarajan, S. Bräse, H. Li, C. N. C. Boddy, F. Rubsam, Chem. Commun. 1997, 1899-1900.)

N-reprotection of H—B-A-c1-OH can be achieved applying standard amino acid protection protocols. Chloroformates or N-hydroxy-succinimidyl carbonates in solvents like dioxane, if required in the presence of a base such as aqueous K$_2$CO$_3$ solution, react to give the N-protected amino acid PG³-B-A-c1-OH.

Coupling of an additional amino acid can be effected applying classical peptide coupling conditions.

Building blocks c1-c3 can be derived from tri-functionalized aminoacids (e.g. derivatives of Dap, Dab, Orn, Lys, Asp, Glu), main chain- or side chain-functional groups of which may be part of the macrocyclic scaffold.

Non proteinogenic tri-functionalized amino acid building blocks can be obtained by various synthetic methods, among others formal alkylation of the side chain hydroxyl group of Ser, HomoSer, Thr or derivation of the mercapto group of Cys, HomoCys with Ω-haloalkyl carboxylic esters.

An alternative route for synthesizing macrocyclic compounds of the invention comprises a²) synthesis of the H-A-c1-OPG² fragment as described above;

b²) N-acylation of the aminoalcohol HO—B—H with a suitably N-terminal protected amino acid PG⁴-c2-OH to afford the amidoalcohol PG⁴-c2-B—OH;

c²) aryl or thioaryl ether synthesis starting from H-A-c1-OPG² and PG⁴-c2-B—OH, applying conditions as described above;

d²) release of the "main chain" protective groups to give the cyclization precursor H-c2-B-A-c1-OH; and e²) macrolactamization as described above, affording the protected macrocycles of general formula I (cyclo-(c2-B-A-c1), side chain functional groups still carrying orthogonal protective groups).

The fragment PG⁴-c3-B—OH can be prepared by N-Acylation of the amino alcohol HO—B—H with suitable N-terminal protected amino acid PG4-C3-OH. N-deprotection and coupling to an appropriately N-terminal protected amino acid PG$^5$-c2-OH affords the alcohol PG$^5$-c2-c3-B—OH which can then be converted—by effecting steps corresponding to c$^2$), d$^2$) and e$^2$)—into the protected macrocycles of general formula I (cyclo(c2-c3-B-1'-c1), side chain functional groups still carrying orthogonal protective groups).

As a further alternative, cyclization can be obtained by ring closing metathesis. The orthogonally protected macrocycles of general structure I are synthesized applying a process which comprises a$^3$) coupling of an optionally substituted alkenyl amine containing building block c1(alkenyl) of type C to the acyloxy or hydroxy or acylmercapto aryl/heteroaryl carboxylic acid PG$^1$-A-OH;

b$^3$) if required release of the aryl/heteroaryl (phenolic) OH group or mercapto group, respectively;

c$^3$) N-acylation of the aminoalcohol HO—B—H with an optionally suitably substituted alkenyl carboxylic acid PG$^6$-c2(alkenyl)-OH to afford the amido alcohol PG$^6$-c2(alkenyl)-B—OH;

d$^3$) aryl or thioaryl ether formation as described above to yield the cyclization precursor PG$^6$-c2(alkenyl)-B-A-c1(alkenyl);

e$^3$) ring closure metathesis; and f$^3$) optional hydrogenation of the newly generated olefinic double bond of the metathesis product of step e$^3$).

Ring closure metathesis to form macrocyclic compounds from olefinic precursors is well known (for examples see A. Fürstner, O. Guth, A. Duffels, G. Seidel, M. Liebl, B. Gabor, and R. Mynott, Chem. Eur. J. 2001, 7 (22), 4811-4820).

Ring closure metathesis of PG$^6$-c2(alkenyl)-B-A-c1(alkenyl) is conveniently performed in suitable solvents, like CH$_2$Cl$_2$ or toluene, at 20 to 100° C. in the presence of indenylidene-ruthenium complexes including dichloro-(3-phenyl-1H-inden-1-ylidene)bis(tricyclohexylphosphine)-ruthenium (II), [1,3-Bis(2,4,6-trimethylphenyl)-2-imidazolidinylidene]-dichloro-(3-phenyl-1H-inden-1-ylidene (tricyclohexylphosphine)-ruthenium(II), [1,3-Bis(2,4,6-trimethylphenyl)-2-imidazolidinylidene]-dichloro-(3-phenyl-1H-inden-1-ylidene) (pyridyl)ruthenium(II) (see S. Monsaert, R. Drozdzak, V. Dragutan, I. Dragutan, and F. Verpoort, Eur. J. Inorg. Chem. 2008, 432-440 and references therein).

Derivatization of the macrocyclic core structures with variable R-groups can be effected as described hereinbelow.

Orthogonally protected attachment points (e.g. exocyclic amino groups, carboxyl groups, hydroxyl groups) allow stepwise deprotection and derivatization.

The reactions can be carried out in a parallel fashion to generate libraries of final products. The following general process can be applied:

a$^4$) Cleavage of the first protective group;
b$^4$) derivatization of the free functional group;
c$^4$) cleavage of the second protective group, and
d$^4$) derivatiszation or the free functional group.

Amine protecting groups such as preferably Boc, Cbz, Teoc, Alloc, Fmoc are removed applying standard conditions, cf. T. W. Greene, P. G. M. Wuts, Protective Groups in Organic Synthesis, 3rd edition, John Wiley & Sons, 1999; P. J. Koncienski, Protecting Groups, 3rd edition, Georg Thieme Verlag, 2005. Carboxylic acid protecting groups such as tert.butyl, benzyl, allyl, methyl are removed applying standard conditions.

Alcohol protecting groups such as tert.butyl, benzyl, allyl, acetyl, benzoyl, pivaloyl are removed applying standard conditions.

Attachment point amino groups can be converted into amides by reaction with carbonyl chlorides, carboxylic acid anhydrides active esters or by treatment with carboxylic acids in the presence of soluble or polymer-supported coupling reagents such as for example HATU, T3P or polymer-supported carbodiimides.

Reductive alkylation of the attachment point amino groups or their reaction with alkyl halides, alkylsulfonates or Michael acceptors affords higher alkylated amines.

The reaction of attachment point amino groups with isocyanates or equivalents like carbamoyl chlorides or hydroxysuccinimidyl esters affords ureas.

The reaction of attachment point amino groups with isothiocyanates provides thioureas.

The reaction of attachment point amino groups with chloroformates or equivalents such as hydroxysuccinimidyl carbonates affords carbamates.

The reaction of attachment point amino groups with sulfonyl chlorides yields sulfonamides.

The reaction of attachment point amino groups with suitably activated aromatic or heteroaromatic halides or sulfonates—in the presence of auxiliary base and if required a Pd catalyst (e.g. Buchwald couplings)—affords the corresponding N-aryl or N-heteroaryl derivatives.

Attachment point carboxyl groups are converted into amides using amines and coupling reagents.

Attachment point alcoholic hydroxyl groups can be alkylated with alkyl halides or alkylsulfonates to give alkylethers. Their reaction with phenols in the presence of azodicarboxylic acid derivatives and triaryl or trialkyl phosphines as well as their reaction with suitably activated aryl or heteroaryl halides or sulfonates affords aryl or heteroaryl ethers.

Attachment point secondary alcoholic hydroxyl groups can be oxidized to the corresponding ketones which in turn may be submitted to a reductive amination using amines and a suitable reducing agent.

Attachment point alcoholic hydroxyl groups can be converted into esters.

Appropriate macrocyclic compounds of general formula I with one or more (orthogonally) protected exocyclic functional groups and a free primary amino group can be converted into fully derivatized products on solid support.

A process, which allows an efficient parallel array derivatization, comprises a$^5$) attachment of the macrocyclic amine to an appropriately functionalized solid support in a reductive amination step;

b$^5$) acylation, carbamoylation, oxycarbonylation or sulfonylation of the secondary amine thus obtained in step a$^5$);

c$^5$) Removal of the protective group of the next attachment point;

d$^5$) Derivatisation of the second free functional group whereby amino groups can be converted into amides, ureas, thioureas carbamates, or sulfonamides, or can be alkylated; and carboxylic acids can be converted into amides;

e$^5$) repetition of steps c$^5$) and d$^5$) if an additional derivatisation site is available; and f$^5$) Release of the final product from solid support.

In principle a macrocyclic carbocylic acid can be coupled to polymer-supported amines and be converted into final products by effecting steps corresponding c$^5$) to f$^5$).

The functionalized solid support is a derivative of polystyrene cross-linked with preferably 1-5% divinylbenzene, of polystyrene coated with polyethyleneglycol (Tentagel®), and of polyacrylamid resins (see D. Obrecht, J.-M. Villalgordo, "Solid-Supported zombinatorial and Parallel Synthesis of Small-Molecular-Weight Compound Libraries", Tetrahedron Organic Chemistry Series, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention, linkers are used which are designed to release an N-acyl derivative (amide, urea, carbamate) or a sulfonamide under acidic conditions. Such linkers have been applied in the backbone amide linker (BAL) strategy for solid-phase synthesis of C-terminal modified and cyclic peptides (K. J. Jensen, J. Alsina, M. F. Songster, J. Vagner, F. Albericio, and G. Barnay, J. Am. Chem. Soc. 1998, 120, 5441-5452; J. Alsina, K. J. Jensen, F. Albericio, and G. Barany, Chem. Eur. J. 1999, 5 (10), 2787-2795) as well as for the synthesis of heterocyclic compounds (T. F. Herpin, K. G. Van Kirk, J. M. Savino, S. T. Yu, and R. F. Labaudinière, J. Comb. Chem. 2000, 2, 513-521, M. del Fresno, J. Alsina, M. Royo, G. Barany, and F. Albericio, Tetrahedron Lett. 1998, 39, 2639-2642; N. S. Gray, S. Kwon, P. G. Schultz, Tetrahedron Lett. 1997, 38 (7), 1161-1164).

Examples of resins functionalized by such linker structures include DFPE polystyrene (2-(3,5-dimethoxy-4-formylphenoxy)ethyl polystyrene), DFPEM polystyrene (2-(3,5-dimethoxy-4-formylphenoxy)ethoxymethyl polystyrene), FMPB resins (4-(4-formyl-3-methoxyphenoxy)butyryl AM resin), FMPE polystyrene HL (2-(4-formyl-3-methoxyphenoxy)ethyl polystyrene HL), FMPB NovaGel™ (4-(4-formyl-3-methoxyphenoxy)butyryl NovaGel™; a PEG PS resin).

The macrocyclic primary amine is attached to such solid support by means of reductive amination preferably using $NaBH(OAc)_3$ in 1,2 dichloroethane in the presence of trimethyl orthoformate.

The use of reductive amination to couple amines to resins with the above mentioned linker is well documented; for example $NaBH_3CN$ in DMF or in methanol, or $NaBH(OAc)_3$ in DMF/acetic acid or in dichloromethane/acetic acid have been used (see K. J. Jensen, J. Alsina, M. F. Songster, J. Vagner, F. Albericio, and G. Barany, J. Am. Chem. Soc. 1998, 120, 5441-5452; J. Alsina, K. J. Jensen, F. Albericio, and G. Barnay, Chem. Eur. J. 1999, 5 (10), 2787-2795; T. F. Herpin, K. G. Van Kirk, J. M. Savino, S. T. Yu, and R. F. Labaudinière, J. Comb. Chem. 2000, 2, 513-521; A. L. Vergnon, R. S. Pottorf, M. R. Player, J. Comb. Chem. 2004, 6, 91-98.). These authors also describe a variety of conditions for the acylation of the resulting secondary amine, using carboxylic acid and coupling reagents including PyBOP, PyBroP, HATU as well as carboxylic acid fluorides or carboxylic acid anhydrides.

The second functional group is an Alloc or Fmoc protected amino group or a carboxyl group protected as allyl ester. Standard conditions are applied to deprotect and derivatize these functional groups.

The final products are detached from the solid support by means of acid in organic solvents or in $H_2O$. The use of TFA in dichloromethane, TFA in dichloromethane in the presence of a scavenger such as $H_2O$ or dimethyl sulfide, or of $TFA/H_2O$ and $TFA/H_2O$/dimethylsulfide has been described, references see above.

Macrocyclic compounds of general formula I with highly variable amino acid side chain motifs in bridge c can advantageously be prepared in a parallel array synthesis on solid support. This synthesis comprises immobilization of an appropriately protected and functionalized precursor comprising building blocks A, B and subsequent coupling of one to three amino acids c1, c2 and c3, followed by cyclization and release of the product thus obtained.

The corresponding process comprises:

$a^6$) condensation of a suitable hydroxy or mercapto aryl/heteroaryl carboxylic acid ester $H-A-OPG^7$ with an appropriately N-protected amino alcohol $HO-B-PG^8$, substituted with an orthogonally protected primary amino group, applying the methods discussed above;

$b^6$) removal of the protective group of the primary amine;

$c^6$) attachment of the product obtained in step $b^6$) to the solid support in a reductive alkylation step in analogy to the previously described process providing a polymer-supported fragment $PG^8-B-A-O-PG^7$ with free secondary side chain amino group;

$d^6$) acylation, carbamoylation, oxycarbonylation or sulfonylation of the secondary amine obtained in step $c^6$);

$e^6$) cleavage of the "main chain" amine protective group ($PG^8$);

$f^6$) coupling of a appropriately N-terminal protected amino acid PG9-c3-OH;

$g^6$) removal of the N-terminal protective group ($PG^9$) of the product obtained in step $f^6$);

$h^6$) next coupling to introduce amino acid $PG^9$-c1-OH (for target compounds with bridges comprising two amino acid building blocks), or coupling/deprotection cycle to introduce amino $PG^9$-c2-OH followed by coupling of amino acid $PG^9$-c1-OH (for target compounds with bridges comprising three amino acid building blocks) by effecting steps corresponding to $f^6$) and $g^6$);

$i^6$) cleavage of the aryl/heteroaryl ester group ($PG^7$);

$j^6$) cleavage of the N-terminal protective group ($PG^9$);

$k^6$) macrolactamization of the linear cyclization precursor on solid support (for an example of cyclization on solid support see the synthesis of cyclic peptides attached to the solid support with the side chain as described by C. Cabrele, M. Langer, and A. G. Beck-Sickinger, J. Org. Chem. 1999, 64, 4353-4361.); and $l^6$) detachment of the final product.

As an alternative, the linear cyclization precursor obtained in step $j^6$) can be released from the solid support and cyclized in solution by $k^{6'}$) detachment of the linear cyclization precursor; and $l^{6'}$) macrolactamization in solution.

In a parallel array synthesis soluble coupling reagents as described above as well as polymer supported coupling reagents such as N-cyclohexyl-carbodiimide-N'-methylpolystyrene or N-alkyl-2-chloro pyridinium triflate resin (S. Crosignani, J. Gonzales, D. Swinnen, Org. Lett. 2004, 6 (24), 4579-4582) may be used.

Further alternatives include ring closure in other positions, for example between amino acids c1 and c2.

Thus a precursor with two amino acids coupled to the immobilized precursor would be prepared (polymer supported $PG^9$-c2-c3-B-A-$OPG^7$) by effecting steps corresponding to steps $a^6$) to $h^6$) described in the above paragraph. The subsequent steps then comprise $i^{6'}$) cleavage of the aryl/heteroaryl ester group ($PG^7$);

$j^{6'}$) coupling of an appropriately C-terminal protected amino acid
H-c1-$OGP^7$;

$k^{6'}$) cleavage of the c-terminal protective group ($PG^7$);

$l^{6'}$) cleavage of the N-terminal protective group ($PG^9$) and $m^{6'}$) macrolactamization either on solid support or in solution after detachment of the linear precursor from the solid support.

The macrocycles of formula I of the present invention interact with specific biological targets. In particular, they show agonistic or antagonistic activity on the motilin receptor (MR receptor), on the serotonin receptor of subtype 5-HT$_{2B}$ (5-HT$_{2B}$ receptor), and on the prostaglandin F2α receptor (FP receptor). Accordingly, these compounds are useful for the treatment of hypomotility disorders of the gastrointestinal tract such as diabetic gastroparesis and constipation type irritable bowl syndrome; for the treatment of CNS related diseases like migraine, schizophrenia, psychosis or depression; for the treatment of ocular hypertension such as associated with glaucoma and for preterm labour.

The macrocycles, as such or after further optimization, may be administered per se or may be applied as an appropriate formulation together with carriers, diluents or excipients well-known in the art.

When used to treat or prevent the diseases mentioned above the macrocycles can be administered singly, as mixtures of several macrocycles, or in combination with other pharmaceutically active agents. The macrocycles can be administered per se or as pharmaceutical compositions.

Pharmaceutical compositions comprising macrocycles of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active macrocycles into preparations which can be used pharmaceutically. Proper formulation depends upon the method of administration chosen.

For topical administration the macrocycles of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the macrocycles of type I may be formulated in adequate solutions, preferably in physiologically compatible buffers such as Hank's solution, Ringer's solution, or physiological saline buffer. The solutions may contain formulatory agents such as suspending, stabilizing and/or dispersing agents. Alternatively, the macrocycles of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated per se or by combining the active macrocycle of the invention with pharmaceutically acceptable carriers well known in the art. Such carriers enable the macrocycles of type I to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, (e.g. lactose, sucrose, mannitol or sorbitol) or such as cellulose preparations (e.g. maize starch, wheat starch, rice starch, potato starch, gelatin, gum tragacanth, methyl cellulose, hydroxypropylmethyl cellulose, sodium carboxymethylcellulose); and/or granulating agents; and/or binding agents such as polyvinylpyrrolidone (PVP). If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the macrocycles of the invention are conveniently delivered in form of an aerosol spray from pressurized packs or a nebulizer, with the use of a suitable propellant, e.g. hydrofluoroalkanes (HFA) such as HFA 134a (1,1,1,2,-tetrafluoroethane); carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the macrocycles of the invention and a suitable powder base such as lactose or starch.

The compounds may also be formulated in rectal or vaginal compositions such as suppositories together with appropriate suppository bases like cocoa butter or other glycerides.

In addition to the formulations described afore, the macrocycles of the invention may also be formulated as depot preparations. Such slow release, long acting formulations may be administered by implantation (e.g. subcutaneously or intramuscularly) or by intramuscular injection. For the manufacture of such depot preparations the macrocycles of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the macrocycles of type I may be delivered using a sustained-release system, such as semi-permeable matrices of solid polymers containing the therapeutic agent. Various sustained-release materials have been established and are well-known by those skilled in the art. Sustained-release capsules may, depending on their chemical nature, release the compounds over a period of a few days up to several months. Depending on the chemical nature and the biological stability of the therapeutic agent, additional strategies for stabilization may be employed.

As the macrocycles of the invention may contain charged residues, they may be included in any of the above-described formulations as such or as pharmaceutically acceptable salts. Pharmaceutically acceptable salts tend to be more soluble in aqueous and other protic solvents than the corresponding free base or acid forms.

The macrocycles of the invention, or compositions thereof, will generally be used in an amount effective to achieve the intended purpose. It is to be understood that the amount used will depend on a particular application.

For example, the therapeutically effective dose for an systemic administration can be estimated initially from in vitro assays: A dose can be formulated in animal models to achieve a circulating macrocycle concentration range that includes the IC$_{50}$ or EC$_{50}$ as determined in the cell culture (i.e. the concentration of a test compound that shows half maximal inhibitory concentration in case of antagonists or half maximal effective concentration in case agonists). Such information can be used to more accurately determine useful doses in humans. Initial dosages can also be determined from in vivo data, e.g. animal models, using techniques that are well known in the art. One having ordinary skill in the art could readily optimize administration to humans based on animal data.

Dosage amounts for applications such as gastroparesis or schizophrenia etc. may be adjusted individually to provide plasma levels of the active compound that are sufficient to maintain the therapeutic effect. Therapeutically effective serum levels may be achieved by administering multiple doses each day.

In cases of local administration or selective uptake, the effective local concentration of the macrocycles of the invention may not be related to plasma concentration. Those having the ordinary skill in the art will be able to optimize therapeutically effective local dosages without undue experimentation.

The amount of macrocycle administered will, of course, be dependent on the subject being treated, on the subject's weight, the severity of the affliction, the manner of administration and the judgment of the prescribing physician.

Normally, a therapeutically effective dose of the macrocycles described herein will provide therapeutic benefit without causing substantial toxicity.

Toxicity of the macrocycles of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from cell culture assays and animal studies can be used in formulating a dosage range that is not toxic for use in humans. The dosage of the macrocycles of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (cf. E. Fingl et al., *The Pharmacological Basis of Therapeutics*, 5th ed. 1975 (Ed. L. Goodman and A. Gilman), Ch.1, p. 1).

A further embodiment of the present invention may also include compounds, which are identical to the compounds of formula I, except that one or more atoms are replaced by an atom having an atomic mass number or mass different from the atomic mass number or mass usually found in nature, e.g. compounds enriched in $^2H$ (D), $^3H$, $^{11}C$, $^{14}C$, $^{125}I$ etc. These isotopic analogs and their pharmaceutical salts and formulations are considered useful agents in the therapy and/or diagnostic, for example, but not limited to, where a fine-tuning of in vivo half-life time could let to an optimized dosage regimen.

EXAMPLES

The following Examples illustrate the invention in more detail but are not intended to limit its scope in any way. The following abbreviations are used in these Examples:
ADDP: azodicarboxylic dipiperidide
All: allyl
Alloc: allyloxycarbonyl
AllocCl: allyl chloroformate
AllocOSu: allyloxycarbonyl-N-hydroxysuccinimide
AM-resin: aminomethyl resin
aq.: aqueous
arom.: aromatic
BnBr: benzyl bromide
Boc: tert-butoxycarbonyl
br.: broad
Cbz: benzyloxycarbonyl
CbzOSu: N-(benzyloxycarbonyloxy)succinimide
Cl-HOBt: 6-chloro-1-hydroxybenzotriazole
CMBP: cyanomethylenetributyl-phosphorane
m-CPBA: 3-chloroperbenzoic acid
d: day(s) or doublet (spectral)
DBU: 1,8-diazabicyclo[5.4.0]undec-7-ene
DCE: 1,2-dichloroethane
DEAD: diethyl azodicarboxylate
DFPE polystyrene: 2-(3,5-dimethoxy-4-formylphenoxy) ethyl polystyrene
DIAD: diisopropyl azodicarboxylate
DIC: N,N'-diisopropylcarbodiimide
DMF: dimethylformamide
DMSO: dimethyl sulfoxide
DPPA: diphenyl phosphoryl azide
DVB: divinylbenzene
EDC: 1-[3-(dimethylamino)propyl-3-ethylcarbodiimide
equiv.: equivalent
$Et_3N$: triethylamine
EtOAc: ethyl acetate
FC: flash chromatography
FDPP: pentafluorophenyl diphenylphosphinate
Fmoc: 9-fluorenylmethoxycarbonyl
h: hour(s)
HATU: O-(7-azobenzotriazol-1-yl)-N,N,N',N'-tetramethyluronium hexafluorophosphate
HBTU: O-(benortriazol-1-yl)-N,N,N',N'-tetramethyluronium hexafluorophosphate
HCTU: O-(1H-6-chlorobenortriazol-1-yl)-N,N,N',N'-tetramethyluronium hexafluorophosphate
HOAt: 1-hydroxy-7-azabenzotriazole
$HOBt.H_2O$: 1-hydroxybenzotriazole hydrate
HMPA: hexamethylphosphoramide
i.v.: in vacuo
m: multiplet (spectral)
MeOH: methanol
NMP: 1-methyl-2-pyrrolidinone
$Pd(PPh_3)_4$: Tetrakis(triphenylphosphine)palladium(0)
PEG PS resin: polyethyleneglycol coated polystyrene resin
PG: protective group
$PPh_3$: triphenylphosphine
prep.: preparative
i-$Pr_2NEt$: N-ethyl-N,N-diisopropylamine
PyBOP: (Benzotriazol-1-yloxy)tripyrrolidinophosphonium hexafluorophosphate
PyBroP: Bromotripyrrolidinophosphonium hexafluorophosphate
q: quartet (spectral)
quant.: quantitative
sat.: saturated
soln: solution
t: triplet (spectral)
TBAF: tetrabutylammonium fluoride
Teoc: 2-(trimethylsilyl)ethoxycarbonyl
TeocONp: 2-(trimethylsilyl)ethyl 4-nitrophenyl carbonate
TFA: trifluoroacetic acid
THF: tetrahydrofuran
tlc: thin layer chromatography
T3P™: propanphosphonic acid cyclic anhydride
p-TsOH: p-toluenesulfonic acid General Methods
  TLC: Merck (silica gel 60 F254, 0.25 mm).
  Flash chromatography (FC): Fluka silica gel 60 (0.04-0.063 mm) and Interchim Puriflash IR 60 silica gel (0.04-0.063 mm).
I. Analytical HPLC-MS Methods:
  $R_t$ in min (purity at 220 nm in %), m/z $[M+H]^+$
  Volume of injection: 5 μL for all methods Method 1a and 1b

| | | | | |
|---|---|---|---|---|
| Column: | XBridge C18 2.5 μm, 2.1 × 50 mm (186003085 - Waters) | | | |
| Mobile Phases | A: 0.1% TFA in Water | | | |
| | B: 0.085% TFA in Acetonitrile | | | |
| Column oven temp. | 45° C. | | | |
| | Time (min.) | Flow (μl/min) | % A | % B |
| Gradient | 0 | 500 | 97 | 3 |
| | 0.1 | 500 | 97 | 3 |
| | 3 | 500 | 3 | 97 |
| | 3.6 | 500 | 3 | 97 |
| | 3.7 | 500 | 97 | 3 |
| | 4.3 | 500 | 97 | 3 |

Method 1, cont.

| | |
|---|---|
| UV Wavelenght: | 220 nm  254 nm |
| MS scan Range: | Method 1a 100-800 Da |
| | Method 1b  Centroid |
| | 300-2000 Da  mode |
| Scan Time: | 1 sec. |
| Ionization type: | Electrospray |

Method 2

| | | | | |
|---|---|---|---|---|
| Column: | Gemini NX C18 3 μm, 2.1 × 50 mm (00B-4453-B0 - Phenomenex) | | | |
| Mobile Phases | A: 0.1% TFA in Water | | | |
| | B: 0.085% TFA in Acetonitrile | | | |
| Column oven temp. | 45° C. | | | |
| | Time (min.) | Flow (μl/min) | % A | % B |
| Gradient | 0 | 800 | 97 | 3 |
| | 0.1 | 800 | 97 | 3 |
| | 2.2 | 800 | 3 | 97 |
| | 2.5 | 800 | 3 | 97 |
| | 2.55 | 1000 | 97 | 3 |
| | 2.75 | 1000 | 97 | 3 |
| | 2.8 | 800 | 97 | 3 |
| UV Wavelenght: | 220 nm  254 nm | | | |
| MS scan Range: | 100-2000 Da  Centroid mode | | | |
| Scan Time: | 1 sec. | | | |
| Ionization type: | Electrospray | | | |

Method 3

| | | | | |
|---|---|---|---|---|
| Column: | Gemini NX C18 3 μm, 2.1 × 50 mm (00B-4453-B0 - Phenomenex) | | | |
| Mobile Phases | A: 1 mM ammonium bicarbonate pH 10 | | | |
| | B: Acetonitrile | | | |
| Column oven temp. | 45° C. | | | |
| | Time (min.) | Flow (μl/min) | % A | % B |
| Gradient | 0 | 800 | 97 | 3 |
| | 0.1 | 800 | 97 | 3 |
| | 2.2 | 800 | 3 | 97 |
| | 2.5 | 800 | 3 | 97 |
| | 2.55 | 1000 | 97 | 3 |
| | 2.75 | 1000 | 97 | 3 |
| | 2.8 | 800 | 97 | 3 |

Method 3, cont.

| | |
|---|---|
| UV Wavelenght: | 220 nm  254 nm |
| MS scan Range: | 100-2000 Da  Centroid mode |
| Scan Time: | 1 sec. |
| Ionization type: | Electrospray |

Method 4a-4-b

| | | | | |
|---|---|---|---|---|
| Column: | Gemini NX C18 3 μm, 2.1 × 50 mm (00B-4453-B0 - Phenomenex) | | | |
| Mobile Phases | A: 0.1% TFA in Water | | | |
| | B: 0.085% TFA in Acetonitrile | | | |
| Column oven temp. | 45° C. | | | |
| | Time (min.) | Flow (μl/min) | % A | % B |
| Gradient | 0 | 800 | 97 | 3 |
| | 0.1 | 800 | 97 | 3 |
| | 2.7 | 800 | 3 | 97 |
| | 3 | 800 | 3 | 97 |
| | 3.05 | 1000 | 97 | 3 |
| | 3.25 | 1000 | 97 | 3 |
| | 3.3 | 800 | 97 | 3 |
| UV Wavelenght: | 220 nm  254 nm | | | |
| MS scan Range: | Method 4a  Centroid | | | |
| | 100-2000 Da  mode | | | |
| | Method 4b  Profile | | | |
| | 350-2000 Da  mode | | | |
| Scan Time: | 1 sec. | | | |
| Ionization type: | Electrospray | | | |

Method 5a-5b

| | | | | |
|---|---|---|---|---|
| Column: | Gemini NX C18 3 μm, 2.1 × 50 mm (00B-4453-B0 - Phenomenex) | | | |
| Mobile Phases | A: 1 mM ammonium bicarbonate pH 10 | | | |
| | B: Acetonitrile | | | |
| Column oven temp. | 45° C. | | | |
| | Time (min.) | Flow (μl/min) | % A | % B |
| Gradient | 0 | 800 | 97 | 3 |
| | 0.1 | 800 | 97 | 3 |
| | 2.7 | 800 | 3 | 97 |
| | 3 | 800 | 3 | 97 |
| | 3.05 | 1000 | 97 | 3 |
| | 3.25 | 1000 | 97 | 3 |
| | 3.3 | 800 | 97 | 3 |

Method 5, cont.

| | |
|---|---|
| UV Wavelenght: | 220 nm  254 nm |
| MS scan Range: | Method 5a  Centroid |
| | 100-2000 Da  mode |
| | Method 5b  Profile |
| | 350-2000 Da  mode |
| Scan Time: | 1 sec. |
| Ionization type: | Electrospray |

Method 6

| | |
|---|---|
| Column: | Acquity UPLC BEH C18 1.7 μm, 2.1 × 50 mm (cod. 186002350 - Waters) |
| Mobile Phases | A: 0.1% TFA in Water |
| | B: 0.085% TFA in Acetonitrile |
| Column oven temp. | 55° C. |

Method 7

| | Time (min.) | Flow (μl/min) | % A | % B |
|---|---|---|---|---|
| Gradient | 0 | 1250 | 97 | 3 |
| | 0.05 | 1250 | 97 | 3 |
| | 1.65 | 1250 | 3 | 97 |
| | 1.95 | 1250 | 3 | 97 |
| | 2.00 | 1250 | 97 | 3 |
| | 2.30 | 1250 | 97 | 3 |
| UV Wavelenght: | 220 nm | 254 nm | | |
| MS scan Range: | 100-1650 Da | Centroid mode | | |
| Scan Time: | 0.5 sec. | | | |
| Ionization type: | Electrospray | | | |

| | |
|---|---|
| Column: | Acquity UPLC BEH C18 1.7 μm, 2.1 × 50 mm (cod. 186002350 - Waters) |
| Mobile Phases | A: 0.1% TFA in Water<br>B: 0.085% TFA in Acetonitrile |
| Column oven temp. | 55° C. |

| | Time (min.) | Flow (μl/min) | % A | % B |
|---|---|---|---|---|
| Gradient | 0 | 1250 | 97 | 3 |
| | 0.05 | 1250 | 97 | 3 |
| | 1.65 | 1250 | 3 | 97 |
| | 1.95 | 1250 | 3 | 97 |
| | 2.00 | 1250 | 97 | 3 |
| | 2.30 | 1250 | 97 | 3 |

Method 7, cont.

| | | |
|---|---|---|
| UV Wavelenght: | 220 nm | 254 nm |
| MS scan Range: | 100-1650 Da | Profile mode |
| Scan Time: | 0.5 sec. | |
| Ionization type: | Electrospray | |

Method 8

| | |
|---|---|
| Column: | Acquity UPLC BEH C18 1.7 μm, 2.1 × 50 mm (cod. 186002350 - Waters) |
| Mobile Phases | A: 1 mM ammonium bicarbonate pH 10<br>B: Acetonitrile |
| Column oven temp. | 55° C. |
| Volume of injection: | 5 μl |

| | Time (min.) | Flow (μl/min) | % A | % B |
|---|---|---|---|---|
| Gradient | 0 | 1250 | 97 | 3 |
| | 0.05 | 1250 | 97 | 3 |
| | 1.65 | 1250 | 3 | 97 |
| | 1.95 | 1250 | 3 | 97 |
| | 2.00 | 1250 | 97 | 3 |
| | 2.30 | 1250 | 97 | 3 |
| UV Wavelenght: | 220 nm | 254 nm | | |
| MS scan Range: | 100-1650 Da | Profile mode | | |
| Scan Time: | 0.5 sec. | | | |
| Ionization type: | Electrospray | | | |

Method 9a-9c

| | |
|---|---|
| Column: | Acquity UPLC BEH C18 1.7 μm, 2.1 × 100 mm (cod. 186002352 - Waters) |
| Mobile Phases | A: 0.1% TFA in Water/Acetonitrile<br>B: 95/5 v/v 0.085% TFA in Acetonitrile |
| Column oven temp. | 55° C. |

Method 9, cont.

| | Time (min.) | Flow (μl/min) | % A | % B |
|---|---|---|---|---|
| Gradient | 0 | 700 | 99 | 1 |
| | 0.2 | 700 | 99 | 1 |
| | 2.5 | 700 | 3 | 97 |
| | 2.85 | 700 | 3 | 97 |
| | 2.86 | 700 | 99 | 1 |
| | 3.20 | 700 | 99 | 1 |
| UV Wavelenght: | 220 nm | | | |
| MS scan Range: | Method 9a: 100-800 Da;<br>Method 9b: 100-1200 Da;<br>Method 9c: 200-1400 Da | | Profile mode | |
| Scan Time: | 1 sec. | | | |
| Ionization type: | Electrospray | | | |

Analytical HPLC (x % CH$_3$CN): R$_t$ in min (purity at 220 nm in %)
Column: Develosil RPAq 5 μm, 4.6×50 mm;
Flow rate: 1.5 ml/min
0.0-0.5 min (x % CH$_3$CN, 100-x % H$_2$O containing 0.1% TFA);
0.5-5.0 min (x % CH$_3$CN, 100-x % H$_2$O containing 0.1% TFA to 100% CH$_3$CN) 5.0-6.2 min (100% CH$_3$CN)
II. Preparative HPLC Methods:
1. Reverse Phase—Acidic Conditions
Column: XBridge C18 5 μm, 30×150 mm (Waters)
Mobile Phases:
A: 0.1% TFA in Water/Acetonitrile 95/5 v/v
1B: 0.1% TFA in Water/Acetonitrile 5/95 v/v
2. Reverse Phase—Basic Conditions
Column: XBridge C18 5 μm, 30×150 mm (Waters)
Mobile Phases:
A: 10 mM Ammonium Bicarbonate pH 10/Acetonitrile 95/5 v/v
B: Acetonitrile
3. Normal Phase

| | |
|---|---|
| Column: (Macherey-Nagel) | VP 100/21 NUCLEOSIL 50-10, 21 × 100 mm |
| Mobile phases: | A: Hexane<br>B: Ethylacetate<br>C: Methanol |

NMR Spectroscopy: Bruker Avance 300, $^1$H-NMR (300 MHz) in the indicated solvent at ambient temperature. Chemical shifts δ in ppm, coupling constants J in Hz.

The term "isomers" comprises in the present invention species of identical chemical formula, constitution and thus molecular mass, such as but not limited to amide cis/trans isomers, rotamers, conformers, diastereomers.

Examples

Starting Materials

Building Blocks of Type A (Scheme 1)

2-Acetoxy-5-fluoro benzoic acid (2) was prepared according to the method of C. M. Suter and A. W. Weston, *J. Am. Chem. Soc.* 1939, 61, 2317-2318.

3-Acetoxybenzoic acid (3) is commercially available.

4-Acetoxybenzoic acid (4) is commercially available.

5-Hydroxy nicotinic acid (5) is commercially available.

8-Acetoxyquinoline-2-carboxylic acid (8) was prepared according to the method of R. W. Hay, C. R. Clark, *J. Chem. Soc. Dalton* 1977, 1993-1998.

(S)-2-tert-Butoxycarbonylamino-8-hydroxy-1,2,3,4-tetrahydro-naphthalene-2-carboxylic acid (10) was prepared according to the method of M. M. Altorfer, Dissertation Universität Zürich, 1996.

3-Mercaptobenzoic acid (11) is commercially available

Building Blocks of Type B (Scheme 2)

tert-Butyl (3S,5S)-5-(hydroxymethyl)pyrrolidin-3-ylcarbamate (13) as well as the corresponding HCl salt (13.HCl) are commercially available.

tert-Butyl (3R,5S)-5-(hydroxymethyl)pyrrolidin-3-ylcarbamate (17) as well as the corresponding HCl salt (17.HCl) are commercially available.

(S)-tert-Butyl 3-(hydroxymethyl)piperazine-1-carboxylate hydrochloride (21.HCl) is commercially available.

(R)-tert-Butyl 3-(hydroxymethyl)piperazine-1-carboxylate hydrochloride (83.HCl) (Scheme 5) is commercially available.

(2S,4S)-Allyl 2-(hydroxymethyl)-4-((2-(trimethylsilyl) ethoxy)carbonylamino)pyrrolidine-1-carboxylate (16) was prepared in three steps (1. Alloc protection of the secondary amino group with allyloxycarbonyl-N-hydroxysuccinimide (AllocOSu) in $CH_2Cl_2$, 2. cleavage of the Boc group with dioxane-HCl;

3. Teoc protection of the primary amino group with 2-(trimethylsilyl)ethyl 4-nitrophenyl carbonate (Teoc-ONp) in $CH_2Cl_2$ in the presence of $Et_3N$) from amino alcohol 13, applying standard conditions; as leading references cf. T. W. Greene, P. G. M. Wuts, *Protective Groups in Organic Synthesis,* 3rd edition, John Wiley & Sons, 1999; P. J. Kocienski, *Protecting Groups,* 3rd edition, Georg Thieme Verlag, 2005.

Data of 16: $C_{15}H_{28}N_2O_5Si$ (344.5): Flow injection MS (APCI): 689 ([2M+H]$^+$), 345 ([M+H]$^+$). $^1$H-NMR (DMSO-$d_6$): 7.28 (d, J=6.1, 1 H), 5.90 (m, 1 H), 5.25 (qd, J=1.7, 17.2, 1 H), 5.16 (qd, J=1.5, 10.5, 1 H), 4.90 (br. t, 1 H), 4.54-4.42 (m, 2 H), 4.04-3.97 (m, 2 H), 3.90 (q, J=6.8, 1 H), 3.80-3.66 (br. m and dd, 2 H), 3.57-3.43 (br. m, 2 H), 2.96 (br. m, 1 H), 2.19 (br. m, 1 H), 1.78 (br. m, 1 H), 0.89 (t, J ca 8.3, 2 H), 0.00 (s, 9 H)

(2S,4R)-Allyl 2-(hydroxymethyl)-4-((2-(trimethylsilyl) ethoxy)carbonylamino)pyrrolidine-1-carboxylate (20) was prepared from amino alcohol hydrochloride 17.HCl, applying the same transformations as described for the synthesis of diastereomer 16 with the exception of the Alloc protection step which was performed using allyl chloroformate in $CH_2Cl_2$ in the presence of aqueous $NaHCO_3$ solution.

Data of 20: $C_{15}H_{28}N_2O_5Si$ (344.5): LC-MS (method 9a): $R_f$=1.98, 345 ([M+H]$^+$); 317; 259. $^1$H-NMR (DMSO-$d_6$): 7.26 (d, J=6.6, 1 H), 5.89 (m, 1 H), 5.25 (br. d, J=17.0, 1 H), 5.15 (br. d, J=10.2, 1 H), 4.75 (m, 1 H), 4.48 (m, 2 H), 4.16-3.98 (m, 3 H), 3.82 (br. m, 1 H), 3.48-3.30 (m, 3 H), 3.21 (m, 1 H), 2.01 (m, 1 H), 1.80 (m, 1 H), 0.89 (t, J=8.3, 2H), 0.00 (s, 9 H).

(S)-1-Allyl 4-tert-butyl 2-(hydroxymethyl)piperazine-1,4-dicarboxylate (22) was prepared from amino alcohol hydrochloride 21.HCl, applying allyl chloroformate in $CH_2Cl_2$ in the presence of aqueous $NaHCO_3$ solution; as leading references cf. T. W. Greene, P. G. M. Wuts, *Protective Groups in Organic Synthesis,* 3rd edition, John Wiley & Sons, 1999; P. J. Kocienski, *Protecting Groups,* 3rd edition, Georg Thieme Verlag, 2005.

Data of 22: $C_{14}H_{24}N_2O_5$ (300.4): LC-MS (method 9a): $R_f$=1.70, 201 ([M+H]$^+$). $^1$H-NMR (DMSO-$d_6$): 5.90 (m, 1 H), 5.29 (qd, J=1.7, 17.3, 1 H), 5.18 (qd, J=1.5, 10.5, 1 H), 4.81 (t, J=4.9, 1 H), 4.53 (d-like m, J ca. 5.1, 2 H), 4.04-3.75 (br. m, 4 H), 3.39 (m, 2 H), 2.95-2.70 (br. m, 3 H), 1.40 (s, 9 H).

Building Blocks of Type C (Scheme 3)

(S)-5-Allyl 1-benzyl 2-(methylamino)pentanedioate hydrochloride (27.HCl)

A mixture of Boc-L-Glu(OAll)OH (23; 33 g, 115 mmol) and $NaHCO_3$ (27 g, 322 mmol) in DMF (500 mL) was stirred for 1 h at room temperature followed by the slow addition of benzyl bromide (35 mL, 299 mmol) in DMF (15 mL). Stirring was continued for 16 h followed by aqueous workup (diethyl ether, sat. aq. $NaHCO_3$ soln, sat aq. NaCl soln) and purification by FC($CH_2Cl_2$/MeOH 100:0 to 98:2) to give the corresponding benzyl ester (34.4 g, 79%), which was dissolved in dioxane (40 mL) and treated with 4 M HCl-dioxane (400 mL) for 1 h. The volatiles were evaporated. The residue was crystallized from diethyl ether to afford 24.HCl (23.8 g, 83%).

4-Nitrobenzenesulfonyl chloride (39 g, 178 mmol) was added at 0° C. to a solution of 24.HCl (46.5 g, 148 mmol) and pyridine (42 mL, 519 mmol) in $CH_2Cl_2$ (700 mL). The mixture was stirred for 15 h followed by aqueous workup ($CH_2Cl_2$, 1 M aq. HCl soln) and purification of the crude by FC (hexane/EtOAc 80:20 to 75:25) to yield 25 (55.54 g, 81%).

A solution of 25 (41.3 g, 89 mmol) in dry DMF (200 mL) was cooled to 0° C. Methyliodide (5.8 mL, 94 mmol) in DMF (100 mL) was slowly added, followed by a solution of DBU (14 mL, 94 mmol) in DMF (100 mL). The mixture was stirred for 4 h at room temperature followed by aqueous workup (EtOAc, 1 M aq. HCl soln., $H_2O$, sat. aq. $NaHCO_3$ soln, sat. aq. NaCl soln) to afford 26 (42.8 g, 99%).

A solution of 26 (17.4 g, 37 mmol) in dry, degassed $CH_3CN$ (270 mL) was treated with thiophenol (6.7 mL, 66 mmol) and $Cs_2CO_3$ (39 g, 121 mmol) at room temperature for 16 h. The mixture was filtered and the residue was washed with diethyl ether. The filtrate was carefully concentrated (bath temperature 20° C.) and immediately purified by FC (hexane/EtOAc 80:20 to 50:50). The combined product fractions were carefully concentrated, immediately treated with 4 M HCl-dioxane (20 mL) for 5 min and concentrated to give 27.HCl (8.62 g, 72%).

Data of 27.HCl: $C_{16}H_{21}NO_4$.HCl (291.3, free base). LC-MS (method 9b): $R_f$=1.44, 292 ([M+H]$^+$). $^1$H-NMR (DMSO-$d_6$): 9.57 (br. s, $NH_2^+$), 7.45-7.34 (m, 5 arom. H), 5.88 (M, 1 H), 5.32-5.19 (m, 4 H), 4.53 (td, J=1.3, 5.4, 1 H), 4.13 (br. t, J ca. 6.0, 1 H), 2.69-2.40 (m, 2 H), 2.56 (s, 3 H), 2.30-2.05 (m, 2 H).

(R)-5-Allyl 1-benzyl 2-(methylamino)pentanedioate hydrochlorided (29.HCl) was prepared from Boc-D-Glu (OAll)OH (28) applying the methods described above for the synthesis of the enantiomer (27.HCl).

Data of 29.HCl: $C_{16}H_{21}NO_4$.HCl (291.3, free base). LC-MS (method 9b): $R_f$=1.44, 292 ([M+H]$^+$). $^1$H-NMR (DMSO-$d_6$): 9.92 (br. s, NH$^+$), 9.54 (br. s, NH$^+$), 7.45-7.34 (m, 5 arom. H), 5.88 (M, 1 H), 5.32-5.19 (m, 4 H), 4.53 (td, J=1.3, 5.4, 1 H), 4.13 (br. t, J ca. 6.0, 1 H), 2.69-2.40 (m, 2 H), 2.56 (s, 3 H), 2.30-2.05 (m, 2 H).

(S)-Allyl 2-(benzyloxycarbonylamino)-3-(methylamino)propanoate hydrochloride (32.HCl)

Cbz-L-SerOH (30) was converted into amino acid 31 by β-lactone formation and opening with HNCH$_3$Si(CH$_3$)$_3$ (see J. Kim, S. G. Bott, D. M. Hoffman *Inorg. Chem.* 1998, 37, 3835-3841), following the procedures of J. K. Kretsinger and J. P. Schneider, *J. Am. Chem. Soc.* 2003, 125, 7907-7913 and E. S. Ratemi and J. C. Vederas, *Tetrahedron Lett.* 1994, 35, 7605-7608.

A solution of 31.HCl (2.2 g, 7.6 mmol) in allyl alcohol (55 mL) was treated with thionyl chloride (1.7 mL, 23 mmol) for 15 min at room temperature and for 1.5 h at 70° C. The volatiles were evaporated. The crude product was dissolved in CH$_2$Cl$_2$ and washed with aq. NaHCO$_3$ solution. The aqueous layers were extracted with CH$_2$Cl$_2$ and with EtOAc. The combined organic phase was dried (Na$_2$SO$_4$), filtered, and concentrated. The resulting oil (2.18 g) was dissolved in CH$_2$Cl$_2$ (80 mL), treated with 4 M HCl-dioxane (20 mL), stirred for 5 min and concentrated to afford 32.HCl (2.5 g, quantitative).

Data of 32.HCl: C$_{15}$H$_{20}$N$_2$O$_4$.HCl (292.3, free base). LC-MS (method 9a): R$_t$=1.26, 293 ([M+H]$^+$). $^1$H-NMR (DMSO-d$_6$):
9.20 (br. s, NH$^+$), 9.03 (br. s, NH$^+$), 8.02 (d, J=8.2, NH), 7.38-7.30 (m, 5 arom. H), 5.89 (m, 1 H), 5.33 (d, J=17.3, 1 H), 5.23 (d, J=10.5, 1 H), 5.08 (s, 2 H), 4.63 (d, J=5.3, 2 H), 4.56 (m, 1 H), 3.35 (br. m, 1 H), 3.25 (br. m, 1 H), 2.56 (br. s, 3 H).

As an alternative, 32.HCl was prepared from Cbz-L-DapOH applying the method described below for the synthesis of the enantiomer 36.HCl.

(R)-Allyl 2-(benzyloxycarbonylamino)-3-(methylamino)propanoate hydrochloride (36.HCl)

Cbz-D-DapOH was converted into the allylester-pTsOH salt 33 pTsOH according to the procedure of T. M. Kamenecka and S. J. Danishefsky, *Chem. Eur. J.* 2001, 7, 41-63, describing the synthesis of D-threonine allyl ester.

The amino ester 33 pTsOH was converted into the free base by extraction (CH$_2$Cl$_2$, sat. aq. NaHCO$_3$ soln) and treated with 4-nitrobenzenesulfonyl chloride (1.05 equiv.) in CH$_2$Cl$_2$ in the presence of pyridine (3.0 equiv.) to give the p-nitrophenyl sulfonamide 34.

At 0° C., a solution of methyl iodide (2.3 mL, 37 mmol) in DMF (80 mL) was added to a solution of 34 (16.4 g, 35 mmol) in DMF (80 mL). A solution of DBU (5.6 mL, 37 mmol) in DMF (80 mL) was slowly added over 2 h. The mixture was stirred at room temperature for 1.5 h, followed by an aqueous workup (EtOAC, 1 M HCl soln, H$_2$O, sat. aq. NaHCO$_3$ soln, sat. aq. NaCl soln) to afford 35 (17.07 g, quant.).

At 0° C., thiophenol (3.02 mL, 29.6 mmol) was added (dropwise, rapidly) to a mixture of 35 (7.85 g, 16.5 mmol) and K$_2$CO$_3$ (7.95 g, 57.5 mmol) in DMF (78 mL). The mixture was stirred for 2.5 h at 0-10° C. The mixture was diluted with EtOAc and washed with H$_2$O and sat. aq. NaCl soln. The organic layer was extracted with ice-cold 1 M aqueous HCl soln. The aqueous phase (base extract) was poured onto aqueous Na$_2$CO$_3$ soln to reach pH ca 7; 2 M aq. NaOH soln. was added to reach pH ca 10, followed by extraction with EtOAc. The organic phase was dried (Na$_2$SO$_4$) and concentrated. The remaining oil (2.72 g) was dissolved in CH$_2$Cl$_2$ (30 mL) and treated with 4 M HCl-dioxane (10 mL) to afford after evaporation of the volatiles 36.HCl (3.34 g, 62%).

Data of 36.HCl: C$_{25}$H$_{20}$N$_2$O$_4$.HCl (292.3, free base). LC-MS (method 7): R$_t$=0.88, 293 ([M+H]$^+$). $^1$H-NMR (DMSO-d$_6$): 9.06 (br. s, NH$^+$), 8.94 (br. s, NH$^+$), 8.00 (d, J=8.3, NH), 7.38-7.30 (m, 5 arom. H), 5.88 (m, 1 H), 5.33 (d, J=17.3, 1 H), 5.23 (d, J=10.5, 1 H), 5.08 (s, 2 H), 4.63 (d, J=5.3, 2 H), 4.56 (m, 1 H), 3.35 (br. m, 1 H), 3.20 (br. m, 1 H), 2.57 (br. s, 3 H).

(S)-Allyl 2-(benzyloxycarbonylamino)-4-(methylamino)butanoate hydrochloride (40.HCl)

Cbz-L-DabOH (37) was converted into the allylester-pTsOH salt 38.pTsOH according to the procedure of T. M. Kamenecka and S. J. Danishefsky, *Chem. Eur. J.* 2001, 7, 41-63, describing the synthesis of D-threonine allyl ester.

A mixture of 38.pTsOH (45 g, 97 mmol) in CH$_2$Cl$_2$ (600 mL) was cooled to 0° C. MeOH (60 mL) was added, followed by ethyl trifluoroacetate (23 mL, 194 mmol). Et$_3$N (53 mL, 387 mmol) was added dropwise. The mixture was stirred at 0° C. for 15 min, then at room temperature for 4 h. The volatiles were evaporated. The residue was dissolved in EtOAc, washed (1 M aq. HCl soln, sat. aq. Na$_2$CO$_3$ soln), dried (Na$_2$SO$_4$), filtered and concentrated to afford the corresponding trifluoroacetamide (32 g, 84%). N-Methylation of the acetamide (21.78 g, 56 mmol; applying CH$_3$I and K$_2$CO$_3$ in DMF) following the procedure described by Chu-Biao Xue et al. *J. Med. Chem.* 2001, 44, 2636-2660—with the exception that the transformation was performed at room temperature for 4 h—afforded 39 (25 g, ca 90%). Treatment of 39 (8.0 g, ca 18 mmol) in THF (80 mL) with Pd(PPh$_3$)$_4$ (0.2 g) and morpholine (8.5 mL, 98 mmol) at room temperature for 3 h afforded after aqueous workup (EtOAc, 1 M aq HCl soln.) the corresponding trifluoroacetamido acid (7.3 g) which was treated with NH$_3$ (25% in H$_2$O; 50 mL) for 2 h and concentrated to give the corresponding aminoacid (8 g). This material was dissolved in allyl alcohol (150 mL) and treated at 0° C. with thionyl chloride (6.6 mL, 91 mmol). The mixture was stirred at 0° C. for 15 min and at room temperature for 3 h and concentrated to give 40.HCl (7.6 g, used in the next step without further purification).

Data of 40.HCl: C$_{16}$H$_{22}$N$_2$O$_4$.HCl (306.3, free base). Flow injection MS (ESI, positive modus): 307 ([M+H]$^+$). $^1$H-NMR (DMSO-d$_6$): 8.97 (br. s, NH$_2^+$), 7.92 (d, J=7.8, NH), 7.40-7.25 (m, 5 arom. H), 5.88 (m, 1 H), 5.32 (d, J=17.2, 1 H), 5.22 (d, J=10.5, 1 H), 5.05 (s, 2 H), 4.60 (d, J=5.2, 2 H), 4.22 (m, 1 H), 2.94 (m, 2 H), 2.50 (s, 3 H, superimposed by DMSO-d signal), 2.10 (m, 1 H), 2.00 (m, 1 H).

(S)-Allyl 2-(benzyloxycarbonylamino)-5-(methylamino)pentanoate hydrochloride (44.HCl)

Cbz-L-OrnOH (41) was converted into the allylester-pTsOH salt 42.pTsOH according to the procedure of T. M. Kamenecka and S. J. Danishefsky, *Chem. Eur. J.* 2001, 7, 41-63, describing the synthesis of D-threonine allyl ester.

The ester 42.pTsOH (5.5 g, 11 mmol) was converted into 43 (3.97 g, 83%) applying the conditions described for the synthesis of 39, with the exception that the N-methylation was continued at room temperature for 8 h.

The allyl ester group was then cleaved applying the conditions described for the treatment of 39. The saponification of the resulting trifluoroacetamido acid was performed according to the procedure of Chu-Biao Xue et al. *J. Med. Chem.* 2001, 44, 2636-2660, with the exception that 2 equiv. of LiOH were used. The resulting amino acid (3.80 g, containing LiCl ca. 9 mmol) was treated at room temperature with allyl alcohol (100 mL) and thionyl chloride (3.0 mL, 41 mmol). The mixture was heated for 2 h at 70° C. Stirring was continued at room temperature for 17 h. The volatiles were evaporated. The resulting solid was washed with $CH_2Cl_2$ to afford 44.HCl (3.62 g, ca 75% w/w; yield 83%, used without further purification).

Data of 44.HCl: $C_{17}H_{24}N_2O_4$.HCl (320.4, free base). LC-MS (method 9b): $R_t$=1.48, 321 ([M+H]$^+$). $^1$H-NMR (DMSO-$d_6$): 9.26 (br. s, $NH_2^+$), 7.86 (d, J=7.7, NH), 7.39-7.13 (m, 5 arom. H), 5.89 (m, 1 H), 5.31 (br. d, J=17.3, 1 H), 5.20 (br. d, J=10.4, 1 H), 5.04 (s, 2 H), 4.58 (d, J=5.2, 2 H), 4.05 (br. m, 1 H), 2.81 (br. m, 2 H), 2.44 (s, 3 H), 1.80-1.60 (br. m, 4 H), Sarcosine allyl ester (46) was prepared as p-TsOH salt applying the procedure of T. M. Kamenecka and S. J. Danishefsky, *Chem. Eur. J.* 2001, 7, 41-63, describing the synthesis of D-threonine allyl ester.

2-((Allyloxycarbonyl) (methyl)amino)acetic acid (47) was prepared according to the method of M. Mori, A. Somada, S. Oida, *Chem. Pharm. Bull.* 2000, 48, 716-728.

3-((Allyloxycarbonyl) (methyl)amino)propanoic acid (49) was prepared applying the method of M. Mori, A. Somada, S. Oida, *Chem. Pharm. Bull.* 2000, 48, 716-728, describing the synthesis of N-allyloxycarbonylsarcosine.

(S)-2-(Benzyloxycarbonylamino)pent-4-enoic acid (51) was prepared from (S)-allylglycine by N-protection (CB-zOSu, dioxane, aqueous $Na_2CO_3$) in analogy to the procedure of D. R. Ijzendoorn, P. N. M. Botman, R. H. Blaauw, *Org. Lett* 2006, 8, 239-242.

Acid 51 was also described by Z-Y Sun, C—H. Kwon, J. N. D. Wurpel, *J. Med. Chem.* 1994, 37, 2841-2845.

General Procedures
Synthesis of the A-c1 Fragment
Procedure A
A.1: Acid Chloride Formation Oxalyl chloride (3.5-5.0 equiv.) was added to a mixture of the acetoxyaryl carboxylic acid (Ac-A-OH) and dry diethyl ether or $CH_2Cl_2$. The resulting mixture was stirred at room temperature for 15 min followed by the addition of a few drops (ca 50-100 μL) of dry DMF. Stirring was continued for 16 h. The mixture was filtered. The filtrate was concentrated and the residue dried i.v. to afford the crude acetoxyaryl carboxylic acid chloride (Ac-A-Cl), which was immediately used in the next step.

A.2: Amide Coupling

A mixture of the amino ester salt (H-c1-OAll.HCl), the crude acetoxyaryl carboxylic acid chloride (Ac-A-Cl, 1.1-1.5 equiv.) and dry $CH_2Cl_2$ or THF was cooled to 0° C. An auxiliary base (sym-collidine or i-$Pr_2$NEt; 3.0 equiv.) was added dropwise. The mixture was stirred at room temperature for 16 h. The mixture was distributed between EtOAc and 1 M aq. HCl solution. The organic phase was washed (1 M aq. HCl soln., then sat. aq. $NaHCO_3$ soln. or sat aq. NaCl soln.), dried ($Na_2SO_4$), filtered and concentrated. FC (hexane/EtOAc gradients) gave the acetoxyaryl amide (Ac-A-c1-OAll).

A.3: Deacetylation

A solution of acetoxyarylamide (Ac-A-c1-OAll) in dry THF was treated at 0° C. with 3-dimethylaminopropylamine (3.0-4.5 equiv.). The mixture was stirred at room temperature for 1-5 h. The mixture was distributed between EtOAc and icecold 0.1 M or 1 M aq. HCl solution. The organic phase was washed (0.1 or 1 M aq. HCl soln., sat. aq. NaCl soln.), dried ($Na_2SO_4$), filtered and concentrated to afford the hydroxyaryl amide (H-A-c1-OAll).

Synthesis of the Linear Cyclization Precursor H—B-A-c1-OH
Procedure B
B.1.1: Mitsunobu Aryl Ether Synthesis Using $PPh_3$/DEAD A mixture of the hydroxyaryl amide (H-A-c1-OAll) and $PPh_3$ (1.5 equiv.) was dried i.v. for 15 min. Under argon a solution of alcohol (HO—B-Alloc, 1.2 equiv.) in dry benzene was added and the resulting solution was cooled to 0° C. A solution DEAD (40% in toluene, 1.2 equiv.) in benzene was slowly added (by syringe pump). The mixture was stirred at room temperature for 18 h and concentrated. FC (hexane/EtOAc gradients) gave the protected amino acid (Alloc-B-A-c1-OAll, sometimes contaminated with byproducts such as e.g. triphenylphosphine oxide, however acceptable for the use in the next step without further purification).

B.1.2: Mitsunobu Aryl Ether Synthesis Using CMBP

A solution of the hydroxyaryl amide (HO-A-c1-OAll), the alcohol (HO—B-Alloc, 1.2-1.3 equiv) and CMBP (2 equiv) was heated in dry toluene at reflux for 3-4 h. The solution was concentrated. FC (hexane/EtOAc gradients) afforded the protected amino acid (Alloc-B-A-c1-OAll).

B.2: Cleavage of the Allyl/Alloc Protective Groups $Pd(PPh_3)_4$ (0.05-0.1 equiv.) was added to a mixture of the protected amino acid (Alloc-B-A-c1-OAll) and 1,3-dimethylbarbituric acid (2.5 equiv.) in degassed EtOAc/$CH_2Cl_2$ (ca. 1:1). The resulting solution was stirred at room temperature for 1-3 h and concentrated. FC (EtOAC, $CH_2Cl_2$/EtOH, or $CH_2Cl_2$/MeOH gradients) afforded the free amino acid (H—B-A-c1-OH)

Synthesis of the Linear Cyclization Precursor H—B-a-c1-c2-Oh
Procedure C
C.1: Alloc Carbamate Formation At 0° C., allylchloroformate (1.1 equiv.) was slowly added to a mixture of aminoacid (H—B-A-c1-OH) and $Na_2CO_3$ (1.5-3 equiv.) in dioxane/$H_2O$ 1:1. The mixture was stirred at room temperature for 15 h. The mixture was diluted with EtOAc and treated with 1 M aq. HCl solution until pH ca 2 was reached. The organic phase was separated, washed (sat. aq. NaCl soln.), dried ($Na_2SO_4$), filtered, concentrated and dried i.v. to afford the alloc protected amino acid (Alloc-B-A-c1-OH).

C.2: Amid Coupling i-$Pr_2$NEt (5.0 equiv.) was slowly added to a mixture of the alloc protected amino acid (Alloc-B-A-c1-OH), the aminoacid ester salt (H-c2-0All.p-TsOH, 1.2 equiv.), HOAt (1.5 equiv.) and HATU (1.5 equiv.) in DMF. The mixture was stirred at room temperature for 20 h followed by distribution between EtOAc and ice-cold 0.5 M aq, HCl solution. The organic phase was washed (0.5 M aq. HCl soln., $H_2O$, sat. aq. $NaHCO_3$ soln., sat. aq. NaCl soln.), dried ($Na_2SO_4$), filtered and concentrated. FC (hexane/EtOAc gradients) afforded the protected amino acid (Alloc-B-A-c1-c2-OAll)

C.3: Cleavage of the Allyl/Alloc Protective Groups $Pd(PPh_3)_4$ (0.1 equiv.) was added to a mixture of the protected amino acid (Alloc-B-A-c1-c2-OAll) and 1,3-dimethylbarbituric acid (2.5 equiv.) in degassed EtOAc/$CH_2Cl_2$ 1:1. The resulting solution was stirred at room temperature for 1-2 h and concentrated. FC (EtOAC, $CH_2Cl_2$/EtOH, or $CH_2Cl_2$/MeOH gradients) afforded the free amino acid (H—B-A-c1-c2-OH).

Synthesis of the c2-B Fragment
Procedure D
Synthesis in Two Steps, Via Amidoester and Subsequent Saponification i-Pr$_2$NEt (5.0 equiv.) was slowly added to a mixture of the N-protected amino acid (Alloc-c2-OH, 2.2 equiv.), the aminoalcohol hydrochloride (HO—B—H HCl), Cl-HOBt (0.25 equiv.) and HCTU (2.5 equiv.) in DMF. The resulting solution was stirred at room temperature for 17 h, followed by distribution between EtOAc and sat. aq. Na$_2$CO$_3$ solution. The organic phase was washed (1 M aq. HCl soln, sat. aq. NaCl soln), dried (Na$_2$SO$_4$), filtered and concentrated. FC (hexane/EtOAc or CH$_2$Cl$_2$/MeOH gradients) afforded the corresponding amidoester, which was dissolved in THF/H$_2$O 4:1 and treated with lithium hydroxide monohydrate (3.0 equiv.) for 2 h at room temperature. The mixture was concentrated to about 50% of the original volume, diluted with EtOAc and extracted with 1 M aq. NaOH solution. The organic phase was washed (H$_2$O, sat. aq. NaCl soln), dried (Na$_2$SO$_4$), filtered and concentrated to afford the amidoalcohol (HO—B-c2-Alloc).

Synthesis of the Linear Cyclization Precursor H-c2-B-A-c1-OH
Procedure E
E.1.1: Mitsunobu Aryl Ether Synthesis Using PPh$_3$/DEAD A mixture of the hydroxyaryl amide (HO-A-c1-OAll) and PPh$_3$ (1.5-4.5 equiv.) was dissolved in benzene. The solution was concentrated and the residue was dried i.v. for 15-30 min. Under argon, a solution of the alcohol (HO—B-c2-Alloc, 1.2-2.3 equiv.) in dry and degassed benzene was added and the resulting mixture was cooled to 0° C. A solution of DEAD (40% in toluene, 1.2-4.5 equiv.) was slowly added. The mixture was stirred at room temperature for 18 h. In case of incomplete consumption of the hydroxyaryl amide, additional triphenylphosphine (1.0-1.3 equiv.) and DEAD (40% in toluene, 1.0 equiv.) and alcohol (1.0 equiv.)—if consumed according to tlc—were added and stirring was continued for 18 h. The mixture was concentrated.

FC (hexane/EtOAc, CH$_2$Cl$_2$/EtOH, or CH$_2$Cl$_2$/MeOH gradients) afforded Alloc-c2-B-A-c1-OAll (possibly contaminated with byproducts such as e.g. triphenylphosphine oxide, however acceptable for the use in the next step without further purification).

E.1.2: Mitsunobu Aryl Ether Synthesis Using CMBP

CMBP (2-3 equiv.) was added to a mixture of the hydroxyaryl amide (H-A-c1-OAll) and the alcohol (HO—B-c2-Alloc, 1.2-2.2 equiv.) in dry toluene. The mixture was heated at reflux for 16 h and concentrated. FC (hexane/EtOAc gradients) afforded the protected amino acid (Alloc-c2-B-A-c1-OAll).

E.2: Cleavage of the Allyl/Alloc Protective Groups

Pd(PPh$_3$)$_4$ (0.05-0.1 equiv.) was added to a mixture of the protected amino acid (Alloc-c2-B-A-c1-OAll) and 1,3-dimethylbarbituric acid (2.4 equiv.) in degassed EtOAc/CH$_2$Cl$_2$ 1:1. The resulting solution was stirred at room temperature for 1-3 h and concentrated. FC(EtOAC, CH$_2$Cl$_2$/EtOH, or CH$_2$Cl$_2$/MeOH gradients) afforded the free amino acid (H-c2-B-A-c1-OH).

Synthesis of the Macrocycles Cyclo-(B-A-c1), and Cyclo-(c2-B-A-c1)
Procedure F

The macrolactamization was typically performed at final concentrations ranging from 0.01 M to 0.001 M
F.1.1: T3P Mediated Lactam Formation A solution of the precursor (H—B-A-c1-OH or H-c2-B-A-c1-OH or H—B-A-c1-c2-OH, respectively) in dry CH$_2$Cl$_2$ was added within 2 h by syringe pump to a solution of T3P (50% in EtOAc, 2 equiv.) and i-Pr$_2$NEt (4 equiv.) in dry CH$_2$Cl$_2$. The solution was stirred at room temperature for 20 h, extracted with sat. aq. Na$_2$CO$_3$ solution and with H$_2$O, dried (Na$_2$SO$_4$), filtered and then concentrated. FC (hexane/EtOAc/MeOH or CH$_2$Cl$_2$/MeOH gradients) afforded the macrocyclic compound (cyclo-(B-A-c1) or cyclo-(c2-B-A-c1), respectively).

F.1.2: FDPP Mediated Lactam Formation

A solution of the precursor (H—B-A-c1-OH or H-c2-B-A-c1-OH or H—B-A-c1-c2-OH, respectively) in dry DMF was added within 2 h to a solution of FDPP (2.0 equiv.) in dry DMF. The solution was stirred at room temperature for 20 h. The volatiles were evaporated and the residue taken up in EtOAc and washed (sat. aq. NaHCO$_3$ soln, H$_2$O, sat. aq. NaCl soln). The organic phase was dried (Na$_2$SO$_4$), filtered and concentrated. FC (hexane/EtOAc/MeOH or CH$_2$Cl$_2$/MeOH gradients gradients) afforded the macrocyclic compound (cyclo-(B-A-c1) or cyclo-(c2-B-A-c1), respectively).

Attachment of Substituents to the Macrocyclic Core Structures: Synthesis of the Final Products
Procedure H A solution of a macrocyclic benzylester in MeOH or MeOH/THF (ca 100 mL per g of starting material) was hydrogenated for 2 h at room temperature and at normal pressure in the presence of palladium hydroxide on activated charcoal (moistened with 50% H$_2$O; 0.5 g per g of starting material). The mixture was filtered trough a pad of celite. The residue was washed (MeOH, MeOH/CH$_2$Cl$_2$ 1:1, THF). The combined filtrate and washings were concentrated to obtain a macrocyclic acid.

Procedure I
I.1: Teoc Deprotection with Dioxane-HCl

A solution of a macrocyclic Teoc-amine (1.5 mmol) in dioxane (18 mL) was treated with 4 M HCl in dioxane (18 mL) and stirred at room temperature for 4-16 h. The mixture was treated with diethyl ether and filtered. The solid was washed with diethyl ether and dried i.v. to give the macrocyclic amine hydrochloride.

I.2: Teoc Deprotection with TBAF in THF

A solution of TBAF (1 M in THF, 3 equiv.) was added at 0° C. to a solution of a macrocyclic Teoc-amine (1.3 mmol) in THF (34 mL). Stirring at 0° C. to room temperature was continued for 3 h. The solution was distributed between CH$_2$Cl$_2$ and H$_2$O. The organic phase was washed (H$_2$O), dried (Na$_2$SO$_4$), filtered and concentrated to provide after FC the macrocyclic amine.

Procedure J

A solution of a macrocyclic Boc-amine in dioxane (10 mL per g of starting material) was treated with 4 M HCl in dioxane (20 mL per g of starting material) and stirred at room temperature for 2 h. The mixture was filtered. The solid was washed with diethyl ether and dried i.v. to give the macrocyclic amine hydrochloride.

Procedure K

A solution of a macrocyclic benzylcarbamate (0.9 mmol) in MeCH (52 mL) was hydrogenated for 4 h at room temperature and at normal pressure in the presence of palladium hydroxide on activated charcoal (moistened with 50% H$_2$O; 0.3 g). The mixture was filtered trough a pad of celite. The residue was washed (MeOH). The combined filtrate and washings were concentrated to obtain the macrocyclic amine.

Procedure L

Amide Coupling

L.1.1: with Carboxylic Acid Anhydrides or Acylchlorides

A Solution of an Amino macrocycle (free amine or hydrochloride; 0.09 mmol) in $CH_2Cl_2$ (1 mL) was at 0° C. subsequently treated with pyridine (10 equiv.) and the carboxylic acid anhydride (1.05-5 equiv.) or a carboxylic acid chloride (1.05-2.0 equiv.), respectively. The solution was stirred at room temperature for 15 h. After the addition of MeOH (0.1 mL) the solution was stirred for 10 min and concentrated. The resulting crude product was coevaporated with toluene and purified by chromatography (FC, normal phase or reversed phase prep. HPLC) to give an N-acylamino macrocycle.

L.1.2: with Carboxylic Acid and Polymersupported Carbodiimide

A solution of an amino macrocycle (free amine or hydrochloride; 0.09 mmol), a carboxylic acid (1.2 equiv.), HOBt.$H_2O$ (1.2 equiv.) in $CH_2Cl_2$ (1 mL) was treated with N-cyclohexyl-carbodiimide-N'-methylpolystyrene (1.9 mmol/g; 1.5 equiv.) and i-$Pr_2NEt$ (3.0 equiv.). The mixture was stirred for 15 h at room temperature. (Polystyrylmethyl) trimethylammonium bicarbonate (3.5 mmol/g; 3 equiv.) was added and stirring was continued for 1 h. The mixture was diluted with $CH_2Cl_2$/MeOH 9:1 (2 mL) and filtered. The polymer was washed twice with $CH_2Cl_2$/MeOH 8:2 (5 mL). The combined filtrate and washings were concentrated. Purification of the crude product by chromatography (FC, normal phase or reversed phase prep. HPLC) afforded an N-acylamino macrocycle L.1.3: with a Carboxylic Acid and HATU A solution of an amino macrocycle (free amine or hydrochloride; 0.145 mmol), a carboxylic acid (2.0 equiv.), HATU (2.0 equiv.), HOAt (2.0 equiv.) in DMF (2 mL) was treated with i-$Pr_2NEt$ (4.0 equiv.). The mixture was stirred for 15 h at room temperature. The solvent was removed. The residue was distributed between $CHCl_3$ and sat. aq. $NaHCO_3$ solution. The organic phase was washed ($H_2O$), dried ($Na_2SO_4$), filtered and concentrated. Purification of the crude product by chromatography (FC, normal phase or reversed phase prep. HPLC) afforded an N-acylamino macrocycle.

L.2: with an Amine and HATU

A solution of a macrocyclic carboxylic acid (0.78 mmol), an amine (2.0 equiv.), HATU (2.0 equiv.), HOAt (2.0 equiv.) in DMF (6 mL) was treated with i-$Pr_2NEt$ (4.0 equiv.). The mixture was stirred for 15 h at room temperature. The solvent was removed. The residue was distributed between $CHCl_3$ and sat. aq. $NaHCO_3$ solution. The organic phase was washed ($H_2O$), dried ($Na_2SO_4$), filtered and concentrated. Purification of the crude product by chromatography (FC, normal phase or reversed phase prep. HPLC) afforded a macrocycle amide.

Procedure M

N,N-Diethylamino macrocycles by Reductive Amination

At 0° C. $NaBH(OAc)_3$ (5 equiv.) and acetaldehyde (1 mL) were added to a solution of an the amino macrocycle (free amine or hydrochloride; 0.09 mmol) in THF (1 mL). The mixture was stirred at 0° C. to room temperature for 15 h. The mixture was diluted with $CHCl_3$ and washed with sat. aq. $NaHCO_3$ soln. The organic phase was dried ($Na_2SO_4$), filtered and concentrated. Purification of the crude product by chromatography (FC, normal phase or reversed phase prep. HPLC) afforded the diethylamino macocycle.

Procedure N

Methylester Cleavage

A solution of the methylester (57 µmol) in THF (1.5 mL) and MeOH (0.5 mL) was treated with $H_2O$ (0.5 mL) and lithium hydroxide monohydrate (3 equiv.) for 2 h at room temperature.

The mixture was acidified by addition of aqueous 1 M HCl and concentrated. The crude product was purified by prep. HPLC.

Synthesis of A-c1 Fragments

1. Synthesis of (S)-5-allyl 1-benzyl 2-(5-fluoro-2-hydroxy-N-methylbenzamido)pentanedioate (54) (Scheme 4)

Following procedure A (steps A.1-A.3), the reaction of 2-acetoxy-5-fluoro benzoic acid (2, 11.78 g, 59 mmol) and oxalylchloride (18 mL, 206 mmol) in dry $CH_2Cl_2$ (516 mL) in the presence of DMF (50 µL) afforded 2-acetoxy-5-fluoro benzoyl chloride (52).

Reaction of acid chloride 52 with (S)-5-allyl 1-benzyl 2-(methylamino)pentanedioate hydrochloride (27HCl, 15.0 g, 46 mmol) in THF (260 mL) in the presence of i-$Pr_2NEt$ (23 mL, 137 mmol) yielded the acetate 53 (19.35 g, 90%), which was treated with 3-dimethylamino-1-propylamine (23 mL, 185 mmol) in THF (200 mL) to afford after aqueous workup (EtOAc, 0.1 M aq. HCl soln, sat. aq. NaCl soln) and after FC (hexane/EtOAc 8:2 to 7:3) the phenol 54 (14.4 g, 81%).

Data of 54: $C_{23}H_{24}FNO_6$ (429.4). HPLC (30% $CH_3CN$): $R_t$=3.79 (87%). LC-MS (method 9a): $R_t$=2.09, 430 ([M+H]$^+$).

2. Synthesis of (R)-5-allyl 1-benzyl 2-(5-fluoro-2-hydroxy-N-methylbenzamido)pentanedioate (56) (Scheme 4)

Following procedure A (steps A.1-A.3), the reaction of 2-acetoxy-5-fluoro benzoic acid (2, 13.0 g, 67 mmol) and oxalylchloride (20 mL, 233 mmol) in dry $CH_2Cl_2$ (585 mL) in the presence of DMF (50 µL) afforded 2-acetoxy-5-fluoro benzoyl chloride (52).

Reaction of acid chloride 52 with (R)-5-allyl 1-benzyl 2-(methylamino)pentanedioate hydrochloride (29.HCl, 17.0 g, 52 mmol) in THF (280 mL) in the presence of i-$Pr_2NEt$ (27 mL, 156 mmol) yielded 55 (21.5 g, 88%), which was treated with 3-dimethylamino-1-propylamine (26 mL, 205 mmol) in THF (200 mL) to afford after aqueous workup (EtOAc, 0.1 M aq. HCl soln, sat. aq. NaCl soln) and after FC (hexane/EtOAc 8:2 to 7:3) the phenol 56 (14.8 g, 75%).

Data of 56: $C_{23}H_{24}FNO_6$ (429.4). HPLC (30% $CH_3CN$): $R_t$=3.79 (89). LC-MS (method 9c): $R_t$=2.11, 430 ([M+H]$^+$).

3. Synthesis of (S)-allyl 2-(benzyloxycarbonylamino)-3-(3-hydroxy-N-methylbenzamido)propanoate (59) (Scheme 4)

Following procedure A (steps A.1-A.3), the reaction of 3-acetoxybenzoic acid (3, 6.0 g, 33 mmol) and oxalylchloride (14 mL, 164 mmol) in dry diethyl ether (216 mL) in the presence of DMF (50 µL) afforded 3-acetoxybenzoyl chloride (57, 7.0 g, quant.).

Reaction of 57 (7.0 g, 35 mmol) with (S)-allyl 2-(benzyloxycarbonylamino)-3-(methylamino)propanoate hydrochloride (32.HCl, 10.5 g, 32 mmol) in $CH_2Cl_2$ (285 mL) in the presence of 2,4,6-collidine (12.8 mL, 96 mmol) yielded 58 (12.34 g, 82%).

The acetate 58 (12.82 g, 28.2 mmol) was treated with 3-dimethylamino-1-propylamine (10.6 mL, 84.6 mmol) in THF (114 mL) to afford the phenol 59 (10.45 g, 90%).

Data of 59: $C_{22}H_{24}N_2O_6$ (412.4). HPLC (10% $CH_3CN$): $R_t$=3.91 (96). LC-MS (method 9a): $R_t$=1.77, 413 ([M+H]$^+$).

4. Synthesis of (R)-allyl 2-(benzyloxycarbonylamino)-3-(3-hydroxy-N-methylbenzamido)propanoate (61) (Scheme 4)

Following procedure A (steps A.1-A.3), the reaction of 3-acetoxybenzoic acid (3, 5.82 g, 32.3 mmol) and oxalylchloride (11.1 mL, 129 mmol) in dry diethyl ether (210 mL) in the presence of DMF (50 μL) afforded 3-acetoxybenzoyl chloride (57, 6.5 g, 100%).

Reaction of 57 (6.5 g, 32.3 mmol) with (R)-allyl 2-(benzyloxycarbonylamino)-3-(methylamino)propanoate hydrochloride (36.HCl, 8.5 g, 26 mmol) in $CH_2Cl_2$ (220 mL) in the presence of 2,4,6-collidine (10.3 mL, 77.6 mmol) yielded 60 (10.73 g, 92%).

The acetate 60 (15.46 g, 34 mmol) was treated with 3-dimethylamino-1-propylamine (12.8 mL, 102 mmol) in THF (140 mL) to afford the phenol 61 (12.92 g, 92%).

Data of 61: $C_{22}H_{24}N_2O_6$ (412.4). LC-MS (method 2): $R_t$=1.77 (98), 413 ([M+H]$^+$).

5. Synthesis of (S)-allyl 2-(benzyloxycarbonylamino)-4-(3-hydroxy-N-methylbenzamido)butanoate (63) (Scheme 4)

Following procedure A (steps A.1-A.3), the reaction of 3-acetoxybenzoic acid (3, 7.65 g, 43 mmol) and oxalylchloride (18.2 mL, 213 mmol) in dry $CH_2Cl_2$ (140 mL) in the presence of DMF (300 μL) afforded after 3 h at room temperature 3-acetoxybenzoyl chloride (57).

Reaction of 57 thus obtained with (S)-allyl 2-(benzyloxycarbonylamino)-5-(methylamino)butanoate hydrochloride (40.HCl, 8.7 g, 28 mmol) in THF (140 mL) in the presence of i-Pr$_2$NEt (15 mL, 85 mmol) yielded 62 (8.1 g, 61%).

The acetate 62 (4.85 g, 10 mmol) was treated with 3-dimethylamino-1-propylamine (3.8 mL, 31 mmol) in THF (90 mL) to afford the phenol 63 (4.23 g, 95%).

Data of 63: $C_{23}H_{26}N_2O_6$ (426.5). LC-MS: (method 6): $R_t$=1.06 (99), 427 ([M+H]$^+$).

6. Synthesis of (S)-allyl 2-(benzyloxycarbonylamino)-5-(3-hydroxy-N-methylbenzamido)pentanoate (65) (Scheme 4)

Following procedure A (steps A.1-A.3), the reaction of 3-acetoxybenzoic acid (3, 10 g, 58 mmol) and oxalylchloride (19 mL, 218 mmol) in dry $CH_2Cl_2$ (450 mL) in the presence of DMF (500 μL) afforded 3-acetoxybenzoyl chloride (57).

Reaction of 57 thus obtained with (S)-allyl 2-(benzyloxycarbonylamino)-5-(methylamino)pentanoate hydrochloride (44.HCl, 17.3 g, 48 mmol) in THF (200 mL) in the presence of i-Pr$_2$NEt (25 mL, 145 mmol) yielded 64 (12.08 g, 51%), which was treated with 3-dimethylamino-1-propylamine (9.3 mL, 75 mmol) in THF (240 mL) to afford after aqueous workup (EtOAc, 1 M aq. HCl soln, sat. aq. NaHCO$_3$ soln, sat.-aq. NaCl soln) the phenol 65 (10.84 g, 98%).

Data of 65: $C_{24}H_{28}N_2O_6$ (440.5). LC-MS (method 6): $R_t$=1.15 (91), 441 ([M+H]$^+$).

7. Synthesis of (S)-5-allyl 1-benzyl 2-(4-hydroxy-N-methylbenzamido)pentanedioate (68) (Scheme 4)

Following procedure A (steps A.1-A.3), the reaction of 4-acetoxybenzoic acid (4, 10.7 g, 59.5 mmol) and oxalylchloride (17.7 mL, 206 mmol) in dry $CH_2Cl_2$ (350 mL) in the presence of DMF (50 μL) afforded 4-acetoxybenzoyl chloride (66).

Reaction of 66 with (S)-5-allyl 1-benzyl 2-(methylamino)pentanedioate hydrochloride (27.HCl, 15.0 g, 46 mmol) in THF (250 mL) in the presence of i-Pr$_2$NEt (23.3 mL, 137 mmol) yielded 67 (16.24 g, 78%).

The treatment of 67 (15.2 g, 33.5 mmol) with 3-dimethylamino-1-propylamine (12.6 mL, 101 mmol) in THF (140 mL) afforded the phenol 68 (14.86 g, quant.; the product was contaminated with 9% EtOAc).

Data of 68: $C_{23}H_{25}NO_6$ (411.4). LC-MS (method 9b): $R_t$=1.96, 412 ([M+H]$^+$).

8. Synthesis of (S)-allyl 2-(benzyloxycarbonylamino)-3-(5-hydroxy-N-methylnicotinamido)propanoate (71) (Scheme 4)

A mixture of 5-hydroxy nicotinic acid (5, 3.5 g, 25.1 mmol) and acetic anhydride (23 mL, 243 mmol) was heated at 95° C. for 45 min and cooled to room temperature. The mixture was filtered. The solid was washed (H$_2$O, diethyl ether) and dried i.v. to give 5-acetoxynicotinic acid (6; 3.76 g, 82%) (Scheme 1) 5-Acetoxynicotinic acid (6; 5.7 g, 31.5 mmol) was suspended in CHCl$_3$ (stabilized with amylene, 230 mL). Oxalylchloride (9.0 mL, 105 mmol) was added followed by DMF (ca. 50 μl). The mixture was stirred at room temperature for 15 h, then concentrated, coevaporated with dry $CH_2Cl_2$ and dried i.v. to afford 5-acetoxynicotinoyl chloride (69). (S)-allyl 2-(benzyloxycarbonylamino)-3-(methylamino)propanoate hydrochloride (32, 8.6 g, 26.2 mmol) and THF (225 mL) were added. The mixture was cooled to 0° C. Et$_3$N (13 mL, 92 mmol) was slowly added. The mixture was stirred at 0° C. to room temperature for 18 h. 3-dimethylamino-1-propylamine (9.9 mL, 78.6 mmol) was added and stirring at room temperature was continued for 2 h. The mixture was distributed between EtOAc and 1 M aq. NaH PO$_4$ solution. The organic layer was separated, washed (sat. aq. NaCl soln), dried (Na$_2$SO$_4$), filtered and concentrated. FC(CH$_2$Cl$_2$/MeOH 19:1) afforded the phenol 71 (8.81 g, 81%).

Data of 71: $C_{21}H_{23}N_3O_6$ (413.4). LC-MS (method 6): $R_t$=0.94 (92), 414 ([M+H]$^+$).

9. Synthesis of allyl (2S)-2-[(benzyloxy)carbonyl]amino-3-[((2S)-2-[(tert-butoxycarbonyl)amino]-8-hydroxy-1,2,3,4-tetrahydro-2-naphthalenylcarbonyl)(methyl)amino]propanoate (72) (Scheme 4)

A mixture of 10 (3.0 g, 9.76 mmol), HATU (5.57 g, 14.6 mmol), HOAt (1.99 g, 14.6 mmol) and 32.HCl (6.4 g, 19.5 mmol) were dissolved in DMF (113 mL). i-Pr$_2$NEt (8.36 mL, 48.8 mmol) was added. The mixture was stirred at room temperature for 3 d. The mixture was distributed between H$_2$O and EtOAc. The organic phase was dried (Na$_2$SO$_4$), filtered, and concentrated. FC (hexane/EtOAc 75:25 to 50:50) afforded 72 (2.58 g, 45%).

Data of 72: $C_{31}H_{39}N_3O_8$ (581.3). LC-MS (method 7): $R_t$=1.27 (97), 582 ([M+H]$^+$).

10. Synthesis of 5-allyl 1-benzyl (2S)-2-[[(8-hydroxy-2-quinolinyl)carbonyl] (methyl)amino]pentanedioate (75) (Scheme 4)

Following procedure A (steps A.1-A.3), the reaction of 8-Acetoxyquinoline-2-carboxylic acid (8, 2.22 g 9.6 mmol) and oxalylchloride (2.1 mL, 24 mmol) in dry $CH_2Cl_2$ (90 mL) (no addition of DMF) afforded after 2 h at room temperature acetoxyquinoline-2-carboxylic acid chloride (73).

Reaction of 73 with (S)-5-allyl 1-benzyl 2-(methylamino) pentanedioate hydrochloride (27.HCl, 2.3 g, 8.0 mmol) in $CH_2Cl_2$ (200 mL) in the presence of i-Pr$_2$NEt (5.5 mL, 32 mmol) yielded after 2.5 h at room temperature and purification by FC (hexane/EtOAc gradient) 74 (3.03 g, 74%), which was treated with 3-dimethylamino-1-propylamine (2.3 mL, 18 mmol) in THF (54 mL) to afford after aqueous workup (EtOAc, 1 M aq. HCl soln, sat. aq. NaHCO$_3$ soln, sat.-aq. NaCl soln) the phenol 75 (2.79 g, 99%).

Data of 75: $C_{26}H_{26}N_2O_6$ (462.5). LC-MS (method 7): $R_t$=1.29 (94), 463 ([M+H]$^+$).

11. Synthesis of N-allyl-3-hydroxy-N-methylbenzamide (77) (Scheme 4)

Following procedure A (steps A.1-A.3), the reaction of 3-acetoxybenzoic acid (3, 23.7 g, 132 mmol) and oxalylchloride (45.3 mL, 527 mmol) in dry diethyl ether (800 mL) in the presence of DMF (100 μL) afforded 3-acetoxybenzoyl chloride (57).

Reaction of 57 thus obtained with N-allylmethylamine (10.1 ml, 105 mmol) in $CH_2Cl_2$ (500 mL) in the presence of 2,4,6-collidine (42 mL, 316 mmol) yielded 76 (24 g, 98%).

The acetate 76 (10.9 g, 46.7 mmol) was treated with 3-dimethylamino-1-propylamine (17.5 mL, 140 mmol) in THF (90 mL) to afford after aqueous workup (EtOAc, 1 M aq. HCl soln, sat. aq. NaCl soln) the phenol 77 (9.0 g, 100%).

Data of 77: $C_{11}H_{13}NO_2$ (191.2). LC-MS (method 2): $R_t$=1.52 (99), 192 ([M+H]$^+$).

12. Synthesis of (S)-5-allyl-1-benzyl 2-(3-mercapto-N-methylbenzamido)pentanedioate (80) (Scheme 4)

Acetic anhydride (0.46 mL, 4.86 mmol) was added at 0° C. to a solution of 3-mercaptobenzoic acid (11, 250 mg, 1.62 mmol) in 1 M aqueous NaOH solution (5.0 mL, 5.0 mmol). The mixture was stirred at 0° C. for 1 h. A precipitate was formed. The mixture was acidified by the addition of 1 M aqueous HCl solution and filtered. The solid was dried i.v. to afford 3-(acetylthio)benzoic acid (12; 280 mg, 88%).

Oxalyl chloride (0.34 mL, 3.97 mmol) was added to a mixture of 12 (260 mg, 1.33 mmol) and CHCl$_3$ (stabilized with amylene; 16 mL). DMF (7 μL) was added. The mixture was stirred at room temperature for 2 h. The volatiles were evaporated to afford 3-(acetylthio)benzoyl chloride (78).

(S)-5-allyl 1-benzyl 2-(methylamino)pentanedioate hydrochloride (27.HCl, 434 mg, 1.33 mmol) and dry THF (5 mL) were added. The mixture was cooled to 0° C., followed by the addition of i-Pr$_2$NEt (0.79 mL, 4.6 mmol). The mixture was stirred at room temperature for 16 h and distributed between EtOAc and 1 M aqueous HCl solution. The organic phase was separated, dried (Na$_2$SO$_4$), filtered and concentrated. FC (hexane/EtOAc 2:1) afforded the acetate 79 (420 mg, 67%).

At room temperature, a solution of 79 (246 mg, 0.52 mmol) in degassed THF (3.6 mL) was treated with 3-dimethylamino-1-propylamine (0.13 mL, 1.05 mmol) for 1 h. The mixture was distributed between EtOAc and 1 M aqueous HCl solution. The organic phase was separated, dried (Na$_2$SO$_4$), filtered and concentrated. FC (hexane/EtOAc 2:1) afforded 80 (153 mg, 68%).

Data of 80: $C_{23}H_{25}NO_5S$ (427.5): LC-MS (method 7): $R_t$=1.39 (84), 428 ([M+H]$^+$).

Synthesis of c2-B Fragments

1. Synthesis of allyl N-2-[(2S,4S)-4-[(tert-butoxycarbonyl)amino]-2-(hydroxymethyl)tetrahydro-1H-pyrrol-1-yl]-2-oxoethyl-N-methylcarbamate (81) (Scheme 5)

A solution of (2-((allyloxycarbonyl) (methyl)amino)acetic acid (47, 8.0 g, 46 mmol) and aminoalcohol 13 (11.0 g, 51 mmol) in DMF (120 mL) was cooled to 0° C. 2,4,6-Collidine (11 mL, 82 mmol) was added followed by HATU (22 g, 58 mmol). The mixture was stirred for 1 h at 0° C. then for 16 h at room temperature followed by distribution between EtOAc and sat. aq. Na$_2$CO$_3$ solution. The organic phase was washed (1 M aq. HCl soln, sat. aq. NaCl soln), dried (Na$_2$SO$_4$), filtered and concentrated. FC (EtOAc/MeOH 100:0 to 95:5) afforded the amidoalcohol 81 (14.7 g, 86%).

Data of 81: $C_{17}H_{29}N_3O_6$ (371.4). HPLC (20% $CH_3CN$): $R_t$=2.94 (97). LC-MS (method 9c): $R_t$=1.55; 743 ([2M+H]$^+$), 372 ([M+H]$^+$).

2. Synthesis of allyl N-2-[(2S,4R)-4-[(tert-butoxycarbonyl)amino]-2-(hydroxymethyl)tetrahydro-1H-pyrrol-1-yl]-2-oxoethyl-N-methylcarbamate (82) (Scheme 5)

Following procedure D, the reaction of the amnioalcohol 17.HCl (10.0 g, 39.6 mmol) and 2-((allyloxycarbonyl) (methyl)amino)acetic acid (47, 15.1 g, 87 mmol) in DMF (100 mL) in the presence of HCTU (40.9 g, 98.9 mmol), Cl-HOBt (1.68 g, 9.89 mmol) and i-Pr$_2$NEt (33.6 mL, 198 mmol) afforded after FC (hexane/EtOAc 20:80 to 0:100) the corresponding amido ester intermediate (13.7 g) which was saponified with lithium hydroxide monohydrate (3.28 g, 78.1 mmol) in THF (350 mL) and H$_2$O (90 mL) to yield the amidoalcohol 82 (8.89 g, 61%).

Data of 82: $C_{17}H_{29}N_3O_6$ (371.4). LC-MS (method 9b): $R_t$=1.57; 372 ([M+H]$^+$), 316, 272 ([M+H-Boc]$^+$), 156.

3. Synthesis of tert-butyl (3R)-4-{2-[[(allyloxy)carbonyl](methyl)amino]acetyl}-3-(hydroxymethyl)tetrahydro-1(2H)-pyrazinecarboxylate (84) (Scheme 5)

Following procedure D, the reaction of (R)-tert-butyl 3-(hydroxymethyl)piperazine-1-carboxylate hydrochloride (83.HCl, 19.7 g, 78 mmol) and 3-((allyloxycarbonyl) (methyl)amino)acetic acid (47, 30 g, 172 mmol) in DMF (188 mL) in the presence of HCTU (81.0 g, 195 mmol), Cl-HOBt (3.3 g, 19 mmol) and i-Pr$_2$NEt (67 mL, 390 mmol) afforded after FC (EtOAc) the corresponding amido ester intermediate (40 g) which was saponified with lithium hydroxide monohydrate (9.5 g, 228 mmol) in THF (1020 mL) and H$_2$O (245 mL) to yield after FC (EtOAc) amidoalcohol 84; 22.8 g, 79%).

Data of 84: C$_{17}$H$_{29}$N$_3$O$_6$ (371.4). LC-MS (method 7): R$_t$=0.99 (93), 372 ([M+H]$^+$).

4. Synthesis of benzyl N-MS)-1-[(2S,4S)-4-[(tert-butoxycarbonyl)amino]-2-(hydroxymethyl)tetrahydro-1H-pyrrol-1-yl]carbonyl-3-butenyl)carbamate (85) (Scheme 5)

Aminoalcohol-hydrochloride 13.HCl (3.7 g, 14.7 mmol) was added to a solution of acid 51 (5.22 g, 14.7 mmol) in DMF (80 ml). The mixture was cooled to 0° C. HATU (7.0 g, 18.4 mmol) and 2,4,6-collidine (3.51 ml, 26.4 mmol) were added. The solution was stirred at 0° C. to room temperature for 17 h, followed by distribution between EtOAc and sat. aq. Na$_2$CO$_3$ solution. The organic phase was washed (1 M aq. HCl soln, sat. aq. NaHCO$_3$ soln, sat. aq. NaCl soln), dried (Na$_2$SO$_4$), filtered and concentrated. FC (hexane/EtOAc 30:70 to 20:80) afforded the amidoalcohol (85, 5.78 g, 88%)

Data of 85: C$_{23}$H$_{33}$N$_3$O$_6$ (447.5). LC-MS (method 2): R$_t$=1.92 (92), 448 ([M+H]$^+$).

5. Synthesis of allyl N-3-[(2S,4R)-4-[(tert-butoxycarbonyl)amino]-2-(hydroxymethyl)tetrahydro-1H-pyrrol-1-yl]-3-oxopropyl-N-methylcarbamate (86) (Scheme 5)

Following procedure D, the reaction of aminoalcohol 17.HCl (7.5 g, 30 mmol) and 3-((allyloxycarbonyl) (methyl)amino)propanoic acid (49, 12.3 g, 66 mmol) in DMF (77 mL) in the presence of HCTU (31.0 g, 75.0 mmol), Cl-HOBt (1.27 g, 7.5 mmol) and i-Pr$_2$NEt (25.6 mL, 150 mmol) afforded after FC(CH$_2$Cl$_2$/MeOH 100:0 to 97:3) the corresponding amido ester intermediate (17.1 g) which was saponified with lithium hydroxide monohydrate (3.8 g, 90 mmol) in THF (388 mL) and H$_2$O (105 mL) to yield the amidoalcohol 86 (10.48 g, 86%).

Data of 86: C$_{18}$H$_{31}$N$_3$O$_6$ (385.4). HPLC (10% CH$_3$CN): R$_t$=3.49 (88). LC-MS (method 9a): R$_t$=1.62; 386 ([M+H]$^+$), 330 ([M+H-tBu]$^+$), 286 ([M+H-Boc]$^+$).

Core 01: Synthesis of Ex.1 (Scheme 6)

Synthesis of the Mitsunobu Product 87

To a solution of 54 (350 mg, 0.82 mmol), 16 (590 mg, 1.7 mmol) and PPh$_3$ (1069 mg, 4.08 mmol) in dry degassed CHCl$_3$ (11 mL) was added ADDP (1028 mg, 4.08 mmol) in one portion at 0° C., under a N$_2$ atmosphere. The resulting mixture was stirred for 16 h at room temperature. The mixture was filtered and the slurry washed further with diethyl ether. The combined filtrates were concentrated in vacuo. The crude residue was purified by FC (CH$_2$Cl$_2$/EtOH 100:0 to 99:1) to afford 87 (1.05 g, contains triphenylphosphine oxide; used in the next step without further purification).

Synthesis of the Amino Acid 88

Following procedure B.2, the reaction of 87 (441 mg, contaminated with triphenylphosphine oxide, ca 0.5 mmol), 1,3-dimethylbarbituric acid (219 mg, 1.4 mmol) and Pd(PPh$_3$)$_4$ (34 mg) in EtOAc/CH$_2$Cl$_2$ (55:45, 10 mL) yielded after 1.5 h and subsequent FC(CH$_2$Cl$_2$/MeOH 100:0 to 80:20) amino acid 88 (267 mg, 72%).

Data of 88: C$_{31}$H$_{42}$FN$_3$O$_8$Si (631.7). LC-MS (method 9a): R$_t$=2.02, 632 ([M+H]$^+$). HPLC (30% CH$_3$CN): R$_t$=3.41 (96).

Synthesis of the Macrolactam Ex.1

According to procedure F.1.1 the amino acid 88 (75 mg, 0.12 mmol) in dry CH$_2$Cl$_2$ (6 mL) was added within 4 h to T3P (50% in EtOAc, 0.21 mL, 0.36 mmol) and i-Pr$_2$NEt (0.1 mL, 0.59 mmol) in dry CH$_2$Cl$_2$ (6 mL) to give after FC(CH$_2$Cl$_2$/MeOH 100:0 to 96:4) the macrolactam Ex.1 (45 mg, 61%).

Data of Ex.1: C$_{34}$H$_{40}$FN$_3$O$_7$Si (613.7). LC-MS (method 7):

R$_t$=1.45 (41), 614 ([M+H]$^+$); 1.47 (44), 614 ([M+H]$^+$).
$^1$H-NMR (DMSO-d$_6$): complex spectrum, several isomers; 7.45-7.01 (m, 8 H), 6.78-6.58 (2 m, 1 H), 5.42-5.06 (m, 3 H), 4.50-3.50 (several m, 7 H), 3.30-1.40 (several m, 7 H), 2.84, 2.70, 2.66 (s, 3 H), 0.97-0.82 (m, 2 H), 0.03, 0.02, 0.00 (s 9 H).

Core 02: Synthesis of Ex.2 (Scheme 11)

Synthesis of the Protected Macrolactam Ex.2

A solution of T3P (50% in EtOAc, 0.75 mL, 1.27 mmol) and i-Pr$_2$NEt (0.36 mL, 2.2 mmol) in dry CH$_2$Cl$_2$ (20 mL) was added within 2 h to a solution of the amino acid 98 (250 mg, 0.43 mmol) in dry CH$_2$Cl$_2$ (730 mL). The solution was stirred at room temperature for 20 h, followed by extraction with sat. aq. Na$_2$CO$_3$ solution. The organic phase was dried (Na$_2$SO$_4$), filtered and concentrated. FC(CH$_2$Cl$_2$/MeOH 100:0 to 95:5) afforded Ex.2 (187 mg, 77%).

Data of Ex.2: C$_{30}$H$_{36}$FN$_3$O$_7$ (569.6) LC-MS (method 7): R$_t$=1.35 (62), 570 ([M+H]$^+$); 1.39 (15), 570 ([M+H]$^+$)
$^1$H-NMR (DMSO-d$_6$): complex spectrum, several isomers; 7.46-7.30 (m, 5 H), 7.27-7.06 (m, 2 H), 6.98-6.67 (4 dd, 1 H), 5.54-5.06 (m, 3 H), 4.68-3.48 (m, 6 H), 3.05-1.98 (m 10 H; s at 2.82, 2.69, 2.64), 1.44-1.41 (3s, 9 H).

Core 03: Synthesis of Ex.3, Ex.4, and Ex.5 (Scheme 7)

Synthesis of the Mitsunobu Product 89

Following procedure E.1.1, the reaction of phenol 54 (7.8 g, 18 mmol), alcohol 81 (16 g, 43 mmol), DEAD (40% in toluene, 37 mL, 82 mmol), and PPh$_3$ (21 g, 80 mmol) in dry benzene (250 mL) afforded after FC(CH$_2$Cl$_2$/EtOH 100:0 to 95:5) the protected amino acid 89 (15.9 g, contaminated with ca. 30% triphenylphosphine oxide; used in the next step without further purification).

Synthesis of the Amino Acid 90

Following procedure E.2, the reaction of 89 (9.6 g, contaminated with triphenylphosphine oxide, ca 9 mmol), 1,3-dimethylbarbituric acid (5.0 g, 32.0 mmol) and Pd(PPh$_3$)$_4$ (0.4 g) in EtOAc/CH$_2$Cl$_2$ (55:45, 266 mL) yielded after 1.5 h and after FC(CH$_2$Cl$_2$/MeOH 90:10 to 50:50) amino acid 90 (4.34 g, 76%).

Data of 90: C$_{33}$H$_{43}$FN$_4$O$_9$ (658.7). HPLC (10% CH$_3$CN): R$_t$=3.87 (99).

LC-MS (method 9a): R$_t$=1.77, 659 ([M+H]$^+$).
Synthesis of the Protected Macrolactam Ex.3

According to procedure F.1.2, the amino acid 90 (2.5 g, 3.80 mmol) in dry DMF (50 mL) was treated with FDPP (2.51 g, 6.53 mmol) in DMF (400 mL) to afford after FC (EtOAc/MeOH 100:0 to 95:5) the macrolactam Ex.3 (2.29 g, 94%).

Data of Ex.3: C$_{33}$H$_{41}$FN$_4$O$_8$ (640.7). HPLC (30% CH$_3$CN): R$_t$=3.20 (96). LC-MS (method 9c): R$_t$=2.06, 641 ([M+H]$^+$). $^1$H-NMR (CDCl$_3$): 7.45-7.32 (m, 5 H), 7.06 (m, 1 H), 6.94-6.88 (m, 2 H), 5.57 (dd, J=2.8, 12.6, 1 H), 5.42

(br. m, 1 H), 5.26 (d, J=12.2, 1 H), 5.15 (d, J=12.2, 1 H), 4.90 (dd, J=2.5, 11.0, 1 H), 4.34 (d, J=17.2, 1 H), 4.35-4.11 (m, 3 H), 3.82 (br. t, J ca. 8.5, 1 H), 3.65 (d, J=17.3, 1 H), 3.29 (t, J ca 8.8, 1 H), 3.14 (s, 3 H), 2.65 (s, 3 H), 2.51-1.98 (several m, 5 H), 1.76 (td, J=8.2, 12.7, 1 H), 1.36 (s, 9 H).

Synthesis of the Acid Ex.4:

According to procedure H, ester Ex.3 (2.0 g, 3.1 mmol) was hydrogenated in MeOH (120 mL)/THF (40 mL) in the presence of the catalyst (1 g) for 2 h to afford Ex.4 (1.68 g, 97%).

Data of Ex.4: $C_{26}H_{35}FN_4O_8$ (550.6). HPLC (5% $CH_3CN$): $R_f$=3.60 (86). LC-MS: (method 9c): $R_t$=1.53; 551 ([M+H]$^+$), 451 ([M+H-Boc]$^+$).

Synthesis of the Amine Ex.5:

According to procedure J, ester Ex.3 (100 mg, 0.16 mmol) in dioxane (3 mL) was treated with 4 M HCl-dioxane (3 mL) to afford Ex.5.HCl (100 mg, quant.).

Data of Ex.5.HCl: $C_{28}H_{33}FN_4O_6$.HCl (540.6, free base). LC-MS: (method 9c): $R_t$=1.44, 541 ([M+H]$^+$).

Core 04: Synthesis of Ex.56 and Ex.57 (Scheme 8)

Synthesis of the Mitsunobu Product 91

Following procedure E.1.1 the reaction of phenol 54 (8.0 g, 19 mmol), alcohol 82 (16.0 g, 43 mmol), DEAD (40% in toluene, 38 mL, 84 mmol), and PPh$_3$ (22 g, 84 mmol) in dry benzene (260 mL) afforded after FC the protected amino acid 91 (33.5 g, contaminated with triphenylphosphine oxide. The material was used in the next step without further purification).

Synthesis of the Amino Acid 92

Following procedure E.2, the reaction of 91 (33.5 g, impure material), 1,3-dimethylbarbituric acid (16 g, 102 mmol) and Pd(PPh$_3$)$_4$ (0.2 g) in EtOAc/CH$_2$Cl$_2$ (45:55, 340 mL) yielded after 3 h and after FC(CH$_2$Cl$_2$/EtOH 100:0 to 70:30 then CH$_2$Cl$_2$/MeOH 90:10 to 70:30) amino acid 92 (4.8 g, 39% over the two steps, based on phenol 54).

Data of 92: $C_{33}H_{43}FN_4O_9$ (658.7). HPLC (10% $CH_3CN$): $R_f$=3.80 (95). LC-MS (method 9c): $R_t$=1.81, 659 ([M+H]$^+$).

Synthesis of the Protected Macrolactam Ex.56

According to procedure F.1.1, amino acid 92 (3.8 g, 5.80 mmol) in dry CH$_2$Cl$_2$ (40 mL) was treated with T3P (50% in EtOAc, 6.8 mL, 12 mmol) and i-Pr$_2$NEt (4.0 mL, 23 mmol) in dry CH$_2$Cl$_2$ (510 mL) to afford after FC (EtOAc/ MeOH 100:0 to 95:5) the macrolactam Ex.56 (3.23 g, 87%).

Data of Ex.56: $C_{33}H_{41}FN_4O_8$ (640.7). HPLC (30% $CH_3CN$): $R_f$=3.49 (88). LC-MS (method 9c): $R_t$=2.02, 641 ([M+H]$^+$). $^1$H-NMR (CDCl$_3$): 7.41-7.32 (m, 5 H), 7.04 (m, 1 H), 6.94-6.83 (m, 2 H), 5.54 (dd, J=3.0, 12.7, 1 H), 5.25 (d, J=12.2, 1 H), 5.14 (d, J=12.2, 1 H), 4.89 (dd, J=2.1, 11.0, 1 H), 4.63 (br. m, 1 H), 4.39-4.10 (m, 4 H), 3.79-3.64 (m, 2 H), 3.49 (br. m, 1 H), 3.12 (s, 3 H), 2.64 (s, 3 H), 2.51-2.36 (m, 2 H), 2.23-1.98 (m, 4 H), 1.44 (s, 9 H).

Synthesis of the Acid Ex.57:

According to procedure H, the ester Ex.56 (2.25 g, 3.5 mmol) was hydrogenated in MeOH (120 mL)/THF (40 mL) in the presence of the catalyst (1.1 g) for 2 h to afford—after washing of the filtration residue with warm (50° C.) MeOH/ THF 3:1—the acid Ex.57 (1.9 g, 98%).

Data of Ex.57: $C_{26}H_{35}FN_4O_8$ (550.6). HPLC LC-MS: (method 2): $R_t$=1.54 (82), 551 ([M+H]$^+$).

Core 05: Synthesis of Ex.85 and Ex.86 (Scheme 9)

Synthesis of the Mitsunobu Product 93

Following procedure E.1.1, the reaction of phenol 56 (6.6 g, 15 mmol), alcohol 81 (13 g, 35 mmol), DEAD (40% in toluene, 32 mL, 69 mmol), and PPh$_3$ (18 g, 69 mmol) in dry benzene (220 mL) afforded after FC(CH$_2$Cl$_2$/MeOH 100:0 to 94:6) the protected amino acid 93 (34.5 g, contaminated with triphenylphosphine oxide and diethyl hydrazine-1,2-dicarboxylate; acceptable for the use in the next step without further).

Synthesis of the Amino Acid 94

Following procedure E.2, the reaction of 93 (34.5 g, impure material), 1,3-dimethylbarbituric acid (17 g, 106 mmol) and Pd(PPh$_3$)$_4$ (0.1 g) in EtOAc/CH$_2$Cl$_2$ (55:45, 350 mL) yielded after 3 h and after FC(CH$_2$Cl$_2$/EtOH 100:0 to 70:30 then CH$_2$Cl$_2$/MeOH 90:10 to 70:30) the amino acid 94 (5.6 g, 55% over the two steps, based on phenol 56).

Data of 94: $C_{33}H_{43}FN_4O_9$ (658.7). HPLC (10% $CH_3CN$): $R_f$=3.79 (96). LC-MS (method 9c): $R_t$=1.77, 659 ([M+H]$^+$).

Synthesis of the Protected Macrolactam Ex.85

According to procedure F.1.1, amino acid 94 (2.75 g, 4.2 mmol) in dry CH$_2$Cl$_2$ (35 mL) was treated with T3P (50% in EtOAc, 4.9 mL, 8.3 mmol) and i-Pr$_2$NEt (2.9 mL, 17 mmol) in dry CH$_2$Cl$_2$ (355 mL) to yield after FC (EtOAc/ MeOH 100:0 to 95:5) macrolactam Ex.85 (2.47 g, 92%).

Data of Ex.85: $C_{33}H_{41}FN_4O_8$ (640.7). HPLC (30% $CH_3CN$): $R_f$=3.52 (96). LC-MS (method 9c): $R_t$=2.06; 641 ([M+H]$^+$), 541 ([M+H-Boc]$^+$). $^1$H-NMR (CDCl$_3$): two isomers, ratio 85:15, 7.42-7.31 (m, 5 H), 7.08-6.77 (m, 3 H), 5.33 (d, J=8.3, 1 H), 5.23 (d, J=12.2, 1 H), 5.17 (d, J=12.1, 1 H), 4.84 (dd, J=2.9, 8.9, 1 H), 4.37-4.25 (m, 3 H), 4.11 (dd, J=4.2, 12.0, 1 H), 3.89 (t, J=8.3, 1 H), 3.80 (d, J=8.9, 1 H), 3.61 (d, J=17.1, 1 H), 3.16 (t, J=9.1, 1 H), 3.13 (s, 2.55 H, NCH$_3$ of major isomer), 3.03 (s, 0.45 H, NCH$_3$ of minor isomer), 2.98 (s, 2.55 H, NCH$_3$ of major isomer), 2.87 (0.45 H, NCH$_3$ of minor isomer), 2.64-2.41 (m, 2 H), 2.27-2.09 (m, 1 H), 1.98-1.83 (m, 2 H), 1.79-1.66 (m, 2 H), 1.45 (s, 7.65 H, Boc, major isomer), 1.35 (s, 1.35 H, Boc, minor isomer).

Synthesis of the Acid Ex.86:

According to procedure H, ester Ex.85 (2.0 g, 3.1 mmol) was hydrogenated in MeOH (120 mL)/THF (40 mL) in the presence of the catalyst (1 g) for 2 h to afford—after washing of the filtration residue with warm (50° C.) MeOH/TFH 3:1—the acid Ex.86 (1.67 g, 97%).

Data of Ex.86: $C_{26}H_{35}FN_4O_8$ (550.6). LC-MS: (method 3): $R_t$=1.10 (83), 551 ([M+H]$^+$); 1.17 (15), 551 ([M+H]$^+$).

Core 06: Synthesis of Ex.104 and Ex.105 (Scheme 10)

Synthesis of the Mitsunobu Product 95

Following procedure E.1.2, the reaction of phenol 56 (13.1 g, 30.5 mmol), alcohol 82 (13.6 g, 36.6 mmol), and CMBP (14.7 g, 61 mmol) in dry toluene (500 mL) afforded after FC (hexane/EtOAc 50:50 to 30:70) the protected amino acid 95 (16 g, 67%).

Synthesis of the Amino Acid 96

Following procedure E.2, the reaction of 95 (16.0 g, 20 mmol), 1,3-dimethylbarbituric acid (8 g, 49 mmol) and Pd(PPh$_3$)$_4$ (0.1 g) in EtOAc/CH$_2$Cl$_2$ (55:45, 220 mL) yielded after 3 h and after FC(CH$_2$Cl$_2$/EtOH 100:0 to 70:30 then CH$_2$Cl$_2$/MeOH 90:10 to 70:30) amino acid 96 (11 g, 81%).

Data of 96: $C_{33}H_{43}FN_4O_9$ (658.7). LC-MS (method 2): $R_t$=1.63 (97), 659 ([M+H]$^+$).

Synthesis of the Protected Macrolactam Ex.104

According to procedure F.1.1, amino acid 96 (4.0 g, 6.1 mmol) in dry CH$_2$Cl$_2$ (40 mL) was treated with T3P (50% in EtOAc, 7.2 mL, 12.1 mmol) and i-Pr$_2$NEt (4.2 mL, 24.3 mmol) in dry CH$_2$Cl$_2$ (1160 mL) to give after FC(CH$_2$Cl$_2$/MeOH 100:0 to 95:5) macrolactam Ex.104 (2.32 g, 60%).

Data of Ex.104: C$_{33}$H$_{41}$FN$_4$O$_8$ (640.7). LC-MS (method 7): R$_t$=1.21 (47), 641 ([M+H]$^+$); 1.24 (53), 641 ([M+H]). $^1$H-NMR (DMSO-d$_6$): complex spectrum, mixture of isomers, 7.44-6.65 (m, 9 H), 5.32-5.05 (m, 2 H), 4.70-3.30 (several m, 9 H), 2.92 (s, NCH$_3$ of major isomer), 2.84 (s, NCH$_3$ of major isomer), 2.30-1.70 (several m, 6 H), 1.40, 1.38 (2 s, 9 H).

Synthesis of the Acid Ex.105:

According to procedure H, ester Ex.104 (2.15 g, 3.3 mmol) was hydrogenated in MeOH (215 mL) in the presence of the catalyst (1.07 g) for 4 h to afford acid Ex.105 (1.72 g, 93%).

Data of Ex.105: C$_{26}$H$_{35}$FN$_4$O$_8$ (550.6). LC-MS: (method 7): R$_t$=0.91 (45), 551 ([M+H]$^+$); 0.95 (38), 551 ([M+H]$^+$).

Core 07: Synthesis of Ex.115 and Ex.116 (Scheme 11)

Synthesis of the Mitsunobu Product 97

A mixture of the phenol 54 (6.42 g, 14.9 mmol), alcohol 22 (4.04 g, 13.5 mmol), and PPh$_3$ (9.73 g, 37.1 mmol) was dried i.v. for 15 min. and dissolved in dry, degassed chloroform (130 mL). The solution was cooled to 0° C. A solution of ADDP (9.36 g, 37.1 mmol) in chloroform (20 mL) was slowly added. The mixture was stirred at room temperature for 3 h followed by the addition of more 22 (4.04 g, 13.5 mmol) and PPh$_3$ (5.97 g, 22.8 mmol) in chloroform (20 mL). The mixture was cooled to 0° C. A solution of ADDP (5.74 g, 22.7 mmol) in chloroform (20 mL) was slowly added. The solution was stirred at room temperature for 16 h and concentrated. The residue was suspended in diethyl ether and filtered. The solid was washed with diethyl ether. The combined filtrate and washings were concentrated. FC (CH$_2$Cl$_2$/EtOAc 10:1) gave 97 (7.73 g, 73%).

Synthesis of the Amino Acid 98

Following procedure B.2, the reaction of 97 (7.72 g, 11 mmol), 1,3-dimethylbarbituric acid (4.1 g, 26.0 mmol) and Pd(PPh$_3$)$_4$ (0.63 g) in EtOAc/CH$_2$Cl$_2$ (53:47, 190 mL) yielded after 2 h and after FC (EtOAc, then CH$_2$Cl$_2$/MeOH 95:5 to 90:10) amino acid 98 (4.31 g, 67%).

Data of 98: C$_{30}$H$_{38}$FN$_3$O$_8$ (587.6). HPLC (10% CH$_3$CN): R$_t$=3.86 (84). LC-MS (method 9a): R$_t$=1.76; 588 ([M+H]$^+$), 488 ([M+H-Boc]$^+$).

Synthesis of the Alloc Protected Amino Acid 99

Following procedure C.1, the reaction of the amino acid 98 (4.3 g, 7.3 mmol), allyl choroformate (0.86 mL, 8.0 mmol) and Na$_2$CO$_3$ (1.2 g, 11 mmol) in dioxane (62 mL) and H$_2$O (60 mL) gave acid 99 (5.07 g, 100%).

Synthesis of the Protected Diamide 100

Following procedure C.2, the acid 99 (4.9 g, 7.3 mmol) was reacted with sarcosine allylester p-toluenesulfonate (46.p-TsOH, 2.6 g, 8.8 mmol), HOAt (1.5 g, 11 mmol), HATU (4.2 g, 11 mmol) and i-Pr$_2$NEt (6.2 mL, 36 mmol) in DMF (75 mL) to afford the protected amino acid 100 (4.37 g, 76%).

Data of 100: C$_{40}$H$_{51}$FN$_4$O$_{11}$ (782.8). HPLC (50% CH$_3$CN): R$_t$=3.56 (99). LC-MS (method 9a): R$_t$=2.45; 783 ([M+H]$^+$), 683 ([M+H-Boc]$^+$).

Synthesis of the Deprotected Amino Acid 101

Following procedure C.3, the reaction of the protected amino acid 100 (4.36 g, 5.6 mmol), 1,3-dimethylbarbituric acid (2.1 g, 13 mmol) and Pd(PPh$_3$)$_4$ (0.32 g) in EtOAc/CH$_2$Cl$_2$ (45:55, 106 mL) yielded amino acid 101 (3.46 g, 93%).

Data of 101: C$_{33}$H$_{43}$FN$_4$O$_9$ (658.7). LC-MS (method 9b): R$_t$=1.74; 659 ([M+H]$^+$), 559 ([M+H-Boc]$^+$).

Synthesis of the Protected Macrolactam Ex.115

According to procedure F.1.1, amino acid 101 (3.44 g, 5.2 mmol) in dry CH$_2$Cl$_2$ (50 mL) was treated with T3P (50% in EtOAc, 6.2 mL, 10 mmol) and i-Pr$_2$NEt (3.6 mL, 21 mmol) in dry CH$_2$Cl$_2$ (470 mL) to give after FC(CH$_2$Cl$_2$/MeOH 95:5) macrolactam Ex.115 (2.95 g, 90%).

Data of Ex.115: C$_{33}$H$_{41}$FN$_4$O$_8$ (640.7). HPLC (20% CH$_3$CN): R$_t$=4.05 (93). LC-MS (method 9c): R$_t$=2.08; 641 ([M+H]$^+$). $^1$H-NMR (DMSO-d$_6$): complex spectrum, mixture of isomers, 7.38 (s, 5 H), 7.35-6.95 (several m, 2 H), 6.81-6.72 (several m, 0.4 H), 6.64 (dd, J=3.1, 8.2, 0.25 H), 6.39 (dd, J=3.2, 7.7, 0.25 H), 6.30 (dd, J=3.3, 8.2, 0.1 H), 5.37-4.99 (m, 3 H), 4.60-3.60 (several m, 9 H), 3.20-2.60 (several m and s, 8 H), 2.40-1.70 (several m, 4 H), 1.45, 1.43, 1.42, 1.38 (4 s, Boc).

Synthesis of the Acid Ex.116:

According to procedure H, the ester Ex.115 (1.2 g, 1.9 mmol) was hydrogenated in MeOH (120 mL) in the presence of the catalyst (0.6 g) for 2 h to afford the acid Ex.116 (1.02 g, 99%).

Data of Ex.116: C$_{26}$H$_{35}$FN$_4$O$_8$ (550.6). HPLC (10% CH$_3$CN): R$_t$=3.47 (20), 3.55 (75). LC-MS: (method 9c): R$_t$=1.53, 1.58; 551 ([M+H]$^+$).

Core 08: Synthesis of Ex.132 and Ex.133 (Scheme 12)

Synthesis of the Mitsunobu Product 102

Following procedure E.1.2, the reaction of phenol 56 (2.0 g, 4.7 mmol), alcohol 84 (2.08 g, 5.6 mmol), and CMBP (2.25 g, 9.3 mmol) in dry toluene (80 mL) afforded after 3 h and after FC (hexane/EtOAc 1:1 to 1:2) the protected amino acid 102 (2.06 g, 56%).

Synthesis of the Amino Acid 103

Following procedure E.2, the reaction of 102 (2.05 g, 2.6 mmol), 1,3-dimethylbarbituric acid (1.0 g, 6.3 mmol) and Pd(PPh$_3$)$_4$ (0.15 g) in EtOAc/CH$_2$Cl$_2$ (55:45; 45 mL) yielded after 2 h and after FC (EtOAc, then CH$_2$Cl$_2$/MeOH 95:5 to 70:30) amino acid 103 (1.45 g, 85%).

Data of 103: C$_{33}$H$_{43}$FN$_4$O$_9$ (658.7). HPLC (5% CH$_3$CN): R$_t$=4.04 (97). LC-MS (method 9c): R$_t$=1.87, 659 ([M+H]$^+$).

Synthesis of the Protected Macrolactam Ex.132

According to procedure F.1.1, the amino acid 103 (1.44 g, 2.19 mmol) in dry CH$_2$Cl$_2$ (40 mL) was treated with T3P (50% in EtOAc, 2.6 mL, 4.37 mmol) and i-Pr$_2$NEt (1.5 mL, 8.74 mmol) in dry CH$_2$Cl$_2$ (170 mL) to give after FC(CH$_2$Cl$_2$/MeOH 95:5) the macrolactam Ex.132 (1.36 g, 96%).

Data of Ex.132: C$_{33}$H$_{41}$FN$_4$O$_8$ (640.7). LC-MS (method 2): R$_t$=1.93 (100), 641 ([M+H]$^+$); LC-MS (method 9c): R$_t$=2.12, 641 ([M+H]$^+$).

$^1$H-NMR (DMSO-d$_6$): complex spectrum, mixture of isomers, 7.38 (s, 5 H), 7.35-6.99 (several m, 2 H), 6.85-6.73 (several m, 0.4 H), 6.65 (dd, J=3.1, 8.2, 0.25 H), 6.39 (dd, J=3.1, 7.9, 0.25 H), 6.30 (dd, J=3.3, 8.1, 0.1 H), 5.37-4.99 (m, 3 H), 4.6-3.6 (several m, 9 H), 3.2-2.6 (several m and s, 8 H), 2.4-1.7 (several m, 4 H), 1.45, 1.43, 1.41, 1.38 (4 s, Boc).

Synthesis of the Acid Ex.133:

According to procedure H, ester Ex.132 (1.13 g, 1.7 mmol) was hydrogenated in MeOH (110 mL) in the presence of the catalyst (0.56 g) for 4 h to afford acid Ex.133 (0.92 g, 94%).

Data of Ex.133: $C_{26}H_{35}FN_4O_8$ (550.6). HPLC (5% $CH_3CN$): $R_t$=3.65 (27), 3.72 (71). LC-MS: (method 9c): $R_t$=1.53, 551 ([M+H]$^+$); 1.57, 551 ([M+H]$^+$).

Core 09: Synthesis of Ex.142 and Ex.143 (Scheme 13)

Synthesis of the Mitsunobu Product 104

Following procedure E.1.2, the reaction of the phenol 54 (3.1 g, 7.2 mmol), alcohol 86 (3.34 g, 8.7 mmol), and CMBP (3.49 g, 14.4 mmol) in dry toluene (123 mL) afforded after 3 h and after FC (hexane/EtOAc 1:1 to 1:2) the protected amino acid 104 (4.11 g, 71%).

Synthesis of the Amino Acid 105

Following procedure E.2, the reaction of 104 (4.07 g, 5.1 mmol), 1,3-dimethylbarbituric acid (1.9 g, 12 mmol) and Pd(PPh$_3$)$_4$ (0.3 g) in EtOAc/CH$_2$Cl$_2$ (45:55, 90 mL) yielded after 2 h and after FC (EtOAc, then CH$_2$Cl$_2$/MeOH 95:5 to 70:30) the amino acid 105 (3.19 g, 93%).

Data of 105: $C_{34}H_{45}FN_4O_9$ (672.7). HPLC (5% CH$_3$CN): $R_t$=3.96 (88). LC-MS (method 9c): $R_t$=1.83, 673 ([M+H]$^+$).

Synthesis of the Protected Macrolactam Ex.142

According to procedure F.1.1, amino acid 105 (2.4 g, 3.6 mmol) in dry CH$_2$Cl$_2$ (40 mL) was treated with T3P (50% in EtOAc, 4.2 mL, 7.1 mmol) and i-Pr$_2$NEt (2.4 mL, 14.2 mmol) in dry CH$_2$Cl$_2$ (300 mL) to give after FC(CH$_2$Cl$_2$/MeOH 95:5) the macrolactam Ex.142 (1.92 g, 82%).

Data of Ex.142: $C_{34}H_{43}FN_4O_8$ (654.7). HPLC (30% CH$_3$CN): $R_t$=3.50 (89). LC-MS (method 9b): $R_t$=2.01; 655 ([M+H]$^+$), 599 ([M+H-tBu]$^+$), 555 ([M+H-Boc]$^+$). $^1$H-NMR (DMSO-d$_6$): complex spectrum, mixture of isomers, 7.41-7.38 (m, 5 H), 7.37-7.14 (m, 3 H), 6.80-6.67 (m, 1 H), 5.45-5.13 (m, 3 H), 4.60-3.30 (several m, 8 H), 3.10-2.50 (several m and s, 8 H), 2.50-1.80 (several m, 6 H), 1.39, 1.38, 1.36 (3 s, Boc).

Synthesis of the Acid Ex.143:

According to procedure H, ester Ex.142 (1.07 g, 1.6 mmol) was hydrogenated in MeOH (100 mL) in the presence of the catalyst (0.53 g) for 4 h to afford acid Ex.143 (0.92 g, 99%).

Data of Ex.143: $C_{27}H_{37}FN_4O_8$ (564.6). LC-MS: (method 2): $R_t$=1.54 (91), 565 ([M+H]$^+$).

Core 10: Synthesis of Ex.164 and Ex.165 (Scheme 14)

Synthesis of the Mitsunobu Product 106

Following procedure B.1.2, the reaction of phenol 63 (4.2 g, 9.8 mmol), alcohol 16 (4.4 g, 13 mmol), and CMBP (4.8 g, 20 mmol) in dry toluene (120 mL) afforded after 4 h and FC (hexane/EtOAc 50:50) the protected amino acid 106 (6.37 g, 86%).

Synthesis of the Amino Acid 107

Following procedure B.2, the reaction of 106 (1.18 g, 1.6 mmol), 1,3-dimethylbarbituric acid (0.6 g, 3.8 mmol) and Pd(PPh$_3$)$_4$ (90 mg) in EtOAc/CH$_2$Cl$_2$ (60:40, 15 mL) yielded after 3 h and after FC(CH$_2$Cl$_2$/EtOH 100:0 to 80:20) the amino acid 107 (0.86 g, 87%).

Data of 107: $C_{31}H_{44}N_4O_8Si$ (628.8). LC-MS: (method 6): $R_t$=1.08 (88), 629 ([M+H]$^+$).

Synthesis of the Protected Macrolactam Ex.164

According to procedure F.1.2, amino acid 107 (310 mg, 0.49 mmol) in dry DMF (5 mL) was treated with FDPP (379 mg, 0.99 mmol) in dry DMF (500 mL) to afford after FC (hexane/EtOAc/MeOH 50:50:0 to 0:95:5) the macrolactam Ex.164 (131 mg, 43%).

Data of Ex.164: $C_{31}H_{42}N_4O_7Si$ (610.8). LC-MS: (method 7): $R_t$=1.34 (98), 611 ([M+H]$^+$). $^1$H-NMR (DMSO-d$_6$): 7.42-7.27 (m, 8 H), 6.98 (dd, J=1.4, 8.2, 1 H), 6.91 (d, J=7.5, 1 H), 6.84 (s, 1 H), 4.98 (s, 2 H), 4.50 (d, J=11.9, 1 H), 4.35-4.15 (m, 3 H), 4.06-3.96 (m, 4 H), 3.21 (m, 1 H), 3.10-2.95 (m, 2 H), 2.87 (s, 3 H), 2.30-1.80 (m, 4 H), 0.91 (t, J=8.3, 2 H), 0.00 (s, 9 H).

Synthesis of the Amine Ex.165

At 0° C., a solution of TBAF in THF (1 M, 3.9 mL, 3.9 mmol) was added to a solution of Ex.164 (1.2 g, 1.96 mmol) in THF (42 mL). The solution was allowed to stir at 0° C. to room temperature for 15 h, followed by the addition of more TBAF in THF (1 M, 1.18 mL, 1.18 mmol). Stirring was continued for 2 h. The solution was distributed between CH$_2$Cl$_2$ and H$_2$O. The aqueous phase was repeatedly extracted with CH$_2$Cl$_2$. The combined organic phase was dried (Na$_2$SO$_4$), filtered and concentrated. FC (CH$_2$Cl$_2$/MeOH 100:0 to 90:10) afforded Ex.165 (0.76 g, 83%).

Data of Ex.165: $C_{25}H_{30}N_4O_5$ (466.52). LC-MS: (method 4a): $R_t$=1.49 (99), 467 ([M+H]$^+$).

Core 11: Synthesis of Ex.181 and Ex.182 (Scheme 15)

Synthesis of the Mitsunobu Product 108

Following procedure B.1.2, the reaction of phenol 65 (10.7 g, 24 mmol), alcohol 16 (10.0 g, 29 mmol), and CMBP (12.0 g, 49 mmol) in dry toluene (362 mL) afforded after FC (hexane/EtOAc 50:50 to 70:30) the protected amino acid 108 (14.55 g, 78%).

Synthesis of the Amino Acid 109

Following procedure B.2, the reaction of 108 (14.50 g, 19 mmol), 1,3-dimethylbarbituric acid (7.0 g, 47.0 mmol) and Pd(PPh$_3$)$_4$ (0.1 g) in EtOAc/CH$_2$Cl$_2$ (55:45, 203 mL) yielded after 3 h and after FC(CH$_2$Cl$_2$/MeOH 99:1 to 90:10) the amino acid 109 (11.26 g, 92%).

Data of 109: $C_{32}H_{46}N_4O_8Si$ (642.8). LC-MS: (method 6): $R_t$=1.13 (94), 643 ([M+H]$^+$).

Synthesis of the Protected Macrolactam Ex.181

According to procedure F.1.1, the amino acid 109 (4.0 g, 6.2 mmol) in dry CH$_2$Cl$_2$ (100 mL) was treated with T3P (50% in EtOAc, 7.4 mL, 12.4 mmol) and i-Pr$_2$NEt (4.3 mL, 24.8 mmol) in dry CH$_2$Cl$_2$ (560 mL). Prior to aqueous workup, the CH$_2$Cl$_2$ was replaced by EtOAc. FC (hexane/EtOAc 50:50 to 0:100) afforded the macrolactam Ex.181 (2.11 g, 54%).

Data of Ex.181: $C_{32}H_{44}N_4O_7Si$ (624.8). LC-MS (method 7): $R_t$=1.37 (99), 625 ([M+H]$^+$). $^1$H-NMR (DMSO-d$_6$): 7.46 (d, J=8.0, 1 H), 7.42 (d, J=7.2, 1 H), 7.34-7.23 (m, 6 H), 7.06 (d, J=8.2, 1 H), 6.82 (d, J=7.4, 1 H), 6.78 (s, 1 H), 5.02-4.86 (m, 3 H), 4.13 (t, J=8.5, 1 H), 4.06-3.67 (m, 7 H), 3.05 (br. m, 1 H), 2.88 (br. m, 1 H), 2.88 (s, 3 H), 2.15 (m, 2 H), 1.51 (br. m, 2 H), 1.33 (br. m, 1 H), 1.12 (br. m, 1 H), 0.91 (t-like m, J ca. 8.4, 2 H), 0.00 (s, 9 H).

Synthesis of the Amine Ex.182

According to procedure I.2, carbamate Ex.181 (844 mg, 1.3 mmol) in THF (34 mL) was treated with TBAF solution (4.1 mL) to afford after FC(CH$_2$Cl$_2$/MeOH 90:10) the amine Ex.182 (620 mg, 95%)

Data of Ex.182: $C_{26}H_{32}N_4O_5$ (480.5). LC-MS: (method 2): $R_t$=1.35 (99), 481 ([M+H]$^+$).

Core 12: Linear Synthesis of Ex.196 and Ex.197 (Scheme 16)

Synthesis of the Mitsunobu Product 110

Following procedure B.1.1, the reaction of phenol 59 (5.22 g, 12.6 mmol), alcohol 16 (5.2 g, 15.2 mmol), PPh$_3$ (5.0 g, 19 mmol) in dry benzene (124 mL) and DEAD (40% in toluene, 7.0 mL, 15.2 mmol) in dry benzene (36 mL) afforded after FC (hexane/EtOAc 60:40 to 40:60) the protected amino acid 110 (8.3 g, 88%, contaminated with some triphenylphosphine oxide; acceptable for the use in the next stop without further purification).

Synthesis of the Amino Acid 111

Following procedure B.2, the reaction of 110 (4.15 g, 5.62 mmol), 1,3-dimethylbarbituric acid (2.19 g, 14.0 mmol) and Pd(PPh$_3$)$_4$ (0.71 g) in EtOAc/CH$_2$Cl$_2$ 1:1 (60 mL) yielded after 1 h and after FC(CH$_2$Cl$_2$/EtOH 95:5 to 90:10 then CH$_2$Cl$_2$/MeOH 90:10 to 70:30) amino acid 111 (2.75 g, 80%).

Data of 111: C$_{30}$H$_{42}$N$_4$O$_8$Si (614.8). HPLC (10% CH$_3$CN): R$_t$=3.82 (99). LC-MS (method 9a): R$_t$=1.81; 615 ([M+H]$^+$).

Synthesis of the Alloc Protected Amino Acid 112

Following procedure C.1, the reaction of the amino acid 111 (1.5 g, 2.4 mmol), allyl choroformate (0.29 mL, 2.68 mmol) and Na$_2$CO$_3$ (0.72 g, 6.83 mmol) in dioxane (40 mL) and H$_2$O (40 mL) gave acid 112 (1.7 g, 100%).

Synthesis of the Protected Amino Acid 113

Following procedure C.2, the acid 112 (1.7 g, 2.4 mmol) was reacted with sarcosine allylester p-toluenesulfonate (46.p-TsOH, 0.88 g, 2.9 mmol), HOAt (0.5 g, 3.6 mmol), HATU (1.4 g, 3.6 mmol) and i-Pr$_2$NEt (2.1 mL, 12 mmol) in DMF (25 mL) to afford the protected amino acid 113 (1.51 g, 75%).

Data of 113: C$_{40}$H$_{55}$N$_5$O$_{22}$Si (809.9). HPLC (40% CH$_3$CN): R$_t$=4.43 (91). LC-MS (method 9c): R$_t$=2.51, 810 ([M+H]$^+$).

Deprotection to Amino Acid 114

Following procedure C.3, the reaction of the protected amino acid 113 (1.5 g, 1.85 mmol), 1,3-dimethylbarbituric acid (0.72 g, 4.6 mmol) and Pd(PPh$_3$)$_4$ (0.23 g) in EtOAc/CH$_2$Cl$_2$ (1:1, 25 mL) yielded amino acid 114 (1.05 g, 83%).

Data of 114: C$_{33}$H$_{47}$N$_5$O$_9$Si (685.8). HPLC (10% CH$_3$CN): R$_t$=3.85 (95). LC-MS (method 9c): R$_t$=1.78, 686 ([M+H]$^+$).

Synthesis of the Protected Macrolactam Ex.196

According to procedure F.1.2, amino acid 114 (1.0 g, 1.46 mmol) in dry DMF (20 mL) was treated with FDPP (1.12 g, 2.92 mmol) in dry DMF (130 mL) to yield after FC (EtOAc) the macrolactam Ex.196 (0.61 g, 63%).

Data of Ex.196: C$_{33}$H$_{45}$N$_5$O$_8$Si (667.8). LC-MS (method 1a): R$_t$=2.66 (100), 668 ([M+H]$^+$). LC-MS (method 9c): R$_t$=2.12, 668 ([M+H]$^+$), 640. $^1$H-NMR (CDCl$_3$): 7.34-7.26 (m, 6 H), 7.17 (d, J=7.6, 1 H), 7.02 (s, 1 H), 6.91 (d, J=9.5, 1 H), 5.49 (d, J=9.5, 2 H), 5.10 (m, 1 H), 5.06 (s, 2 H), 4.39-4.13 (m, 5 H), 4.00-3.95 (m, 2 H), 3.65 (m, 1 H), 3.36 (br. s, 2 H), 3.14 (m, 2 H), 3.09 (s, 3 H), 2.74 (s, 3 H), 2.45 (m, 1 H), 2.08 (m, 1 H), 0.98 (m, 2 H), 0.00 (s, 9 H). $^1$H-NMR (DMSO-d$_6$): 7.98 (d, J=9.9, 1 H), 7.52 (d, J=7.9, 1 H), 7.36-7.27 (m, 6 H), 7.18 (s, 1 H), 7.06 (dd, J=1.8, 8.1, 1 H), 6.83 (d, J=7.5, 1 H), 5.12 (d, J=12.5, 1 H), 5.04 (d, J=12.5, 1 H), 4.87 (d, J=8.8, 1 H), 4.25-3.89 (m, 8 H), 3.71-3.66 (m, 2 H), 3.20 (m, 1 H), 3.02 (m, 1 H), 2.97 (s, 3 H), 2.65 (s, 3 H), 2.20 (m, 1 H), 2.09 (m, 1 H), 0.92 (t, J=8.2, 2 H), 0.00 (s, 9 H).

Synthesis of the Amine Ex.197

According to procedure I.1, carbamate Ex.196 (120 mg, 0.18 mmol) in dioxane (3 mL) was treated with 4 M HCl-dioxane (3 mL) to afford Ex.197.HCl (59 mg, 58%).

Data of Ex.197.HCl: C$_{27}$R$_{33}$N$_5$O$_6$.HCl (523.5, free base). HPLC (5% CH$_3$CN): R$_t$=3.05 (83). LC-MS (method 9c): R$_t$=1.12, 524 ([M+H]$^+$). $^1$H-NMR (DMSO-d$_6$): 8.53 (br. s, NH$_3$), 8.03 (d, =9.9, 1 H), 7.41-7.31 (m, 7 H), 7.15 (m, 1 H), 6.85 (d, J=7.5, 1 H), 5.14 (d, J=12.5, 1 H), 5.04 (d, J=12.5, 1 H), 4.86 (dd, J ca. 2.2, 11.0, 1 H), 4.42-4.13 (m, 2 H), 4.05 (t, J=8.5, 1 H), 3.96 (d, J=17.8, 1 H), 3.85-3.75 (m, 2 H), 3.65 (br. m, 1 H), ca. 3.3-3.1 (m, 3 H, partially superimposed by the H$_2$O signal), 2.97 (s, 3 H), 2.67 (s, 3 H), 2.42 (m, 1 H), 2.18 (br. q, J ca. 11.1, 1 H).

Core 12: Convergent Synthesis of Ex.197 and Ex.198 (Scheme 17)

Synthesis of the Mitsunobu Product 115

Following procedure E.1.1, phenol 59 (4.6 g, 11 mmol) was treated for 40 h with alcohol 81 (5.0 g, 13 mmol), DEAD (40% in toluene, 6.1 mL, 13 mmol) and PPh$_3$ (4.4 g, 17 mmol) in dry benzene (150 mL). After 2 h and after 18 h, more PPh$_3$ (1.82 g, 6.9 mmol), alcohol 81 (2.04 g, 5.5 mmol) in benzene (50 mL), and DEAD (40% in toluene, 2.55 mL, 5.6 mmol) in benzene (13 mL) were added. FC (hexane/EtOAc 50:50 to 90:10) afforded the protected amino acid 115.1 (2.5 g, 29%).

Following procedure E.1.2, the reaction of phenol 59 (2.9 g, 7.0 mmol), alcohol 81, (5.7 g, 15 mmol) and CMBP (5.1 g, 21 mmol) in dry toluene (121 mL) afforded after FC (hexane/EtOAc 20:80 to 90:10) the protected amino acid 115.2 (2.92 g, 54%).

Synthesis of the Amino Acid 116

Following procedure E.2, the reaction of 115.1 (3.17 g, 4.14 mmol), 1,3-dimethylbarbituric acid (1.62 g, 10.3 mmol) and Pd(PPh$_3$)$_4$ (0.53 g) in EtOAc/CH$_2$Cl$_2$ (1:1, 46 mL) yielded after 1 h and after FC(CH$_2$Cl$_2$/MeOH 90:10 to 70:30) the amino acid 116.1 (1.86 g, 70%).

Data of 116.1: C$_{32}$H$_{43}$N$_5$O$_9$ (641.7). HPLC (5% CH$_3$CN): R$_t$=3.65 (100). LC-MS (method 9c): R$_t$=1.60, 642 ([M+H]$^+$).

Following procedure E.2, the reaction of 115.2 (2.9 g, 3.8 mmol), 1,3-dimethylbarbituric acid (1.5 g, 9.5 mmol) and Pd(PPh$_3$)$_4$ (0.48 g) in EtOAc/CH$_2$Cl$_2$ (1:1, 46 mL) yielded after 1 h and after FC(CH$_2$Cl$_2$/MeOH 90:10 to 70:30) the amino acid 116.2 (2.0 g, 83%).

Data of 116.2: C$_{32}$H$_{43}$N$_5$O$_9$ (641.7). HPLC (5% CH$_3$CN): R$_t$=3.73 (98). LC-MS (method 9c): R$_t$=1.61, 642 ([M+H]$^+$).

Synthesis of the Protected Macrolactam Ex.198

According to procedure F.1.1, the amino acid 116.1 (1.0 g, 1.6 mmol) in dry CH$_2$Cl$_2$ (200 mL) was treated with T3P (50% in EtOAc, 1.8 mL, 3.1 mmol) and i-Pr$_2$NEt (1.1 mL, 6.2 mmol) in dry CH$_2$Cl$_2$ (1400 mL) to afford after FC (EtOAc/MeOH 95:5 to 80:20) the macrolactam Ex.198 (containing 15% of the epimer Ex.231; 0.38 g, 39%).

Data of Ex.198: C$_{32}$H$_{41}$N$_5$O$_8$ (623.7). LC-MS: (method 2): R$_t$=1.78 (84), 624 ([M+H]$^+$); 1.82 (15). LC-MS (method 9c): R$_t$=1.87, 624 ([M+H]$^+$).

$^1$H-NMR (CDCl$_3$): 7.42-7.25 (m, 7 H), 7.07 (s, 1 H), 7.00 (d, J=8.2, 1 H), 5.59 (d, J=9.5, 1 H), 5.38 (br. d, J ca 7.9, 1 H), 5.18 (dd, J=2.5, 12.2, 1 H), 5.13 (s, 2 H), 4.43-4.01 (m, 5 H), 3.73 (m, 1 H), 3.47 (d, J=17.7, 1 H), 3.33 (d, J=17.7, 1 H), 3.20-3.11 (m, 2 H), 3.17 (s, 3 H), 2.81 (s, 3 H), 2.50 (m, 1 H), 2.15 (m, 1 H), 1.51 (s, Boc, major isomer), 1.45 (s, Boc, minor isomer); $^1$H-NMR (DMSO-d$_6$): 7.97 (d, J=10.3, 1 H), 7.41-7.30 (m, 7 H), 7.18 (s, 1 H), 7.09 (d, J=8.2, 1 H), 6.85 (J=7.6, 1 H), 5.12 (d, J=12.5, 1 H), 5.05 (d, J=12.6, 1 H), 4.89 (J=9.6, 1 H), 4.30-3.55 (m, 6 H), 3.40 (2 H, superimposed by $H_2O$ signal), 3.25-3.00 (m, 2 H), 2.99 (s, 3 H), 2.65 (s, 3 H), 2.22 (m, 1 H), 2.05 (br. q, 1 H), 1.41, (s, 9 H).

According to procedure F.1.1, amino acid 116.2 (0.85 g, 1.3 mmol) in dry $CH_2Cl_2$ (170 mL) was treated with T3P (50% in EtOAc, 1.56 mL, 2.6 mmol) and i-$Pr_2$NEt (0.91 mL, 5.3 mmol) in dry $CH_2Cl_2$ (1190 mL) to afford after FC (EtOAc/MeOH 95:5 to 80:20) the macrolactam Ex.198 and its epimer Ex.231 (ca 1:1 mixture; 0.61 g, 73%).

Data of the mixture Ex.198/Ex.231: $C_{32}H_{41}N_5O_8$ (623.7). LC-MS: (method 2): $R_t$=1.78 (44), 624 ([M+H]$^+$); 1.82 (56), 624 ([M+H]$^+$). $^1$H-NMR (CDCl$_3$): complex spectrum, mixture of epimers, 7.41-7.20 (m, 6 H), 7.07-6.92 (m, 3 H) 5.8-4.8 (several m, 5 H), 4.3-3.0 (several m, 10 H), 3.16 (s, NCH$_3$), 2.81 (s, NCH$_3$), 2.58-2.45 (m, 1 H), 2.19-2.03 (m, 1 H), 1.51, 1.41 (2 s, 9 H)

Synthesis of the Amine Ex.197

According to procedure J, carbamate Ex.198/Ex.231 (ca. 85:15, 749 mg, 1.2 mmol) in dioxane (7.5 mL) was treated with 4 M HCl-dioxane (15 mL) to afford Ex.197.HCl/Ex.232.HCl (607 mg, 90%). Data of Ex.197.HCl/Ex.232.HCl: $C_{27}H_{33}N_5O_6$.HCl (523.5, free base). LC-MS (method 2): $R_t$=1.26 (75), 1.33 (14); 524 ([M+H]$^+$).

$^1$H-NMR (DMSO-d$_6$), major component Ex.197'HCl: spectrum identical with the one described above for compound Ex.197'HCl (cf. Scheme 16).

According to procedure J, carbamate Ex.198/Ex.231 (ca. 1:1, 1.32 g, 2.12 mmol) in dioxane (13 mL) was treated with 4 M HCl-dioxane (26 mL) to afford after separation of the isomers by preparative RP-HPLC (method 1) Ex.197 TFA (460 mg, 34%) and Ex.232 TFA (470 mg, 35%).

Data of Ex.197 TFA: $C_{27}H_{33}N_5O_6 \cdot C_2HF_3O_2$ (523.5, free base). LC-MS (method 2): $R_t$=1.25 (99), 524 ([M+H]$^+$). LC-MS (method 7): $R_t$=0.74 (97), 524 ([M+H]$^+$). $^1$H-NMR (DMSO-d$_6$): 8.34 (br. s, NH$_3^+$), 8.07 (d, J=9.9, 1 H), 7.43-7.33 (m, 6 H), 7.20 (s, 1 H), 7.10 (dd, J=1.5, 8.2, 1 H), 6.87 (d, J=7.4, 1 H), 5.17 (d, J=12.5, 1 H), 5.05 (d, J=12.5, 1 H), 4.87 (br. dd, 1 H), 4.27-4.16 (m, 2 H), 4.06 (t, J=8.6, 1 H), 4.01-3.91 (m, 2 H), 3.82 (t-like dd, J ca. 8.1, 1 H), 3.70 (br. m, 1 H), 3.35-3.20 (m, 3 H), 2.98 (s, 3 H), 2.70 (s, 3 H), 2.49 (m, 1 H), 2.18 (br. q, J ca 11.0, 1 H).

Data of Ex.232 TFA: See below; Core 14.

Core 13: Synthesis of Ex.215 and Ex.216 (Scheme 18)

Synthesis of the Mitsunobu Product 117

Following procedure B.1.1, the reaction of phenol 59 (2.1 g, 5.1 mmol), alcohol 20 (2.1 g, 6.1 mmol), PPh$_3$ (2.0 g, 7.6 mmol) in dry benzene (50 mL) and DEAD (40% in toluene, 2.8 mL, 6.1 mmol) in dry benzene (14 mL) afforded, after further addition of PPh$_3$ (0.84 g, 3.2 mmol), alcohol 20 (0.88 g, 2.6 mmol) in benzene (21 mL) and DEAD (40% in toluene, 1.2 mL, 2.6 mmol) in benzene (6 mL) and after FC (hexane/EtOAc 50:50) the protected amino acid 117 (3.8 g, 100%).

Synthesis of the Amino Acid 118

Following procedure B.2, the reaction of 117 (7.63 g, 10.3 mmol), 1,3-dimethylbarbituric acid (4.03 g, 25.8 mmol) and Pd(PPh$_3$)$_4$ (1.31 g) in EtOAc/CH$_2$Cl$_2$ (1:1, 110 mL) yielded after 1 h and after FC(CH$_2$Cl$_2$/MeOH 95:5 to 70:30) the amino acid 118 (3.48 g, 60%).

Data of 118: $C_{30}H_{42}N_4O_8Si$ (614.8). HPLC (10% CH$_3$CN): $R_t$=3.88 (100). LC-MS (method 9a): $R_t$=1.80, 615 ([M+H]$^+$).

Synthesis of the Alloc Protected Amino Acid 119

Following procedure C.1, the reaction of the amino acid 118 (3.36 g, 5.5 mmol), allyl choroformate (0.64 mL, 6.0 mmol) and Na$_2$CO$_3$ (0.87 g, 8.2 mmol) in dioxane (51 mL) and H$_2$O (51 mL) gave the acid 119 (3.51 g, 92%).

Synthesis of the Protected Amino Acid 120

Following procedure C.2, acid 119 (3.47 g, 5.0 mmol) was reacted with sarcosine allylester p-toluenesulfonate (46.p-TsOH, 1.8 g, 6.0 mmol), HOAt (1.0 g, 7.4 mmol), HATU (2.8 g, 7.4 mmol) and i-Pr$_2$NEt (4.2 mL, 25 mmol) in DMF (108 mL) to afford the protected amino acid 120 (3.52 g, 88%).

Data of 120: $C_{40}H_{55}N_5O_{22}Si$ (809.9). LC-MS: (method 4b): $R_t$=2.51 (95), 810 ([M+H]$^+$)

Deprotection to Amino Acid 121

Following procedure C.3, the reaction of the protected amino acid 120 (3.49 g, 4.31 mmol), 1,3-dimethylbarbituric acid (1.68 g, 10.8 mmol) and Pd(PPh$_3$)$_4$ (0.55 g) in EtOAc/CH$_2$Cl$_2$ (1:1; 50 mL) yielded the amino acid 121 (2.72 g, 92%).

Data of 121: $C_{33}H_{47}N_5O_9Si$ (685.8). LC-MS: (method 4b): $R_t$=1.84 (94), 686 ([M+H]$^+$)

Synthesis of the Protected Macrolactam Ex.215

According to procedure F.1.2, amino acid 121 (1.33 g, 1.94 mmol) in dry DMF (27 mL) was treated with FDPP (1.49 g, 3.88 mmol) in dry DMF (164 mL) to yield after FC (EtOAc/MeOH 95:5) macrolactam Ex.215 (0.89 g, 68%).

Data of Ex.215: $C_{33}H_{45}N_5O_8Si$ (667.8). LC-MS: (method 1b): $R_t$=2.60 (99), 668 ([M+H]$^+$). LC-MS: (method 9c): $R_t$=2.14, 668 ([M+H]$^+$). $^1$H-NMR (DMSO-d$_6$): 7.94 (d, J=9.8, 1 H), 7.39-7.27 (m, 7 H), 7.11 (s, 1 H), 6.97 (dd, J=1.5, 8.2, 1 H), 6.82 (d, J=7.5, 1 H), 5.05 (s, 2 H), 4.83 (br. d, 1 H), 4.25 (br. m, 1 H), 4.17-3.96 (m, 5 H), 3.73 (br. q, J ca. 16.8, 2 H), 3.47 (m, 1 H), 3.33 (m, 1 H), 3.19 (m, 2 H), 2.96 (s, 3 H), 2.67 (s, 3 H), 2.20 (m, 1 H), 2.00 (m, 1 H), 0.91 (t, J=8.4, 2 H), 0.00 (s, 9 H).

Synthesis of the Amine Ex.216

According to procedure I.1, carbamate Ex.215 (881 mg, 1.3 mmol) in dioxane (16 mL) was treated with 4 M HCl-dioxane (16 mL) to afford Ex.216.HCl (666 mg, 90%).

Data of Ex.216.HCl: $C_{27}H_{33}N_5O_6$.HCl (523.5, free base). HPLC (5% CH$_3$CN): $R_t$=3.11 (91). LC-MS (method 9c): $R_t$=1.19, 524 ([M+H]$^+$).

Core 14: Synthesis of Ex.231 and Ex.232 (Scheme 19)

Synthesis of the Mitsunobu Product 122

A mixture of phenol 61 (4.6 g, 11.2 mmol) and PPh$_3$ (5.27 g, 20.1 mmol) was dissolved in benzene. The solution was concentrated and the residue was dried i.v. for 20 min. A solution of the alcohol 81, (7.46 g, 20.1 mmol) in dry, degassed benzene (120 mL) was added. The resulting mixture was cooled to 0° C. DEAD (40% in toluene, 11.5 mL, 25.1 mmol) in benzene (10 mL) was slowly added. The solution was stirred at room temperature for 16 h. More PPh$_3$ (1.46 g, 5.6 mmol), alcohol 81 (1.04 g, 2.8 mmol) and at 0° C., a solution of DEAD (40% in toluene, 2.6 mL, 5.7 mmol) in benzene (2 mL) were added and stirring at room temperature was continued for 7 h. More PPh$_3$ (1.46 g, 5.6 mmol), alcohol 81 (1.04 g, 2.8 mmol), and at 0° C., a solution of DEAD (40% in toluene, 2.6 mL, 5.7 mmol) in benzene (2 mL) were added. Stirring at room temperature was continued for 16 h. The mixture was concentrated. FC (hexane/EtOAc 30:70 to 0:100) afforded 122 (12.8 g, contaminated with ca 40% triphenylphosphinoxide, yield ca 90%). The material was used for the next step without further purification)

Synthesis of the Amino Acid 123

Following procedure E.2, the reaction of the protected amino acid 122 (contaminated with ca 40% of triphenylphosphine oxide, 12.8 g, ca 10 mmol), 1,3-dimethylbarbituric acid (3.91 g, 25.1 mmol) and Pd(PPh$_3$)$_4$ (1.27 g) in EtOAc/CH$_2$Cl$_2$ (1:1, 120 mL) yielded after 1 h and after FC(CH$_2$Cl$_2$/MeOH 100:0 to 70:30 then CHCl$_3$/MeOH 70:30) the amino acid 123 (2.80 g, 44%).

Data of 123: C$_{32}$H$_{43}$N$_5$O$_9$ (641.7). LC-MS: (method 2): R$_t$=1.56 (94), 642 ([M+H]$^+$).

Synthesis of the Protected Macrolactam Ex.231

According to procedure F.1.2, amino acid 123 (3.29 g, 5.13 mmol) in dry DMF (150 mL) was added within 4 h at 60° C. to FDPP (3.94 g, 10.3 mmol) in dry DMF (4980 mL) to afford after 16 h at 60° C. and after FC (EtOAc/MeOH 100:0 to 95:5) the macrolactam Ex.231 (contained ca 15% of its epimer Ex.198; 2.5 g, 78%).

Data of Ex.231: C$_{32}$H$_{41}$N$_5$O$_8$ (623.7). LC-MS: (method 2): R$_t$=1.78 (12), 1.82 (83), 624 ([M+H]$^+$). LC-MS: (method 7): R$_t$=1.16 (18), 624 ([M+H]$^+$); 1.18 (80), 624 ([M+H]$^+$). $^1$H-NMR (CDCl$_3$): complex spectrum, two epimers; 7.38-7.22 (m, 6H), 7.06-6.90 (m, 3H), 5.80-4.80 (several m, 4 H), 5.08, 5.12 (2s, 2 H), 4.43-2.80 (several br. m, 15 H), 2.51 (m, 1 H), 2.19-2.03 (m, 1 H), 1.50, 1.42 (2 s, 9 H).

Synthesis of the Amine Ex.232

According to procedure J, carbamate Ex.231 (containing 15% of the epimer Ex.198; 1.42 g, 2.3 mmol) in dioxane (30 mL) was treated with 4 M HCl-dioxane (45 mL) to afford after preparative RP-HPLC (method 1) Ex.232 TFA (1.10 g, 71%) and Ex.197 TFA (0.27 g, 17%).

Data of Ex.232 TFA: C$_{27}$H$_{33}$N$_5$O$_6$.C$_2$HF$_3$O$_2$ (523.5, free base). LC-MS (method 2): R$_t$=1.32 (99), 524 ([M+H]$^+$). $^1$H-NMR (DMSO-d$_6$): complex spectrum, mixture of isomers; 8.40 (br. s), 8.20 (br. s), 7.84 (d, J=7.1), 7.50-6.80 (several m), 5.25-3.40 (several m, partially superimposed by the H$_2$O signal), 3.30-2.80 (m), 3.04 (s, NCH$_3$), 2.98 (s, NCH$_3$), 2.67 (s, NCH$_3$), 2.64 (s, NCH$_3$), 2.6-1.9 (several m).

Data of Ex.197 TFA: See above; Core 12.

Core 15 and Core 16

Synthesis of Ex.238 and Ex.239 (Scheme 20)

Synthesis of the Mitsunobu Product 124

Following procedure E.1.1, phenol 77 (1.63 g, 8.5 mmol), alcohol 85 (5.72 g, 12.8 mmol) and PPh$_3$ (4.02 g, 15.3 mmol) in dry benzene (80 mL) were treated with DEAD (40% in toluene, 8.79 mL, 19.2 mmol) for 20 h. Purification by FC (hexane/EtOAc 20:80 to 100:0) then (hexane/EtOAc 50:50 to 20:80) afforded the protected amino acid 124 (1.96 g, 37%).

Synthesis of the Macrocycle Ex.238

Dichloro-[1,3-bis(mesityl)-2-imidazoldinylidene]-(3-phenyl-1H-inden-1-ylidene) (tricyclohexylphosphine)ruthenium (II) (Umicore M2 catalyst; 88 mg) was added to a solution of 124 (1160 mg, 1.29 mmol) in dry, degassed CH$_2$Cl$_2$ (170 mL). The solution was stirred in a sealed tube at 40° C. for 68 h, followed by 45 h at room temperature. During this period further equal portions of catalyst (in total 350 mg) were added after 20 h, 28 h, 44 h, and 52 h. The solution was concentrated. FC (hexane/EtOAc 70:30 to 0:100) gave Ex.238 (350 mg, 46%, mixture of two isomers, ratio>9:1, acceptable for the use in the next step). An analytical sample (69 mg) was further purified by preparative RP-HPLC (method 2) to afford pure Ex.238 (major isomer; 45 mg).

Data of Ex.238 (major isomer): C$_{32}$H$_{40}$N$_4$O$_7$ (592.6). LC-MS: (method 4a): R$_t$=2.23 (92), 593 ([M+H]$^+$). $^1$H-NMR (CDCl$_3$): 7.62-7.31 (m, 6 H), 7.07 (d, J=7.6, 1 H), 6.99 (dd, J=2.0, 7.9, 1 H), 6.85 (s, 1 H), 5.69-5.61 (m, 2 H), 5.48 (d, J=8.2, 1 H), 5.21 (m, 1 H), 5.10 (s, 2 H), 4.76 (d, J=10.1, 1 H), 4.54 (dt, J=3.5, 7.9, 1 H), 4.41-4.25 (m, 2 H), 4.13 (d, J=10.7, 1 H), 3.97 (m, 1 H), 3.62 (m, 2 H), 3.48 (m, 1 H), 3.10 (s, 3 H), 2.73 (m, 1 H), 2.60-2.45 (m, 2 H), 2.02 (m, 1 H), 1.46 (s, 9 H).

Synthesis of Amine Ex.239

A solution of Ex.238 (430 mg, 0.73 mmol) in MeOH/THF 1:3, 36 mL) was hydrogenated for 3.5 h at room temperature and at normal pressure in the presence of palladium hydroxide on activated charcoal (moistened with 50% H$_2$O; 215 mg). The mixture was filtered through a pad of celite. The filtrate was concentrated to give Ex.239 (355 mg, quantitative; used in the next step without further purification).

An analytical sample (68 mg) was purified by preparative RP-HPLC (method 2) to afford pure Ex.239 (37 mg).

Data of Ex.239: C$_{24}$H$_{36}$N$_4$O$_5$ (460.6): LC-MS (method 7): R$_t$=0.88 (97), 461 ([M+H]$^+$). $^1$H-NMR (DMSO-d$_6$): 7.36 (t, J=7.8, 1 H), 7.25 (d, J=6.1, 1 H), 7.03 (dd, J=1.6, 8.2, 1 H), 6.88-6.65 (m, 2 H), 4.51 (d, J=8.3, 1 H), 4.18 (t, J=10.3, 2 H), 4.09 (br. s, 1 H), 3.96 (br. m, 2 H), 3.19-2.72 (m, 3 H), 2.92 (s, 3 H), 2.34 (m, 2 H), 2.05 (br. q, 1 H), 1.82 (m, 1 H), 1.60-0.85 (m, 5 H), 1.40 (s, 9 H), 0.82 (m, 1 H).

Core 17: Synthesis of Ex.248 and Ex.249 (Scheme 21)

Synthesis of the Mitsunobu Product 125

Following procedure E.1.1, phenol 68 (6.0 g, 14.6 mmol), alcohol 82 (9.75 g, 26.2 mmol), and PPh$_3$ (6.88 g, 26.2 mmol) were treated in dry benzene (160 mL) with DEAD (40% in toluene, 15 mL, 32.8 mmol) for 40 h. After 18 h and after 25 h, more PPh$_3$ (1.27 g, 4.8 mmol) and DEAD (40% in toluene, 2.23 mL, 4.9 mmol) in benzene (2 mL) were added. FC (hexane/EtOAc 30:70 to 20:80) afforded the protected amino acid 125 (16.85 g, contaminated with ca 40% triphenylphosphinoxide, yield ca 85%). The material was used for the next step without further purification)

Synthesis of the Amino Acid 126

Following procedure E.2, the reaction of 125 (16.8 g, contaminated with ca 40% of triphenylphosphine oxide, ca. 12 mmol), 1,3-dimethylbarbituric acid (4.80 g, 30.8 mmol) and Pd(PPh$_3$)$_4$ (1.56 g) in EtOAc/CH$_2$Cl$_2$ (1:1, 170 mL) yielded after 1 h and after FC(CH$_2$Cl$_2$/MeOH 0:100 to 70:30, then CHCl$_3$/MeOH 70:30) amino acid 126 (4.15 g, ca. 52%).

Data of 126: C$_{33}$H$_{44}$N$_4$O$_9$ (640.7). HPLC (10% CH$_3$CN): R$_t$=3.67 (69). LC-MS (method 9c): R$_t$=1.75, 641 ([M+H]$^+$).

Synthesis of the Protected Macrolactam Ex.248

According to procedure F.1.1, amino acid 126 (4.55 g, 7.1 mmol) in dry CH$_2$Cl$_2$ (120 mL) was added within 3 h to T3P (50% in EtOAc, 8.37 ml, 14.2 mmol) and i-Pr$_2$NEt (4.83 ml, 28.4 mmol) in dry CH$_2$Cl$_2$ (6660 mL). Prior to aqueous workup, CH$_2$Cl$_2$ was replaced with EtOAc. FC(CH$_2$Cl$_2$/MeOH 100:0 to 95:5) yielded the macrolactam Ex.248 (2.38 g, 54%).

Data of Ex.248: C$_{33}$H$_{42}$N$_4$O$_8$ (622.7). LC-MS: (method 2): R$_t$=1.83 (100), 623 ([M+H]$^+$). LC-MS: (method 9c): R$_t$=1.97, 623 ([M+H]$^+$). $^1$H-NMR (DMSO-d$_6$): 7.45-7.34 (m, 5 H), 7.15-6.78 (m, 5 H), 5.25 (s, 2 H), 5.08 (d, J=12.8, 1 H), 4.62 (d, J=13.5, 2 H), 4.29 (m, 1 H), 4.09 (d, J=7.3, 1

H), 3.89 (d, J=12.4, 1 H), 3.54 (br. t, 1 H), 3.27 (m, 1 H), 3.07 (s, 3 H), 2.80 (m, 1 H), 2.71 (s, 3 H), 2.28-2.06 (m, 4 H), 1.94 (m, 1 H), 1.71 (m, 1 H), 1.39 (s, 9 H).

Synthesis of the Acid Ex.249:

According to procedure H, the ester Ex.248 (2.16 g, 3.5 mmol) was hydrogenated in MeOH (130 mL)/THF (40 mL) in the presence of the catalyst (1.09 g) for 2.5 h to afford the acid Ex.249 (1.83 g, 99%).

Data of Ex.249: $C_{26}H_{36}N_4O_8$ (532.6). LC-MS: (method 2): $R_t$=1.42 (95), 533 ([M+H]$^+$).

Core 18: Synthesis of Ex.272, Ex.273, and Ex.274 (Scheme 22)

Synthesis of the Mitsunobu Product 127

Following procedure E.1.1, the reaction of phenol 71 (6.47 g, 15.7 mmol), the alcohol 81 (10.5 g, 28.2 mmol), DEAD (40% in toluene, 26 mL, 56.3 mmol), and PPh$_3$ (14.8 g, 56.3 mmol) in dry benzene (380 mL) afforded after 2 h at room temperature and after aqueous workup (EtOAc, sat. aq. Na$_2$CO$_3$ soln, sat. aq. NaCl soln), drying (Na$_2$SO$_4$), concentration of the organic layer and FC (hexane/EtOAc 30:70, 0:100, then CH$_2$Cl$_2$/MeOH 90:10) the protected amino acid 127 (12.0 g, 99%).

Synthesis of the Amino Acid 128

Following procedure E.2, the reaction of 127 (12.0 g, 16 mmol), 1,3-dimethylbarbituric acid (5.9 g, 38.0 mmol) and Pd(PPh$_3$)$_4$ (0.9 g) in EtOAc/CH$_2$Cl$_2$ (55:45, 275 mL) yielded after 2 h and after FC (EtOAc, then CH$_2$Cl$_2$/MeOH 90:10 to 60:40) the amino acid 128 (9.05 g, 90%).

Data of 128: $C_{31}H_{42}N_6O_9$ (642.7). LC-MS: (method 7): $R_t$=0.90 (94), 643 ([M+H]$^+$).

Synthesis of the Protected Macrolactam Ex.272

According to procedure F.1.1, the amino acid 128 (5.04 g, 7.8 mmol) in dry CH$_2$Cl$_2$ (100 mL) was treated with T3P (50% in EtOAc, 9.2 mL, 16 mmol) and i-Pr$_2$NEt (5.4 mL, 31 mmol) in dry CH$_2$Cl$_2$ (700 mL) to afford after FC(CH$_2$Cl$_2$/MeOH 39:1 to 19:1) the epimeric macrolactams Ex.272 (1.90 g, 38%).

Data of Ex.272: $C_{34}H_{40}N_6O_8$ (624.7). LC-MS: (method 2): $R_t$=1.61 (99), 625 ([M+H]$^+$). LC-MS: (method 7): $R_t$=1.01 (99), 625 ([M+H]$^+$). $^1$H-NMR (DMSO-d$_6$): 8.47 (d, J=2.6, 1 H), 8.12 (s, 1 H), 7.95 (d, J=9.6, 1 H), 7.61 (s, 1 H), 7.40-7.29 (m, 6 H), 5.10 (d, J=12.6, 1 H), 5.04 (d, J=12.6, 1 H), 4.98 (br. d, J=10.7, 1 H), 4.16 (br. d, J=11.8, 1 H), 4.10-3.90 (m, 4 H), 3.71 (br. t, J ca. 8.4, 1 H), 3.65-3.40 (m, 2 H), 3.23 (br. dd, J=11.1, 15.2, 1 H), 3.04 (s, 3 H), 2.92 (t, J=9.6, 1 H), 2.66 (s, 3 H), 2.12 (m, 1 H), 2.09 (br. q, 1 H), 1.42 (s, 9 H).

Synthesis of the Amine Ex.273

According to procedure J, carbamate Ex.272 (3.12 g, 5 mmol) in dioxane (31 mL) was treated with 4 M HCl-dioxane (62 mL) to afford Ex.273.2HCl (2.9 g, 97%)

Data of Ex.273.2HCl: $C_{26}H_{32}N_6O_6$.2HCl (524.5, free base). LC-MS (method 2): $R_t$=1.31 (92), 525 ([M+H]$^+$).

Synthesis of the Amine Ex.274

According to procedure K, carbamate Ex.272 (200 mg, 0.32 mmol) was hydrogenated in MeOH (20 mL) in the presence of the catalyst (100 mg) to afford Ex.274 (154 mg, 97%).

Data of Ex.274: $C_{23}H_{34}N_6O_6$. (490.5). LC-MS (method 2): $R_t$=1.26 (98), (491 ([M+H]$^+$).

Core 19: Synthesis of Ex.297 and Ex.298 (Scheme 23)

Synthesis of the Mitsunobu Product 129

Following procedure E.1.2, the reaction of phenol 75 (4.58 g, 9.9 mmol), alcohol 81 (5.5 g, 15 mmol), and CMBP (4.8 g, 20 mmol) in dry toluene (24 mL) afforded after FC (hexane/EtOAc 1:3) the protected amino acid 129 (5.54 g, 68%).

Synthesis of the Amino Acid 130

Following procedure E.2, the reaction of 129 (5.53 g, 6.8 mmol), 1,3-dimethylbarbituric acid (2.5 g, 16 mmol) and Pd(PPh$_3$)$_4$ (0.39 g) in EtOAc/CH$_2$Cl$_2$ 55:45 (118 mL) yielded after 2 h and after FC(CH$_2$Cl$_2$/MeOH 95:5 to 70:30) the amino acid 130 (1.45 g, 85%).

Data of 130: $C_{36}H_{45}N_5O_9$ (691.7). LC-MS (method 7): $R_t$=1.09 (96), 692 ([M+H]$^+$).

Synthesis of the Protected Macrolactam Ex.297

According to procedure F.1.1, amino acid 130 (2.57 g, 3.7 mmol) in dry CH$_2$Cl$_2$ (40 mL) was treated with T3P (50% in EtOAc, 4.4 mL, 7.4 mmol) and i-Pr$_2$NEt (2.5 mL, 14.9 mmol) in dry CH$_2$Cl$_2$ (330 mL) to give after FC(CH$_2$Cl$_2$/MeOH 99:1 to 90:10) the macrolactam Ex.297 (2.5 g, contaminated with ca 20% i-Pr$_2$NEt; yield 80%).

Data of Ex.297: $C_{36}H_{43}N_5O_8$ (673.7). LC-MS: (method 7): $R_t$=1.18 (93), 674 ([M+H]$^+$).

Aqueous workup (EtOAc, 1 M aq. NaH PO$_4$ soln) of ananalytical sample (100 mg) afforded pure Ex.297 (81 mg).

LC-MS: (method 2): $R_t$=2.20 (93), 674 ([M+H]$^+$). $^1$H-NMR (DMSO-d$_6$):complex spectrum, several isomers, 8.51 (d, J=8.5, 0.2; H), 8.47 (d, J=8.7, 0.1 H), 8.40 (d, J=8.5, 0.55 H), 8.32 (d, J=8.5, 0.15 H), 7.68-7.10 (several m, 10 H), 5.96 (br. s, 0.3 H), 5.90 (br. s, 0. 3 H), 5.4-5.0 (m, 2.4 H), 4.8-3.8 (several m, 8 H), 3.3-2.5 (several m and s, 8 H), 2.5-1.6 (several m, 4 H), 1.42, 1.41, 1.36, 1.26 (4 s, Boc).

Synthesis of the Acid Ex.298:

According to procedure H, the ester Ex.297 (2.0 g, contaminated with ca 20% i-Pr$_2$NEt 2.4 mmol) was hydrogenated in MeOH (200 mL) in the presence of the catalyst (1 g) for 3 h.

The crude product was suspended in diethyl ether (20 mL) stirred for 20 min, filtered, washed (diethyl ether) and dried to afford Ex.298 (1.63 g, contaminated with 15% i-Pr$_2$NEt, quantitative yield).

Aqueous workup (CH$_2$Cl$_2$, 1 M aq. NaH PO$_4$ soln) of an analytical sample (200 mg) afforded pure Ex.298 (135 mg).

Data of Ex.298: $C_{29}H_{37}N_5O_8$ (583.6). LC-MS: (method 4a): $R_t$=1.78 (86), 584 ([M+H]$^+$).

Core 20: Synthesis of Ex.311 (Scheme 24)

Synthesis of the Mitsunobu Product 131

A solution of phenol 72 (200 mg, 0.34 mmol), alcohol 16 (178 mg, 0.52 mmol) and PPh$_3$ (180 mg, 0.69 mmol) in benzene (5 mL) was degassed. At 0° C., DEAD (40% in toluene, 0.32 mL, 0.69 mmol) was added. The mixture was stirred at room temperature for 15 h. More of alcohol 16 (178 mg, 0.52 mmol) and PPh$_3$ (180 mg, 0.69 mmol) were added. DEAD (40% in toluene, 0.32 mL, 0.69 mmol) was added at 0° C. The mixture was stirred for 20 h and concentrated. FC(CH$_2$Cl$_2$/EtOAc 100:0 to 80:20) afforded 131 (containing ca. 20% of diethyl hydrazine-1,2-dicarboxylate; used without any further purification).

Synthesis of the Amino Acid 132

Following procedure B.2, the reaction of 131 (250 mg, ca. 80%, 0.22 mmol), 1,3-dimethylbarbituric acid (107 mg, 0.69 mmol) and Pd(PPh$_3$)$_4$ (16 mg) in EtOAc/CH$_2$Cl$_2$ (55:45, 4.8 mL) yielded after 3 h and after FC (EtOAc/MeOH 100:0 to 90:10, then CH$_2$Cl$_2$/MeOH 90:10 to 80:20) 132 (177 mg, yield over the two steps: 73%).

Data of 132: C$_{39}$H$_{57}$N$_5$O$_{10}$Si (784.0): LC-MS: (method 7): R$_t$=1.31, 784.2 ([M+H]$^+$).

Synthesis of the Alloc Protected Amino Acid 133

Following procedure C.1, the reaction of 132 (150 mg, 0.19 mmol), allyl chloroformate (23 µL, 0.21 mmol) and Na$_2$CO$_3$ (61 mg, 0.57 mmol) in dioxane (1.5 mL) and H$_2$O (1.5 mL) gave, after 2 h at 0° C., acid 133 (154 mg, 92%).

Synthesis of the Protected Amino Acid 134

Following procedure C.2, acid 133 (140 mg, 0.16 mmol) was reacted with sarcosine allylester p-toluenesulfonate (46 pTsOH, 58 mg, 0.194 mmol), HOAt (33 mg, 0.24 mmol), HATU (92 mg, 0.24 mmol) and i-Pr$_2$NEt (0.138 mL, 0.81 mmol) in DMF (2.4 mL) to afford the protected amino acid 134 (106 mg, 67%).

Data of 134: C$_{49}$H$_{70}$N$_6$O$_{13}$Si (979.2). LC-MS: (method 7): R$_t$=1.68, 979.3 ([M+H]$^+$).

Synthesis of Amino acid 135

Following procedure C.3, the reaction of the protected amino acid 134 (100 mg, 0.10 mmol), 1.3-dimethylbarbituric acid (38 mg, 0.25 mmol) and Pd(PPh$_3$)$_4$ (6 mg) in EtOAc/CH$_2$Cl$_2$ (45:55, 1.9 mL) yielded after 16 h and after FC (EtOAc, then CH$_2$Cl$_2$/MeOH 90:10) 135 (70 mg, 80%).

Data of 135: C$_{42}$H$_{62}$N$_6$O$_{11}$Si (855.1). LC-MS: (method 7): R$_t$=1.30, 855.5 ([M+H]$^+$).

Synthesis of the Protected Macrolactam Ex.311

According to procedure F.1.1, a solution of the amino acid 135 (60 mg, 0.07 mmol) in dry CH$_2$Cl$_2$ (2 mL), was added within 2 h to T3P (50% in EtOAc; 84 µL, 0.14 mmol) and i-Pr$_2$NEt (48 µL, 0.28 mmol) in CH$_2$Cl$_2$ (5 mL). Then sat. aq. NaHCO$_3$ solution was added and the mixture was extracted with CH$_2$Cl$_2$. The organic phase was dried (Na$_2$SO$_4$), filtered and concentrated. FC (EtOAc) afforded Ex.311 (26 mg, 44%).

Data of Ex.311: (C$_{42}$H$_{60}$N$_6$O$_{10}$Si (837.0): LC-MS: (method 7): R$_t$=1.51 (90), 837.4 ([M+H]$^+$). $^1$H-NMR (CDCl$_3$): 7.26 (s, 5 H), 7.09 (t, J=8.4, 1 H), 6.78 (d-like m, 1 H), 6.61 (d, J=7.4, 1 H), 5.50-4.90 (several br. m, 5 H), 4.90-3.80 (several br. m, 8 H), 3.69 (br. t, J ca. 8.5, 1 H), 3.6-2.3 (several br. m, 14 H), 2.12 (m, 1 H), 1.61 (m, 1 H), 1.38 (s, 9 H), 1.24 (s, 2 H), 0.93 (br. t, J ca. 8.0, 2 H), 0.00, −0.03 (2 s, 9 H).

Core 21: Synthesis of Ex.312 and Ex.313 (Scheme 25)

Synthesis of the Mitsunobu Product 136

Alcohol 82 (217 mg, 0.58 mmol) and CMBP (212 mg, 0.88 mmol) were dissolved in dry degassed toluene (7 mL) and heated at 100° C. for 30 min. A solution of 80 (250 mg, 0.58 mmol) in toluene (2 mL) was added dropwise. Stirring at 100° C. was continued for 1 h. The volatiles were evaporated. FC (hexane/EtOAc 2:1 to 1:1) yielded 136 (290 mg, 63%).

Synthesis of Amino Acid 137

Following procedure E.2 the reaction of 136 (250 mg, 0.32 mmol), 1,3-dimethylbarbituric acid (120 mg, 0.77 mmol) and Pd(PPh$_3$)$_4$ (18 mg) in EtOAc/CH$_2$Cl$_2$ (45:55, 5.5 mL) yielded after 0.5 h and after FC(CH$_2$Cl$_2$/MeOH 95:5 to 70:30) the aminoacid 137 (164 mg, 78%).

Data of 137: C$_{33}$H$_{44}$N$_4$O$_8$S (656.8). LC-MS (method 7): R$_t$=1.15 (95), 657 ([M+H]$^+$).

Synthesis of the Protected Macrolactam Ex.312

According to procedure F.1.1, a solution of the amino acid 137 (100 mg, 0.15 mmol) in dry CH$_2$Cl$_2$ (2 mL) was added over 2 h to T3P (50% in EtOAc, 0.18 mL, 0.31 mmol) and i-Pr$_2$NEt (0.1 mL, 0.61 mmol) in dry CH$_2$Cl$_2$ (13 mL). Stirring at room temperature was continued for 1 h, followed by aqueous workup (EtOAc, sat. aq. NaHCO$_3$ soln, Na$_2$SO$_4$) and FC (EtOAc) to afford Ex.312 (56 mg, 57%).

Data of Ex.312: C$_{33}$H$_{42}$N$_4$O$_7$S (638.7). LC-MS (method 7): R$_t$=1.33 (95), 639 ([M+H]$^+$). $^1$H-NMR (CDCl$_3$): 7.37-7.23 (m, 8 H), 6.92 (br. s, 1 H), 5.25 (m, 2 H), 5.17 (s, 1 H), 4.88 (d, J=16.2, 1 H), 4.62 (br. m, 1 H), 4.46 (br. t-like m, 1 H), 4.31 (br. m, 1 H), 4.17 (dd, J=4.1, 14.2, 1 H), 3.72 (dd, J=4.8, 10.7, 1 H), 3.50 (m, 1 H), 3.30-2.80 (several m, 2 H), 3.14 (s, 3 H), 3.01 (s, 3 H), 2.60-1.90 (several m, 6 H), 1.46 (s, 9 H).

Synthesis of Sulfon Ex.313 m-CPBA (70% w/w; 10 mg, 41 µmol) was added at 0° C. to a solution of Ex.312 (20 mg, 31 µmol) in CH$_2$Cl$_2$ (0.5 mL). The mixture was stirred for 15 min followed by the addition of m-CPBA (9 mg, 37 µmol). The mixture was allowed to warm to room temperature over 1 h, diluted with CH$_2$Cl$_2$ and washed with aq. Na$_2$S$_2$O$_3$ soln and with aq. NaHCO$_3$ soln. The organic phase was dried (Na$_2$SO$_4$), filtered and concentrated. FC (EtOAc/MeOH 100:0 to 90:10) afforded Ex.313 (8 mg, 38%).

Data of Ex.313: C$_{33}$H$_{42}$N$_4$O$_9$S (670.7). LC-MS (method 6): R$_t$=1.24 (95), 671 ([M+H]$^+$). $^1$H-NMR (CDCl$_3$): 7.89 (td, J=1.7, 7.3, 1 H), 7.71 (s, 1 H), 7.43-7.28 (m, 7 H), 5.17 (d, J=12.0, 1 H), 5.10 (d, J=12.0, 1 H), 5.01 (dd, J=5.9, 9.1, 1 H), 4.96-4.85 (m, 2 H), 4.71 (d, J=15.4, 1 H), 4.57 (br. m, 1 H), 4.33 (br. m, 2 H), 3.85 (dd, J=7.8, 12.3, 1 H), 3.25 (s, 3 H), 3.20 (m, 1 H), 3.10 (m, 1 H), 2.97 (s, 3 H), 2.73-2.54 (m, 2 H), 2.45-2.23 (m, 2 H), 2.17 (m, 1 H), 1.99 (m, 1 H), 1.46 (s, 9 H).

Synthesis of Final Products

Advanced macrocyclic intermediates and final products depicted in Tables 21a-36a (Scheme 26) and were prepared starting from the suitable precursor macrocyclic acid or macrocyclic amine applying the general procedures (H—N) described above. Deviations from general procedures are indicated in Tables 21a-36a.

Analytical data of these intermediates and final products are depicted in Tables 21b-36b.

IUPAC names of all examples are listed in Tables 20, 21c-36c, and 37.

Detailed Description of Selected Examples

Core 03

Synthesis of Selected Advanced Intermediates and Final Products (Scheme 27)

Synthesis of Amide Ex.27

A mixture of Ex.4 (432 mg, 0.79 mmol), HATU (597 mg, 1.57 mmol) and HOAt (214 mg, 1.57 mmol) was dissolved in DMF (6 mL). N,N-dimethylethylenediamine (173 µL, 1.57 mmol) and i-Pr$_2$NEt (537 µL, 3.14 mmol) were added. The solution was stirred at room temperature for 15 h and concentrated. The residue was dissolved in CHCl$_3$ and washed with sat. aq. NaHCO$_3$ solution and with H$_2$O. The organic phase was dried (Na$_2$SO$_4$), filtered and concentrated. FC(CH$_2$Cl$_2$/MeOH/conc. aq. NH$_3$ soln 100:0:0 to 90:10:0.5) afforded Ex.27 (405 mg, 83%).

Data of Ex.27: Cf. Table 21b

Synthesis of Amine Ex.28

A solution of Ex.27 (400 mg, 0.64 mmol) in dioxane (4 mL) was treated at room temperature with 4 M HCl-dioxane (8 mL) for 2 h. The volatiles were evaporated. The residue was dissolved in CH$_2$Cl$_2$/MeOH, concentrated and dried i.v. to afford Ex.28.HCl (343 mg, 90%).

Data of Ex.28: Cf. Table 21b

Synthesis of Amide Ex.11

A mixture of Ex.28.HCl (75 mg, 0.126 mmol), 1H-indole-3-acetic acid (44 mg, 0.253 mmol), HATU (96 mg, 0.253 mmol) and HOAt (34 mg, 0.253 mmol) was dissolved in DMF (2 mL). i-Pr$_2$NEt (87 µL, 0.505 mmol) was added. The solution was stirred at room temperature for 15 h and concentrated. The residue was dissolved in CHCl$_3$ and washed with sat. aq. NaHCO$_3$ solution and with H$_2$O. The organic phase was dried (Na$_2$SO$_4$), filtered and concentrated. FC(CH$_2$Cl$_2$/MeOH/conc. aq. NH$_3$ soln 100:0:0 to 90:10:1) afforded Ex.11 (50 mg, 58%).

Data of Ex.11: Cf. Table 21b $^1$H-NMR (DMSO-d$_6$): 10.81 (s, 1 H), 8.26 (d, J=7.4, 1 H), 7.62 (t, J=5.5, 1 H), 7.46 (d, J=7.9, 1 H), 7.37-7.15 (m, 4 H), 7.09 (d, J=2.2, 1 H), 7.04 (t, J=7.5, 1 H), 6.92 (t, J ca. 7.4, 1 H), 5.08 (d, J ca. 12.5, 1 H), 4.74 (d, J=8.9, 1 H), 4.37 (d, J=11.0, 1 H), 4.25 (d, J=17.7, 1 H), 4.22-4.13 (m, 2 H), 3.97 (d, J=17.6, 1 H), 3.78 (t, J=8.3, 1 H), 3.41 (s, 2 H), 3.24 (m, 1 H), 3.15 (m, 1 H), 2.98 (t, J=9.2, 1 H), 2.88 (s, 3 H), 2.53 (s, 3 H), 2.41-2.27 (m, 4 H), 2.17 (s, 6 H), 2.04 (m, 1 H), 1.83 (t-like m, 2 H), 1.69 (q-like m, 1 H).

Synthesis of Amide Ex.49

A mixture of Ex.28.HCl (60 mg, 0.101 mmol), 1-naphthylacetic acid (23 mg, 0.121 mmol), and HOBt.H$_2$O (19 mg, 0.121 mmol) was dissolved in CH$_2$Cl$_2$ (1 mL). N-Cyclohexyl-carbodiimide-N'-methylpolystyrene (1.9 mmol/g; 80 mg, 0.152 mmol) and i-Pr$_2$NEt (52 µL, 0.303 mmol) were added. The mixture was stirred for 15 h at room temperature. (Polystyrylmethyl)-trimethylammonium bicarbonate (3.5 mmol/g; 87 mg, 0.303 mmol) was added and stirring was continued for 1 h. The mixture was diluted with CH$_2$Cl$_2$/MeOH 9:1 (2 mL) and filtered. The polymer was washed with twice with CH$_2$Cl$_2$/MeOH 8:2 (5 mL). The combined filtrate and washings were concentrated. Purification of the crude product by FC(CH$_2$Cl$_2$/MeOH/conc. aq. NH$_3$ soln. 100:0:0 to 90:10:1) afforded Ex.49 (58 mg, 83%).

Data of Ex.49: Cf. Table 21b $^1$H-NMR (DMSO-d$_6$): 8.45 (d, J=7.3, 1 H), 8.00-7.87 (m, 2 H), 7.79 (d, J=8.0, 1 H), 7.62 (t, J=5.5, 1 H), 7.53-7.25 (m, 6 H), 7.19 (dd, J=3.0, 8.4, 1 H), 5.10 (d, J=12.3, 1 H), 4.75 (d, J=8.9, 1 H), 4.39 (d, J=10.8, 1 H), 4.27 (d, J=17.8, 1 H), 4.28-4.08 (m, 2 H), 3.95 (d, J=17.9, 1 H), 3.83 (m, 1 H), 3.81 (s, 2 H), 3.24 (m, 1 H), 3.16 (m, 1 H), 3.03 (t, J=9.2, 1 H), 2.87 (s, 3 H), 2.54 (s, 3 H), 2.42-2.27 (m, 4 H), 2.16 (s, 6 H), 2.02 (m, 1 H), 1.84 (t-like m, 2 H), 1.71 (q, J ca. 9.4, 1 H).

Synthesis of Amide Ex.30

A mixture of Ex.4 (400 mg, 0.73 mmol), HATU (552 mg, 1.45 mmol), HOAt (198 mg, 1.45 mmol) and tryptamine (233 mg, 1.45 mmol) was dissolved in DMF (6 mL). i-Pr$_2$NEt (497 µL, 2.91 mmol) was added. The solution was stirred at room temperature for 15 h followed by aqueous workup (CHCl$_3$, sat. aq. NaHCO$_3$ soln, H$_2$O). The organic phase was dried (Na$_2$SO$_4$), filtered and concentrated. FC(CH$_2$Cl$_2$/MeOH 100:0 to 95:5) afforded Ex.30 (410 mg, 81%).

Data of Ex.30: Cf. Table 21b $^1$H-NMR (DMSO-d$_6$): 10.80 (s, 1 H), 7.91 (t, J=5.6, 1 H), 7.56 (d, J=7.7, 1 H), 7.32 (d, J=8.0, 1 H), 7.27-7.12 (m, 5 H), 7.06 (t, J=7.5, 1 H), 6.97 (t, J=7.4, 1 H), 5.08 (d, J=12.4, 1 H), 4.75 (d, J=9.3, 1 H), 4.34 (d, J=10.9, 1 H), 4.24 (d, J=17.8, 1 H), 4.10 (t-like m, 1 H), 3.97 (d, J=17.7, 1 H), 3.86 (m, 1 H), 3.77 (m, 1 H), 3.42-3.30 (m, 2 H), 2.96-2.83 (m, 3 H), 2.89 (s, 3 H), 2.50 (s, 3 H, superimposed by DMSO-d signal), 2.27 (m, 2 H), 2.08 (m, 1 H), 1.84 (t-like m, 2 H), 1.65 (q, J=10.8, 1 H), 1.34 (s, 9 H).

Synthesis of Amine Ex.55

A solution of Ex.30 (380 mg, 0.55 mmol) in dioxane (4 mL) was treated at room temperature with 4 M HCl-dioxane (8 mL) for 4 h. The volatiles were evaporated. The residue was dissolved in dioxane (4 mL) and treated again for 2 h with 4 M HCl-dioxane (8 mL). The volatiles were evaporated. The residue was washed with diethyl ether and purified by FC(CH$_2$Cl$_2$/MeOH/conc. aq. NH$_3$ soln 90:10:0 to 90:10:1) to afford Ex.55 (136 mg, 42%).

Data of Ex.55: Cf. Table 21b

Synthesis of Amide Ex.12

A mixture of Ex.55 (68 mg, 0.092 mmol), 1H-indole-3-acetic acid (32 mg, 0.184 mmol), HATU (70 mg, 0.184 mmol) and HOAt (25 mg, 0.184 mmol) was dissolved in DMF (2 mL). i-Pr$_2$NEt (63 µL, 0.367 mmol) was added. The solution was stirred at room temperature for 15 h and concentrated. The residue was dissolved in CHCl$_3$ and washed with sat. aq. NaHCO$_3$ solution and with H$_2$O. The organic phase was dried (Na$_2$SO$_4$), filtered and concentrated. Purification by prep. HPLC, method 1, afforded Ex.12 (38 mg, 55%).

Data of Ex.12: Cf. Table 21b $^1$H-NMR (DMSO-d$_6$): 10.81 (s, 2 H), 8.26 (d, J=7.2, 1 H), 7.93 (t, J=5.7, 1 H), 7.57 (d, J=7.8, 1 H), 7.46 (d, J=7.7, 1 H), 7.38-6.90 (m, 11 H); 5.10 (d, J=12.1, 1 H), 4.76 (d, J=9.3, 1 H), 4.38 (d, J=10.8, 1 H), 4.26 (d, J=17.8, 1 H), 4.23-4.11 (m, 2 H), 3.96 (d, J=18.0, 1 H), 3.78 (t, J=8.3, 1 H), 3.7-3.25 (m, 3 H), 3.60 (s, 2 H), 3.01-2.81 (m, 2 H), 2.88 (s, 3 H), ca. 2.5 (s, 3 H, superimposed by DMSO-d signal), 2.33 (m, 2 H), 2.06 (m, 1 H), 1.85 (t-like m, 2 H), 1.63 (q, J ca. 10.7, 1 H).

Synthesis of Amide Ex.16

A mixture of Ex.55 (68 mg, 0.092 mmol), N,N-dimethyl glycine (19 mg, 0.184 mmol), HATU (70 mg, 0.184 mmol) and HOAt (25 mg, 0.184 mmol) was dissolved in DMF (2 mL). i-Pr$_2$NEt (63 µL, 0.367 mmol) was added. The solution was stirred at room temperature for 15 h and concentrated. The residue was dissolved in CHCl$_3$ and washed with sat. aq. NaHCO$_3$ solution and with H$_2$O. The organic phase was dried (Na$_2$SO$_4$), filtered and concentrated. Purification by prep. HPLC, method 1, afforded Ex.16 TFA (40 mg, 55%).

Data of Ex.16 TFA: Cf. Table 21b $^1$H-NMR (DMSO-d$_6$): 10.81 (s, 1 H), 9.66 (br. s, NH$^+$), 8.75 (d, J=6.9, 1 H), 7.90 (t, J=5.6, 1 H), 7.56 (d, J=7.8, 1 H), 7.34-7.14 (m, 5 H), 7.06 (t, J ca. 7.5, 1 H), 6.97 (t, J=7.4, 1 H), 5.08 (d, J=12.3, 1 H), 4.78 (d, J=9.2, 1 H), 4.39 (d, J=10.7, 1 H), 4.24 (d, J=17.8, 1 H), 4.24-4.14 (m, 2 H), 4.00 (d, J=17.8, 1 H), 3.96-3.75 (m, 3 H), 3.45-3.35 (m, 2 H), 3.0-2.67 (m, 3 H), 2.90 (s, 3 H), 2.75 (s, 6 H), 2.50 (s, 3 H, superimposed by DMSO-d signal), 2.5-2.27 (m, 2 H), 2.08 (m, 1 H), 1.85 (t-like m, 2 H), 1.64 (q, J=10.8, 1 H).

Synthesis of Amide Ex.53

Pyridine (2 mL) and acetic anhydride (0.14 mL, 1.48 mmol) were added to a solution of Ex.5.HCl (95 mg, 0.15 mmol) in dry CH$_2$Cl$_2$ (2 mL). The solution was stirred at room temperature for 20 h. The solution was diluted with EtOAc and washed with 1 M aq. HCl soln, sat. aq. NaCl soln, sat. aq. NaHCO$_3$ soln, and sat. aq. NaCl soln. The organic phase was dried (Na$_2$SO$_4$), filtered and concentrated. FC of the crude product afforded Ex.53 (60 mg, 70%).

Data of Ex.53: Cf. Table 21b

Synthesis of Acid Ex.54

A solution of Ex.53 (58 mg, 0.01 mmol) in MeOH (5 mL) was hydrogenated at room temperature and normal pressure for 2 h in the presence of palladium hydroxide on activated charcoal (moistened with 50% H$_2$O; 50 mg). The mixture was filtered through a pad of celite. The residue was washed (MeOH). The combined filtrate and washings were concentrated and dried i.v. to yield Ex.54 (45 mg, 92%).

Data of Ex.54: Cf. Table 21b

Synthesis of Amide Ex.9

A mixture of Ex.54 (45 mg, 0.091 mmol), HATU (52 mg, 0.137 mmol) HOAt (19 mg, 0.137 mmol) and tryptamine (22 mg, 0.137 mmol) was dissolved in DMF (1 mL). i-Pr$_2$NEt (47 µL, 0.274 mmol) was added. The solution was stirred at room temperature for 20 h followed by aqueous workup (CHCl$_3$, sat. aq. NaHCO$_3$ soln, H$_2$O). The organic phase was dried (Na$_2$SO$_4$), filtered and concentrated. FC(CH$_2$Cl$_2$/MeOH 100:0 to 86:14) afforded Ex.9 (36 mg, 62%).

Data of Ex.9: Cf. Table 21b $^1$H-NMR (DMSO-d$_6$): 10.81 (s, 1 H), 8.06 (d, J=7.0, 1 H), 7.93 (t, J=5.6, 1 H), 7.56 (d, J=7.8, 1 H), 7.34-7.14 (m, 5 H), 7.05 (t, J ca. 7.5, 1 H), 6.97 (t, J ca. 7.4, 1 H), 5.09 (d, J=12.4, 1 H), 4.75 (d, J=9.1, 1 H), 4.38 (d, J=10.8, 1 H), 4.26 (d, J=17.7, 1 H), 4.19-4.10 (m, 2 H), 3.97 (d, J=17.9, 1 H), 3.78 (t, J=8.3, 1 H), 3.43-3.30 (m, 2 H), 2.96-2.83 (m, 3 H), 2.89 (s, 3 H), 2.50 (s, 3 H, superimposed by DMSO-d signal), 2.40-2.27 (m, 2 H), 2.08 (m, 1 H), 1.85 (m, 2 H), 1.71 (s, 3 H), 1.62 (q, J ca. 10.6, 1 H).

Core 11 and Core 12

Synthesis of Selected Advanced Intermediates and Final Products (Scheme 28)

Synthesis of Amide Ex.184

A mixture of Ex 182 (500 mg, 1.04 mmol), 2-naphthylacetic acid (232 mg, 1.25 mmol), HATU (791 mg, 2.08 mmol) and HOAt (283 mg, 2.08 mmol) was dissolved in DMF (15 mL). i-Pr$_2$NEt (712 µL, 4.16 mmol) was added. The solution was stirred at room temperature for 20 h and concentrated. The residue was dissolved in CHCl$_3$ and washed with sat. aq. NaHCO$_3$ solution and with H$_2$O. The organic phase was dried (Na$_2$SO$_4$), filtered and concentrated. FC (EtOAc, then CH$_2$Cl$_2$/MeOH 95:5) afforded Ex.184 (637 mg, 94%).

Data of Ex.184: Cf. Table 29b $^1$H-NMR (DMSO-d$_6$): 8.41 (d, J=7.0, 1 H), 7.90-7.83 (m, 3 H), 7.77 (s, 1 H), 7.53-7.44 (m, 4 H), 7.32-7.22 (m, 6 H), 7.04 (d, J=8.4, 1 H), 6.86 (d, J=7.4, 1 H), 6.81 (s, 1 H), 5.02-4.90 (m, 3 H), 4.19 (t, J ca. 8.6, 1 H), 4.14-3.96 (m, 2 H), 3.83 (t-like m, 2 H), 3.63 (s, 2 H), ca. 3.3 (m, 1 H, superimposed by H$_2$O signal), 3.05 (m, 1 H), 2.95 (m, 1 H), 2.91 (s, 3 H), 2.27 (m, 1 H), 2.16 (br. q, J ca. 11.3, 1 H), 1.54 (m, 2 H), 1.31 (m, 1 H), 1.15 (m, 1 H).

Synthesis of Amide Ex.200

A mixture of Ex.197 TFA (60 mg, 0.094 mmol), 1H-indole-3-acetic acid (25 mg, 0.14 mmol), HATU (54 mg, 0.14 mmol) and HOAt (19 mg, 0.14 mmol) was dissolved in DMF (1.5 mL). i-Pr$_2$NEt (81 µL, 0.471 mmol) was added. The solution was stirred for 18 h at room temperature and concentrated. The residue was dissolved in CHCl$_3$ and washed (sat. aq. NaHCO$_3$ soln, H$_2$O). The organic phase was dried (Na$_2$SO$_4$), filtered and concentrated, followed by FC (EtOAc, then CH$_2$Cl$_2$/MeOH 95:5) to afford Ex.200 (50 mg, 78%).

Data of Ex.200: Cf. Table 30b $^1$H-NMR (DMSO-d$_6$): 10.86 (s, 1 H), 8.42 (d, J=7.8, 1 H), 8.01 (d, J=10.0, 1 H), 7.58 (d, J=7.8, 1 H), 7.36-7.19 (m, 9 H), 7.07-7.02 (m, 2 H), 6.97 (t, J=7.1, 1 H), 6.86 (d, J=7.6, 1 H), 5.08 (s, 2 H), 4.88 (d, J=8.7, 1 H), 4.30-4.10 (m, 2 H), 4.13 (d, J=10.9, 1 H), 4.01 (t-like m, 1 H), 3.95 (d, J=18.0, 1 H), 3.75-3.70 (m, 2 H), 3.56 (s, 2 H), 3.4-3.2 (m, 2 H, partially superimposed by H$_2$O signal), 3.04 (t, J=9.9, 1 H), 2.98 (s, 3 H), 2.65 (s, 3 H), 2.27 (m, 1 H), 2.09 (q, J=11.7, 1 H).

Synthesis of Amine Ex.202

A solution of Ex.200 (320 mg, 0.47 mmol) in MeOH (28 mL) was hydrogenated at normal pressure and at room temperature for 4 h in the presence of palladium hydroxide on activated charcoal (moistened with 50% H$_2$O; 158 mg). The mixture was filtered through a pad of celite. The residue was washed (MeOH). The combined filtrate and washings were concentrated and dried i.v. to yield Ex.202 (250 mg, 97%).

Data of Ex.202: Cf. Table 30b

Synthesis of Amide Ex.213

A solution of Ex.202 (60 mg, 0.11 mmol) in dry CH$_2$Cl$_2$ (1 mL) was treated with pyridine (89 µL, 1.1 mmol). Decanoyl chloride (46 µL, 0.22 mmol) was slowly added at 0° C. The mixture was stirred at 0° C. to room temperature for 18 h followed by the addition of MeOH (0.1 mL). Stirring was continued for 10 min. The volatiles were evaporated. The residue was three times treated with toluene and evaporated. Purification by prep. HPLC, method 1 and subsequent FC (EtOAc/MeOH 90:10 to 80:20) afforded Ex.213 (27 mg, 35%).

Data of Ex.213: Cf. Table 30b $^1$H-NMR (DMSO-d$_6$): 10.86 (s, 1 H), 8.53 (d, J=9.8, 1 H), 8.44 (d, J=7.7, 1 H), 7.57 (d, J=7.7, 1 H), 7.35-7.30 (m, 3 H), 7.27 (s, 1 H), 7.19-6.95 (m, 3 H), 6.84 (d, J=7.5, 1 H), 4.86 (dd, J=2.4, 11.2, 1 H), 4.60 (q, J=8.4, 1 H), 4.25 (q-like m, 1 H), 4.14 (d, J=10.7, 1 H), 4.04-3.82 (m, 3 H), 3.73 (t, J ca. 8.5, 1 H), 3.55 (s, 2 H), 3.24 (d, J=7.8, 2 H), 3.09 (t, J=9.5, 1 H), 2.99 (s, 3 H), 2.67 (s, 3 H), 2.26 (m, 1 H), 2.15 (t, J=7.2, 2 H), 2.09 (m, 1 H), 1.51 (t-like m, 2 H), 1.24 (s, 12 H), 0.85 (t, J=6.6, 3 H).

Core 11

Synthesis of Ex.186 on Solid Support (Scheme 29)

Synthesis of Amine 139

A solution of Ex.181 (2.0 g, 3.2 mmol) in MeOH (200 mL) was hydrogenated for 3 h at room temperature and at normal pressure in the presence of palladium hydroxide on activated charcoal (15-20% Pd, moistened with 50% H$_2$O; 400 mg). The mixture was filtered through a pad of celite. The residue was washed (MeOH). The combined filtrate and washings were concentrated and dried i.v. to give the corresponding amine (1.57 g), which was dissolved in CH$_2$Cl$_2$ (8 mL) and treated with sat. aqueous NaHCO$_3$ solution (2.9 mL) and allyl chloroformate (0.36 mL, 3.43 mmol). The mixture was stirred at room temperature for 2 h. The organic phase was separated and concentrated. Purification of the residue by FC (EtOAc) afforded the allyl carbamate 138 (1.65 g, 92%).

TBAF solution (1 M in THF, 7 mL, 7 mmol) was added at 0° C. to a solution of 138 (1.29 g, 2.24 mmol) in THF (53 mL). The solution was stirred at 0° C. to room temperature for 3 h and concentrated. The residue was distributed between CH$_2$Cl$_2$ and sat. aq. NaHCO$_3$ solution. The aqueous phase was separated and extracted with CH$_2$Cl$_2$. The combined organic phase was dried (Na$_2$SO$_4$), filtered and concentrated. The residue was dissolved in CH$_2$Cl$_2$ (10 mL) and treated for 20 min with 25% aq. HCl solution (0.29 mL). The volatiles were evaporated and the residue was dried i.v. to afford 139.HCl (1.14 g; contaminated with ca 15% tetrabutylammonium salt and used without further purification; yield ca 90%)

Data of 139.HCl: $C_{22}H_{30}N_4O_5 \cdot HCl$ (430.5, free base). LC-MS (method 4a): $R_t$=1.22 (92), 431.3 $[M+H]^+$.

Synthesis of the Resin 140

DFPE polystyrene (1% DVB, 100-200 mesh, loading 0.89 mmol/g; 200 mg, 0.178 mmol) was swollen in DCE (2 mL) for 1 h. The resin was filtered. A solution of amine hydrochloride 139.HCl (ca 85% w/w, 166 mg, 0.303 mmol) in DCE (1.33 mL) and trimethyl orthoformate (0.66 mL, 6.02 mmol) were added. The resin was shaken for 1 h at room temperature, followed by the addition of sodium triacetoxyborohydride (75 mg, 0.356 mmol). The mixture was shaken for 15 h and the resin was filtered. The resin was successively washed three times each with DMF, 10% i-Pr$_2$NEt in DMF, DMF, CH$_2$Cl$_2$ and dried i.v. to afford resin 140 (293 mg).

Synthesis of the Resin 141

1st Acid coupling step: The resin 140 (loading 0.77 mmol/g; 50 mg, 0.038 mmol) was swollen in DMF (1 mL) for 30 min and filtered. CH$_2$Cl$_2$ (0.5 mL), DMF (0.5 mL), 2-naphthylacetic acid (65 mg, 0.35 mmol), i-Pr$_2$NEt (0.13 mL, 0.76 mmol) and HATU (144 mg, 0.38 mmol) were successively added. The resin was shaken for 1 h, filtered and washed with DMF. CH$_2$Cl$_2$ (0.5 mL), DMF (0.5 mL), 2-naphthylacetic acid (65 mg, 0.35 mmol), i-Pr$_2$NEt (0.13 mL, 0.76 mmol) and then HATU (144 mg, 0.38 mmol) were added to the resin. The mixture was shaken for 1 h and filtered. The resin was washed three times with DMF and two times with CH$_2$Cl$_2$.

Cleavage of the Alloc group: CH$_2$Cl$_2$ (1 mL), phenylsilane (41 mg, 0.375 mmol) and Pd(PPh$_3$)$_4$ (9 mg) were added to the resin. The mixture was shaken for 15 min and filtered. The resin was washed with CH$_2$Cl$_2$ and treated again for 15 min with CH$_2$Cl$_2$ (1 mL), phenylsilane (41 mg, 0.375 mmol) and Pd(PPh$_3$)$_4$ (9 mg). The resin was filtered, washed three times each with CH$_2$Cl$_2$, DMF and twice with MeOH and CH$_2$Cl$_2$.

2nd Acid coupling step: DMF (0.5 mL), CH$_2$Cl$_2$ (1 mL), 2-naphthylacetic acid (70 mg, 0.375 mmol), i-Pr$_2$NEt (0.13 mL, 0.75 mmol) and PyBOP (195 mg, 0.375 mmol) were added to the resin. The mixture was shaken for 1 h and filtered. The resin was washed three times each with DMF and CH$_2$Cl$_2$ to afford resin 141, which was immediately used in the next step.

Release of the Amide Ex.186

The resin 141 was treated with 20% TFA in CH$_2$Cl$_2$ (1 mL) for 10 min, filtered and washed with CH$_2$Cl$_2$. The resin was treated again for 10 min with 20% TFA in CH$_2$Cl$_2$ (1 mL), filtered and washed three times with CH$_2$Cl$_2$. The combined filtrates and washings were concentrated. The residue was treated with CH$_3$CN, evaporated and dried i.v. Purification of the crude product by prep. HPLC, method 3, afforded Ex.186 (11 mg, yield: overall 32% based on 139).

Data of Ex.186: $C_{42}H_{42}N_4O_5$ (682.8). LC-MS (method 4a): $R_t$=2.26 (98). $^1$H-NMR (DMSO-d$_6$): 8.38 (d, J=7.0, 2 H), 7.91-7.69 (m, 8 H), 7.54-7.27 (m, 7 H), 7.03 (dd, J=1.5, 8.2, 1 H), 6.86-6.82 (m, 2 H), 4.94 (d, J=12.7, 1 H), 4.19 (t, J=8.6, 1 H), 4.11-3.94 (m, 3 H), 3.71 (dd, J=9.2, 16.5, 1 H), 3.62 (s, 2 H), 3.58 (s, 2 H), 3.08 (m, 1 H), 2.89 (m, 1 H), 2.89 (s, 3 H), 2.5 (m, 1 H, superimposed by DMSO-d signal), 2.30 (m, 1 H), 2.14 (q-like m, 1 H), 1.64-1.49 (m, 2 H), 1.34 (m, 1 H), 1.14 (m, 1 H).

The $^1$H-NMR spectrum is identical with the spectrum of the sample prepared in solution, cf. Table 29

TABLE 20

Examples of Core 01 and Core 02 (Ex. 1-Ex. 2)

| No | | | IUPAC name |
|---|---|---|---|
| Core 01 | R2 | R50 | |
| Ex. 1 | (trimethylsilylethyl carbamate group) | OCH$_2$Ph | 8-benzyl 2-[2-(trimethylsilyl)ethyl] (2S,8S,16aS)-12-fluoro-9-methyl-5,10-dioxo-2,3,5,6,7,8,9,10,16,16a-decahydro-1H-pyrrolo[2,1-c][1,4,9]benzoxadiazacyclododecine-2,8-dicarboxylate |
| Core 02 | R11 | R50 | |
| Ex. 2 | (tert-butyl carbamate group) | OCH$_2$Ph | 9-benzyl 2-(tert-butyl) (9s,17aS)-13-fluoro-10-methyl-6,11-dioxo-3,4,6,7,8,9,10,11,17,17a-decahydropyrazino[2,1-c][1,4,9]benzoxadiazacyclododecine-2,9(1H)-dicarboxylate |

TABLE 21a

Examples of Core 03 (Ex. 3-Ex. 55,)

| No | R50 | R2 | Starting material | General Procedure | Reagent | Purification Method | Yield, (isolated salt) |
|---|---|---|---|---|---|---|---|
| Ex. 3-Ex. 5: cf. experimental description | | | | | | | |
| Ex. 6 | OH | (dimethylaminoacetamide group) | Ex. 52 | H | H$_2$, Pd(OH)$_2$—C*) | Crude product | 70% |

TABLE 21a-continued

Examples of Core 03 (Ex. 3-Ex. 55,)

| No | R50 | R2 | Starting material | General Procedure | Reagent | Purification Method | Yield, (isolated salt) |
|---|---|---|---|---|---|---|---|
| Ex. 7 | methylamino | acetamido | Ex. 25 | L.1.1 | acetic anhydride (5 equiv.) | prep. HPLC, method 1 | 56% |
| Ex. 8 | N,N-dimethylaminoethylamino | acetamido | Ex. 28 | L.1.1 | acetic anhydride (10 equiv.) | prep. HPLC, method 1 | 26% (TFA salt) |
| Ex. 9 | tryptaminyl | acetamido | Ex. 53 | L.2 | tryptamine (1.5 equiv.) HATU (1.5 equiv.) HOAt (1.5 equiv.) i-Pr$_2$NEt (3 equiv.) | FC (CH$_2$Cl$_2$/ MeOH) | 62% |
| Ex. 10 | β-alanyl | acetamido | Ex. 31 | N | LiOH•H$_2$O | prep. HPLC, method 1 | 57% |
| Ex. 11 | N,N-dimethylaminoethylamino | 3-indoleacetamido | Ex. 28 | L.1.3 | 3-indoleacetic acid | FC (CH$_2$Cl$_2$/ MeOH/ aq. NH$_3$) | 58% |
| Ex. 12 | tryptaminyl | 3-indoleacetamido | Ex. 55 | L.1.3 | 3-indoleacetic acid | prep. HPLC, method 1 | 55% |
| Ex. 13 | β-alanyl | 3-indoleacetamido | Ex. 34 | N | LiOH•H$_2$O | prep. HPLC, method 1 | 60% |
| Ex. 14 | methylamino | N,N-dimethylglycinamido | Ex. 25 | **) | N,N-dimethyl glycine | prep. HPLC, method 1 | 22% (TFA salt) |
| Ex. 15 | N,N-dimethylaminoethylamino | N,N-dimethylglycinamido | Ex. 28 | L.1.3 | N,N-dimethyl glycine | prep. HPLC, method 1 | 42% (TFA salt) |

TABLE 21a-continued

Examples of Core 03 (Ex. 3-Ex. 55,)

| No | R50 | R2 | Starting material | General Procedure | Reagent | Purification Method | Yield, (isolated salt) |
|---|---|---|---|---|---|---|---|
| Ex. 16 | tryptamine-derived (indole-ethyl-NH-Me) | N,N-dimethyl-glycinamide | Ex. 55 | L.1.3 | N,N-dimethyl glycine | prep. HPLC, method 1 | 56% (TFA salt) |
| Ex. 17 | HN-CH2CH2-COOH | N,N-dimethyl-glycinamide | Ex. 33 | N | LiOH•H2O | prep. HPLC, method 1 | 77% (TFA salt) |
| Ex. 18 | MeNH- | HOOC-CH2CH2-C(O)NH- | Ex. 25 | L.1.1 | succinic anhydride (1.05 equiv) | prep. HPLC, method 1 | 62% |
| Ex. 19 | Me2N-CH2CH2-NH- | HOOC-CH2CH2-C(O)NH- | Ex. 28 | L.1.1 | succinic anhydride (1.05 equiv) pyridine (49 equiv.) | prep. HPLC, method 1 | 67% (TFA salt) |
| Ex. 20 | HN-CH2CH2-COOH | HOOC-CH2CH2-C(O)NH- | Ex. 32 | N | LiOH•H2O | prep. HPLC, method 1 | 72% |
| Ex. 21 | Me2N-CH2CH2-NMe- | 3-indolyl-CH2-C(O)NH- | Ex. 23 | L.1.3 | 3-indoleacetic acid | prep. HPLC, method 1 | 32% |
| Ex. 22 | Me2N-CH2CH2-NMe- | CH3-C(O)NH- | Ex. 23 | L.1.1 | acetic anhydride (10 equiv) pyridine (120 equiv.) | prep. HPLC, method 1 | 53% (TFA salt) |
| Ex. 23 | Me2N-CH2CH2-NMe- | NH2 | Ex. 29 | J | HCl-dioxane | prep. HPLC, method 1 | 52% (TFA salt) |
| Ex. 24 | MeNH- | Boc-NH- | Ex. 4 | L.2 | methylamine-HCl (10 equiv.), HATU (1.5 equiv.) HOAt (1.5 equiv.) i-Pr2NEt (13 equiv.) | FC (CH2Cl2/MeOH) | 89% |
| Ex. 25 | MeNH- | NH2 | Ex. 24 | J | HCl-dioxane | crude product | 84% (HCl salt) |

TABLE 21a-continued

Examples of Core 03 (Ex. 3-Ex. 55,)

| No | R50 | R2 | Starting material | General Procedure | Reagent | Purification Method | Yield, (isolated salt) |
|---|---|---|---|---|---|---|---|
| Ex. 26 | (structure) | (structure) | Ex. 4 | L.2 | β-alaninemethylester hydrochloride | FC (CH$_2$Cl$_2$/MeOH) | 97% |
| Ex. 27 | (structure) | (structure) | Ex. 4 | L.2 | N,N-dimethyl-ethylenediamine | FC (CH$_2$Cl$_2$/MeOH/aq. NH$_3$) | 83% |
| Ex. 28 | (structure) | NH$_2$ | Ex. 27 | J | HCl-dioxane | (crude product) | 90% (HCl salt) |
| Ex. 29 | (structure) | (structure) | Ex. 4 | L.2 | N,N,N'-trimethyl-ethylenediamine | FC (CH$_2$Cl$_2$/MeOH/aq. NH$_3$) | 74% |
| Ex. 30 | (structure) | (structure) | Ex. 4 | L.2 | tryptamine | FC (CH$_2$Cl$_2$/MeOH) | 81% |
| Ex. 31 | (structure) | (structure) | Ex. 51 | L.1.1 | acetic anhydride (5 equiv) | prep. HPLC, method 1 | 72% |
| Ex. 32 | (structure) | (structure) | Ex. 51 | L.1.1 | succinic anhydride (1.05 equiv) | prep. HPLC, method 1 | 68% |
| Ex. 33 | (structure) | (structure) | Ex. 51 | L.1.3 | N,N-dimethyl glycine | prep. HPLC, method 1 | 64% (TFA salt) |
| Ex. 34 | (structure) | (structure) | Ex. 51 | L.1.3 | 3-indoleacetic acid | prep. HPLC, method 1 | 24% |
| Ex. 35 | (structure) | (structure) | Ex. 23 | L.1.1 | succinic anhydride (1.05 equiv) | prep. HPLC, method 1 | 63% (TFA salt) |

TABLE 21a-continued

Examples of Core 03 (Ex. 3-Ex. 55.)

| No | R50 | R2 | Starting material | General Procedure | Reagent | Purification Method | Yield, (isolated salt) |
|---|---|---|---|---|---|---|---|
| Ex. 36 | N,N-dimethylaminoethyl-N-methyl | N,N-dimethylglycinamide | Ex. 23 | L.1.3 | N,N-dimethyl glycine | prep. HPLC, method 1 | 40% (TFA salt) |
| Ex. 37 | pyrrolidinyl | acetamide | Ex. 42 | L.1.1 | acetic anhydride (5 equiv) | prep. HPLC, method 1 | 61% |
| Ex. 38 | pyrrolidinyl | 3-indolyl acetamide | Ex. 42 | L.1.3 | 3-indoleacetic acid | prep. HPLC, method 1 | 43% |
| Ex. 39 | pyrrolidinyl | N,N-dimethylglycinamide | Ex. 42 | L.1.3 | N,N-dimethyl glycine | prep. HPLC, method 1 | 56% (TFA salt) |
| Ex. 40 | pyrrolidinyl | succinamide | Ex. 42 | L.1.1 | succinic anhydride (1.05 equiv) | prep. HPLC, method 1 | 37% |
| Ex. 41 | pyrrolidinyl | Boc-NH | Ex. 4 | L.2 | pyrrolidine | FC (CH$_2$Cl$_2$/MeOH) | 76% |
| Ex. 42 | pyrrolidinyl | NH$_2$ | Ex. 41 | J | HCl-dioxane | (crude product) | 90% (HCl salt) |
| Ex. 43 | pyrrolidinyl | N,N-diethylamino | Ex. 42 | M | acetaldehyde | prep. HPLC, method 1 | 67% (TFA salt) |
| Ex. 44 | methylamino | N,N-diethylamino | Ex. 25 | M | acetaldehyde | prep. HPLC, method 1 | 33% (TFA salt) |
| Ex. 45 | methylamino | 2-naphthyl acetamide | Ex. 25 | L.1.3 | 2-naphthylacetic acid | prep. HPLC, method 1 | 46% |
| Ex. 46 | N,N-dimethylaminoethylamino | 2-naphthyl carboxamide | Ex. 28 | L.1.1 | 2-naphthoyl chloride (3.6 equiv.) | FC (CH$_2$Cl$_2$/MeOH/aq. NH$_3$) | 85% |

TABLE 21a-continued

Examples of Core 03 (Ex. 3-Ex. 55,)

| No | R50 | R2 | Starting material | General Procedure | Reagent | Purification Method | Yield, (isolated salt) |
|---|---|---|---|---|---|---|---|
| Ex. 47 | (dimethylaminoethylamino) | 1-naphthamide | Ex. 28 | L.1.2 | 1-naphthoic acid | FC (CH$_2$Cl$_2$/ MeOH/ aq. NH$_3$) | 85% |
| Ex. 48 | (dimethylaminoethylamino) | 2-naphthylacetamide | Ex. 28 | L.1.2 | 2-naphthylacetic acid | FC (CH$_2$Cl$_2$/ MeOH/ aq. NH$_3$) | 83% |
| Ex. 49 | (dimethylaminoethylamino) | 1-naphthylacetamide | Ex. 28 | L.1.2 | 1-naphthylacetic acid | FC (CH$_2$Cl$_2$/ MeOH/ aq. NH$_3$) | 83% |
| Ex. 50 | (dimethylaminoethylamino) | 3-CF$_3$-benzamide | Ex. 28 | L.1.1 | 3-(trifluoromethyl)-benzoyl chloride (4 equiv.) | FC (CH$_2$Cl$_2$/ MeOH/ aq. NH$_3$) | 24% |
| Ex. 51 | H-N-CH$_2$CH$_2$-C(O)-OCH$_3$ | NH$_2$ | Ex. 26 | J | HCl-dioxane | crude product | 93% (HCl salt) |
| Ex. 52 | OCH$_2$Ph | N,N-dimethylglycinamide | Ex. 5 | L.1.3 | N,N-dimethylglycine (1.7 equiv.) HATU (1.0 equiv.) HOAt (2.0 equiv.) i-Pr$_2$NEt (4.0 equiv.) | prep. HPLC, method 1 | 88% (TFA salt) |
| Ex. 53 | OCH$_2$Ph | acetamide | Ex. 5 | L.1.1 | Acetic anhydride (10 equiv.) pyridine/CH$_2$Cl$_2$ 1:1 | FC | 70% |
| Ex. 54 | OH | acetamide | Ex. 54 | H | H$_2$, Pd(OH)$_2$—C | crude product | 92% |
| Ex. 55 | tryptamine-N | NH$_2$ | Ex. 30 | J | HCl-dioxane | FC (CH$_2$Cl$_2$/ MeOH/ aq. NH$_3$) | 42% |

*)Prior to debenzylation, the starting material Ex. 52•TFA was converted into the free base (CHCl$_3$, aq. Na$_2$CO$_3$ soln.)
**)The amide coupling reaction was performed at room temperature with N,N-dimethyl glycine (2.2 equiv.) in CH$_2$Cl$_2$, in the presence of T3P (50% in EtOAc; 2.2 equiv.) and i-Pr$_2$NEt (3 equiv.).

267
268
TABLE 21b
Examples of Core 03 (Ex. 3-Ex. 55,)
| No | R50 | R2 | Formula | Monoisotopic Mass | Rt (purity at 220 nm) | [M + H]+ found | LC-MS-Method |
|---|---|---|---|---|---|---|---|
| Ex. 3-Ex. 5: cf. experimental description | | | | | | | |
| Ex. 6 | OH | 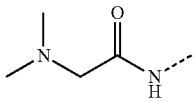 | C25H34FN5O7 | 535.2 | 1.05 (99) | 536.3 | Method 2 |
| Ex. 7 |  | 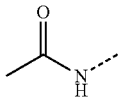 | C24H32FN5O6 | 505.2 | 1.21 (87) | 506.3 | Method 2 |
| Ex. 9 | 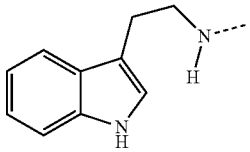 | 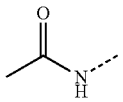 | C33H39FN6O6 | 634.3 | 2.12 (99) | 635.4 | Method 1a |
| Ex. 10 | 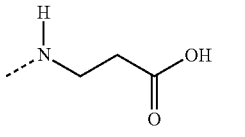 | 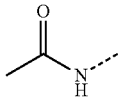 | C26H34FN5O8 | 563.2 | 1.20 (91) | 564.2 | Method 2 |
| Ex. 11 | 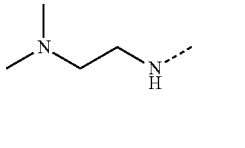 | 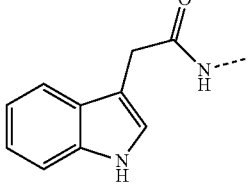 | C35H44FN7O6 | 677.3 | 1.34 (93) | 678.4 | Method 2 |
| Ex. 12 | 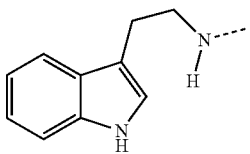 |  | C41H44FN7O6 | 749.3 | 1.73 (92) | 750.4 | Method 2 |
| Ex. 13 | 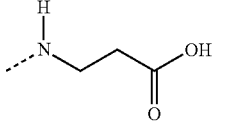 | 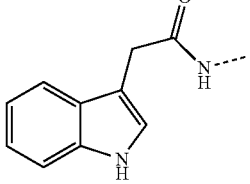 | C34H39FN6O8 | 678.3 | 1.45 (87) | 679.3 | Method 2 |
| Ex. 14 |  | 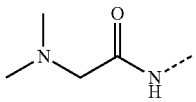 | C26H37FN6O6 | 548.3 | 1.08 (88) | 549.3 | Method 2 |
| Ex. 15 | 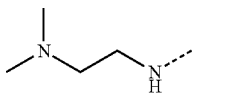 | 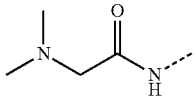 | C29H44FN7O6 | 605.3 | 0.99 (96) | 606.4 | Method 2 |

TABLE 21b-continued

Examples of Core 03 (Ex. 3-Ex. 55.)

| No | R50 | R2 | Formula | Monoisotopic Mass | Rt (purity at 220 nm) | [M + H]+ found | LC-MS-Method |
|---|---|---|---|---|---|---|---|
| Ex. 16 | tryptamine-derived group | N,N-dimethylglycinamide | C35H44FN7O6 | 677.3 | 1.41 (97) | 678.4 | Method 2 |
| Ex. 17 | β-alanine | N,N-dimethylglycinamide | C28H39FN6O8 | 606.3 | 1.09 (94) | 607.3 | Method 2 |
| Ex. 18 | methylamine | succinamide | C26H34FN5O8 | 563.2 | 1.20 (88) | 564.3 | Method 2 |
| Ex. 19 | N,N-dimethylethylenediamine | succinamide | C29H41FN6O8 | 620.3 | 1.08 (100) | 621.3 | Method 2 |
| Ex. 20 | β-alanine | succinamide | C28H36FN5O10 | 621.2 | 1.18 (91) | 622.2 | Method 2 |
| Ex. 21 | N,N-dimethylethylenediamine | indole-acetamide | C36H46FN7O6 | 691.4 | 1.35 (88) | 692.4 | Method 2 |
| Ex. 22 | N,N,N'-trimethylethylenediamine | acetamide | C28H41FN6O6 | 576.3 | 1.12 (96) | 577.4 | Method 2 |
| Ex. 23 | N,N,N'-trimethylethylenediamine | NH2 | C26H39FN6O5 | 534.3 | 0.96 (88) | 535.4 | Method 2 |
| Ex. 24 | methylamine | Boc-carbamate | C27H38FN5O7 | 563.3 | 1.54 (93) | 564.3 | Method 2 |
| Ex. 25 | methylamine | NH2 | C22H30FN5O5 | 463.2 | 1.06 (91) | 464.2 | Method 2 |
| Ex. 26 | β-alanine methyl ester | Boc-carbamate | C30H42FN5O9 | 635.3 | 1.61 (87) | 636.4 | Method 2 |

TABLE 21b-continued

Examples of Core 03 (Ex. 3-Ex. 55.)

| No | R50 | R2 | Formula | Monoisotopic Mass | Rt (purity at 220 nm) | [M + H]+ found | LC-MS-Method |
|---|---|---|---|---|---|---|---|
| Ex. 27 | (dimethylaminoethylamino) | Boc-NH | C30H45FN6O7 | 620.3 | 1.53 (92) | 621.3 | Method 4a |
| Ex. 28 | (dimethylaminoethylamino) | NH2 | C25H37FN6O5 | 520.3 | 0.93 (94) | 521.3 | Method 2 |
| Ex. 29 | (dimethylamino-N-methyl-ethylamino) | Boc-NH | C31H47FN6O7 | 634.4 | 1.41 (96) | 635.4 | Method 2 |
| Ex. 30 | (tryptaminyl) | Boc-NH | C36H45FN6O7 | 692.3 | 1.79 (99) | 693.4 | Method 2 |
| Ex. 31 | (methyl β-alaninate) | AcNH | C27H36FN5O8 | 577.3 | 1.32 (90) | 578.3 | Method 2 |
| Ex. 32 | (methyl β-alaninate) | HOOC-CH2CH2-C(O)NH | C29H38FN5O10 | 635.3 | 1.30 (83) | 636.2 | Method 2 |
| Ex. 33 | (methyl β-alaninate) | Me2N-CH2-C(O)NH | C29H41FN6O8 | 620.3 | 1.18 (100) | 621.3 | Method 2 |
| Ex. 34 | (methyl β-alaninate) | indol-3-yl-CH2-C(O)NH | C35H41FN6O8 | 692.3 | 1.56 (90) | 693.3 | Method 2 |
| Ex. 35 | (dimethylaminoethylamino) | HOOC-CH2CH2-C(O)NH | C30H43FN6O8 | 634.3 | 1.10 (94) | 635.3 | Method 2 |
| Ex. 36 | (dimethylaminoethylamino) | Me2N-CH2-C(O)NH | C30H46FN7O6 | 619.4 | 1.00 (91) | 620.3 | Method 2 |
| Ex. 37 | (pyrrolidin-1-yl) | AcNH | C27H36FN5O6 | 545.3 | 1.36 (93) | 546.3 | Method 2 |

TABLE 21b-continued
Examples of Core 03 (Ex. 3-Ex. 55,)
| No | R50 | R2 | Formula | Monoisotopic Mass | Rt (purity at 220 nm) | [M + H]+ found | LC-MS-Method |
|---|---|---|---|---|---|---|---|
| Ex. 38 | 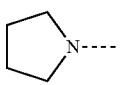 | 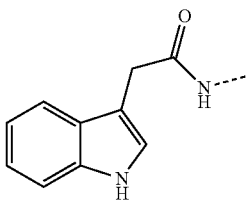 | C35H41FN6O6 | 660.3 | 1.60 (94) | 661.3 | Method 2 |
| Ex. 39 | 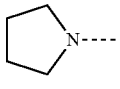 | 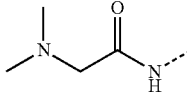 | C29H41FN6O6 | 588.3 | 1.19 (94) | 589.3 | Method 2 |
| Ex. 40 | 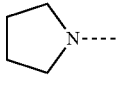 | 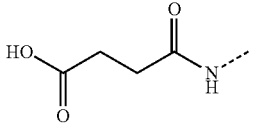 | C29H38FN5O8 | 603.3 | 1.33 (94) | 604.3 | Method 2 |
| Ex. 41 | 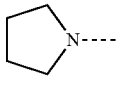 | 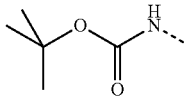 | C30H42FN5O7 | 603.3 | 1.67 (90) | 604.3 | Method 2 |
| Ex. 42 | 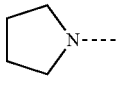 | NH$_2$ | C25H34FN5O5 | 503.3 | 1.17 (92) | 504.2 | Method 2 |
| Ex. 43 | 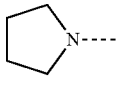 | 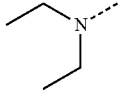 | C29H42FN5O5 | 559.3 | 1.26 (96) | 560.3 | Method 2 |
| Ex. 44 | 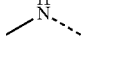 | 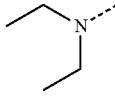 | C26H38FN5O5 | 519.3 | 1.13 (97) | 520.3 | Method 2 |
| Ex. 45 | 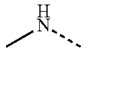 | 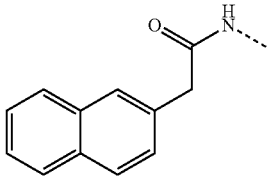 | C34H38FN5O6 | 631.3 | 1.65 (97) | 632.2 | Method 2 |
| Ex. 46 | 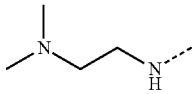 | 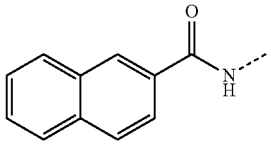 | C36H43FN6O6 | 674.3 | 1.49 (97) | 675.5 | Method 2 |
| Ex. 47 | 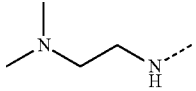 | 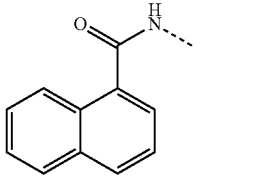 | C36H43FN6O6 | 674.3 | 1.43 (96) | 675.5 | Method 2 |

TABLE 21b-continued

Examples of Core 03 (Ex. 3-Ex. 55.)

| No | R50 | R2 | Formula | Monoisotopic Mass | Rt (purity at 220 nm) | [M + H]+ found | LC-MS-Method |
|---|---|---|---|---|---|---|---|
| Ex. 48 | 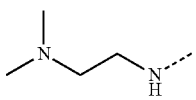 | 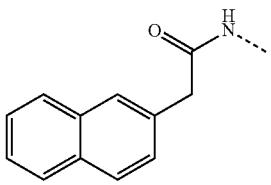 | C37H45FN6O6 | 688.3 | 1.50 (95) | 689.5 | Method 2 |
| Ex. 49 | 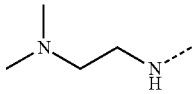 | 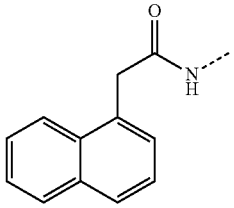 | C37H45FN6O6 | 688.3 | 1.48 (95) | 689.5 | Method 2 |
| Ex. 50 | 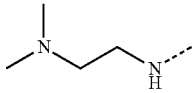 | 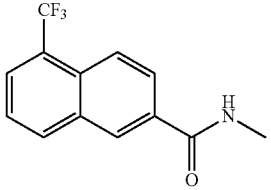 | C33H40F4N6O6 | 692.3 | 1.49 (97) | 693.5 | Method 2 |
| Ex. 51 | 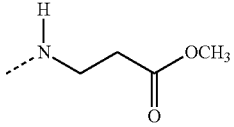 | NH2 | C25H34FN5O7 | 535.2 | 1.05 | 536.3 | Method 9c |
| Ex. 52 | OCH2Ph | 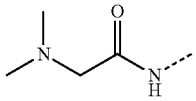 | C32H40FN5O7 | 625.3 | 1.47 | 626.3 | Method 9c |
| Ex. 53 | OCH2Ph | 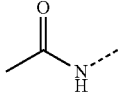 | C30H35FN4O7 | 582.3 | 1.65 | 582.9 | Method 9c |
| Ex. 54 | OH | 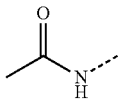 | C23H29FN4O7 | 492.2 | 1.04 | 493.1 | Method 9c |
| Ex. 55 | 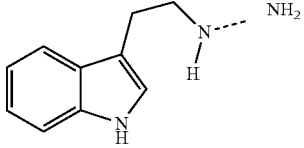 | NH2 | C31H37FN6O5 | 592.3 | 1.38 | 593.0 | Method 9c |

TABLE 21c

Examples of Core 03 (Ex. 3-Ex.55.)

| No | R50 | R2 | IUPAC name |
|---|---|---|---|
| Ex. 3 | OCH2Ph | 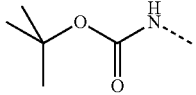 | benzyl (2S,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |

TABLE 21c-continued

Examples of Core 03 (Ex. 3-Ex.55,)

| No | R50 | R2 | IUPAC name |
|---|---|---|---|
| Ex. 4 | OH | (tert-butoxycarbonyl)amino CH2 group | (2S,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 5 | OCH₂Ph | NH₂ | benzyl (2S,11S,19aS)-2-amino-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex. 6 | OH | 2-(dimethylamino)acetamido | (2S,11S,19aS)-2-{[2-(dimethylamino)acetyl]amino}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 7 | methylamino | acetamido | (2S,11S,19aS)-2-(acetylamino)-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 8 | 2-(dimethylamino)ethylamino | acetamido | (2S,11S,19aS)-2-(acetylamino)-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 9 | 2-(1H-indol-3-yl)ethylamino | acetamido | (2S,11S,19aS)-2-(acetylamino)-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 10 | 2-carboxyethylamino | acetamido | 3-({[(2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl]carbonyl}amino)propanoic acid |
| Ex. 11 | 2-(dimethylamino)ethylamino | 2-(1H-indol-3-yl)acetamido | (2S,11S,19aS)-N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 12 | 2-(1H-indol-3-yl)ethylamino | 2-(1H-indol-3-yl)acetamido | (2S,11S,19aS)-15-fluoro-2-{[2-(1H-indol-3-yl)acetyl]amino}-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 13 | 2-carboxyethylamino | 2-(1H-indol-3-yl)acetamido | 3-{[(((2S,11S,19aS)-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl)carbonyl]amino}propanoic acid |

TABLE 21c-continued

Examples of Core 03 (Ex. 3-Ex.55,)

| No | R50 | R2 | IUPAC name |
|---|---|---|---|
| Ex. 14 | (methylamino) | [2-(dimethylamino)acetyl]amino | (2S,11S,19aS)-2-{[2-(dimethylamino)acetyl]amino}-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 15 | [2-(dimethylamino)ethyl]amino | [2-(dimethylamino)acetyl]amino | (2S,11S,19aS)-2-{[2-(dimethylamino)acetyl]amino}-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 16 | 2-(1H-indol-3-yl)ethylamino | [2-(dimethylamino)acetyl]amino | (2S,11S,19aS)-2-{[2-(dimethylamino)acetyl]amino}-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 17 | 3-(methylamino)propanoic acid | [2-(dimethylamino)acetyl]amino | 3-{[((2S,11S,19aS)-2-{[2-(dimethylamino)acetyl]amino}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl)carbonyl]amino}propanoic acid |
| Ex. 18 | (methylamino) | 4-oxo-4-amino-butanoic acid | 4-({(2S,11S,19aS)-15-fluoro-7,12-dimethyl-11-[(methylamino)carbonyl]-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl}amino)-4-oxobutanoic acid |
| Ex. 19 | [2-(dimethylamino)ethyl]amino | 4-oxo-4-amino-butanoic acid | 4-{[(2S,11S,19aS)-11-({[2-(dimethylamino)ethyl]amino}carbonyl)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]amino}-4-oxobutanoic acid |
| Ex. 20 | 3-(methylamino)propanoic acid | 4-oxo-4-amino-butanoic acid | 4-[((2S,11S,19aS)-15-fluoro-11-{[(3-hydroxy-3-oxopropyl)amino]carbonyl}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)amino]-4-oxobutanoic acid |
| Ex. 21 | [2-(dimethylamino)ethyl]amino | [2-(1H-indol-3-yl)acetyl]amino | (2S,11S,19aS)-N-[2-(dimethylamino)ethyl]-15-fluoro-2-{[2-(1H-indol-3-yl)acetyl]amino}-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 22 | [2-(dimethylamino)ethyl]amino | acetylamino | (2S,11S,19aS)-2-(acetylamino)-N-[2-(dimethylamino)ethyl]-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 23 | [2-(dimethylamino)ethyl]amino | NH$_2$ | (2S,11S,19aS)-2-amino-N-[2-(dimethylamino)ethyl]-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 24 | (methylamino) | tert-butoxycarbonylamino | tert-butyl N-{(2S,11S,19aS)-15-fluoro-7,12-dimethyl-11-[(methylamino)carbonyl]-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl}carbamate |

TABLE 21c-continued

Examples of Core 03 (Ex. 3-Ex.55,)

| No | R50 | R2 | IUPAC name |
|---|---|---|---|
| Ex. 25 | H, N-methyl | NH₂ | (2S,11S,19aS)-2-amino-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 26 | methyl 3-(N-H)propanoate | Boc-NH | methyl 3-[({(2S,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl}carbonyl)amino]propanoate |
| Ex. 27 | Me₂N-CH₂CH₂-NH- | Boc-NH | tert-butyl N-[(2S,11S,19aS)-11-({[2-(dimethylamino)ethyl]amino}carbonyl)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 28 | Me₂N-CH₂CH₂-NH- | NH₂ | (2S,11S,19aS)-2-amino-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 29 | Me₂N-CH₂CH₂-N(Me)- | Boc-NH | tert-butyl N-(2S,11S,19aS)-11-{[[2-(dimethylamino)ethyl]methyl)amino]carbonyl}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex. 30 | indol-3-yl-CH₂CH₂-NH- | Boc-NH | tert-butyl N-[(2S,11S,19aS)-15-fluoro-11-({[2-(1H-indol-3-yl)ethyl]amino}carbonyl)-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 31 | methyl 3-(NH)propanoate | Ac-NH | methyl 3-({[(2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl]carbonyl}amino)propanoate |
| Ex. 32 | methyl 3-(NH)propanoate | HOOC-CH₂CH₂-C(O)NH- | 4-[((2S,11S,19aS)-15-fluoro-11-{[(3-methoxy-3-oxopropyl)amino]carbonyl}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)amino]-4-oxobutanoic acid |
| Ex. 33 | methyl 3-(NH)propanoate | Me₂N-CH₂-C(O)NH- | methyl 3-{[((2S,11S,19aS)-2-{[2-(dimethylamino)acetyl]amino}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl)carbonyl]amino}propanoate |
| Ex. 34 | methyl 3-(NH)propanoate | indol-3-yl-CH₂-C(O)NH- | methyl 3-{[((2S,11S,19aS)-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl)carbonyl]amino}propanoate |
| Ex. 35 | Me₂N-CH₂CH₂-N(Me)- | HOOC-CH₂CH₂-C(O)NH- | 4-[((2S,11S,19aS)-11-{[[2-(dimethylamino)ethyl](methyl)amino]carbonyl}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)amino]-4-oxobutanoic acid |

TABLE 21c-continued

Examples of Core 03 (Ex. 3-Ex.55,)

| No | R50 | R2 | IUPAC name |
|---|---|---|---|
| Ex. 36 | 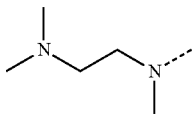 | 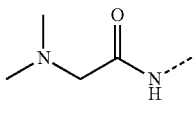 | (2S,11S,19aS)-2-{[2-(dimethylamino)acetyl]amino}-N-[2-(dimethylamino)ethyl]-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 37 | 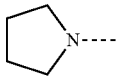 | 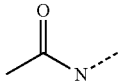 | N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]acetamide |
| Ex. 38 | 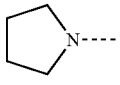 | 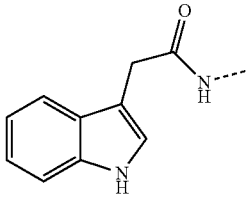 | N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(1H-indol-3-yl)acetamide |
| Ex. 39 | 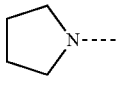 | 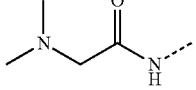 | N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(dimethylamino)acetamide |
| Ex. 40 | 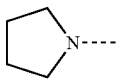 | 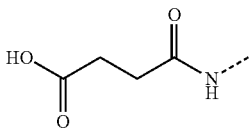 | 4-{[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]amino}-4-oxobutanoic acid |
| Ex. 41 | 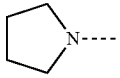 | 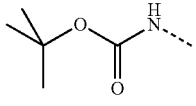 | tert-butyl N-[(2S,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 42 | 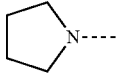 | NH$_2$ | (2S,11S,19aS)-2-amino-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12]benzoxatriazacyclopentadecine-5,8,13-trione |
| Ex. 43 | 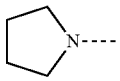 | 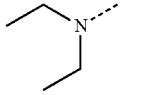 | (2S,11S,19aS)-2-(diethylamino)-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12]benzoxatriazacyclopentadecine-5,8,13-trione |
| Ex. 44 |  | 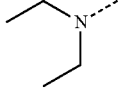 | (2S,11S,19aS)-2-(diethylamino)-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 45 |  | 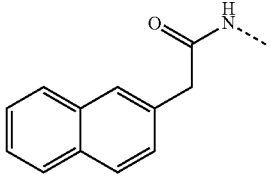 | (2S,11S,19aS)-15-fluoro-N,7,12-trimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 46 | 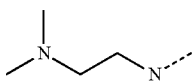 | 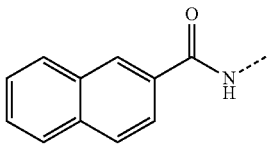 | (2S,11S,19aS)-N-[2-(dimethylamino)ethyl]-15-fluoro-7,12-dimethyl-2-(2-naphthoylamino)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 21c-continued

Examples of Core 03 (Ex. 3-Ex.55,)

| No | R50 | R2 | IUPAC name |
|---|---|---|---|
| Ex. 47 | 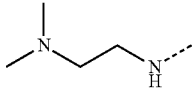 | 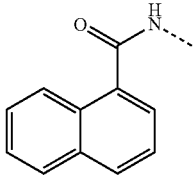 | (2S,11S,19aS)-N-[2-(dimethylamino)ethyl]-15-fluoro-7,12-dimethyl-2-(1-naphthoylamino)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 48 | 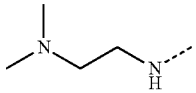 | 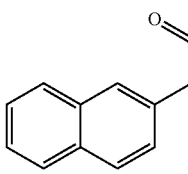 | (2S,11S,19aS)-N-[2-(dimethylamino)ethyl]-15-fluoro-7,12-dimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 49 | 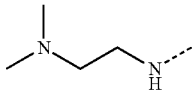 | 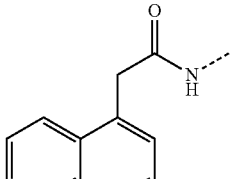 | (2S,11S,19aS)-N-[2-(dimethylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 50 | 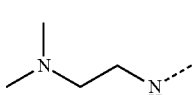 | 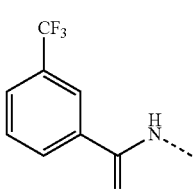 | (2S,11S,19aS)-N-[2-(dimethylamino)ethyl]-15-fluoro-7,12-dimethyl-5,8,13-trioxo-2-{[3-(trifluoromethyl)benzoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 51 | 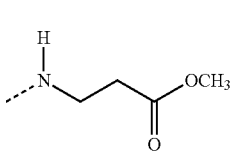 | $NH_2$ | methyl 3-({[(2S,11S,19aS)-2-amino-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-11-yl]carbonyl}amino)propanoate |
| Ex. 52 | OCH$_2$Ph | 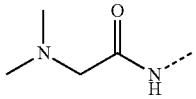 | benzyl (2S,11S,19aS)-2-{[2-(dimethylamino)acetyl]amino}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex. 53 | OCH$_2$Ph | 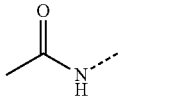 | benzyl (2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex. 54 | OH | 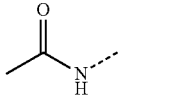 | (2S,11S,19aS)-2-(acetylamino)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 55 | 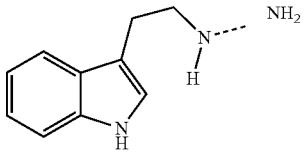 | $NH_2$ | (2S,11S,19aS)-2-amino-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 22a

Examples of Core 04 (Ex. 56-Ex. 84,)

| No | R50 | R2 | Starting material | General Procedure | Reagent | Purification Method | Yield, (isolated salt) |
|---|---|---|---|---|---|---|---|
| Ex. 56-Ex 57: cf. experimental description | | | | | | | |
| Ex. 58 | dimethylaminoethyl-methylamino | Boc-NH- | Ex. 57 | L.2 | N,N,N'-trimetylethylenediamine | FC (CH$_2$Cl$_2$/MeOH/aq. NH$_3$) | 86% |
| Ex. 59 | 2-naphthylmethylamino | Boc-NH- | Ex. 57 | L.2 | 2-naphthyl-methylamine | FC (CH$_2$Cl$_2$/MeOH) | 91% |
| Ex. 60 | pyrrolidin-1-yl | Boc-NH- | Ex. 57 | L.2 | pyrrolidine | FC (CH$_2$Cl$_2$/MeOH) | 79% |
| Ex. 61 | pyridin-4-ylmethylamino | Boc-NH- | Ex. 57 | L.2 | 4-(aminomethyl) pyridine | FC (CH$_2$Cl$_2$/MeOH) | 81% |
| Ex. 62 | dimethylaminoethyl-methylamino | NH$_2$ | Ex. 58 | J | HCl-dioxane | crude product | 98% (HCl salt) |
| Ex. 63 | 2-naphthylmethylamino | NH$_2$ | Ex. 59 | J | HCl-dioxane | crude product | 76% (HCl salt) |
| Ex. 64 | pyrrolidin-1-yl | NH$_2$ | Ex. 60 | J | HCl-dioxane | crude product | 94% (HCl salt) |
| Ex. 65 | pyridin-4-ylmethylamino | NH$_2$ | Ex. 61 | J | HCl-dioxane | crude product | 91% (HCl salt) |
| Ex. 66 | dimethylaminoethyl-methylamino | 2-naphthylacetamido | Ex. 62 | L.1.3 | 2-naphthylacetic acid | prep. HPLC, method 1 | 67% (TFA salt) |
| Ex. 67 | dimethylaminoethyl-methylamino | 3-(pyridin-4-yl)propanamido | Ex. 62 | L.1.2 | 3-(pyridine-4-yl)propanoic acid | prep. HPLC, method 2 | 56% |

TABLE 22a-continued

Examples of Core 04 (Ex. 56-Ex. 84,)

| No | R50 | R2 | Starting material | General Procedure | Reagent | Purification Method | Yield, (isolated salt) |
|---|---|---|---|---|---|---|---|
| Ex. 68 | | | Ex. 62 | L.1.2 | 1-naphthylacetic acid (1.5 equiv.) | prep. HPLC, method 1 | 24% (TFA salt) |
| Ex. 69 | | | Ex. 63 | L.1.1 | acetic anhydride (5 equiv.) | prep. HPLC, method 1 | 75% |
| Ex. 70 | | | Ex. 63 | L.1.3 | 1-pyrrolidinacetic acid | prep. HPLC, method 1 | 62% (TFA salt) |
| Ex. 71 | | | Ex. 63 | L.1.2 | 3-(pyridine-4-yl)propanoic acid | prep. HPLC, method 1 | 22% (TFA salt) |
| Ex. 72 | | | Ex. 64 | L.1.3 | 2-naphthylacetic acid | prep. HPLC, method 2 | 51% |
| Ex. 73 | | | Ex. 64 | L.1.2 | 1-pyrrolidinacetic acid (1.7 equiv.) | prep. HPLC, method 1 | 39% (TFA salt) |
| Ex. 74 | | | Ex. 64 | L.1.2 | 3-(pyridine-4-yl)propanoic acid | prep. HPLC, method 2 | 29% |
| Ex. 75 | | | Ex. 65 | L.1.3 | 2-naphthylacetic acid | prep. HPLC, method 1 | 37% (TFA salt) |
| Ex. 76 | | | Ex. 65 | L.1.2 | 1-pyrrolidinacetic acid (1.7 equiv.) | prep. HPLC, method 2 | 45% |

TABLE 22a-continued

Examples of Core 04 (Ex. 56-Ex. 84,)

| No | R50 | R2 | Starting material | General Procedure | Reagent | Purification Method | Yield, (isolated salt) |
|---|---|---|---|---|---|---|---|
| Ex. 77 | pyridin-4-ylmethylamino | 3-(pyridin-3-yl)propanamide | Ex. 65 | L.1.2 | 3-(pyridine-4-yl)propanoic acid | prep. HPLC, method 2 | 45% |
| Ex. 78 | 2-(dimethylamino)ethylamino | pentanamide | Ex. 62 | L.1.1 | valeroyl chloride (1.6 equiv.) | prep. HPLC, method 1 | 56% |
| Ex. 79 | naphthalen-2-ylmethylamino | pentanamide | Ex. 63 | L.1.1 | valeroyl chloride (1.6 equiv.) | prep. HPLC, method 1 | 77% |
| Ex. 80 | pyrrolidin-1-yl | pentanamide | Ex. 64 | L.1.1 | valeroyl chloride (1.3 equiv.) | prep. HPLC, method 1 | 64% |
| Ex. 81 | 2-(dimethylamino)ethylamino | NH$_2$ | Ex. 84 | J | HCl-dioxane | crude product | 99% (HCl salt) |
| Ex. 82 | 2-(dimethylamino)ethylamino | 2-(1H-indol-3-yl)acetamide | Ex. 81 | L.1.3 | 3-indoleacetic acid (1.5 equiv.) HATU (1.5 equiv.) HOAt (1.5 equiv.) i-Pr$_2$NEt (5 equiv.) | prep. HPLC, method 1, then FC (CH$_2$Cl$_2$/ MeOH/aq. NH$_3$) | 15% |
| Ex. 83 | 2-(dimethylamino)ethylamino | 2-(naphthalen-2-yl)acetamide | Ex. 81 | L.1.3 | 2-naphthylacetic acid (1.2 equiv.) | FC (CH$_2$Cl$_2$/ MeOH/aq. NH$_3$), then prep. HPLC, method 1 | 58% |
| Ex. 84 | 2-(dimethylamino)ethylamino | tert-butyl carbamate | Ex. 57 | L.2 | 2-dimethylaminoethylamine | FC (CH$_2$Cl$_2$/ MeOH) | 89% |

TABLE 22b

Examples of Core 04 (Ex. 56-Ex. 84,)

| No | R50 | R2 | Formula | Monoisotopic Mass | Rt (purity at 220 nm) | [M + H]$^+$ found | LC-MS-Method |
|---|---|---|---|---|---|---|---|
| Ex. 56-Ex. 57: cf. experimental description | | | | | | | |
| Ex. 58 | 2-(dimethylamino)ethylamino | tert-butyl carbamate | C31H47FN6O7 | 634.4 | 1.44 (91) | 635.5 | Method 2 |

TABLE 22b-continued
Examples of Core 04 (Ex. 56-Ex. 84,)
| No | R50 | R2 | Formula | Monoisotopic Mass | Rt (purity at 220 nm) | [M + H]+ found | LC-MS-Method |
|---|---|---|---|---|---|---|---|
| Ex. 59 | 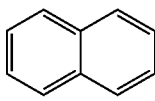 | 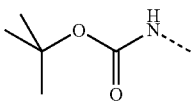 | C37H44FN5O7 | 689.3 | 1.89 (87) | 690.5 | Method 2 |
| Ex. 60 | 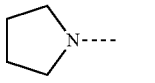 | 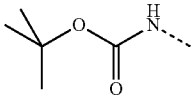 | C30H42FN5O7 | 603.3 | 1.67 (84) | 604.4 | Method 2 |
| Ex. 61 | 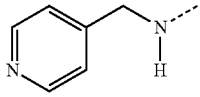 | 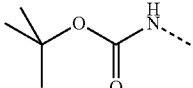 | C32H41FN6O7 | 640.3 | 1.42 (92) | 641.4 | Method 2 |
| Ex. 62 | 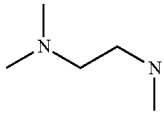 | NH$_2$ | C26H39FN6O5 | 534.3 | 0.97 (91) | 535.4 | Method 2 |
| Ex. 63 | 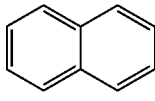 | NH$_2$ | C32H36FN5O5 | 589.3 | 1.53 (95) | 590.4 | Method 2 |
| Ex. 64 | 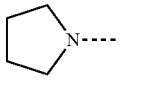 | NH$_2$ | C25H34FN5O5 | 503.3 | 1.23 (82) | 504.3 | Method 2 |
| Ex. 65 | 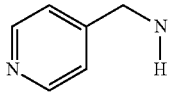 | NH$_2$ | C27H33FN6O5 | 540.3 | 0.97 (97) | 541.4 | Method 2 |
| Ex. 66 | 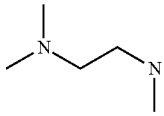 | 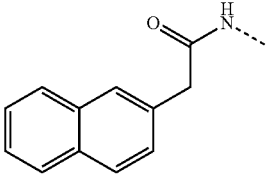 | C38H47FN6O6 | 702.4 | 1.51 (97) | 703.5 | Method 2 |
| Ex. 67 | 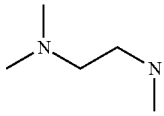 | 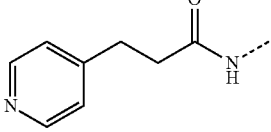 | C34H46FN7O6 | 667.4 | 1.08 (94) | 668.5 | Method 2 |
| Ex. 68 | 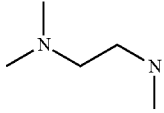 | 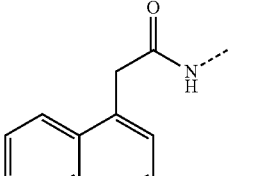 | C38H47FN6O6 | 702.4 | 1.51 (88) | 703.5 | Method 2 |
| Ex. 69 | 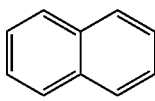 | 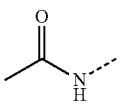 | C34H38FN5O6 | 631.3 | 1.66 (90) | 632.3 | Method 2 |

TABLE 22b-continued
Examples of Core 04 (Ex. 56-Ex. 84,)
| No | R50 | R2 | Formula | Monoisotopic Mass | Rt (purity at 220 nm) | [M + H]+ found | LC-MS-Method |
|---|---|---|---|---|---|---|---|
| Ex. 70 | 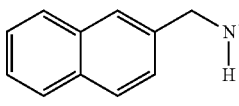 | 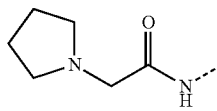 | C38H45FN6O6 | 700.3 | 1.56 (95) | 701.5 | Method 2 |
| Ex. 71 | 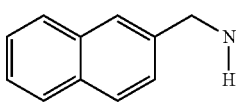 | 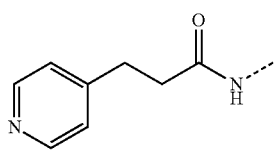 | C40H43FN6O6 | 722.3 | 1.55 (93) | 723.5 | Method 2 |
| Ex. 72 | 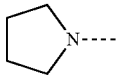 | 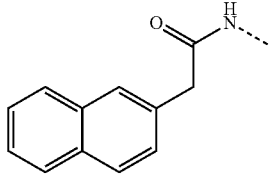 | C37H42FN5O6 | 671.3 | 1.73 (87) | 672.4 | Method 2 |
| Ex. 73 | 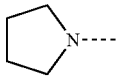 | 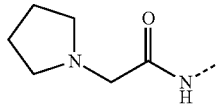 | C31H43FN6O6 | 614.3 | 1.28 (90) | 615.4 | Method 2 |
| Ex. 74 | 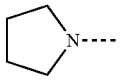 | 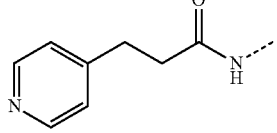 | C33H41FN6O6 | 636.3 | 1.29 (91) | 637.4 | Method 2 |
| Ex. 75 | 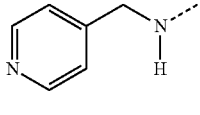 | 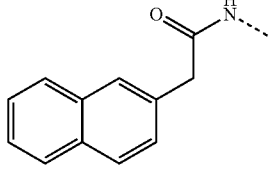 | C39H41FN6O6 | 708.3 | 1.50 (92) | 709.4 | Method 2 |
| Ex. 76 | 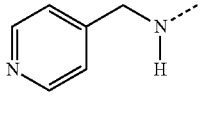 | 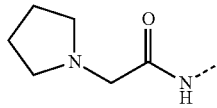 | C33H42FN7O6 | 651.3 | 1.07 (91) | 652.4 | Method 2 |
| Ex. 77 |  | 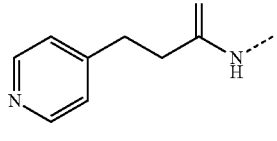 | C35H40FN7O6 | 673.3 | 1.07 (90) | 674.5 | Method 2 |
| Ex. 78 | 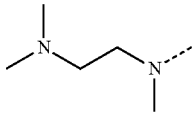 | 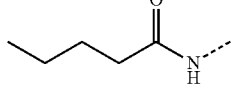 | C31H47FN6O6 | 618.4 | 1.33 (98) | 619.4 | Method 2 |
| Ex. 79 | 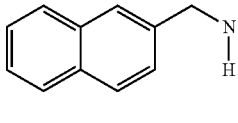 | 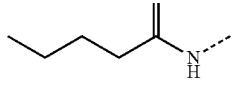 | C37H44FN5O6 | 673.3 | 1.81 (91) | 674.4 | Method 2 |

TABLE 22b-continued

Examples of Core 04 (Ex. 56-Ex. 84,)

| No | R50 | R2 | Formula | Monoisotopic Mass | Rt (purity at 220 nm) | [M + H]+ found | LC-MS-Method |
|---|---|---|---|---|---|---|---|
| Ex. 80 | pyrrolidinyl | pentanamide | C30H42FN5O6 | 587.3 | 1.56 (93) | 588.4 | Method 2 |
| Ex. 81 | N,N-dimethylaminoethylamino | NH2 | C25H37FN6O5 | 520.3 | 1.10 (88) | 521.4 | Method 2 |
| Ex. 82 | N,N-dimethylaminoethylamino | indol-3-ylacetamide | C35H44FN7O6 | 677.3 | 1.36 (93) | 678.5 | Method 2 |
| Ex. 83 | N,N-dimethylaminoethylamino | 2-naphthylacetamide | C37H45FN6O6 | 688.3 | 1.49 (93) | 689.5 | Method 2 |
| Ex. 84 | N,N-dimethylaminoethylamino | Boc-NH | C30H45FN6O7 | 620.3 | 1.38 (87) | 621.5 | Method 2 |

TABLE 22c

Examples of Core 04 (Ex. 56-Ex. 84,)

| No | R50 | R2 | IUPAC name |
|---|---|---|---|
| Ex. 56 | OCH2Ph | Boc-NH | benzyl (2R,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex. 57 | OH | Boc-NH | (2R,11S,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 58 | N,N-dimethylaminoethyl(methyl)amino | Boc-NH | tert-butyl N-((2R,11S,19aS)-11-{[[2-(dimethylamino)ethyl](methyl)amino]carbonyl}-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex. 59 | 2-naphthylmethylamino | Boc-NH | tert-butyl N-((2R,11S,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex. 60 | pyrrolidinyl | Boc-NH | tert-butyl N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]carbamate |

TABLE 22c-continued

Examples of Core 04 (Ex. 56-Ex. 84,)

| No | R50 | R2 | IUPAC name |
|---|---|---|---|
| Ex. 61 | 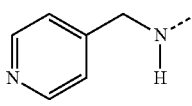 | 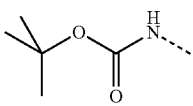 | tert-butyl N-((2R,11S,19aS)-15-fluoro-7,12-dimethyl-5,8,13-trioxo-11-{[(4-pyridinylmethyl)amino]carbonyl}-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex. 62 | 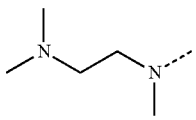 | NH$_2$ | (2R,11S,19aS)-2-amino-N-[2-(dimethylamino)ethyl]-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 63 | 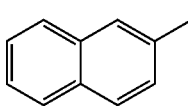 | NH$_2$ | (2R,11S,19aS)-2-amino-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 64 | 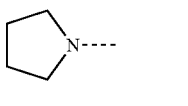 | NH$_2$ | (2R,11S,19aS)-2-amino-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12]benzoxatriazacyclopentadecine-5,8,13-trione |
| Ex. 65 | 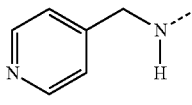 | NH$_2$ | (2R,11S,19aS)-2-amino-15-fluoro-7,12-dimethyl-5,8,13-trioxo-N-(4-pyridinylmethyl)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 66 | 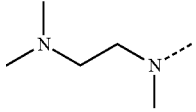 | 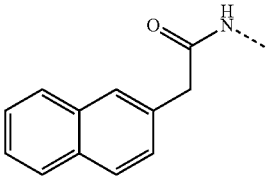 | (2R,11S,19aS)-N-[2-(dimethylamino)ethyl]-15-fluoro-N,7,12-trimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 67 | 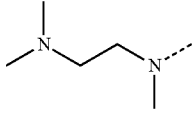 | 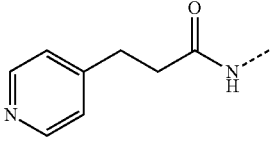 | (2R,11S,19aS)-N-[2-(dimethylamino)ethyl]-15-fluoro-N,7,12-trimethyl-5,8,13-trioxo-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 68 | 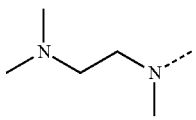 | 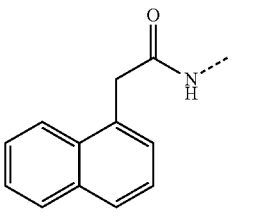 | (2R,11S,19aS)-N-[2-(dimethylamino)ethyl]-15-fluoro-N,7,12-trimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 69 | 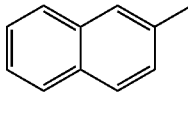 | 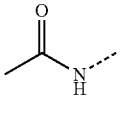 | (2R,11S,19aS)-2-(acetylamino)-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 70 | 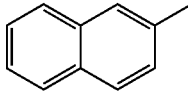 | 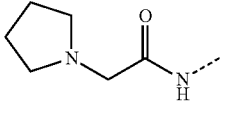 | (2R,11S,19aS)-15-fluoro-7,12-dimethyl-N-(2-naphthylmethyl)-5,8,13-trioxo-2-{[2-(1-pyrrolidinyl)acetyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 71 | 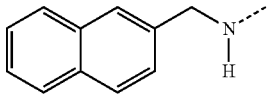 | 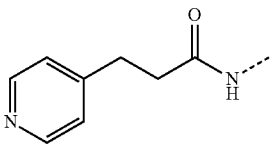 | (2R,11S,19aS)-15-fluoro-7,12-dimethyl-N-(2-naphthylmethyl)-5,8,13-trioxo-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 22c-continued

Examples of Core 04 (Ex. 56-Ex. 84,)

| No | R50 | R2 | IUPAC name |
|---|---|---|---|
| Ex. 72 | pyrrolidinyl | 2-naphthylacetamide group | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(2-naphthyl)acetamide |
| Ex. 73 | pyrrolidinyl | (1-pyrrolidinyl)acetamide | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(1-pyrrolidinyl)acetamide |
| Ex. 74 | pyrrolidinyl | 3-(4-pyridinyl)propanamide | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-3-(4-pyridinyl)propanamide |
| Ex. 75 | 4-pyridinylmethylamino | 2-naphthylacetamide group | (2R,11S,19aS)-15-fluoro-7,12-dimethyl-2-{[2-(2-naphthyl)acetyl]amino}-5,8,13-trioxo-N-(4-pyridinylmethyl)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 76 | 4-pyridinylmethylamino | (1-pyrrolidinyl)acetamide | (2R,11S,19aS)-15-fluoro-7,12-dimethyl-5,8,13-trioxo-N-(4-pyridinylmethyl)-2-{[2-(1-pyrrolidinyl)acetyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 77 | 4-pyridinylmethylamino | 3-(4-pyridinyl)propanamide | (2R,11S,19aS)-15-fluoro-7,12-dimethyl-5,8,13-trioxo-N-(4-pyridinylmethyl)-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 78 | 2-(dimethylamino)ethylamino | pentanoylamino | (2R,11S,19aS)-N-[2-(dimethylamino)ethyl]-15-fluoro-N,7,12-trimethyl-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 79 | 2-naphthylmethylamino | pentanoylamino | (2R,11S,19aS)-15-fluoro-7,12-dimethyl-N-(2-naphthylmethyl)-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 80 | pyrrolidinyl | pentanamide | N-[(2R,11S,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]pentanamide |
| Ex. 81 | 2-(dimethylamino)ethylamino | NH₂ | (2R,11S,19aS)-2-amino-N-[2-(dimethylamino)ethyl]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 22c-continued

Examples of Core 04 (Ex. 56-Ex. 84,)

| No | R50 | R2 | IUPAC name |
|---|---|---|---|
| Ex. 82 |  |  | (2R,11S,19aS)-N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 83 |  |  | (2R,11S,19aS)-N-[2-(dimethylamino)ethyl]-15-fluoro-7,12-dimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 84 |  |  | tert-butyl N-[(2R,11S,19aS)-11-({[2-(dimethylamino)ethyl]amino}carbonyl)-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate |

TABLE 23a

Examples of Core 05 (Ex. 85-Ex. 103,)

| No | R2 | R50 | Starting material | General Procedure | Reagent | Purification Method | Yield, (isolated salt) |
|---|---|---|---|---|---|---|---|
| Ex. 85-Ex 86: cf. experimental description | | | | | | | |
| Ex. 87 | tert-butyl carbamate | methylamino | Ex. 86 | L.2 | methylamine-hydrochloride (10 equiv.) HATU (1.5 equiv.) HOAt (1.5 equiv.) i-Pr$_2$NEt (13 equiv.) | FC (CH$_2$Cl$_2$/MeOH) | 76% |
| Ex. 88 | tert-butyl carbamate | pyrrolidinyl | Ex. 86 | L.2 | pyrrolidine | FC (CH$_2$Cl$_2$/MeOH) then prep. HPLC, method 2 | 64% |
| Ex. 89 | tert-butyl carbamate | 2-naphthylmethylamino | Ex. 86 | L.2 | 2-naphthyl-methyl-amine | FC (EtOAc/MeOH) | 93% |
| Ex. 90 | NH$_2$ | methylamino | Ex. 87 | J | HCl-dioxane | crude product | 86% (HCl salt) |
| Ex. 91 | NH$_2$ | 2-naphthylmethylamino | Ex. 89 | J | HCl-dioxane | crude product | 98% (HCl salt) |
| Ex. 92 | NH$_2$ | pyrrolidinyl | Ex. 88 | J | HCl-dioxane | crude product | 94% (HCl salt) |

TABLE 23a-continued

Examples of Core 05 (Ex. 85-Ex. 103.)

| No | R2 | R50 | Starting material | General Procedure | Reagent | Purification Method | Yield, (isolated salt) |
|---|---|---|---|---|---|---|---|
| Ex. 93 | 2-naphthyl-CH2-C(O)NH- | CH3-NH- | Ex. 90 | L.1.2 | 2-naphthyl-acetic acid | prep. HPLC, method 3 | 66% |
| Ex. 94 | 1-pyrrolidinyl-CH2-C(O)NH- | 2-naphthyl-CH2-NH- | Ex. 91 | L.1.2 | 1-pyrrolidine-acetic acid (1.7 equiv.) | prep. HPLC, method 1 | 46% (TFA salt) |
| Ex. 95 | HOOC-CH2CH2-C(O)NH- | 2-naphthyl-CH2-NH- | Ex. 91 | L.1.1 | succinic anhydride (1.05 equiv.) | prep. HPLC, method 2 | 47% (NH4+ salt) |
| Ex. 96 | 4-pyridyl-CH2CH2-C(O)NH- | 2-naphthyl-CH2-NH- | Ex. 91 | L.1.2 | 3-(pyridine-4-yl)propanoic acid (3.7 equiv.) | FC (CH2Cl2/MeOH) | 74% |
| Ex. 97 | 1-naphthyl-CH2-C(O)NH- | 2-naphthyl-CH2-NH- | Ex. 91 | L.1.2 | 1-naphthyl-acetic acid (1.7 equiv.) | prep. HPLC, method 3 | 72% |
| Ex. 98 | 1-pyrrolidinyl-CH2-C(O)NH- | 1-pyrrolidinyl- | Ex. 92 | L.1.2 | 1-pyrrolidine-acetic acid | prep. HPLC, method 1 | 68% (TFA salt) |
| Ex. 99 | HOOC-CH2CH2-C(O)NH- | 1-pyrrolidinyl- | Ex. 92 | L.1.1 | succinic anhydride (1.05 equiv.) | prep. HPLC, method 2 | 40% (NH4+ salt) |
| Ex. 100 | 1-naphthyl-CH2-C(O)NH- | 1-pyrrolidinyl- | Ex. 92 | L.1.2 | 1-naphthyl-acetic acid | FC (EtOAc/MeOH) | 83% |
| Ex. 101 | 2-naphthyl-C(O)NH- | 1-pyrrolidinyl- | Ex. 92 | L.1.1 | 2-naphthoyl chloride (1.6 equiv.) | FC (EtOAc/MeOH) | 84% |

TABLE 23a-continued

Examples of Core 05 (Ex. 85-Ex. 103,)

| No | R2 | R50 | Starting material | General Procedure | Reagent | Purification Method | Yield, (isolated salt) |
|---|---|---|---|---|---|---|---|
| Ex. 102 | *nonanoyl-NH structure* | *naphthalen-2-ylmethyl-NH* | Ex. 91 | L.1.1 | decanoyl chloride (4.1 equiv.) pyridine (15 equiv.) | prep. HPLC, method 3 | 64% |
| Ex. 103 | *valeroyl-NH structure* | *naphthalen-2-ylmethyl-NH* | Ex. 91 | L.1.1 | valeroyl chloride (2.0 equiv.) | prep. HPLC, method 3 | 87% |

TABLE 23b

Examples of Core 05 (Ex. 85-Ex. 103,)

| No | R2 | R50 | Formula | Monoisotopic Mass | Rt (purity at 220 nm) | [M + H]+ found | LC-MS-Method |
|---|---|---|---|---|---|---|---|
| Ex. 85-Ex 86: cf. experimental description | | | | | | | |
| Ex. 87 | *Boc-NH* | *MeNH* | C27H38FN5O7 | 563.3 | 1.52 (78) | 564.4 | Method 2 |
| Ex. 88 | *Boc-NH* | *pyrrolidine* | C30H42FN5O7 | 603.3 | 1.59 (64), 1.63 (27) | 604.4/ 604.4 | Method 2 |
| Ex. 89 | *Boc-NH* | *naphthalen-2-ylmethyl-NH* | C37H44FN5O7 | 689.3 | 1.89 (97) | 690.5 | Method 2 |
| Ex. 90 | NH₂ | *MeNH* | C22H30FN5O5 | 463.2 | 1.02 (95) | 464.3 | Method 2 |
| Ex. 91 | NH₂ | *naphthalen-2-ylmethyl-NH* | C32H36FN5O5 | 589.3 | 1.51 (98) | 590.4 | Method 2 |
| Ex. 92 | NH₂ | *pyrrolidine* | C25H34FN5O5 | 503.3 | 1.20 (97) | 504.3 | Method 2 |
| Ex. 93 | *2-naphthylacetyl-NH* | *MeNH* | C34H38FN5O6 | 631.3 | 1.65 (98) | 632.3 | Method 2 |
| Ex. 94 | *pyrrolidinylacetyl-NH* | *naphthalen-2-ylmethyl-NH* | C38H45FN6O6 | 700.3 | 1.55 (100) | 701.5 | Method 2 |

TABLE 23b-continued
Examples of Core 05 (Ex. 85-Ex. 103,)
| No | R2 | R50 | Formula | Monoisotopic Mass | Rt (purity at 220 nm) | [M + H]+ found | LC-MS-Method |
|---|---|---|---|---|---|---|---|
| Ex. 95 | 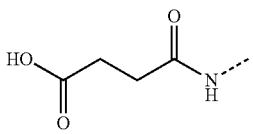 | 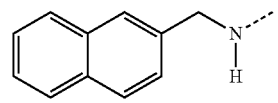 | C36H40FN5O8 | 689.3 | 1.65 (98) | 690.5 | Method 2 |
| Ex. 96 | 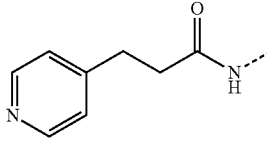 | 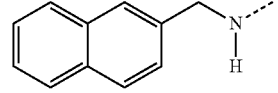 | C40H43FN6O6 | 722.3 | 1.51 (96) | 723.5 | Method 2 |
| Ex. 97 | 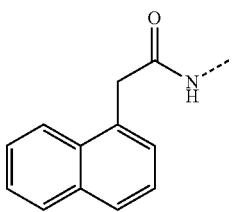 | 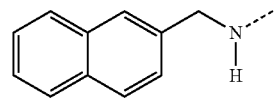 | C44H44FN5O6 | 757.3 | 1.96 (92) | 758.5 | Method 2 |
| Ex. 98 | 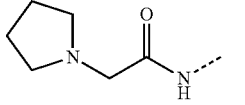 |  | C31H43FN6O6 | 614.3 | 1.25 (98) | 615.3 | Method 2 |
| Ex. 99 | 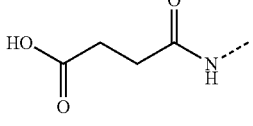 |  | C29H38FN5O8 | 603.3 | 1.34 (100) | 604.4 | Method 2 |
| Ex. 100 | 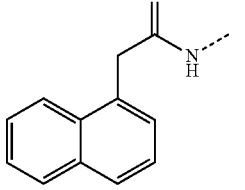 | 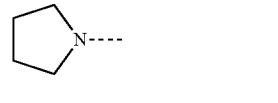 | C37H42FN5O6 | 671.3 | 1.73 (85) | 672.4 | Method 3 |
| Ex. 101 | 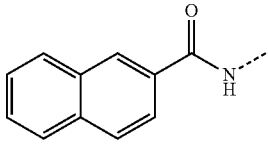 |  | C36H40FN5O6 | 657.3 | 1.73 (98) | 658.4 | Method 2 |
| Ex. 102 | 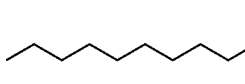 | 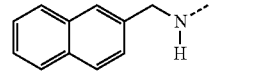 | C42H54FN5O6 | 743.4 | 2.16 (95) | 744.6 | Method 3 |
| Ex. 103 | 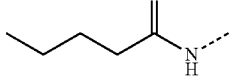 | 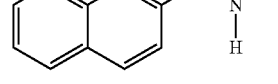 | C37H44FN5O6 | 673.3 | 1.83 (96) | 674.5 | Method 2 |

TABLE 23c

Examples of Core 05 (Ex. 85-Ex. 103,)

| No | R2 | R50 | IUPAC name |
|---|---|---|---|
| Ex. 85 | tert-butyl carbamate group | OCH₂Ph | benzyl (2S,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylate |
| Ex. 86 | tert-butyl carbamate group | OH | (2S,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 87 | tert-butyl carbamate group | methylamino | tert-butyl N-{(2S,11R,19aS)-15-fluoro-7,12-dimethyl-11-[(methylamino)carbonyl]-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl}carbamate |
| Ex. 88 | tert-butyl carbamate group | pyrrolidinyl | tert-butyl N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 89 | tert-butyl carbamate group | (2-naphthylmethyl)amino | tert-butyl N-((2S,11R,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex. 90 | NH₂ | methylamino | (2S,11R,19aS)-2-amino-15-fluoro-N,7,12-trimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 91 | NH₂ | (2-naphthylmethyl)amino | (2S,11R,19aS)-2-amino-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 92 | NH₂ | pyrrolidinyl | (2S,11R,19aS)-2-amino-15-fluoro-7,12-dimethyl-11-(1-pyrrolidinylcarbonyl)-2,3,6,7,9,10,11,12,19,19a-decahydro-1H,5H-pyrrolo[2,1-c][1,4,7,12]benzoxatriazacyclopentadecine-5,8,13-trione |
| Ex. 93 | 2-(2-naphthyl)acetamido | methylamino | (2S,11R,19aS)-15-fluoro-N,7,12-trimethyl-2-{[2-(2-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 94 | 2-(1-pyrrolidinyl)acetamido | (2-naphthylmethyl)amino | (2S,11R,19aS)-15-fluoro-7,12-dimethyl-N-(2-naphthylmethyl)-5,8,13-trioxo-2-{[2-(1-pyrrolidinyl)acetyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 95 | 3-carboxypropanoylamino | (2-naphthylmethyl)amino | 4-[((2S,11R,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)amino]-4-oxobutanoic acid |
| Ex. 96 | 3-(4-pyridinyl)propanoylamino | (2-naphthylmethyl)amino | (2S,11R,19aS)-15-fluoro-7,12-dimethyl-N-(2-naphthylmethyl)-5,8,13-trioxo-2-{[3-(4-pyridinyl)propanoyl]amino}-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 23c-continued

Examples of Core 05 (Ex. 85-Ex. 103,)

| No | R2 | R50 | IUPAC name |
|---|---|---|---|
| Ex. 97 | 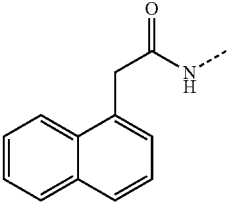 | 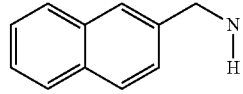 | (2S,11R,19aS)-15-fluoro-7,12-dimethyl-2-{[2-(1-naphthyl)acetyl]amino}-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 98 | 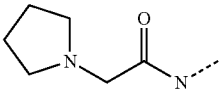 | 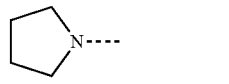 | N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(1-pyrrolidinyl)acetamide |
| Ex. 99 | 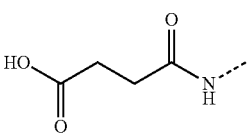 | 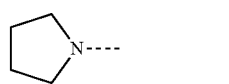 | 4-{[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]amino}-4-oxobutanoic acid |
| Ex. 100 | 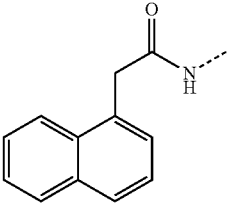 | 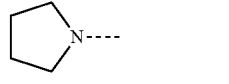 | N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-(1-naphthyl)acetamide |
| Ex. 101 | 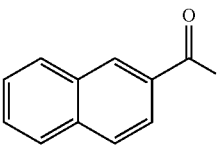 |  | N-[(2S,11R,19aS)-15-fluoro-7,12-dimethyl-5,8,13-trioxo-11-(1-pyrrolidinylcarbonyl)-2,3,6,7,8,9,10,11,12,13,19,19a-dodecahydro-1H,5H-pyrrolo[2,1-c][1,4,7,12]benzoxatriazacyclopentadecin-2-yl]-2-naphthamide |
| Ex. 102 | 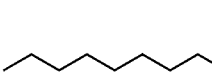 | 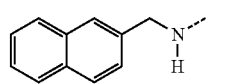 | (2S,11S,19aS)-2-(decanoylamino)-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 103 | 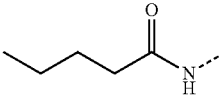 | 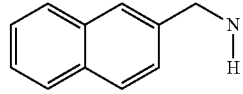 | (2S,11S,19aS)-15-fluoro-7,12-dimethyl-N-(2-naphthylmethyl)-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 24a

Examples of Core 06 (Ex. 104-Ex. 114,)

| No | R2 | R50 | Starting material | General Procedure | Reagent | Purification Method | Yield, (isolated salt) |
|---|---|---|---|---|---|---|---|
| Ex. 104-Ex. 105: cf. experimental description | | | | | | | |
| Ex. 106 | 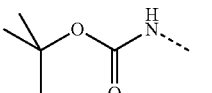 | 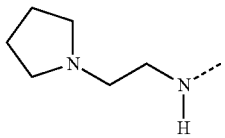 | Ex. 105 | L.2 | N-(2-aminoethyl)pyrrolidine | FC (CH$_2$Cl$_2$/ MeOH/ aq. NH$_3$) | 78% |

TABLE 24a-continued

Examples of Core 06 (Ex. 104-Ex. 114,)

| No | R2 | R50 | Starting material | General Procedure | Reagent | Purification Method | Yield, (isolated salt) |
|---|---|---|---|---|---|---|---|
| Ex. 107 | *tert*-butoxycarbonylamino | 2-naphthylmethyl-NH- | Ex. 105 | L.2 | 2-naphthylmethyl-amine | FC (CH$_2$Cl$_2$/MeOH) | 96% |
| Ex. 108 | NH$_2$ | pyrrolidin-1-yl-ethyl-NH- | Ex. 106 | J | HCl-dioxane | crude product | 99% (HCl salt) |
| Ex. 109 | NH$_2$ | 2-naphthylmethyl-NH- | Ex. 107 | J | HCl-dioxane | crude product | 95% (HCl salt) |
| Ex. 110 | 2-naphthylacetamido | pyrrolidin-1-yl-ethyl-NH- | Ex. 108 | L.1.2 | 2-naphthylacetic acid | prep. HPLC, method 1 and workup (CHCl$_3$/aq. NaHCO$_3$ soln.) | 51% |
| Ex. 111 | 1-naphthylacetamido | pyrrolidin-1-yl-ethyl-NH- | Ex. 108 | L.1.2 | 1-naphthylacetic acid | prep. HPLC, method 1 | 55% (TFA salt) |
| Ex. 112 | diethylamino | pyrrolidin-1-yl-ethyl-NH- | Ex. 108 | M | acetaldehyde | FC (CH$_2$Cl$_2$/MeOH/aq. NH$_3$) | 48% |
| Ex. 113 | 1-naphthylacetamido | 2-naphthylmethyl-NH- | Ex. 109 | L.1.2 | 1-naphthylacetic acid (3.7 equiv.) | prep. HPLC, method 3 | 77% |
| Ex. 114 | valeroylamido | 2-naphthylmethyl-NH- | Ex. 109 | L.1.1 | valeroyl chloride (2 equiv.) | prep. HPLC, method 3 | 84% |

TABLE 24b

Examples of Core 06 (Ex. 104-Ex. 114,)

| No | R2 | R50 | Formula | Monoisotopic Mass | Rt (purity at 220 nm) | [M + H]+ found | LC-MS-Method |
|---|---|---|---|---|---|---|---|
| Ex. 104-Ex. 105: cf. experimental description | | | | | | | |
| Ex. 106 | Boc-NH- | pyrrolidine-ethyl-NH- | C32H47FN6O7 | 646.4 | 1.36 (43), 1.42 (27), 1.44 (27) | 647.5/647.5 647.5 | Method 2 |
| Ex. 107 | Boc-NH- | naphthyl-CH2-NH- | C37H44FN5O7 | 689.3 | 1.94 (42)/ 1.98 (50) | 690.5/690.5 | Method 2 |
| Ex. 108 | NH2 | pyrrolidine-ethyl-NH- | C27H39FN6O5 | 546.3 | 1.37 (50), 1.44 (38) | 547.5/547.5 | Method 3 |
| Ex. 109 | NH2 | naphthyl-CH2-NH- | C32H36FN5O5 | 589.3 | 1.55 (96) | 590.3 | Method 2 |
| Ex. 110 | 2-naphthyl-CH2-C(O)NH- | pyrrolidine-ethyl-NH- | C39H47FN6O6 | 714.4 | 1.62 (44), 1.66 (52) | 715.4/715.4 | Method 2 |
| Ex. 111 | 1-naphthyl-CH2-C(O)NH- | pyrrolidine-ethyl-NH- | C39H47FN6O6 | 714.4 | 1.51 (46), 1.56 (54) | 715.5/715.5 | Method 2 |
| Ex. 112 | Et2N- | pyrrolidine-ethyl-NH- | C31H47FN6O5 | 602.4 | 1.14 (57), 1.18 (39) | 603.4/603.5 | Method 2 |
| Ex. 113 | 1-naphthyl-CH2-C(O)NH- | naphthyl-CH2-NH- | C44H44FN5O6 | 757.3 | 2.15 (52), 2.19 (41) | 758.4/758.4 | Method 4a |
| Ex. 114 | butyl-C(O)NH- | naphthyl-CH2-NH- | C37H44FN5O6 | 673.3 | 2.00 (58), 2.05 (41) | 674.4/674.4 | Method 4a |

TABLE 24c

Examples of Core 06 (Ex. 104-Ex. 114,)

| No | R2 | R50 | IUPAC name |
|---|---|---|---|
| Ex. 104 | tert-butoxycarbonylamino (Boc-NH-) | OCH₂Ph | benzyl (2R,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H, 5H-pyrrolo [2,1-c][1,4,7,12]benzoxatriazacyclopentadecine-11-carboxylate |
| Ex. 105 | tert-butoxycarbonylamino (Boc-NH-) | OH | (2R,11R,19aS)-2-[(tert-butoxycarbonyl)amino]-15-fluoro-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxylic acid |
| Ex. 106 | tert-butoxycarbonylamino (Boc-NH-) | 2-(1-pyrrolidinyl)ethylamino | tert-butyl N-[(2R,11R,19aS)-15-fluoro-7,12-dimethyl-5,8,13-trioxo-11-({[2-(1-pyrrolidinyl)ethyl]amino}carbonyl)-2,3,6,7,8,9,10,11,12,13,19,19a-dodecahydro-1H,5H-pyrrolo[2,1-c][1,4,7,12]benzoxatriazacyclopentadecin-2-yl]carbamate |
| Ex. 107 | tert-butoxycarbonylamino (Boc-NH-) | (2-naphthylmethyl)amino | tert-butyl N-((2R,11R,19aS)-15-fluoro-7,12-dimethyl-11-{[(2-naphthylmethyl)amino]carbonyl}-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl)carbamate |
| Ex. 108 | NH₂ | 2-(1-pyrrolidinyl)ethylamino | (2R,11R,19aS)-2-amino-15-fluoro-7,12-dimethyl-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 109 | NH₂ | (2-naphthylmethyl)amino | (2R,11R,19aS)-2-amino-15-fluoro-7,12-dimethyl-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 110 | [2-(2-naphthyl)acetyl]amino | 2-(1-pyrrolidinyl)ethylamino | (2R,11R,19aS)-15-fluoro-7,12-dimethyl-2-{[2-(2-naphthyl)acetyl]amino}-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 111 | [2-(1-naphthyl)acetyl]amino | 2-(1-pyrrolidinyl)ethylamino | (2R,11R,19aS)-15-fluoro-7,12-dimethyl-2-{[2-(1-naphthyl)acetyl]amino}-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 112 | diethylamino (Et₂N-) | 2-(1-pyrrolidinyl)ethylamino | (2R,11R,19aS)-2-(diethylamino)-15-fluoro-7,12-dimethyl-5,8,13-trioxo-N-[2-(1-pyrrolidinyl)ethyl]-2,3,6,7,8,9,10,11,12,13,19,19a-dodecahydro-1H,5H-pyrrolo[2,1-c][1,4,7,12]benzoxatriazacyclopentadecine-11-carboxamide |
| Ex. 113 | [2-(1-naphthyl)acetyl]amino | (2-naphthylmethyl)amino | (2R,11R,19aS)-15-fluoro-7,12-dimethyl-2-{[2-(1-naphthyl)acetyl]amino}-N-(2-naphthylmethyl)-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 24c-continued

Examples of Core 06 (Ex. 104-Ex. 114,)

| No | R2 | R50 | IUPAC name |
|---|---|---|---|
| Ex. 114 | (butanoylamino, CH3(CH2)3C(O)NH-) | (2-naphthylmethylamino, naphthalen-2-ylCH2NH-) | (2R,11R,19aS)-15-fluoro-7,12-dimethyl-N-(2-naphthylmethyl)-5,8,13-trioxo-2-(pentanoylamino)-2,3,6,7,8,9,10,11,12,13,19,19a-dodecahydro-1H,5H-pyrrolo[2,1-c][1,4,7,12]benzoxatriazacyclopentadecine-11-carboxamide |

TABLE 25a

Examples of Core 07 (Ex. 115-Ex. 131,)

| No | R11 | R50 | Starting material | General Procedure | Reagent | Purification Method | Yield, (isolated salt) |
|---|---|---|---|---|---|---|---|
| Ex. 115-Ex. 116: cf. experimental description | | | | | | | |
| Ex. 117 | Boc-O- | Me2N-CH2CH2-NH- | Ex. 116 | L.2 | N,N-dimethylethylendiamine | FC (CH2Cl2/MeOH/aq. NH3) | 73% |
| Ex. 118 | Boc-O- | tryptamine-NH- | Ex. 116 | L.2 | tryptamine | FC (CH2Cl2/MeOH) | 98% |
| Ex. 119 | Boc-O- | Me2N-CH2CH2-N(Me)- | Ex. 116 | L.2 | N,N,N'-trimethylethylene-diamine | FC (CH2Cl2/MeOH) | 79% |
| Ex. 120 | Boc-O- | (R)-PhCH(Me)NH- | Ex. 116 | L.2 | D-(+)-α-methylbenzylamine | prep. HPLC, method 1 | 70% |
| Ex. 121 | H | Me2N-CH2CH2-NH- | Ex. 117 | J | HCl-dioxane | crude product | 98% (HCl salt) |
| Ex. 122 | H | tryptamine-NH- | Ex. 118 | J | HCl-dioxane | crude product | 98% (HCl salt) |
| Ex. 123 | H | Me2N-CH2CH2-N(Me)- | Ex. 119 | J | HCl-dioxane THF/CH2Cl2 as cosolvent | crude product | quant. (HCl salt) |
| Ex. 124 | H | (R)-PhCH(Me)NH- | Ex. 120 | J | HCl-dioxane | crude product | 95% (HCl salt) |

TABLE 25a-continued

Examples of Core 07 (Ex. 115-Ex. 131,)

| No | R11 | R50 | Starting material | General Procedure | Reagent | Purification Method | Yield, (isolated salt) |
|---|---|---|---|---|---|---|---|
| Ex. 125 | (acetyl) | (tryptamine-NH) | Ex. 122 | L.1.1 | acetic anhydride (1.1 equiv.) pyridine/CH$_2$Cl$_2$ 1:1 (3 mL) | prep. HPLC, method 1 | 62% |
| Ex. 126 | (N,N-dimethylglycyl) | (N-methyl-N'-methylethylenediamine) | Ex. 121 | L.1.3 | N,N-dimethylglycine | prep. HPLC, method 1 | 39% (TFA salt) |
| Ex. 127 | (3-indoleacetyl) | (N-methyl-N'-methylethylenediamine) | Ex. 121 | L.1.3 | 3-indoleacetic acid | prep. HPLC, method 1 | 20% (TFA salt) |
| Ex. 128 | (N,N-dimethylglycyl) | (tryptamine-NH) | Ex. 122 | L.1.3 | N,N-dimethylglycine | prep. HPLC, method 1 | 21% (TFA salt) |
| Ex. 129 | (3-indoleacetyl) | (tryptamine-NH) | Ex. 122 | L.1.3 | 3-Indoleacetic acid | prep. HPLC, method 1 | 45% |
| Ex. 130 | (acetyl) | (N,N,N'-trimethylethylenediamine) | Ex. 123 | L.1.1 | acetic anhydride (5 equiv.) | prep. HPLC, method 1 | 14% (TFA salt) |
| Ex. 131 | (N,N-dimethylglycyl) | (N,N,N'-trimethylethylenediamine) | Ex. 123 | L.1.3 | N,N-dimethylglycine | prep. HPLC, method 1 | 44% (TFA salt) |

TABLE 25b

Examples of Core 07 (Ex. 115-Ex. 131,)

| No | R11 | R50 | Formula | Monoisotopic Mass | Rt (purity at 220 nm) | [M + H]$^+$ found | LC-MS-Method |
|---|---|---|---|---|---|---|---|
| Ex. 115-Ex. 116: cf. experimental description | | | | | | | |
| Ex. 117 | (Boc) | (N-methyl-N'-methylethylenediamine) | C30H45FN6O7 | 620.3 | 1.45 | 621.2 | Method 9c |

TABLE 25b-continued
Examples of Core 07 (Ex. 115-Ex. 131,)
| No | R11 | R50 | Formula | Monoisotopic Mass | Rt (purity at 220 nm) | [M + H]+ found | LC-MS-Method |
|---|---|---|---|---|---|---|---|
| Ex. 118 | 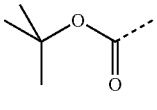 | 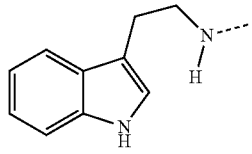 | C36H45FN6O7 | 692.3 | 1.94 | 693.1 | Method 9c |
| Ex. 119 | 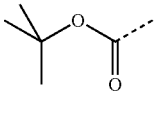 | 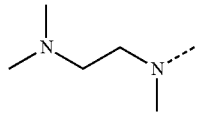 | C31H47FN6O7 | 634.4 | 1.48 | 635.4 | Method 9c |
| Ex. 120 | 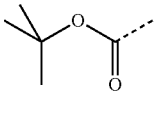 | 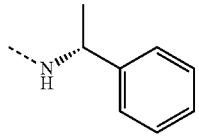 | C34H44FN5O7 | 653.3 | 1.99 | 653.9 | Method 9c |
| Ex. 121 | H | 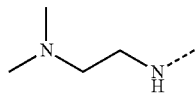 | C25H37FN6O5 | 520.3 | 1.23 (17), 1.29 (80) | 521.3/521.3 | Method 3 |
| Ex. 122 | H | 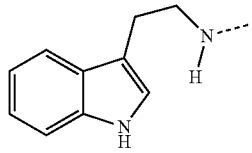 | C31H37FN6O5 | 592.3 | 1.40 (89) | 593.3 | Method 2 |
| Ex. 123 | H | 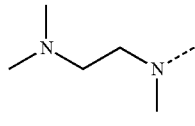 | C26H39FN6O5 | 534.3 | 1.32 (96) | 535.3 | Method 3 |
| Ex. 124 | H | 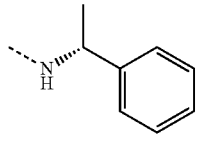 | C29H36FN5O5 | 553.3 | 1.41 (98) | 554.3 | Method 2 |
| Ex. 125 | 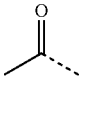 | 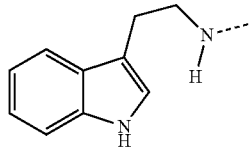 | C33H39FN6O6 | 634.3 | 1.54 (100) | 635.3 | Method 2 |
| Ex. 126 | 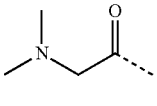 | 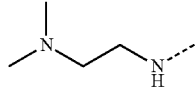 | C29H44FN7O6 | 605.3 | 1.37 (83) | 606.4 | Method 3 |
| Ex. 127 | 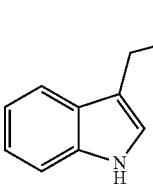 | 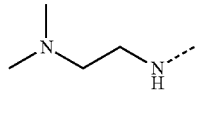 | C35H44FN7O6 | 677.3 | 1.32 (12), 1.38 (84) | 678.3/678.3 | Method 2 |

TABLE 25b-continued

Examples of Core 07 (Ex. 115-Ex. 131,)

| No | R11 | R50 | Formula | Monoisotopic Mass | Rt (purity at 220 nm) | [M + H]+ found | LC-MS-Method |
|---|---|---|---|---|---|---|---|
| Ex. 128 | (dimethylaminoacetyl) | (tryptamine) | C35H44FN7O6 | 677.3 | 1.40 (98) | 678.4 | Method 2 |
| Ex. 129 | (indol-3-ylacetyl) | (tryptamine) | C41H44FN7O6 | 749.3 | 1.73 (85) | 750.4 | Method 2 |
| Ex. 130 | (acetyl) | (N,N,N'-trimethylethylenediamine) | C28H41FN6O6 | 576.3 | 1.10 (98) | 577.3 | Method 2 |
| Ex. 131 | (dimethylaminoacetyl) | (N,N,N'-trimethylethylenediamine) | C30H46FN7O6 | 619.4 | 1.41 (96) | 620.4 | Method 3 |

TABLE 25c

Examples of Core 07 (Ex. 115-Ex. 131,)

| No | R11 | R50 | IUPAC name |
|---|---|---|---|
| Ex. 115 | (Boc) | OCH2Ph | 12-benzyl 2-(tert-butyl) (12S,20aS)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2,12(1H)-dicarboxylate |
| Ex. 116 | (Boc) | OH | (12S,20aS)-2-(tert-butoxycarbonyl)-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxylic acid |
| Ex. 117 | (Boc) | (N,N-dimethylethylenediamine) | tert-butyl (12S,20aS)-12-({[2-(dimethylamino)ethyl]amino}carbonyl)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex. 118 | (Boc) | (tryptamine) | tert-butyl (12S,20aS)-16-fluoro-12-({[2-(1H-indol-3-yl)ethyl]amino}carbonyl)-8,13-dimethyl-6,9,14-trioxo-3,4,7,8,9,10,11,12,13,14,20,20a-dedecahydro-6H-pyrazino[2,1-c][1,4,7,12]benzoxatriazacyclopentadecine-2(1H)-carboxylate |
| Ex. 119 | (Boc) | (N,N,N'-trimethylethylenediamine) | tert-butyl (12S,20aS)-12-{[[2-(dimethylamino)ethyl]methyl)amino]carbonyl}-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |

TABLE 25c-continued

Examples of Core 07 (Ex. 115-Ex. 131,)

| No | R11 | R50 | IUPAC name |
|---|---|---|---|
| Ex. 120 | (tert-butyl carbamate group) | (1R)-1-phenylethylamino | tert-butyl (12S,20aS)-16-fluoro-8,13-dimethyl-6,9,14-trioxo-12-({[(1R)-1-phenylethyl]amino}carbonyl)-3,4,7,8,9,10,11,12,13,14,20,20a-dodecahydro-6H-pyrazino[2,1-c][1,4,7,12]benzoxatriazacyclopentadecine-2(1H)-carboxylate |
| Ex. 121 | H | 2-(dimethylamino)ethylamino | (12S,20aS)-N-[2-(dimethylamino)ethyl]-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 122 | H | tryptamine | (12S,20aS)-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 123 | H | N-methyl-2-(dimethylamino)ethylamino | (12S,20aS)-N-[2-(dimethylamino)ethyl]-16-fluoro-N,8,13-trimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 124 | H | (1R)-1-phenylethylamino | (12S,20aS)-16-fluoro-8,13-dimethyl-6,9,14-trioxo-N-[(1R)-1-phenylethyl]-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 125 | acetyl | tryptamine | (12S,20aS)-2-acetyl-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 126 | 2-(dimethylamino)acetyl | 2-(dimethylamino)ethylamino | (12S,20aS)-2-[2-(dimethylamino)acetyl]-N-[2-(dimethylamino)ethyl]-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 127 | 2-(1H-indol-3-yl)acetyl | 2-(dimethylamino)ethylamino | (12S,20aS)-N-[2-(dimethylamino)ethyl]-16-fluoro-2-[2-(1H-indol-3-yl)acetyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 128 | 2-(dimethylamino)acetyl | tryptamine | (12S,20aS)-2-[2-(dimethylamino)acetyl]-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 129 | 2-(1H-indol-3-yl)acetyl | tryptamine | (12S,20aS)-16-fluoro-2-[2-(1H-indol-3-yl)acetyl]-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 25c-continued

Examples of Core 07 (Ex. 115-Ex. 131,)

| No | R11 | R50 | IUPAC name |
|---|---|---|---|
| Ex. 130 | (acetyl group) | (N,N-dimethylaminoethyl-N-methyl) | (12S,20aS)-2-acetyl-N-[2-(dimethylamino)ethyl]-16-fluoro-N,8,13-trimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 131 | (dimethylaminoacetyl) | (N,N-dimethylaminoethyl-N-methyl) | (12S,20aS)-2-[2-(dimethylamino)acetyl]-N-[2-(dimethylamino)ethyl]-16-fluoro-N,8,13-trimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 26a

Examples of Core 08 (Ex. 132-Ex. 141,)

| No | R11 | R50 | Starting material | General Procedure | Reagent | Purification Method | Yield, (isolated salt) |
|---|---|---|---|---|---|---|---|
| Ex. 132-Ex. 133: cf. experimental description | | | | | | | |
| Ex. 134 | Boc-O- | (N,N-dimethylaminoethyl-NH) | Ex. 133 | L.2 | N,N-dimethylethylenediamine | FC (CH$_2$Cl$_2$/MeOH/aq. NH$_3$) | 80% |
| Ex. 135 | H | (N,N-dimethylaminoethyl-NH) | Ex. 134 | J | HCl-dioxane | crude product | 100% (HCl salt) |
| Ex. 136 | Boc-O- | (tryptamine-NH) | Ex. 133 | L.2 | tryptamine | FC (CH$_2$Cl$_2$/MeOH/aq. NH$_3$) | 89% |
| Ex. 137 | H | (tryptamine-NH) | Ex. 136 | J | HCl-dioxane | crude product | 100% (HCl salt) |
| Ex. 138 | 2-naphthylacetyl | (N,N-dimethylaminoethyl-NH) | Ex. 135 | L.1.2 | 2-naphthylacetic acid | prep. HPLC, method 1 | 71% (TFA salt) |
| Ex. 139 | N,N-dimethylglycyl | (tryptamine-NH) | Ex. 137 | L.1.2 | N,N-dimethyl glycine | prep. HPLC, method 1 | 40% (TFA salt) |

TABLE 26a-continued

Examples of Core 08 (Ex. 132-Ex. 141,)

| No | R11 | R50 | Starting material | General Procedure | Reagent | Purification Method | Yield, (isolated salt) |
|---|---|---|---|---|---|---|---|
| Ex. 140 | (acetyl group) | (tryptamine-N-methyl) | Ex. 137 | L.1.1 | acetic anhydride (5 equiv.) | prep. HPLC, method 1 | 50% |
| Ex. 141 | (2-naphthylacetyl group) | (tryptamine-N-methyl) | Ex. 137 | L.1.2 | 2-naphthylacetic acid | prep. HPLC, method 3, then FC (EtOAc/MeOH) | 39% |

TABLE 26b

Examples of Core 08 (Ex. 132-Ex. 141,)

| No | R11 | R50 | Formula | Monoisotopic Mass | Rt (purity at 220 nm) | [M + H]+ found | LC-MS-Method |
|---|---|---|---|---|---|---|---|
| Ex. 132-Ex. 133: cf. experimental description | | | | | | | |
| Ex. 134 | (Boc-O-) | (N,N-dimethylaminoethyl-NH) | C30H45FN6O7 | 620.3 | 1.40 (20), 1.45 (77) | 621.5/621.5 | Method 2 |
| Ex. 135 | H | (N,N-dimethylaminoethyl-NH) | C25H37FN6O5 | 520.3 | 0.94 (85) | 521.4 | Method 2 |
| Ex. 136 | (Boc-O-) | (tryptamine-N-methyl) | C36H45FN6O7 | 692.3 | 1.83 (91) | 693.5 | Method 2 |
| Ex. 137 | H | (tryptamine-N-methyl) | C31H37FN6O5 | 592.3 | 1.41 (80) | 593.4 | Method 2 |
| Ex. 138 | (2-naphthylacetyl) | (N,N-dimethylaminoethyl-NH) | C37H45FN6O6 | 688.3 | 1.46 (15), 1.51 (84) | 689.5/689.5 | Method 2 |
| Ex. 139 | (N,N-dimethylaminoacetyl) | (tryptamine-N-methyl) | C35H44FN7O6 | 677.3 | 1.43 (92) | 678.5 | Method 2 |

TABLE 26b-continued

Examples of Core 08 (Ex. 132-Ex. 141,)

| No | R11 | R50 | Formula | Monoisotopic Mass | Rt (purity at 220 nm) | [M + H]+ found | LC-MS-Method |
|---|---|---|---|---|---|---|---|
| Ex. 140 | (acetyl) | (tryptamine) | C33H39FN6O6 | 634.3 | 1.57 (97) | 635.5 | Method 2 |
| Ex. 141 | (2-naphthylacetyl) | (tryptamine) | C43H45FN6O6 | 760.3 | 1.86 (95) | 761.5 | Method 2 |

TABLE 26c

Examples of Core 08 (Ex. 132-Ex. 141,)

| No | R11 | R50 | IUPAC name |
|---|---|---|---|
| Ex. 132 | Boc | OCH2Ph | 12-benzyl 2-(tert-butyl) (12R,20aR)-16-fluoro-8,13-dimethyl-6,9,14-trioxo-3,4,7,8,9,10,11,12,13,14,20,20a-dodeeanydro-6H-pyrazino[2,1-c][1,4,7,12]benzoxatriazacyclopentadecine-2,12(1H)-dicarboxylate |
| Ex. 133 | Boc | OH | (12R,20aR)-2-(tert-butoxycarbonyl)-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxylic acid |
| Ex. 134 | Boc | (dimethylaminoethylamino) | tert-butyl (12R,20aR)-12-({[2-(dimethylamino)ethyl]amino}carbonyl)-16-fluoro-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex. 135 | H | (dimethylaminoethylamino) | (12R,20aR)-N-[2-(dimethylamino)ethyl]-16-fluoro-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 136 | Boc | (tryptamine) | tert-butyl (12R,20aR)-16-fluoro-12-({[2-(1H-indol-3-yl)ethyl]amino}carbonyl)-8,13-dimethyl-6,9,14-trioxo-3,4,7,8,9,10,11,12,13,14,20,20a-dodecahydro-6H-pyrazino[2,1-c][1,4,7,12]benzoxatriazacyclopentadecine-2(1H)-carboxylate |
| Ex. 137 | H | (tryptamine) | (12R,20aR)-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 138 | (2-naphthylacetyl) | (dimethylaminoethylamino) | (12R,20aR)-N-[2-(dimethylamino)ethyl]-16-fluoro-8,13-dimethyl-2-[2-(2-naphthyl)acetyl]-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 26c-continued

Examples of Core 08 (Ex. 132-Ex. 141,)

| No | R11 | R50 | IUPAC name |
|---|---|---|---|
| Ex. 139 | 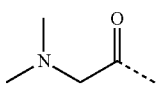 | 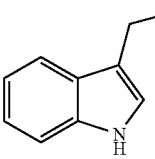 | (12R,20aR)-2-[2-(dimethylamino)acetyl]-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 140 |  | 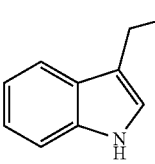 | (12R,20aR)-2-acetyl-16-fluoro-N-[2-(1H-indol-3-yl)ethyl]-8,13-dimethyl-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |
| Ex. 141 | 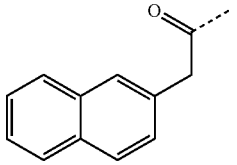 | 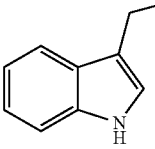 | (12R,20aR)-16-fluoro-N-[2-(1H-indol-3-yl)ethyl]-8,13-dimethyl-2-[2-(2-naphthyl)acetyl]-6,9,14-trioxo-1,2,3,4,7,8,9,10,11,12,13,14,20,20a-tetradecahydro-6H-pyrazino[2,1-c][1,4,7,12]benzoxatriazacyclopentadecine-12-carboxamide |

TABLE 27a

Examples of Core 09 (Ex. 142-Ex. 163,)

| No | R2 | R50 | Starting material | General Procedure | Reagent | Purification Method | Yield, (isolated salt) |
|---|---|---|---|---|---|---|---|
| Ex. 142-Ex. 143: cf. experimental description | | | | | | | |
| Ex. 144 | 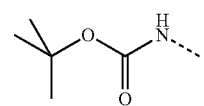 | 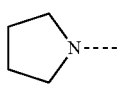 | Ex. 143 | L.2 | pyrrolidine | FC (CH$_2$Cl$_2$/MeOH) | 91% |
| Ex. 145 | 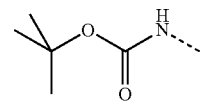 | 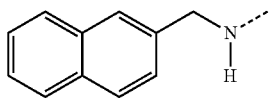 | Ex. 143 | L.2 | 2-naphthyl-methylamine | FC (CH$_2$Cl$_2$/MeOH) | 72% |
| Ex. 146 | 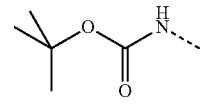 | 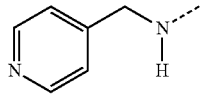 | Ex. 143 | L.2 | 4-(aminomethyl)pyridine | FC (CH$_2$Cl$_2$/MeOH) | 87% |
| Ex. 147 | NH$_2$ | 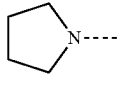 | Ex. 144 | J | HCl-dioxane | crude product | 100% (HCl salt) |
| Ex. 148 | NH$_2$ | 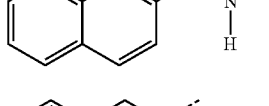 | Ex. 145 | J | HCl-dioxane | crude product | 97% (HCl salt) |
| Ex. 149 | NH$_2$ | 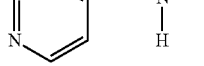 | Ex. 146 | J | HCl-dioxane | crude product | 87% (HCl salt) |

TABLE 27a-continued

Examples of Core 09 (Ex. 142-Ex. 163,)

| No | R2 | R50 | Starting material | General Procedure | Reagent | Purification Method | Yield, (isolated salt) |
|---|---|---|---|---|---|---|---|
| Ex. 150 | | | Ex. 147 | L.1.2 | 2-naphthylacetic acid | Prep. HPLC, method 3 | 72% |
| Ex. 151 | | | Ex. 147 | L.1.1 | valeroyl chloride (2.0 equiv.) | Prep. HPLC, method 3 | 73% |
| Ex. 152 | | | Ex. 147 | L.1.2 | 1-pyrriolidin-acetic acid | Prep. HPLC, method 2 | 26% |
| Ex. 153 | | | Ex. 148 | L.1.2 | 2-naphthylacetic acid | Prep. HPLC, method 3 | 68% |
| Ex. 154 | | | Ex. 148 | L.1.1 | valeroyl chloride (2.0 equiv.) | Prep. HPLC, method 3 | 76% |
| Ex. 155 | | | Ex. 148 | L.1.1 | acetic anhydride (5.0 equiv.) | Prep. HPLC, method 3 | 72% |
| Ex. 156 | | | Ex. 148 | L.1.1 | succinic anhydride (1.05 equiv.) | Prep. HPLC, method 2 | 69% (NH4+ salt) |
| Ex. 157 | | | Ex. 149 | L.1.2 | 2-naphthylacetic acid (1.7 equiv.) | Prep. HPLC, method 2 | 24% |
| Ex. 158 | | | Ex. 149 | L.1.1 | valeroyl chloride (2.0 equiv.) | Prep. HPLC, method 2 | 42% |
| Ex. 159 | | | Ex. 149 | L.1.2 | 1-pyrriolidin-acetic acid (2.5 equiv.) | Prep. HPLC, method 2 | 55% |

TABLE 27a-continued

Examples of Core 09 (Ex. 142-Ex. 163.)

| No | R2 | R50 | Starting material | General Procedure | Reagent | Purification Method | Yield, (isolated salt) |
|---|---|---|---|---|---|---|---|
| Ex. 160 | HOOC-CH2-CH2-C(O)-NH- | pyridin-4-ylmethyl-NH- | Ex. 149 | L.1.1 | succinic anhydride (1.05 equiv.) | Prep. HPLC, method 2 | 69% (NH4+ salt) |
| Ex. 161 | 3-(pyridin-4-yl)propanoyl-NH- | pyrrolidin-1-yl | Ex. 147 | L.1.2 | 3-(pyridine-4-yl)propanoic acid | Prep. HPLC, method 2 | 53% |
| Ex. 162 | 3-(pyridin-4-yl)propanoyl-NH- | naphthalen-2-ylmethyl-NH- | Ex. 148 | L.1.2 | 3-(pyridine-4-yl)propanoic acid | Prep. HPLC, method 2 | 48% |
| Ex. 163 | 3-(pyridin-4-yl)propanoyl-NH- | pyridin-4-ylmethyl-NH- | Ex. 149 | L.1.2 | 3-(pyridine-4-yl)propanoic acid (1.7 equiv.) | Prep. HPLC, method 2 | 63% |

TABLE 27b

Examples of Core 09 (Ex. 142-Ex. 163.)

| No | R2 | R50 | Formula | Monoisotopic Mass | Rt (purity at 220 nm) | [M + H]+ found | LC-MS-Method |
|---|---|---|---|---|---|---|---|
| Ex. 142-Ex. 143: cf. experimental description | | | | | | | |
| Ex. 144 | Boc-NH- | pyrrolidin-1-yl | C31H44FN5O7 | 617.3 | 1.66 (90) | 618.4 | Method 2 |
| Ex. 145 | Boc-NH- | naphthalen-2-ylmethyl-NH- | C38H46FN5O7 | 703.3 | 1.90 (90) | 704.5 | Method 2 |
| Ex. 146 | Boc-NH- | pyridin-4-ylmethyl-NH- | C33H43FN6O7 | 654.3 | 1.39 (92) | 655.5 | Method 2 |
| Ex. 147 | NH2 | pyrrolidin-1-yl | C26H36FN5O5 | 517.3 | 1.36 (79) | 518.4 | Method 3 |
| Ex. 148 | NH2 | naphthalen-2-ylmethyl-NH- | C33H38FN5O5 | 603.3 | 1.53 (98) | 604.4 | Method 2 |

TABLE 27b-continued

Examples of Core 09 (Ex. 142-Ex. 163.)

| No | R2 | R50 | Formula | Monoisotopic Mass | Rt (purity at 220 nm) | [M + H]+ found | LC-MS-Method |
|---|---|---|---|---|---|---|---|
| Ex. 149 | NH₂ | pyridin-4-ylmethylamino | C28H35FN6O5 | 554.3 | 1.25 (8), 1.31 (85) | 555.4 | Method 3 |
| Ex. 150 | naphthalen-2-yl-acetamide | pyrrolidin-1-yl | C38H44FN5O6 | 685.3 | 1.72 (98) | 686.5 | Method 2 |
| Ex. 151 | pentanamide | pyrrolidin-1-yl | C31H44FN5O6 | 601.3 | 1.55 (98) | 602.5 | Method 2 |
| Ex. 152 | 2-(pyrrolidin-1-yl)acetamide | pyrrolidin-1-yl | C32H45FN6O6 | 628.3 | 1.52 (94) | 629.5 | Method 3 |
| Ex. 153 | naphthalen-2-yl-acetamide | naphthalen-2-ylmethylamino | C45H46FN5O6 | 771.3 | 1.94 (96) | 772.5 | Method 2 |
| Ex. 154 | pentanamide | naphthalen-2-ylmethylamino | C38H46FN5O6 | 687.3 | 1.82 (97) | 688.5 | Method 2 |
| Ex. 155 | acetamide | naphthalen-2-ylmethylamino | C35H40FN5O6 | 645.3 | 1.67 (99) | 646.4 | Method 2 |
| Ex. 156 | succinamide | naphthalen-2-ylmethylamino | C37H42FN5O8 | 703.3 | 1.65 (99) | 704.5 | Method 2 |
| Ex. 157 | naphthalen-2-yl-acetamide | pyridin-4-ylmethylamino | C40H43FN6O6 | 722.3 | 1.48 (94) | 723.8 | Method 2 |
| Ex. 158 | pentanamide | pyridin-4-ylmethylamino | C33H43FN6O6 | 638.3 | 1.50 (95) | 639.5 | Method 3 |
| Ex. 159 | 2-(pyrrolidin-1-yl)acetamide | pyridin-4-ylmethylamino | C34H44FN7O6 | 665.3 | 1.47 (96) | 666.5 | Method 3 |

TABLE 27b-continued

Examples of Core 09 (Ex. 142-Ex. 163.)

| No | R2 | R50 | Formula | Monoisotopic Mass | Rt (purity at 220 nm) | [M + H]+ found | LC-MS-Method |
|---|---|---|---|---|---|---|---|
| Ex. 160 | HOOC-CH2-CH2-C(O)-NH- | 4-pyridinyl-CH2-NH- | C32H39FN6O8 | 654.3 | 1.04 (96) | 655.4 | Method 3 |
| Ex. 161 | 4-pyridinyl-CH2-CH2-C(O)-NH- | pyrrolidinyl-N- | C34H43FN6O6 | 650.3 | 1.47 (91) | 651.5 | Method 3 |
| Ex. 162 | 4-pyridinyl-CH2-CH2-C(O)-NH- | 2-naphthyl-CH2-NH- | C41H45FN6O6 | 736.3 | 1.55 (96) | 737.6 | Method 2 |
| Ex. 163 | 4-pyridinyl-CH2-CH2-C(O)-NH- | 4-pyridinyl-CH2-NH- | C36H42FN7O6 | 687.3 | 1.42 (99) | 688.5 | Method 3 |

TABLE 27c

Examples of Core 09 (Ex. 142-Ex. 163.)

| No | R2 | R50 | IUPAC name |
|---|---|---|---|
| Ex. 142 | tBuO-C(O)-NH- | OCH2Ph | benzyl (2R,12S,20aS)-2-[(tert-butoxycarbonyl)amino]-16-fluoro-8,13-dimethyl-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxylate |
| Ex. 143 | tBuO-C(O)-NH- | OH | (2R,12S,20aS)-2-[(tert-butoxycarbonyl)amino]-16-fluoro-8,13-dimethyl-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxylic acid |
| Ex. 144 | tBuO-C(O)-NH- | pyrrolidinyl-N- | tert-butyl N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]carbamate |
| Ex. 145 | tBuO-C(O)-NH- | 2-naphthyl-CH2-NH- | tert-butyl N-((2R,12S,20aS)-16-fluoro-8,13-dimethyl-12-{[(2-naphthylmethyl)amino]carbonyl}-5,9,14-trioxo-2,3,5,6,7,8,9,10,11,12,13,14,20,20a-tetradecahydro-1H-pyrrolo[2,1-c][1,4,8,13]benzoxatriazacyclohexadecin-2-yl)carbamate |
| Ex. 146 | tBuO-C(O)-NH- | 4-pyridinyl-CH2-NH- | tert-butyl N-((2R,12S,20aS)-16-fluoro-8,13-dimethyl-5,9,14-trioxo-12-{[(4-pyridinylmethyl)amino]carbonyl}-2,3,5,6,7,8,9,10,11,12,13,14,20,20a-tetradecahydro-1H-pyrrolo[2,1-c][1,4,8,13]benzoxatriazacyclohexadecin-2-yl)carbamate |
| Ex. 147 | NH2 | pyrrolidinyl-N- | (2R,12S,20aS)-2-amino-16-fluoro-8,13-dimethyl-12-(1-pyrrolidinylcarbonyl)-2,3,7,8,10,11,12,13,20,20a-decahydro-1H-pyrrolo[2,1-c][1,4,8,13]benzoxatriazacyclohexadecine-5,9,14(6H)-trione |

TABLE 27c-continued

Examples of Core 09 (Ex. 142-Ex. 163,)

| No | R2 | R50 | IUPAC name |
|---|---|---|---|
| Ex. 148 | NH₂ | (2-naphthylmethylamino) | (2R,12S,20aS)-2-amino-16-fluoro-8,13-dimethyl-N-(2-naphthylmethyl)-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 149 | NH₂ | (4-pyridinylmethylamino) | (2R,12S,20aS)-2-amino-16-fluoro-8,13-dimethyl-5,9,14-trioxo-N-(4-pyridinylmethyl)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 150 | (2-naphthyl)acetamido | 1-pyrrolidinyl | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]-2-(2-naphthyl)acetamide |
| Ex. 151 | pentanoylamino | 1-pyrrolidinyl | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]pentanamide |
| Ex. 152 | (1-pyrrolidinyl)acetamido | 1-pyrrolidinyl | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]-2-(1-pyrrolidinyl)acetamide |
| Ex. 153 | (2-naphthyl)acetamido | (2-naphthylmethylamino) | (2R,12S,20aS)-16-fluoro-8,13-dimethyl-2-{[2-(2-naphthyl)acetyl]amino}-N-(2-naphthylmethyl)-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 154 | pentanoylamino | (2-naphthylmethylamino) | (2R,12S,20aS)-16-fluoro-8,13-dimethyl-N-(2-naphthylmethyl)-5,9,14-trioxo-2-(pentanoylamino)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 155 | acetylamino | (2-naphthylmethylamino) | (2R,12S,20aS)-2-(acetylamino)-16-fluoro-8,13-dimethyl-N-(2-naphthylmethyl)-5,9,14-trioxo-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 156 | 3-carboxypropanoylamino | (2-naphthylmethylamino) | 4-[((2R,12S,20aS)-16-fluoro-8,13-dimethyl-12-{[(2-naphthylmethyl)amino]carbonyl}-5,9,14-trioxo-2,3,5,6,7,8,9,10,11,12,13,14,20,20a-tetradecahydro-1H-pyrrolo[2,1-c][1,4,8,13]benzoxatriazacyclohexadecin-2-yl)amino]-4-oxobutanoic acid |
| Ex. 157 | (2-naphthyl)acetamido | (4-pyridinylmethylamino) | (2R,12S,20aS)-16-fluoro-8,13-dimethyl-2-{[2-(2-naphthyl)acetyl]amino}-5,9,14-trioxo-N-(4-pyridinylmethyl)-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 158 | pentanoylamino | (4-pyridinylmethylamino) | (2R,12S,20aS)-16-fluoro-8,13-dimethyl-5,9,14-trioxo-2-(pentanoylamino)-N-(4-pyridinylmethyl)-2,3,5,6,7,8,9,10,11,12,13,14,20,20a-tetradecahydro-1H-pyrrolo[2,1-c][1,4,8,13]benzoxatriazacyclohexadecine-12-carboxamide |

TABLE 27c-continued

Examples of Core 09 (Ex. 142-Ex. 163,)

| No | R2 | R50 | IUPAC name |
|---|---|---|---|
| Ex. 159 | pyrrolidinyl-CH2-C(O)-NH- | 4-pyridinyl-CH2-NH- | (2R,12S,20aS)-16-fluoro-8,13-dimethyl-5,9,14-trioxo-N-(4-pyridinylmethyl)-2-{[2-(1-pyrrolidinyl)acetyl]amino}-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 160 | HOOC-CH2CH2-C(O)-NH- | 4-pyridinyl-CH2-NH- | 4-[((2R,12S,20aS)-16-fluoro-8,13-dimethyl-5,9,14-trioxo-12-{[(4-pyridinylmethyl)amino]carbonyl}-2,3,5,6,7,8,9,10,11,12,13,14,20,20a-tetradecahydro-1H-pyrrolo[2,1-c][1,4,8,13]benzoxatriazacyclohexadecin-2-yl)amino]-4-oxobutanoic acid |
| Ex. 161 | 4-pyridinyl-CH2CH2-C(O)-NH- | pyrrolidinyl-C(O)- | N-[(2R,12S,20aS)-16-fluoro-8,13-dimethyl-5,9,14-trioxo-12-(1-pyrrolidinylcarbonyl)-2,3,5,6,7,8,9,10,11,12,13,14,20,20a-tetradecahydro-1H-pyrrolo[2,1-c][1,4,8,13]benzoxatriazacyclohexadecin-2-yl]-3-(4-pyridinyl)propanamide |
| Ex. 162 | 4-pyridinyl-CH2CH2-C(O)-NH- | 2-naphthyl-CH2-NH- | (2R,12S,20aS)-16-fluoro-8,13-dimethyl-N-(2-naphthylmethyl)-5,9,14-trioxo-2-{[3-(4-pyridinyl)propanoyl]amino}-2,3,5,6,7,8,9,10,11,12,13,14,20,20a-tetradecahydro-1H-pyrrolo[2,1-c][1,4,8,13]benzoxatriazacyclohexadecine-12-carboxamide |
| Ex. 163 | 4-pyridinyl-CH2CH2-C(O)-NH- | 4-pyridinyl-CH2-NH- | (2R,12S,20aS)-16-fluoro-8,13-dimethyl-5,9,14-trioxo-N-(4-pyridinylmethyl)-2-{[3-(4-pyridinyl)propanoyl]amino}-2,3,5,6,7,8,9,10,11,12,13,14,20,20a-tetradecahydro-1H-pyrrolo[2,1-c][1,4,8,13]benzoxatriazacyclohexadecine-12-carboxamide |

TABLE 28a

Examples of Core 10 (Ex. 164-Ex. 180,)

| No | R2 | R5 | Starting material | General Procedure | Reagent | Purification Method | Yield, (isolated salt) |
|---|---|---|---|---|---|---|---|
| Ex. 164-Ex. 165: cf. experimental description | | | | | | | |
| Ex. 166 | n-butyl-C(O)-NH- | benzyl-O-C(O)-NH- | Ex. 165 | L.1.1 | valeroyl chloride (2.0 equiv.) | FC (EtOAc/MeOH) | ca.70% |
| Ex. 167 | n-butyl-C(O)-NH- | NH2 | Ex. 166 | K | H2, Pd(OH)2—C | crude product | quant. |
| Ex. 168 | 2-naphthyl-CH2-C(O)-NH- | benzyl-O-C(O)-NH- | Ex. 165 | L.1.3 | 2-naphthylacetic acid | FC (EtOAc) | 68% |

TABLE 28a-continued

Examples of Core 10 (Ex. 164-Ex. 180,)

| No | R2 | R5 | Starting material | General Procedure | Reagent | Purification Method | Yield, (isolated salt) |
|---|---|---|---|---|---|---|---|
| Ex. 169 | 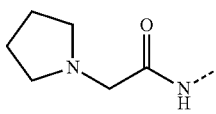 | 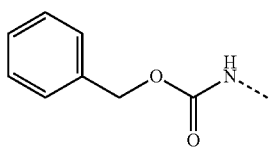 | Ex. 165 | L.1.3 | 1-pyrrolidinacetic acid | FC (EtOAc/MeOH) | 76% |
| Ex. 170 | 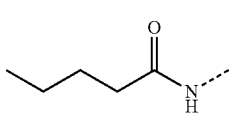 | 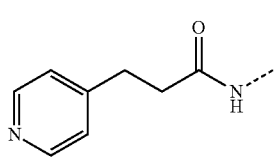 | Ex. 167 | L.1.2 | 3-(pyridine-4-yl)propanoic acid | FC (CH$_2$Cl$_2$/MeOH) | 78% |
| Ex. 171 | 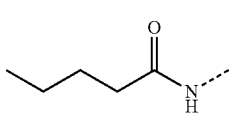 | 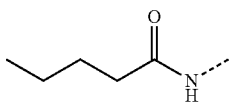 | Ex. 167 | L.1.1 | 2-naphthoyl chloride (2.6 equiv.) | Prep. HPLC, method 3 | 42% |
| Ex. 172 | 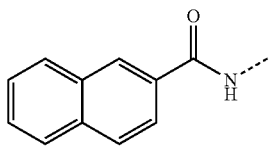 | NH$_2$ | Ex. 168 | K | H$_2$, Pd(OH)$_2$—C | crude product | 97% |
| Ex. 173 | 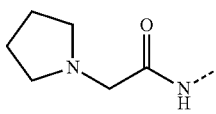 | NH$_2$ | Ex. 169 | K | H$_2$, Pd(OH)$_2$—C | crude product | 96% |
| Ex. 174 | 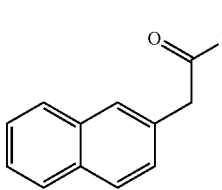 | 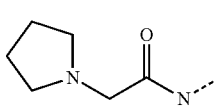 | Ex. 172 | L.1.1 | acetic anhydride (5 equiv.) | Prep. HPLC, method 3 | 97% |
| Ex. 175 | 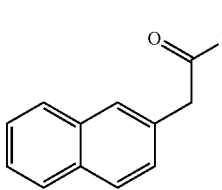 | 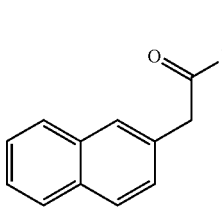 | Ex. 172 | L.1.2 | 1-pyrrolidinacetic acid (2.2 equiv.) | Prep. HPLC, method 3 | 58% |
| Ex. 176 | 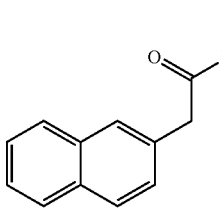 | 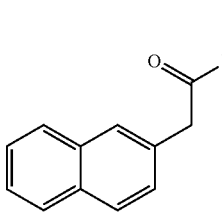 | Ex. 172 | L.1.2 | 3-(pyridine-4-yl)propanoic acid | Prep. HPLC, method 3 | 71% |

TABLE 28a-continued

Examples of Core 10 (Ex. 164-Ex. 180.)

| No | R2 | R5 | Starting material | General Procedure | Reagent | Purification Method | Yield, (isolated salt) |
|---|---|---|---|---|---|---|---|
| Ex. 177 | 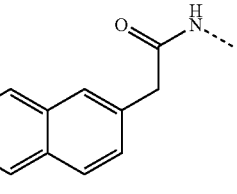 | 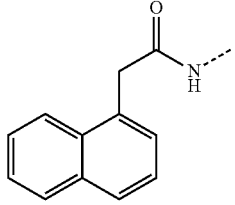 | Ex. 172 | L.1.2*) | 1-naphthylacetic acid | Prep. HPLC, method 3 | 68% |
| Ex. 178 | 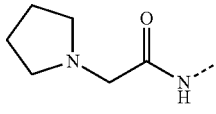 | 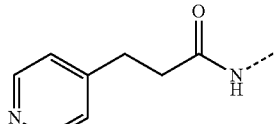 | Ex. 173 | L.1.2 | 3-(pyridine-4-yl)propanoic acid | Prep. HPLC, method 2 | 48% |
| Ex. 179 | 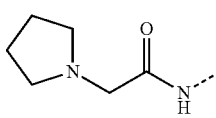 | 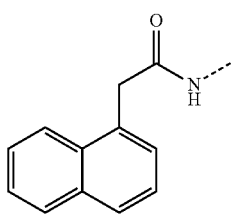 | Ex. 173 | L.1.2*) | 1-naphthylacetic acid | Prep. HPLC, method 3 | 84% |
| Ex. 180 | 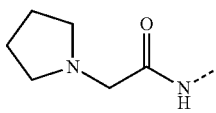 | 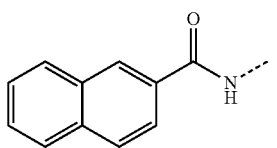 | Ex. 173 | L.1.1*) | 2-naphthoyl chloride (1.5 equiv.) | Prep. HPLC, method 3 | 78% |

*)The treatment with (polystyrylmethyl)trimethylammonium bicarbonate was replaced by an aqueous workup (CHCl₃, sat. aq. NaHCO₃ soln)

TABLE 28b

Examples of Core 10 (Ex. 164-Ex. 180.)

| No | R2 | R5 | Formula | Monoisotopic Mass | Rt (purity at 220 nm) | [M + H]+ found | LC-MS-Method |
|---|---|---|---|---|---|---|---|
| Ex. 164-Ex. 165: cf. experimental description | | | | | | | |
| Ex. 166 | 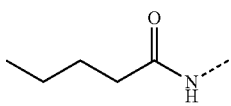 | 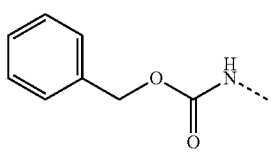 | C30H38N4O6 | 550.3 | 1.96 (99) | 551.3 | Method 4a |
| Ex. 167 | 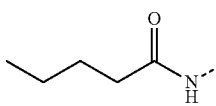 | NH₂ | C22H32N4O4 | 416.2 | 1.4 (99) | 417.3 | Method 4a |
| Ex. 168 | 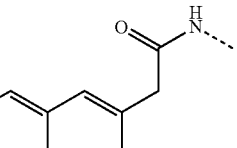 | 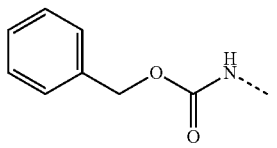 | C37H38N4O6 | 634.3 | 2.2 (98) | 635.3 | Method 4a |

TABLE 28b-continued

Examples of Core 10 (Ex. 164-Ex. 180,)

| No | R2 | R5 | Formula | Monoisotopic Mass | Rt (purity at 220 nm) | [M + H]+ found | LC-MS-Method |
|---|---|---|---|---|---|---|---|
| Ex. 169 | | | C31H39N5O6 | 577.3 | 1.57 (99) | 578.4 | Method 4a |
| Ex. 170 | | | C30H39N5O5 | 549.3 | 1.47 (97) | 550.4 | Method 4a |
| Ex. 171 | | | C33H38N4O5 | 570.3 | 2.1 (100) | 571.3 | Method 4a |
| Ex. 172 | | NH2 | C29H32N4O4 | 500.2 | 1.60 (91) | 501.3 | Method 4a |
| Ex. 173 | | NH2 | C23H33N5O4 | 443.3 | 1.48 (99) | 444.2 | Method 5a |
| Ex. 174 | | | C31H34N4O5 | 542.3 | 1.82 (99) | 543.2 | Method 4a |
| Ex. 175 | | | C35H41N5O5 | 611.3 | 1.69 (96) | 612.2 | Method 4a |
| Ex. 176 | | | C37H39N5O5 | 633.3 | 1.68 (99) | 634.3 | Method 4a |

TABLE 28b-continued

Examples of Core 10 (Ex. 164-Ex. 180,)

| No | R2 | R5 | Formula | Monoisotopic Mass | Rt (purity at 220 nm) | [M + H]+ found | LC-MS-Method |
|---|---|---|---|---|---|---|---|
| Ex. 177 | 2-naphthylacetamide | 1-naphthylacetamide | C41H40N4O5 | 668.3 | 2.24 (92) | 669.3 | Method 4a |
| Ex. 178 | pyrrolidinylacetamide | 4-pyridylpropanamide | C31H40N6O5 | 576.3 | 1.07 (98) | 577.3 | Method 4a |
| Ex. 179 | pyrrolidinylacetamide | 1-naphthylacetamide | C35H41N5O5 | 611.3 | 1.69 (93) | 612.3 | Method 4a |
| Ex. 180 | pyrrolidinylacetamide | 2-naphthylcarboxamide | C34H39N5O5 | 597.3 | 1.69 (97) | 597.8 | Method 4a |

TABLE 28c

Examples of Core 10 (Ex. 164-Ex. 180,)

| No | R2 | R5 | IUPAC name |
|---|---|---|---|
| Ex. 164 | 2-(trimethylsilyl)ethoxycarbonylamino | benzyl carbamate | benzyl N-[(4S,6S,10S)-13-methyl-9,14-dioxo-6-({[2-(trimethylsilyl)ethoxy]carbonyl}amino)-2-oxa-8,13-diazatricyclo[13.3.1.0^{4,8}]nonadeca-1(19),15,17-trien-10-yl]carbamate |
| Ex. 165 | NH2 | benzyl carbamate | benzyl N-[(4S,6S,10S)-6-amino-13-methyl-9,14-dioxo-2-oxa-8,13-diazatricyclo[13.3.1.0^{4,8}]nonadeca-1(19),15,17-trien-10-yl]carbamate |
| Ex. 166 | pentanoylamino | benzyl carbamate | benzyl N-[(4S,6S,10S)-13-methyl-9,14-dioxo-6-(pentanoyl-amino)-2-oxa-8,13-diazatricyclo[13.3.1.0^{4,8}]nonadeca-1(19),15,17-trien-10-yl]carbamate |

TABLE 28c-continued

Examples of Core 10 (Ex. 164-Ex. 180,)

| No | R2 | R5 | IUPAC name |
|---|---|---|---|
| Ex. 167 | (butyl-C(O)-NH-) | NH$_2$ | N-[(4S,6S,10S)-10-amino-13-methyl-9,14-dioxo-2-oxa-8,13-diazatricyclo[13.3.1.0$^{4,8}$]nonadeca-1(19),15,17-trien-6-yl]pentanamide |
| Ex. 168 | (2-naphthyl-CH$_2$-C(O)-NH-) | (benzyl-O-C(O)-NH-) | benzyl N-[(4S,6S,10S)-13-methyl-6-{[2-(2-naphthyl)acetyl]amino}-9,14-dioxo-2-oxa-8,13-diazatricyclo[13.3.1.0$^{4,8}$]nonadeca-1(19),15,17-trien-10-yl]carbamate |
| Ex. 169 | (pyrrolidinyl-CH$_2$-C(O)-NH-) | (benzyl-O-C(O)-NH-) | benzyl N-[(4S,6S,10S)-13-methyl-9,14-dioxo-6-{[2-(1-pyrrolidinyl)acetyl]amino}-2-oxa-8,13-diazatricyclo[13.3.1.0$^{4,8}$]nonadeca-1(19),15,17-trien-10-yl]carbamate |
| Ex. 170 | (butyl-C(O)-NH-) | (4-pyridinyl-CH$_2$CH$_2$-C(O)-NH-) | N-[(4S,6S,10S)-13-methyl-9,14-dioxo-10-{[3-(4-pyridinyl)propanoyl]amino}-2-oxa-8,13-diazatricyclo[13.3.1.0$^{4,8}$]nonadeca-1(19),15,17-trien-6-yl]pentanamide |
| Ex. 171 | (butyl-C(O)-NH-) | (2-naphthyl-C(O)-NH-) | N-[(4S,6S,10S)-13-methyl-9,14-dioxo-6-(pentanoylamino)-2-oxa-8,13-diazatricyclo[13.3.1.0$^{4,8}$]nonadeca-1(19),15,17-trien-10-yl]-2-naphthamide |
| Ex. 172 | (2-naphthyl-CH$_2$-C(O)-NH-) | NH$_2$ | N-[(4S,6S,10S)-10-amino-13-methyl-9,14-dioxo-2-oxa-8,13-diazatricyclo[13.3.1.0$^{4,8}$]nonadeca-1(19),15,17-trien-6-yl]-2-(2-naphthyl)acetamide |
| Ex. 173 | (pyrrolidinyl-CH$_2$-C(O)-NH-) | NH$_2$ | N-[(4S,6S,10S)-10-amino-13-methyl-9,14-dioxo-2-oxa-8,13-diazatricyclo[13.3.1.0$^{4,8}$]nonadeca-1(19),15,17-trien-6-yl]-2-(1-pyrrolidinyl)acetamide |
| Ex. 174 | (2-naphthyl-CH$_2$-C(O)-NH-) | (CH$_3$-C(O)-NH-) | N-[(4S,6S,10S)-10-(acetylamino)-13-methyl-9,14-dioxo-2-oxa-8,13-diazatricyclo[13.3.1.0$^{4,8}$]nonadeca-1(19),15,17-trien-6-yl]-2-(2-naphthyl)acetamide |
| Ex. 175 | (2-naphthyl-CH$_2$-C(O)-NH-) | (pyrrolidinyl-CH$_2$-C(O)-NH-) | N-[(4S,6S,10S)-13-methyl-9,14-dioxo-10-{[2-(1-pyrrolidinyl)acetyl]amino}-2-oxa-8,13-diazatricyclo[13.3.1.0$^{4,8}$]nonadeca-1(19),15,17-trien-6-yl]-2-(2-naphthyl)acetamide |

TABLE 28c-continued

Examples of Core 10 (Ex. 164-Ex. 180.)

| No | R2 | R5 | IUPAC name |
|---|---|---|---|
| Ex. 176 | 2-naphthyl-CH2-C(O)NH- | pyridin-4-yl-CH2CH2-C(O)NH- | N-[(4S,6S,10S)-13-methyl-6-{[2-(2-naphthyl)acetyl]amino}-9,14-dioxo-2-oxa-8,13-diazatricyclo[13.3.1.0$^{4,8}$]nonadeca-1(19),15,17-trien-10-yl]-3-(4-pyridinyl)propanamide |
| Ex. 177 | 2-naphthyl-CH2-C(O)NH- | 1-naphthyl-CH2-C(O)NH- | N-[(4S,6S,10S)-13-methyl-6-{[2-(2-naphthyl)acetyl]amino}-9,14-dioxo-2-oxa-8,13-diazatricyclo[13.3.1.0$^{4,8}$]nonadeca-1(19),15,17-trien-10-yl]-2-(1-naphthyl) acetamide |
| Ex. 178 | pyrrolidin-1-yl-CH2-C(O)NH- | pyridin-4-yl-CH2CH2-C(O)NH- | N-[(4S,6S,10S)-13-methyl-9,14-dioxo-6-{[2-(1-pyrrolidinyl)acetyl]amino}-2-oxa-8,13-diazatricyclo[13.3.1.0$^{4,8}$]nonadeca-1(19),15,17-trien-10-yl]-3-(4-pyridinyl)propanamide |
| Ex. 179 | pyrrolidin-1-yl-CH2-C(O)NH- | 1-naphthyl-CH2-C(O)NH- | N-[(4S,6S,10S)-13-methyl-9,14-dioxo-6-{[2-(1-pyrrolidinyl)acetyl]amino}-2-oxa-8,13-diazatricyclo[13.3.1.0$^{4,8}$]nonadeca-1(19),15,17-trien-10-yl]-2-(1-naphthyl)acetamide |
| Ex. 180 | pyrrolidin-1-yl-CH2-C(O)NH- | 2-naphthyl-C(O)NH- | N-[(4S,6S,10S)-13-methyl-9,14-dioxo-6-{[2-(1-pyrrolidinyl)acetyl]amino}-2-oxa-8,13-diazatricyclo[13.3.1.0$^{4,8}$]nonadeca-1(19),15,17-trien-10-yl]-2-naphthamide |

TABLE 29a

Examples of Core 11 (Ex. 181-Ex. 195)

| No | R2 | R5 | Starting material | General Procedure | Reagent | Purification Method | Yield, (isolated salt) |
|---|---|---|---|---|---|---|---|
| Ex. 181-Ex. 182: cf. experimental description | | | | | | | |
| Ex. 183 | CH3-C(O)NH- | Bn-O-C(O)NH- | Ex. 182 | L.1.1 | acetic anhydride (5 equiv.) | FC (CH2Cl2/MeOH) | 75% |
| Ex. 184 | 2-naphthyl-CH2-C(O)NH- | Bn-O-C(O)NH- | Ex. 182 | L.1.3 | 2-naphthylacetic acid (1.2 equiv.) | FC (EtOAc, then CH2Cl2/MeOH) | 94% |

TABLE 29a-continued

Examples of Core 11 (Ex. 181-Ex. 195)

| No | R2 | R5 | Starting material | General Procedure | Reagent | Purification Method | Yield, (isolated salt) |
|---|---|---|---|---|---|---|---|
| Ex. 185 | naphthyl-CH2-C(O)-NH- | NH2 | Ex. 184 | K | H2, Pd(OH)2—C | crude product | 99% |
| Ex. 186 | naphthyl-CH2-C(O)-NH- | naphthyl-CH2-C(O)-NH- | Ex. 185 | L.1.3 | 2-naphthylacetic acid (1.2 equiv.) | prep. HPLC, method 3 | 60% |
| Ex. 186 | naphthyl-CH2-C(O)-NH- | naphthyl-CH2-C(O)-NH- | 139 | Synthesis on solid support | 2-naphthylacetic acid | prep. HPLC, method 3 | 32% |
| Ex. 187 | naphthyl-CH2-C(O)-NH- | pyrrolidin-1-yl-CH2-C(O)-NH- | Ex. 185 | L.1.3 | pyrrolidin-1-acetic acid (1.2 equiv.) | prep. HPLC, method 3 then prep. HPLC, method 1 | 38% (TFA salt) |
| Ex. 188 | naphthyl-CH2-C(O)-NH- | pyridin-4-yl-CH2CH2-C(O)-NH- | Ex. 185 | L.1.3 | 3-(pyridine-4-yl)propanoic acid (1.2 equiv.) | prep. HPLC, method 3 then prep. HPLC, method 1 | 32% (TFA salt) |
| Ex. 189 | naphthyl-CH2-C(O)-NH- | CH3(CH2)3-C(O)-NH- | Ex. 185 | L.1.1 | valeroyl chloride (2 equiv.) | prep. HPLC, method 3 | 52% |
| Ex. 190 | NH2 | 3,5-difluorobenzoyl-NH- | Ex. 193 | 1.2 | TBAF (4 equiv.) in THF | crude product, contaminated with TBAF | ca 70% |

TABLE 29a-continued

Examples of Core 11 (Ex. 181-Ex. 195)

| No | R2 | R5 | Starting material | General Procedure | Reagent | Purification Method | Yield, (isolated salt) |
|---|---|---|---|---|---|---|---|
| Ex. 191 | (acetamide structure) | (3,5-difluorobenzamide structure) | Ex. 190 | L.1.1 | Acetic anhydride (10 equiv.) Pyridine/CH$_2$Cl$_2$ 1:1 (3 mL) | prep. HPLC, method 3 | 62% |
| Ex. 192 | (3-(pyridin-4-yl)propanamide structure) | (3,5-difluorobenzamide structure) | Ex. 190 | L.1.3 | 3-(pyridine-4-yl)propanoic acid (1.2 equiv.) | prep. HPLC, method 3 | 63% |
| Ex. 193 | (2-(trimethylsilyl)ethyl carbamate structure) | (3,5-difluorobenzamide structure) | Ex. 194 | L.1.1 | 3,5-difluorbenzoyl chloride (2 equiv.) | FC (EtOAc) | 85% |
| Ex. 194 | (2-(trimethylsilyl)ethyl carbamate structure) | NH$_2$ | Ex. 181 | K | H$_2$, Pd(OH)$_2$—C | crude product | quant. |
| Ex. 195 | (benzamide structure) | (3,5-difluorobenzamide structure) | Ex. 190 | L.1.1 | benzoyl chloride (2 equiv.) | preparative HPLC method 3 | 78% |

TABLE 29b

Examples of Core 11 (Ex. 181-Ex. 195, continued on the following pages)

| No | R2 | R5 | Formula | Mono-isotopic Mass | Rt (purity at 220 nm) | [M + H]$^+$ found | LC-MS-Method |
|---|---|---|---|---|---|---|---|
| Ex. 181-Ex. 182: cf. experimental description | | | | | | | |
| Ex. 183 | (acetamide structure) | (benzyl carbamate structure) | C28H34N4O6 | 522.3 | 1.56 (99) | 523.3 | Method 2 |

US 9,695,191 B2
TABLE 29b-continued
Examples of Core 11 (Ex. 181-Ex. 195, continued on the following pages)
| No | R2 | R5 | Formula | Mono-isotopic Mass | Rt (purity at 220 nm) | [M + H]+ found | LC-MS-Method |
|---|---|---|---|---|---|---|---|
| Ex. 184 | 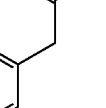 | 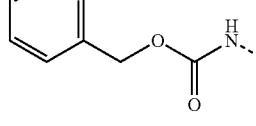 | C38H40N4O6 | 648.3 | 1.92 (96) | 649.5 | Method 2 |
| Ex. 185 | 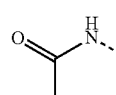 | NH2 | C30H34N4O4 | 514.3 | 1.48 (98) | 515.4 | Method 2 |
| Ex. 186 | 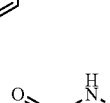 |  | C42H42N4O5 | 682.3 | 2.00 (91) | 683.5 | Method 2 |
| Ex. 186 | 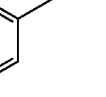 | 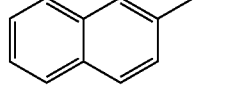 | C42H42N4O5 | 682.3 | 2.26 (98) | 683.3 | Method 4a |
| Ex. 187 | 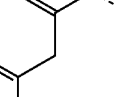 | 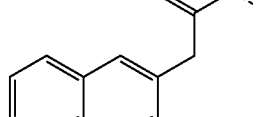 | C36H43N5O5 | 625.3 | 1.62 (100) | 626.4 | Method 2 |
| Ex. 188 | 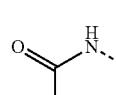 | 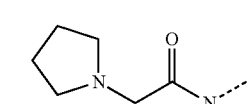 | C38H41N5O5 | 647.3 | 1.60 (99) | 648.3 | Method 2 |
| Ex. 189 | 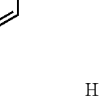 |  | C35H42N4O5 | 598.3 | 1.88 (85), 1.93 (8) | 599.5 | Method 2 |

TABLE 29b-continued

Examples of Core 11 (Ex. 181-Ex. 195, continued on the following pages)

| No | R2 | R5 | Formula | Mono-isotopic Mass | Rt (purity at 220 nm) | [M + H]+ found | LC-MS-Method |
|---|---|---|---|---|---|---|---|
| Ex. 190 | NH2 | 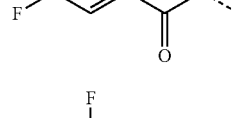 | C25H28F2N4O4 | 486.2 | 1.42 (98) | 487.3 | Method 4a |
| Ex. 191 | 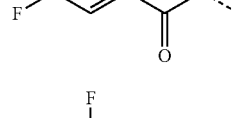 | 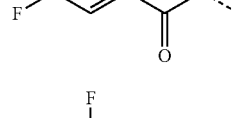 | C27H30F2N4O5 | 528.2 | 1.69 (99) | 529.3 | Method 4a |
| Ex. 192 |  | 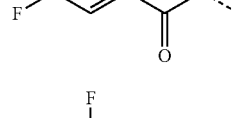 | C33H35F2N5O5 | 619.3 | 1.50 (99) | 620.3 | Method 4a |
| Ex. 193 | 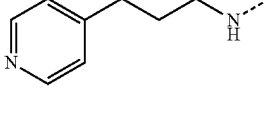 | 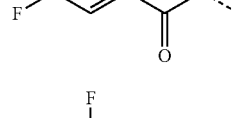 | C31H40F2N4O6Si | 630.3 | 2.13 (97) | 631.4 | Method 2 |
| Ex. 194 | 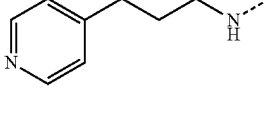 | NH2 | C24H38N4O5Si | 490.3 | 1.62 (99) | 491.3 | Method 2 |
| Ex. 195 | 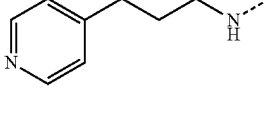 | 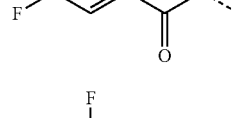 | C32H32F2N4O5 | 590.2 | 1.99 (98) | 591.3 | Method 4a |

TABLE 29c

Examples of Core 11 (Ex. 181-Ex. 195, continued on the following pages)

| No | R2 | R5 | IUPAC name |
|---|---|---|---|
| Ex. 181 |  | 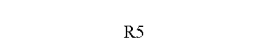 | benzyl N-[(4S,6S,10S)-14-methyl-9,15-dioxo-6-({[2-(trimethylsilyl)ethoxy]carbonyl}amino)-2-oxa-8,14-diazatricyclo[14.3.1.0$^{4,8}$]icosa-1(20),16,18-trien-10-yl]carbamate |

TABLE 29c-continued

Examples of Core 11 (Ex. 181-Ex. 195, continued on the following pages)

| No | R2 | R5 | IUPAC name |
|---|---|---|---|
| Ex. 182 | NH$_2$ | benzyl carbamate (Cbz-NH-) | benzyl N-[(4S,6S,10S)-6-amino-14-methyl-9,15-dioxo-2-oxa-8,14-diazatricyclo[14.3.1.0$^{4,8}$]icosa-1(20),16,18-trien-10-yl]carbamate |
| Ex. 183 | acetamido (AcNH-) | benzyl carbamate (Cbz-NH-) | benzyl N-[(4S,6S,10S)-6-(acetylamino)-14-methyl-9,15-dioxo-2-oxa-8,14-diazatricyclo[14.3.1.0$^{4,8}$]icosa-1(20),16,18-trien-10-yl]carbamate |
| Ex. 184 | 2-(2-naphthyl)acetamido | benzyl carbamate (Cbz-NH-) | benzyl N-[(4S,6S,10S)-14-methyl-6-{[2-(2-naphthyl)acetyl]amino}-9,15-dioxo-2-oxa-8,14-diazatricyclo[14.3.1.0$^{4,8}$]icosa-1(20),16,18-trien-10-yl]carbamate |
| Ex. 185 | 2-(2-naphthyl)acetamido | NH$_2$ | N-[(4S,6S,10S)-10-amino-14-methyl-9,15-dioxo-2-oxa-8,14-diazatricyclo[14.3.1.0$^{4,8}$]icosa-1(20),16,18-trien-6-yl]-2-(2-naphthyl)acetamide |
| Ex. 186 | 2-(2-naphthyl)acetamido | 2-(2-naphthyl)acetamido | N-[(4S,6S,10S)-14-methyl-10-{[2-(2-naphthyl)acetyl]amino}-9,15-dioxo-2-oxa-8,14-diazatricyclo[14.3.1.0$^{4,8}$]icosa-1(20),16,18-trien-6-yl]-2-(2-naphthyl)acetamide |
| Ex. 187 | 2-(2-naphthyl)acetamido | 2-(1-pyrrolidinyl)acetamido | N-[(4S,6S,10S)-14-methyl-9,15-dioxo-10-{[2-(1-pyrrolidinyl)acetyl]amino}-2-oxa-8,14-diazatricyclo[14.3.1.0$^{4,8}$]icosa-1(20),16,18-trien-6-yl]-2-(2-naphthyl)acetamide |
| Ex. 188 | 2-(2-naphthyl)acetamido | 3-(4-pyridinyl)propanamido | N-[(4S,6S,10S)-14-methyl-6-{[2-(2-naphthyl)acetyl]amino}-9,15-dioxo-2-oxa-8,14-diazatricyclo[14.3.1.0$^{4,8}$]icosa-1(20),16,18-trien-10-yl]-3-(4-pyridinyl)propanamide |
| Ex. 189 | 2-(2-naphthyl)acetamido | pentanamido | N-[(4S,6S,10S)-14-methyl-6-{[2-(2-naphthyl)acetyl]amino}-9,15-dioxo-2-oxa-8,14-diazatricyclo[14.3.1.0$^{4,8}$]icosa-1(20),16,18-trien-10-yl]pentanamide |

TABLE 29c-continued

Examples of Core 11 (Ex. 181-Ex. 195, continued on the following pages)

| No | R2 | R5 | IUPAC name |
|---|---|---|---|
| Ex. 190 | NH₂ | 3,5-difluorobenzamide (F, F-substituted benzamide) | N-[(4S,6S,10S)-6-amino-14-methyl-9,15-dioxo-2-oxa-8,14-diazatricyclo[14.3.1.0$^{4,8}$]icosa-1(20),16,18-trien-10-yl]-3,5-difluorobenzamide |
| Ex. 191 | acetylamino (CH₃C(O)NH–) | 3,5-difluorobenzamide | N-[(4S,6S,10S)-6-(acetylamino)-14-methyl-9,15-dioxo-2-oxa-8,14-diazatricyclo[14.3.1.0$^{4,8}$]icosa-1(20),16,18-trien-10-yl]-3,5-difluorobenzamide |
| Ex. 192 | 3-(4-pyridinyl)propanoylamino | 3,5-difluorobenzamide | 3,5-difluoro-N-[(4S,6S,10S)-14-methyl-9,15-dioxo-6-{[3-(4-pyridinyl)propanoyl]amino}-2-oxa-8,14-diazatricyclo[14.3.1.0$^{4,8}$]icosa-1(20),16,18-trien-10-yl]benzamide |
| Ex. 193 | 2-(trimethylsilyl)ethyl carbamate | 3,5-difluorobenzamide | 2-(trimethylsilyl)ethyl N-[(4S,6S,10S)-10-[(3,5-difluorobenzoyl)amino]-14-methyl-9,15-dioxo-2-oxa-8,14-diazatricyclo[14.3.1.0$^{4,8}$]icosa-1(20),16,18-trien-6-yl]carbamate |
| Ex. 194 | 2-(trimethylsilyl)ethyl carbamate | NH₂ | 2-(trimethylsilyl)ethyl N-[(4S,6S,10S)-10-amino-14-methyl-9,15-dioxo-2-oxa-8,14-diazatricyclo[14.3.1.0$^{4,8}$]icosa-1(20),16,18-trien-6-yl]carbamate |
| Ex. 195 | benzoylamino (PhC(O)NH–) | 3,5-difluorobenzamide | N-[(4S,6S,10S)-6-(benzoylamino)-14-methyl-9,15-dioxo-2-oxa-8,14-diazatricyclo[14.3.1.0$^{4,8}$]icosa-1(20),16,18-trien-10-yl]-3,5-difluorobenzamide |

TABLE 30a

Examples of Core 12 (Ex. 196-Ex. 214 continued on the following pages)

| No | R2 | R5 | Starting material | General Procedure | Reagent | Purification Method | Yield, (isolated salt) |
|---|---|---|---|---|---|---|---|
| Ex. 196-Ex. 198: cf. experimental description | | | | | | | |
| Ex. 199 | acetylamino (CH₃C(O)NH–) | benzyl carbamate (PhCH₂OC(O)NH–) | Ex. 197•HCl | L.1.1 | acetic anhydride (10 equiv.) pyridine (2 mL) | FC (CH₂Cl₂/MeOH) then prep HPLC, method 1 | 36% |

TABLE 30a-continued

Examples of Core 12 (Ex. 196-Ex. 214 continued on the following pages)

| No | R2 | R5 | Starting material | General Procedure | Reagent | Purification Method | Yield, (isolated salt) |
|---|---|---|---|---|---|---|---|
| Ex. 200 | 3-indolylacetamide group | benzyl carbamate group | Ex. 197•HCl | L.1.3 | 3-indoleacetic acid (1.5 equiv.), HATU (1.5 equiv.), HOAt (1.5 equiv), i-Pr$_2$NEt (5 equiv.) | FC (CH$_2$Cl$_2$/MeOH) then prep HPLC, method 1 | 22% |
| Ex. 200 | 3-indolylacetamide group | benzyl carbamate group | Ex. 197•TFA | L.1.3 | 3-indoleacetic acid (1.5 equiv.), HATU (1.5 equiv.), HOAt (1.5 equiv), i-Pr$^2$NEt (5 equiv.) | FC (EtOAc, then CH$_2$Cl$_2$/MeOH) | 78% |
| Ex. 201 | N,N-dimethylglycinamide group | benzyl carbamate group | Ex. 197•HCl | L.1.3 | N,N-dimethyl glycine (1.7 equiv.) | FC (CH$_2$Cl$_2$/MeOH) and prep HPLC, method 1 | 91% *) (TFA salt) |
| Ex. 202 | 3-indolylacetamide group | NH$_2$ | Ex. 200 | K | H$_2$, Pd(OH)$_2$—C | crude product | 97% |
| Ex. 203 | N,N-dimethylglycinamide group | NH$_2$ | Ex. 201 | K | H$_2$, Pd(OH)$_2$—C | crude product | 99% |
| Ex. 204 | acetamide group | 3-indolylacetamide group | Ex. 214 | L.1.3 | 3-indoleacetic acid (1.2 equiv.), HATU (1.5 equiv.), HOAt (1.5 equiv), i-Pr$_2$NEt (3 equiv.) | FC (CH$_2$Cl$_2$/MeOH) | 64% |
| Ex. 205 | acetamide group | N,N-dimethylglycinamide group | Ex. 214 | L.1.3 | N,N-dimethyl glycine (1.7 equiv.) | prep HPLC, method 1 | 47% (TFA salt) |
| Ex. 206 | 3-indolylacetamide group | N,N-dimethylglycinamide group | Ex. 202 | L.1.3 | N,N-dimethyl glycine (1.7 equiv.) | prep HPLC, method 1 | 39% (TFA salt) |

TABLE 30a-continued

Examples of Core 12 (Ex. 196-Ex. 214 continued on the following pages)

| No | R2 | R5 | Starting material | General Procedure | Reagent | Purification Method | Yield, (isolated salt) |
|---|---|---|---|---|---|---|---|
| Ex. 207 | (indol-3-yl-CH2-C(O)-NH-) | HOOC-CH2-CH2-C(O)-NH- | Ex. 202 | L.1.1 | succinic anhydride (1.05 equiv.) pyridine (49 equiv.) | prep HPLC, method 2 | 48% |
| Ex. 208 | (CH3)2N-CH2-C(O)-NH- | CH3-C(O)-NH- | Ex. 203 | L.1.1 | acetic anhydride (10 equiv.) pyridine/CH2Cl2 1:1 (3 mL) | prep HPLC, method 2 | 59% |
| Ex. 209 | (CH3)2N-CH2-C(O)-NH- | HOOC-CH2-CH2-C(O)-NH- | L.1.1 | Ex. 203 | succinic anhydride (1.05 equiv.) pyridine (49 equiv.) | prep HPLC, method 2 | 35% |
| Ex. 210 | (CH3)2N-CH2-C(O)-NH- | 2-naphthyl-CH2-C(O)-NH- | Ex. 203 | L.1.3 | 2-naphthylacetic acid (1.2 equiv.) | prep HPLC, method 1 | 38% (TFA salt) |
| Ex. 211 | (indol-3-yl-CH2-C(O)-NH-) | pyridin-4-yl-CH2CH2-C(O)-NH- | Ex. 202 | L.1.2 | 3-(pyridine-4-yl)propanoic acid | prep HPLC, method 1 | 44% (TFA salt) |
| Ex. 212 | (indol-3-yl-CH2-C(O)-NH-) | 2-naphthyl-CH2-C(O)-NH- | Ex. 202 | L.1.3 | 2-naphthylacetic acid (1.2 equiv.) | prep HPLC, method 1 then FC (EtOAc/MeOH) | 53% |
| Ex. 213 | (indol-3-yl-CH2-C(O)-NH-) | CH3(CH2)8CONH | Ex. 202 | L.1.1 | decanoyl chloride (2 equiv.) | prep HPLC, method 1 then FC (EtOAc/MeOH) | 35% |
| Ex. 214 | CH3-C(O)-NH- | NH2 | Ex. 199 | K | H2, Pd(OH)2—C | crude product | 98% |

\*)An analytical sample was further purified by prep. HPLC (method 1), to afford the TFA salt of the corresponding product TABLE 30b
Examples of Core 12 (Ex. 196-Ex. 214, continued on the following pages)
| No | R2 | R5 | Formula | Monoisotopic Mass | Rt (purity at 220 nm) | [M + H]+ found | LC-MS-Method |
|---|---|---|---|---|---|---|---|
| | | Ex. 196-Ex. cf.198: experimental description | | | | | |
| Ex. 199 | 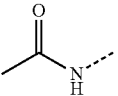 | 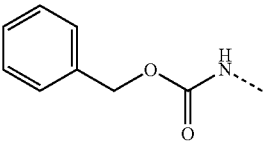 | C29H35N5O7 | 565.3 | 1.92 (100) | 566.4 | Method 1a |
| Ex. 200 | 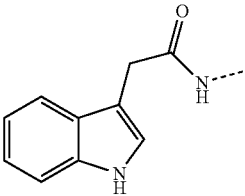 | 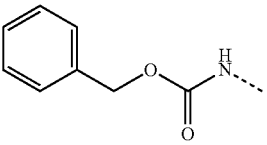 | C37H40N6O7 | 680.3 | 2.23 (98) | 681.4 | Method 1a |
| Ex. 200 | 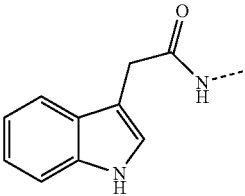 | 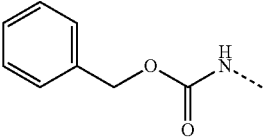 | C37H40N6O7 | 680.3 | 1.68 (93) | 681.5 | Method 2 |
| Ex. 201 | 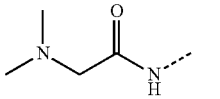 | 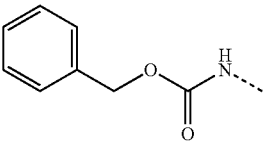 | C31H40N6O7 | 608.3 | 1.28 (99) | 609.4 | Method 2 |
| Ex. 202 | 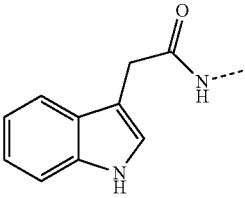 | NH2 | C29H34N6O5 | 546.3 | 1.32 (76) | 547.4 | Method 2 |
| Ex. 203 | 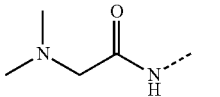 | NH2 | C23H34N6O5 | 474.3 | 0.77 | 475.5 | Method 9c |
| Ex. 204 | 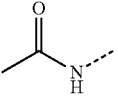 | 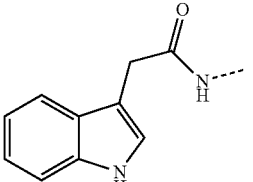 | C31H36N6O6 | 588.3 | 1.49 (87) | 589.2 | Method 4a |
| Ex. 205 | 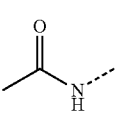 | 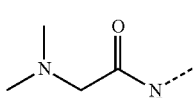 | C25H36N6O6 | 516.3 | 1.42 (100) | 517.3 | Method 1a |

TABLE 30b-continued
Examples of Core 12 (Ex. 196-Ex. 214, continued on the following pages)
| No | R2 | R5 | Formula | Monoisotopic Mass | Rt (purity at 220 nm) | [M + H]+ found | LC-MS-Method |
|---|---|---|---|---|---|---|---|
| Ex. 206 | 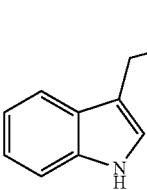 | 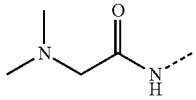 | C33H41N7O6 | 631.3 | 1.84 (97) | 632.4 | Method 1a |
| Ex. 207 | 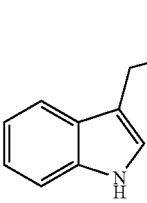 | 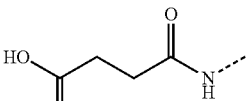 | C33H38N6O8 | 646.3 | 1.42 (100) | 647.4 | Method 2 |
| Ex. 208 | 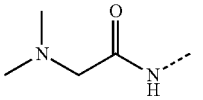 | 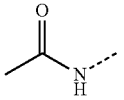 | C25H36N6O6 | 516.3 | 0.95 (100) | 517.4 | Method 2 |
| Ex. 209 | 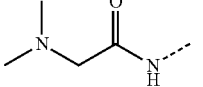 | 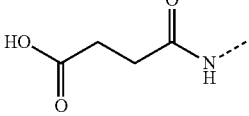 | C27H38N6O8 | 574.3 | 1.02 (92) | 575.4 | Method 3 |
| Ex. 210 | 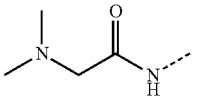 | 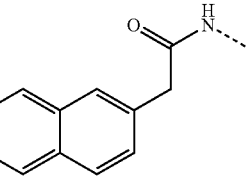 | C35H42N6O6 | 642.3 | 1.37 (100) | 643.4 | Method 2 |
| Ex. 211 | 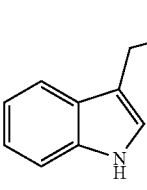 | 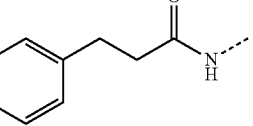 | C37H41N7O6 | 679.3 | 1.34 (92) | 680.5 | Method 2 |
| Ex. 212 | 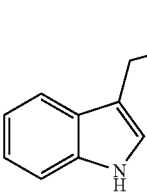 | 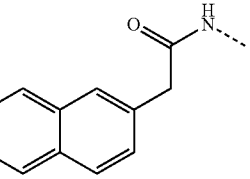 | C41H42N6O6 | 714.3 | 1.75 (86) | 715.5 | Method 2 |
| Ex. 213 | 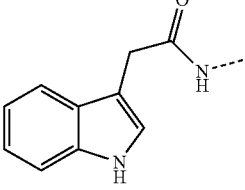 | CH3(CH2)8CONH | C39H52N6O6 | 700.4 | 1.96 (99) | 701.6 | Method 2 |

TABLE 30b-continued

Examples of Core 12 (Ex. 196-Ex. 214, continued on the following pages)

| No | R2 | R5 | Formula | Monoisotopic Mass | Rt (purity at 220 nm) | [M + H]+ found | LC-MS- Method |
|---|---|---|---|---|---|---|---|
| Ex. 214 | 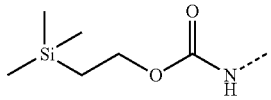 | NH2 | C21H29N5O5 | 431.2 | 0.81*) | 432.2 | Method 9c |

*) Analytical HPLC (5% CH3CN): 2.52 (93)

TABLE 30c

Examples of Core 12 (Ex. 196-Ex. 214, continued on the following pages)

| No | R2 | R5 | IUPAC name |
|---|---|---|---|
| Ex. 196 | 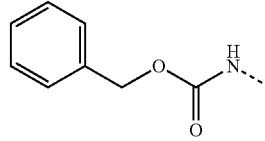 | 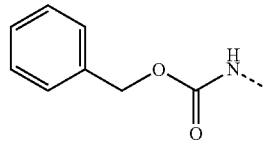 | benzyl N-[(4S,6S,13S)-11,15-dimethyl-9,12,16-trioxo-6-({[2-(trimethylsilyl)ethoxy]carbonyl]amino)-2-oxa-8,11,15-triazatricyclo[15.3.1.0^{4,8}]henicosa-1(21),17,19-trien-13-yl]carbamate |
| Ex. 197 | NH2 | 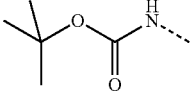 | benzyl N-[(4S,6S,13S)-6-amino-11,15-dimethyl-9,12,16-trioxo-2-oxa-8,11,15-triazatricyclo[15.3.1.0^{4,8}]henicosa-1(21),17,19-trien-13-yl]carbamate |
| Ex. 198 | 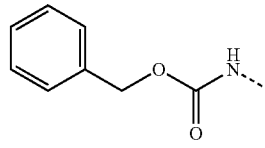 | 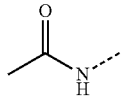 | benzyl N-[(4S,6S,13S)-6-[(tert-butoxycarbonyl)amino]-11,15-dimethyl-9,12,16-trioxo-2-oxa-8,11,15-triazatricyclo[15.3.1.0^{4,8}]henicosa-1(21),17,19-trien-13-yl]carbamate |
| Ex. 199 | 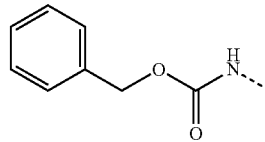 | 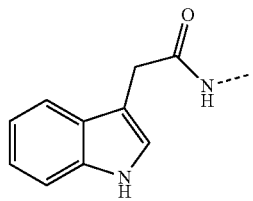 | benzyl N-[(4S,6S,13S)-6-(acetylamino)-11,15-dimethyl-9,12,16-trioxo-2-oxa-8,11,15-triazatricyclo[15.3.1.0^{4,8}]henicosa-1(21),17,19-trien-13-yl]carbamate |
| Ex. 200 | 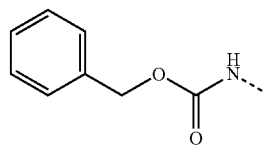 | 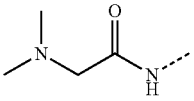 | benzyl N-[(4S,6S,13S)-6-{[2-(1H-indol-3-yl)acetyl]amino}-11,15-dimethyl-9,12,16-trioxo-2-oxa-8,11,15-triazatricyclo[15.3.1.0^{4,8}]henicosa-1(21),17,19-trien-13-yl]carbamate |
| Ex. 201 | 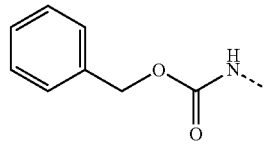 | 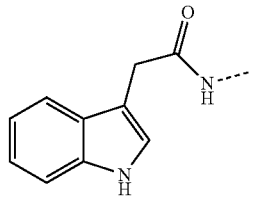 | benzyl N-[(4S,6S,13S)-6-{[2-(dimethylamino)acetyl]amino}-11,15-dimethyl-9,12,16-trioxo-2-oxa-8,11,15-triazatricyclo[15.3.1.0^{4,8}]henicosa-1(21),17,19-trien-13-yl]carbamate |
| Ex. 202 | 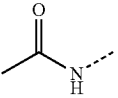 | NH2 | N-[(4S,6S,13S)-13-amino-11,15-dimethyl-9,12,16-trioxo-2-oxa-8,11,15-triazatricyclo[15.3.1.0^{4,8}]henicosa-1(21),17,19-trien-6-yl]-2-(1H-indol-3-yl)acetamide |

TABLE 30c-continued

Examples of Core 12 (Ex. 196-Ex. 214, continued on the following pages)

| No | R2 | R5 | IUPAC name |
|---|---|---|---|
| Ex. 203 | (CH₃)₂N-CH₂-C(=O)-NH- | NH₂ | N-[(4S,6S,13S)-13-amino-11,15-dimethyl-9,12,16-trioxo-2-oxa-8,11,15-triazatricyclo[15.3.1.0$^{4,8}$]henicosa-1(21),17,19-trien-6-yl]-2-(dimethylamino)acetamide |
| Ex. 204 | CH₃-C(=O)-NH- | (1H-indol-3-yl)-CH₂-C(=O)-NH- | N-[(4S,6S,13S)-6-(acetylamino)-11,15-dimethyl-9,12,16-trioxo-2-oxa-8,11,15-triazatricyclo[15.3.1.0$^{4,8}$]henicosa-1(21),17,19-trien-13-yl]-2-(1H-indol-3-yl)acetamide |
| Ex. 205 | CH₃-C(=O)-NH- | (CH₃)₂N-CH₂-C(=O)-NH- | N-[(4S,6S,13S)-6-(acetylamino)-11,15-dimethyl-9,12,16-trioxo-2-oxa-8,11,15-triazatricyclo[15.3.1.0$^{4,8}$]henicosa-1(21),17,19-trien-13-yl]-2-(dimethylamino)acetamide |
| Ex. 206 | (1H-indol-3-yl)-CH₂-C(=O)-NH- | (CH₃)₂N-CH₂-C(=O)-NH- | 2-(dimethylamino)-N-[(4S,6S,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]acetamide |
| Ex. 207 | (1H-indol-3-yl)-CH₂-C(=O)-NH- | HOOC-CH₂-CH₂-C(=O)-NH- | 4-{[(4S,6S,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]amino}-4-oxobutanoic acid |
| Ex. 208 | (CH₃)₂N-CH₂-C(=O)-NH- | CH₃-C(=O)-NH- | N-[(4S,6S,13S)-13-(acetylamino)-11,15-dimethyl-9,12,16-trioxo-2-oxa-8,11,15-triazatricyclo[15.3.1.0$^{4,8}$]henicosa-1(21),17,19-trien-6-yl]-2-(dimethylamino)acetamide |
| Ex. 209 | (CH₃)₂N-CH₂-C(=O)-NH- | HOOC-CH₂-CH₂-C(=O)-NH- | 4-{[(4S,6S,13S)-6-{[2-(dimethylamino)acetyl]amino}-11,15-dimethyl-9,12,16-trioxo-2-oxa-8,11,15-triazatricyclo[15.3.1.0$^{4,8}$]henicosa-1(21),17,19-trien-13-yl]amino}-4-oxobutanoic acid |
| Ex. 210 | (CH₃)₂N-CH₂-C(=O)-NH- | (2-naphthyl)-CH₂-C(=O)-NH- | 2-(dimethylamino)-N-[(4S,6S,13S)-11,15-dimethyl-13-{[2-(2-naphthyl)acetyl]amino}-9,12,16-trioxo-2-oxa-8,11,15-triazatricyclo[15.3.1.0$^{4,8}$]henicosa-1(21),17,19-trien-6-yl]acetamide |
| Ex. 211 | (1H-indol-3-yl)-CH₂-C(=O)-NH- | (4-pyridinyl)-CH₂-CH₂-C(=O)-NH- | N-[(4S,6S,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]-3-(4-pyridinyl)propanamide |

TABLE 30c-continued

Examples of Core 12 (Ex. 196-Ex. 214, continued on the following pages)

| No | R2 | R5 | IUPAC name |
|---|---|---|---|
| Ex. 212 | [indol-3-yl-CH2-C(=O)-NH- structure] | [2-naphthyl-CH2-C(=O)-NH- structure] | N-[(4S,6S,13S)-11,15-dimethyl-13-{[2-(2-naphthyl)acetyl]amino}-9,12,16-trioxo-2-oxa-8,11,15-triazatricyclo[15.3.1.04,8]henicosa-1(21),17,19-trien-6-yl]-2-(1H-indol-3-yl)acetamide |
| Ex. 213 | [indol-3-yl-CH2-C(=O)-NH- structure] | $CH_3(CH_2)_8CONH$ | N-[(4S,6S,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]decanamide |
| Ex. 214 | [CH3-C(=O)-NH- structure] | $NH_2$ | N-[(4S,6S,13S)-13-amino-11,15-dimethyl-9,12,16-trioxo-2-oxa-8,11,15-triazatricyclo[15.3.1.0$^{4,8}$]henicosa-1(21),17,19-trien-6-yl]acetamide |

TABLE 31a

Examples of Core 13 (Ex. 215-Ex. 230, continued on the following pages)

| No | R2 | R5 | Starting material | General Procedure | Reagent | Purification Method | Yield, (isolated salt) |
|---|---|---|---|---|---|---|---|
| Ex. 215-Ex. 216: cf experimental description | | | | | | | |
| Ex. 217 | [indol-3-yl-CH2-C(=O)-NH- structure] | [CH3-C(=O)-NH- structure] | Ex. 221 | L.1.1 | acetic anhydride (10 equiv.) pyridine/CH2Cl2 1:1 (2 mL) | prep. HPLC, method 1 | 41% |
| Ex. 218 | [(CH3)2N-CH2-C(=O)-NH- structure] | [PhCH2-O-C(=O)-NH- structure] HCl | Ex. 216 •HCl | L.1.3 | N,N-dimetyl glycine (1.7 equiv.) | FC (CH2Cl2/MeOH) | 85%*) |
| Ex. 219 | [indol-3-yl-CH2-C(=O)-NH- structure] | [PhCH2-O-C(=O)-NH- structure] HCl | Ex. 216 •HCl | L.1.3 | 3-indoleacetic acid (1.1 equiv.) HATU (1.5 equiv.) HOAt (1.5 equiv.) i-Pr2NEt (5 equiv.) | FC (CH2Cl2/MeOH) | 63% |
| Ex. 220 | [(CH3)2N-CH2-C(=O)-NH- structure] | $NH_2$ | Ex. 218 | K | H2, Pd(OH)2—C | crude product | 93%*) |

TABLE 31a-continued

Examples of Core 13 (Ex. 215-Ex. 230, continued on the following pages)

| No | R2 | R5 | Starting material | General Procedure | Reagent | Purification Method | Yield, (isolated salt) |
|---|---|---|---|---|---|---|---|
| Ex. 221 | (3-indolylacetamide) | NH₂ | Ex. 219 | K | H₂, Pd(OH)₂—C | crude product | 94%*) |
| Ex. 222 | (N,N-dimethylglycinamide) | (acetamide) | Ex. 220 | L.1.1 | acetic anhydride (5 equiv.) | prep. HPLC, method 1 | 25% (TFA salt) |
| Ex. 223 | (N,N-dimethylglycinamide) | (N,N-dimethylglycinamide) | Ex. 220 | L.1.3 | N,N-dimetyl glycine (1.7 equiv.) | prep. HPLC, method 1 | 24% (TFA salt) |
| Ex. 224 | (N,N-dimethylglycinamide) | (succinamide) | Ex. 220 | L.1.1 | succinic anhydride (1.05 equiv.) | prep. HPLC, method 1 | 37% (TFA salt) |
| Ex. 225 | (N,N-dimethylglycinamide) | (3-indolylacetamide) | Ex. 220 | L.1.3 | 3-indoleacetic acid (1.2 equiv.) HATU (1.5 equiv.) HOAt (1.5 equiv.) i-Pr₂NEt (3 equiv.) | prep. HPLC, method 1 | 28% (TFA salt) |
| Ex. 226 | (3-indolylacetamide) | (N,N-dimethylglycinamide) | Ex. 221 | L.1.3 | N,N-dimetyl glycine (1.7 equiv.) | prep. HPLC, method 1 | 45% (TFA salt) |
| Ex. 227 | (3-indolylacetamide) | (succinamide) | Ex. 221 | L.1.1 | succinic anhydride (1.05 equiv.) pyridine (49 equiv.) | prep. HPLC, method 1 | 49% |
| Ex. 228 | (3-indolylacetamide) | (3-indolylacetamide) | Ex. 221 | L.1.3 | 3-indoleacetic acid (1.2 equiv.) HATU (1.5 equiv.) HOAt (1.5 equiv.) i-Pr₂NEt (3 equiv.) | prep. HPLC, method 1 | 33% |

TABLE 31a-continued

Examples of Core 13 (Ex. 215-Ex. 230, continued on the following pages)

| No | R2 | R5 | Starting material | General Procedure | Reagent | Purification Method | Yield, (isolated salt) |
|---|---|---|---|---|---|---|---|
| Ex. 229 | indol-3-yl-acetamide | 2-naphthyl-acetamide | Ex. 221 | L.1.3 | 2-naphthylacetic acid (1.2 equiv.) | prep. HPLC, method 1 | 56% |
| Ex. 230 | N,N-dimethylglycinamide | 2-naphthyl-acetamide | Ex. 220 | L.1.3 | 2-naphthylacetic acid (1.2 equiv.) | prep. HPLC, method 1 | 52% (TEA salt) |

*) Analytical sample further purified by prep. HPLC, method 1 to afford the TFA salt of the corresponding product

TABLE 31b

Examples of Core 13 (Ex. 215-Ex. 230, continued on the following pages)

| No | R2 | R5 | Formula | Monoisotopic Mass | Rt (purity at 220 nm) | [M + H]+ found | LC-MS-Method |
|---|---|---|---|---|---|---|---|
| Ex. 215-Ex. 216: cf. experimental description ||||||||
| Ex. 217 | indol-3-yl-acetamide | acetamide | C31H36N6O6 | 588.3 | 1.82 (94) | 589.2 | Method 1b |
| Ex. 218 | N,N-dimethylglycinamide | benzyl carbamate | C31H40N6O7 | 608.3 | 1.36 (100) | 609.2 | Method 4b |
| Ex. 219 | indol-3-yl-acetamide | benzyl carbamate | C37H40N6O7 | 680.3 | 1.64 (96) | 681.3 | Method 2 |
| Ex. 220 | N,N-dimethylglycinamide | NH2 | C23H34N6O5 | 474.3 | 1.19 (92) | 475.2 | Method 5b |

TABLE 31b-continued

Examples of Core 13 (Ex. 215-Ex. 230, continued on the following pages)

| No | R2 | R5 | Formula | Monoisotopic Mass | Rt (purity at 220 nm) | [M + H]+ found | LC-MS-Method |
|---|---|---|---|---|---|---|---|
| Ex. 221 | (indol-3-yl)acetamide | NH₂ | C29H34N6O5 | 546.3 | 1.38 (96) | 547.2 | Method 4b |
| Ex. 222 | N,N-dimethylglycinamide | acetamide | C25H36N6O6 | 516.3 | 1.23 (97) | 517.2 | Method 5b |
| Ex. 223 | N,N-dimethylglycinamide | N,N-dimethylglycinamide | C27H41N7O6 | 559.3 | 1.33 (94) | 560.3 | Method 5b |
| Ex. 224 | N,N-dimethylglycinamide | succinamide | C27H38N6O8 | 574.3 | 1.04 (100) | 575.2 | Method 5b |
| Ex. 225 | N,N-dimethylglycinamide | (indol-3-yl)acetamide | C33H41N7O6 | 631.3 | 1.30 (97) | 632.3 | Method 4b |
| Ex. 226 | (indol-3-yl)acetamide | N,N-dimethylglycinamide | C33H41N7O6 | 631.3 | 1.39 (92) | 632.2 | Method 4b |
| Ex. 227 | (indol-3-yl)acetamide | succinamide | C33H38N6O8 | 646.3 | 1.49 (94) | 647.2 | Method 4b |
| Ex. 228 | (indol-3-yl)acetamide | (indol-3-yl)acetamide | C39H41N7O6 | 703.3 | 1.75 (91) | 704.3 | Method 4b |

TABLE 31b-continued

Examples of Core 13 (Ex. 215-Ex. 230, continued on the following pages)

| No | R2 | R5 | Formula | Monoisotopic Mass | Rt (purity at 220 nm) | [M + H]+ found | LC-MS-Method |
|---|---|---|---|---|---|---|---|
| Ex. 229 | indol-3-yl-CH2-C(=O)-NH- | naphthalen-2-yl-CH2-C(=O)-NH- | C41H42N6O6 | 714.3 | 1.91 (92) | 715.3 | Method 4b |
| Ex. 230 | (CH3)2N-CH2-C(=O)-NH- | naphthalen-2-yl-CH2-C(=O)-NH- | C35H42N6O6 | 642.3 | 1.50 (100) | 643.2 | Method 4b |

TABLE 31c

Examples of Core 13 (Ex. 215-Ex. 230)

| No | R2 | R5 | IUPAC name |
|---|---|---|---|
| Ex. 215 | (trimethylsilyl)ethoxycarbonyl-NH- | benzyloxycarbonyl-NH- | benzyl N-[(4S,6R,13S)-11,15-dimethyl-9,12,16-trioxo-6-({[2-(trimethylsilyl)ethoxy]carbonyl}amino)-2-oxa-8,11,15-triazatricyclo[15.3.1.0$^{4,8}$]henicosa-1(21),17,19-trien-13-yl]carbamate |
| Ex. 216 | NH2 | benzyloxycarbonyl-NH- | benzyl N-[(4S,6R,13S)-6-amino-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 217 | indol-3-yl-CH2-C(=O)-NH- | CH3-C(=O)-NH- | N-[(4S,6R,13S)-13-(acetylamino)-11,15-dimethyl-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 218 | (CH3)2N-CH2-C(=O)-NH- | benzyloxycarbonyl-NH- | benzyl N-[(4S,6R,13S)-6-{[2-(dimethylamino)acetyl]amino}-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 219 | indol-3-yl-CH2-C(=O)-NH- | benzyloxycarbonyl-NH- | benzyl N-[(4S,6R,13S)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]carbamate |

TABLE 31c-continued

Examples of Core 13 (Ex. 215-Ex. 230)

| No | R2 | R5 | IUPAC name |
|---|---|---|---|
| Ex. 220 | 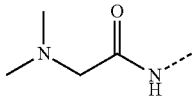 | NH₂ | N-[(4S,6R,13S)-13-amino-11,15-dimethyl-9,12,16-trioxo-2-oxa-8,11,15-triazatricyclo[15.3.1.0⁴,⁸]henicosa-1(21),17,19-trien-6-yl]-2-(dimethylamino)acetamide |
| Ex. 221 |  | NH₂ | N-[(4S,6R,13S)-13-amino-11,15-dimethyl-9,12,16-trioxo-2-oxa-8,11,15-triazatricyclo[15.3.1.0⁴,⁸]henicosa-1(21),17,19-trien-6-yl]-2-(1H-indol-3-yl)acetamide |
| Ex. 222 | 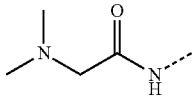 | 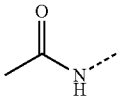 | N-[(4S,6R,13S)-13-(acetylamino)-11,15-dimethyl-9,12,16-trioxo-2-oxa-8,11,15-triazatricyclo[15.3.1.0⁴,⁸]henicosa-1(21),17,19-trien-6-yl]-2-(dimethylamino)acetamide |
| Ex. 223 | 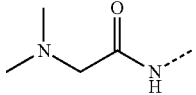 | 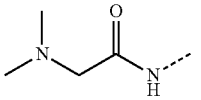 | 2-(dimethylamino)-N-[(4S,6R,13S)-13-{[2-(dimethylamino)acetyl]amino}-11,15-dimethyl-9,12,16-trioxo-2-oxa-8,11,15-triazatricyclo[15.3.1.0⁴,⁸]henicosa-1(21),17,19-trien-6-yl]acetamide |
| Ex. 224 | 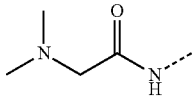 | 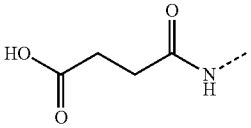 | 4-{[(4S,6R,13S)-6-{[2-(dimethylamino)acetyl]amino}-11,15-dimethyl-9,12,16-trioxo-2-oxa-8,11,15-triazatricyclo[15.3.1.0⁴,⁸]henicosa-1(21),17,19-trien-13-yl]amino}-4-oxobutanoic acid |
| Ex. 225 | 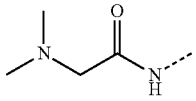 |  | 2-(dimethylamino)-N-[(4S,6R,13S)-13-{[2-(1H-indol-3-yl)acetyl]amino}-11,15-11-dimethyl-9,12,16-trioxo-2-oxa-8,11,15-triazatricyclo[15.3.1.0⁴,⁸]henicosa-1(21),17,19-trien-6-yl]acetamide |
| Ex. 226 |  | 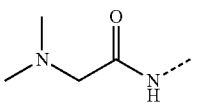 | 2-(dimethylamino)-N-[(4S,6R,13S)-6-{[2-(1H-indol-3-yl)acetyl]amino}-11,15-dimethyl-9,12,16-trioxo-2-oxa-8,11,15-triazatricyclo[15.3.1.0⁴,⁸]henicosa-1(21),17,19-trien-13-yl]acetamide |
| Ex. 227 | 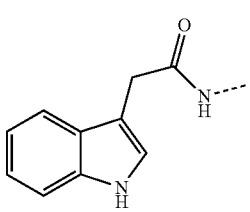 | 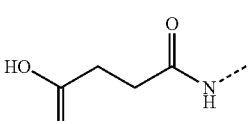 | 4-{[(4S,6R,13S)-6-{[2-(1H-indol-3-yl)acetyl]amino}-11,15-dimethyl-9,12,16-trioxo-2-oxa-8,11,15-triazatricyclo[15.3.1.0⁴,⁸]henicosa-1(21),17,19-trien-13-yl]amino}-4-oxobutanoic acid |
| Ex. 228 | 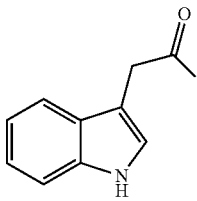 | 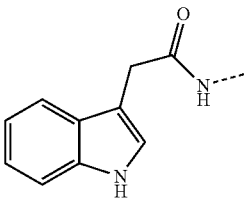 | 2-(1H-indol-3-yl)-N-[(4S,6R,13S)-13-{[2-(1H-indol-3-yl)acetyl]amino}-11,15-dimethyl-9,12,16-trioxo-2-oxa-8,11,15-triazatricyclo[15.3.1.0⁴,⁸]henicosa-1(21),17,19-trien-6-yl]acetamide |

TABLE 31c-continued

Examples of Core 13 (Ex. 215-Ex. 230)

| No | R2 | R5 | IUPAC name |
|---|---|---|---|
| Ex. 229 | (indol-3-yl acetamide) | (2-naphthyl acetamide) | N-[(4S,6R,13S)-11,15-dimethyl-13-{[2-(2-naphthyl)acetyl]amino}-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 230 | (dimethylaminoacetamide) | (2-naphthyl acetamide) | 2-(dimethylamino)-N-[(4S,6R,13S)-11,15-dimethyl-13-{[2-(2-naphthyl)acetyl]amino}-9,12,16-trioxo-2-oxa-8,11,15-triazatricyclo[15.3.1.0$^{4,8}$]henicosa-1(21),17,19-trien-6-yl]acetamide |

TABLE 32a

Examples of Core 14 (Ex. 231-Ex. 237)

| No | R2 | R5 | Starting material | General Procedure | Reagent | Purification Method | Yield, (isolated salt) |
|---|---|---|---|---|---|---|---|
| Ex. 231-Ex. 232: cf. experimental description | | | | | | | |
| Ex. 233 | (indol-3-yl acetamide) | (benzyl carbamate) | Ex. 232·TFA | L.1.3 | 3-indoleacetic acid (1.5 equiv.) HATU (1.5 equiv.) HOAt (1.5 equiv.) i-Pr$_2$NEt (5 equiv) | FC (EtOAc, then CH$_2$Cl$_2$/ MeOH) | 68% |
| Ex. 234 | (indol-3-yl acetamide) | NH$_2$ | Ex. 233 | K | H$_2$, Pd(OH)$_2$—C | crude product | 99% |
| Ex. 235 | (indol-3-yl acetamide) | (2-naphthyl acetamide) | Ex. 234 | L.1.3 | 2-naphthylacetic acid (1.2 equiv.) | prep. HPLC, method 3 | 68% |
| Ex. 236 | (indol-3-yl acetamide) | (pyrrolidin-1-yl acetamide) | Ex. 234 | L.1.3 | pyrrolidin-1-acetic acid (1.2 equiv.) | prep. HPLC, method 3 | 28% |

TABLE 32a-continued

Examples of Core 14 (Ex. 231-Ex. 237)

| No | R2 | R5 | Starting material | General Procedure | Reagent | Purification Method | Yield, (isolated salt) |
|---|---|---|---|---|---|---|---|
| Ex. 237 | (indol-3-yl-acetamide) | (3-phenylpropanamide) | Ex. 234 | L.1.3 | 3-phenylpropionic acid | prep. HPLC, method 3 | 66% |

TABLE 32b

Examples of Core 14 (Ex. 231-Ex. 237)

| No | R2 | R5 | Formula | Monoisotopic Mass | Rt (purity at 220 nm) | [M + H]+ found | LC-MS-Method |
|---|---|---|---|---|---|---|---|
| Ex. 231-Ex. 232: cf. experimental description | | | | | | | |
| Ex. 233 | (indol-3-yl-acetamide) | (benzyl carbamate) | C37H40N6O7 | 680.3 | 1.80 (96) | 681.4 | Method 2 |
| Ex. 234 | (indol-3-yl-acetamide) | NH2 | C29H34N6O5 | 546.3 | 1.47 (93) | 547.3 | Method 2 |
| Ex. 235 | (indol-3-yl-acetamide) | (naphthalen-2-yl-acetamide) | C41H42N6O6 | 714.3 | 1.80 (90) | 715.4 | Method 2 |
| Ex. 236 | (indol-3-yl-acetamide) | (pyrrolidin-1-yl-acetamide) | C35H43N7O6 | 657.3 | 1.45 (94) | 658.4 | Method 2 |
| Ex. 237 | (indol-3-yl-acetamide) | (3-phenylpropanamide) | C38H42N6O6 | 678.3 | 1.81 (96) | 679.4 | Method 2 |

TABLE 32c

Examples of Core 14 (Ex. 231-Ex. 237)

| No | R2 | R5 | IUPAC name |
| --- | --- | --- | --- |
| Ex. 231 | tert-butoxycarbonylamino group | benzyl carbamate group | benzyl N-[(4S,6S,13R)-6-[(tert-butoxycarbonyl)amino]-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 232 | NH$_2$ | benzyl carbamate group | benzyl N-[(4S,6S,13R)-6-amino-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 233 | 2-(1H-indol-3-yl)acetamido group | benzyl carbamate group | benzyl N-[(4S,6S,13R)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]carbamate |
| Ex. 234 | 2-(1H-indol-3-yl)acetamido group | NH$_2$ | N-[(4S,6S,13R)-13-amino-11,15-dimethyl-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 235 | 2-(1H-indol-3-yl)acetamido group | 2-(2-naphthyl)acetamido group | N-[(4S,6S,13R)-11,15-dimethyl-13-{[2-(2-naphthyl)acetyl]amino}-9,12,16-trioxo-2-oxa-8,11,15-triazatricyclo[15.3.1.0$^{4,8}$]henicosa-1(21),17,19-trien-6-yl]-2-(1H-indol-3-yl)acetamide |
| Ex. 236 | 2-(1H-indol-3-yl)acetamido group | 2-(1-pyrrolidinyl)acetamido group | N-[(4S,6S,13R)-11,15-dimethyl-9,12,16-trioxo-13-{[2-(1-pyrrolidinyl)acetyl]amino}-2-oxa-8,11,15-triazatricyclo[15.3.1.0$^{4,8}$]henicosa-1(21),17,19-trien-6-yl]-2-(1H-indol-3-yl)acetamide |
| Ex. 237 | 2-(1H-indol-3-yl)acetamido group | 3-phenylpropanamido group | N-[(4S,6S,13R)-6-{[2-(1H-indol-3-yl)acetyl]amino}-11,15-dimethyl-9,12,16-trioxo-2-oxa-8,11,15-triazatricyclo[15.3.1.0$^{4,8}$]henicosa-1(21),17,19-trien-13-yl]-3-phenylpropanamide |

Table 33a

Examples of Core 15 and Core 16 (Ex. 238-Ex. 247)

| No | R2 | R5 | Starting material | General Procedure | Reagent | Purification Method | Yield, (isolated salt) |
|---|---|---|---|---|---|---|---|
| Ex. 238-Ex. 239: cf. experimental description | | | | | | | |
| Ex. 240 | 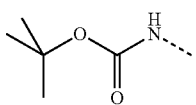 | 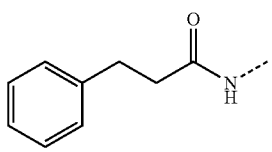 | Ex. 239 | L.1.3 | 3-phenylpoanoic acid | FC (EtOAc/ MeOH)*) | 47% |
| Ex. 241 | 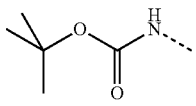 | 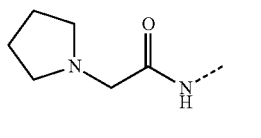 | Ex. 239 | L.1.3 | pyrrolidin-1-acetic acid | FC (CH$_2$Cl$_2$/ MeOH/aq. NH$_3$) | 56% |
| Ex. 242 | NH$_2$ | 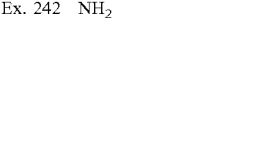 | Ex. 240 | J | HCl-dioxane | crude product | quant. (HCl salt) |
| Ex. 243 | NH$_2$ | 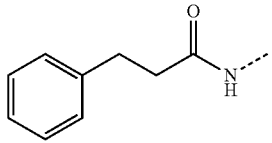 | Ex.241 | J | HCl-dioxane | crude product | quant. (HCl salt) |
| Ex. 244 | 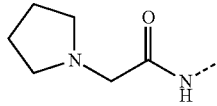 | 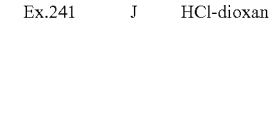 | Ex. 242 | L.1.3 | pyrrolidin-1-acetic acid | FC (CH$_2$Cl$_2$/ MeOH/aq. NH$_3$) | 81% |
| Ex. 245 | 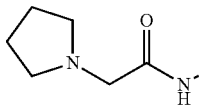 | 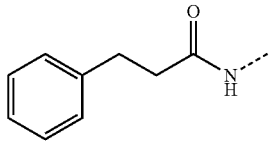 | Ex. 242 | L.1.3 | 3-indoleacetic acid | FC (CH$_2$Cl$_2$/ MeOH/aq. NH$_3$) | 59% |
| Ex. 246 | 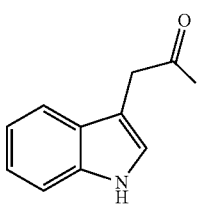 | 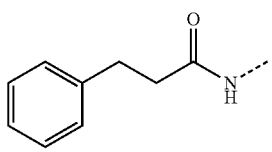 | Ex. 243 | L.1.3 | 2-naphthylacetic acid | FC (CH$_2$Cl$_2$/ MeOH/aq. NH$_3$) | 51% |
| Ex. 247 | 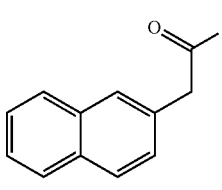 | 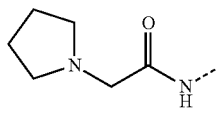 | Ex. 243 | L.1.3 | 3-indoleacetic acid | FC (CH$_2$Cl$_2$/ MeOH/aq. NH$_3$) | 58% |

*) An analytical sample was further purified by prep. HPLC, method 2

TABLE 33b

Examples of Core 15 and Core 16 (Ex. 238-Ex. 247)

| No | R2 | R5 | Formula | Monoisotopic Mass | Rt (purity at 220 nm) | [M + H]+ found | LC-MS-Method |
|---|---|---|---|---|---|---|---|
| Ex. 238-Ex. 239: cf. experimental description | | | | | | | |
| Ex. 240 | Boc-NH- | phenylpropanamide | C33H44N4O6 | 592.3 | 2.12 (90) | 593.3 | Method 4a |
| Ex. 241 | Boc-NH- | pyrrolidinylacetamide | C30H45N5O6 | 571.3 | 1.58 (91) | 572.3 | Method 4a |
| Ex. 242 | NH2 | phenylpropanamide | C28H36N4O4 | 492.3 | 1.53 (88), 1.59 (6) | 493.2 | Method 4a |
| Ex. 243 | NH2 | pyrrolidinylacetamide | C25H37N5O4 | 471.3 | 1.08 (91) | 472.4 | Method 4a |
| Ex. 244 | pyrrolidinylacetamide | phenylpropanamide | C34H45N5O5 | 603.3 | 1.63 (93) | 604.4 | Method 4a |
| Ex. 245 | indolylacetamide | phenylpropanamide | C38H43N5O5 | 649.3 | 2.01 (91) | 650.3 | Method 4a |
| Ex. 246 | naphthylacetamide | pyrrolidinylacetamide | C37H45N5O5 | 639.3 | 1.69 (90) | 640.3 | Method 4a |
| Ex. 247 | indolylacetamide | pyrrolidinylacetamide | C35H44N6O5 | 628.3 | 1.52 (94) | 629.3 | Method 4a |

TABLE 33c

Examples of Core 15 and Core 16 (Ex. 238-Ex. 247)

| No | R2 | R5 | IUPAC name |
|---|---|---|---|
| Core 15 | | | |
| Ex. 238 | tert-butoxycarbonyl amino | benzyloxycarbonyl amino | benzyl N-[(4S,6S,10S)-6-[(tert-butoxycarbonyl)amino]-15-methyl-9,16-dioxo-2-oxa-8,15-diazatricyclo[15.3.1.0$^{4,8}$]henicosa-1(21),12,17,19-tetraen-10-yl]carbamate |
| Core 16 | | | |
| Ex. 239 | tert-butoxycarbonyl amino | NH$_2$ | tert-butyl N-[(4S,6S,10S)-10-amino-15-methyl-9,16-dioxo-2-oxa-8,15-diazatricyclo[15.3.1.0$^{4,8}$]henicosa-1(21),17,19-trien-6-yl]carbamate |
| Ex. 240 | tert-butoxycarbonyl amino | 3-phenylpropanoylamino | tert-butyl N-[(4S,6S,10S)-15-methyl-9,16-dioxo-10-[(3-phenylpropanoyl)amino]-2-oxa-8,15-diazatricyclo[15.3.1.0$^{4,8}$]henicosa-1(21),17,19-trien-6-yl]carbamate |
| Ex. 241 | tert-butoxycarbonyl amino | 2-(1-pyrrolidinyl)acetylamino | tert-butyl N-[(4S,6S,10S)-15-methyl-9,16-dioxo-10-{[2-(1-pyrrolidinyl)acetyl]amino}-2-oxa-8,15-diazatricyclo[15.3.1.0$^{4,8}$]henicosa-1(21),17,19-trien-6-yl]carbamate |
| Ex. 242 | NH$_2$ | 3-phenylpropanoylamino | N-[(4S,6S,10S)-6-amino-15-methyl-9,16-dioxo-2-oxa-8,15-diazatricyclo[15.3.1.0$^{4,8}$]henicosa-1(21),17,19-trien-10-yl]-3-phenylpropanamide |
| Ex. 243 | NH$_2$ | 2-(1-pyrrolidinyl)acetylamino | N-[(4S,6S,10S)-6-amino-15-methyl-9,16-dioxo-2-oxa-8,15-diazatricyclo[15.3.1.0$^{4,8}$]henicosa-1(21),17,19-trien-10-yl]-2-(1-pyrrolidinyl) acetamide |
| Ex. 244 | 2-(1-pyrrolidinyl)acetylamino | 3-phenylpropanoylamino | N-[(4S,6S,10S)-15-methyl-9,16-dioxo-6-{[2-(1-pyrrolidinyl)acetyl]amino}-2-oxa-8,15-diazatricyclo[15.3.1.0$^{4,8}$]henicosa-1(21),17,19-trien-10-yl]-3-phenylpropanamide |
| Ex. 245 | 2-(1H-indol-3-yl)acetylamino | 3-phenylpropanoylamino | N-[(4S,6S,10S)-6-{[2-(1H-indol-3-yl)acetyl]amino}-15-methyl-9,16-dioxo-2-oxa-8,15-diazatricyclo[15.3.1.0$^{4,8}$]henicosa-1(21),17,19-trien-10-yl]-3-phenylpropanamide |
| Ex. 246 | 2-(2-naphthyl)acetylamino | 2-(1-pyrrolidinyl)acetylamino | N-[(4S,6S,10S)-15-methyl-9,16-dioxo-10-{[2-(1-pyrrolidinyl)acetyl]amino}-2-oxa-8,15-diazatricyclo[15.3.1.0$^{4,8}$]henicosa-1(21),17,19-trien-6-yl]-2-(2-naphthyl) acetamide |

TABLE 33c-continued

Examples of Core 15 and Core 16 (Ex. 238-Ex. 247)

| No | R2 | R5 | IUPAC name |
|---|---|---|---|
| Ex. 247 | (1H-indol-3-yl-CH2-C(O)-NH-) structure | (pyrrolidin-1-yl-CH2-C(O)-NH-) structure | 2-(1H-indol-3-yl)-N-[(4S,6S,10S)-15-methyl-9,16-dioxo-10-{[2-(1-pyrrolidinyl)acetyl]amino}-2-oxa-8,15-diazatricyclo[15.3.1.0$^{4,8}$]henicosa-1(21),17,19-trien-6-yl]acetamide |

TABLE 34a

Examples of Core 17 (Ex. 248-Ex. 271)

| No | R2 | R50 | Starting material | General Procedure | Reagent | Purification Method | Yield, (isolated salt) |
|---|---|---|---|---|---|---|---|
| Ex. 248-Ex. 249: cf. experimental description | | | | | | | |
| Ex. 250 | Boc-NH- | pyrrolidin-1-yl | Ex. 249 | L.2 | pyrrolidine | FC (CH$_2$Cl$_2$/MeOH) | 81% |
| Ex. 251 | Boc-NH- | pyrrolidin-1-yl-CH2CH2-NH- | Ex. 249 | L.2 | N-(2-aminoethyl)pyrrolidine | FC (CH$_2$Cl$_2$/MeOH/aq. NH$_3$ soln.) | 88% |
| Ex. 252 | Boc-NH- | 2-naphthylmethyl-NH- | Ex. 249 | L.2 | 2-naphthylmethylamine (1.5 equiv.) HATU (1.5 equiv.) HOAt (1.5 equiv.) i-Pr$_2$NEt (3 equiv.) | FC (CH$_2$Cl$_2$/MeOH) | 91% |
| Ex. 253 | Boc-NH- | pyridin-4-ylmethyl-NH- | Ex. 249 | L.2 | 4-(aminomethyl)pyridine (1.5 equiv.) HATU (1.5 equiv.) HOAt (1.5 equiv.) i-Pr$_2$NEt (3 equiv.) | FC (CH$_2$Cl$_2$/MeOH)*) | 97% |
| Ex. 254 | NH$_2$ | pyrrolidin-1-yl-CH2CH2-NH- | Ex. 251 | J | HCl-dioxane | crude product | 96% (HCl salt) |
| Ex. 255 | NH$_2$ | 2-naphthylmethyl-NH- | Ex. 252 | J | HCl-dioxane | crude product | 100% (HCl salt) |
| Ex. 256 | NH$_2$ | pyrrolidin-1-yl | Ex. 250 | J | HCl-dioxane | crude product | 93% (HCl salt) |
| Ex. 257 | NH$_2$ | pyridin-4-ylmethyl-NH- | Ex. 253 | J | HCl-dioxane | crude product | 91% (HCl salt) |

TABLE 34a-continued

Examples of Core 17 (Ex. 248-Ex. 271)

| No | R2 | R50 | Starting material | General Procedure | Reagent | Purification Method | Yield, (isolated salt) |
|---|---|---|---|---|---|---|---|
| Ex. 258 | pyrrolidinyl-CH2-C(O)-NH- | 2-naphthyl-CH2-NH- | Ex. 255 | L.1.2 | 1-pyrrolidinacetic acid (2.7 equiv.) i-Pr2NEt v(4 equiv.) | FC (CH2Cl2/ MeOH) | 61% |
| Ex. 259 | HOOC-CH2CH2-C(O)-NH- | 2-naphthyl-CH2-NH- | Ex. 255 | L.1.1 | succinic anhydride (1.05 equiv.) pyridine (49 equiv.) | prep. HPLC, method 1 | 15% |
| Ex. 260 | pyridin-4-yl-CH2CH2-C(O)-NH- | 2-naphthyl-CH2-NH- | Ex. 255 | L.1.2 | 3-(pyridine-4-yl)propanoic acid | prep. HPLC, method 1 | 55% (TFA salt) |
| Ex. 261 | 1-naphthyl-CH2-C(O)-NH- | 2-naphthyl-CH2-NH- | Ex. 255 | L.1.3 | 1-naphthylacetic acid (1.2 equiv.) | prep. HPLC, method 1 | 69% |
| Ex. 262 | Et2N- | 2-naphthyl-CH2-NH- | Ex. 255 | M | acetaldehyde | prep. HPLC, method 1 | 76% (TFA salt) |
| Ex. 263 | CH3-C(O)-NH- | pyrrolidin-1-yl | Ex. 256 | L.1.1 | acetic anhydride (10 equiv.) Pyridine/CH2Cl2 1:1 (3 mL) | prep. HPLC, method 1 | 82% |
| Ex. 264 | 2-naphthyl-CH2-C(O)-NH- | pyrrolidin-1-yl | Ex. 256 | L.1.3 | 2-naphthylacetic acid (1.2 equiv.) | prep. HPLC, method 1 | 61% |
| Ex. 265 | 2-naphthyl-CH2-C(O)-NH- | pyridin-4-yl-CH2-NH- | Ex. 257 | L.1.3 | 2-naphthylacetic acid (1.2 equiv.) | prep. HPLC, method 1 | 59% (TFA salt) |
| Ex. 266 | pyrrolidinyl-CH2-C(O)-NH- | pyridin-4-yl-CH2-NH- | Ex. 257 | L.1.2 | 1-pyrrolidinacetic acid | prep. HPLC, method 2 | 71% |
| Ex. 267 | HOOC-CH2CH2-C(O)-NH- | pyridin-4-yl-CH2-NH- | Ex. 257 | L.1.1 | succinic anhydride (1.5 equiv.) pyridine (49 equiv.) | prep. HPLC, method 1 | 89% (TFA salt) |

TABLE 34a-continued

Examples of Core 17 (Ex. 248-Ex. 271)

| No | R2 | R50 | Starting material | General Procedure | Reagent | Purification Method | Yield, (isolated salt) |
|---|---|---|---|---|---|---|---|
| Ex. 268 | 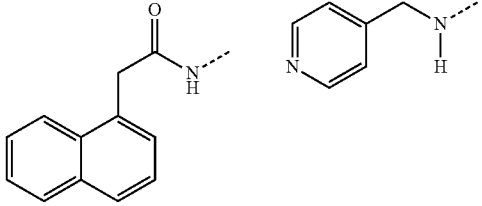 | 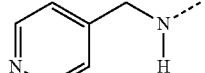 | Ex. 257 | L.1.3 | 1-naphthylacetic acid (1.2 equiv.) | prep. HPLC, method 2 | 45% |
| Ex. 269 |  | 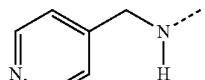 | Ex. 257 | M | Acetaldehyde (0.75 mL) | prep. HPLC, method 2 | 70% |
| Ex. 270 |  | 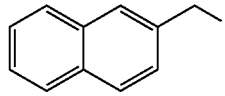 | Ex. 255 | L.1.1 | valeroyl chloride (2 equiv.) | prep. HPLC, method 1 | 77% |
| Ex. 271 | 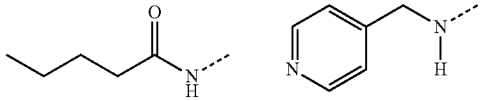 | 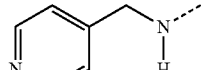 | Ex. 257 | L.1.1 | valeroyl chloride (2 equiv.) | prep. HPLC, method 1 | 58% (TFA salt) |

*) An analytical sample was further purified by prep HPLC, method 1

TABLE 34b

Examples of Core 17 (Ex. 248-Ex. 271)

| No | R2 | R50 | Formula | Monoisotopic Mass | Rt (purity at 220 nm) | [M + H]+ found | LC-MS- Method |
|---|---|---|---|---|---|---|---|
| Ex. 248-Ex. 249: cf. experimental description | | | | | | | |
| Ex. 250 | 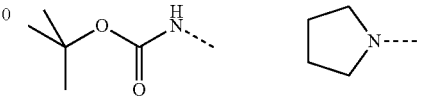 | 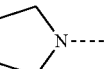 | C30H43N5O7 | 585.4 | 1.58 (96) | 586.4 | Method 2 |
| Ex. 251 | 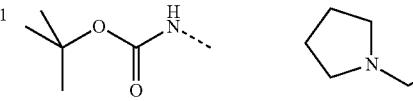 | 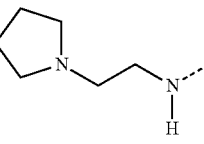 | C32H48N6O7 | 628.4 | 1.35 (98) | 629.5 | Method 2 |
| Ex. 252 | 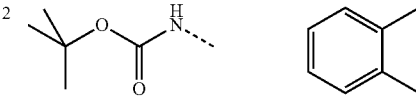 | 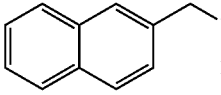 | C37H45N5O7 | 671.3 | 1.86 (88) | 672.4 | Method 2 |
| Ex. 253 | 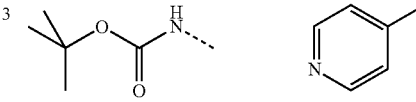 | 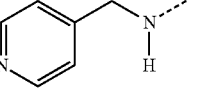 | C32H42N6O7 | 622.3 | 1.29 (92) | 623.4 | Method 2 |
| Ex. 254 | NH2 | 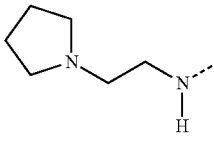 | C27H40N6O5 | 528.3 | 1.31 (97) | 529.5 | Method 3 |

TABLE 34b-continued

Examples of Core 17 (Ex. 248-Ex. 271)

| No | R2 | R50 | Formula | Monoisotopic Mass | Rt (purity at 220 nm) | [M + H]+ found | LC-MS-Method |
|---|---|---|---|---|---|---|---|
| Ex. 255 | NH2 | naphthyl-CH2-NH- | C32H37N5O5 | 571.3 | 1.45 (94) | 572.4 | Method 2 |
| Ex. 256 | NH2 | pyrrolidinyl | C25H35N5O5 | 485.3 | 1.06 (96) | 486.4 | Method 2 |
| Ex. 257 | NH2 | pyridyl-CH2-NH- | C27H34N6O5 | 522.3 | 0.85 (96) | 523.3 | Method 2 |
| Ex. 258 | pyrrolidinyl-CH2-C(O)-NH- | naphthyl-CH2-NH- | C38H46N6O6 | 682.4 | 1.47 (95) | 683.5 | Method 2 |
| Ex. 259 | HOOC-CH2CH2-C(O)-NH- | naphthyl-CH2-NH- | C36H41N5O8 | 671.3 | 1.59 (87) | 672.4 | Method 2 |
| Ex. 260 | pyridyl-CH2CH2-C(O)-NH- | naphthyl-CH2-NH- | C40H44N6O6 | 704.3 | 1.47 (100) | 705.5 | Method 2 |
| Ex. 261 | naphthyl-CH2-C(O)-NH- | naphthyl-CH2-NH- | C44H45N5O6 | 739.3 | 1.93 (99) | 740.5 | Method 2 |
| Ex. 262 | (Et)2N- | naphthyl-CH2-NH- | C36H45N5O5 | 627.3 | 1.50 (100) | 628.5 | Method 2 |
| Ex. 263 | CH3-C(O)-NH- | pyrrolidinyl | C27H37N5O6 | 527.3 | 1.23 (99) | 528.3 | Method 2 |
| Ex. 264 | naphthyl-CH2-C(O)-NH- | pyrrolidinyl | C37H43N5O6 | 653.3 | 1.68 (100) | 654.4 | Method 2 |

TABLE 34b-continued

Examples of Core 17 (Ex. 248-Ex. 271)

| No | R2 | R50 | Formula | Monoisotopic Mass | Rt (purity at 220 nm) | [M + H]+ found | LC-MS-Method |
|---|---|---|---|---|---|---|---|
| Ex. 265 | naphthalen-2-ylacetamide | pyridin-4-ylmethylamine | C39H42N6O6 | 690.3 | 1.44 (99) | 691.5 | Method 2 |
| Ex. 266 | pyrrolidin-1-yl-acetamide | pyridin-4-ylmethylamine | C33H43N7O6 | 633.3 | 0.99 (94) | 634.5 | Method 2 |
| Ex. 267 | succinamide (HOOC-CH2CH2-C(O)NH-) | pyridin-4-ylmethylamine | C31H38N6O8 | 622.3 | 1.05 (94) | 623.3 | Method 2 |
| Ex. 268 | naphthalen-1-ylacetamide | pyridin-4-ylmethylamine | C39H42N6O6 | 690.3 | 1.68 (93) | 691.5 | Method 3 |
| Ex. 269 | diethylaminomethyl | pyridin-4-ylmethylamine | C31H42N6O5 | 578.3 | 0.96 (96) | 579.5 | Method 2 |
| Ex. 270 | pentanamide | naphthalen-2-ylmethylamine | C37H45N5O6 | 655.3 | 1.81 (100) | 656.4 | Method 2 |
| Ex. 271 | pentanamide | pyridin-4-ylmethylamine | C32H42N6O6 | 606.3 | 1.25 (100) | 607.4 | Method 2 |

TABLE 34c

Examples of Core 17 (Ex. 248-Ex. 271)

| No | R2 | R50 | IUPAC name |
|---|---|---|---|
| Ex. 248 | Boc-NH- | OCH2Ph | benzyl (4S,6R,15S)-6-[(tert-butoxycarbonyl)amino]-11,16-dimethyl-9,12,17-trioxo-2-oxa-8,11,16-triazatricyclo[16.2.2.0$^{4,8}$]docosa-1(20),18,21-triene-15-carboxylate |
| Ex. 249 | Boc-NH- | OH | (4S,6R,15S)-6-[(tert-butoxycarbonyl)amino]-11,16-dimethyl-9,12,17-trioxo-2-oxa-8,11,16-triazatricyclo[16.2.2.0$^{4,8}$]docosa-1(20),18,21-triene-15-carboxylic acid |

TABLE 34c-continued

Examples of Core 17 (Ex. 248-Ex. 271)

| No | R2 | R50 | IUPAC name |
|---|---|---|---|
| Ex. 250 | tert-butyl carbamate group | pyrrolidinyl | tert-butyl N-[(4S,6R,15S)-11,16-dimethyl-9,12,17-trioxo-15-(1-pyrrolidinylcarbonyl)-2-oxa-8,11,16-triazatricyclo[16.2.2.0$^{4,8}$]docosa-1(20),18,21-trien-6-yl]carbamate |
| Ex. 251 | tert-butyl carbamate group | 2-(1-pyrrolidinyl)ethylamino group | tert-butyl N-[(4S,6R,15S)-11,16-dimethyl-9,12,17-trioxo-15-({[2-(1-pyrrolidinyl)ethyl]amino}carbonyl)-2-oxa-8,11,16-triazatricyclo[16.2.2.0$^{4,8}$]docosa-1(20),18,21-trien-6-yl]carbamate |
| Ex. 252 | tert-butyl carbamate group | (2-naphthylmethyl)amino group | tert-butyl N-[(4S,6R,15S)-11,16-dimethyl-15-{[(2-naphthylmethyl)amino]carbonyl}-9,12,17-trioxo-2-oxa-8,11,16-triazatricyclo[16.2.2.0$^{4,8}$]docosa-1(20),18,21-trien-6-yl]carbamate |
| Ex. 253 | tert-butyl carbamate group | (4-pyridinylmethyl)amino group | tert-butyl N-[(4S,6R,15S)-11,16-dimethyl-9,12,17-trioxo-15-{[(4-pyridinylmethyl)amino]carbonyl}-2-oxa-8,11,16-triazatricyclo[16.2.2.0$^{4,8}$]docosa-1(20),18,21-trien-6-yl]carbamate |
| Ex. 254 | NH$_2$ | 2-(1-pyrrolidinyl)ethylamino group | (4S,6R,15S)-6-amino-11,16-dimethyl-9,12,17-trioxo-N-[2-(1-pyrrolidinyl)ethyl]-2-oxa-8,11,16-triazatricyclo[16.2.2.0$^{4,8}$]docosa-1(20),18,21-triene-15-carboxamide |
| Ex. 255 | NH$_2$ | (2-naphthylmethyl)amino group | (4S,6R,15S-6-amino-11,16-dimethyl-N-(2-naphthylmethyl)-9,12,17-trioxo-2-oxa-8,11,16-triazatricyclo[16.2.2.0$^{4,8}$]docosa-1(20),18,21-triene-15-carboxamide |
| Ex. 256 | NH$_2$ | pyrrolidinyl | (4S,6R,15S)-6-amino-11,16-dimethyl-15-(1-pyrrolidinylcarbonyl)-2-oxa-8,11,16-triazatricyclo[16.2.2.0$^{4,8}$]docosa-1(20),18,21-triene-9,12,17-trione |
| Ex. 257 | NH$_2$ | (4-pyridinylmethyl)amino group | (4S,6R,15S)-6-amino-11,16-dimethyl-9,12,17-trioxo-N-(4-pyridinylmethyl)-2-oxa-8,11,16-triazatricyclo[16.2.2.0$^{4,8}$]docosa-1(20),18,21-triene-15-carboxamide |
| Ex. 258 | 2-(1-pyrrolidinyl)acetamide group | (2-naphthylmethyl)amino group | (4S,6R,15S)-11,16-dimethyl-N-(2-naphthylmethyl)-9,12,17-trioxo-6-{[2-(1-pyrrolidinyl)acetyl]amino}-2-oxa-8,11,16-triazatricyclo[16.2.2.0$^{4,8}$]docosa-1(20),18,21-triene-15-carboxamide |
| Ex. 259 | 4-oxobutanoic acid group | (2-naphthylmethyl)amino group | 4-{[(4S,6R,15S )-11,16-dimethyl-15-{[(2-naphthylmethyl)amino]carbonyl }-9,12,17-trioxo-2-oxa-8,11,16-triazatricyclo[16.2.2.0$^{4,8}$]docosa-1(20),18,21-trien-6-yl]amino}-4-oxobutanoic acid |
| Ex. 260 | 3-(4-pyridinyl)propanoyl group | (2-naphthylmethyl)amino group | (4S,6R,15S)-11,16-dimethyl-N-(2-naphthylmethyl)-9,12,17-trioxo-6-{[3-(4-pyridinyl)propanoyl]amino}-2-oxa-8,11,16-triazatricyclo[16.2.2.0$^{4,8}$]docosa-1(20),18,21-triene-15-carboxamide |

TABLE 34c-continued

Examples of Core 17 (Ex. 248-Ex. 271)

| No | R2 | R50 | IUPAC name |
|---|---|---|---|
| Ex. 261 | 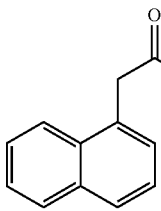 | 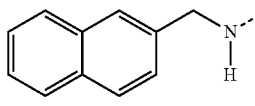 | (4S,6R,15S)-11,16-dimethyl-6-{[2-(1-naphthyl)acetyl]amino}-N-(2-naphthylmethyl)-9,12,17-trioxo-2-oxa-8,11,16-triazatricyclo[16.2.2.0$^{4,8}$]docosa-1(20),18,21-triene-15-carboxamide |
| Ex. 262 | 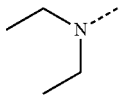 | 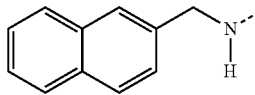 | (4S,6R,15S)-6-(diethylamino)-11,16-dimethyl-N-(2-naphthylmethyl)-9,12,17-trioxo-2-oxa-8,11,16-triazatricyclo[16.2.2.0$^{4,8}$]docosa-1(20),18,21-triene-15-carboxamide |
| Ex. 263 | 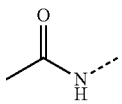 | 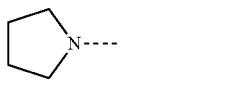 | N-[(4S,6R,15S)-11,16-dimethyl-9,12,17-trioxo-15-(1-pyrrolidinylcarbonyl)-2-oxa-8,11,16-triazatricyclo[16.2.2.0$^{4,8}$]docosa-1(20),18,21-trien-6-yl]acetamide |
| Ex. 264 | 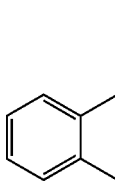 | 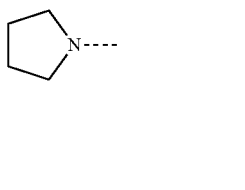 | N-[(4S,6R,15S)-11,16-dimethyl-9,12,17-trioxo-15-(1-pyrrolidinylcarbonyl)-2-oxa-8,11,16-triazatricyclo[16.2.2.0$^{4,8}$]docosa-1(20),18,21-trien-6-yl]-2-(2-naphthyl)acetamide |
| Ex. 265 | 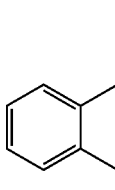 | 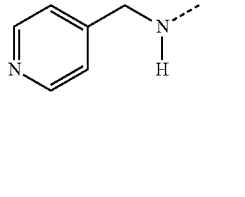 | (4S,6R,15S)-11,16-dimethyl-6-{[2-(2-naphthyl)acetyl]amino}-9,12,17-trioxo-N-(4-pyridinylmethyl)-2-oxa-8,11,16-triazatricyclo[16.2.2.0$^{4,8}$]docosa-1(20),18,21-triene-15-carboxamide |
| Ex. 266 | 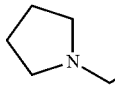 | 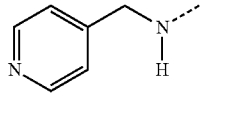 | (4S,6R,15S)-11,16-dimethyl-9,12,17-trioxo-N-(4-pyridinylmethyl)-6-{[2-(1-pyrrolidinyl)acetyl]amino}-2-oxa-8,11,16-triazatricyclo[16.2.2.0$^{4,8}$]docosa-1(20),18,21-triene-15-carboxamide |
| Ex. 267 | 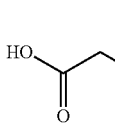 | 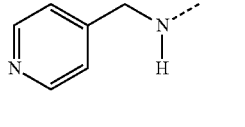 | 4-{[(4S,6R,15S)-11,16-dimethyl-9,12,17-trioxo-15-{[(4-pyridinylmethyl)amino]carbonyl}-2-oxa-8,11,16-triazatricyclo[16.2.2.0$^{4,8}$]docosa-1(20),18,21-trien-6-yl]amino}-4-oxobutanoic acid |
| Ex. 268 | 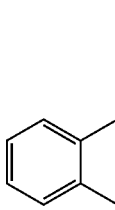 | 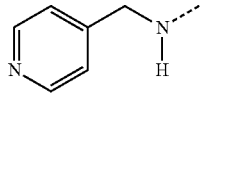 | (4S,6R,15S)-11,16-dimethyl-6-{[2-(1-naphthyl)acetyl]amino}-9,12,17-trioxo-N-(4-pyridinylmethyl)-2-oxa-8,11,16-triazatricyclo[16.2.2.0$^{4,8}$]docosa-1(20),18,21-triene-15-carboxamide |
| Ex. 269 | 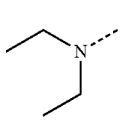 | 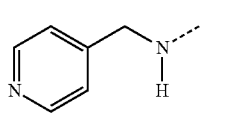 | (4S,6R,15S)-6-(diethylamino)-11,16-dimethyl-9,12,17-trioxo-N-(4-pyridinylmethyl)-2-oxa-8,11,16-triazatricyclo[16.2.2.0$^{4,8}$]docosa-1(20),18,21-triene-15-carboxamide |
| Ex. 270 | 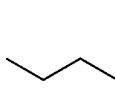 | 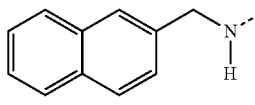 | (4S,6R,15S)-11,16-dimethyl-N-(2-naphthylmethyl)-9,12,17-trioxo-6-(pentanoylamino)-2-oxa-8,11,16-triazatricyclo[16.2.2.0$^{4,8}$]docosa-1(20),18,21-triene-15-carboxamide |

TABLE 34c-continued

Examples of Core 17 (Ex. 248-Ex. 271)

| No | R2 | R50 | IUPAC name |
|---|---|---|---|
| Ex. 271 | 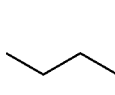 | 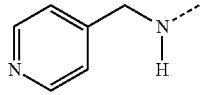 | (4S,6R,15S)-11,16-dimethyl-9,12,17-trioxo-6-(pentanoylamino)-N-(4-pyridinylmethyl)-2-oxa-8,11,16-triazatricyclo[16.2.2.0$^{4,8}$]docosa-1(20),18,21-triene-15-carboxamide |

TABLE 35a

Examples of Core 18 (Ex. 272-Ex. 296)

| No | R2 | R5 | Starting material | General Procedure | Reagent | Purification Method | Yield, (isolated salt) |
|---|---|---|---|---|---|---|---|
| Ex. 272-Ex. 274: cf. experimental description | | | | | | | |
| Ex. 275 | 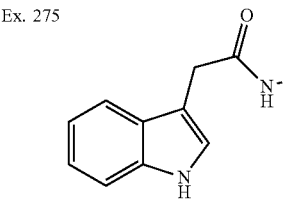 | 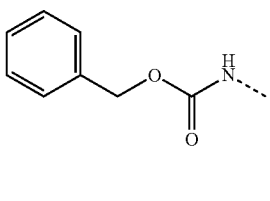 | Ex. 273 (HCl salt) | L.1.3 | 3-indoleacetic acid (1.1 equiv.) HATU (1.5 equiv.) HOAt (1.5 equiv.) i-Pr$_2$NEt (5 equiv.) | FC (CH$_2$Cl$_2$/MeOH) | 53% |
| Ex. 276 | 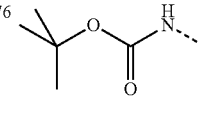 | 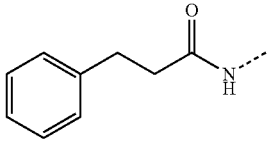 | Ex. 274 | L.1.3 | 3-phenylpropanoic acid (1.2 equiv.) HATU (1.5 equiv.) HOAt (1.5 equiv.) i-Pr$_2$NEt (3 equiv.) | FC (CH$_2$Cl$_2$/MeOH) | 72% |
| Ex. 277 | NH$_2$ | 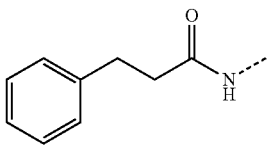 | Ex. 276 | J | HCl-dioxane | crude product | quant. (HCl salt) |
| Ex. 278 | 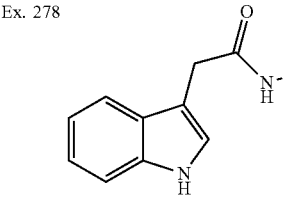 | 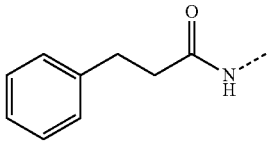 | Ex. 277 | L.1.3 | 3-indoleacetic acid (1.1 equiv.) HATU (1.5 equiv.) HOAt (1.5 equiv.) i-Pr$_2$NEt (5 equiv.) | FC (CH$_2$Cl$_2$/MeOH) | 75% |
| Ex. 279 | 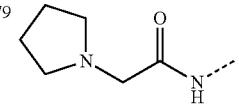 | 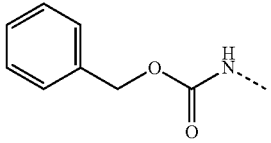 | Ex. 273 (HCl salt) | L.1.3 | pyrrolidine-1-acetic acid (1.2 equiv.) | FC (EtOAc/MeOH) | 67% |
| Ex. 280 | 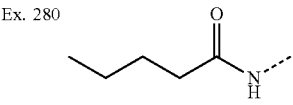 | 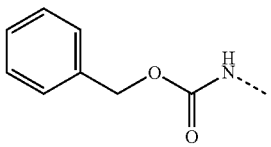 | Ex. 273 (HCl salt) | L.1.1 | valeroyl chloride (2 equiv.) | FC (EtOAc/MeOH) | 71% |
| Ex. 281 | 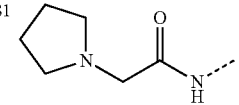 | NH$_2$ | Ex. 279 | K | H$_2$, Pd(OH)$_2$—C | crude product | quant. |

TABLE 35a-continued

Examples of Core 18 (Ex. 272-Ex. 296)

| No | R2 | R5 | Starting material | General Procedure | Reagent | Purification Method | Yield, (isolated salt) |
|---|---|---|---|---|---|---|---|
| Ex. 282 | butanamide | NH₂ | Ex. 280 | K | H₂, Pd(OH)₂—C | crude product | quant. |
| Ex. 283 | pyrrolidin-1-yl-acetamide | 2-naphthylacetamide | Ex. 281 | L.1.3 | 2-naphthylacetic acid (1.2 equiv.) | Prep. HPLC, method 3 | 27% |
| Ex. 284 | pyrrolidin-1-yl-acetamide | succinamic acid | Ex. 281 | L.1.1 | succinic anhydride (1.5 equiv.) Pyridine (49 equiv.) | Prep. HPLC, method 2 | 51% |
| Ex. 285 | pyrrolidin-1-yl-acetamide | 3-(pyridin-4-yl)propanamide | Ex. 281 | L.1.3 | 3-(pyridine-4-yl)propanoic acid (1.2 equiv.) | Prep. HPLC, method 2 | 12% |
| Ex. 286 | pyrrolidin-1-yl-acetamide | pyrrolidin-1-yl-acetamide | Ex. 281 | L.1.3 | pyrrolidine-1-acetic acid (1.2 equiv.) | Prep. HPLC, method 2 | 16% |
| Ex. 287 | butanamide | 2-naphthylacetamide | Ex. 282 | L.1.3 | 2-naphthylacetic acid (1.2 equiv.) | FC (CH₂Cl₂/ MeOH/ aq. NH₃) | 79% |
| Ex. 288 | butanamide | succinamic acid | Ex. 282 | L.1.1 | succinic anhydride (1.5 equiv.) Pyridine (49 equiv.) | Prep. HPLC, method 2 | 57% |
| Ex. 289 | butanamide | 3-(pyridin-4-yl)propanamide | Ex. 282 | L.1.3 | 3-(pyridine-4-yl)propanoic acid (1.2 equiv.) | Prep. HPLC, method 3 | 17% |
| Ex. 290 | butanamide | pyrrolidin-1-yl-acetamide | Ex. 282 | L.1.3 | pyrrolidine-1-acetic acid (1.2 equiv.) | FC (CH₂Cl₂/ MeOH/ aq. NH₃) | 65% |
| Ex. 291 | 2-naphthylacetamide | benzyl carbamate | Ex. 292 (HCl salt) | L.1.3 | 2-naphthylacetic acid (1.2 equiv.) | FC (EtOAc/ MeOH)*) | 79% |

TABLE 35a-continued

Examples of Core 18 (Ex. 272-Ex. 296)

| No | R2 | R5 | Starting material | General Procedure | Reagent | Purification Method | Yield, (isolated salt) |
|---|---|---|---|---|---|---|---|
| Ex. 292 | 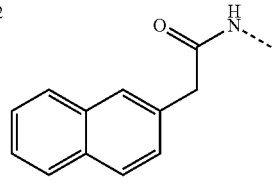 | NH$_2$ | Ex. 291 | K | H$_2$, Pd(OH)$_2$—C | FC (EtOAc/MeOH) | 69% |
| Ex. 293 |  | 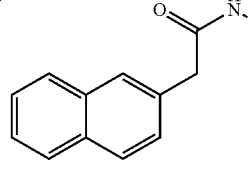 | Ex. 292 | L.1.3 | pyrrolidine-1-acetic acid (1.2 equiv.) | Prep. HPLC, method 3 | 64% |
| Ex. 294 | 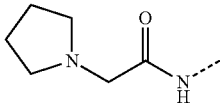 | 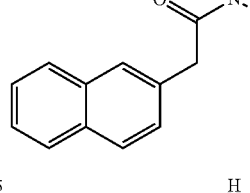 | Ex. 292 | L.1.3 | 3-(pyridine-4-yl)propanoic acid (1.2 equiv.) | Prep. HPLC, method 3 | 70% |
| Ex. 295 | 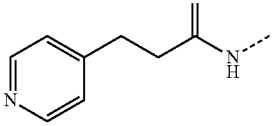 | 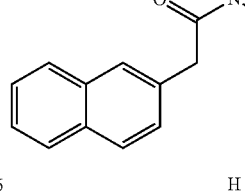 | Ex. 292 | L.1.1 | succinic anhydride (1.5 equiv.) Pyridine (49 equiv.) | Prep. HPLC, method 2 | 73% |
| Ex. 296 | 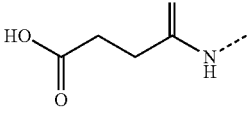 | CH$_3$(CH$_2$)$_8$ CONH | Ex. 292 | L.1.1 | decanoyl chloride (2 equiv.) | Prep. HPLC, method 3 | 40% |

*) An analytical sample was further purified by prep. HPLC, method 3

TABLE 35b

Examples of Core 18 (Ex. 272-Ex. 296)

| No | R2 | R5 | Formula | Monoisotopic Mass | Rt (purity at 220 nm) | [M + H]$^+$ found | LC-MS-Method |
|---|---|---|---|---|---|---|---|

Ex. 272-Ex. 274: cf. experimental description

| Ex. 275 | 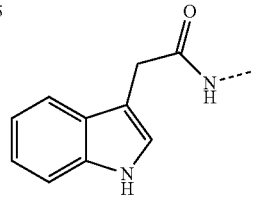 | 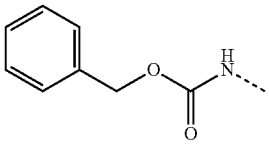 | C36H39N7O7 | 681.3 | 1.53 (97) | 682.5 | Method 2 |

TABLE 35b-continued
Examples of Core 18 (Ex. 272-Ex. 296)
| No | R2 | R5 | Formula | Monoisotopic Mass | Rt (purity at 220 nm) | [M + H]+ found | LC-MS-Method |
|---|---|---|---|---|---|---|---|
| Ex. 276 | 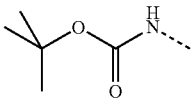 | 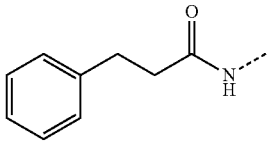 | C32H42N6O7 | 622.3 | 1.57 (95) | 623.4 | Method 2 |
| Ex. 277 | NH2 | 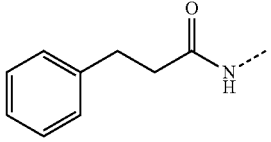 | C27H34N6O5 | 522.3 | 1.10 (98) | 523.4 | Method 2 |
| Ex. 278 | 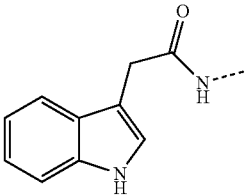 | 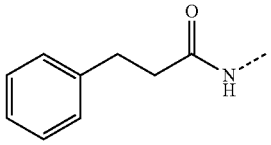 | C37H41N7O6 | 679.3 | 1.50 (98) | 680.5 | Method 2 |
| Ex. 279 | 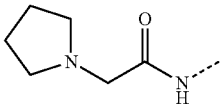 | 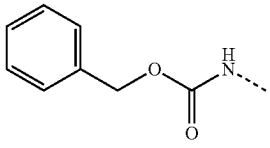 | C32H41N7O7 | 635.3 | 1.32 (98) | 636.3 | Method 2 |
| Ex. 280 | 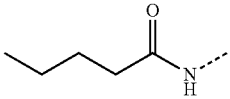 | 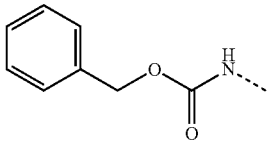 | C31H40N6O7 | 608.3 | 1.54 (98) | 609.3 | Method 2 |
| Ex. 281 | 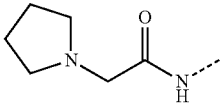 | NH2 | C24H35N7O5 | 501.3 | 1.32 (98) | 502.3 | Method 5a |
| Ex. 282 | 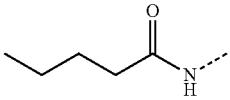 | NH2 | C23H34N6O5 | 474.3 | 1.24 (94) | 475.1 | Method 4a |
| Ex. 283 | 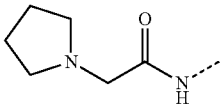 | 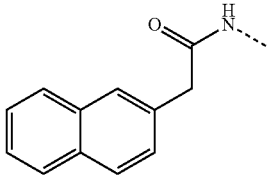 | C36H43N7O6 | 669.3 | 1.42 (95) | 670.3 | Method 4a |
| Ex. 284 | 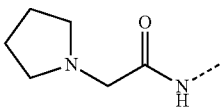 | 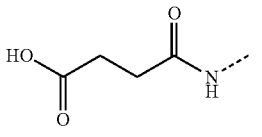 | C28H39N7O8 | 601.3 | 0.99 (100) | 602.2 | Method 5a |

TABLE 35b-continued

Examples of Core 18 (Ex. 272-Ex. 296)

| No | R2 | R5 | Formula | Monoisotopic Mass | Rt (purity at 220 nm) | [M + H]+ found | LC-MS-Method |
|---|---|---|---|---|---|---|---|
| Ex. 285 | pyrrolidine-CH2-C(O)-NH- | pyridin-4-yl-CH2CH2-C(O)-NH- | C32H42N8O6 | 634.3 | 1.47 (98) | 635.2 | Method 5a |
| Ex. 286 | pyrrolidine-CH2-C(O)-NH- | pyrrolidine-CH2-C(O)-NH- | C30H44N8O6 | 612.3 | 1.55 (99) | 613.3 | Method 5a |
| Ex. 287 | butyl-C(O)-NH- | naphthalen-2-yl-CH2-C(O)-NH- | C35H42N6O6 | 642.3 | 1.77 (98) | 643.3 | Method 4a |
| Ex. 288 | butyl-C(O)-NH- | HOOC-CH2CH2-C(O)-NH- | C27H38N6O8 | 574.3 | 1.32 (100) | 575.2 | Method 4a |
| Ex. 289 | butyl-C(O)-NH- | pyridin-4-yl-CH2CH2-C(O)-NH- | C31H41N7O6 | 607.3 | 1.25 (95) | 608.3 | Method 4a |
| Ex. 290 | butyl-C(O)-NH- | pyrrolidine-CH2-C(O)-NH- | C29H43N7O6 | 585.3 | 1.30 (95) | 586.4 | Method 4a |
| Ex. 291 | naphthalen-2-yl-CH2-C(O)-NH- | benzyl-O-C(O)-NH- | C38H40N6O7 | 692.3 | 1.91 (97) | 693.3 | Method 4a |
| Ex. 292 | naphthalen-2-yl-CH2-C(O)-NH- | NH2 | C30H34N6O5 | 558.3 | 1.55 (99) | 559.3 | Method 4a |
| Ex. 293 | naphthalen-2-yl-CH2-C(O)-NH- | pyrrolidine-CH2-C(O)-NH- | C36H43N7O6 | 669.3 | 1.52 (96) | 670.3 | Method 4a |

TABLE 35b-continued

Examples of Core 18 (Ex. 272-Ex. 296)

| No | R2 | R5 | Formula | Monoisotopic Mass | Rt (purity at 220 nm) | [M + H]+ found | LC-MS-Method |
|---|---|---|---|---|---|---|---|
| Ex. 294 | naphthalen-2-yl-acetamide | 3-(pyridin-4-yl)propanamide | C38H41N7O6 | 691.3 | 1.46 (97) | 692.3 | Method 4a |
| Ex. 295 | naphthalen-2-yl-acetamide | HOOC-CH2CH2-C(O)NH- | C34H38N6O8 | 658.3 | 1.58 (99) | 659.2 | Method 4a |
| Ex. 296 | naphthalen-2-yl-acetamide | CH3(CH2)8CONH | C40H52N6O6 | 712.4 | 2.22 (99) | 713.4 | Method 4a |

TABLE 35c

Examples of Core 18 (Ex. 272-Ex. 296)

| No | R2 | R5 | IUPAC name |
|---|---|---|---|
| Ex. 272 | tert-butyl carbamate | benzyl carbamate | benzyl N-[(4S,6S,13S)-6-[(tert-butoxycarbonyl)amino]-11,15-dimethyl-9,12,16-trioxo-2-oxa-8,11,15,19-tetraazatricyclo[15.3.1.0⁴,⁸]henicosa-1(21),17,19-trien-13-yl]carbamate |
| Ex. 273 | NH2 | benzyl carbamate | benzyl N-[(4S,6S,13S)-6-amino-11,15-dimethyl-9,12,16-trioxo-2-oxa-8,11,15,19-tetraazatricyclo[15.3.1.0⁴,⁸]henicosa-1(21),17,19-trien-13-yl]carbamate |
| Ex. 274 | tert-butyl carbamate | NH2 | tert-butyl N-[(4S,6S,13S)-13-amino-11,15-dimethyl-9,12,16-trioxo-2-oxa-8,11,15,19-tetraazatricyclo[15.3.1.0⁴,⁸]henicosa-1(21),17,19-trien-6-yl]carbamate |
| Ex. 275 | 2-(1H-indol-3-yl)acetamide | benzyl carbamate | benzyl N-[(4S,6S,13S)-6-{[2-(1H-indol-3-yl)acetyl]amino}-11,15-dimethyl-9,12,16-trioxo-2-oxa-8,11,15,19-tetraazatricyclo[15.3.1.0⁴,⁸]henicosa-1(21),17,19-trien-13-yl]carbamate |
| Ex. 276 | tert-butyl carbamate | 3-phenylpropanamide | tert-butyl N-[(4S,6S,13S)-11,15-dimethyl-9,12,16-trioxo-13-[(3-phenylpropanoyl)amino]-2-oxa-8,11,15,19-tetraazatricyclo[15.3.1.0⁴,⁸]henicosa-1(21),17,19-trien-6-yl]carbamate |

TABLE 35c-continued

Examples of Core 18 (Ex. 272-Ex. 296)

| No | R2 | R5 | IUPAC name |
|---|---|---|---|
| Ex. 277 | NH₂ | [3-phenylpropanamide group structure] | N-[(4S,6S,13S)-6-amino-11,15-dimethyl-9,12,16-trioxo-2-oxa-8,11,15,19-tetraazatricyclo[15.3.1.0⁴,⁸]henicosa-1(21),17,19-trien-13-yl]-3-phenylpropanamide |
| Ex. 278 | [2-(1H-indol-3-yl)acetamide group structure] | [3-phenylpropanamide group structure] | N-[(4S,6S,13S)-6-{[2-(1H-indol-3-yl)acetyl]amino}-11,15-dimethyl-9,12,16-trioxo-2-oxa-8,11,15,19-tetraazatricyclo[15.3.1.0⁴,⁸]henicosa-1(21),17,19-trien-13-yl]-3-phenylpropanamide |
| Ex. 279 | [2-(1-pyrrolidinyl)acetamide group structure] | [benzyl carbamate group structure] | benzyl N-[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0⁴,⁸]henicosa-1(21),17,19-trien-13-yl]carbamate |
| Ex. 280 | [pentanamide group structure] | [benzyl carbamate group structure] | benzyl N-[(4S,6S,13S)-11,15-dimethyl-9,12,16-trioxo-6-(pentanoylamino)-2-oxa-8,11,15,19-tetraazatricyclo[15.3.1.0⁴,⁸]henicosa-1(21),17,19-trien-13-yl]carbamate |
| Ex. 281 | [2-(1-pyrrolidinyl)acetamide group structure] | NH₂ | N-[(4S,6S,13S)-13-amino-11,15-dimethyl-9,12,16-trioxo-2-oxa-8,11,15,19-tetraazatricyclo[15.3.1.0⁴,⁸]henicosa-1(21),17,19-trien-6-yl]-2-(1-pyrrolidinyl)acetamide |
| Ex. 282 | [pentanamide group structure] | NH₂ | N-[(4S,6S,13S)-13-amino-11,15-dimethyl-9,12,16-trioxo-2-oxa-8,11,15,19-tetraazatricyclo[15.3.1.0⁴,⁸]henicosa-1(21),17,19-trien-6-yl]pentanamide |
| Ex. 283 | [2-(1-pyrrolidinyl)acetamide group structure] | [2-(2-naphthyl)acetamide group structure] | N-[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0⁴,⁸]henicosa-1(21),17,19-trien-13-yl]-2-(2-naphthyl)acetamide |
| Ex. 284 | [2-(1-pyrrolidinyl)acetamide group structure] | [4-oxobutanoic acid amide group structure] | 4-{[[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0⁴,⁸]henicosa-1(21),17,19-trien-13-yl]amino}-4-oxobutanoic acid |
| Ex. 285 | [2-(1-pyrrolidinyl)acetamide group structure] | [3-(4-pyridinyl)propanamide group structure] | N-[(4S,6S,13S)-11,15-dimethyl-9,12,16-trioxo-6-{[2-(1-pyrrolidinyl)acetyl]amino}-2-oxa-8,11,15,19-tetraazatricyclo[15.3.1.0⁴,⁸]henicosa-1(21),17,19-trien-13-yl]-3-(4-pyridinyl)propanamide |
| Ex. 286 | [2-(1-pyrrolidinyl)acetamide group structure] | [2-(1-pyrrolidinyl)acetamide group structure] | N-[(4S,6S,13S)-11,15-dimethyl-9,12,16-trioxo-13-{[2-(1-pyrrolidinyl)acetyl]amino}-2-oxa-8,11,15,19-tetraazatricyclo[15.3.1.0⁴,⁸]henicosa-1(21),17,19-trien-6-yl]-2-(1-pyrrolidinyl)acetamide |

TABLE 35c-continued

Examples of Core 18 (Ex. 272-Ex. 296)

| No | R2 | R5 | IUPAC name |
|---|---|---|---|
| Ex. 287 | (butanoylamino structure) | 2-(2-naphthyl)acetamido structure | N-[(4S,6S,13S)-11,15-dimethyl-13-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-6-yl]pentanamide |
| Ex. 288 | (butanoylamino structure) | HOOC-CH$_2$CH$_2$-C(O)NH- structure | 4-{[(4S,6S,13S)-11,15-dimethyl-9,12,16-trioxo-6-(pentanoylamino)-2-oxa-8,11,15,19-tetraazatricyclo[15.3.1.0$^{4,8}$]henicosa-1(21),17,19-trien-13-yl]amino}-4-oxobutanoic acid |
| Ex. 289 | (butanoylamino structure) | 3-(4-pyridinyl)propanamido structure | N-[(4S,6S,13S)-11,15-dimethyl-9,12,16-trioxo-13-{[3-(4-pyridinyl)propanoyl]amino}-2-oxa-8,11,15,19-tetraazatricyclo[15.3.1.0$^{4,8}$]henicosa-1(21),17,19-trien-6-yl]pentanamide |
| Ex. 290 | (butanoylamino structure) | 2-(1-pyrrolidinyl)acetamido structure | N-[(4S,6S,13S)-11,15-dimethyl-9,12,16-trioxo-13-{[2-(1-pyrrolidinyl)acetyl]amino}-2-oxa-8,11,15,19-tetraazatricyclo[15.3.1.0$^{4,8}$]henicosa-1(21),17,19-trien-6-yl]pentanamide |
| Ex. 291 | 2-(2-naphthyl)acetamido structure | benzyl carbamate structure | benzyl N-[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]carbamate |
| Ex. 292 | 2-(2-naphthyl)acetamido structure | NH$_2$ | N-[(4S,6S,13S)-13-amino-11,15-dimethyl-9,12,16-trioxo-2-oxa-8,11,15,19-tetraazatricyclo[15.3.1.0$^{4,8}$]henicosa-1(21),17,19-trien-6-yl]-2-(2-naphthyl)acetamide |
| Ex. 293 | 2-(2-naphthyl)acetamido structure | 2-(1-pyrrolidinyl)acetamido structure | N-[(4S,6S,13S)-11,15-dimethyl-9,12,16-trioxo-13-{[2-(1-pyrrolidinyl)acetyl]amino}-2-oxa-8,11,15,19-tetraazatricyclo[15.3.1.0$^{4,8}$]henicosa-1(21),17,19-trien-6-yl]-2-(2-naphthyl)acetamide |
| Ex. 294 | 2-(2-naphthyl)acetamido structure | 3-(4-pyridinyl)propanamido structure | N-[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]-3-(4-pyridinyl)propanamide |

TABLE 35c-continued

Examples of Core 18 (Ex. 272-Ex. 296)

| No | R2 | R5 | IUPAC name |
|---|---|---|---|
| Ex. 295 | 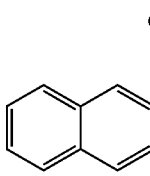 | 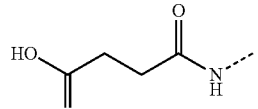 | 4-{[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]amino}-4-oxobutanoic acid |
| Ex. 296 | 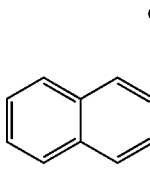 | CH$_3$(CH$_2$)$_8$CONH | N-[(4S,6S,13S)-11,15-dimethyl-6-{[2-(2-naphthyl)acetyl]amino}-9,12,16-trioxo-2-oxa-8,11,15,19-tetraazatricyclo[15.3.1.0$^{4,8}$]henicosa-1(21),17,19-trien-13-yl]decanamide |

TABLE 36a

Examples of Core 19 (Ex. 297-Ex. 310)

| No | R2 | R50 | Starting material | General Procedure | Reagent | Purification Method | Yield, (isolated salt) |
|---|---|---|---|---|---|---|---|
| Ex. 297-Ex. 298: cf. experimental description | | | | | | | |
| Ex. 299 | 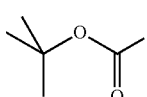 | 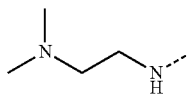 | Ex. 298 | L.2 | N,N-dimethylethylenediamine | Flash Chromatography | 80% |
| Ex. 300 | NH$_2$ | 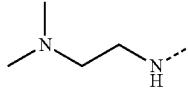 | Ex. 299 | J | HCl-dioxane | No purification | quant. (HCl salt) |
| Ex. 301 | 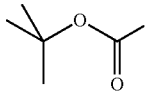 | 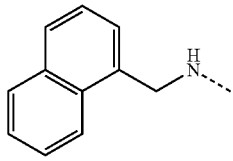 | Ex. 298 | L.2 | 1-naphthylmethylamine | FC (CH$_2$Cl$_2$/MeOH) | 75% |
| Ex. 302 | NH$_2$ | 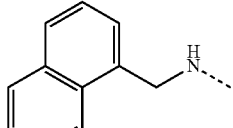 | Ex. 301 | J | HCl-dioxane | Crude product | quant. (HCl salt) |
| Ex. 303 | 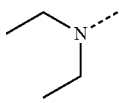 | 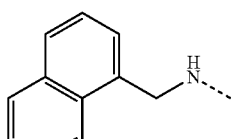 | Ex. 302 | M | acetaldehyde | Prep. HPLC, method 2 | 45% |
| Ex. 304 | 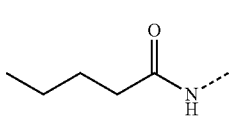 | 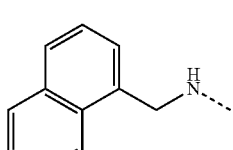 | Ex. 302 | L.1.1 | valeroyl chloride (5 equiv.) | Prep. HPLC, method 2 | 22% |

TABLE 36a-continued

Examples of Core 19 (Ex. 297-Ex. 310)

| No | R2 | R50 | Starting material | General Procedure | Reagent | Purification Method | Yield, (isolated salt) |
|---|---|---|---|---|---|---|---|
| Ex. 305 | 3-(pyridin-4-yl)propanamide (pyridine N, CH2CH2C(O)NH-) | naphthalen-1-ylmethylamine | Ex. 302 | L.1.2 | 3-(pyridine-4-yl)propanoic acid (3.7 equiv.) i-Pr2NEt (4 equiv.) bicarbonate resin (4 equiv.) | FC (CH2Cl2/ MeOH/ aq. NH3) then Prep. HPLC, method 3 | 55% |
| Ex. 306 | N,N-dimethylglycinamide | naphthalen-1-ylmethylamine | Ex. 302 | L.1.2 | N,N-dimethyl glycine (6.2 equiv.) carbodiimide resin (2.5 equiv.) i-Pr2NEt (5 equiv.) bicarbonate resin (5 equiv.) | FC (CH2Cl2/ MeOH) | 43% |
| Ex. 307 | valeramide | N,N-dimethylethylenediamine | Ex. 300 | L.1.1 | valeroyl chloride (2 equiv.) | Prep. HPLC, method 2 | 36% |
| Ex. 308 | 3-(pyridin-4-yl)propanamide | N,N-dimethylethylenediamine | Ex. 300 | L.1.2 | 3-(pyridine-4-yl)propanoic acid (1.2 equiv.) i-Pr2NEt (4 equiv.), bicarbonate resin (4 equiv.) | FC (CH2Cl2/ MeOH) | 77% |
| Ex. 309 | 2-naphthylacetamide | N,N-dimethylethylenediamine | Ex. 300 | L.1.2*) | 2-naphthylacetic acid i-Pr2NEt (4 equiv.) | Prep. HPLC, method 2 | 58% |
| Ex. 310 | 3-indoleacetamide | N,N-dimethylethylenediamine | Ex. 300 | L.1.2 | 3-indoleacetic acid (3.7 equiv.) i-Pr2NEt (4 equiv.) DMF (0.2 mL) bicarbonate resin (4 equiv.) | Prep. HPLC, method 2 | 28% |

*) The treatment with (polystyrylmethyl)trimethylammonium bicarbonate was replaced by an aqueous workup (CHCl3, sat. aq. NaHCO3 soln)

TABLE 36b

Examples of Core 19 (Ex. 297-Ex. 310)

| No | R2 | R5 | Formula | Monoisotopic Mass | Rt (purity at 220 nm) | [M + H]+ found | LC-MS-Method |
|---|---|---|---|---|---|---|---|
| Ex. 297-Ex. 298: cf. experimental description | | | | | | | |
| Ex. 299 | Boc-NH- (tert-butyl carbamate) | N,N-dimethylethylenediamine | C33H47N7O7 | 653.4 | 1.62 (97) | 654.4 | Method 4a |
| Ex. 300 | NH2 | N,N-dimethylethylenediamine | C28H39N7O5 | 553.3 | 1.11 (64), 1.08 (35) | 554.3 | Method 4a |

TABLE 36b-continued

Examples of Core 19 (Ex. 297-Ex. 310)

| No | R2 | R5 | Formula | Monoisotopic Mass | Rt (purity at 220 nm) | [M + H]+ found | LC-MS-Method |
|---|---|---|---|---|---|---|---|
| Ex. 301 | | | C40H46N6O7 | 722.3 | 2.19 (89) | 723.4 | Method 4a |
| Ex. 302 | NH2 | | C35H38N6O5 | 622.3 | 1.70 (79) | 623.3 | Method 4a |
| Ex. 303 | | | C39H46N6O5 | 678.4 | 1.75 (100) | 679.4 | Method 4a |
| Ex. 304 | | | C40H46N6O6 | 706.4 | 2.09 (100) | 707.4 | Method 4a |
| Ex. 305 | | | C43H45N7O6 | 755.3 | 1.67 (57), 1.70 (38) | 756.4 | Method 4a |
| Ex. 306 | | | C39H45N7O6 | 707.3 | 1.71 (86) | 708.3 | Method 4a |
| Ex. 307 | | | C33H47N7O6 | 637.4 | 1.50 (638.3) | 638.3 | Method 4a |
| Ex. 308 | | | C36H46N8O6 | 686.4 | 1.57 (92) | 687.4 | Method 5a |
| Ex. 309 | | | C40H47N7O6 | 721.4 | 1.68 (98) | 722.4 | Method 4a |

TABLE 36b-continued

Examples of Core 19 (Ex. 297-Ex. 310)

| No | R2 | R5 | Formula | Monoisotopic Mass | Rt (purity at 220 nm) | [M + H]+ found | LC-MS-Method |
|---|---|---|---|---|---|---|---|
| Ex. 310 | 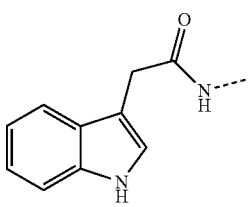 | 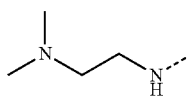 | C38H46N8O6 | 710.4 | 1.52 (97) | 711.4 | Method 4a |

TABLE 36c

Examples of Core 19 (Ex. 297-Ex. 310)

| No | R2 | R5 | IUPAC name |
|---|---|---|---|
| Ex. 297 | 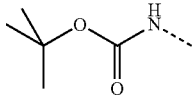 | OCH2Ph | benzyl (4S,6S,15S)-6-[(tert-butoxycarbonyl)amino]-11,16-dimethyl-9,12,17-trioxo-2-oxa-8,11,16,26-tetraazatetracyclo[16.6.2.0$^{4,8}$.0$^{21,25}$]hexacosa-1(24),18,20,22,25-pentaene-15-carboxylate |
| Ex. 298 | 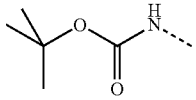 | OH | (4S,6S,15S)-6-[(tert-butoxycarbonyl)amino]-11,16-dimethyl-9,12,17-trioxo-2-oxa-8,11,16,26-tetraazatetracyclo[16.6.2.0$^{4,8}$.0$^{21,25}$]hexacosa-1(24),18,20,22,25-pentaene-15-carboxylic acid |
| Ex. 299 | 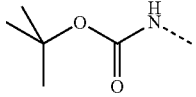 | 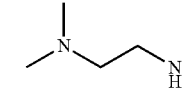 | tert-butyl N-[(4S,6S,15S)-15-({[2-(dimethylamino)ethyl]amino}carbonyl)-11,16-dimethyl-9,12,17-trioxo-2-oxa-8,11,16,26-tetraazatetracyclo[16.6.2.0$^{4,8}$.0$^{21,25}$]hexacosa-1(24),18,20,22,25-pentaen-6-yl]carbamate |
| Ex. 300 | NH2 | 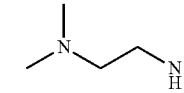 | (4S,6S,15S)-6-amino-N-[2-(dimethylamino)ethyl]-11,16-dimethyl-9,12,17-trioxo-2-oxa-8,11,16,26-tetraazatetracyclo[16.6.2.0$^{4,8}$.0$^{21,25}$]hexacosa-1(24),18,20,22,25-pentaene-15-carboxamide |
| Ex. 301 | 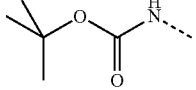 | 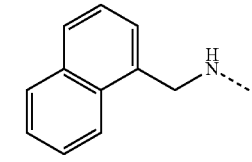 | tert-butyl N-[(4S,6S,15S)-11,16-dimethyl-15-{[(1-naphthylmethyl)amino]carbonyl}-9,12,17-trioxo-2-oxa-8,11,16,26-tetraazatetracyclo[16.6.2.0$^{4,8}$.0$^{21,25}$]hexacosa-1(25),18(26),19,21,23-pentaen-6-yl]carbamate |
| Ex. 302 | NH2 | 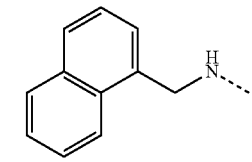 | (4S,6S,15S)-6-amino-11,16-dimethyl-N-(1-naphthylmethyl)-9,12,17-trioxo-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 303 | 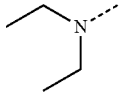 | 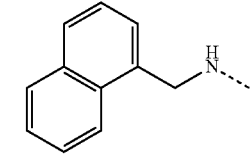 | (4S,6S,15S)-6-(diethylamino)-11,16-dimethyl-N-(1-naphthylmethyl)-9,12,17-trioxo-2-oxa-8,11,16,26-tetraazatetracyclo[16.6.2.0$^{4,8}$.0$^{21,25}$]hexacosa-1(25),18(26),19,21,23-pentaene-15-carboxamide |

TABLE 36c-continued

Examples of Core 19 (Ex. 297-Ex. 310)

| No | R2 | R5 | IUPAC name |
|---|---|---|---|
| Ex. 304 | (butanoylamino structure) | (1-naphthylmethyl structure) | (4S,6S,15S)-11,16-dimethyl-N-(1-naphthylmethyl)-9,12,17-trioxo-6-(pentanoylamino)-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 305 | (3-(4-pyridinyl)propanoyl structure) | (1-naphthylmethyl structure) | (4S,6S,15S)-11,16-dimethyl-N-(1-naphthylmethyl)-9,12,17-trioxo-6-{[3-(4-pyridinyl)propanoyl]amino}-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 306 | (dimethylaminoacetyl structure) | (1-naphthylmethyl structure) | (4S,6S,15S)-6-{[2-(dimethylamino)acetyl]amino}-11,16-dimethyl-N-(1-naphthylmethyl)-9,12,17-trioxo-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 307 | (pentanoyl structure) | (2-(dimethylamino)ethyl structure) | (4S,6S,15S)-N-[2-(dimethylamino)ethyl]-11,16-dimethyl-9,12,17-trioxo-6-(pentanoylamino)-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 308 | (3-(4-pyridinyl)propanoyl structure) | (2-(dimethylamino)ethyl structure) | (4S,6S,15S)-N-[2-(dimethylamino)ethyl]-11,16-dimethyl-9,12,17-trioxo-6-{[3-(4-pyridinyl)propanoyl]amino}-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 309 | (2-(2-naphthyl)acetyl structure) | (2-(dimethylamino)ethyl structure) | (4S,6S,15S)-N-[2-(dimethylamino)ethyl]-11,16-dimethyl-6-{[2-(2-naphthyl)acetyl]amino}-9,12,17-trioxo-2-oxa-8,11,16,26-tetraazatetracyclo[16.6.2.0$^{4,8}$.0$^{21,25}$]hexacosa-1(25),18(26),19,21,23-pentaene-15-carboxamide |
| Ex. 310 | (2-(1H-indol-3-yl)acetyl structure) | (2-(dimethylamino)ethyl structure) | (4S,6S,15S)-N-[2-(dimethylamino)ethyl]-6-{[2-(1H-indol-3-yl)acetyl]amino}-11,16-dimethyl-9,12,17-trioxo-2-oxa-8,11,16,26-tetraazatetracyclo[16.6.2.0$^{4,8}$.0$^{21,25}$]hexacosa-1(25),18(26),19,21,23-pentaene-15-carboxamide |

TABLE 37

Examples of Core 20 and Core 21 (Ex. 311-Ex. 313)

| No Core 20 | R2 | R5 | R38 | IUPAC name |
|---|---|---|---|---|
| Ex. 311 | (2-(trimethylsilyl)ethoxycarbonyl structure) | (benzyl structure) | (tert-butoxycarbonyl structure) | benzyl N-[(4S,6S,13S,17S)-17-[(tert-butoxycarbonyl)amino]-11,15-dimethyl-9,12,16-trioxo-6-({[2-(trimethylsilyl)ethoxy]carbonyl}amino)-2-oxa-8,11,15-triazatetracyclo[15.6.2.0$^{4,8}$.0$^{20,24}$]pentacosa-1(24),20,22-trien-13-yl]carbamate |

TABLE 37-continued
| No Core 21 | R2 | R50 | IUPAC name |
|---|---|---|---|
| Ex. 312 | ![structure] | OCH$_2$Ph | benzyl (4S,6R,15S)-6-[(tert-butoxycarbonyl)amino]-11,16-dimethyl-9,12,17-trioxo-2-thia-8,11,16-triazatricyclo[16.3.1.0$^{4,8}$]docosa-1(22),18,20-triene-15-carboxylate |
| Ex. 313 | ![structure] | OCH$_2$Ph | benzyl (4S,6R,15S)-6-[(tert-butoxycarbonyl)amino]-11,16-dimethyl-2,2,9,12,17-pentaoxo-2λ$^6$-thia-8,11,16-triazatricyclo[16.3.1.0$^{4,8}$]docosa-1(22),18,20-triene-15-carboxylate |
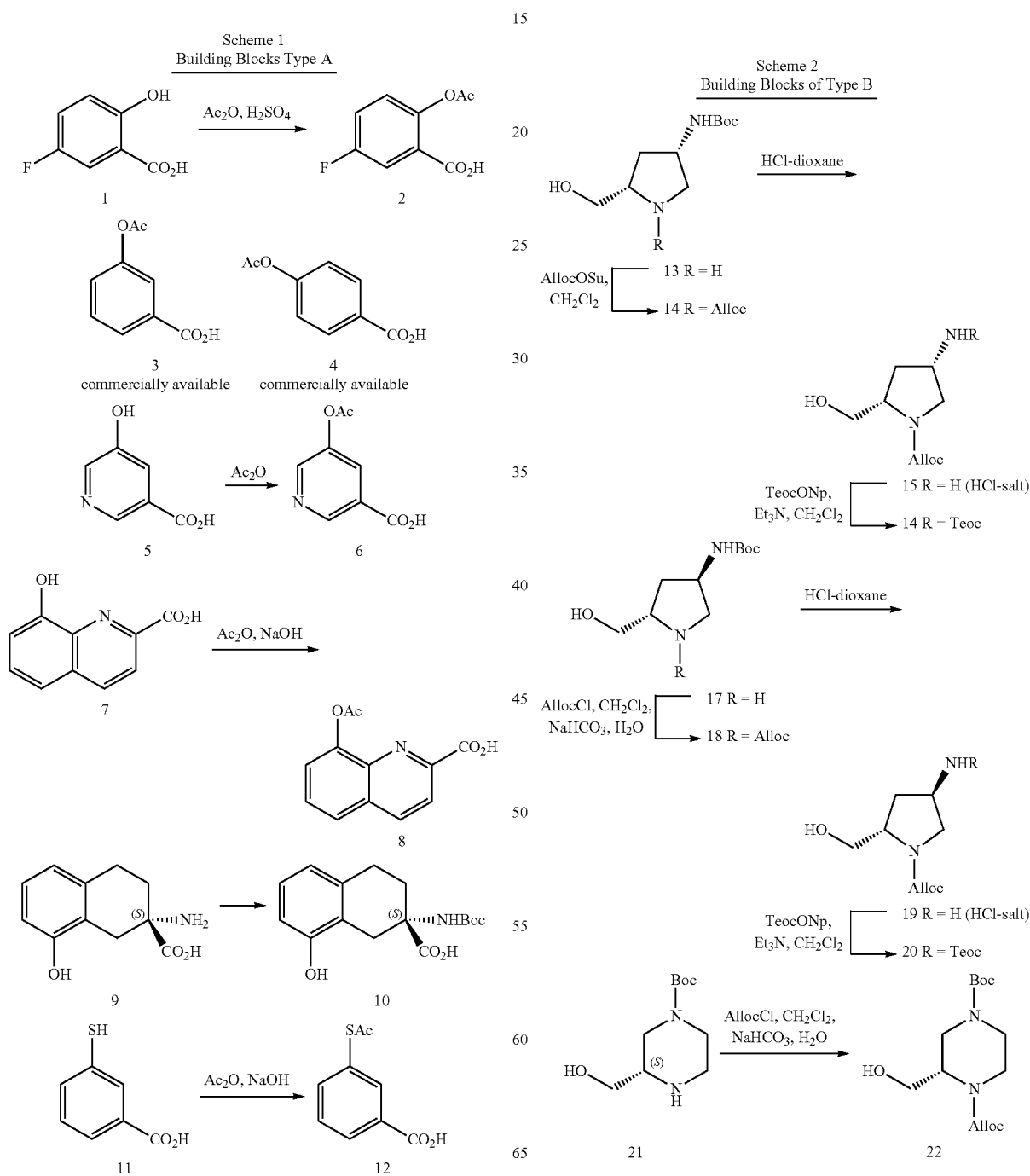

Scheme 3
Building Blocks of Type C:
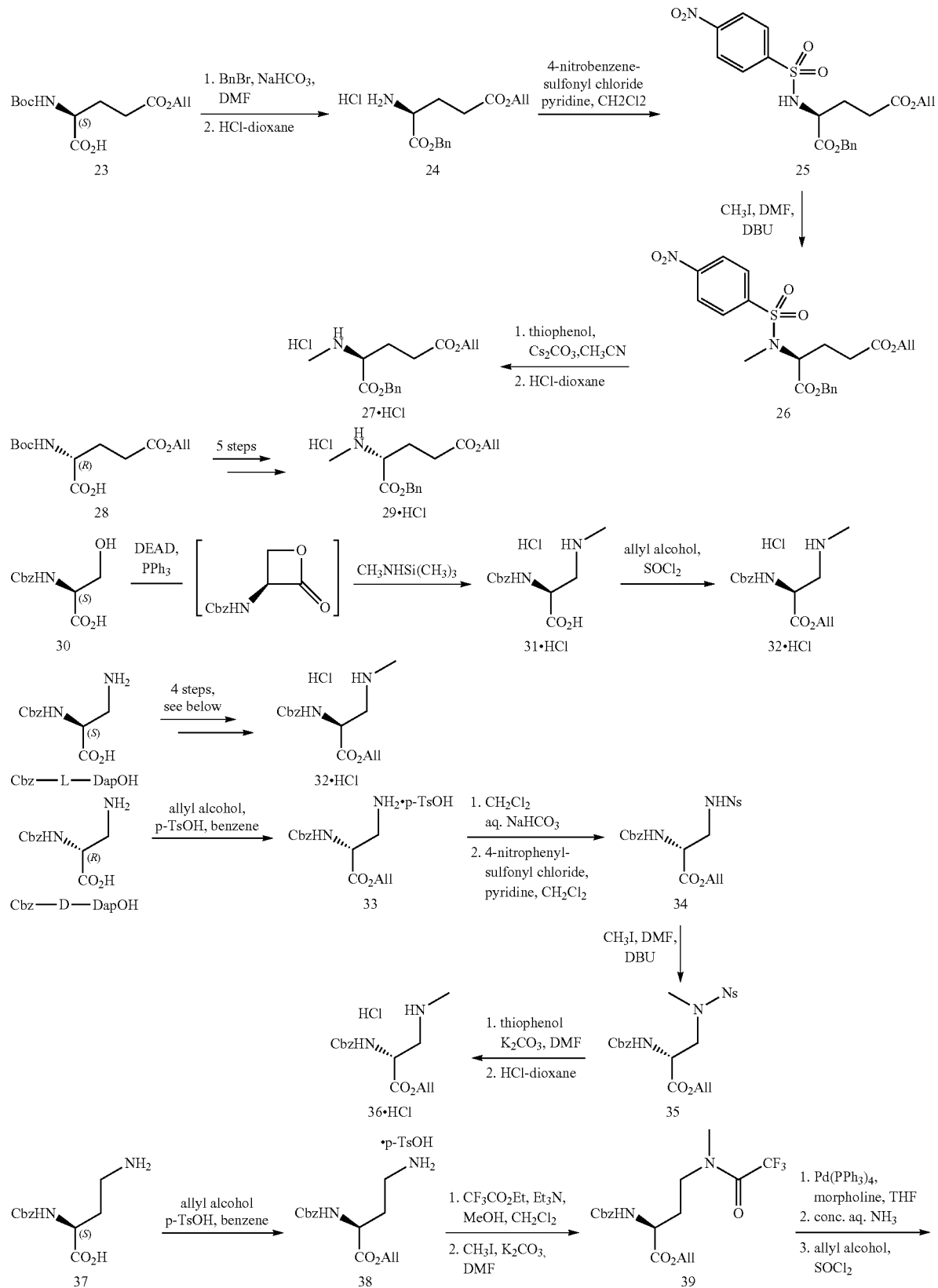

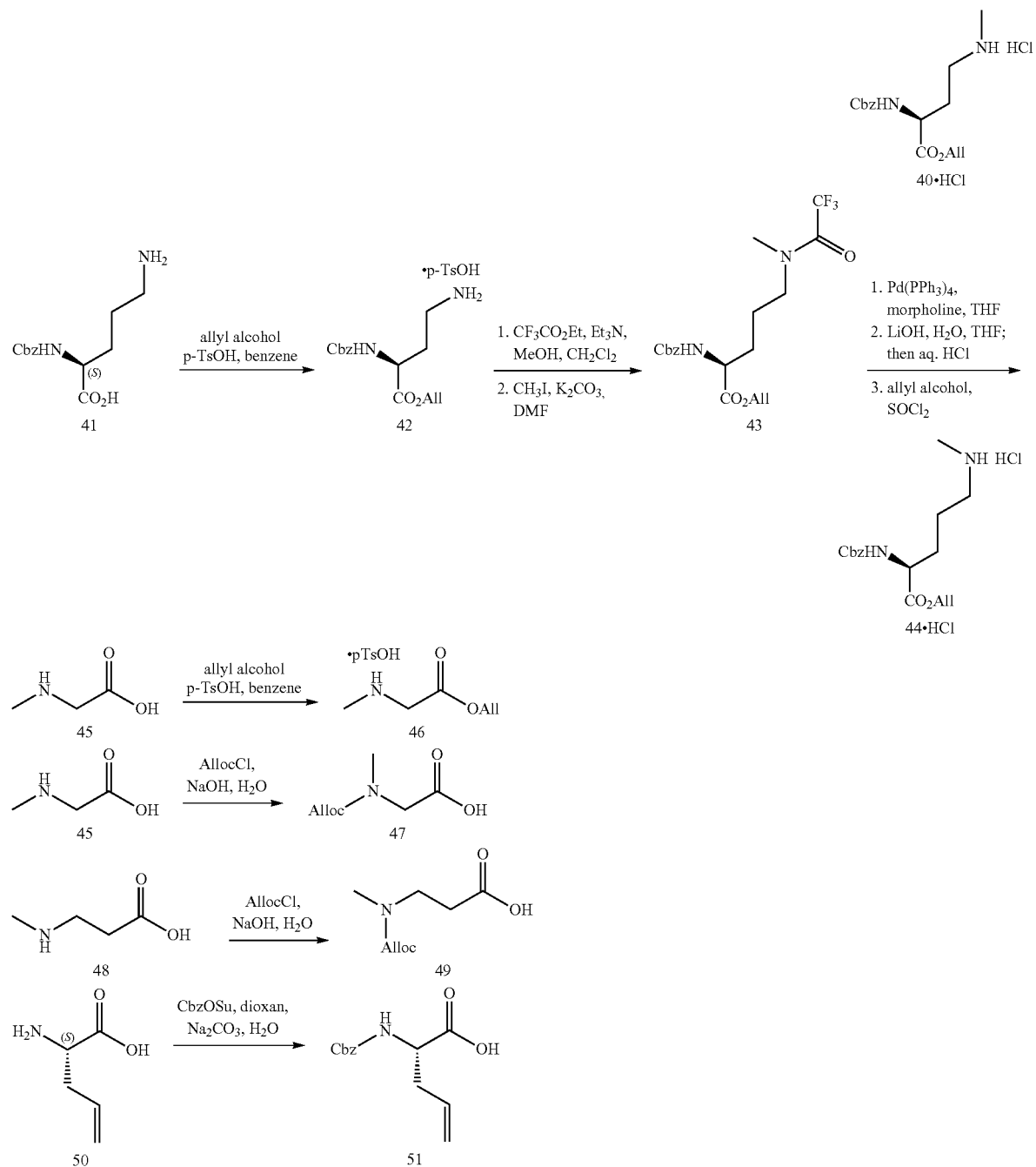
Scheme 4
A-c1 Fragments
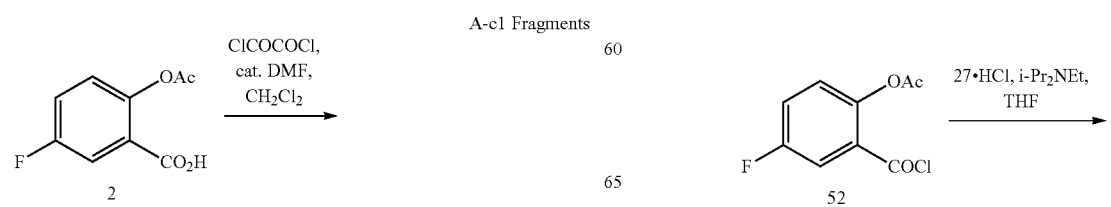

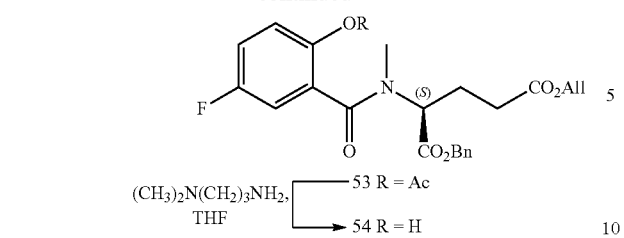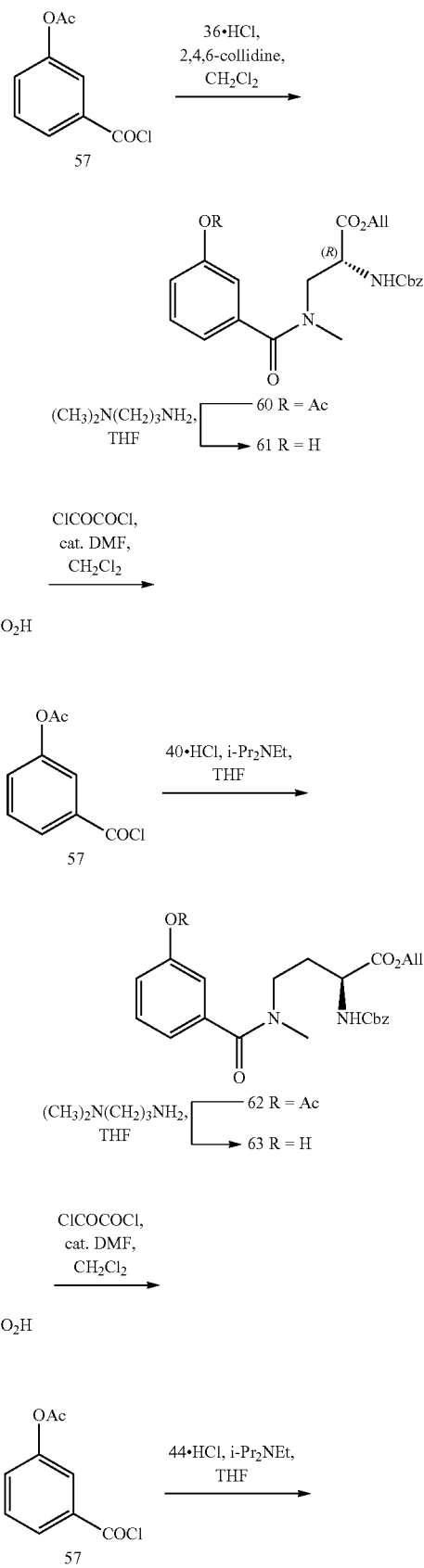

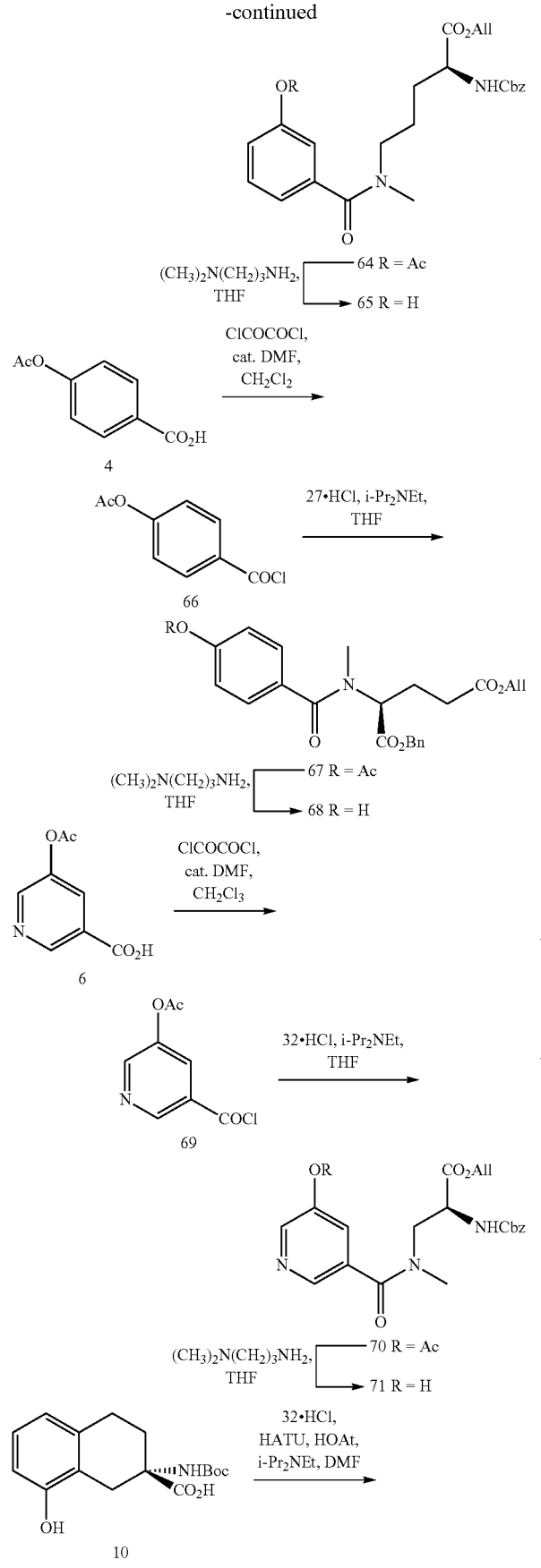
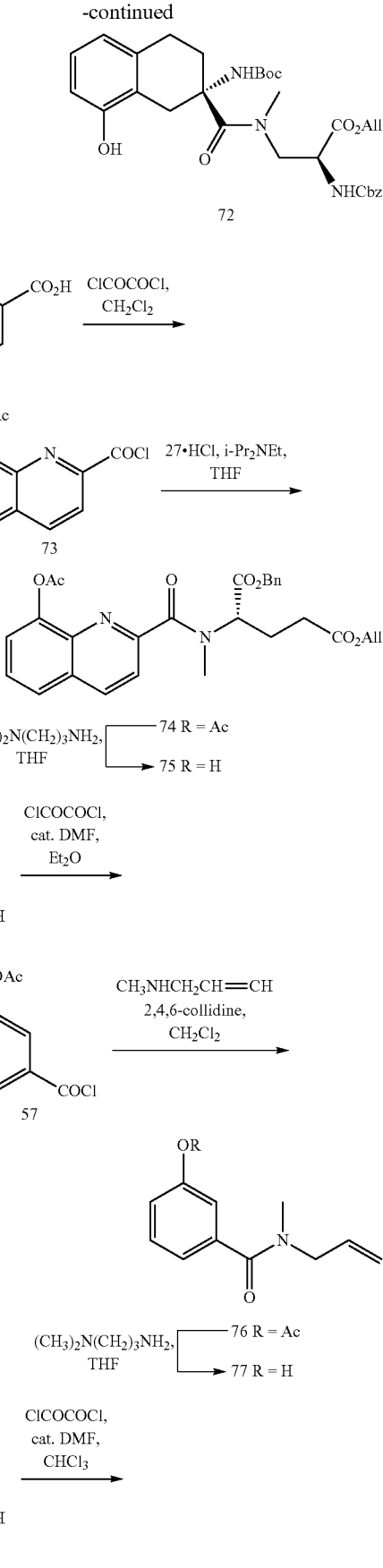

461
-continued
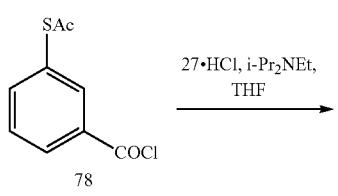
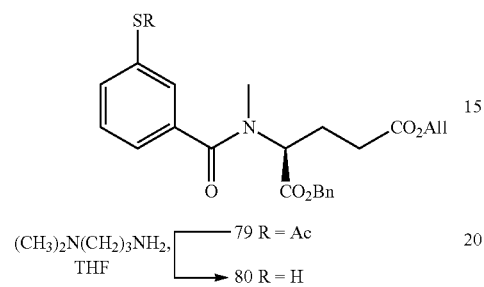
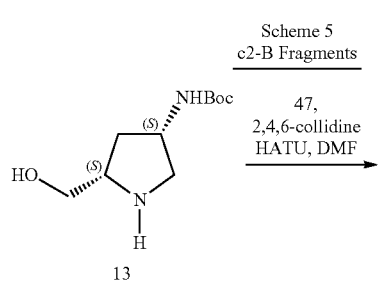
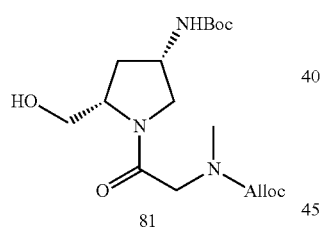
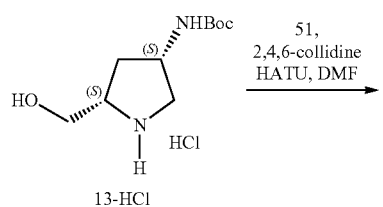
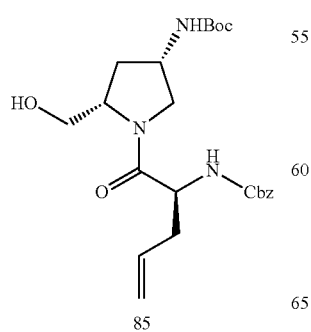
462
-continued
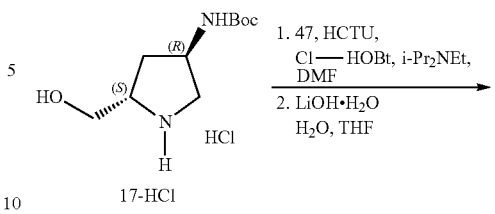
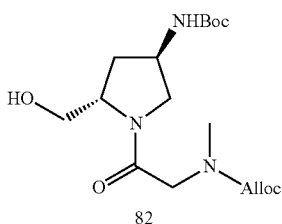
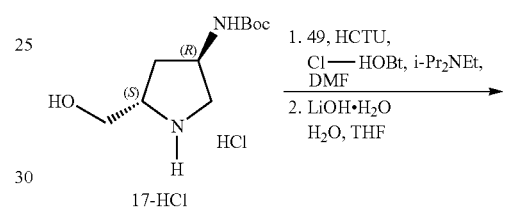
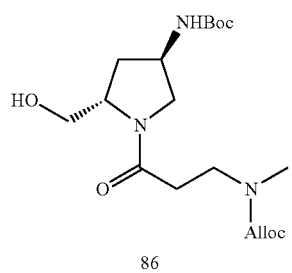
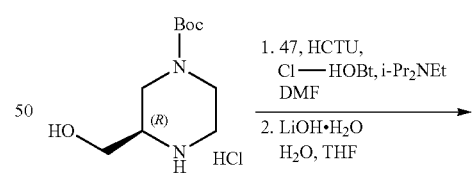
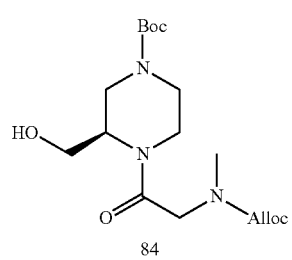

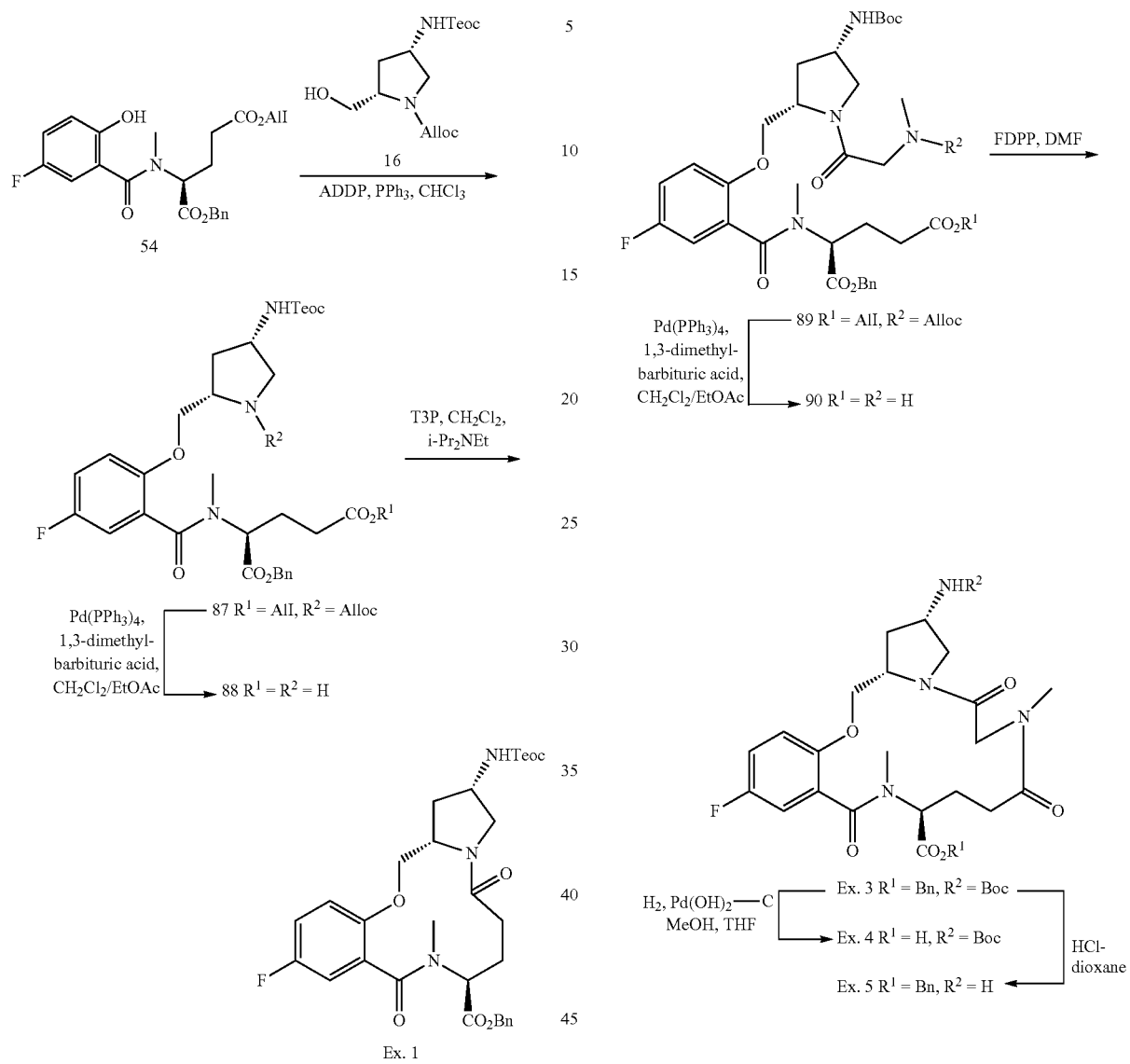
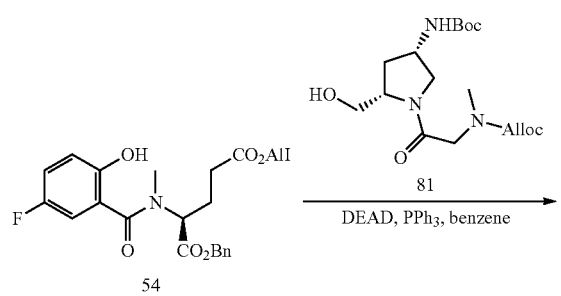
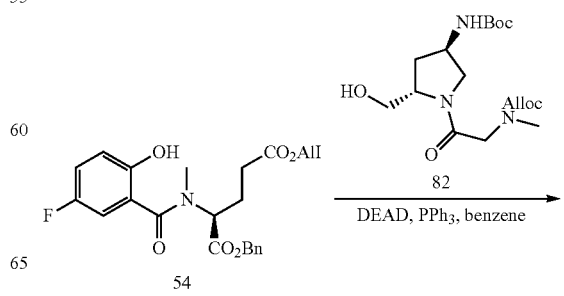

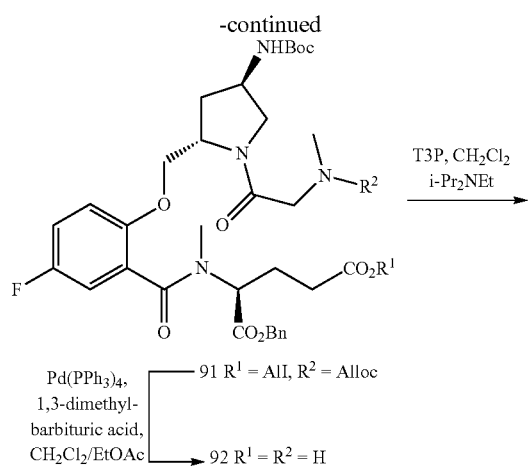
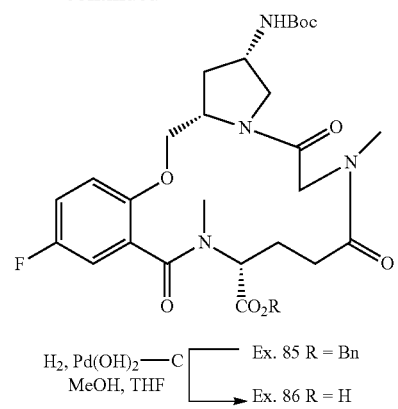
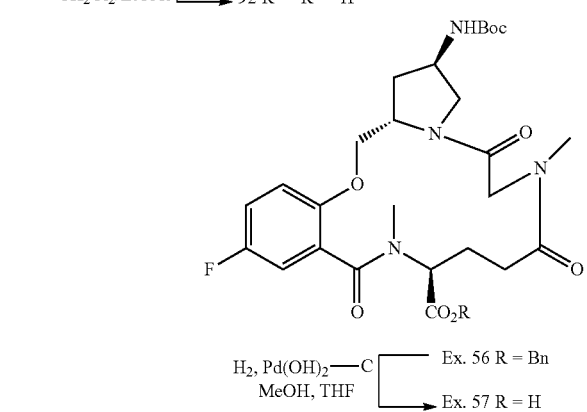
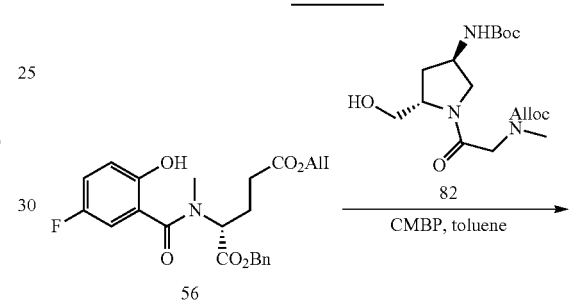
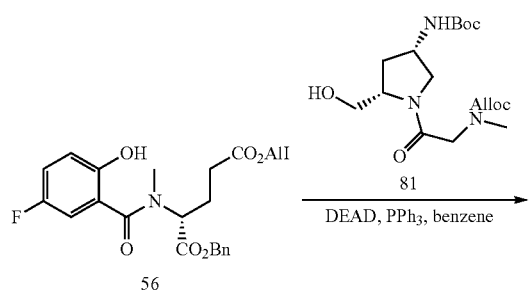
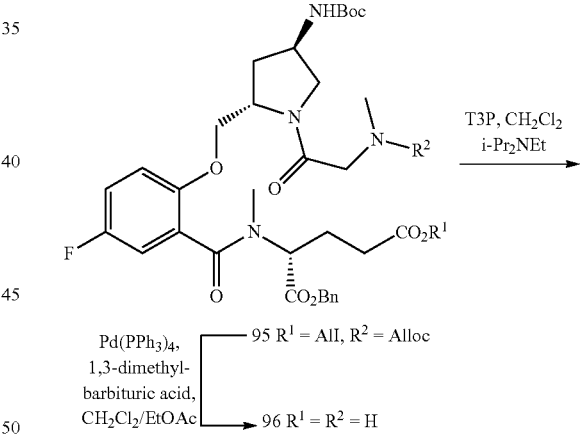
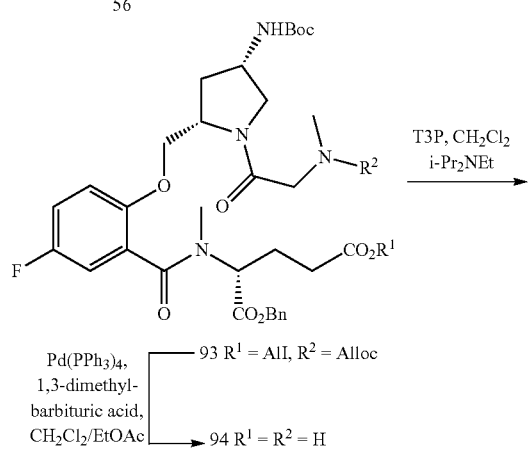
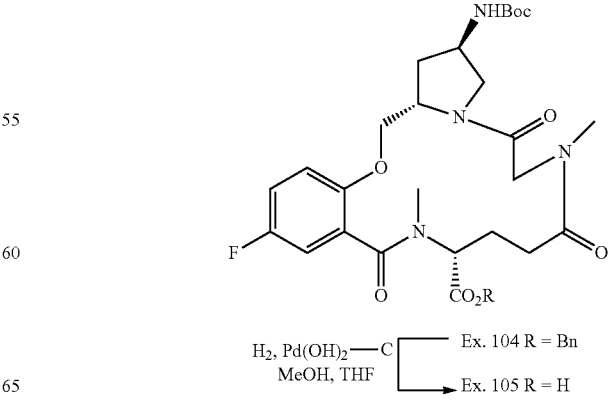

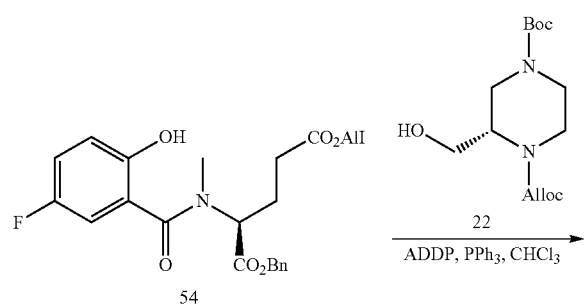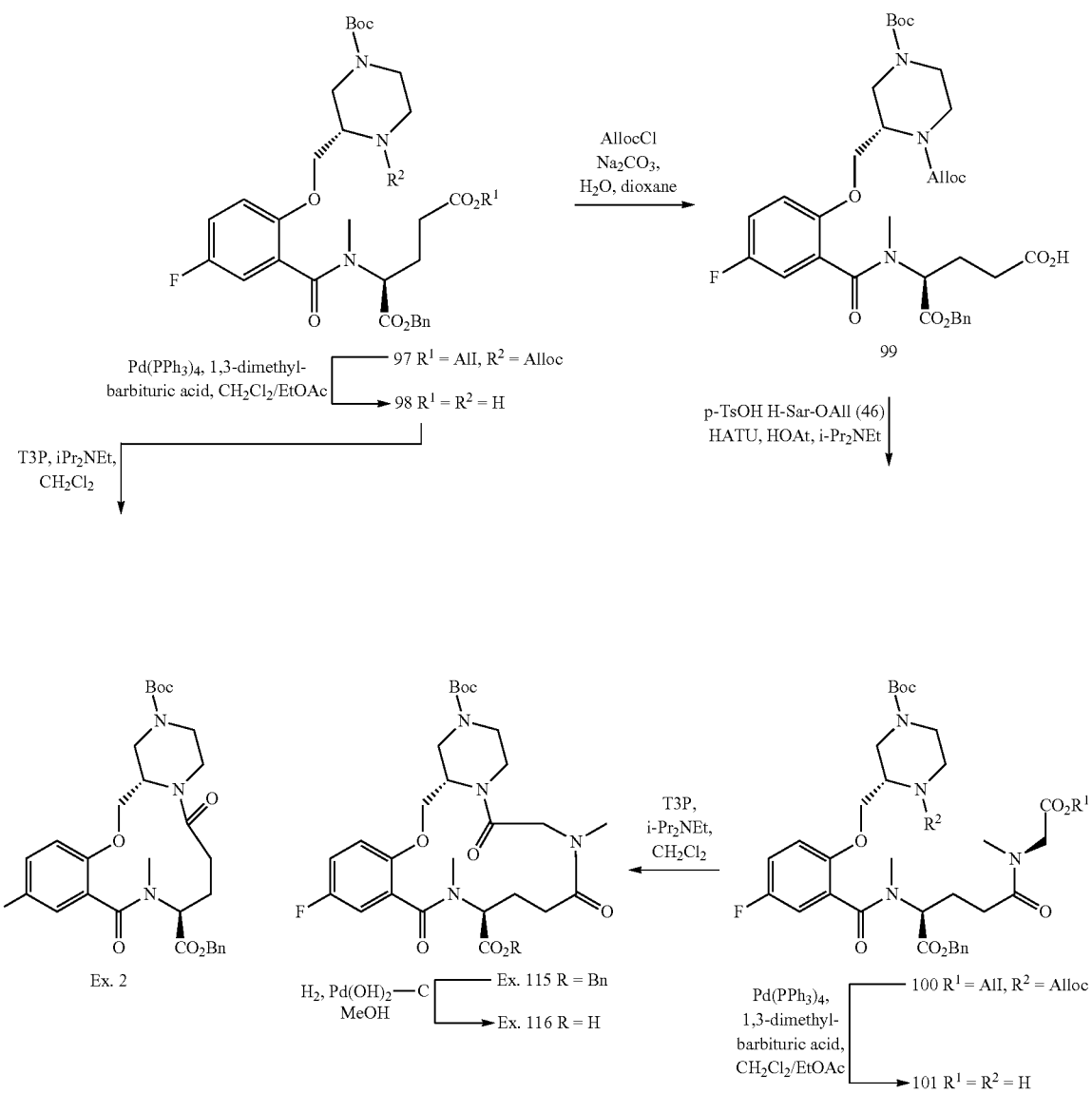

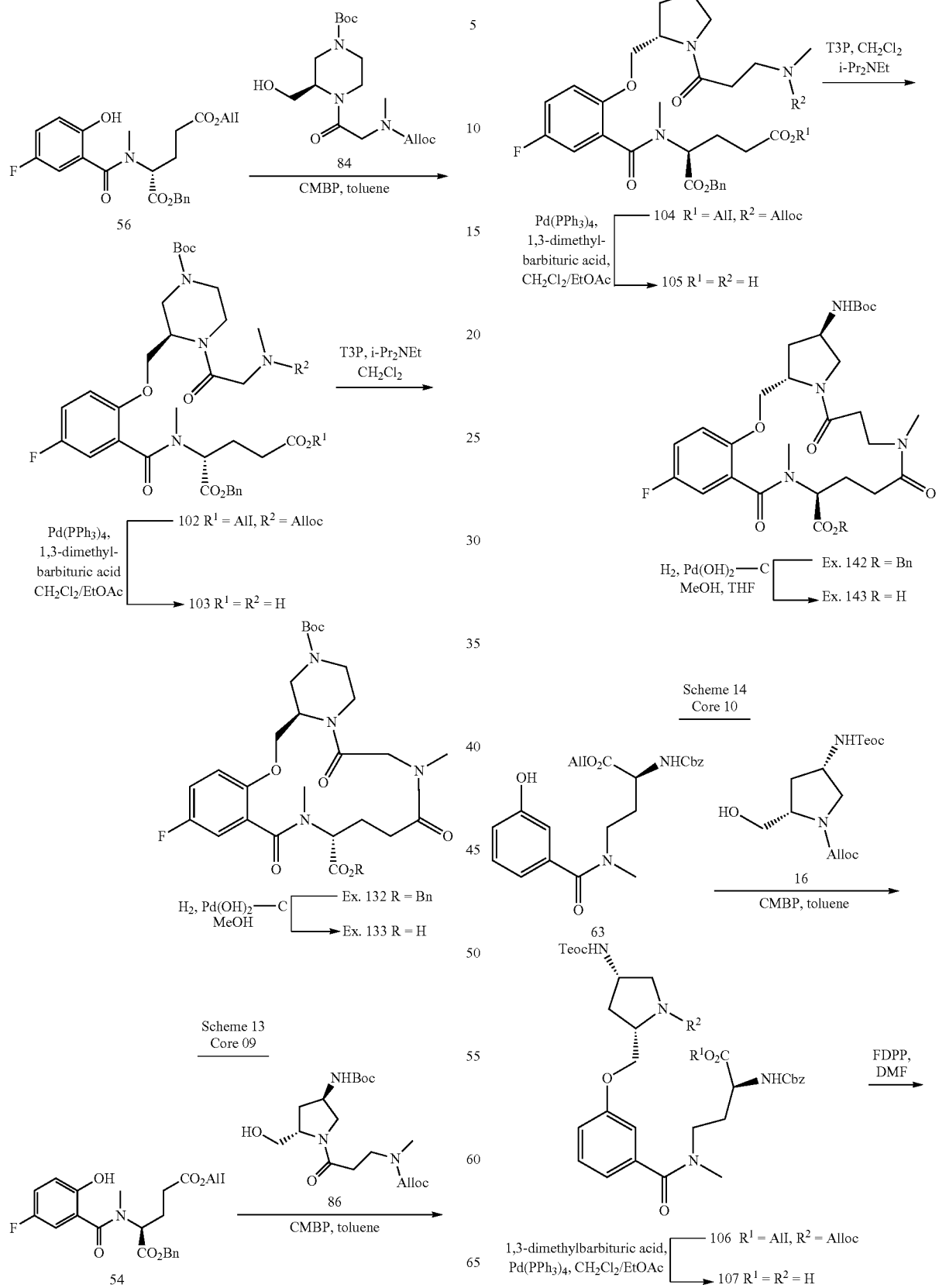

471
-continued
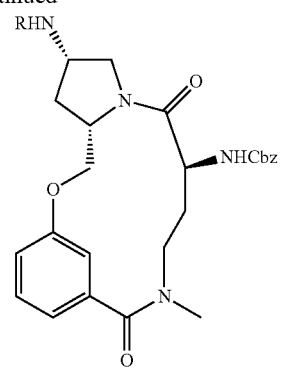
TBAF, THF
Ex. 164 R = Teoc
Ex. 165 R = H
Scheme 15
Core 11
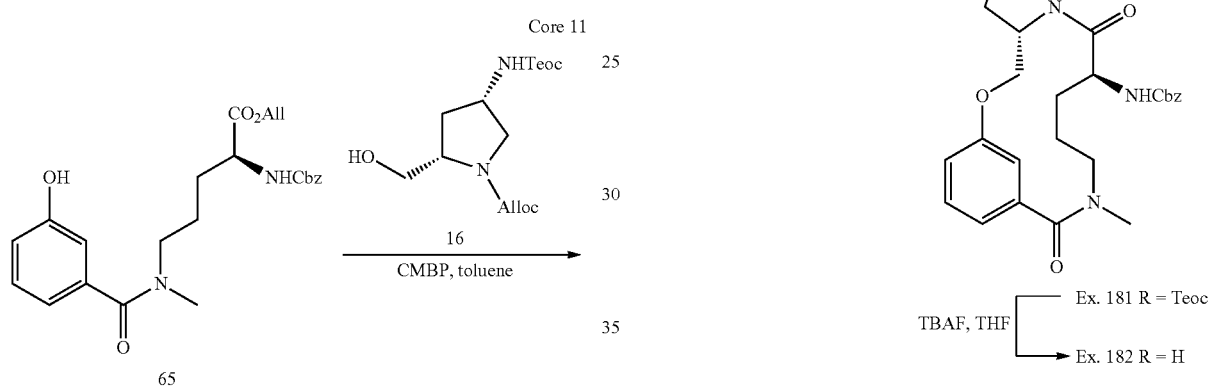
472
-continued
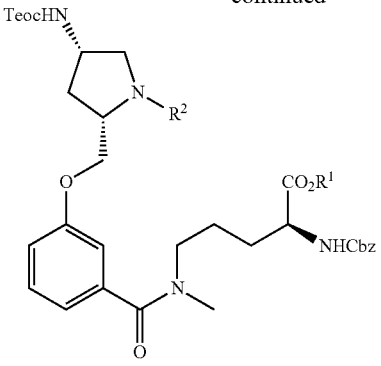
T3P, i-Pr₂NEt, CH₂Cl₂ →
Pd(PPh₃)₄, 1,3-dimethyl-barbituric acid, CH₂Cl₂/EtOAc
108 R¹ = All, R² = Alloc
109 R¹ = R² = H
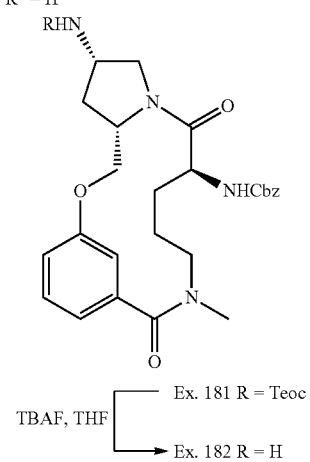
TBAF, THF
Ex. 181 R = Teoc
Ex. 182 R = H
Scheme 16
Core 12 (linear synthesis)
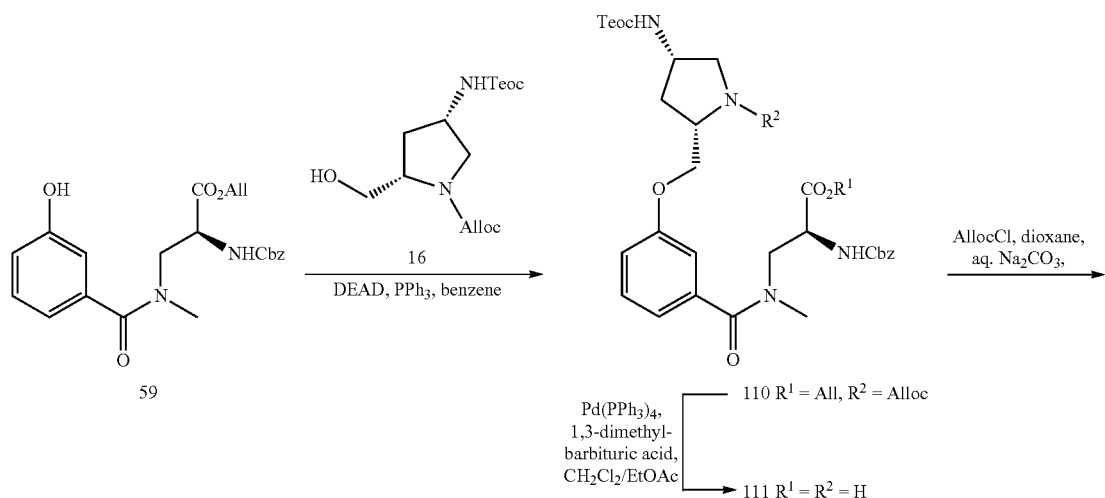
AllocCl, dioxane, aq. Na₂CO₃, →
Pd(PPh₃)₄, 1,3-dimethyl-barbituric acid, CH₂Cl₂/EtOAc
110 R¹ = All, R² = Alloc
111 R¹ = R² = H

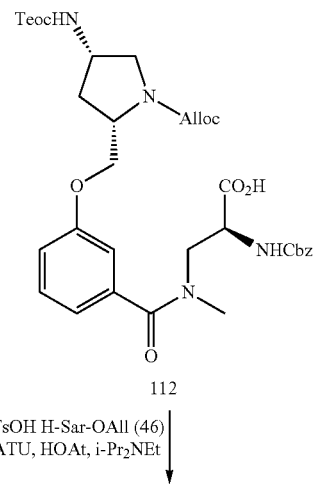
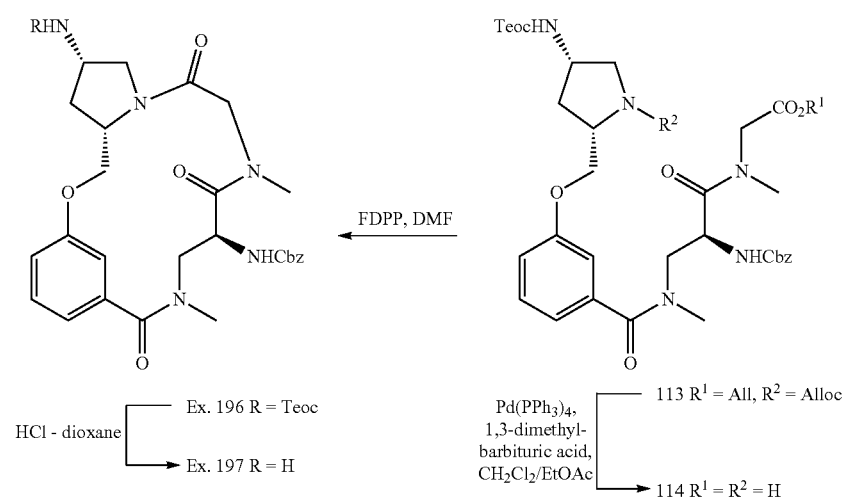
Scheme 17
Core 12 (convergent synthesis)
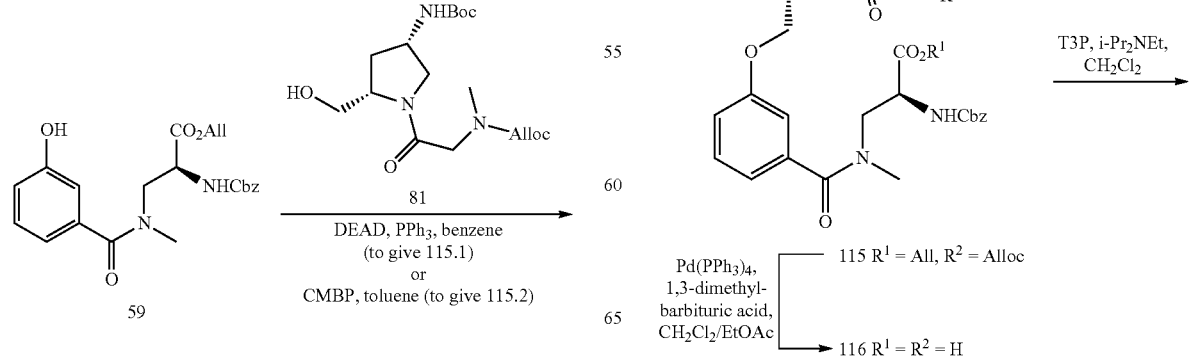

475
-continued
476
-continued
Scheme 18
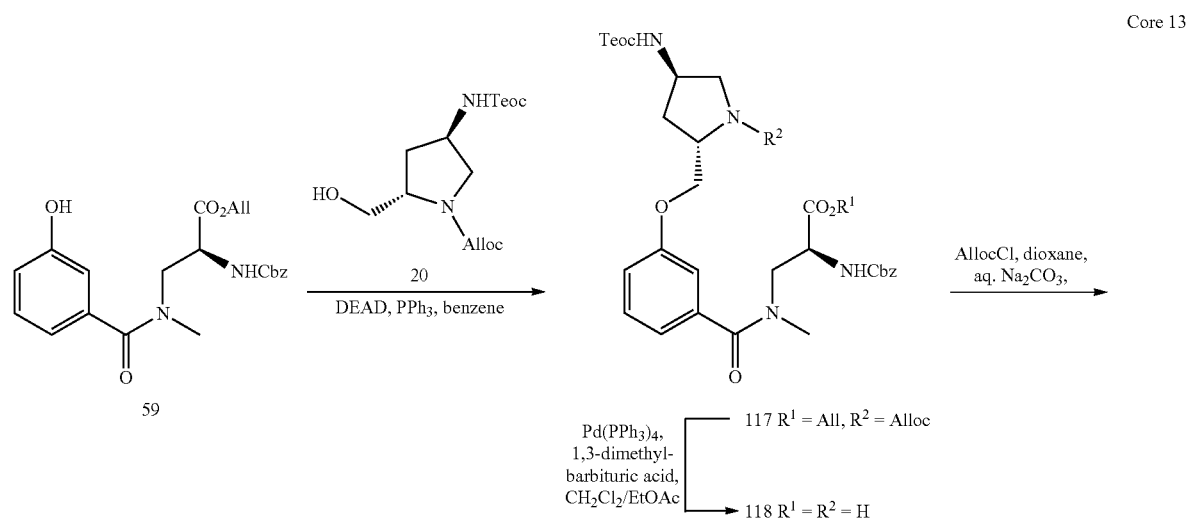
Core 13
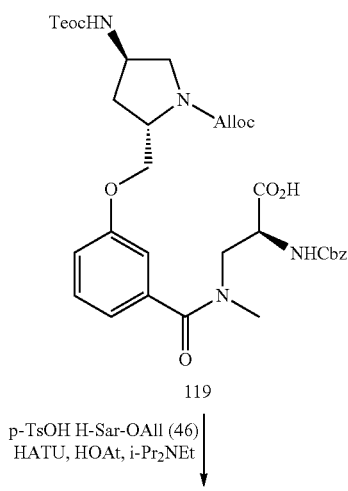

477
478
-continued
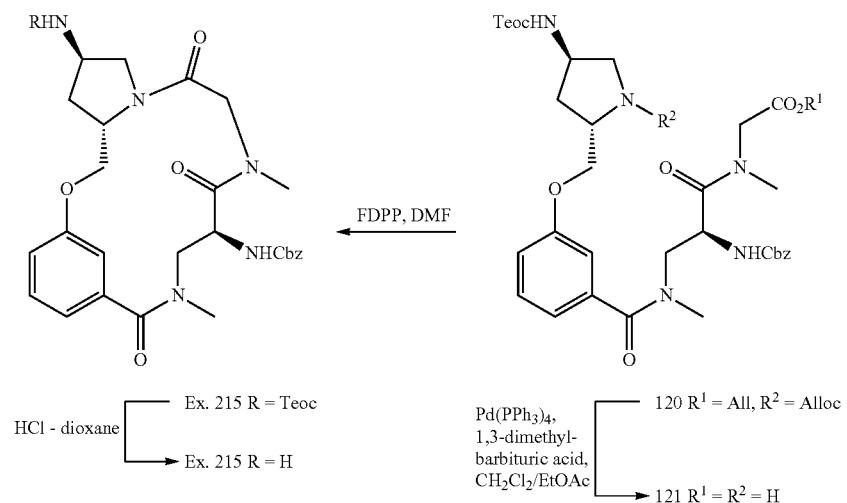
Scheme 19
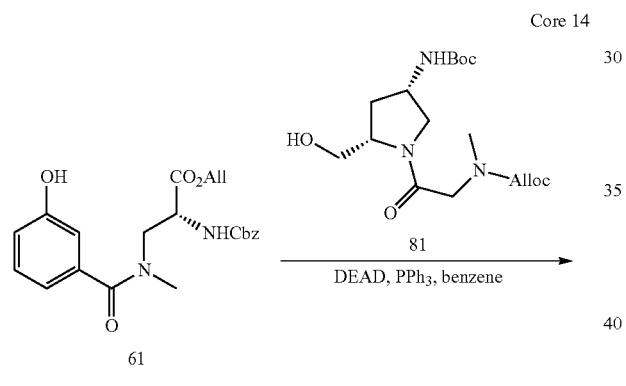
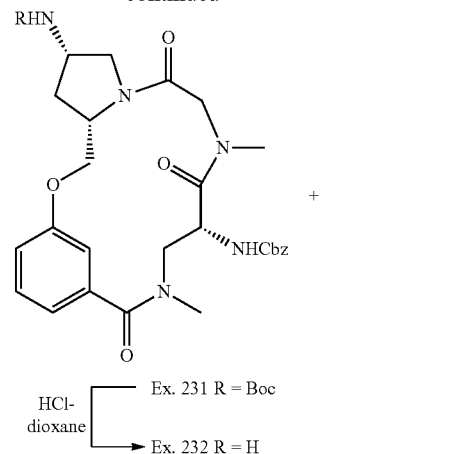
-continued
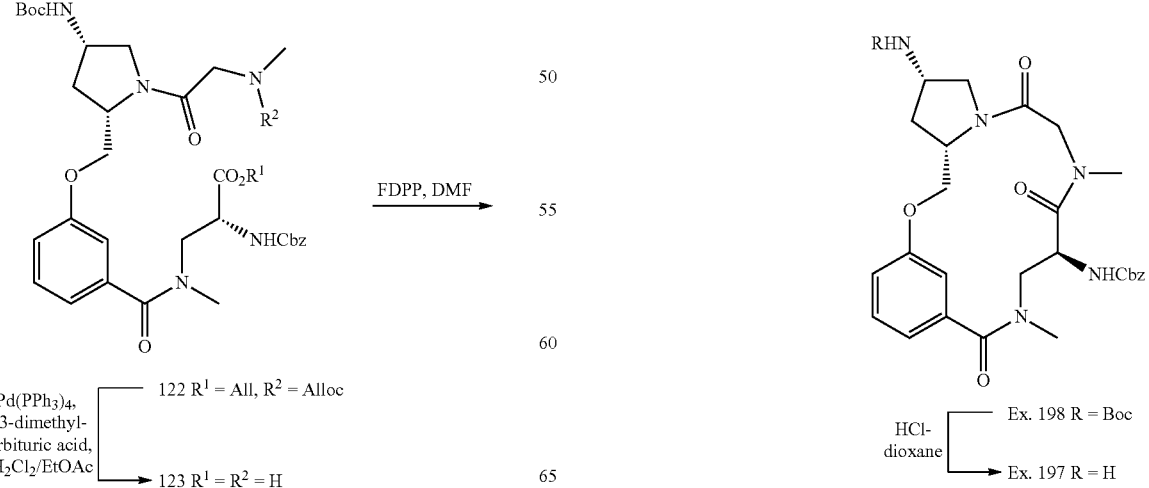

Scheme 20
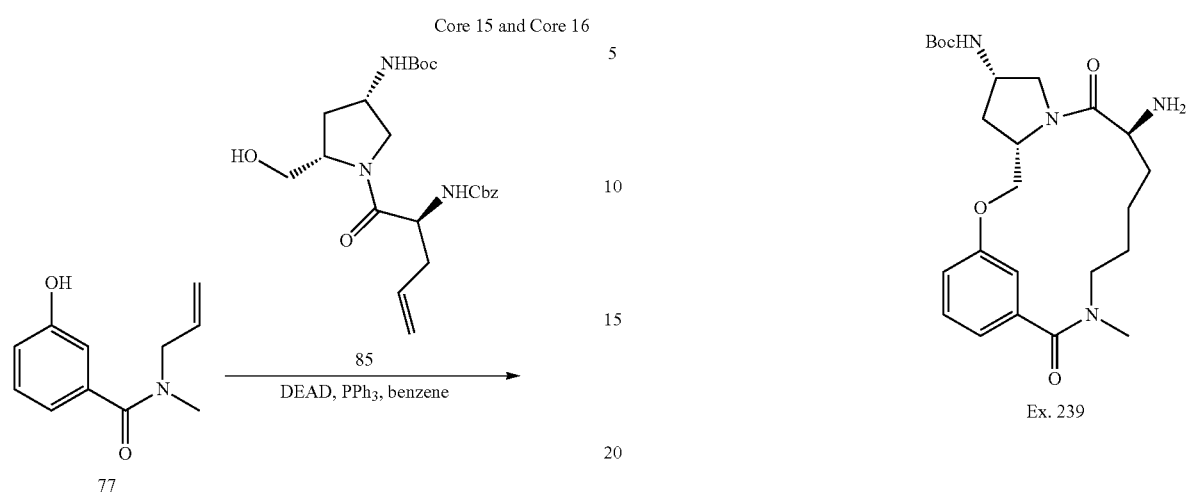
Scheme 21
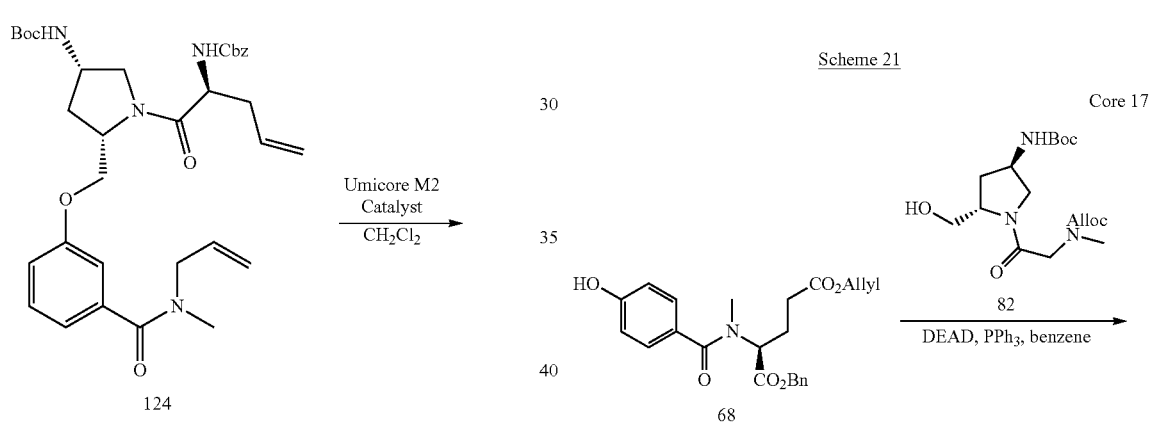

481
-continued
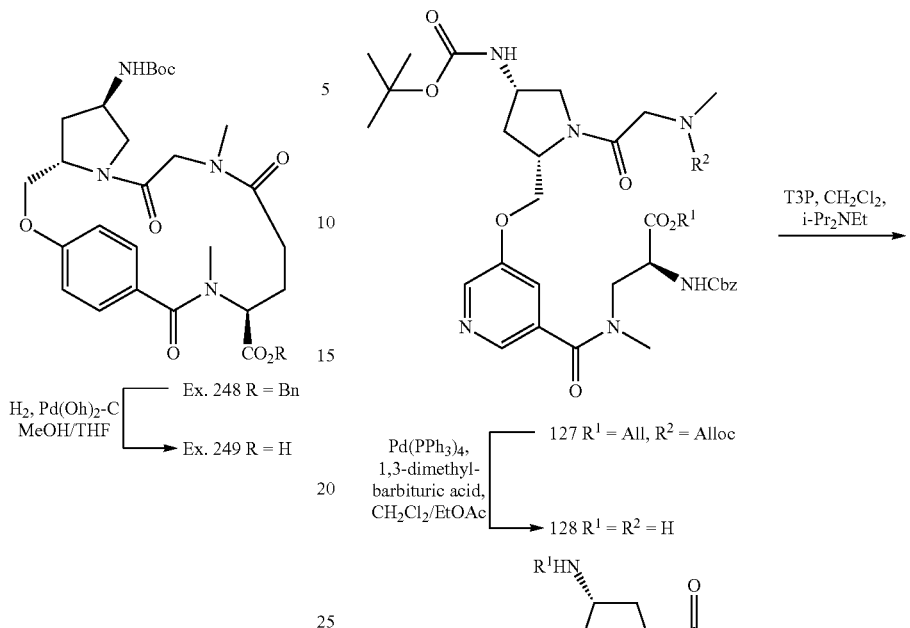
Scheme 22
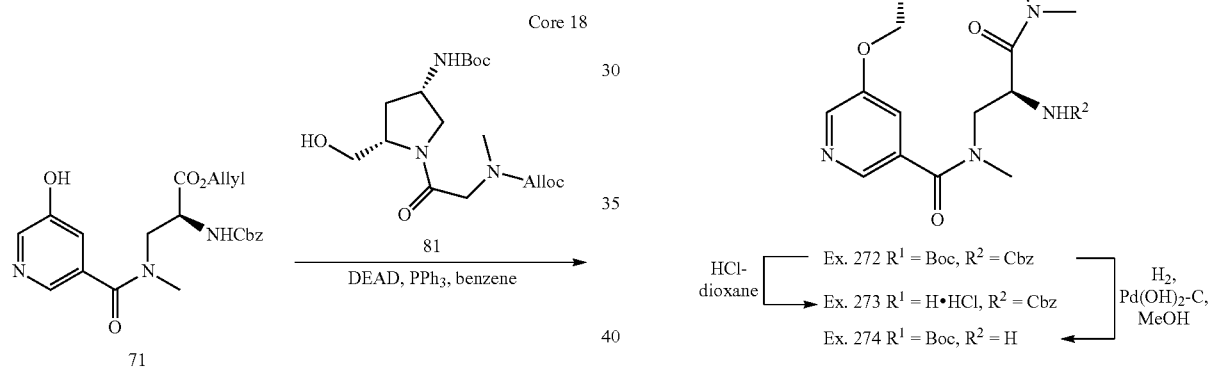
Scheme 23
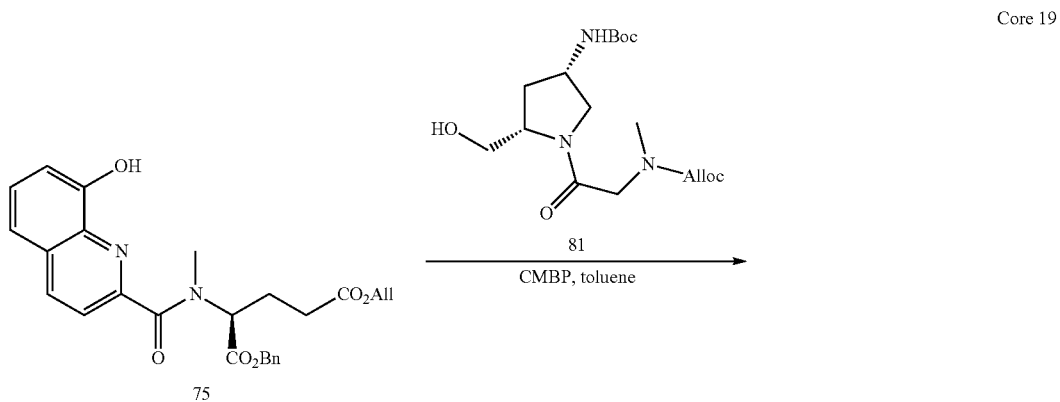

-continued
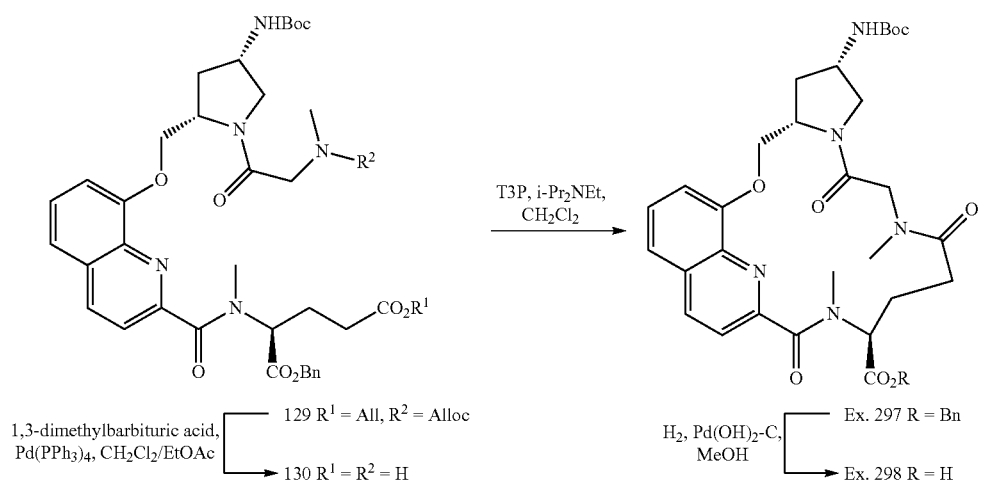
Scheme 24
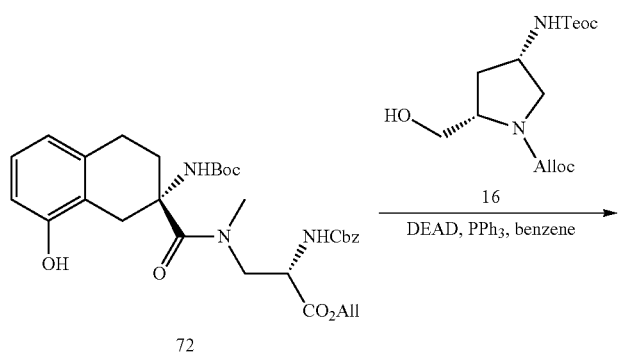
Core 20
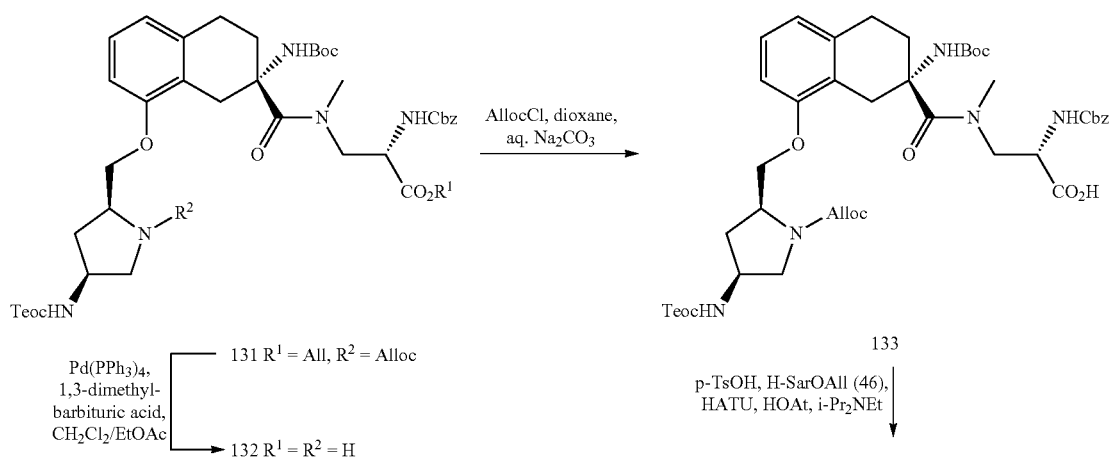

485
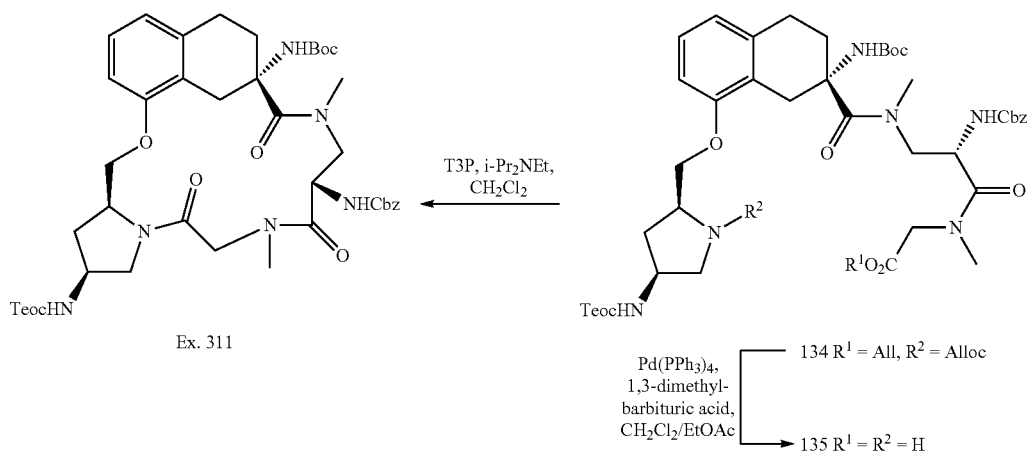
Ex. 311
486
-continued
134 R¹ = All, R² = Alloc
Pd(PPh₃)₄, 1,3-dimethyl-barbituric acid, CH₂Cl₂/EtOAc
135 R¹ = R² = H
-continued
Ex. 312 X = S
m-CPBA, CH₂Cl₂
Ex. 313 X = SO₂
Scheme 25
Core 21
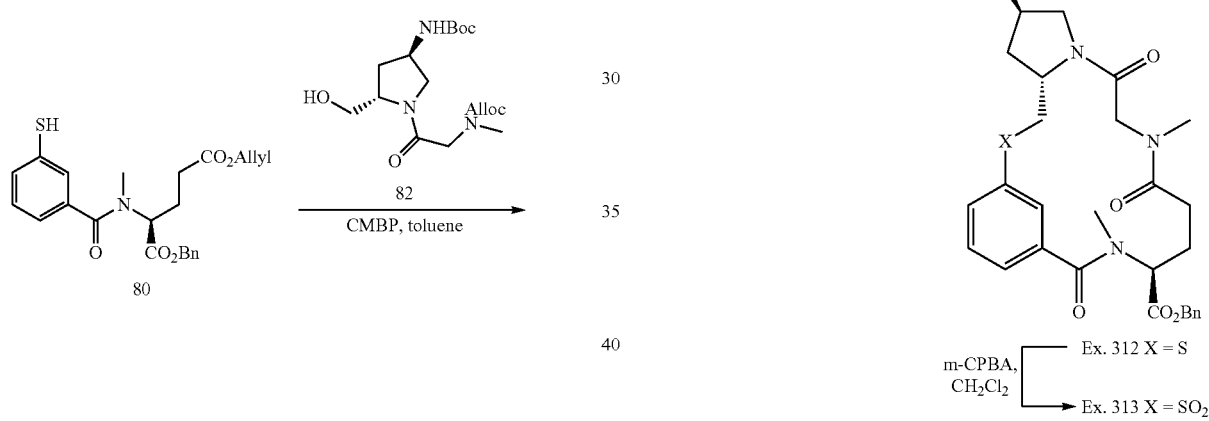
80
82
CMBP, toluene
T3P, i-Pr₂NEt, CH₂Cl₂
136 R¹ = All, R² = Alloc
Pd(PPh₃)₄, 1,3-dimethyl-barbituric acid, CH₂Cl₂/EtOAc
137 R¹ = R² = H
Scheme 26
Structures of Examples
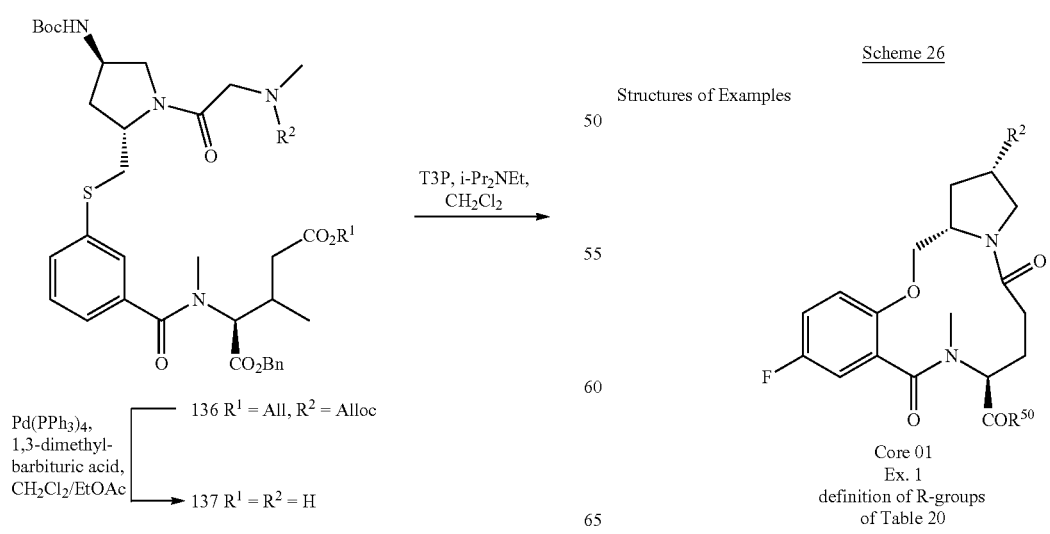
Core 01
Ex. 1
definition of R-groups
of Table 20

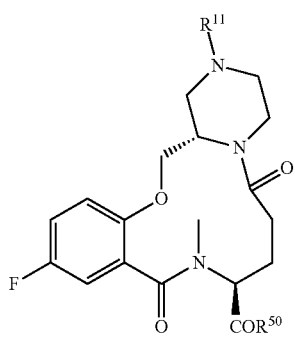
Core 02
Ex. 2
definition of R-groups
of Table 20
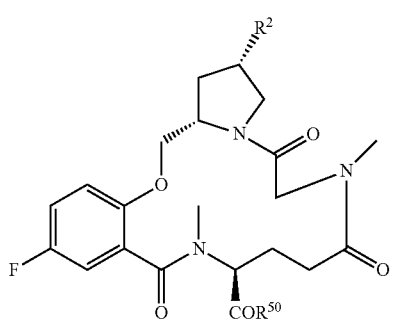
Core 03
Ex. 3 - Ex. 55
definition of R-groups
of Table 21
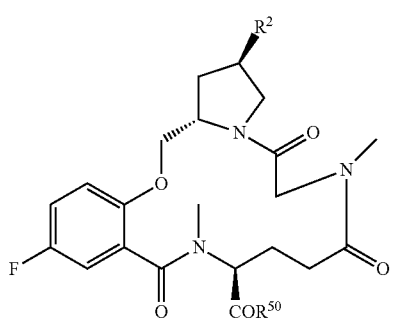
Core 04
Ex. 56 - Ex. 84
definition of R-groups
of Table 22
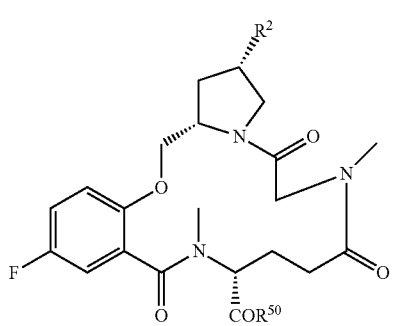
Core 05
Ex. 85 - Ex. 103
definition of R-groups
of Table 23
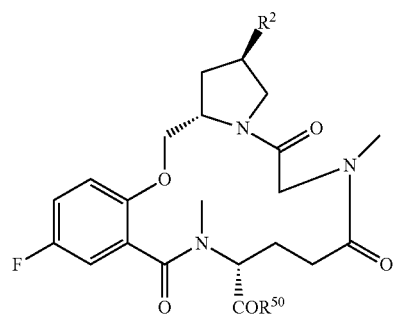
Core 06
Ex. 104 - Ex. 114
definition of R-groups
of Table 24
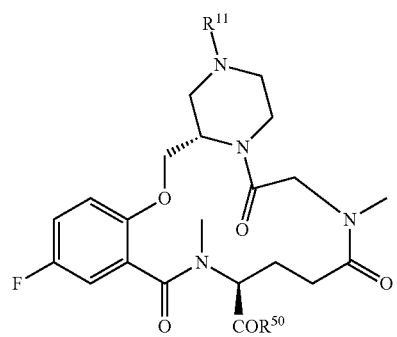
Core 07
Ex. 115 - Ex. 131
definition of R-groups
of Table 25
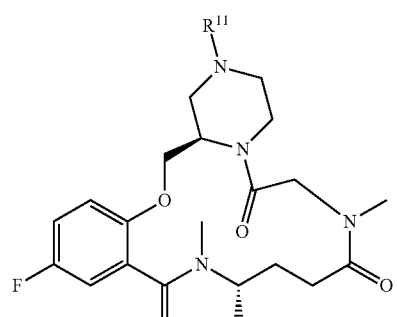
Core 08
Ex. 132 - Ex. 141
definition of R-groups
of Table 26
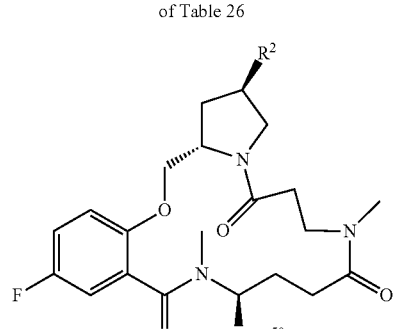
Core 09
Ex. 142 - Ex. 163
definition of R-groups
of Table 27

Structures of Examples

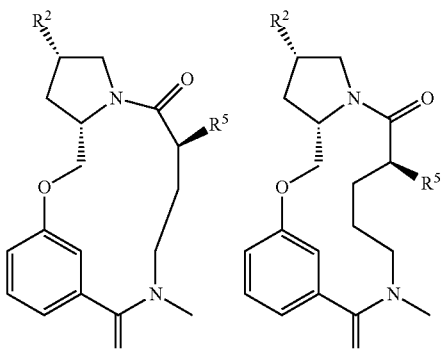

Core 10
Ex. 164 - Ex. 180
definition of R-groups
of Table 28

Core 11
Ex. 181 - Ex. 1950
definition of R-groups
of Table 29

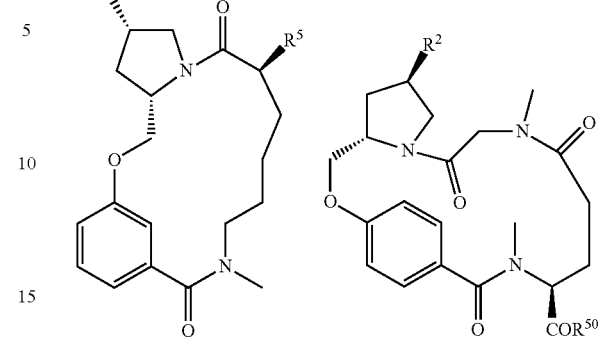

Core 16
Ex. 239 - Ex. 247
definition of R-groups
of Table 33

Core 17
Ex. 248 - Ex. 271
definition of R-groups
of Table 34

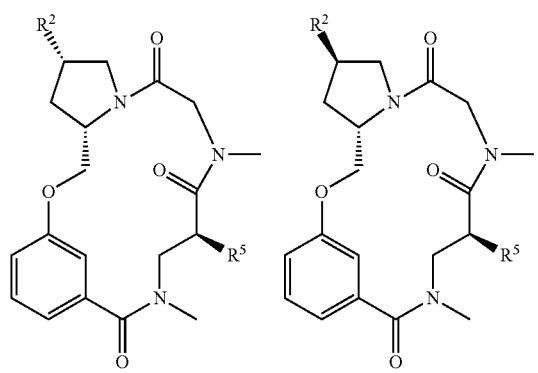

Core 12
Ex. 196 - Ex. 214
definition of R-groups
of Table 30

Core 13
Ex. 215 - Ex. 230
definition of R-groups
of Table 31

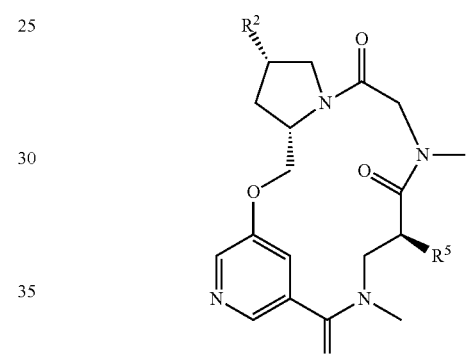

Core 18
Ex. 272 - Ex. 296
definition of R-groups
of Table 35

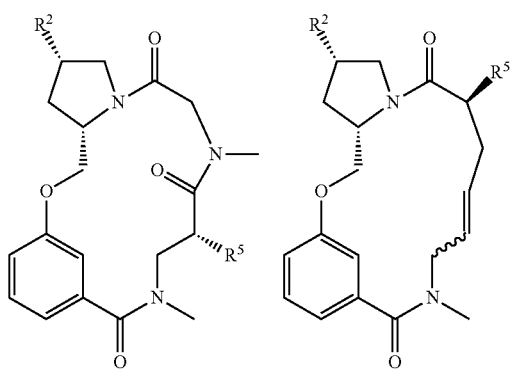

Core 14
Ex. 231 - Ex. 237
definition of R-groups
of Table 32

Core 15
Ex. 238
definition of R-groups
of Table 33

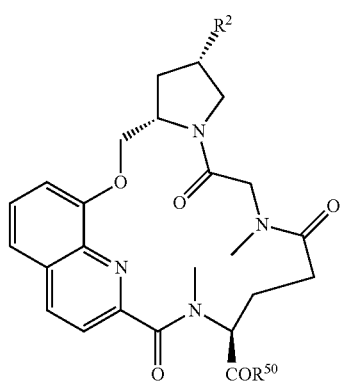

Core 19
Ex. 297 - Ex. 310
definition of R-groups
of Table 36

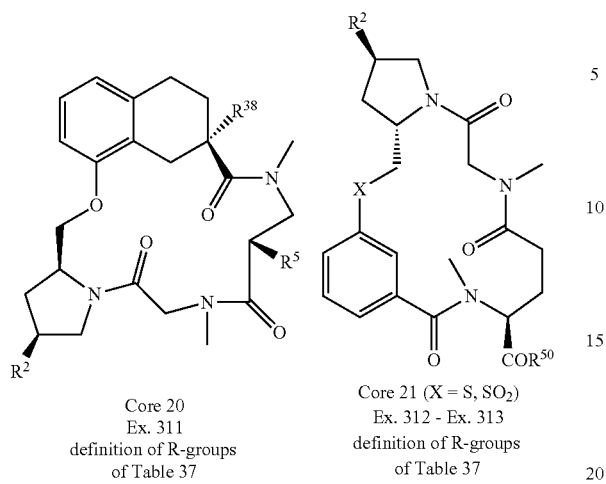
Core 20
Ex. 311
definition of R-groups
of Table 37
Core 21 (X = S, SO$_2$)
Ex. 312 - Ex. 313
definition of R-groups
of Table 37
Scheme 27
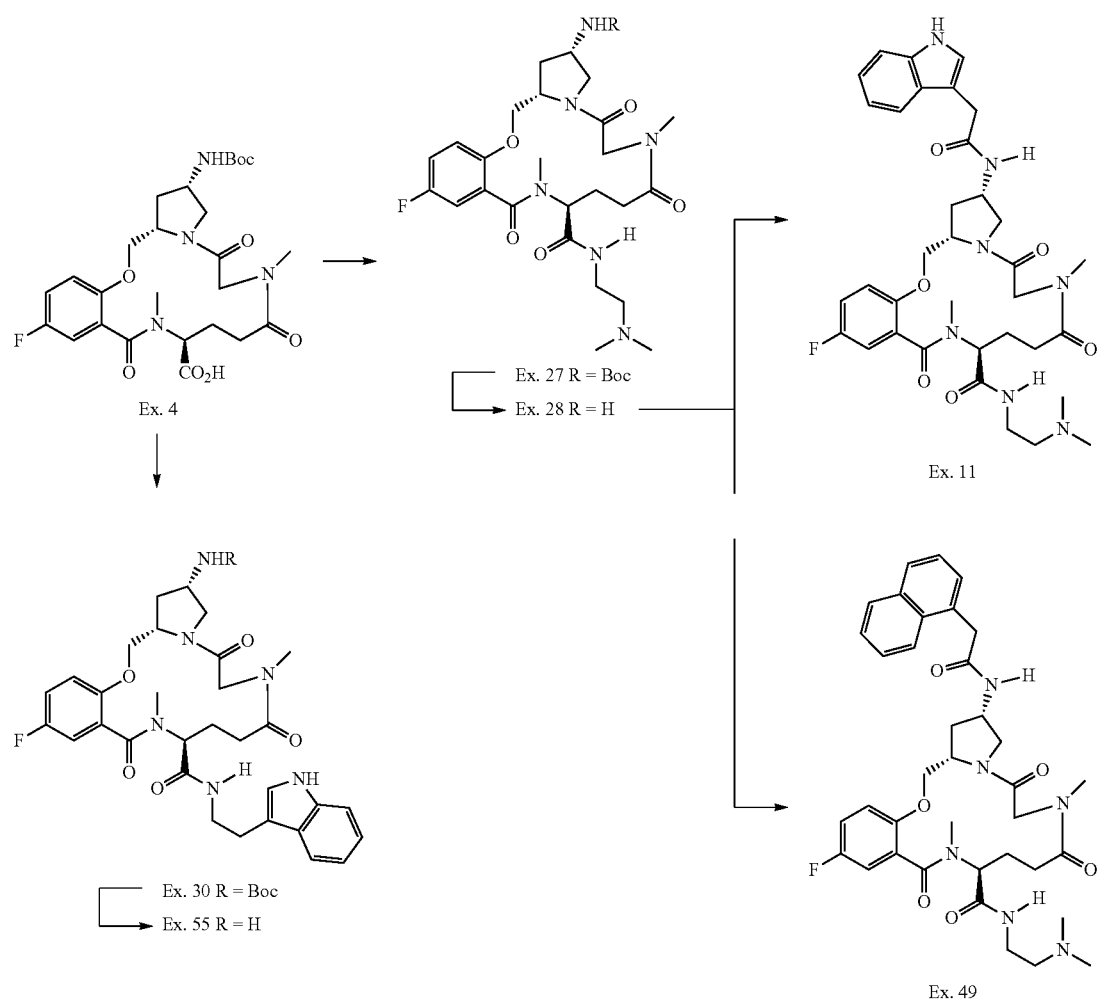

Core 03; Selected Final Products
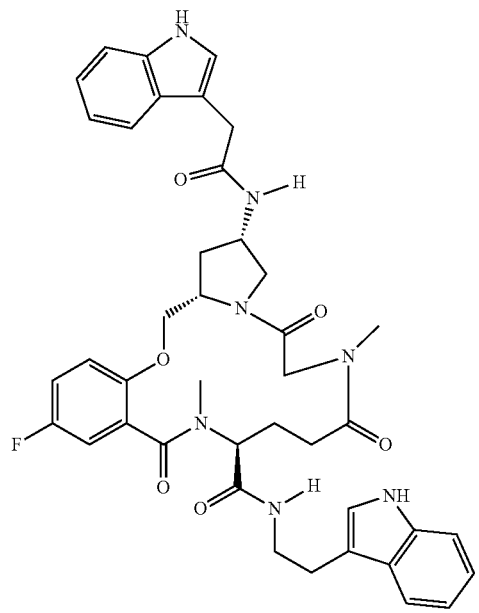
Ex. 12
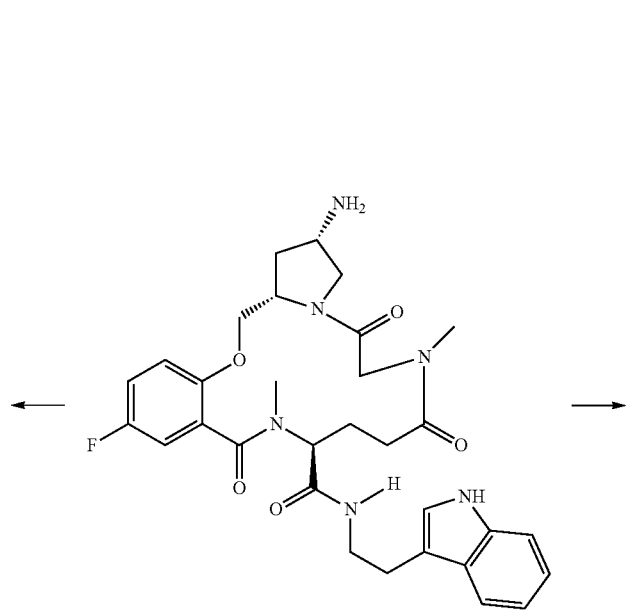
Ex. 55
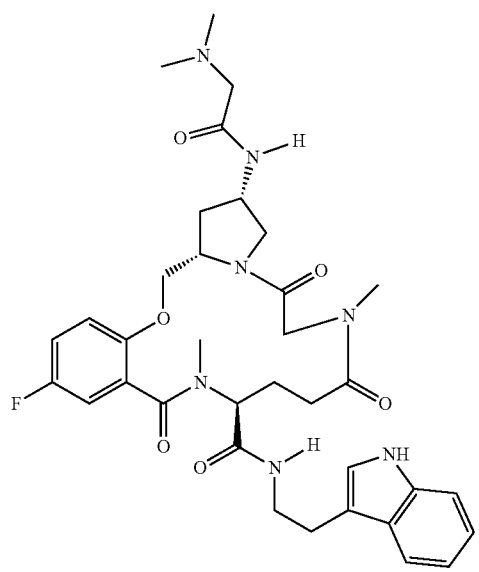
Ex. 16

-continued
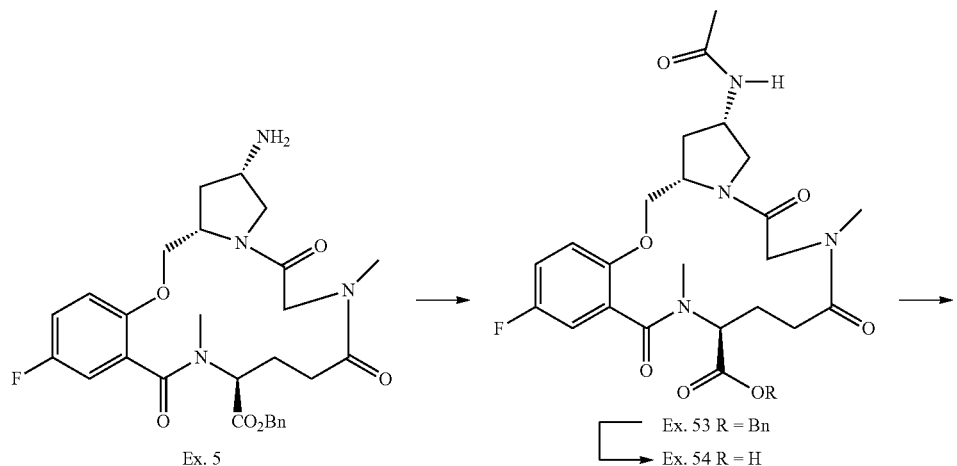
Ex. 5
Ex. 53 R = Bn
Ex. 54 R = H
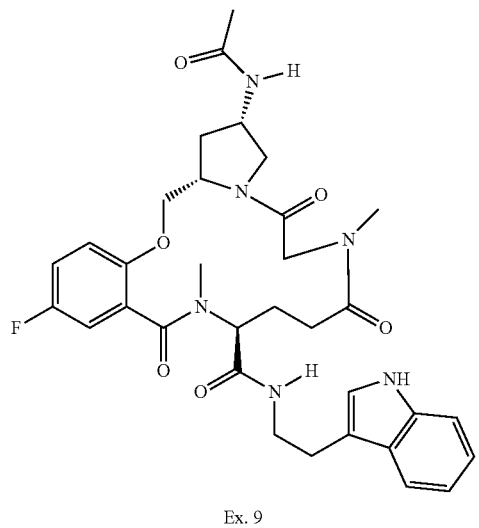
Ex. 9
-continued
Scheme 28
Core 11 and Core 12;
Selected Examples
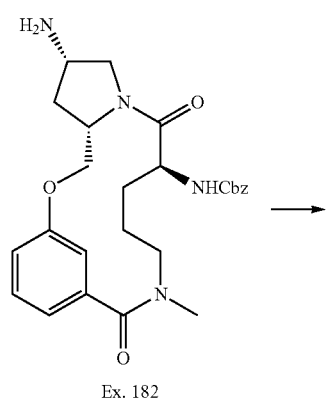
Ex. 182
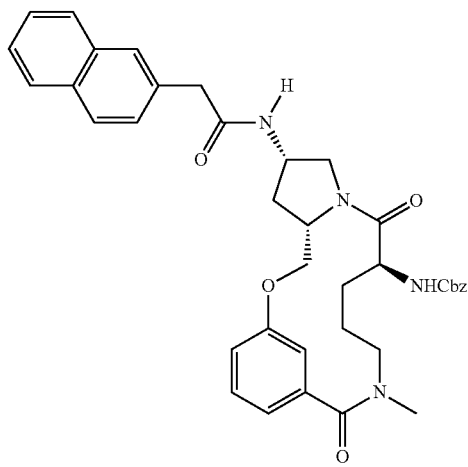
Ex. 184

497
-continued
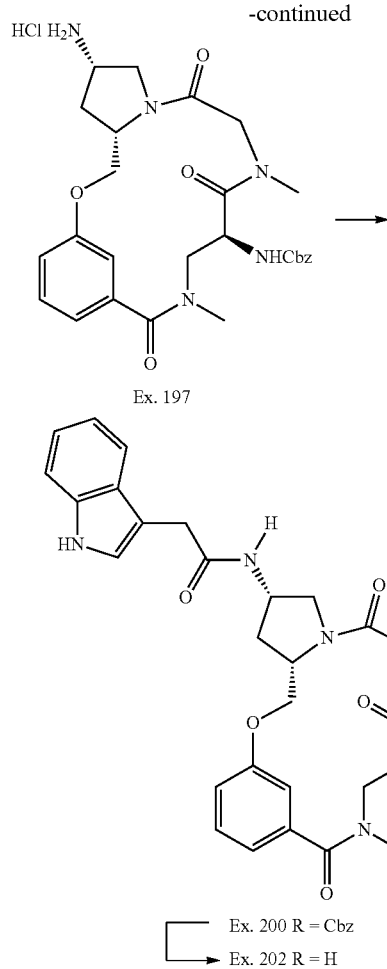
498
-continued
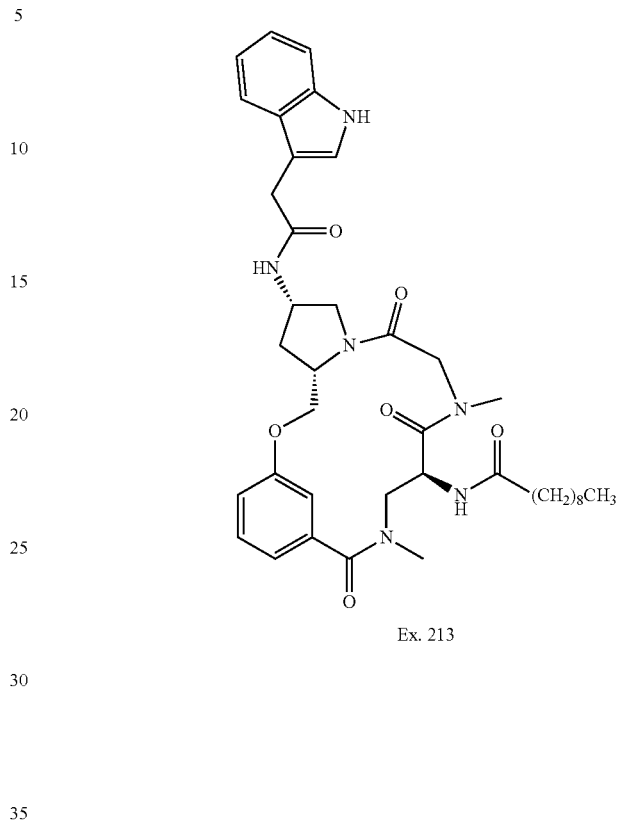
Scheme 29
Core 11;
Derivatization on Solid Support
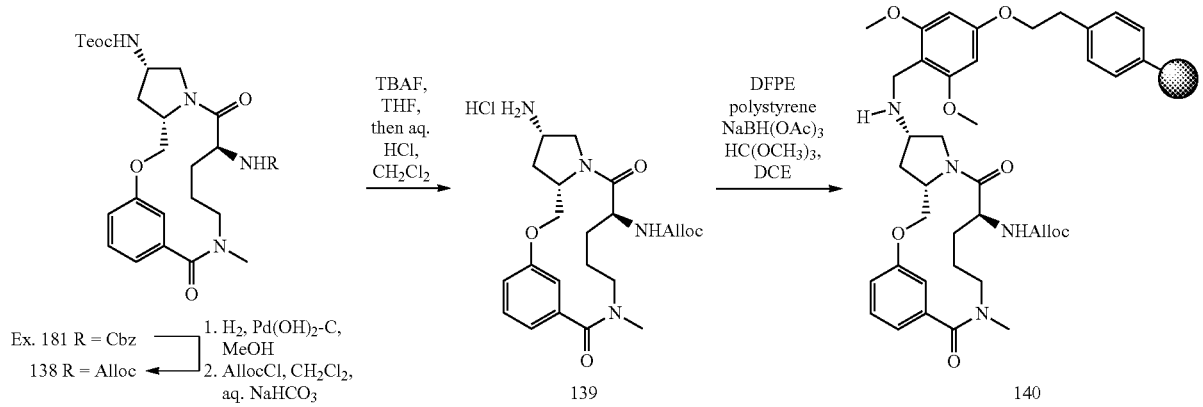

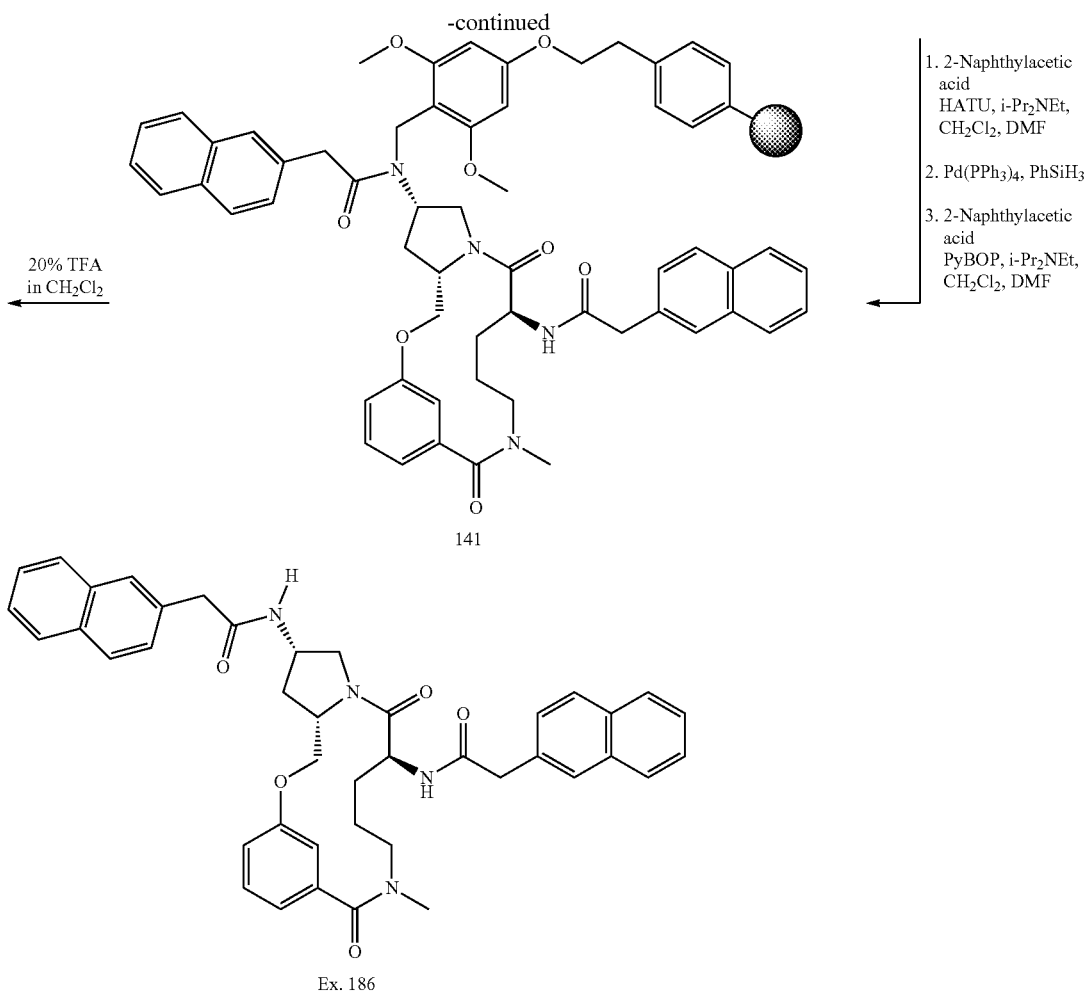

Biological Methods
1. Preparation of the Example Compounds

Example compounds were weighed on a Microbalance (Mettler MX5) and dissolved in 100% DMSO to a final concentration of 2.5 mM for $Ca^{2+}$ assays.

Example compounds were dissolved in $DMSO/H_2O$ 90:10 to a final concentration of 10 mM for plasma stability determination and metabolic stability determination.

2. $Ca^{2+}$ Assays: GPCR Assays for Motilin Receptor, Prostaglandin F (FP) Receptor and 5-Hydroxytryptamine 2B ($5-HT_{2B}$) Receptor Assays were performed using a FLIPR Tetra (Molecular Devices); the data analysis and FLIPR Tetra Operating-Software was ScreenWorks version 2 (Molecular Devices).

Dose dependent agonist and antagonist activities were determined. Percentage activation and percentage inhibition values were determined.

Percentage activation was determined upon initial addition of the sample compounds followed by 10 minutes incubation at 25° C. Following compound incubation, reference agonists were added at $EC_{80}$ to determine percentage inhibition.

Reference agonists were purchased from reputable commercial vendors and prepared according to specifications specific to each ligand. All handling of ligands were done to ensure proper control throughout the experiments.

Test compounds were serially diluted with DMSO. Once the appropriate concentrations were attained, the compounds were diluted into assay buffer.

GPCR Assay Buffer:

Assay buffer was a supplemented HBSS (Hank's Balanced Salt Solution). HBSS was supplemented with 20 mM HEPES (4-(2-hydroxyethyl)-piperazin-1-ethansulfonic acid) and 2.5 mM Probenecid (Sigma P8761).

Assay Plate Seeding:

GPCR assays were performed using $Ca^{2+}$ optimized hematopoietic cell lines (rat) with cultures never exceeding 90% confluency. Cells were harvested and seeded (from cultures at less than 90% confluency) at 50000 cells/well for a 96-well plate (12500 cells/well for 384). After seeding, the assay plates were incubated for forty-five (45) minutes at room temperature. After room temperature incubation, the assay plates were incubated at 37° C. 5% $CO_2$ for 24 hours prior to assaying.

Calcium Dye Loading:

All GPCR assays were performed using Fluo-8 $Ca^{2+}$ dye. $Ca^{2+}$ dye was prepared at 1× dye concentration in GPCR assay buffer. After 24 hours of incubation, cells were washed with GPCR assay buffer, then $Ca^{2+}$-dye (100 μL/well) was added. The plates were incubated for 90 minutes at 30° C. 5% $CO_2$ prior to FLIPR assay.

Agonist Assay:

Compound plates were prepared to add 50 µL/well during the agonist assay mode. During the FLIPR assay, 50 µL/well from the compound plate was diluted 3-fold into the existing 100 µL/well from the dye loading step. Therefore all compounds were prepared as 3× the final concentration desired in the assay.

After completion of the first single addition assay run, assay plate was removed from the FLIPR Tetra and placed at 25° C. for seven (7) minutes before antagonist assay.

Antagonist Assay:

Using the $EC_{80}$ values determined during the agonist assay, all pre-incubated sample compound and reference antagonist (if applicable) wells were stimulated with $EC_{80}$ of reference agonist (motilin; prostaglandin F2α).

After the addition of the reference agonist fluorescence was monitored for 180 sec using FLIPR Tetra.

Data Analysis:

From the FLIPR data, with negative control correction enabled, the maximum statistic for each well was exported and percentage activation relative to $E_{max}$ control was calculated.

3. Plasma Stability

Human plasma (3-5 donors, Blutspendedienst SRK, Basel) and CD-1 mouse plasma (mixed gender pool>50 animals, Innovative Research, CA, USA) are both sodium citrate stabilized. The assay is performed in triplicates at 10 µM compound concentration and 37° C. Samples are taken at 0, 15, 60, and 240 minutes and stopped by precipitation with 2 volumes of acetonitrile. The supernatant is collected, evaporated and reconstituted in a 5% acetonitrile solution to be analyzed by HPLC/MS/MS. The resulting peak area counts are expressed in percent of the 0 value and used to determine the endpoint stability in % and the half life T½ in minutes. In order to monitor assay integrity the degradation of propantheline is assayed with every experimental set 4. Metabolic Stability Microsomes from a human 50 donor mixed gender pool and 1:1 mixtures of microsomes from CD-1 mouse single-gender pools are purchased from Celsis (Belgium). The enzymatic reaction is performed in a buffer containing an NADPH regeneration system and microsomes with the following end concentrations: 100 mM potassium phosphate buffer (all from Sigma), 1 mg/mL glucose-6-phosphate, 1 mg/mL β-nicotinamide adenine dinucleotide phosphate (NADP), 0.65 mg/mL magnesium chloride, 0.8 units/mL of glucose-6-phosphate dehydrogenase (prediluted with 5 mM citrate buffer), 10 µM compound and 1 mg/ml microsomal protein. Compounds are incubated at 37° C. in duplicates and samples are taken after 0, 20 and 60 minutes. After acetonitrile precipitation (2 volumes) and HPLC/MS/MS analysis metabolic turnover is expressed in % of the initial 0 minutes value and half life T½ (min) is calculated. Verapamil for human and propranolol for mouse are used as reference and are assayed with every experimental set.

F. P. Guengerich, *Analysis and Characterization of Enzymes*; in: *Principles and Methods of Toxicology*; A. W. Hayes (Ed.) Raven Press: New York, 1989, 777-813.

R. Singh et al., *In vitro metabolism of a potent HIV-protease inhibitor* (141W94) *using rat, monkey and human liver S9, Rapid Commun. Mass Spectrom.* 1996, 10, 1019-1026.

5. Results

The results of the experiments described under 1.-4. (above) are indicated in Table 38 and Table 39 herein below.

TABLE 38

Biological Data

| No | Motilin receptor antagonist activity [% inhibition at 10 µM] | Motilin receptor antagonist activity $IC_{50}$ [µM]] | FP receptor antagonist activity [% inhibition at 10 µM] | FP receptor antagonist activity $IC_{50}$ [µM] | $5\text{-}HT_{2B}$ receptor agonist activity [% activation at 12.5 µM] | $5\text{-}HT_{2B}$ receptor agonist activity $EC_{50}$ [µM] |
|---|---|---|---|---|---|---|
| Ex. 9   | n.d. | n.d.  | n.d. | n.d. | 48   | 12   |
| Ex. 11  | 79   | 0.78  | n.d. | n.d. | n.d. | n.d. |
| Ex. 12  | 95   | 2.7   | 44   | n.d. | 36   | 3.3  |
| Ex. 16  | n.d. | n.d.  | n.d. | n.d. | 45   | 6.6  |
| Ex. 30  | n.d. | n.d.  | n.d. | n.d. | 48   | 3.3  |
| Ex. 49  | 98   | 0.16  | n.d. | n.d. | n.d. | n.d. |
| Ex. 184 | n.d. | n.d.  | 74   | 0.52 | n.d. | n.d. |
| Ex. 200 | n.d. | n.d.  | 38   | 28   | n.d. | n.d. |
| Ex. 213 | n.d. | n.d.  | 78   | 1.7  | n.d. | n.d. | n.d. not determined

TABLE 39

Plasma Stability and Metabolic Stability

| | Plasma Stability | | | | Metabolic Stability | | | |
|---|---|---|---|---|---|---|---|---|
| No | T ½ [min] hum | 240 min hum | T ½ [min] mouse | 240 min mouse | T ½ [min] hum | 60 min hum | T ½ [min] mouse | 60 min mouse |
| Ex. 9  | 240 | 99  | 240 | 93  | 32 | 20  | 60 | 80 |
| Ex. 11 | 240 | 100 | 240 | 100 | 60 | 74  | 60 | 77 |
| Ex. 12 | 240 | 99  | 240 | 100 | 17 | 7   | 35 | 33 |
| Ex. 16 | 240 | 95  | 240 | 97  | 38 | 31  | 60 | 79 |
| Ex. 30 | 240 | 85  | 240 | 100 | 22 | 2   | 60 | 55 |
| Ex. 37 | 240 | 77  | 240 | 100 | 60 | 100 | 60 | 100 |
| Ex. 43 | 240 | 82  | 240 | 89  | 60 | 100 | 60 | 98 |

TABLE 39-continued

Plasma Stability and Metabolic Stability

| | Plasma Stability | | | | Metabolic Stability | | | |
|---|---|---|---|---|---|---|---|---|
| No | T ½ [min] hum | 240 min hum | T ½ [min] mouse | 240 min mouse | T ½ [min] hum | 60 min hum | T ½ [min] mouse | 60 min mouse |
| Ex. 49 | 240 | 83 | 240 | 96 | 24 | 10 | 60 | 83 |
| Ex. 78 | 240 | 65 | 240 | 100 | 60 | 78 | 60 | 100 |
| Ex. 91 | 240 | 96 | 240 | 88 | 60 | 91 | 60 | 95 |
| Ex. 93 | 240 | 100 | 240 | 100 | 24 | 1 | 29 | 15 |
| Ex. 95 | 240 | 100 | 240 | 93 | 60 | 76 | 60 | 94 |
| Ex. 98 | 240 | 100 | 240 | 78 | 60 | 97 | 60 | 100 |
| Ex. 102 | 240 | 65 | 240 | 75 | 23 | 4 | 42 | 39 |
| Ex. 103 | 240 | 97 | 240 | 75 | 35 | 22 | 36 | 25 |
| Ex. 138 | 240 | 89 | 240 | 78 | 60 | 62 | 60 | 99 |
| Ex. 184 | 240 | 66 | 240 | 58 | 15 | 0 | 22 | 0 |
| Ex. 200 | 240 | 91 | 240 | 100 | 27 | 12 | 30 | 26 |
| Ex. 208 | 240 | 98 | 240 | 90 | 60 | 84 | 60 | 100 |
| Ex. 213 | n.d. | n.d. | n.d. | n.d. | 16 | 0 | 17 | 4 |
| Ex. 230 | 240 | 100 | 240 | 95 | 60 | 61 | 60 | 90 |
| Ex. 260 | 240 | 100 | 240 | 100 | 37 | 19 | 60 | 69 |
| Ex. 262 | 240 | 100 | 240 | 93 | 21 | 0 | 23 | 4 |
| Ex. 264 | 240 | 94 | 240 | 88 | n.d. | n.d. | 42 | 32 |
| Ex. 266 | 240 | 92 | 240 | 74 | 60 | 100 | 60 | 98 |
| Ex. 267 | 240 | 75 | 240 | 79 | 60 | 99 | 60 | 100 |
| Ex. 272 | 240 | 95 | 240 | 92 | 60 | 65 | 60 | 81 | n.d. not determined

The invention claimed is:

1. Compounds of the general formula I incorporating the building blocks A, B and C

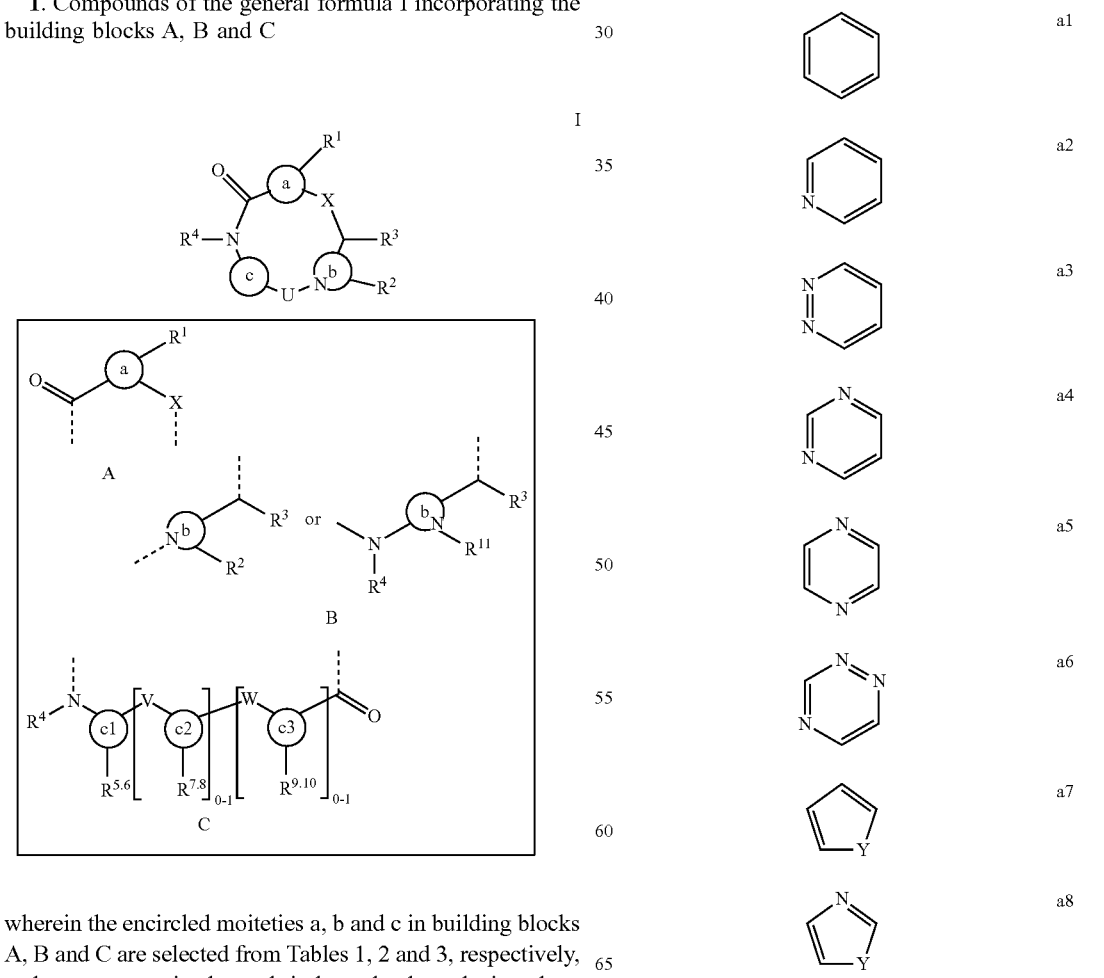

wherein the encircled moieties a, b and c in building blocks A, B and C are selected from Tables 1, 2 and 3, respectively, and are appropriately and independently substituted as defined below:

TABLE 1-continued
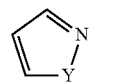 a9
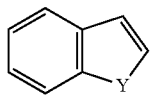 a10
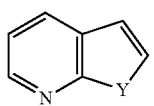 a11
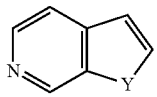 a12
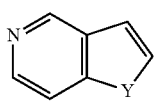 a13
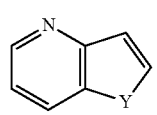 a14
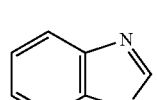 a15
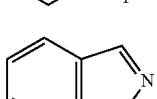 a16
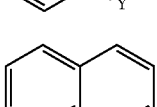 a17
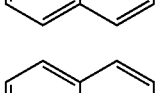 a18
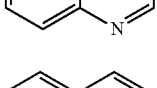 a19
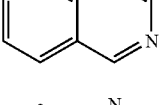 a20
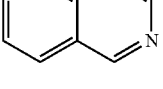 a21
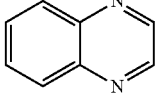 a22
TABLE 1-continued
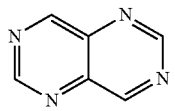 a23
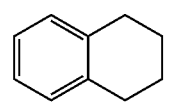 a24
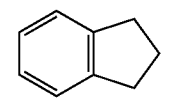 a25
TABLE 2
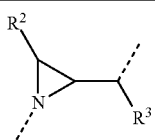 B1 (b1)
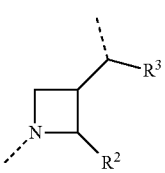 B2 (b2)
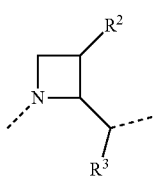 B3 (b2)
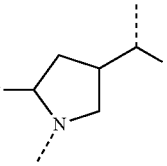 B4 (b3)
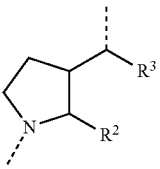 B5 (b3)
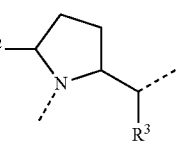 B6 (b3)
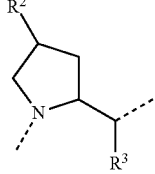 B7 (b3)

TABLE 2-continued

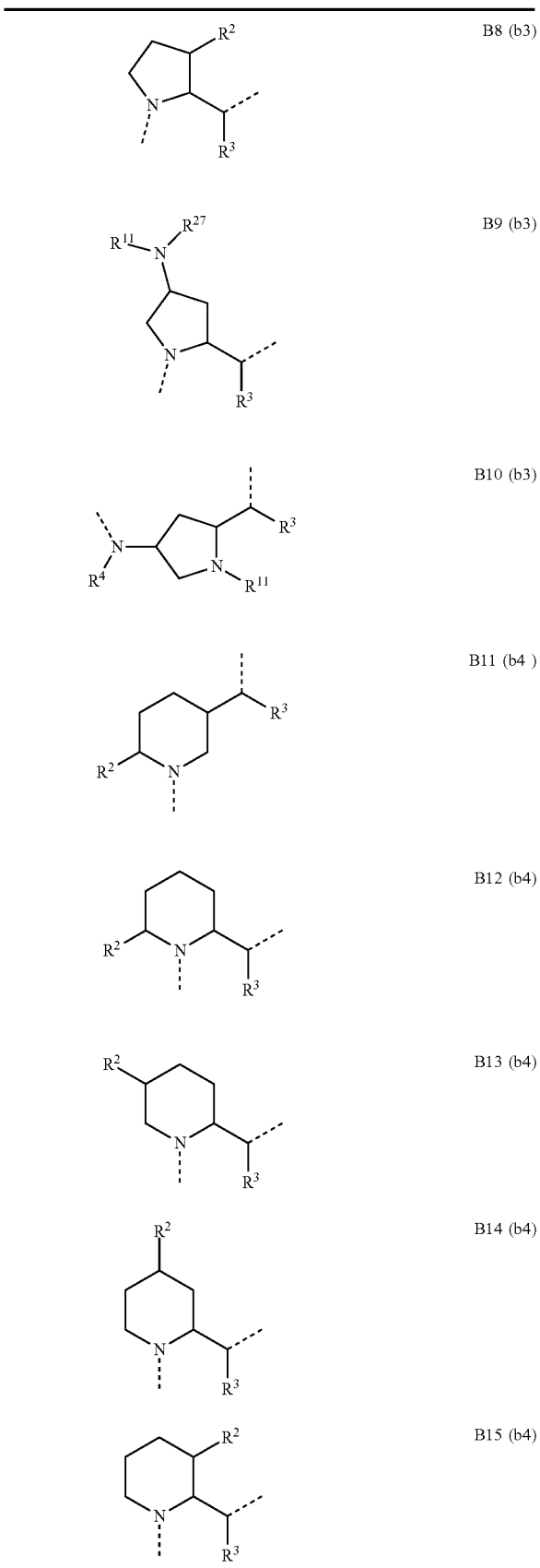

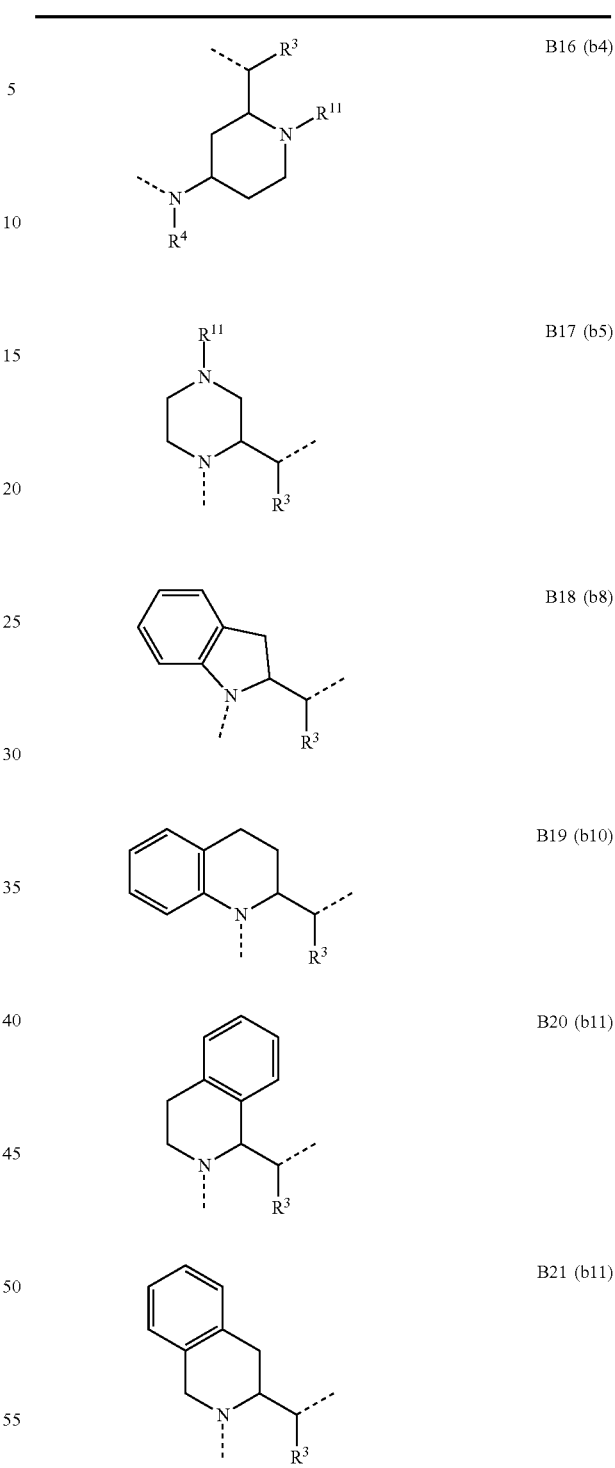

the encircled parts of the bridge subunits c1-c3 representing optionally substitued groups, definitions of c1-c3 being depicted in Table 3, below, each reading from the N-terminus to the C-terminus of the linker C, said linker C being, in the simplest case, constituted by one subunit c1, i.e. c1-1 to c1-6, and for the embodiments consisting of two or three subunits all possible combinations of the subunits c1-c3 and the connectivities U, V and W being possible;

TABLE 3

Scope of Subunits of c1-c3 of the Linker Group C

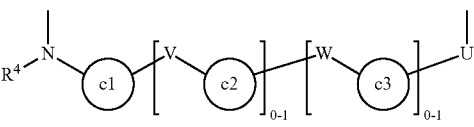

U = 

V, W = 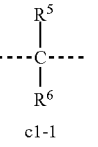

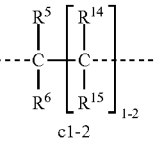

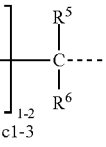

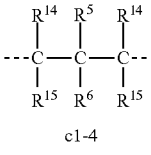

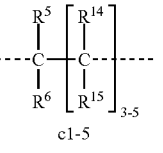

the substituents directly attached to building blocks A, B and C, i.e. $R^1$-$R^{17}$, being defined as follows:

$R^1$ is H; F; Cl; Br; I; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl;

—$(CR^{18}R^{19})_q OR^{20}$; —$(CR^{18}R^{19})_q SR^{20}$; —$(CR^{18}R^{19})_q NR^4R^{11}$;

—$(CR^{18}R^{19})_q OCONR^4R^{11}$; —$(CR^{18}R^{19})_q OCOOR^{21}$; —$(CR^{18}R^{19})_q NR^4COOR^{21}$;

—$(CR^{18}R^{19})_q NR^4COR^{22}$; —$(CR^{18}R^{19})_q NR^4CONR^4R^{11}$; —$(CR^{18}R^{19})_q NR^4SO_2R^{23}$;

—(CR$^{18}$R$^{19}$)$_q$NR$^4$SO$_2$NR$^4$R$^{11}$; —(CR$^{18}$R$^{19}$)$_q$COOR$^{21}$;
—(CR$^{18}$R$^{19}$)$_q$CONR$^4$R$^{11}$;
—(CR$^{18}$R$^{19}$)$_q$SO$_2$NR$^4$R$^{11}$; —(CR$^{18}$R$^{19}$)$_q$PO(OR$^{21}$)$_2$;
—(CR$^{18}$R$^{19}$)$_q$OPO(OR$^{21}$)$_2$;
—(CR$^{18}$R$^{19}$)$_q$COR$^{22}$; —(CR$^{18}$R$^{19}$)$_q$SO$_2$R$^{23}$;
—(CR$^{18}$R$^{19}$)$_q$OSO$_3$R$^{21}$;
—(CR$^{18}$R$^{19}$)$_q$R$^{24}$; —(CR$^{18}$R$^{19}$)$_q$R$^{25}$; or —(CR$^{18}$R$^{19}$)$_q$R$^{26}$;

R$^2$ is H; CF$_3$; alkyl; alkenyl; cycloalkyl; heterocycloalkyl; aryl; heteroaryl; arylalkyl; heteroarylalkyl;
—(CR$^{18}$R$^{19}$)$_q$OR$^{20}$;
—(CR$^{18}$R$^{19}$)$_q$SR$^{20}$; —(CR$^{18}$R1$^9$)$_q$NR$^4$R$^{11}$;
—(CR$^{18}$R$^{19}$)$_q$OCONR$^4$R$^{11}$;
—(CR$^{18}$R$^{19}$)$_q$OCOOR$^{21}$; —(CR$^{18}$R$^{19}$)$_q$NR$^4$COOR$^{21}$;
—(CR$^{18}$R$^{19}$)$_q$NR$^4$COR$^{22}$;
—(CR$^{18}$R$^{19}$)$_q$NR$^4$CONR$^4$R$^{11}$; —(CR$^{18}$R$^{19}$)$_q$NR$^4$SO$_2$R$^{23}$; —(CR$^{18}$R$^{19}$)$_q$NR$^4$SO$_2$NR$^4$R$^{11}$;
—(CR$^{18}$R$^{19}$)$_q$COOR$^{21}$; —(CR$^{18}$R$^{19}$)$_q$CONR$^4$R$^{11}$;
—(CR$^{18}$R$^{19}$)$_q$SO$_2$NR$^4$R$^{11}$;
—(CR$^{18}$R$^{19}$)$_q$R$^{24}$;
—(CR$^{18}$R$^{19}$)$_q$R$^{25}$; or —(CR$^{18}$R$^{19}$)$_q$R$^{26}$;

R$^3$ is H; CF$_3$; alkyl; cycloalkyl; heterocycloalkyl; aryl; heteroaryl; arylalkyl; heteroarylalkyl;

R$^4$ is H; alkyl; alkenyl; cycloalkyl; heterocycloalkyl; aryl; heteroaryl; arylalkyl; or heteroarylalkyl;

R$^5$, R$^7$ and R$^9$ are independently defined as H; F; CF$_3$; alkyl; alkenyl; cycloalkyl; heterocycloalkyl; aryl; heteroaryl; arylalkyl; heteroarylalkyl;
—(CR$^{18}$R$^{19}$)$_s$OR$^{20}$; —(CR$^{18}$R$^{19}$)$_s$SR$^{20}$; —(CR$^{18}$R$^{19}$)$_s$NR$^4$R$^{11}$;
—(CR$^{18}$R$^{19}$)$_s$OCONR$^4$R$^{11}$; —(CR$^{18}$R$^{19}$)$_s$OCOOR$^{21}$;
—(CR$^{18}$R$^{19}$)$_s$NR$^4$COOR$^{21}$;
—(CR$^{18}$R$^{19}$)$_s$NR$^4$COR$^{22}$; —(CR$^{18}$R$^{19}$)$_s$NR$^4$CONR$^4$R$^{11}$;
—(CR$^{18}$R$^{19}$)$_s$NR$^4$SO$_2$R$^{23}$;
—(CR$^{18}$R$^{19}$)$_s$NR$^4$SO$_2$NR$^4$R$^{11}$;
—(CR$^{18}$R$^{19}$)$_q$COOR$^{21}$; —(CR$^{18}$R$^{19}$)$_q$CONR$^4$R$^{11}$;
—(CR$^{18}$R$^{19}$)$_q$SO$_2$NR$^4$R$^{11}$; —(CR$^{18}$R$^{19}$)$_q$PO(OR$^{21}$)$_2$;
—(CR$^{18}$R$^{19}$)$_q$COR$^{22}$; —(CR$^{18}$R$^{19}$)$_q$SO$_2$R$^{23}$;
—(CR$^{18}$R$^{19}$)$_q$R$^{24}$; —(CR$^{18}$R$^{19}$)$_q$R$^{25}$; or —(CR$^{18}$R$^{19}$)$_q$R$^{26}$;

R$^6$, R$^8$ and R$^{10}$ are independently defined as H; F; CF$_3$; alkyl; alkenyl; cycloalkyl; heterocycloalkyl; aryl; heteroaryl; arylalkyl; or heteroarylalkyl;

R$^{11}$ is H; alkyl; alkenyl; cycloalkyl; heterocycloalkyl; aryl; heteroaryl; arylalkyl; heteroarylalkyl;
—(CR$^{18}$R$^{19}$)$_r$OR$^{20}$; —(CR$^{18}$R$^{19}$)$_r$SR$^{20}$; —(CR$^{18}$R$^{19}$)$_r$NR$^4$R$^{27}$;
—(CR$^{18}$R$^{19}$)$_r$OCONR$^4$R$^{27}$; —(CR$^{18}$R$^{19}$)$_r$OCOOR$^{21}$;
—(CR$^{18}$R$^{19}$)$_r$NR$^4$COOR$^{21}$;
—(CR$^{18}$R$^{19}$)$_r$NR$^4$CONR$^4$R$^{27}$; —(CR$^{18}$R$^{19}$)$_r$NR$^4$SO$_2$R$^{23}$; —(CR$^{18}$R$^{19}$)$_r$NR$^4$SO$_2$NR$^4$R$^{27}$;
—(CR$^{18}$R$^{19}$)$_q$COOR$^{21}$; —(CR$^{18}$R$^{19}$)$_q$CONR$^4$R$^{27}$;
—(CR$^{18}$R$^{19}$)$_q$COR$^{22}$;
—(CR$^{18}$R$^{19}$)$_q$SO$_2$R$^{23}$; —(CR$^{18}$R$^{19}$)$_q$SO$_2$NR$^4$R$^{27}$;
—(CR$^{18}$R$^{19}$)$_q$R$^{24}$; —(CR$^{18}$R$^{19}$)$_q$R$^{25}$; or —(CR$^{18}$R$^{19}$)$_q$R$^{26}$;

R$^{12}$ and R$^{13}$ are independently defined as H; or alkyl;
R$^{14}$ and R$^{16}$ are independently defined as H; F; CF$_3$; alkyl; alkenyl; cycloalkyl; heterocycloalkyl; aryl; heteroaryl; arylalkyl; heteroarylalkyl;
—(CR$^{18}$R$^{19}$)$_s$OR$^{20}$; —(CR$^{18}$R$^{19}$)$_s$NR$^4$R$^{11}$; —(CR$^{18}$R$^{19}$)$_s$NR$^4$COOR$^{21}$;
—(CR$^{18}$R$^{19}$)$_s$NR$^4$COR$^{22}$; —(CR$^{18}$R$^{19}$)$_s$NR$^4$CONR$^4$R$^{11}$;
—(CR$^{18}$R$^{19}$)$_s$NR$^4$SO$_2$R$^{23}$;
—(CR$^{18}$R$^{19}$)$_s$NR$^4$SO$_2$NR$^4$R$^{11}$; —(CR$^{18}$R$^{19}$)$_q$COOR$^{21}$;
—(CR$^{18}$R$^{19}$)$_q$CONR$^4$R$^{11}$;
—(CR$^{18}$R$^{19}$)$_q$SO$_2$NR$^4$R$^{11}$; or —(CR$^{18}$R$^{19}$)$_q$COR$^{22}$;

R$^{15}$ and R$^{17}$ are independently defined as H; F; CF$_3$; alkyl; alkenyl; cycloalkyl; heterocycloalkyl; aryl; heteroaryl; arylalkyl; or heteroarylalkyl;

substituents introduced in the sub-definitions of the radical R$^1$-R$^{17}$ being defined as follows:

R$^{18}$ is H; F; CF$_3$; alkyl; alkenyl; cycloalkyl; heterocycloalkyl; aryl; heteroaryl; arylalkyl; heteroarylalkyl;
—(CR$^{29}$R$^{30}$)$_s$OR$^{31}$;
—(CR$^{29}$R$^{30}$)$_s$SR$^{31}$; —(CR$^{29}$R$^{30}$)$_s$NR$^{28}$R$^{31}$;
—(CR$^{29}$R$^{30}$)$_s$OCONR$^{28}$R$^{31}$;
—(CR$^{29}$R$^{30}$)$_s$OCOOR$^{21}$; —(CR$^{29}$R$^{30}$)$_s$NR$^{28}$COOR$^{21}$;
—(CR$^{29}$R$^{30}$)$_s$NR$^{28}$COR$^{31}$; —(CR$^{29}$R$^{30}$)$_s$NR$^{28}$CONR$^{28}$R$^{31}$; —(CR$^{29}$R$^{30}$)$_s$NR$^{28}$SO$_2$R$^{23}$;
—(CR$^{29}$R$^{30}$)$_s$NR$^{28}$SO$_2$NR$^{28}$R$^{31}$; —(CR$^{29}$R$^{30}$)$_q$COOR$^{21}$;
—(CR$^{29}$R$^{30}$)$_q$CONR$^{28}$R$^{31}$;
—(CR$^{29}$R$^{30}$)$_q$SO$_2$NR$^{28}$R$^{31}$; —(CR$^{29}$R$^{30}$)$_q$PO(OR$^{21}$)$_2$;
—(CR$^{29}$R$^{30}$)$_q$COR$^{31}$;
—(CR$^{29}$R$^{30}$)$_q$SO$_2$R$^{23}$;
—(CR$^{29}$R$^{30}$)$_q$R$^{24}$; —(CR$^{29}$R$^{30}$)$_q$R$^{25}$; or —(CR$^{29}$R$^{30}$)$_q$R$^{26}$;

R$^{19}$ is H; CF$_3$; alkyl; alkenyl; cycloalkyl; heterocycloalkyl; aryl; heteroaryl; arylalkyl; heteroarylalkyl;

R$^{20}$ is H; alkyl; alkenyl; cycloalkyl; heterocycloalkyl; aryl; heteroaryl; arylalkyl; heteroarylalkyl;
—(CR$^{29}$R$^{30}$)$_r$OR$^{31}$; —(CR$^{29}$R$^{30}$)$_r$SR$^{31}$;
—(CR$^{29}$R$^{30}$)$_r$NR$^{28}$R$^{31}$; —(CR$^{29}$R$^{30}$)$_r$OCONR$^{28}$R$^{31}$;
—(CR$^{29}$R$^{30}$)$_r$NR$^{28}$COOR$^{21}$;
—(CR$^{29}$R$^{30}$)$_r$NR$^{28}$COR$^{31}$; —(CR$^{29}$R$^{30}$)$_r$NR$^{28}$CONR$^{28}$R$^{31}$; —(CR$^{29}$R$^{30}$)$_r$NR$^{28}$SO$_2$R$^{23}$;
—(CR$^{29}$R$^{30}$)$_r$NR$^{28}$SO$_2$NR$^{28}$R$^{31}$;
—(CR$^{29}$R$^{30}$)$_q$COOR$^{21}$; —(CR$^{29}$R$^{30}$)$_q$CONR$^{28}$R$^{31}$;
—(CR$^{29}$R$^{30}$)$_q$SO$_2$NR$^{28}$R$^{31}$;
—(CR$^{29}$R$^{30}$)$_q$COR$^{31}$; —(CR$^{29}$R$^{30}$)$_q$SO$_2$R$^{23}$;
—(CR$^{29}$R$^{30}$)$_q$R$^{24}$; —(CR$^{29}$R$^{30}$)$_q$R$^{25}$; or —(CR$^{29}$R$^{30}$)$_q$R$^{26}$;

R$^{21}$ is alkyl; alkenyl; cycloalkyl; heterocycloalkyl; aryl; heteroaryl; arylalkyl; or heteroarylalkyl;

R$^{22}$ is alkyl; alkenyl; cycloalkyl; heterocycloalkyl; aryl; heteroaryl; arylalkyl; heteroarylalkyl;
—(CR$^{29}$R$^{30}$)$_s$OR$^{31}$; —(CR$^{29}$R$^{30}$)$_s$SR$^{31}$; —(CR$^{29}$R$^{30}$)$_s$NR$^{28}$R$^{31}$;
—(CR$^{29}$R$^{30}$)$_s$OCONR$^{28}$R$^{31}$; —(CR$^{29}$R$^{30}$)$_s$NR$^{28}$COOR$^{21}$; —(CR$^{29}$R$^{30}$)$_s$NR$^{28}$COR$^{31}$;
—(CR$^{29}$R$^{30}$)$_s$NR$^{28}$CONR$^{28}$R$^{31}$; —(CR$^{29}$R$^{30}$)$_s$NR$^{28}$SO$_2$R$^{23}$;
—(CR$^{29}$R$^{30}$)$_s$NR$^{28}$SO$_2$NR$^{28}$R$^{31}$;
—(CR$^{29}$R$^{30}$)$_s$COOR$^{21}$; —(CR$^{29}$R$^{30}$)$_s$CONR$^{28}$R$^{31}$;
—(CR$^{29}$R$^{30}$)$_s$SO$_2$NR$^{28}$R$^{31}$;
—(CR$^{29}$R$^{30}$)$_t$COR$^{31}$; —(CR$^{29}$R$^{30}$)$_s$SO$_2$R$^{23}$;
—(CR$^{29}$R$^{30}$)$_t$R$^{24}$; —(CR$^{29}$R$^{30}$)$_t$R$^{25}$; or —(CR$^{29}$R$^{30}$)$_t$R$^{26}$;

R$^{23}$ is H; alkyl; alkenyl; cycloalkyl; heterocycloalkyl; aryl; heteroaryl; arylalkyl; heteroarylalkyl; or —(CR$^{32}$R$^{33}$)$_t$R$^{24}$;

R$^{24}$ is aryl, an optionally substituted phenyl group of type C$_6$H$_2$R$^{34}$R$^{35}$R$^{31}$; or a heteroaryl group, one of the groups of formulae H1-H34 (Table 4), below;

TABLE 4

Groups of Formulae H1-H34

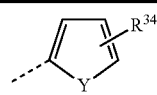

H1

TABLE 4-continued
Groups of Formulae H1-H34
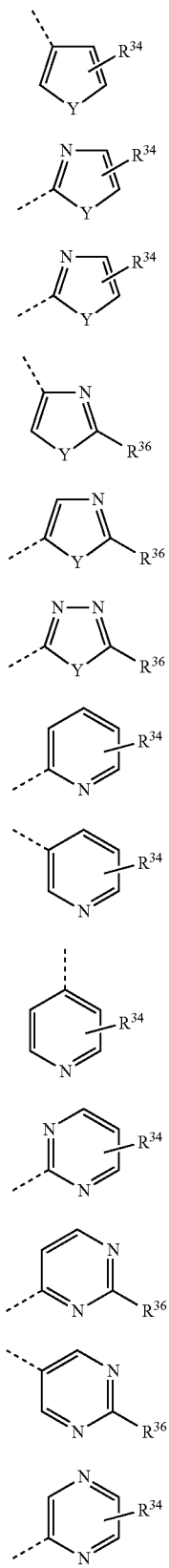
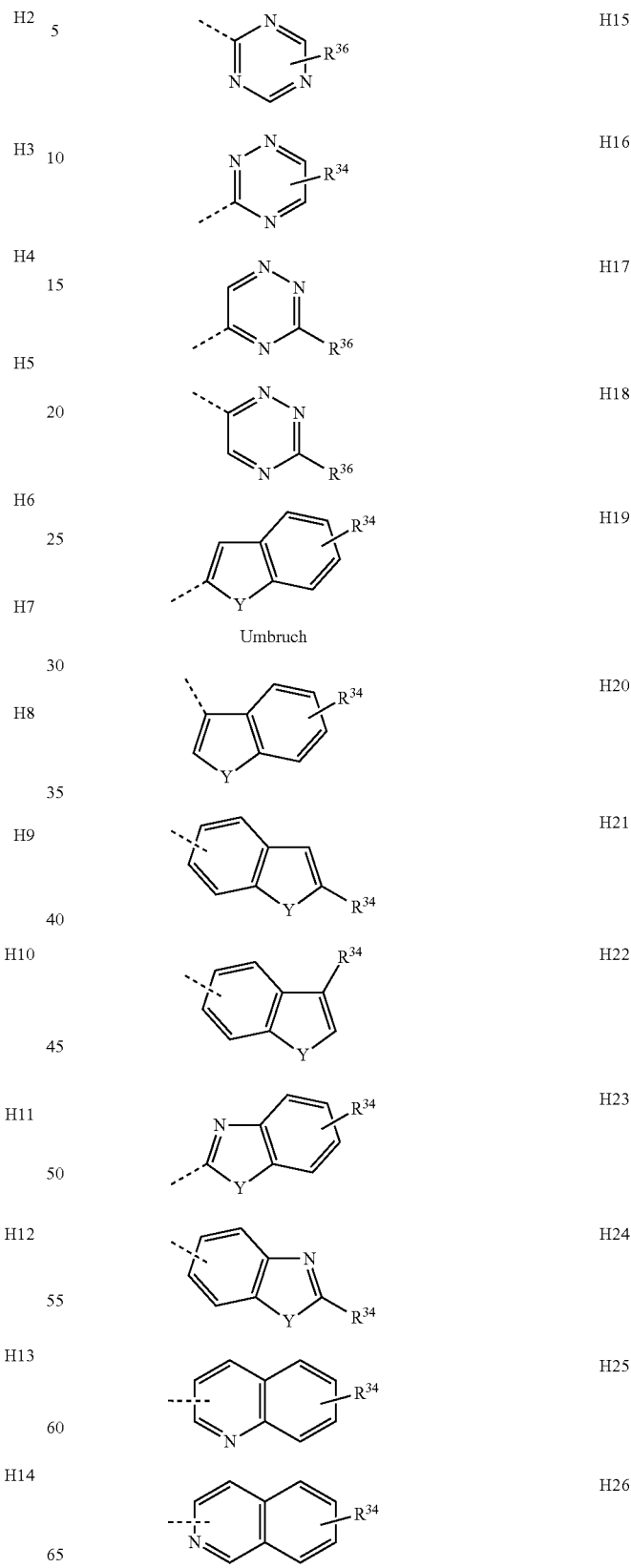

TABLE 4-continued

Groups of Formulae H1-H34

| | |
|---|---|
| H27 | (structure with R³⁴) |
| H28 | (structure with R³⁴) |
| H29 | (structure with R³⁴, R³⁶) |
| H30 | (structure with R³⁴, R³⁶) |
| H31 | (structure with R³⁴) |
| H32 | (structure with R³⁴) |
| H33 | (structure with R³⁴, R³⁶) |
| H34 | (structure with R³⁴) |

$R^{25}$ is one of the groups of formulae H35-H41 as shown in Table 5, below;

TABLE 5

Radicals of formulae H35-H41

| | |
|---|---|
| H35 | (structure with R³⁷, R³⁸) |
| H36 | (structure with R³⁷, R³⁸) |
| H37 | (structure with R³⁷, R³⁸) |
| H38 | (structure with R³⁷, R³⁸) |
| H39 | (structure with R³⁴, R³⁵, R³⁷, R³⁸) |
| H40 | (structure with R³⁴, R³⁵, R³⁷, R³⁸) |
| H41 | (structure with R³⁴, R³⁵, R³⁷, R³⁸) |

$R^{26}$ is one of the groups of formulae H42-H50 as shown in Table 6, below;

TABLE 6

Groups of Formulae H43-H50

| | |
|---|---|
| H42 | (structure with R³⁷, R³⁸) |
| H43 | (structure with R³⁷, R³⁸) |
| H44 | (structure with R³⁷, R³⁸) |

TABLE 6-continued

Groups of Formulae H43-H50

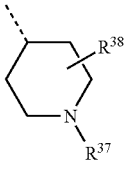
H45

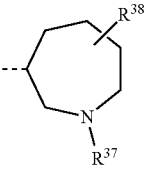
H46

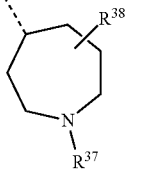
H47

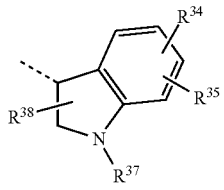
H48

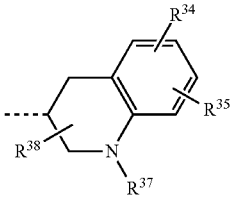
H49

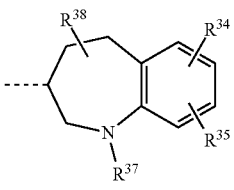
H50

$R^{27}$ is H; alkyl; alkenyl; cycloalkyl; heterocycloalkyl; aryl; heteroaryl; arylalkyl; heteroarylalkyl; or —$(CR^{29}R^{30})R^{24}$;

$R^{28}$ is H; alkyl; alkenyl; cycloalkyl; heterocycloalkyl; aryl; heteroaryl; arylalkyl; heteroarylalkyl;
—$(CR^{32}R^{33})_sOR^{21}$; —$(CR^{32}R^{33})_sNR^{43}R^{42}$; —$(CR^{32}R^{33})_sNR^{42}CONR^{43}R^{42}$;
—$(CR^{32}R^{33})_sNR^{42}COR^{21}$; —$(CR^{32}R^{33})_sNR^{42}SO_2NR^{21}$;
—$(CR^{32}R^{33})_qCOOR^{21}$;
—$(CR^{32}R^{33})_qCOR^{23}$; —$(CR^{32}R^{33})_qSO_2R^{21}$;

$R^{29}$ is H; F; $CF_3$; alkyl; alkenyl; cycloalkyl; heterocycloalkyl; aryl; heteroaryl; arylalkyl; heteroarylalkyl;
—$(CR^{32}R^{33})_sOR^{31}$;
—$(CR^{32}R^{33})_sSR^{31}$; —$(CR^{32}R^{33})_sNR^{28}R^{31}$;
—$(CR^{32}R^{33})_sOCONR^{28}R^{31}$; —$(CR^{32}R^{33})_sO-COOR^{21}$; —$(CR^{32}R^{33})_sNR^{28}COOR^{21}$;
—$(CR^{32}R^{33})_sNR^{28}COR^{31}$; —$(CR^{32}R^{33})_sNR^{28}CONR^{28}R^{31}$; —$(CR^{32}R^{33})_sNR^{28}SO_2R^{23}$;
—$(CR^{32}R^{33})_sNR^{28}SO_2NR^{28}R^{31}$; —$(CR^{32}R^{33})_qCOOR^{21}$;
—$(CR^{32}R^{33})_qCONR^{28}R^{31}$;
—$(CR^{32}R^{33})_sSO_2NR^{28}R^{31}$; —$(CR^{32}R^{33})_2PO(OR^{21})_2$;
—$(CR^{32}R^{33})_qCOR^{31}$;
—$(CR^{32}R^{33})_qSO_2R^{23}$;
—$(CR^{32}R^{33})_qR^{31}$;

$R^{30}$ is H; F; $CF_3$; alkyl; alkenyl; cycloalkyl; heterocycloalkyl; aryl; heteroaryl; arylalkyl; heteroarylalkyl;

$R^{31}$ is H; alkyl; alkenyl; cycloalkyl; heterocycloalkyl; aryl; heteroaryl; arylalkyl; heteroarylalkyl; or one of the groups of formulae H51-H55 as shown in Table 7 below;

TABLE 7

Groups of Formulae H51-H55

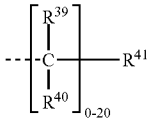
H51

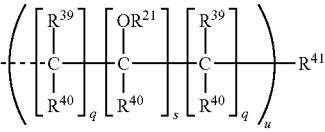
H52

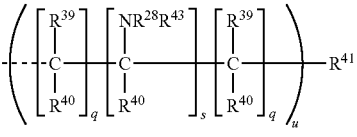
H53

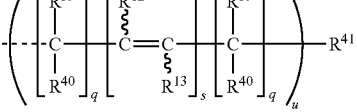
H54

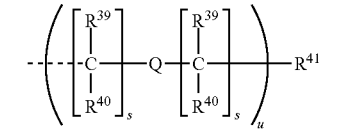
H55

$R^{32}$ and $R^{33}$ are independently defined as H; F; $CF_3$; alkyl; alkenyl; cycloalkyl; heterocycloalkyl; aryl; heteroaryl; arylalkyl; heteroarylalkyl;

$R^{34}$ and $R^{35}$ are independently defined as H; F; Cl; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl; —$(CR^{29}R^{30})_qOR^{31}$;
—$(CR^{29}R^{30})_qSR^{31}$; —$(CR^{29}R^{30})_qNR^{28}R^{31}$;
—$(CR^{29}R^{30})_qOCONR^{28}R^{31}$;
—$(CR^{29}R^{30})_qNR^{28}COOR^{21}$; —$(CR^{29}R^{30})_qNR^{28}COR^{31}$;
—$(CR^{29}R^{30})_qNR^{28}CONR^{28}R^{31}$;
—$(CR^{29}R^{30})_qNR^{28}SO_2R^{23}$; —$(CR^{29}R^{30})_qNR^{28}SO_2NR^{28}R^{31}$;
—$(CR^{29}R^{30})_qCOOR^{21}$;
—$(CR^{29}R^{30})_qCONR^{28}R^{31}$; —$(CR^{29}R^{30})_qSO_2NR^{28}R^{31}$;
—$(CR^{29}R^{30})_qCOR^{31}$;
—$(CR^{29}R^{30})_qSO_2R^{23}$; or —$(CR^{29}R^{30})_qR^{31}$;

$R^{36}$ H; alkyl; alkenyl; alkynyl; cycloalkyl; heterocycloalkyl; aryl; heteroaryl; arylalkyl; heteroarylalkyl; or —$NR^{28}R^{31}$;

$R^{37}$ is H; alkyl; alkenyl; cycloalkyl; heterocycloalkyl; aryl; heteroaryl; arylalkyl; heteroarylalkyl;

—(CR$^{29}$R$^{30}$)$_r$OR$^{31}$;  —(CR$^{29}$R$^{30}$)$_r$SR$^{31}$;  —(CR$^{29}$R$^{30}$)$_r$NR$^{28}$R$^{31}$;  —(CR$^{29}$R$^{30}$)$_r$OCONR$^{28}$R$^{31}$;
—(CR$^{29}$R$^{30}$)$_r$NR$^{28}$COOR$^{21}$;  —(CR$^{29}$R$^{30}$)$_r$NR$^{28}$COR$^{31}$;  —(CR$^{29}$R$^{30}$)$_r$NR$^{28}$CONR$^{28}$R$^{31}$;
—(CR$^{29}$R$^{30}$)$_r$NR$^{28}$SO$_2$R$^{23}$;  —(CR$^{29}$R$^{30}$)$_r$NR$^{28}$SO$_2$NR$^{28}$R$^{31}$;  —(CR$^{29}$R$^{30}$)$_q$COOR$^{21}$;
—(CR$^{29}$R$^{30}$)$_q$CONR$^{28}$R$^{31}$;  —(CR$^{29}$R$^{30}$)$_q$SO$_2$NR$^{28}$R$^{31}$;
—(CR$^{29}$R$^{30}$)$_q$COR$^{31}$;
—(CR$^{29}$R$^{30}$)$_q$SO$_2$R$^{23}$; or —(CR$^{29}$R$^{30}$)$_q$R$^{31}$;

R$^{38}$ is H; alkyl; alkenyl; cycloalkyl; heterocycloalkyl; aryl; heteroaryl; arylalkyl; heteroarylalkyl; —(CR$^{29}$R$^{30}$)$_q$OR$^{31}$; —(CR$^{29}$R$^{30}$)$_q$SR$^{31}$; —(CR$^{29}$R$^{30}$)$_q$NR$^{28}$R$^{31}$;
—(CR$^{29}$R$^{30}$)$_q$NR$^{28}$COOR$^{21}$;  —(CR$^{29}$R$^{30}$)$_q$NR$^{28}$COR$^{31}$;
—(CR$^{29}$R$^{30}$)$_q$NR$^{28}$CONR$^{28}$R$^{31}$;
—(CR$^{29}$R$^{30}$)$_q$COOR$^{21}$;  —(CR$^{29}$R$^{30}$)$_q$CONR$^{28}$R$^{31}$;
—(CR$^{29}$R$^{30}$)$_q$COR$^{31}$; or
—(CR$^{29}$R$^{30}$)$_q$R$^{31}$;

R$^{39}$ is H; F; CF$_3$; alkyl; alkenyl; cycloalkyl; heterocycloalkyl; aryl; heteroaryl; arylalkyl; heteroarylalkyl; —(CR$^{32}$R$^{33}$)$_u$OR$^{21}$;
—(CR$^{32}$R$^{33}$)$_u$NR$^{28}$R$^{43}$;  —(CR$^{32}$R$^{33}$)$_t$COOR$^{21}$; or —(CR$^{32}$R$^{33}$)$_t$CONR$^{28}$R$^{43}$;

R$^{40}$ is H; F; CF$_3$; alkyl; alkenyl; cycloalkyl; heterocycloalkyl; aryl; heteroaryl; arylalkyl; heteroarylalkyl; —(CR$^{32}$R$^{33}$)$_u$OR$^{21}$;
—(CR$^{32}$R$^{33}$)$_u$NR$^{28}$R$^{43}$;  —(CR$^{32}$R$^{33}$)$_t$COOR$^{21}$; or —(CR$^{32}$R$^{33}$)$_t$CONR$^{28}$R$^{43}$;

R$^{41}$ is H; CF$_3$; alkyl; alkenyl; cycloalkyl; heterocycloalkyl; aryl; heteroaryl; arylalkyl; heteroarylalkyl; —OR$^{21}$;  —NR$^{28}$R$^{43}$;  —NR$^{28}$COR$^{23}$; —NR$^{28}$COOR$^{21}$;
—NR$^{28}$SO$_2$R$^{23}$;  —NR$^{28}$CONR$^{28}$R$^{43}$;  —COOR$^{21}$; —CONR$^{28}$R$^{43}$; —C(=NR$^{43}$)NR$^{28}$N$^{43}$;
—NR$^{28}$C(=NR$^{43}$)NR$^{28}$N$^{43}$; or one of the groups of formulae H56-H110 as shown in Table 8 below;

TABLE 8

Groups of Formulae H56-H110

| | |
|---|---|
| H56 | structure with R$^{44}$, R$^{45}$, R$^{46}$ |
| H57 | structure with R$^{44}$, R$^{45}$ |
| H58 | structure with R$^{44}$, R$^{45}$ |
| H59 | structure with R$^{44}$, R$^{45}$ |

TABLE 8-continued

Groups of Formulae H56-H110

| | |
|---|---|
| H60 | structure with R$^{44}$ |
| H61 | structure with R$^{44}$ |
| H62 | structure with R$^{44}$ |
| H63 | structure with R$^{44}$ |
| H64 | structure with R$^{44}$ |
| H65 | structure with R$^{44}$ |
| H66 | structure with R$^{44}$ |
| H67 | structure with R$^{44}$ |
| H68 | structure with R$^{44}$, Q |
| H69 | structure with R$^{44}$, Q |
| H70 | structure with R$^{44}$ |
| H71 | structure with R$^{44}$, Q |

TABLE 8-continued
Groups of Formulae H56-H110
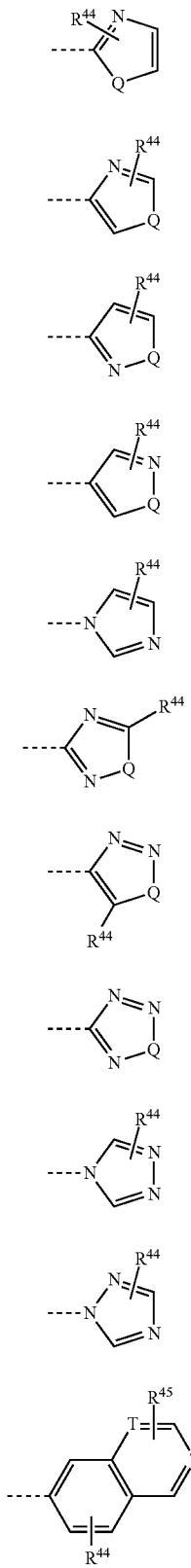
TABLE 8-continued
Groups of Formulae H56-H110
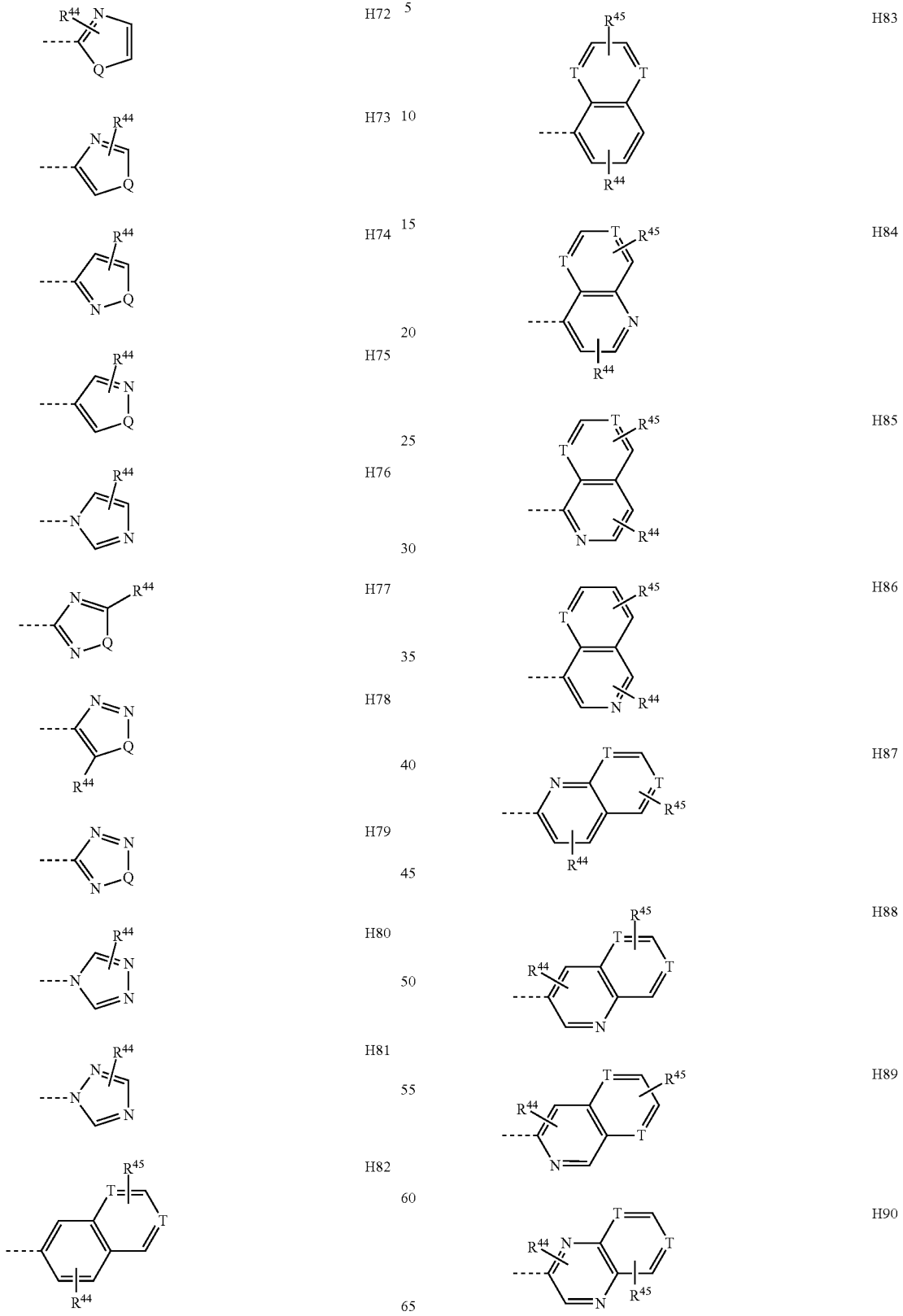

TABLE 8-continued

Groups of Formulae H56-H110

TABLE 8-continued

Groups of Formulae H56-H110

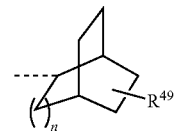
H108

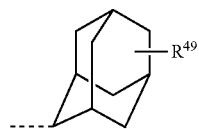
H109

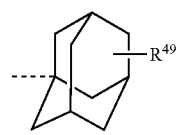
H110

$R^{42}$ is H; alkyl; alkenyl; cycloalkyl; cycloheteroalkyl; aryl; heteroaryl;
—$(CR^{23}R^{33})_sOR^{21}$; —$(CR^{23}R^{33})_sNR^{28}R^{43}$; —$(CR^{23}R^{33})_qCOOR^{21}$; or —$(CR^{23}R^{33})_qCONR^{21}R^{43}$;

$R^{43}$ is H; alkyl; alkenyl; cycloalkyl; heterocycloalkyl; aryl; heteroaryl; arylalkyl; or heteroarylalkyl;

$R^{44}$, $R^{45}$ and $R^{46}$ are independently defined as H; F; $CF_3$; $OCF_3$; $OCHF_2$; $NO_2$; CN; alkyl; alkenyl; alkynyl; cycloalkyl; heterocycloalkyl; aryl; heteroaryl; arylalkyl; heteroarylalkyl; —$OR^{23}$; —$NR^{28}R^{43}$; —$NR^{28}COR^{23}$;
—$NR^{28}SO_2R^{23}$; —$NR^{28}CONR^{28}R^{43}$; —$COR^{23}$; —$SO_2R^{23}$;

$R^{47}$ is H; $CF_3$; alkyl; alkenyl; alkynyl; cycloalkyl; heterocycloalkyl; aryl; heteroaryl; arylalkyl; heteroarylalkyl; —$COOR^{21}$; or —$CONR^{28}R^{43}$;

$R^{48}$ is H; F; $CF_3$; alkyl; alkenyl; cycloalkyl; cycloheteroalkyl; aryl; heteroaryl;
—$(CR^{23}R^{33})_tOR^{21}$; —$(CR^{23}R^{33})_tNR^{28}R^{43}$; —$(CR^{23}R^{33})_t COOR^{21}$;
—$(CR^{23}R^{33})_tCONR^{21}R^{43}$;

$R^{49}$ and $R^{50}$ are independently defined as H; F; $CF_3$; alkyl; alkenyl; cycloalkyl; heterocycloalkyl; aryl; heteroaryl; arylalkyl; heteroarylalkyl;
—$(CR^{32}R^{33})_qOR^{21}$; —$(CR^{32}R^{33})_qNR^{28}R^{43}$; —$(CR^{32}R^{33})_qCOOR^{21}$; or —$(CR^{32}R^{33})_qCONR^{28}R^{43}$;

taken together the following pairs of said substituents can define cyclic structural elements:

($R^4$ and $R^{11}$); ($R^4$ and $R^{27}$); ($R^5$ and $R^6$); ($R^5$ and $R^7$); ($R^5$ and $R^9$); ($R^5$ and $R^{14}$); ($R^5$ and $R^{16}$); ($R^7$ and $R^8$); ($R^7$ and $R^9$); ($R^7$ and $R^{16}$); ($R^9$ and $R^{10}$); ($R^{14}$ and $R^{15}$); ($R^{16}$ and $R^{17}$); ($R^{18}$ and $R^{19}$); ($R^{27}$ and $R^{28}$); ($R^{28}$ and $R^{31}$); ($R^{28}$ and $R^{43}$); ($R^{29}$ and $R^{30}$); ($R^{32}$ and $R^{33}$); ($R^{34}$ and $R^{35}$); ($R^{37}$ and $R^{38}$); ($R^{39}$ and $R^{40}$); ($R^{39}$ and $R^{41}$); ($R^{39}$ and $R^{49}$); ($R^{42}$ and $R^{43}$); ($R^{44}$ and $R^{45}$); or ($R^{44}$ and $R^{46}$) can form optionally substituted cycloalkyl or heterocycloalkyl moieties;

in addition, the structural elements —$NR^4R^{11}$; —$NR^{27}R^{28}$; —$NR^{28}R^{31}$ or —$NR^{28}R^{43}$ can form one of the groups of formulae H111-H118 as shown in Table 9, below;

TABLE 9

Heterocyclic Groups Defined by Linking the Residues of the Disubstituted Amino Groups —$NR^4R^{11}$; —$NR^{27}R^{28}$; —$NR^{28}R^{31}$ or —$NR^{28}R^{43}$.

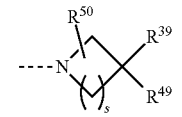
H111

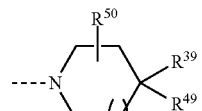
H112

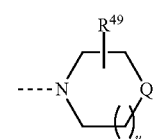
H113

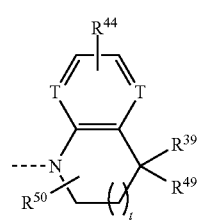
H114

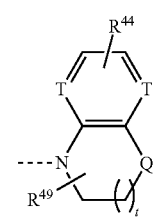
H115

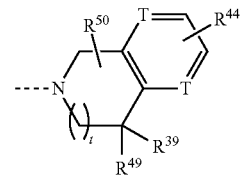
H116

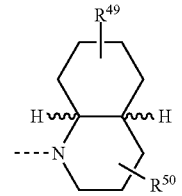
H117

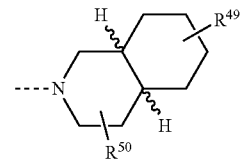
H118 varibale heteroatoms and connector groups in the aforementioned structures being as follows:

Z: O; S; S(=O); S(=O)$_2$; or $NR^{28}$;
Y: O; S; or $NR^{37}$;
X: O; S; S(=O); or S(=O)$_2$;

Q: O; S; or NR$^{28}$;

U, V and W: as defined in Table 3, above;

T: CR$^{46}$ or N;

in case T occurs several times in the same ring structure each T being defined independently of the other; and the indices being defined as follows:

q=0-4; r=2-4; s=1-4; t=0-2; and u=1-2;

all possible stereoismers and pharmaceutical acceptable salts thereof.

2. Compounds according to claim 1 wherein A, B and C are selected from Tables 10, 2 and 12, and are appropriately and independently substituted as defined below:

TABLE 10

| Radicals A1(a1)-A626(a25) | |
|---|---|
| 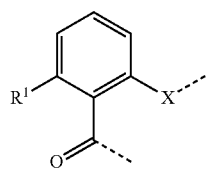 | A1(a1) |
| 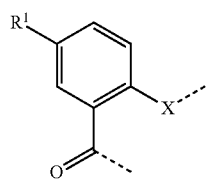 | A2(a1) |
| 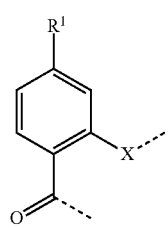 | A3(a1) |
| 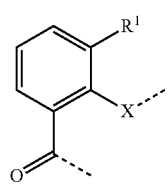 | A4(a1) |
| 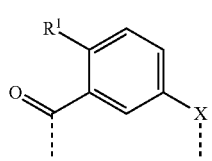 | A5(a1) |
| 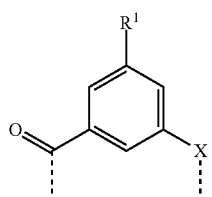 | A6(a1) |

TABLE 10-continued

| Radicals A1(a1)-A626(a25) | |
|---|---|
| 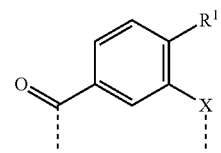 | A7(a1) |
| 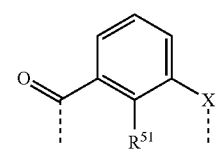 | A8(a1) |
| 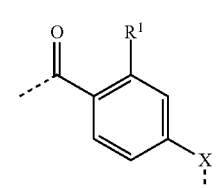 | A9(a1) |
| 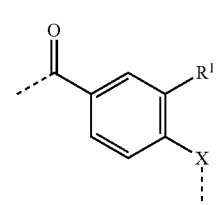 | A10(a1) |
| 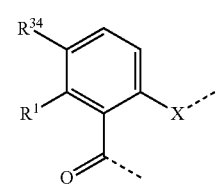 | A11(a1) |
| 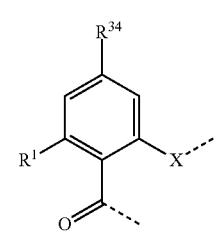 | A12(a1) |
| 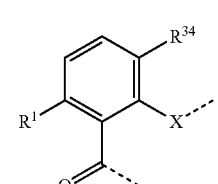 | A13(a1) |
| 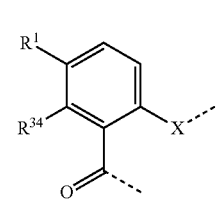 | A14(a1) |

TABLE 10-continued
Radicals A1(a1)-A626(a25)
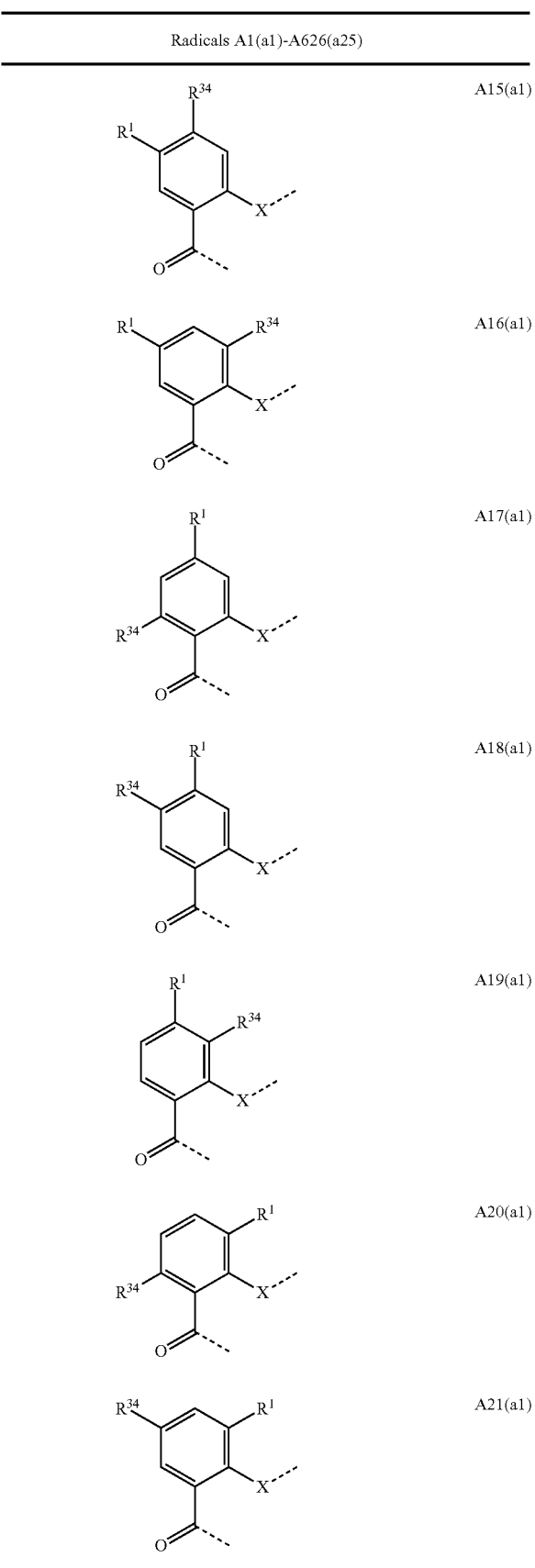
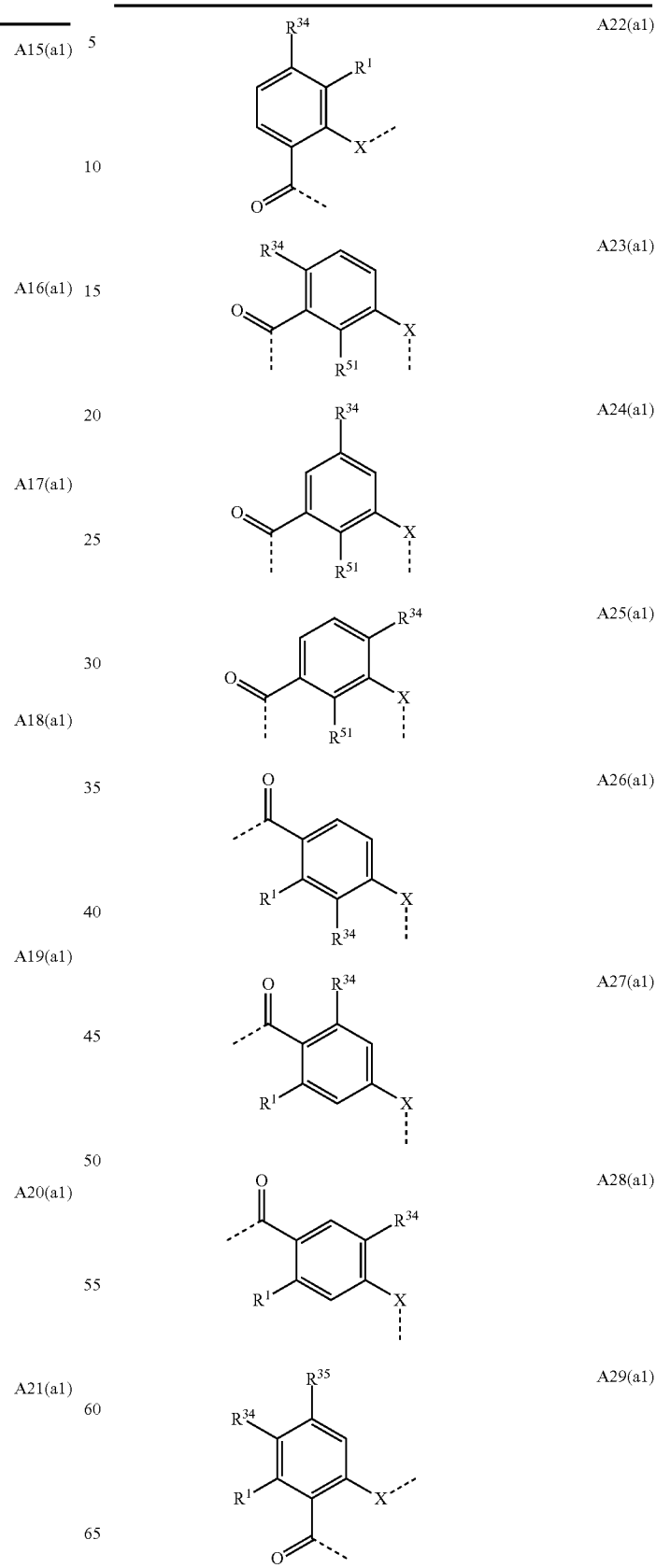

TABLE 10-continued
Radicals A1(a1)-A626(a25)
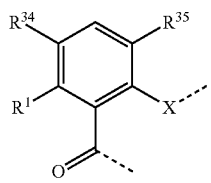 A30(a1)
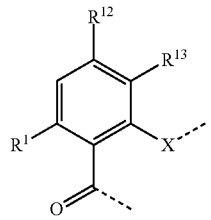 A31(a1)
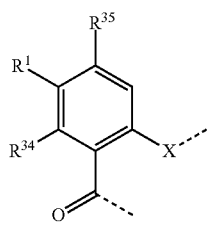 A32(a1)
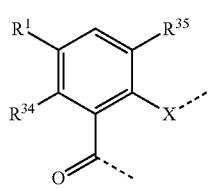 A33(a1)
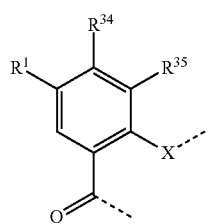 A34(a1)
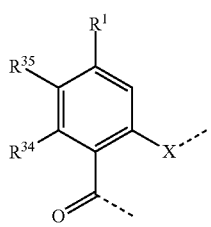 A35(a1)
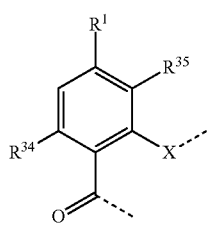 A36(a1)
TABLE 10-continued
Radicals A1(a1)-A626(a25)
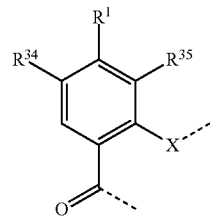 A37(a1)
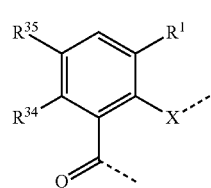 A38(a1)
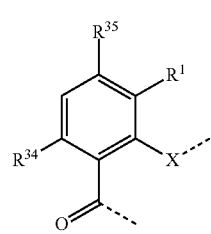 A39(a1)
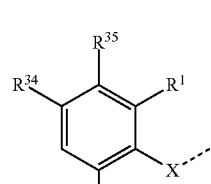 A40(a1)
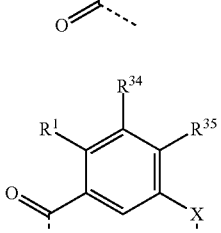 A41(a1)
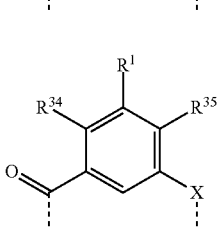 A42(a1)
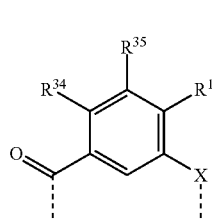 A43(a1)

TABLE 10-continued
Radicals A1(a1)-A626(a25)
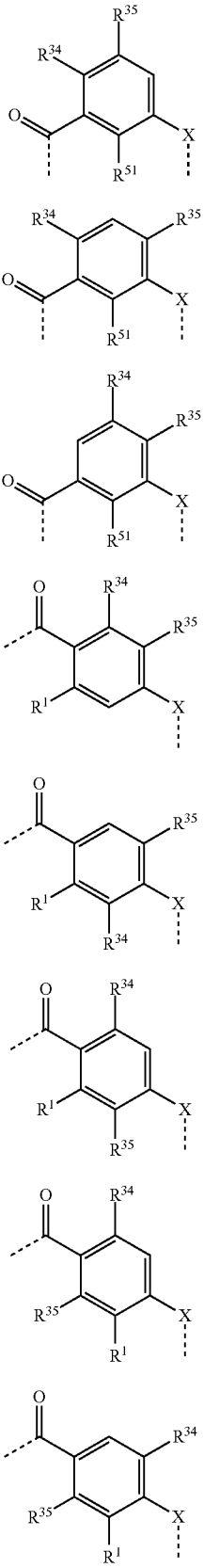
A44(a1)
A45(a1)
A46(a1)
A47(a1)
A48(a1)
A49(a1)
A50(a1)
A51(a1)
TABLE 10-continued
Radicals A1(a1)-A626(a25)
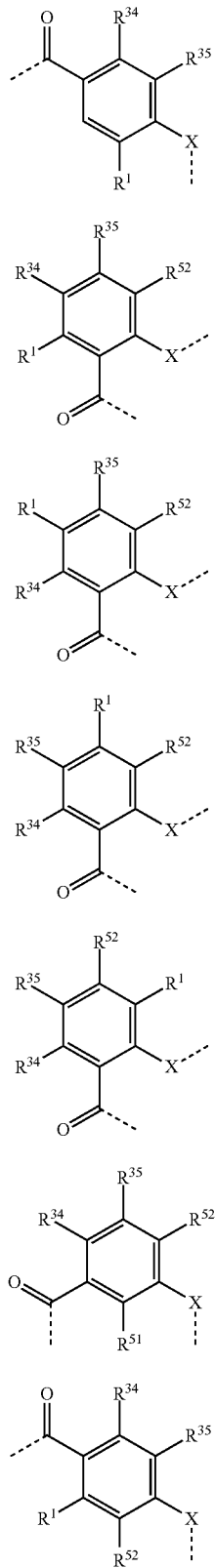
A52(a1)
A53(a1)
A54(a1)
A55(a1)
A56(a1)
A57(a1)
A58(a1)

TABLE 10-continued
Radicals A1(a1)-A626(a25)
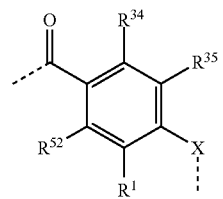 A59(a1)
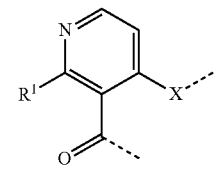 A60(a2)
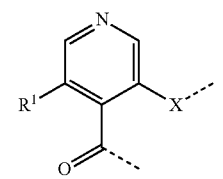 A61(a2)
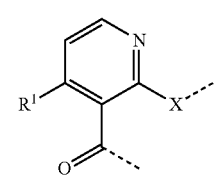 A62(a2)
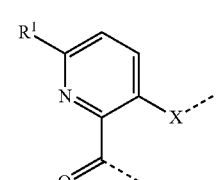 A63(a2)
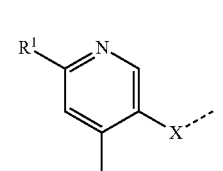 A64(a2)
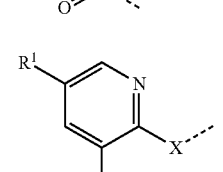 A65(a2)
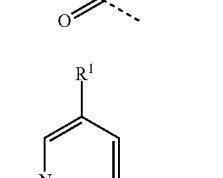 A66(a2)
TABLE 10-continued
Radicals A1(a1)-A626(a25)
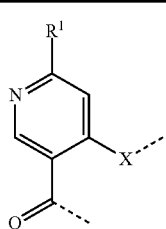 A67(a2)
A68(a2)
A69(a2)
A70(a2)
A71(a2)
A72(a2)
A73(a2)
A74(a2)

TABLE 10-continued

Radicals A1(a1)-A626(a25)

(Structures labeled A75(a2) through A91(a2) — pyridine-based radical structures with R¹, R³⁴, R³⁶, R⁵¹, and X substituents)

TABLE 10-continued
Radicals A1(a1)-A626(a25)
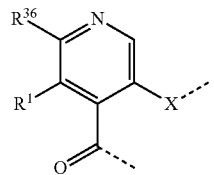 A92(a2)
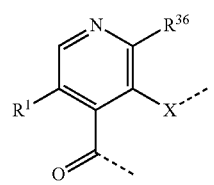 A93(a2)
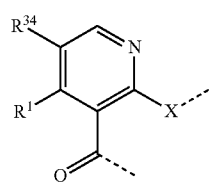 A94(a2)
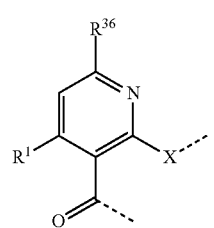 A95(a2)
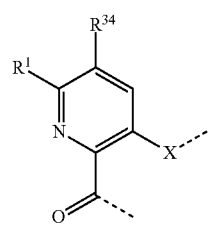 A96(a2)
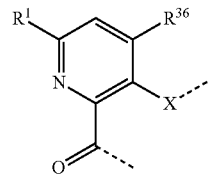 A97(a2)
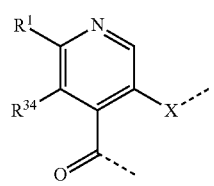 A98(a2)
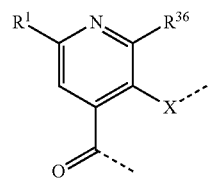 A99(a2)
TABLE 10-continued
Radicals A1(a1)-A626(a25)
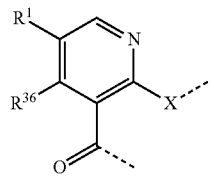 A100(a2)
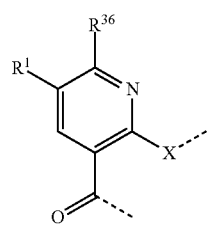 A101(a2)
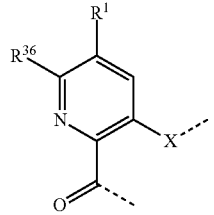 A102(a2)
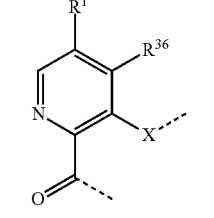 A103(a2)
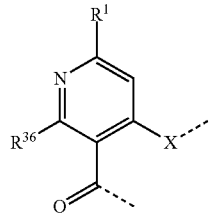 A104(a2)
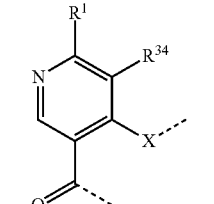 A105(a2)
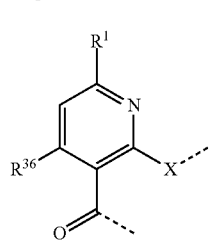 A106(a2)

TABLE 10-continued

Radicals A1(a1)-A626(a25)

A107(a2), A108(a2), A109(a2), A110(a2), A111(a2), A112(a2), A113(a2), A114(a2), A115(a2), A116(a2), A117(a2), A118(a2), A119(a2), A120(a2), A121(a2), A122(a2)

TABLE 10-continued
Radicals A1(a1)-A626(a25)
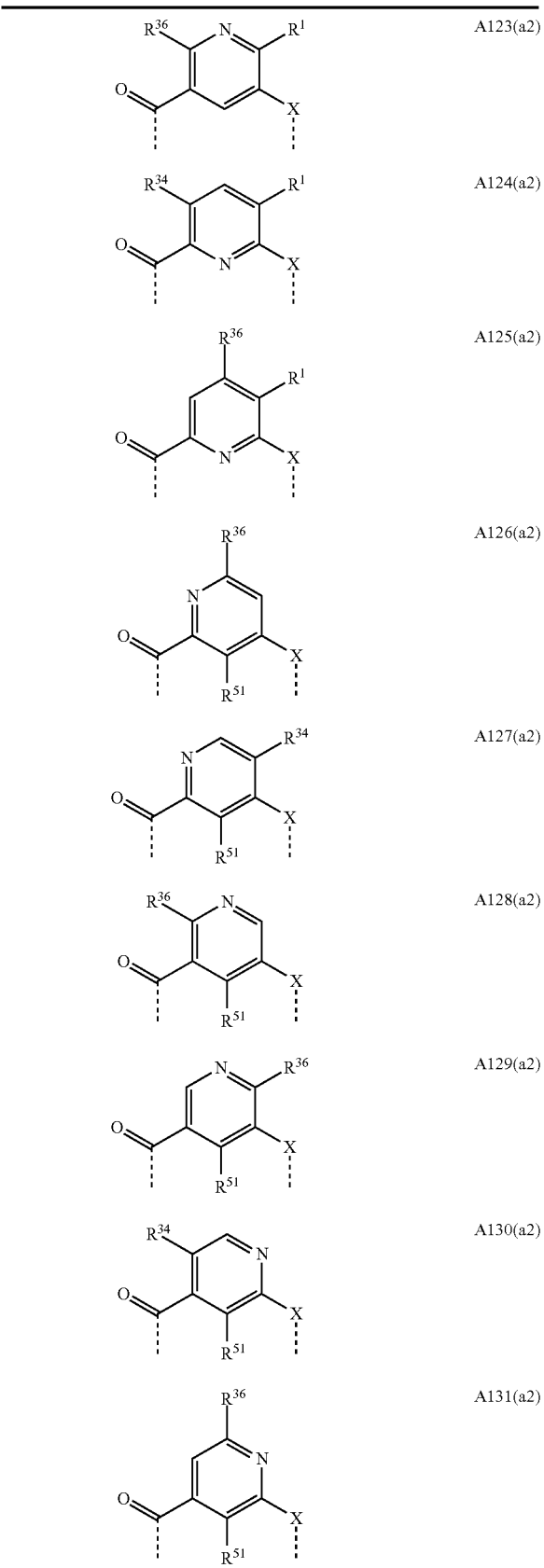
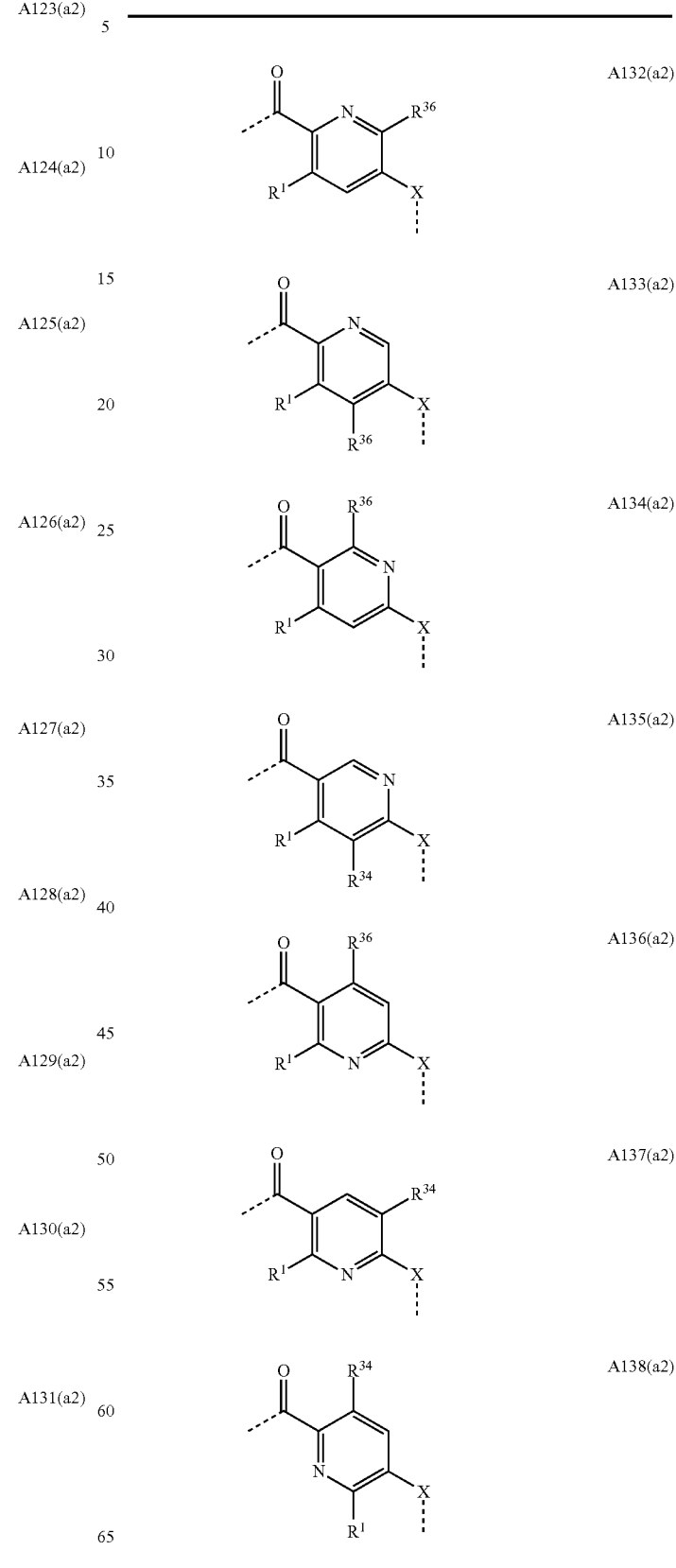

TABLE 10-continued
Radicals A1(a1)-A626(a25)
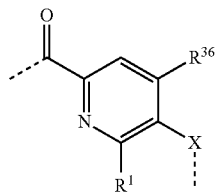 A139(a2)
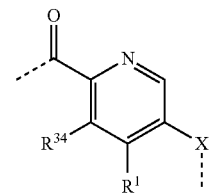 A140(a2)
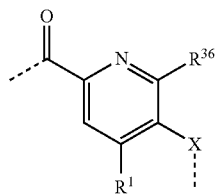 A141(a2)
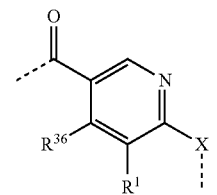 A142(a2)
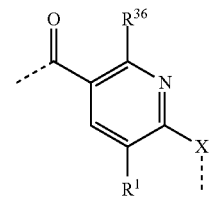 A143(a2)
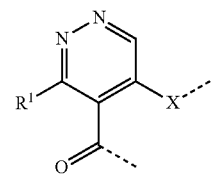 A144(a3)
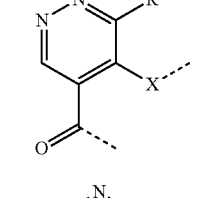 A145(a3)
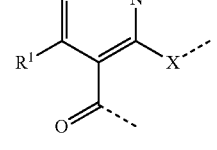 A146(a3)
TABLE 10-continued
Radicals A1(a1)-A626(a25)
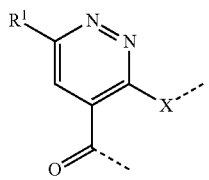 A147(a3)
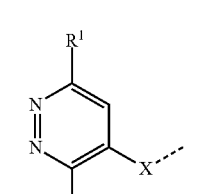 A148(a3)
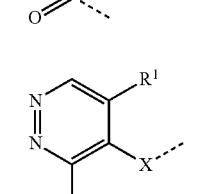 A149(a3)
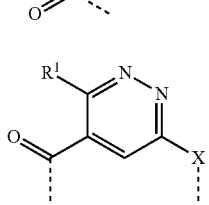 A150(a3)
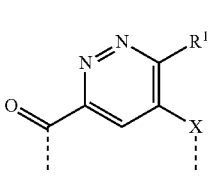 A151(a3)
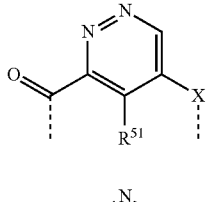 A152(a3)
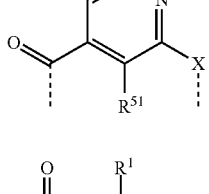 A153(a3)
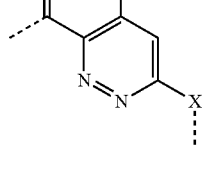 A154(a3)

TABLE 10-continued

Radicals A1(a1)-A626(a25)

TABLE 10-continued
Radicals A1(a1)-A626(a25)
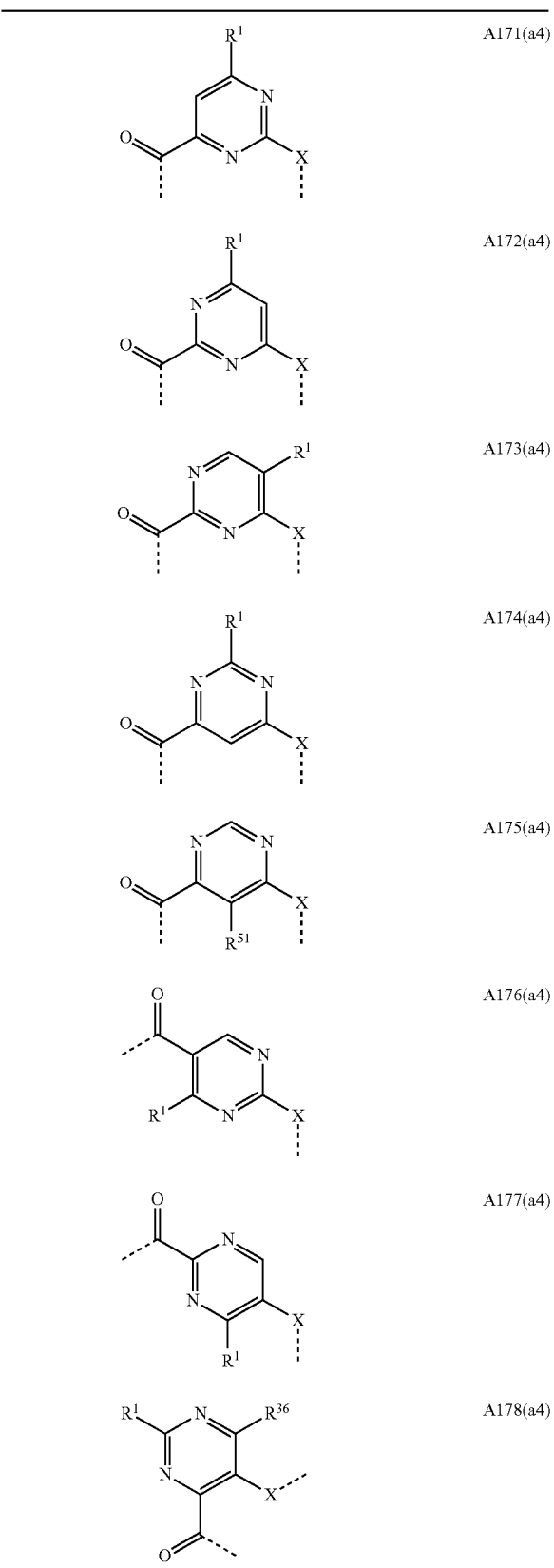
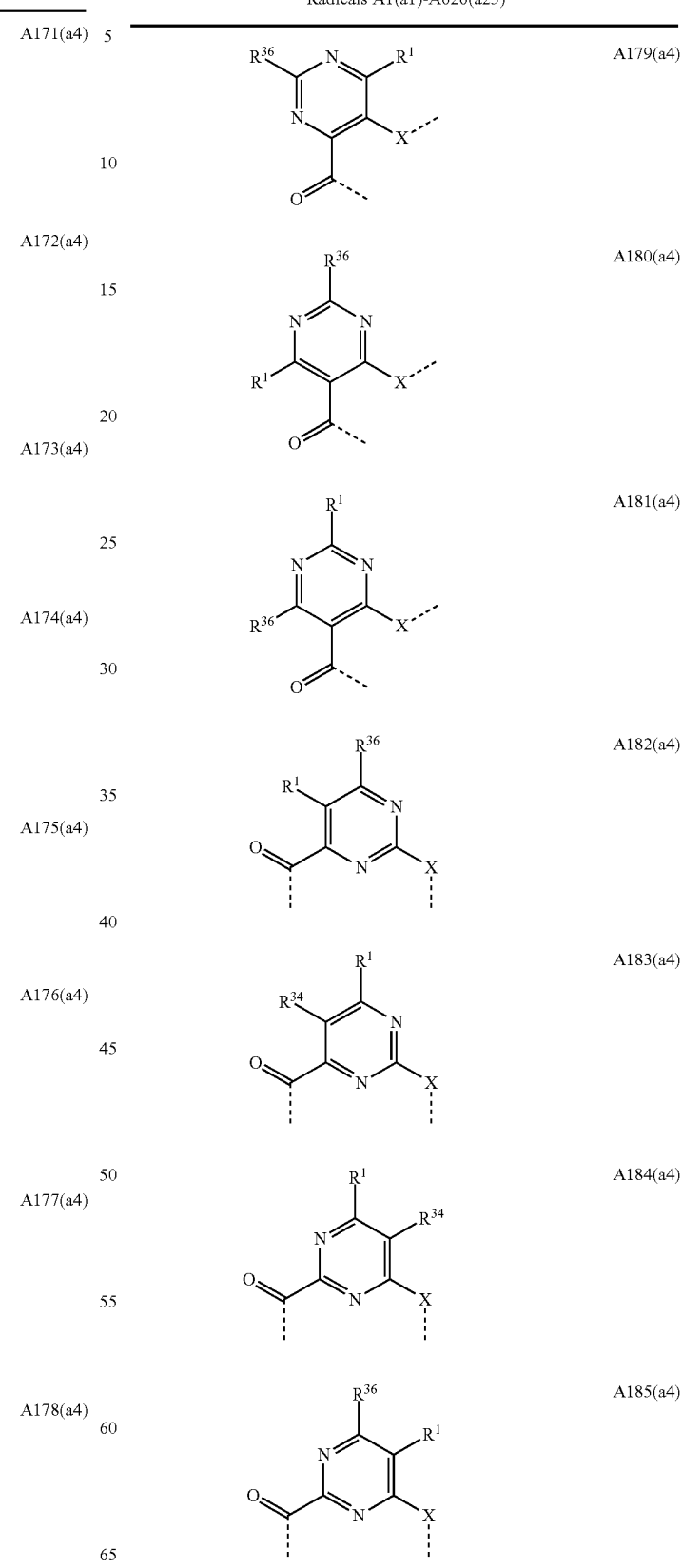

TABLE 10-continued
Radicals A1(a1)-A626(a25)
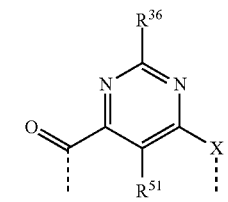 A186(a4)
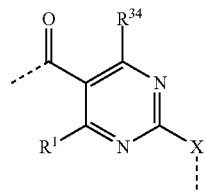 A187(a4)
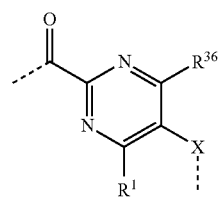 A188(a4)
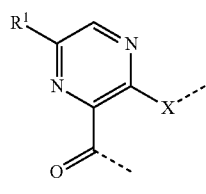 A189(a5)
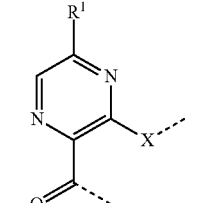 A190(a5)
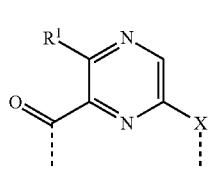 A191(a5)
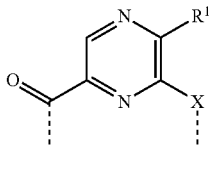 A192(a5)
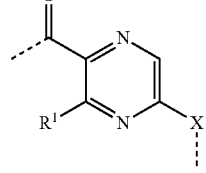 A193(a5)
TABLE 10-continued
Radicals A1(a1)-A626(a25)
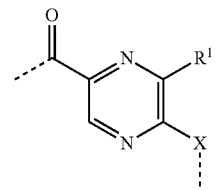 A194(a5)
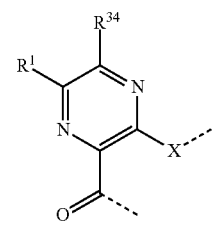 A195(a5)
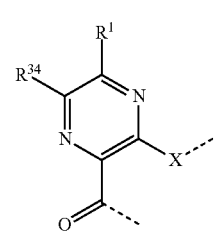 A196(a5)
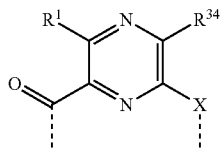 A197(a5)
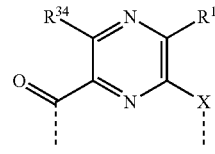 A198(a5)
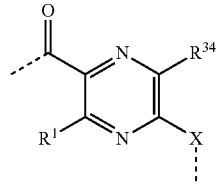 A199(a5)
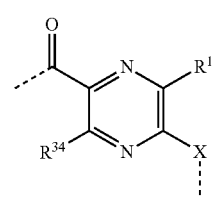 A200(a5)
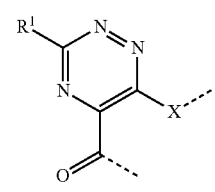 A201(a6)

TABLE 10-continued
Radicals A1(a1)-A626(a25)
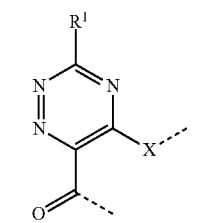 A202(a6)
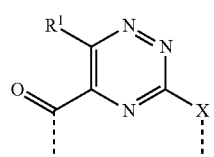 A203(a6)
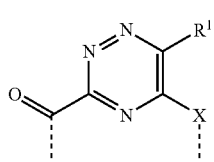 A204(a6)
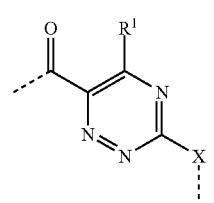 A205(a6)
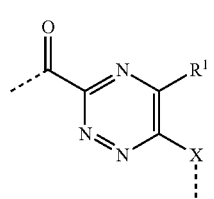 A206(a6)
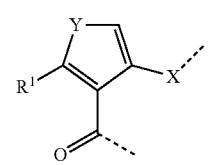 A207(a7)
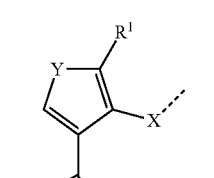 A208(a7)
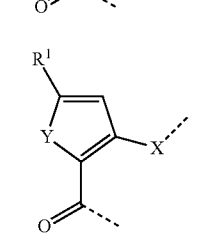 A209(a7)
TABLE 10-continued
Radicals A1(a1)-A626(a25)
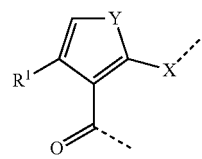 A210(a7)
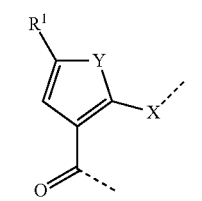 A211(a7)
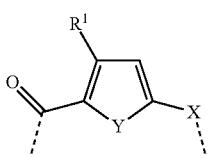 A212(a7)
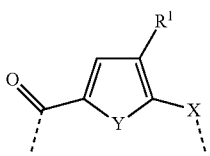 A213(a7)
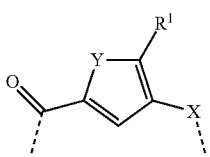 A214(a7)
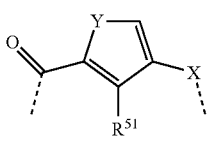 A215(a7)
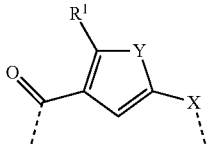 A216(a7)
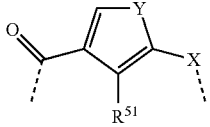 A217(a7)
A218(a7)

TABLE 10-continued

Radicals A1(a1)-A626(a25)

| Structure | Label |
|---|---|
| (thiophene/furan with R¹, R³⁴, X, C=O) | A219(a7) |
| (thiophene/furan with R¹, R³⁴, X, C=O) | A220(a7) |
| (thiophene/furan with R¹, R³⁴, X, C=O) | A221(a7) |
| (thiophene/furan with R¹, R³⁴, X, C=O) | A222(a7) |
| (thiophene/furan with R¹, R³⁴, X, C=O) | A223(a7) |
| (thiophene/furan with R¹, R³⁴, X, C=O) | A224(a7) |
| (thiophene/furan with R¹, R³⁴, X, C=O) | A225(a7) |
| (thiophene/furan with R¹, R³⁴, X, C=O) | A226(a7) |
| (thiophene/furan with R³⁴, R⁵¹, X, C=O) | A227(a7) |
| (thiophene/furan with R³⁴, R⁵¹, X, C=O) | A228(a7) |
| (imidazole/thiazole with R¹, X, C=O) | A229(a8) |
| (imidazole/thiazole with R¹, X, C=O) | A230(a8) |
| (imidazole/thiazole with R¹, X, C=O) | A231(a8) |
| (imidazole/thiazole with R¹, X, C=O) | A232(a8) |
| (imidazole/thiazole with R¹, X, C=O) | A233(a8) |
| (imidazole/thiazole with R¹, X, C=O) | A234(a8) |
| (isoxazole/pyrazole with R¹, X, C=O) | A235(a9) |

TABLE 10-continued

Radicals A1(a1)-A626(a25)

A236(a9)
A237(a9)
A238(a9)
A239(a9)
A240(a10)
A241(a10)
A242(a10)
A243(a10)
A244(a10)
A245(a10)
A246(a10)
A247(a10)
A248(a10)
A249(a10)

TABLE 10-continued
Radicals A1(a1)-A626(a25)
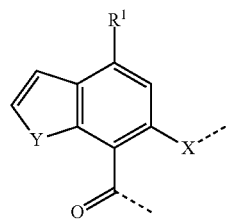 A250(a10)
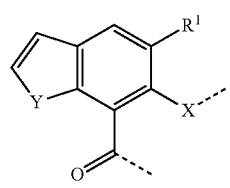 A251(a10)
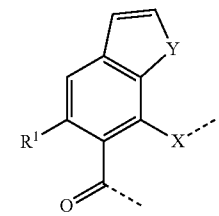 A252(a10)
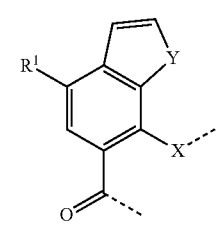 A253(a10)
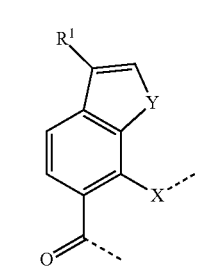 A254(a10)
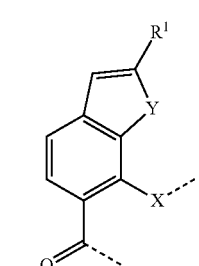 A255(a10)
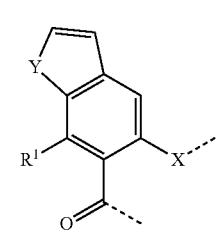 A256(a10)
TABLE 10-continued
Radicals A1(a1)-A626(a25)
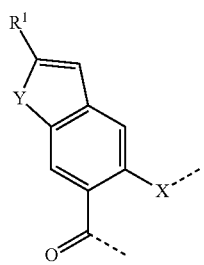 A257(a10)
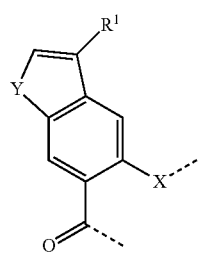 A258(a10)
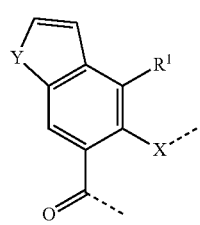 A259(a10)
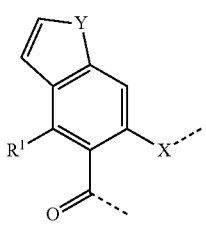 A260(a10)
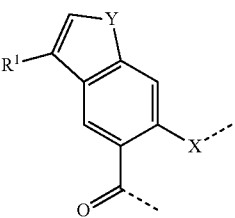 A261(a10)
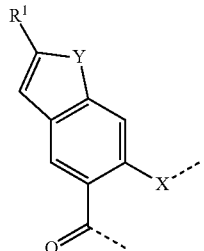 A262(a10)

TABLE 10-continued
Radicals A1(a1)-A626(a25)
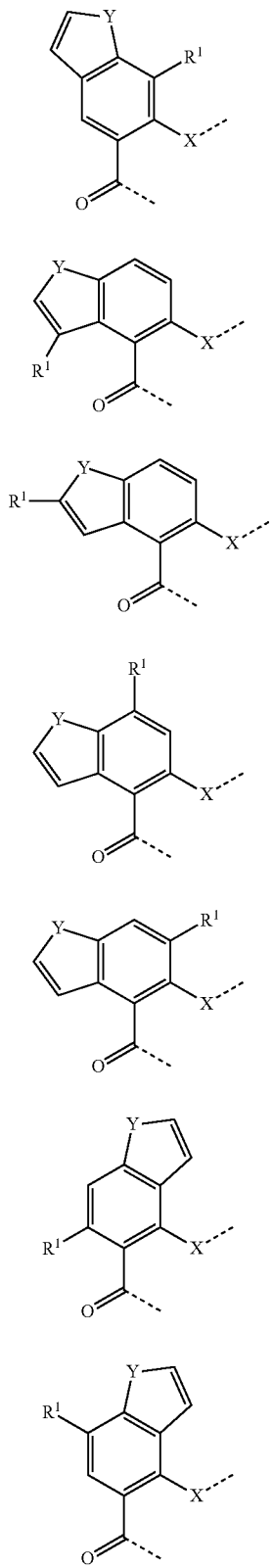
A263(a10)
A264(a10)
A265(a10)
A266(a10)
A267(a10)
A268(a10)
A269(a10)
TABLE 10-continued
Radicals A1(a1)-A626(a25)
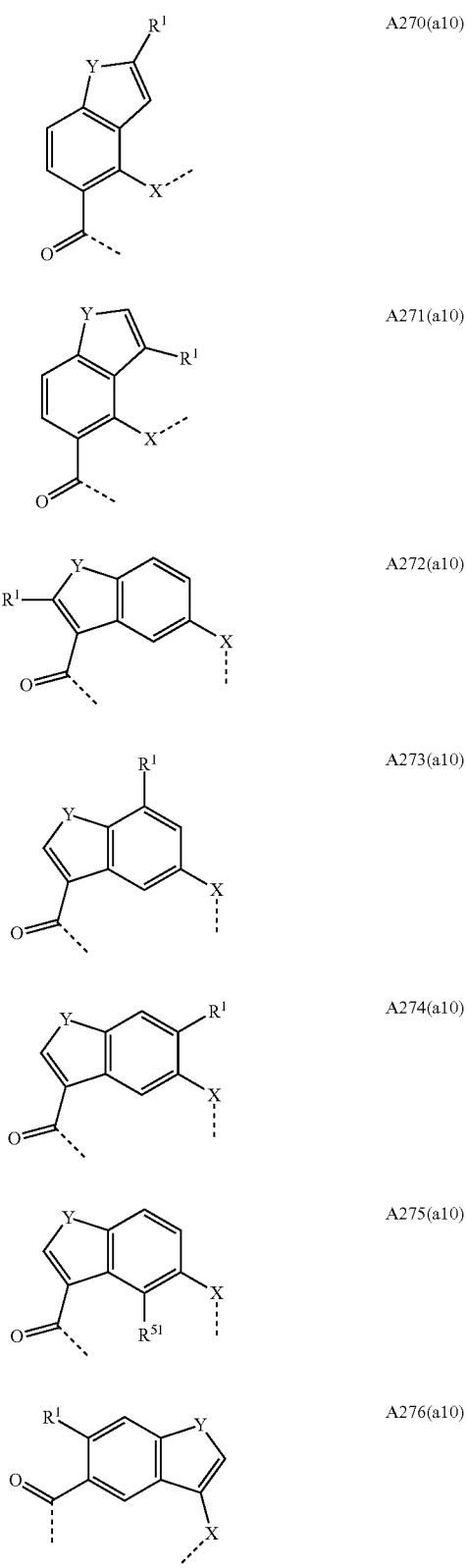
A270(a10)
A271(a10)
A272(a10)
A273(a10)
A274(a10)
A275(a10)
A276(a10)

TABLE 10-continued
Radicals A1(a1)-A626(a25)
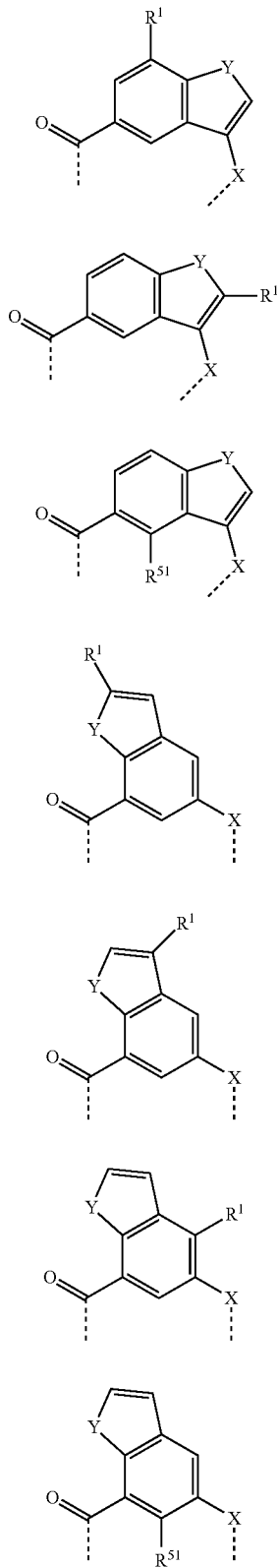
A277(a10)
A278(a10)
A279(a10)
A280(a10)
A281(a10)
A282(a10)
A283(a10)
TABLE 10-continued
Radicals A1(a1)-A626(a25)
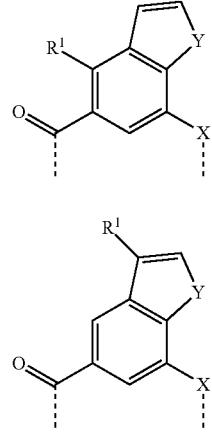
A284(a10)
A285(a10)
A286(a10)
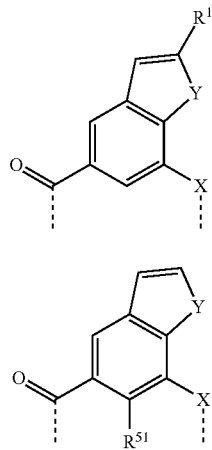
A287(a10)
A288(a10)
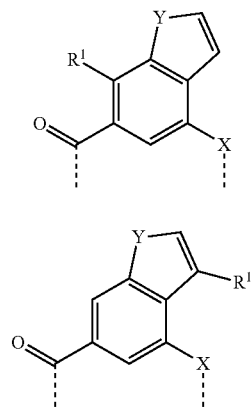
A280(a10)
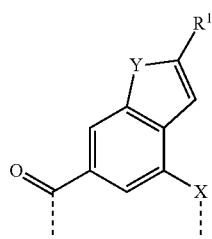
A290(a10)

TABLE 10-continued
Radicals A1(a1)-A626(a25)
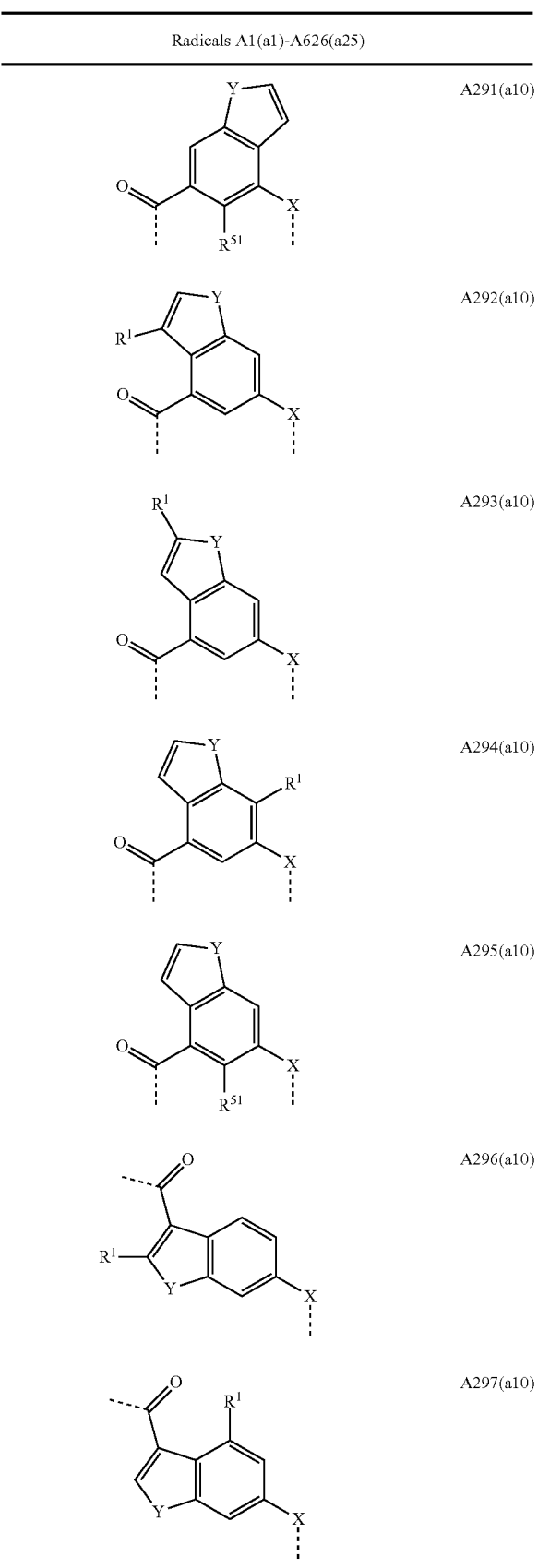
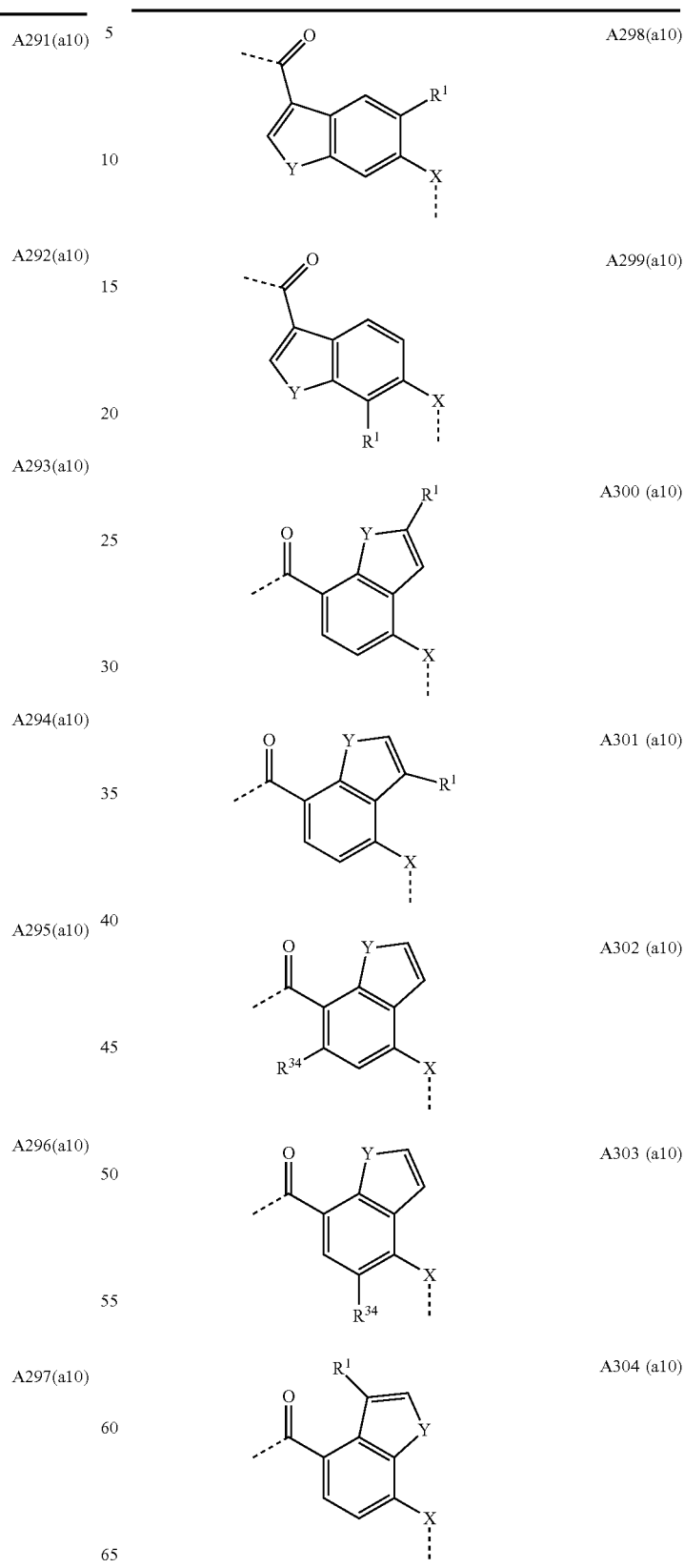

TABLE 10-continued
Radicals A1(a1)-A626(a25)
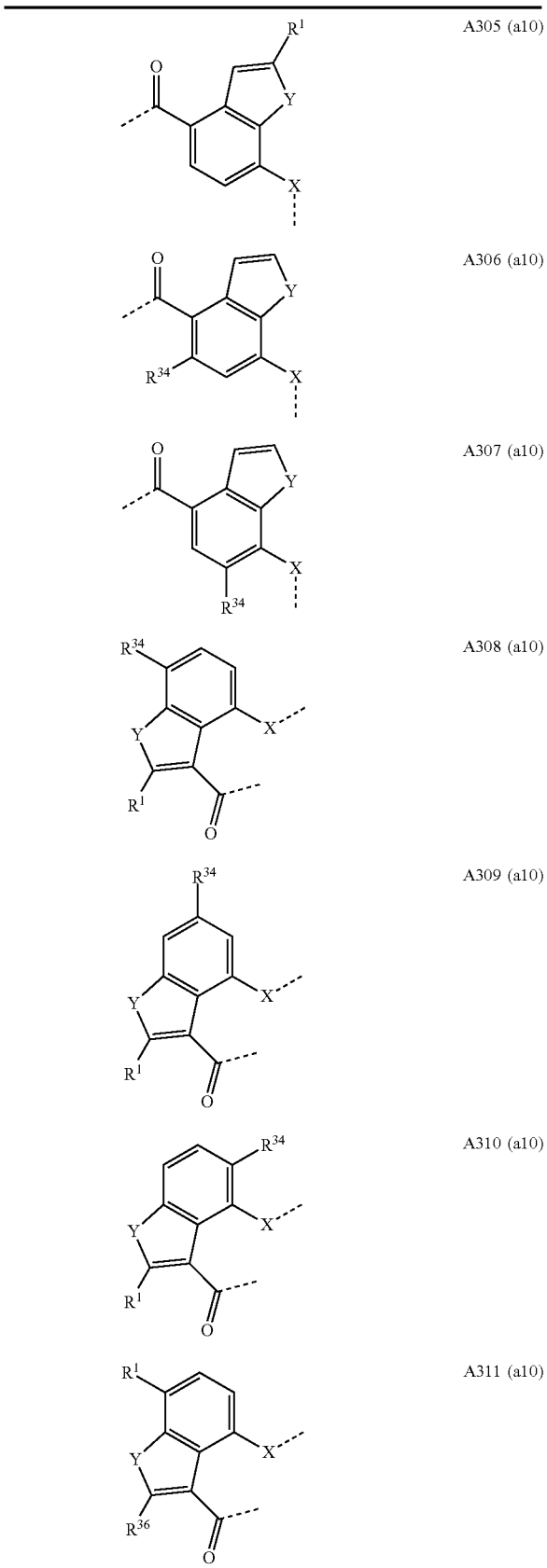
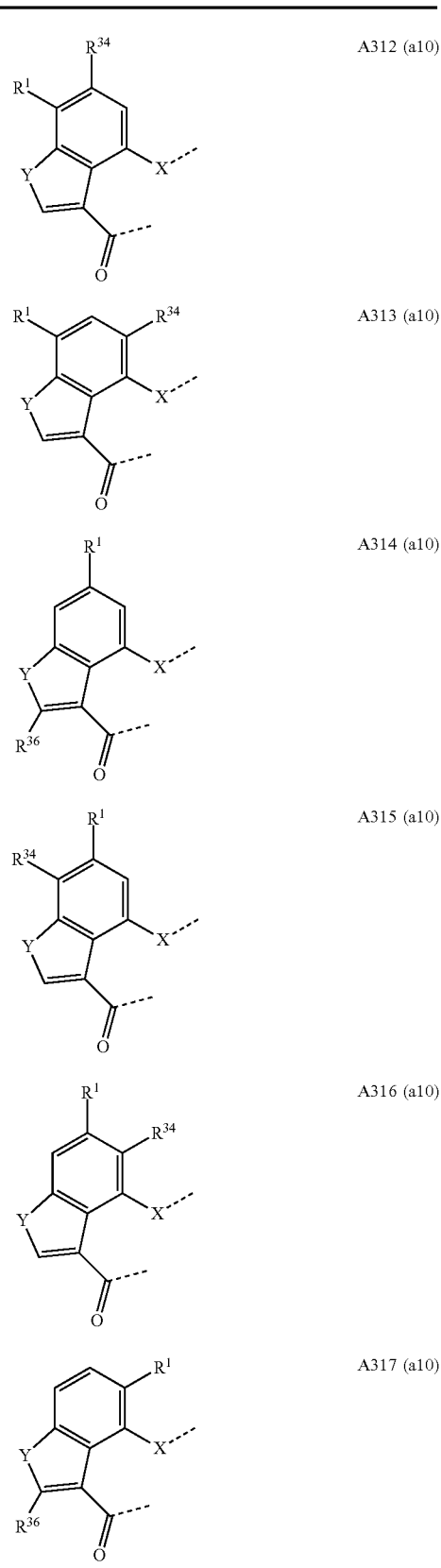

TABLE 10-continued
Radicals A1(a1)-A626(a25)
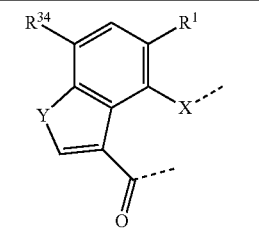 A318 (a10)
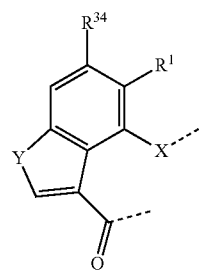 A319 (a10)
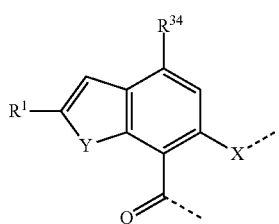 A320 (a10)
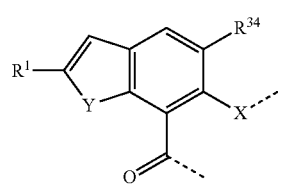 A321 (a10)
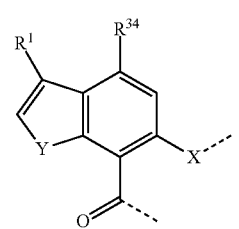 A322 (a10)
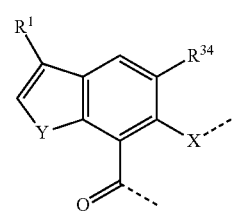 A323 (a10)
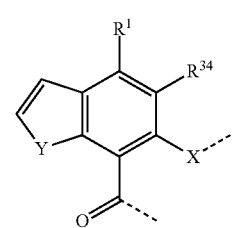 A324 (a10)
TABLE 10-continued
Radicals A1(a1)-A626(a25)
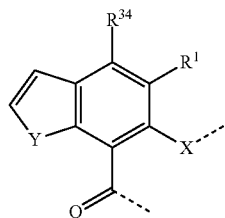 A325 (a10)
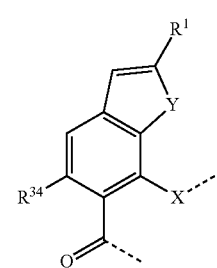 A326 (a10)
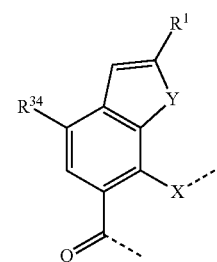 A327 (a10)
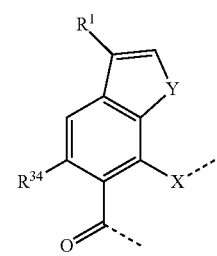 A328 (a10)
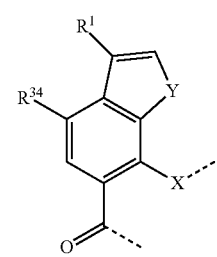 A329 (a10)
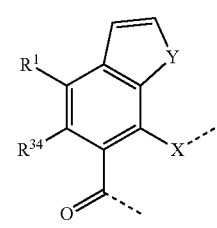 A330 (a10)

TABLE 10-continued

Radicals A1(a1)-A626(a25)

A331 (a10) — A343 (a10) structures

TABLE 10-continued
Radicals A1(a1)-A626(a25)
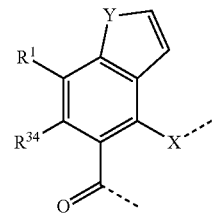 A344 (a10)
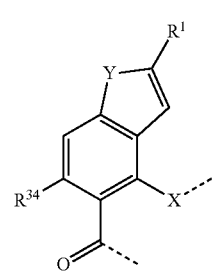 A345 (a10)
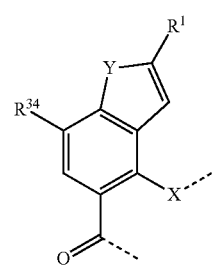 A346 (a10)
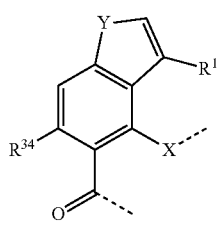 A347 (a10)
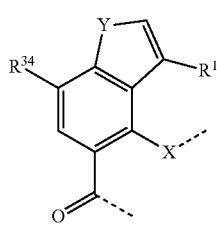 A348 (a10)
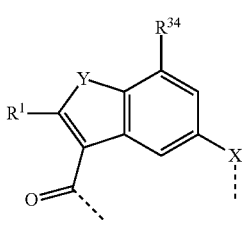 A349 (a10)
TABLE 10-continued
Radicals A1(a1)-A626(a25)
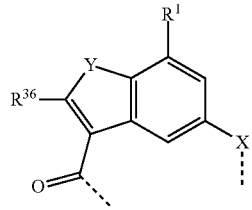 A350 (a10)
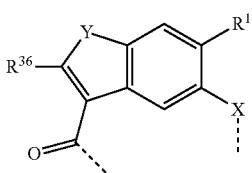 A351 (a10)
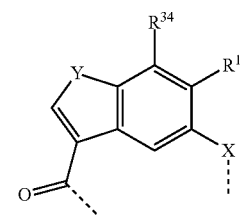 A352 (a10)
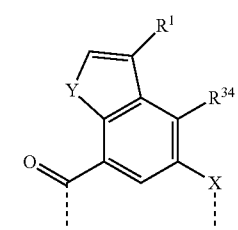 A353 (a10)
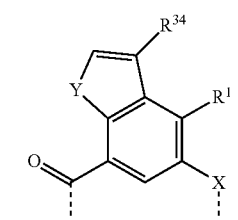 A354 (a10)
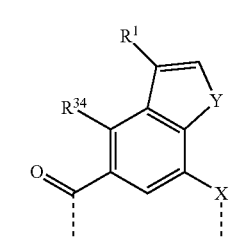 A355 (a10)
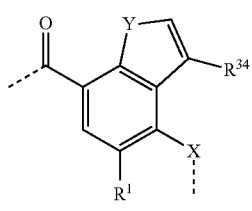 A356 (a10)

TABLE 10-continued

Radicals A1(a1)-A626(a25)

A357 (a10)

A358 (a11)

A359 (a11)

A360 (a11)

A361 (a11)

A362 (a11)

TABLE 10-continued

Radicals A1(a1)-A626(a25)

A363 (a11)

A364 (a11)

A365 (a11)

A366 (a11)

A367 (a11)

A368 (a11)

TABLE 10-continued
Radicals A1(a1)-A626(a25)
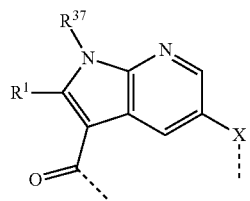 A369 (a11)
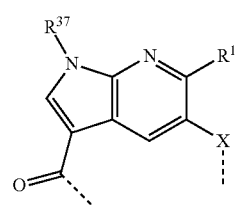 A370 (a11)
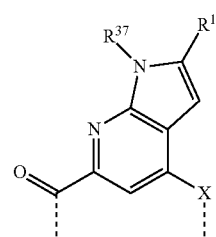 A371 (a11)
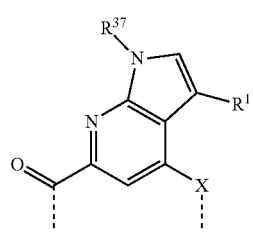 A372 (a11)
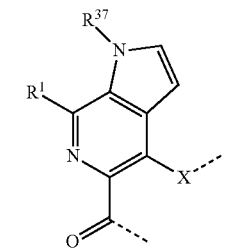 A373 (a12)
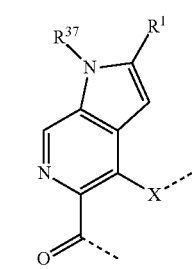 A374 (a12)
TABLE 10-continued
Radicals A1(a1)-A626(a25)
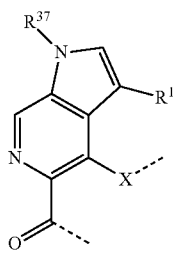 A375 (a12)
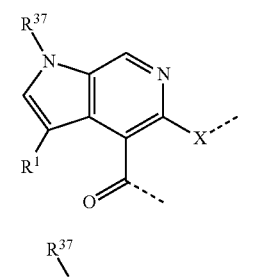 A376 (a12)
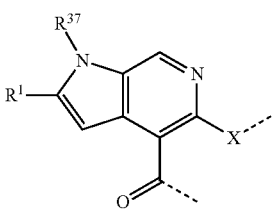 A377 (a12)
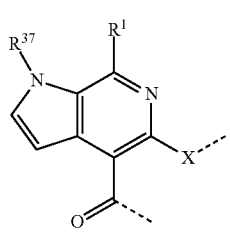 A378 (a12)
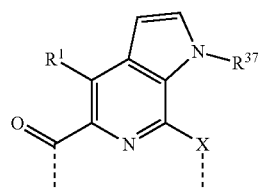 A379 (a12)
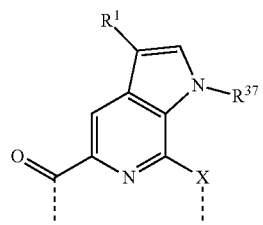 A380 (a12)
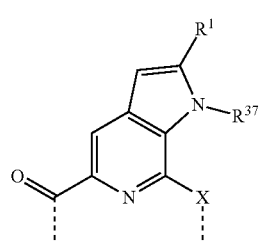 A381 (a12)

TABLE 10-continued
Radicals A1(a1)-A626(a25)
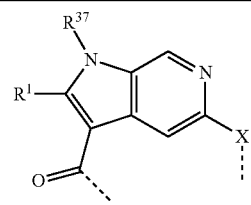 A382 (a12)
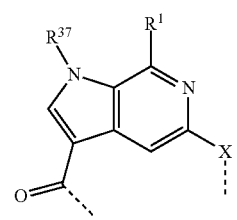 A383 (a12)
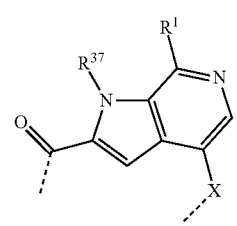 A384 (a12)
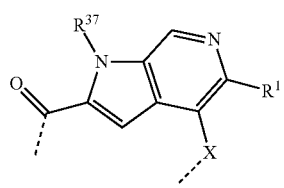 A385 (a12)
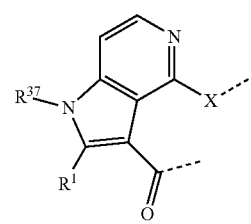 A386 (a13)
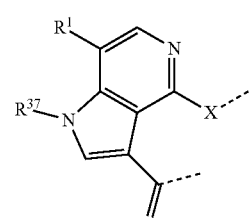 A387 (a13)
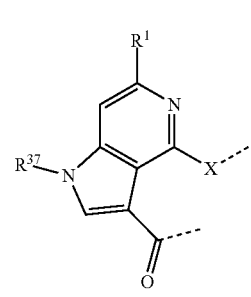 A388 (a13)
TABLE 10-continued
Radicals A1(a1)-A626(a25)
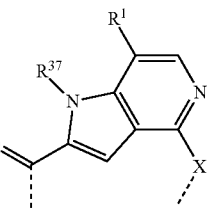 A389 (a13)
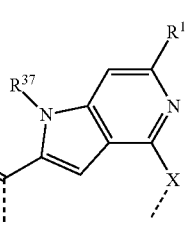 A390 (a13)
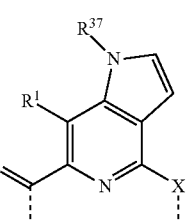 A391 (a13)
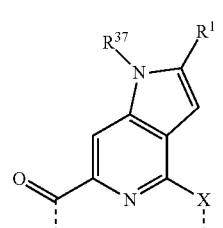 A392 (a13)
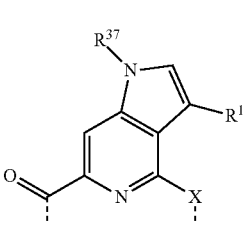 A393 (a13)
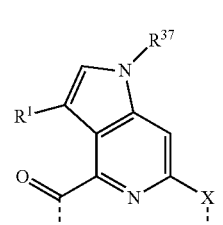 A394 (a13)
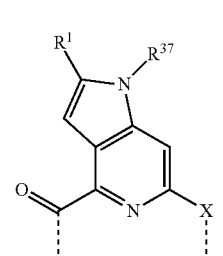 A395 (a13)

TABLE 10-continued
Radicals A1(a1)-A626(a25)
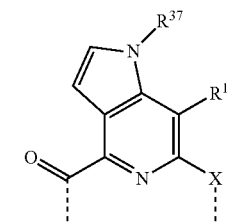 A396 (a13)
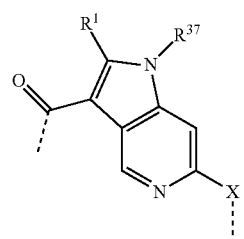 A397 (a13)
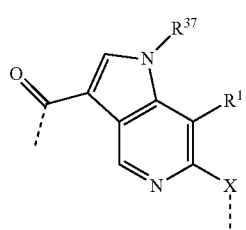 A398 (a13)
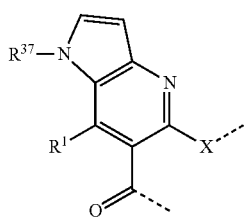 A399 (a14)
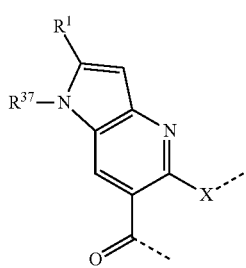 A400 (a14)
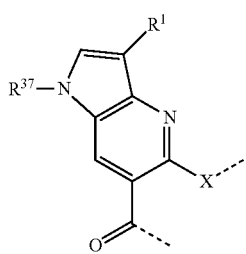 A401 (a14)
TABLE 10-continued
Radicals A1(a1)-A626(a25)
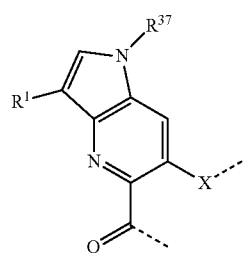 A402 (a14)
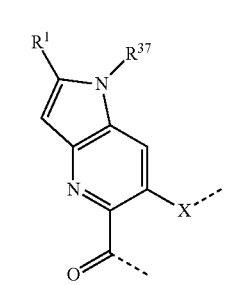 A403 (a14)
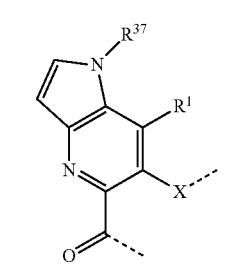 A404 (a14)
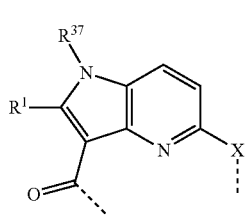 A405 (a14)
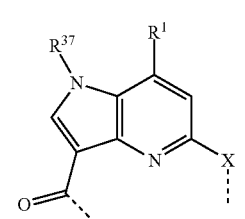 A406 (a14)
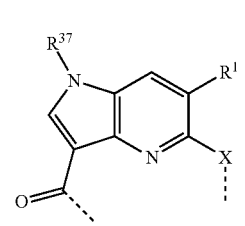 A407 (a14)

TABLE 10-continued
Radicals A1(a1)-A626(a25)
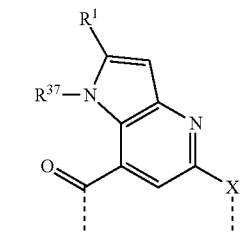 A408 (a14)
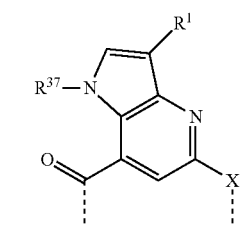 A409 (a14)
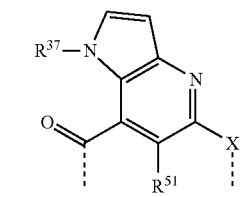 A410 (a14)
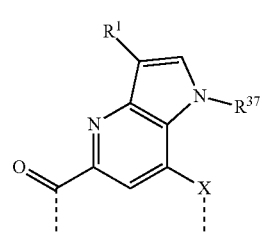 A411 (a14)
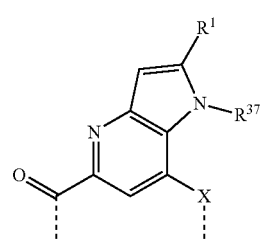 A412 (a14)
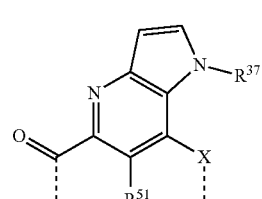 A413 (a14)
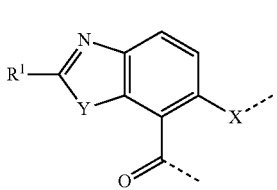 A414 (a15)
TABLE 10-continued
Radicals A1(a1)-A626(a25)
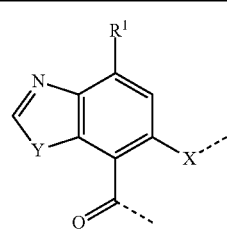 A415 (a15)
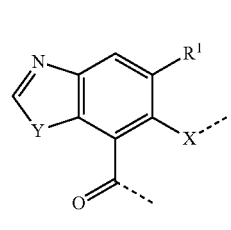 A416 (a15)
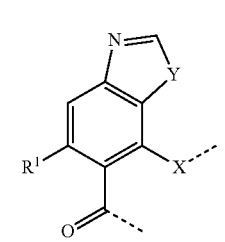 A417 (a15)
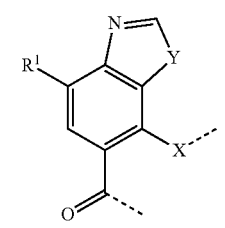 A418 (a15)
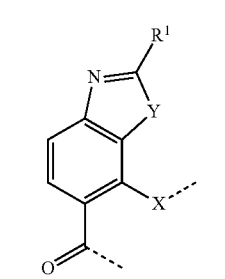 A419 (a15)
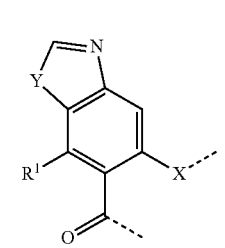 A420 (a15)

TABLE 10-continued

Radicals A1(a1)-A626(a25)

A421 (a15)
A422 (a15)
A423 (a15)
A424 (a15)
A425 (a15)
A426 (a15)
A427 (a15)
A428 (a15)
A429 (a15)
A430 (a15)
A431 (a15)
A432 (a15)
A433 (a15)
A434 (a15)

TABLE 10-continued
Radicals A1(a1)-A626(a25)
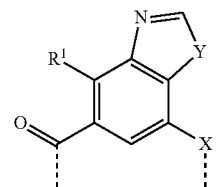 A435 (a15)
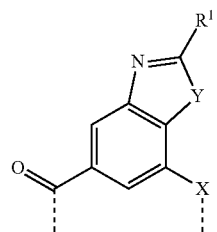 A436 (a15)
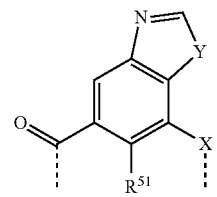 A437 (a15)
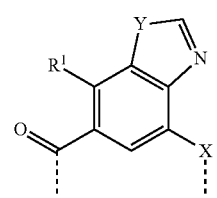 A438 (a15)
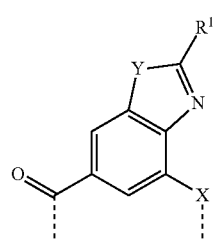 A439 (a15)
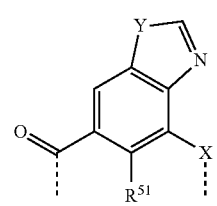 A440 (a15)
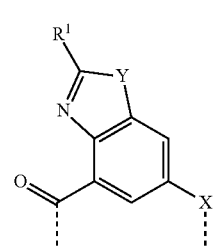 A441 (a15)
TABLE 10-continued
Radicals A1(a1)-A626(a25)
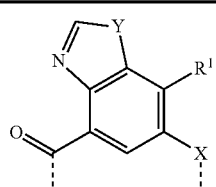 A442 (a15)
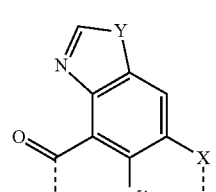 A443 (a15)
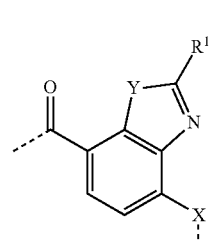 A444 (a15)
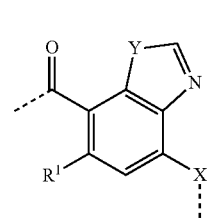 A445 (a15)
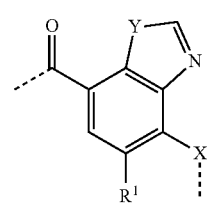 A446 (a15)
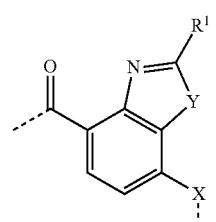 A447 (a15)
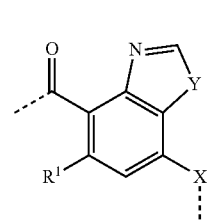 A448 (a15)

TABLE 10-continued
Radicals A1(a1)-A626(a25)
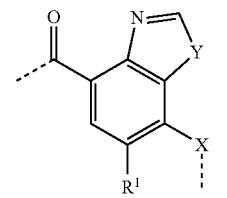 A449 (a15)
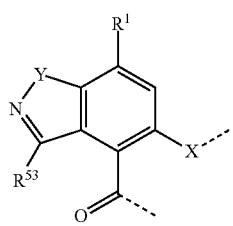 A450 (a16)
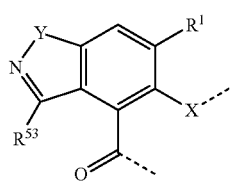 A451 (a16)
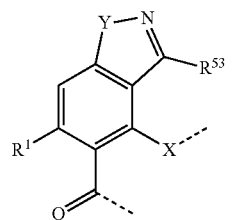 A452 (a16)
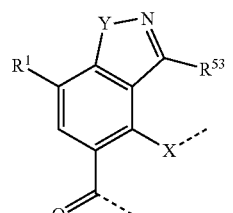 A453 (a16)
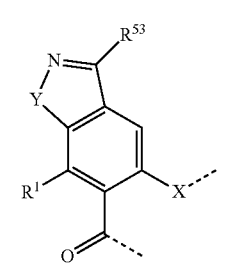 A454 (a16)
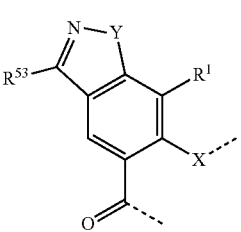 A455 (a16)
TABLE 10-continued
Radicals A1(a1)-A626(a25)
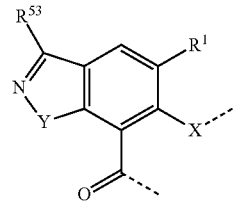 A456 (a16)
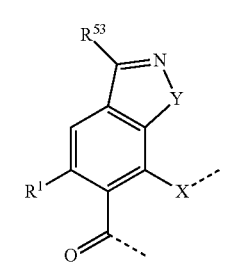 A457 (a16)
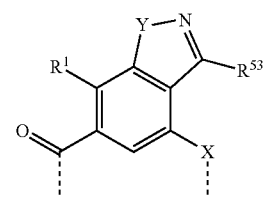 A458 (a16)
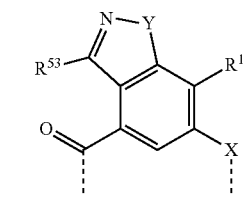 A459 (a16)
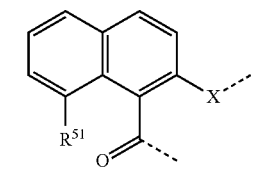 A460 (a17)
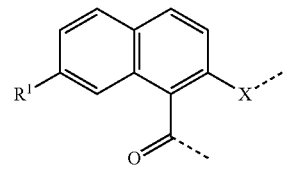 A461 (a17)
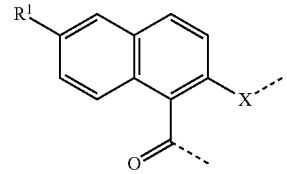 A462 (a17)

TABLE 10-continued
Radicals A1(a1)-A626(a25)
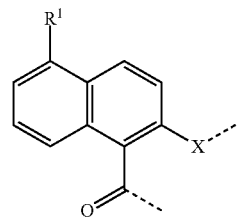 A463 (a17)
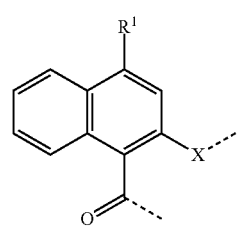 A464 (a17)
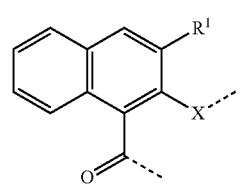 A465 (a17)
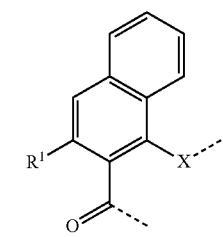 A466 (a17)
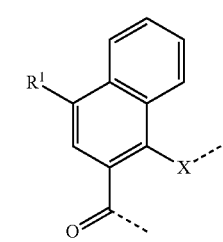 A467 (a17)
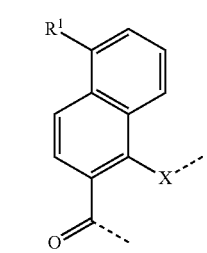 A468 (a17)
TABLE 10-continued
Radicals A1(a1)-A626(a25)
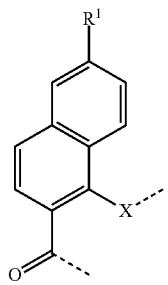 A469 (a17)
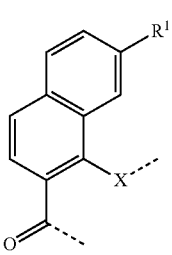 A470 (a17)
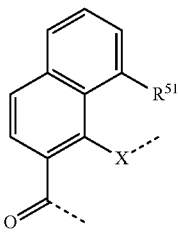 A471 (a17)
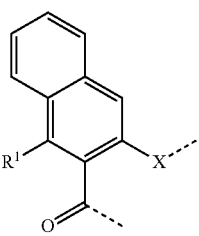 A472 (a17)
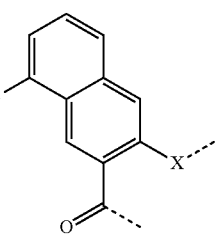 A473 (a17)
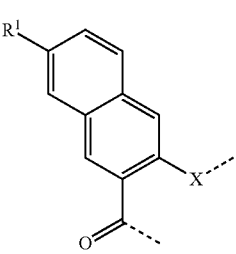 A474 (a17)

TABLE 10-continued

Radicals A1(a1)-A626(a25)

A475 (a17)

A476 (a17)

A477 (a17)

A478 (a17)

A479 (a17)

A480 (a17)

A481 (a17)

A482 (a17)

A483 (a17)

A484 (a17)

A485 (a17)

A486 (a17)

A487 (a17)

TABLE 10-continued
Radicals A1(a1)-A626(a25)
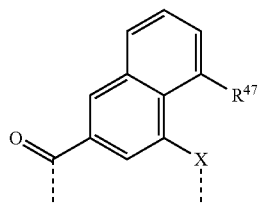
A488 (a17)
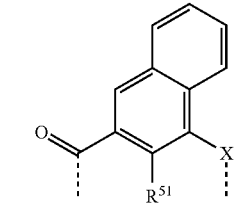
A489 (a17)
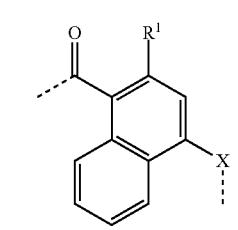
A490 (a17)
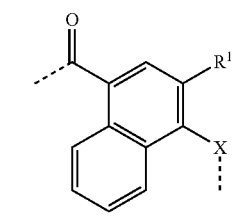
A491 (a17)
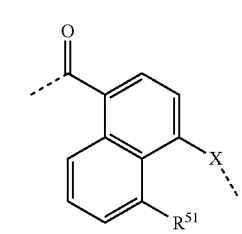
A492 (a17)
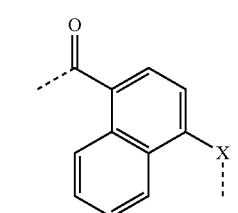
A493 (a17)
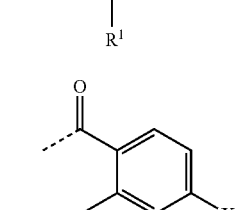
A494 (a17)
TABLE 10-continued
Radicals A1(a1)-A626(a25)
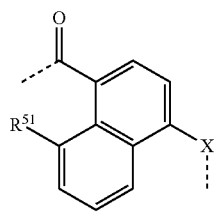
A495 (a17)
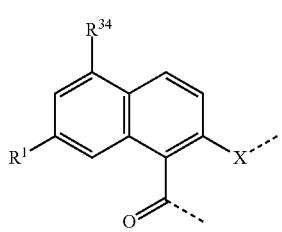
A496 (a17)
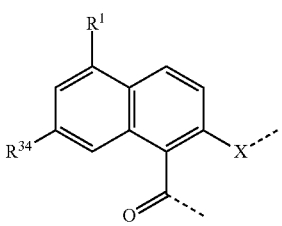
A497 (a17)
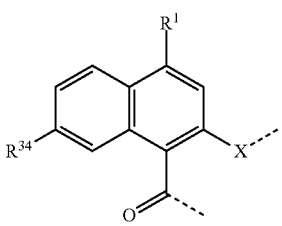
A498 (a17)
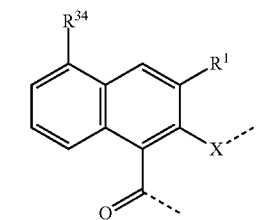
A499 (a17)
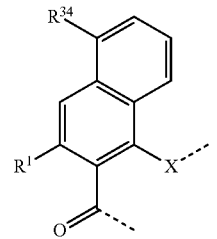
A500 (a17)

TABLE 10-continued
Radicals A1(a1)-A626(a25)
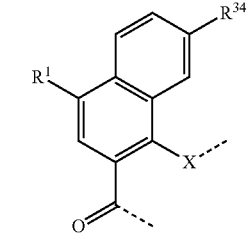 A501 (a17)
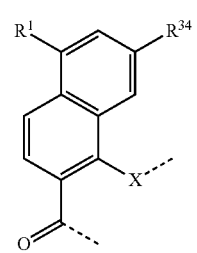 A502 (a17)
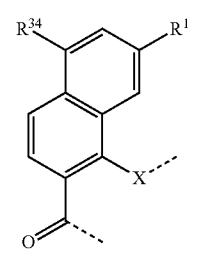 A503 (a17)
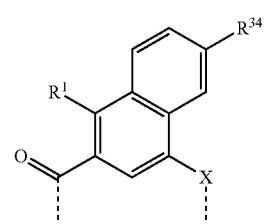 A504 (a17)
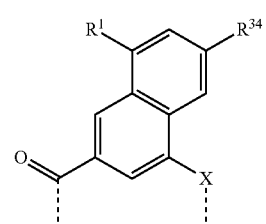 A505 (a17)
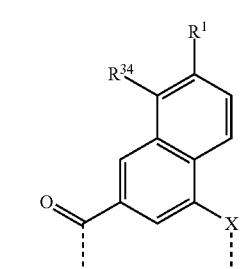 A506 (a17)
TABLE 10-continued
Radicals A1(a1)-A626(a25)
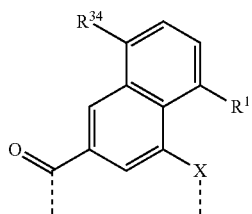 A507 (a17)
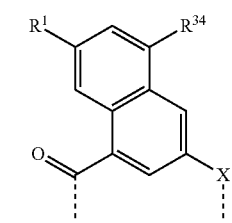 A508 (a17)
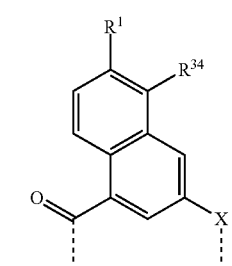 A509 (a17)
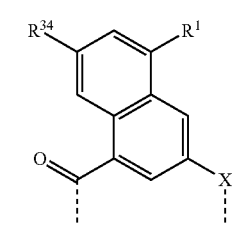 A510 (a17)
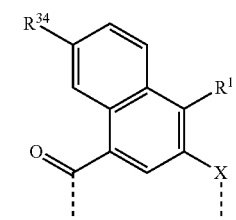 A511 (a17)
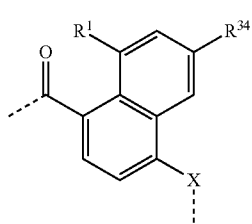 A512 (a17)

TABLE 10-continued
Radicals A1(a1)-A626(a25)
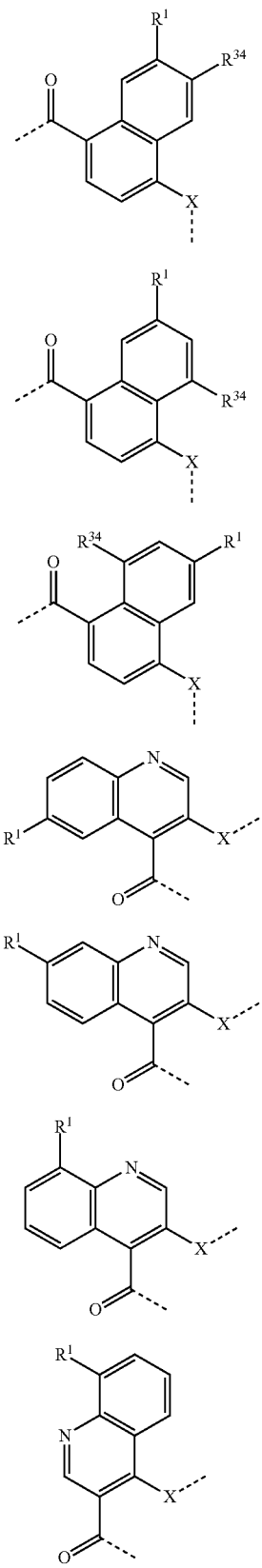
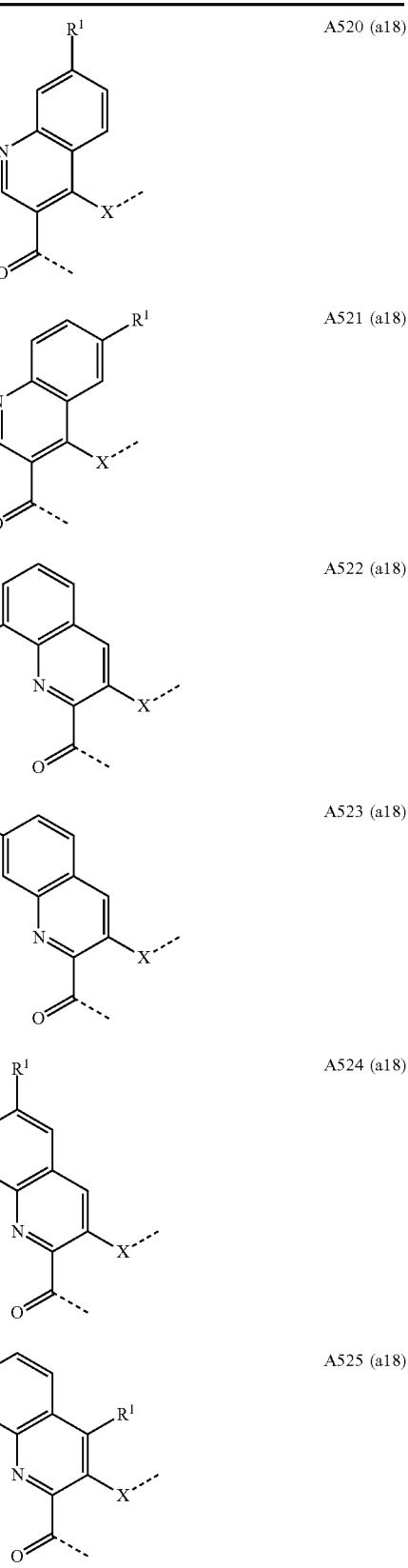

TABLE 10-continued
Radicals A1(a1)-A626(a25)
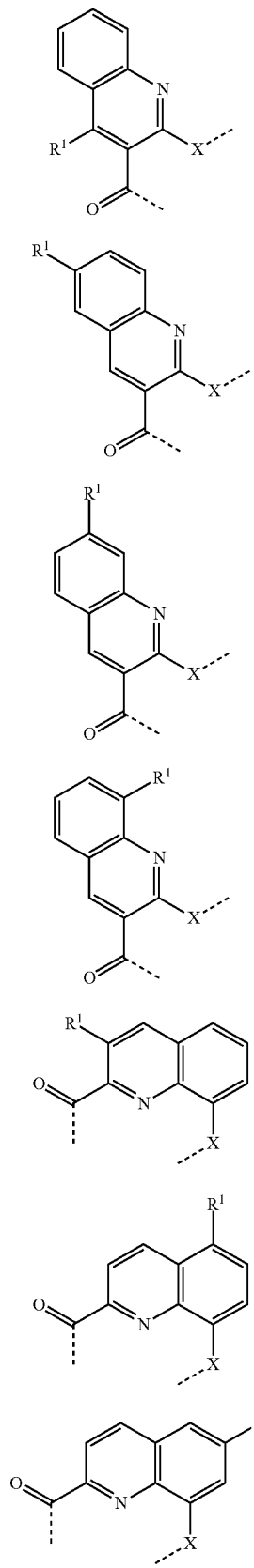
A526 (a18)
A527 (a18)
A528 (a18)
A529 (a18)
A530 (a18)
A531 (a18)
A532 (a18)
TABLE 10-continued
Radicals A1(a1)-A626(a25)
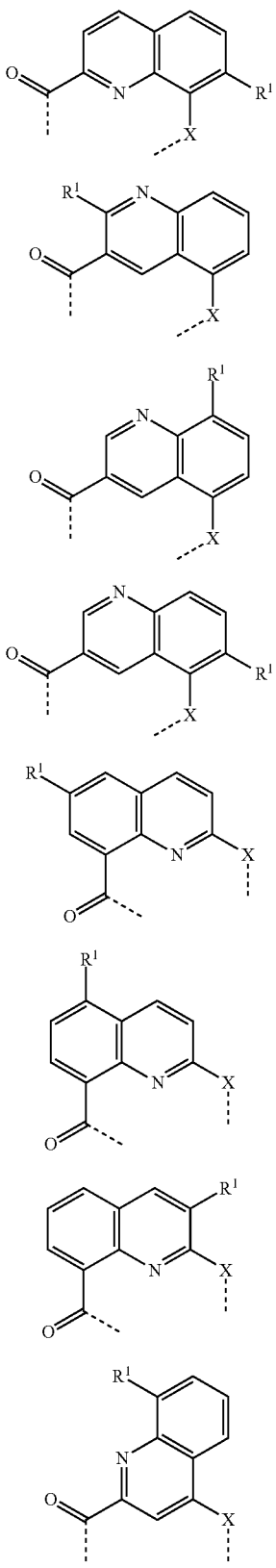
A533 (a18)
A534 (a18)
A535 (a18)
A536 (a18)
A537 (a18)
A538 (a18)
A539 (a18)
A540 (a18)

TABLE 10-continued
Radicals A1(a1)-A626(a25)
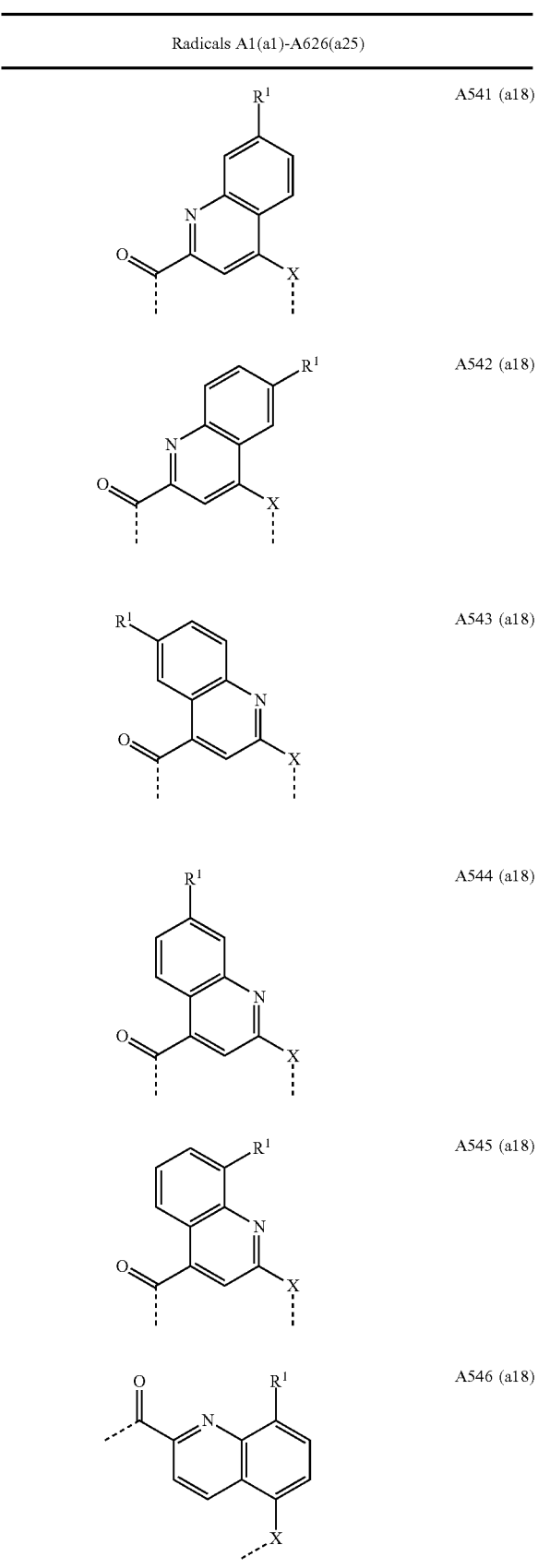
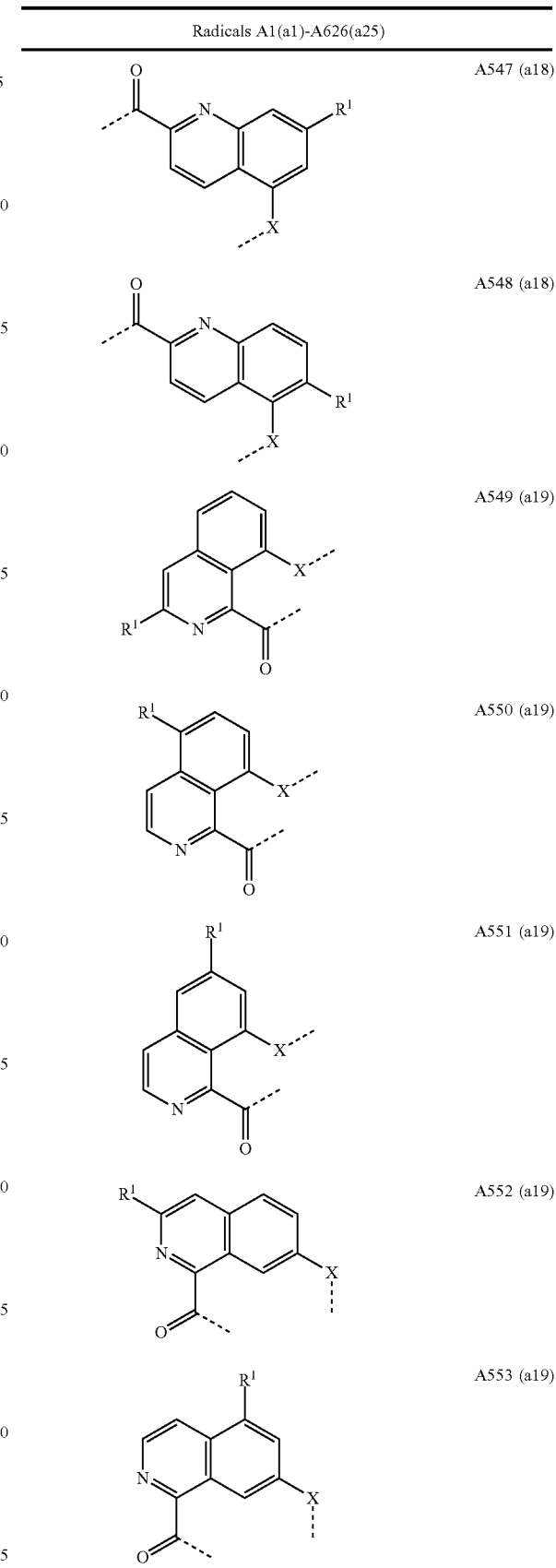

TABLE 10-continued
Radicals A1(a1)-A626(a25)
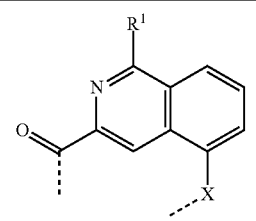 A554 (a19)
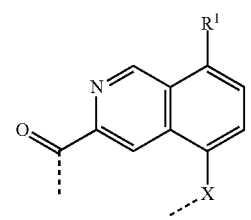 A555 (a19)
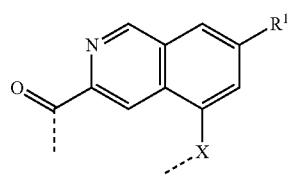 A556 (a19)
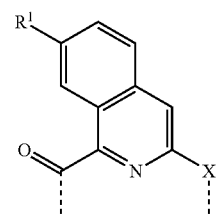 A557 (a19)
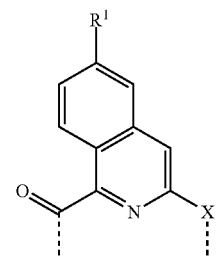 A558 (a19)
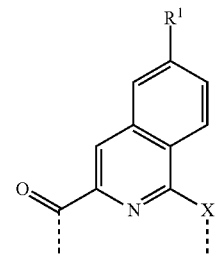 A559 (a19)
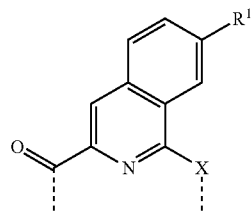 A560 (a19)
TABLE 10-continued
Radicals A1(a1)-A626(a25)
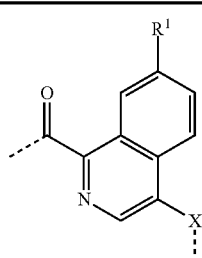 A561 (a19)
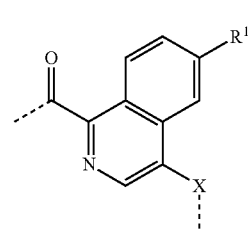 A562 (a19)
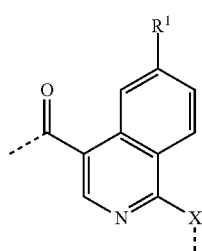 A563 (a19)
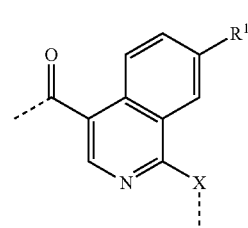 A564 (a19)
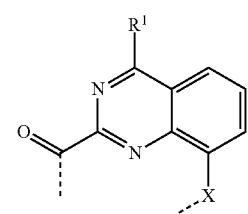 A565 (a20)
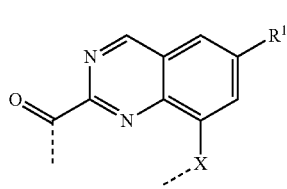 A566 (a20)
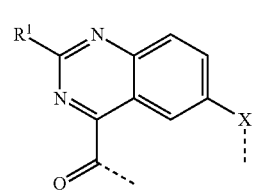 A567 (a20)

TABLE 10-continued
Radicals A1(a1)-A626(a25)
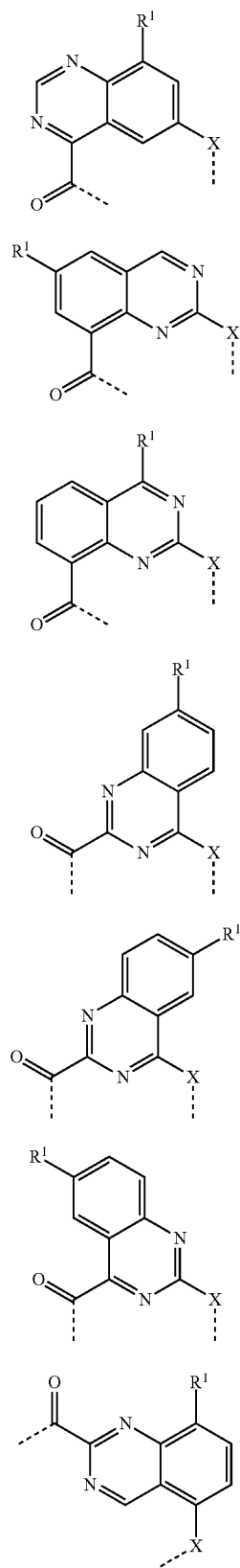
A568 (a20)
A569 (a20)
A570 (a20)
A571 (a20)
A572 (a20)
A573 (a20)
A574 (a20)
TABLE 10-continued
Radicals A1(a1)-A626(a25)
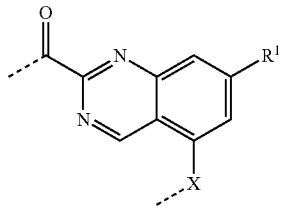
A575 (a20)
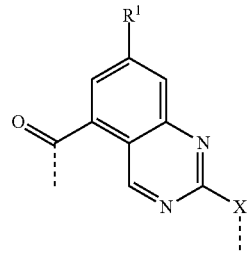
A576 (a20)
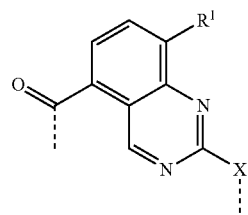
A577 (a20)
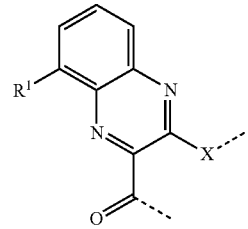
A578 (a21)
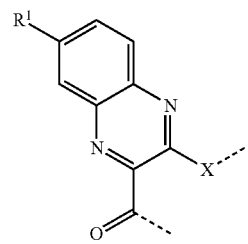
A579 (a21)
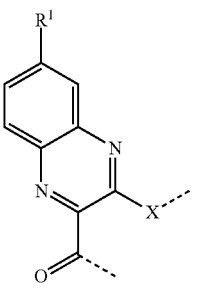
A580 (a21)

TABLE 10-continued
Radicals A1(a1)-A626(a25)
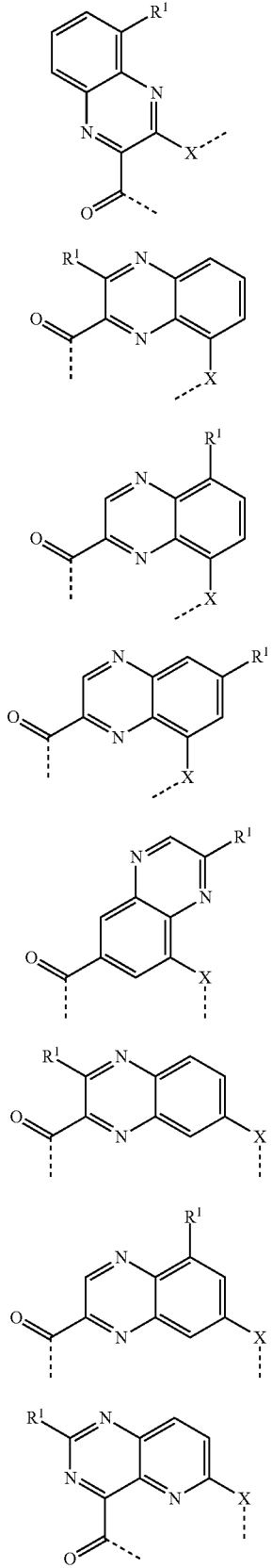
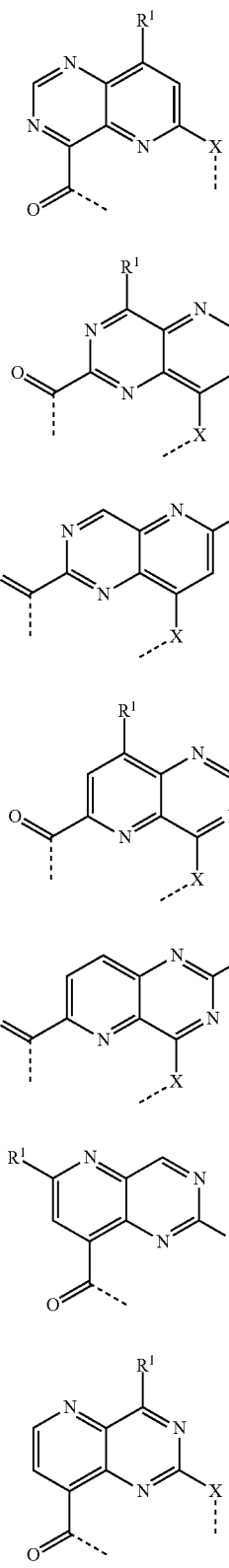

TABLE 10-continued

Radicals A1(a1)-A626(a25)

A596 (a22)
A597 (a22)
A598 (a22)
A599 (a22)
A600 (a22)
A601 (a22)
A602 (a23)
A603 (a23)
A604 (a23)
A605 (a23)
A606 (a23)
A607 (a23)
A608 (a23)
A609 (a24)

TABLE 10-continued
Radicals A1(a1)-A626(a25)
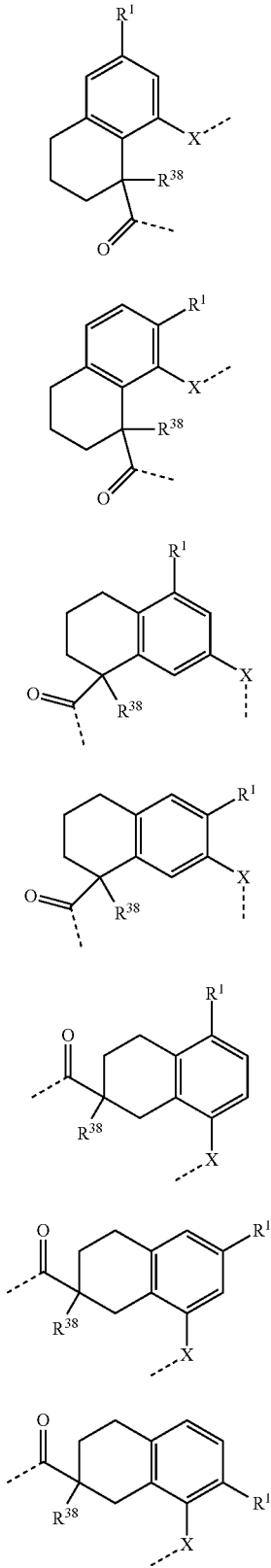
A610 (a24)
A611 (a24)
A612 (a24)
A613 (a24)
A614 (a24)
A615 (a24)
A616 (a24)
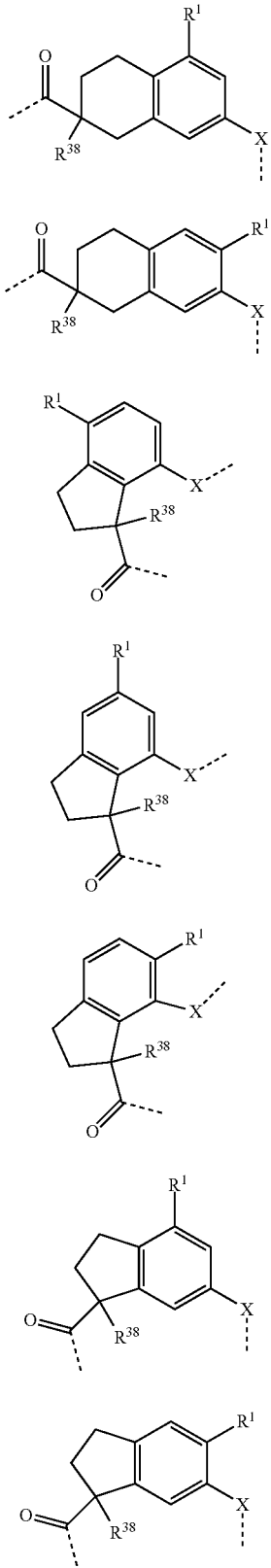
A617 (a24)
A618 (a24)
A619 (a25)
A620 (a25)
A621 (a25)
A622 (a25)
A623 (a25)

TABLE 10-continued

Radicals A1(a1)-A626(a25)

A624 (a25)

A625 (a25)

A626 (a25)

B is selected from the divalent building blocks B1-B21 shown in Table 2, below which are based on optionally substituted cyclic secondary amines carrying a moiety of type —CHR³-LG, wherein LG is a suitable leaving group that can be replaced by the nucleophilic groups of building blocks A thus forming an ether (—O—) or a thioether (—S—) linkage between building blocks of type A and B;

TABLE 2

B1(b1)

B2(b2)

B3(b2)

B4(b3)

TABLE 2-continued

B5(b3)

B6(b3)

B7(b3)

B8(b3)

B9(b3)

B10(b3)

B11(b4)

B12(b4)

B13(b4)

TABLE 2-continued
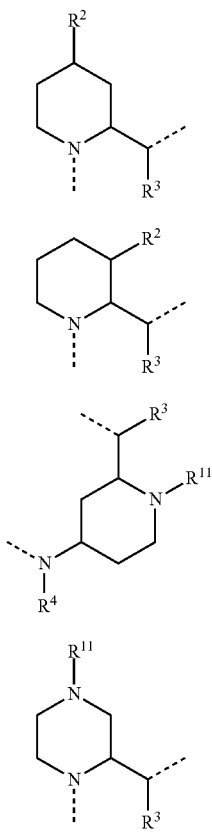
B14(b4)
B15(b4)
B16(b4)
B17(b5)
TABLE 2-continued
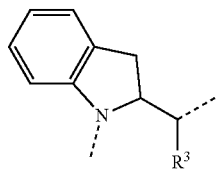
B18(b8)
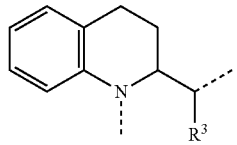
B19(b10)
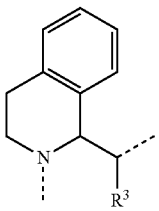
B20(b11)
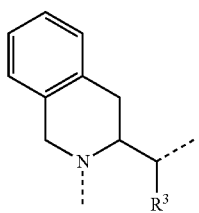
B21(b11)
TABLE 12
Embodiments of Linker C
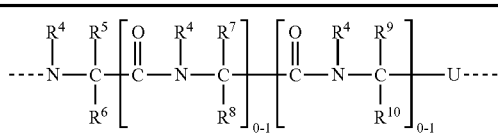
C1
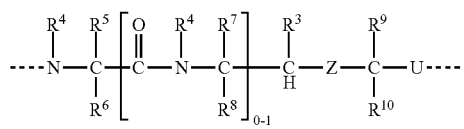
C2
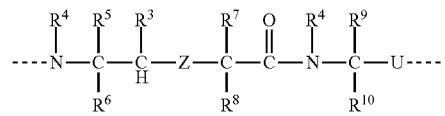
C3
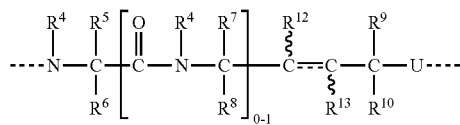
C4
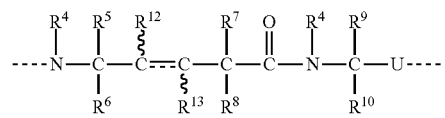
C5

TABLE 12-continued

Embodiments of Linker C

| | |
|---|---|
| (structure) | C6 |
| (structure) | C7 |
| (structure) | C8 |
| (structure) | C9 |
| (structure) | C10 |
| (structure) | C11 |
| (structure) | C12 |
| (structure) | C13 |
| (structure) | C14 |
| (structure) | C15 |
| (structure) | C16 |

TABLE 12-continued

Embodiments of Linker C

| Structure | Label |
|---|---|
| (C17 structure) | C17 |
| (C18 structure) | C18 |
| (C19 structure) | C19 |
| (C20 structure) | C20 |
| (C21 structure) | C21 |
| (C22 structure) | C22 |
| (C23 structure) | C23 |
| (C24 structure) | C24 |
| (C25 structure) | C25 |
| (C26 structure) | C26 |
| (C27 structure) | C27 |

TABLE 12-continued

Embodiments of Linker C

| Structure | Label |
|---|---|
| Chemical structure C28 | C28 |
| Chemical structure C29 | C29 |
| Chemical structure C30 | C30 |
| Chemical structure C31 | C31 |
| Chemical structure C32 | C32 |
| Chemical structure C33 | C33 |
| Chemical structure C34 | C34 |
| Chemical structure C35 | C35 |
| Chemical structure C36 | C36 |
| Chemical structure C37 | C37 |
| Chemical structure C38 | C38 |
| Chemical structure C39 | C39 |

TABLE 12-continued
Embodiments of Linker C
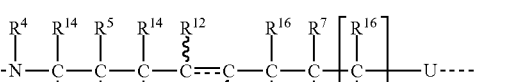 C40
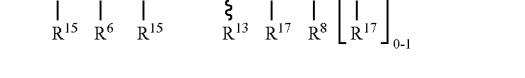 C41
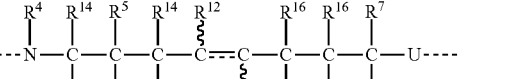 C42
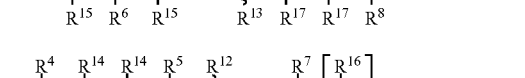 C43
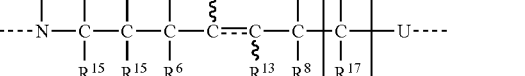 C44
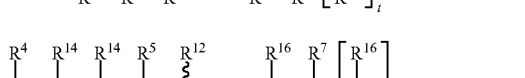 C45
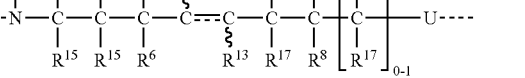 C46
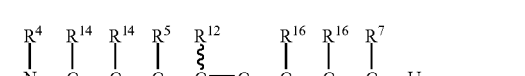 C47
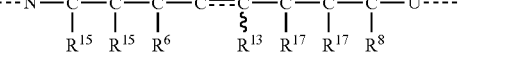 C48
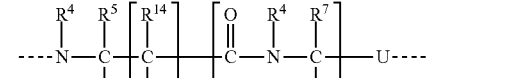 C49
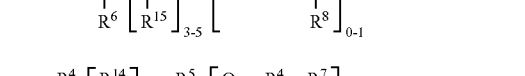 C50
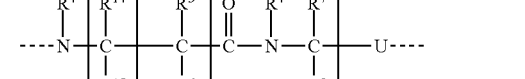 C51

TABLE 12-continued

Embodiments of Linker C (Chemical structures C52 through C62 are shown, which cannot be accurately represented in markdown/LaTeX text format.)

TABLE 12-continued

Embodiments of Linker C

[Structures C63 through C74 depicting chemical linker embodiments with substituents $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, variables $Z$, $U$, and indices $t$, $u$.]

TABLE 12-continued
Embodiments of Linker C
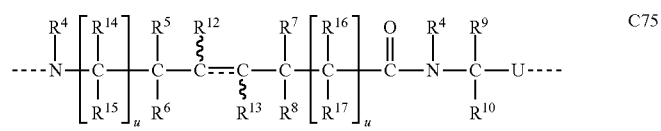 C75
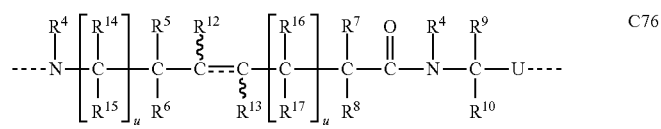 C76
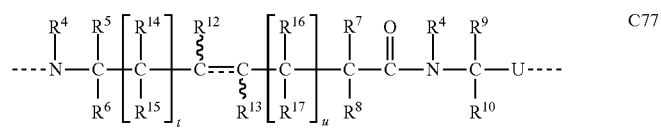 C77
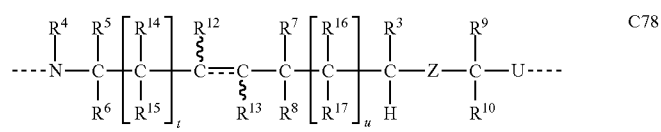 C78
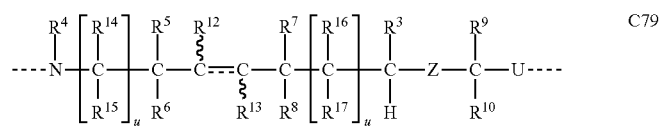 C79
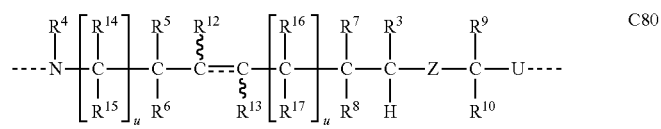 C80
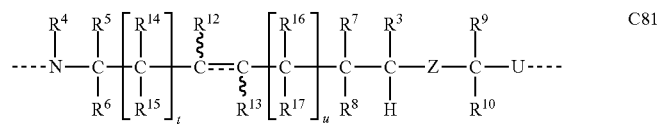 C81
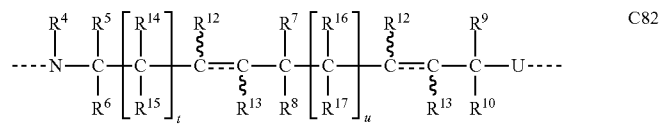 C82
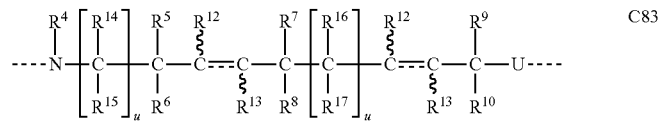 C83
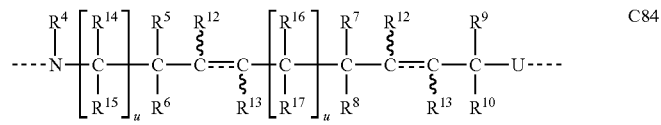 C84
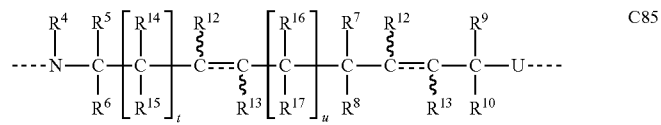 C85

TABLE 12-continued

Embodiments of Linker C

| Structure | Label |
|---|---|
| Chemical structure with groups R⁴, R⁵, R¹⁴, R³, R⁷, R¹⁶, R¹², R⁹, N, C, Z, C=C, U, R⁶, R¹⁵, H, R⁸, R¹⁷, R¹³, R¹⁰ | C86 |
| Chemical structure with similar groups rearranged | C87 |
| Chemical structure with similar groups rearranged | C88 |
| Chemical structure with similar groups rearranged | C89 |
| Chemical structure with amide linkages, groups R⁴, R⁵, R¹⁴, R⁷, R¹⁶, R⁹, O, N, C, U, subscripts 1-5, t, 0-1 | C90 |
| Similar amide-containing structure | C91 |
| Similar amide-containing structure | C92 |
| Similar amide-containing structure | C93 |
| Disulfide-containing structure with S—S linkage, R⁴, R⁵, R¹⁴, R⁷, R¹⁶, R⁹, O, N, C, U, subscripts u, t, 0-1 | C94 |
| Similar disulfide structure | C95 |
| Similar disulfide structure | C96 |

TABLE 12-continued

Embodiments of Linker C

C97: structure with N—C(R⁴)(R⁶)—[C(R⁵)(R¹⁴)(R¹⁵)]ᵤ—S—S—[C(R¹⁶)(R¹⁷)]ₜ—C(R⁷)(R⁸)—C(O)—N(R⁹)—[C(R⁴)(R¹⁰)]₀₋₁—U C98: structure with N—C(R⁴)(R⁶)—[C(R⁵)(R¹⁴)(R¹⁵)]ᵤ—C(O)—C(O)—[C(R¹⁶)(R¹⁷)]ₜ—C(R⁷)(R⁸)—C(O)—N(R⁹)—[C(R⁴)(R¹⁰)]₀₋₁—U C99: structure with N—[C(R⁴)(R¹⁴)(R¹⁵)]ᵤ—C(R⁵)(R⁶)—C(O)—C(O)—[C(R¹⁶)(R¹⁷)]ₜ—C(R⁷)(R⁸)—C(O)—N(R⁹)—[C(R⁴)(R¹⁰)]₀₋₁—U C100: structure with N—[C(R⁴)(R¹⁴)(R¹⁵)]ᵤ—C(R⁵)(R⁶)—C(O)—C(O)—[C(R¹⁶)(R¹⁷)]ₜ—C(R⁷)(R⁸)—C(O)—N(R⁹)—[C(R⁴)(R¹⁰)]₀₋₁—U C101: structure with N—C(R⁴)(R⁶)—[C(R⁵)(R¹⁴)(R¹⁵)]ᵤ—C(O)—C(O)—[C(R¹⁶)(R¹⁷)]ₜ—C(R⁷)(R⁸)—C(O)—N(R⁹)—[C(R⁴)(R¹⁰)]₀₋₁—U $R^1$ is H; F; Cl; Br; I; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl; $-(CR^{18}R^{19})_qOR^{20}$; $-(CR^{18}R^{19})_qNR^4R^{11}$; $-(CR^{18}R^{19})_qNR^4COOR^{21}$; $-(CR^{18}R^{19})_qNR^4COR^{22}$; $-(CR^{18}R^{19})_qNR^4CONR^4R^{11}$; $-(CR^{18}R^{19})_qNR^4SO_2R^{23}$; $-(CR^{18}R^{19})_qNR^4SO_2NR^4R^{11}$; $-(CR^{18}R^{19})_qCOOR^{21}$; $-(CR^{18}R^{19})_qCONR^4R^{11}$; $-(CR^{18}R^{19})_qSO_2NR^4R^{11}$; $-(CR^{18}R^{19})_qPO(OR^{21})_2$; $-(CR^{18}R^{19})_qCOR^{22}$; $-(CR^{18}R^{19})_qSO_2R^{23}$; $-(CR^{18}R^{19})_qOSO_3R^{21}$; $-(CR^{18}R^{19})_qR^{24}$; $-(CR^{18}R^{19})_qR^{25}$; or $-(CR^{18}R^{19})_qR^{26}$.

$R^2$ is H; $CF_3$; lower alkyl; lower alkenyl; lower cycloalkyl; lower heterocycloalkyl; aryl; heteroaryl; lower arylalkyl; lower heteroarylalkyl; $-(CR^{18}R^{19})_qOR^{20}$; $-(CR^{18}R^{19})_qNR^4R^{11}$; $-(CR^{18}R^{19})_qNR^4COOR^{21}$; $-(CR^{18}R^{19})_qNR^4COR^{22}$; $-(CR^{18}R^{19})_qNR^4CONR^4R^{11}$; $-(CR^{18}R^{19})_qNR^4SO_2R^{23}$; $-(CR^{18}R^{19})_qNR^4SO_2NR^4R^{11}$; $-(CR^{18}R^{19})_qCOOR^{21}$; $-(CR^{18}R^{19})_qCONR^4R^{11}$; $-(CR^{18}R^{19})_qSO_2NR^4R^{11}$; $-(CR^{18}R^{19})_qPO(OR^{21})_2$; $-(CR^{18}R^{19})_qCOR^{22}$; $-(CR^{18}R^{19})_qSO_2R^{23}$; $-(CR^{18}R^{19})_qR^{24}$; $-(CR^{18}R^{19})_qR^{25}$; or $-(CR^{18}R^{19})_qR^{26}$.

$R^3$ is defined as in claim 1;

$R^4$ is H; lower alkyl; lower alkenyl; or lower cycloalkyl;

$R^5$, $R^7$ and $R^9$ are independently defined as H; F; $CF_3$; lower alkyl; lower alkenyl; lower cycloalkyl; lower heterocycloalkyl; aryl; heteroaryl; lower arylalkyl; lower heteroarylalkyl; $-(CR^{18}R^{19})_sOR^{20}$; $-(CR^{18}R^{19})_sNR^4R^{11}$; $-(CR^{18}R^{19})_sNR^4COOR^{21}$; $-(CR^{18}R^{19})_sNR^4COR^{22}$; $-(CR^{18}R^{19})_sNR^4CONR^4R^{11}$; $-(CR^{18}R^{19})_sNR^4SO_2R^{23}$; $-(CR^{18}R^{19})_sNR^4SO_2NR^4R^{11}$; $-(CR^{18}R^{19})_qCOOR^{21}$; $-(CR^{18}R^{19})_qCONR^4R^{11}$; $-(CR^{18}R^{19})_qSO_2NR^4R^{11}$; $-(CR^{18}R^{19})_qPO(OR^{21})_2$; $-(CR^{18}R^{19})_qCOR^{22}$; $-(CR^{18}R^{19})_qSO_2R^{23}$; $-(CR^{18}R^{19})_qR^{24}$; $-(CR^{18}R^{19})_qR^{25}$; or $-(CR^{18}R^{19})_qR^{26}$.

$R^6$, $R^8$ and $R^{10}$ are independently defined as H; $CF_3$; or lower alkyl;

$R^{11}$ is H; lower alkyl; lower alkenyl; lower cycloalkyl lower heterocycloalkyl; aryl; heteroaryl; lower arylalkyl; lower heteroarylalkyl; $-(CR^{18}R^{19})_rOR^{20}$; $-(CR^{18}R^{19})_rNR^4R^{27}$; $-(CR^{18}R^{19})_rNR^4COOR^{21}$; $-(CR^{18}R^{19})_rNR^4CONR^4R^{27}$; $-(CR^{18}R^{19})_rNR^4SO_2R^{23}$; $-(CR^{18}R^{19})_rNR^4SO_2NR^4R^{27}$; $-(CR^{18}R^{19})_qCOOR^{21}$; $-(CR^{18}R^{19})_qCONR^4R^{27}$; $-(CR^{18}R^{19})_qCOR^{22}$; $-(CR^{18}R^{19})_qSO_2R^{23}$; $-(CR^{18}R^{19})_qSO_2NR^4R^{27}$; $-(CR^{18}R^{19})_qR^{24}$; $-(CR^{18}R^{19})_sR^{25}$; or $-(CR^{18}R^{19})_qR^{26}$.

$R^{12}$ and $R^{13}$ are independently defined as H; or lower alkyl;

$R^{14}$ and $R^{16}$ are independently defined as H; F; $CF_3$; lower alkyl; lower alkenyl; lower cycloalkyl; lower heterocycloalkyl; aryl; heteroaryl; lower arylalkyl; lower heteroarylalkyl;

$-(CR^{18}R^{19})_sOR^{20}$; $-(CR^{18}R^{19})_sNR^4R^{11}$; $-(CR^{18}R^{19})_sNR^4COOR^{21}$; $-(CR^{18}R^{19})_sNR^4COR^{22}$; $-(CR^{18}R^{19})_sNR^4CONR^4R^{11}$; $-(CR^{18}R^{19})_sNR^4SO_2R^{23}$; $-(CR^{18}R^{19})_qCOOR^{21}$; $-(CR^{18}R^{19})_qCONR^4R^{11}$; $-(CR^{18}R^{19})_qCOR^{22}$;

$R^{15}$ and $R^{17}$ are independently defined as H; $CF_3$; lower alkyl;

$R^{18}$ is H; F; $CF_3$; lower alkyl; lower alkenyl; lower cycloalkyl; lower heterocycloalkyl; aryl; heteroaryl; lower arylalkyl; lower heteroarylalkyl;
—$(CR^{29}R^{30})_sOR^{31}$; —$(CR^{29}R^{30})_sNR^{28}R^{31}$;
—$(CR^{29}R^{30})_sNR^{28}COOR^{21}$;
—$(CR^{29}R^{30})_sNR^{28}COR^{31}$; —$(CR^{29}R^{30})_s$
$NR^{28}CONR^{28}R^{31}$; —$(CR^{29}R^{30})_sNR^{28}SO_2R^{23}$;
—$(CR^{29}R^{30})_sNR^{28}SO_2NR^{28}R^{31}$;
—$(CR^{29}R^{30})_qCOOR^{21}$; —$(CR^{29}R^{30})_qCONR^{28}R^{31}$;
—$(CR^{29}R^{30})_qSO_2NR^{28}R^{31}$;
—$(CR^{29}R^{30})_qPO(OR^{21})_2$; —$(CR^{29}R^{30})_qCOR^{31}$;
—$(CR^{29}R^{30})_qSO_2R^{23}$;
—$(CR^{29}R^{30})_qR^{24}$; —$(CR^{29}R^{30})_qR^{25}$; or —$(CR^{29}R^{30})_qR^{26}$;

$R^{19}$ is H; $CF_3$; or lower alkyl;

$R^{20}$ is H; lower alkyl; lower alkenyl; lower cycloalkyl; lower heterocycloalkyl; aryl; heteroaryl; lower arylalkyl; lower heteroarylalkyl;
—$(CR^{29}R^{30})_rOR^{31}$; —$(CR^{29}R^{30})_rNR^{28}R^{31}$;
—$(CR^{29}R^{30})_rNR^{28}COOR^{21}$;
—$(CR^{29}R^{30})_rNR^{28}COR^{31}$; —$(CR^{29}R^{30})_r$
$NR^{28}CONR^{28}R^{31}$; —$(CR^{29}R^{30})_rNR^{28}SO_2R^{23}$;
—$(CR^{29}R^{30})_qCOOR^{21}$; —$(CR^{29}R^{30})_qCONR^{28}R^{31}$;
—$(CR^{29}R^{30})_qSO_2NR^{28}R^{31}$;
—$(CR^{29}R^{30})_qCOR^{31}$; —$(CR^{29}R^{30})_qSO_2R^{23}$;
—$(CR^{29}R^{30})_qR^{24}$; —$(CR^{29}R^{30})_qR^{25}$; or —$(CR^{29}R^{30})_qR^{26}$;

$R^{21}$ and $R^{23}$ are as defined in claim 1;

$R^{22}$ lower alkyl; lower alkenyl; lower cycloalkyl; lower heterocycloalkyl; aryl; heteroaryl; lower arylalkyl; lower heteroarylalkyl;
—$(CR^{29}R^{30})_sOR^{31}$; —$(CR^{29}R^{30})_sNR^{28}R^{31}$;
—$(CR^{29}R^{30})_sNR^{28}COOR^{21}$;
—$(CR^{29}R^{30})_sNR^{28}COR^{31}$; —$(CR^{29}R^{30})_s$
$NR^{28}CONR^{28}R^{31}$; —$(CR^{29}R^{30})_sNR^{28}SO_2—R^{23}$;
—$(CR^{29}R^{30})_sCOOR^{21}$; —$(CR^{29}R^{30})_sCONR^{28}R^{31}$;
—$(CR^{29}R^{30})_sSO_2NR^{28}R^{31}$;
—$(CR^{29}R^{30})_tCOR^{31}$; —$(CR^{29}R^{30})_sSO_2R^{23}$;
—$(CR^{29}R^{30})_tR^{24}$; —$(CR^{29}R^{30})_tR^{25}$; or —$(CR^{29}R^{30})_tR^{26}$;

$R^{24}$, $R^{25}$ and $R^{26}$, $R^{27}$ and $R^{28}$ are as defined in claim 1;

$R^{29}$ is H; F; $CF_3$; lower alkyl; lower alkenyl; lower cycloalkyl; lower heterocycloalkyl; aryl; heteroaryl; lower arylalkyl; lower heteroarylalkyl;
—$(CR^{32}R^{33})_sOR^{31}$; —$(CR^{32}R^{33})_sNR^{28}R^{31}$;
—$(CR^{32}R^{33})_sNR^{28}COOR^{21}$;
—$(CR^{32}R^{33})_sNR^{28}COR^{31}$; —$(CR^{32}R^{33})_s$
$NR^{28}CONR^{28}R^{31}$; —$(CR^{32}R^{33})_sNR^{28}SO_2R^{23}$;
—$(CR^{32}R^{33})_sCOOR^{21}$; —$(CR^{32}R^{33})_qCONR^{28}R^{31}$;
—$(CR^{32}R^{33})_qSO_2NR^{28}R^{31}$;
—$(CR^{32}R^{33})_qPO(OR^{21})_2$; —$(CR^{32}R^{33})_qCOR^{31}$;
—$(CR^{32}R^{33})_qSO_2R^{23}$;
—$(CR^{32}R^{33})_qR^{31}$;

$R^{30}$ and $R^{33}$ are H; $CF_3$; lower alkyl;

$R^{31}$ and $R^{32}$ are as defined in claim 1;

$R^{34}$ and $R^{35}$ are independently defined as H; F; Cl; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl; —$(CR^{29}R^{30})_qOR^{31}$; —$(CR^{29}R^{30})_qNR^{28}R^{31}$;
—$(CR^{29}R^{30})_qNR^{28}COOR^{21}$; —$(CR^{29}R^{30})_qNR^{28}COR^{31}$;
—$(CR^{29}R^{30})_qNR^{28}CONR^{28}R^{31}$;
—$(CR^{29}R^{30})_qNR^{28}SO_2R^{23}$; —$(CR^{29}R^{30})_qCOOR^{21}$;
—$(CR^{29}R^{30})_qCONR^{28}R^{31}$; —$(CR^{29}R^{30})_qSO_2NR^{28}R^{31}$;
—$(CR^{29}R^{30})_qCOR^{31}$;
—$(CR^{29}R^{30})_qSO_2R^{23}$; or —$(CR^{29}R^{30})_qR^{31}$;

$R^{36}$ is as defined in claim 1;

$R^{37}$ is H; lower alkyl; lower alkenyl; lower cycloalkyl; lower heterocycloalkyl; aryl; heteroaryl; lower arylalkyl; lower heteroarylalkyl;
—$(CR^{29}R^{30})_rOR^{31}$; —$(CR^{29}R^{30})_rNR^{28}R^{31}$;
—$(CR^{29}R^{30})_rNR^{28}COOR^{21}$; —$(CR^{29}R^{30})_rNR^{28}COR^{31}$;
—$(CR^{29}R^{30})_rNR^{28}CONR^{28}R^{31}$;
—$(CR^{29}R^{30})_rNR^{28}SO_2R^{23}$; —$(CR^{29}R^{30})_qCOOR^{21}$;
—$(CR^{29}R^{30})_qCONR^{28}R^{31}$; —$(CR^{29}R^{30})_rSO_2NR^{28}R^{31}$;
—$(CR^{29}R^{30})_qCOR^{31}$;
—$(CR^{29}R^{30})_qSO_2R^{23}$; or —$(CR^{29}R^{30})_qR^{31}$;

$R^{38}$ is H; lower alkyl; lower alkenyl; lower cycloalkyl; lower heterocycloalkyl; aryl; heteroaryl; lower arylalkyl; lower heteroarylalkyl;
—$(CR^{29}R^{30})_qOR^{31}$; —$(CR^{29}R^{30})_qNR^{28}R^{31}$;
—$(CR^{29}R^{30})_qNR^{28}COOR^{21}$;
—$(CR^{29}R^{30})_qNR^{28}COR^{31}$; —$(CR^{29}R^{30})_q$
$NR^{28}CONR^{28}R^{31}$; —$(CR^{29}R^{30})_qCOOR^{21}$;
—$(CR^{29}R^{30})_qCONR^{28}R^{31}$; —$(CR^{29}R^{30})_qCOR^{31}$; or
—$(CR^{29}R^{30})_qR^{31}$;

$R^{39}$; $R^{40}$; $R^{41}$; $R^{42}$; $R^{43}$; $R^{44}$; $R^{45}$; $R^{46}$; $R^{47}$; $R^{48}$; $R^{49}$ and $R^{50}$ are as defined in claim 1;

the variable heteroatom Z and the connector U are defined as:

Z being O; S(=O); or S(=O)$_2$; and

U being —C(=O)—; —NR$^4$—C(=O)—; —C(=O)—C(=O)—; or —C(—OR$^{20}$)$_2$—C(=O)—; and substituents that can be pairwise taken together and form optionally substituted cycloalkyl or heterocycloalkyl moieties;

structural elements that can form one of the groups of formulae H111-H118 (Table 9);

variable heteroatoms Q, T, X and Y; and indices q-u being defined as in claim 1.

3. Compounds according to claim 2 wherein A is A1(a1); A2(a1); A3(a1); A4(a1); A5(a1); A6(a1); A7(a1); A9(a1); A10(a1); A73(a2); A170(a4); A209(a7); A240(a10); A272 (a10); A532(a18); A609(a24); A612(a24) and A614(a24) as shown in Table 13, below;

TABLE 13

Building Blocks of Type A

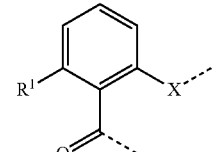

A1(a1)

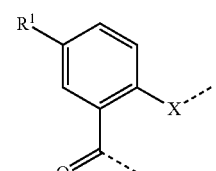

A2(a1)

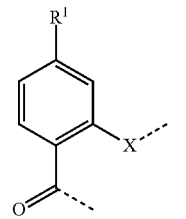

A3(a1)

TABLE 13-continued
Building Blocks of Type A
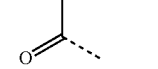
A4(a1)
A5(a1)
A6(a1)
A7(a1)
A9(a1)
A10(a1)
A73(a2)
A170(a4)
TABLE 13-continued
Building Blocks of Type A
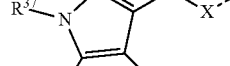
A209(a7)
A240(a10)
A272(a10)
A532(a18)
A609(a24)
A612(a24)
A614(a24)
B is B4(b3); B5(b3); B6(b3); B7(b3); B8(b3); B9(b3); B10(b3); B12(b4); B13(b4); B14(b4); B15(b4); B16(b4) or B17(b5) as shown in Table 14, below;

TABLE 14

Building Blocks of Type B

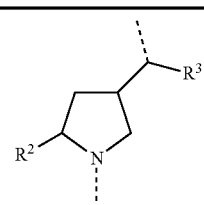 B4(b3)

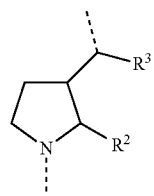 B5(b3)

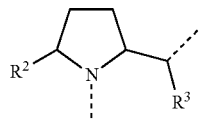 B6(b3)

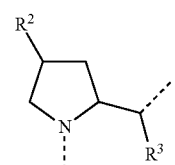 B7(b3)

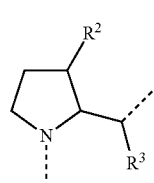 B8(b3)

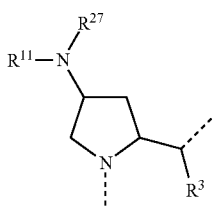 B9(b3)

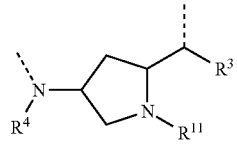 B10(b3)

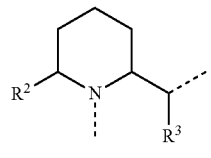 B12(b4)

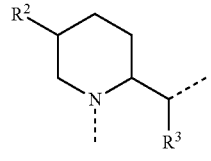 B13(b4)

TABLE 14-continued

Building Blocks of Type B

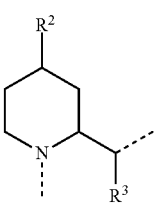 B14(b4)

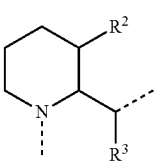 B15(b4)

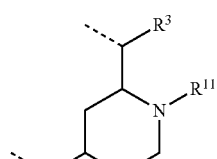 B16(b4)

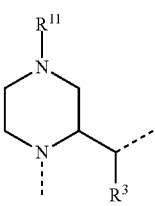 B17(b5)

linker C is one of the groups shown in Table 15, below;

TABLE 15

Linkers of type C $$\text{----N}(R^4)\text{--C}(R^5)(R^6)\text{--[C(=O)--N}(R^4)\text{--C}(R^7)(R^8)]_{0-1}\text{--C(=O)--N}(R^4)\text{--C}(R^9)(R^{10})_{0-1}\text{--U----}$$ C1

$$\text{----N}(R^4)\text{--C}(R^5)(R^6)\text{--[C(=O)--N}(R^4)\text{--C}(R^7)(R^8)]_{0-1}\text{--C}(R^3)(H)\text{--Z--C}(R^9)(R^{10})\text{--U----}$$ C2

$$\text{----N}(R^4)\text{--C}(R^5)(R^6)\text{--C}(R^3)(H)\text{--Z--C}(R^7)(R^8)\text{--C(=O)--N}(R^4)\text{--C}(R^9)(R^{10})\text{--U----}$$ C3

$$\text{----N}(R^4)\text{--C}(R^5)(R^6)\text{--[C(=O)--N}(R^4)\text{--C}(R^7)(R^8)]_{0-1}\text{--C}(R^{12})=C(R^{13})\text{--C}(R^9)(R^{10})\text{--U----}$$ C4

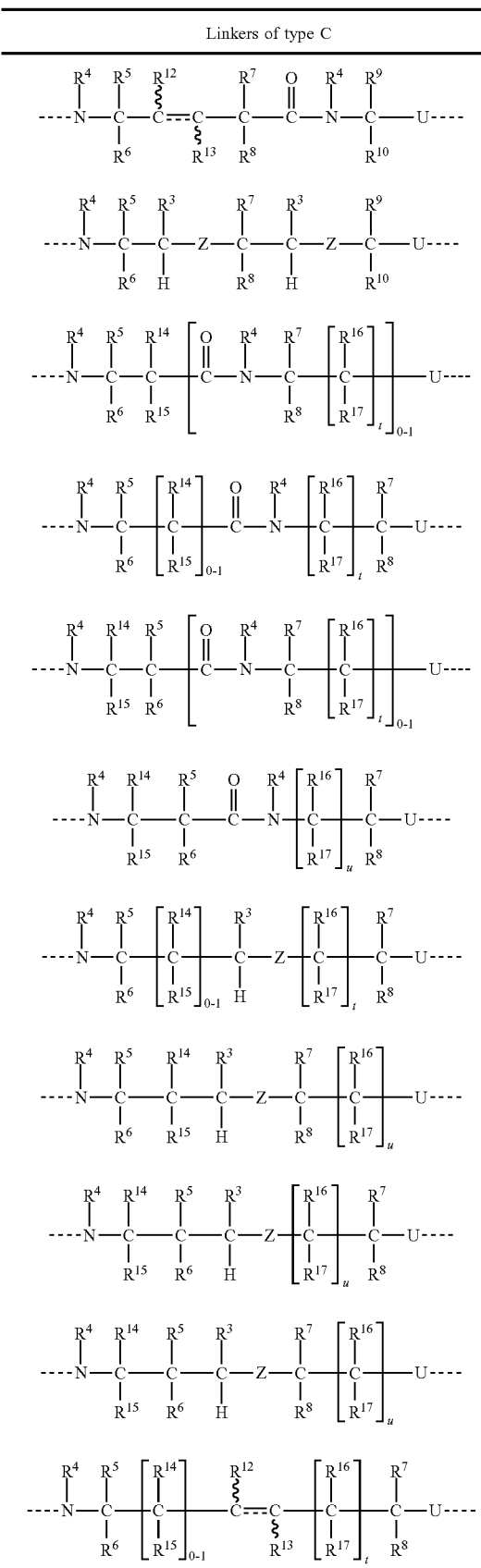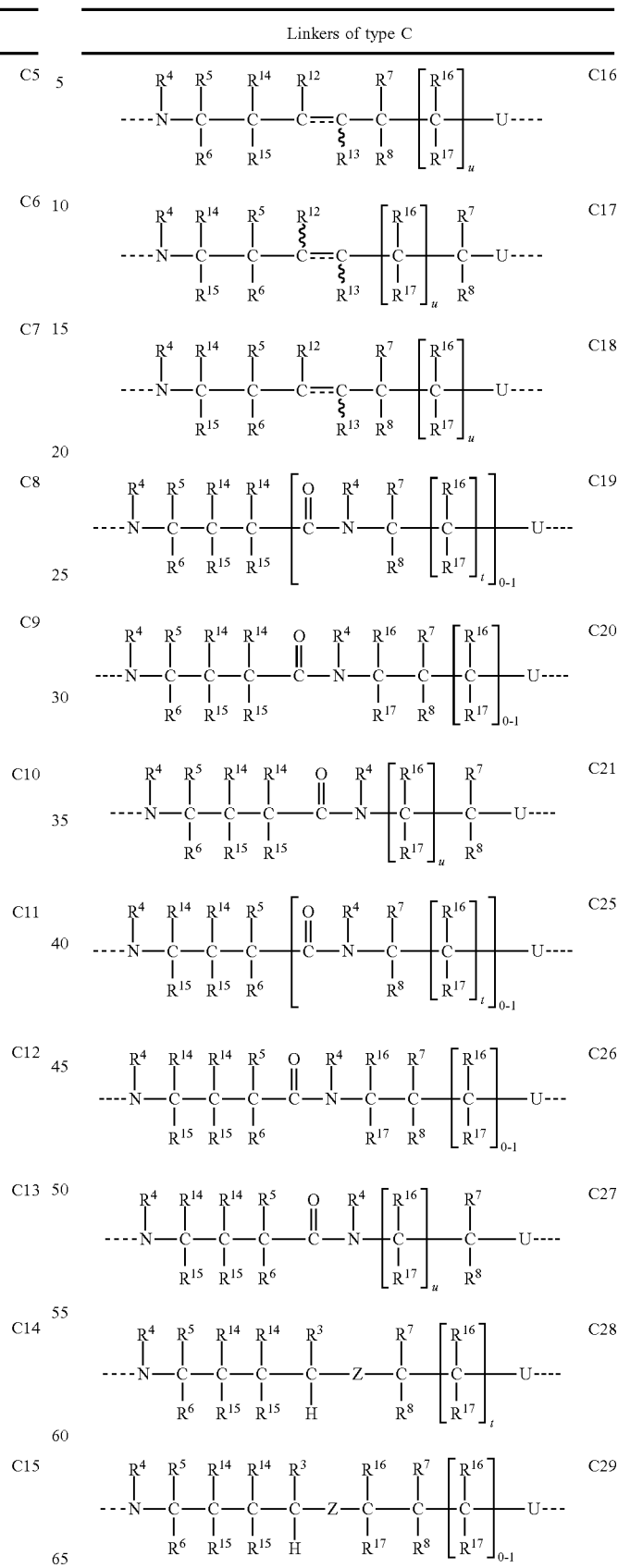

TABLE 15-continued
Linkers of type C
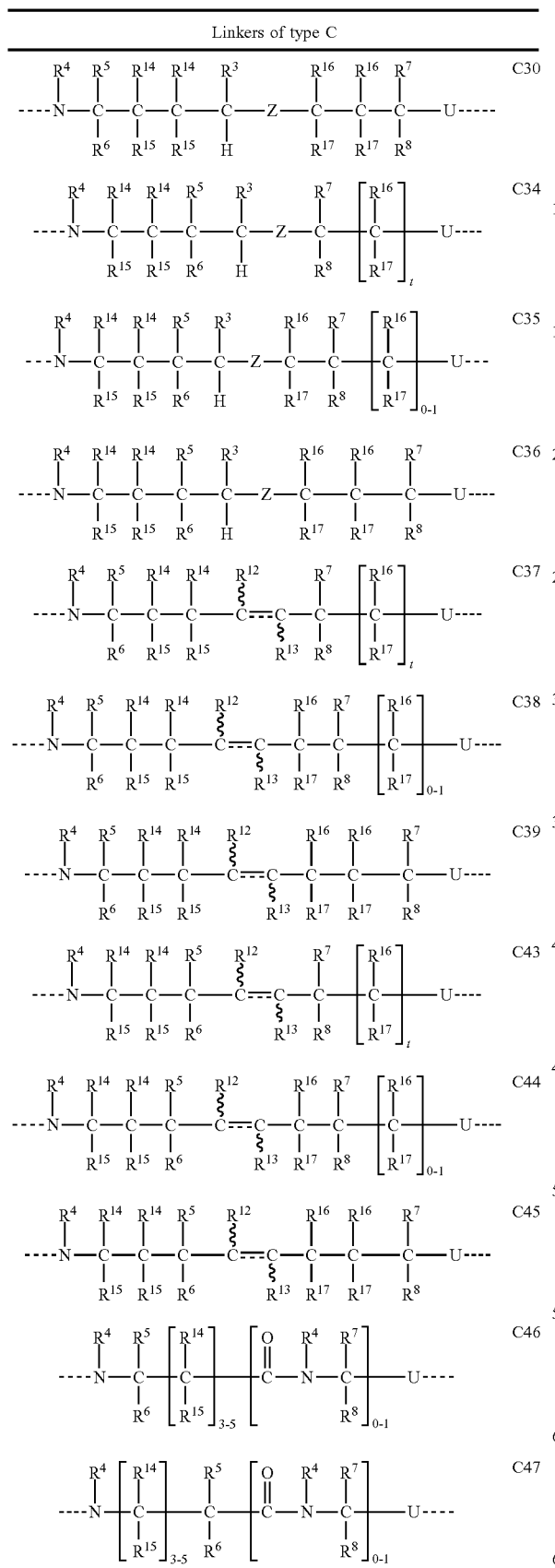
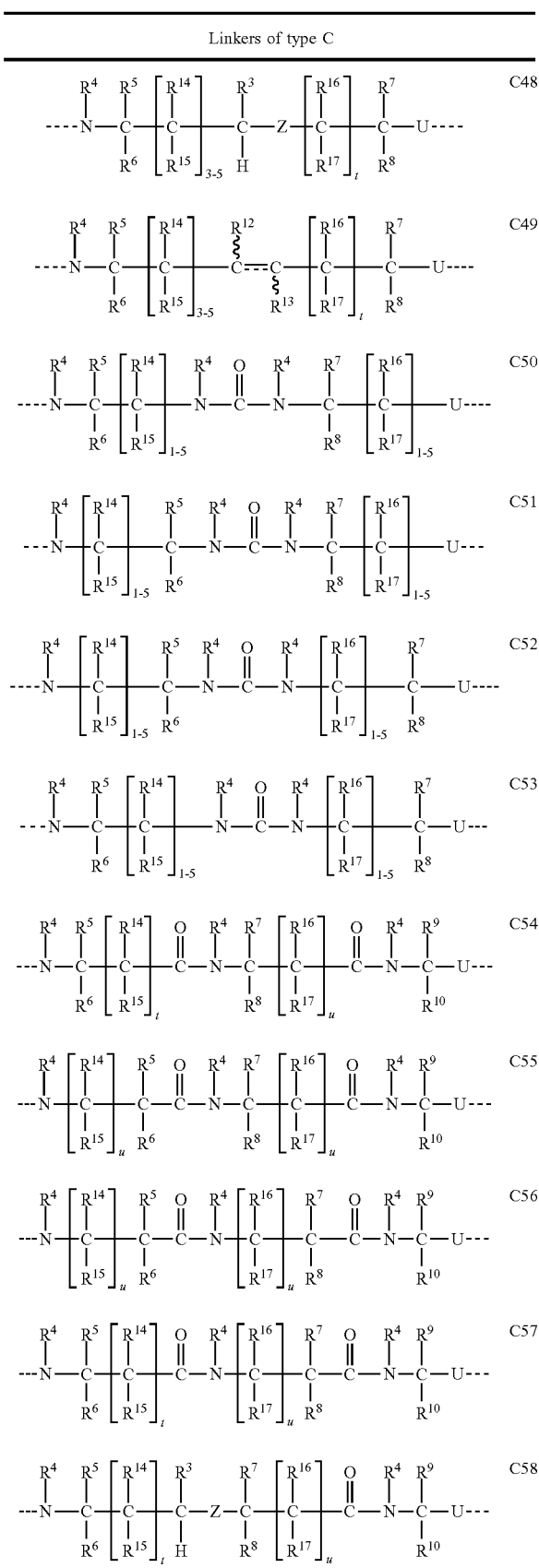

TABLE 15-continued

Linkers of type C (Structures C59 through C81 depicting chemical linker formulas)

TABLE 15-continued

Linkers of type C

[Structures C86 through C93 depicting chemical linker formulas with N, C, Z, U atoms and various R substituents]

4. Compounds according to claim 3 wherein the building blocks of type A are A1(a1); A2(a1); A3(a1); A4(a1); A5(a1); A6(a1); A7(a1); A9(a1); A10(a1); A73(a2); A170 (a4); A209(a7); A240(a10); A272(a10); A532(a18); A614 (a24) as shown in Table 16, below;

TABLE 16

Building Blocks of Type A

[Structures A1(a1), A2(a1), A3(a1), A4(a1), A5(a1), A6(a1), A7(a1), A9(a1), A10(a1) depicting substituted benzene ring building blocks with $R^1$ and X substituents and carbonyl/ether attachment points]

TABLE 16-continued

Building Blocks of Type A

| Structure | Label |
|---|---|
| (pyridine with R¹, C=O, O) | A73(a2) |
| (pyrimidine with R¹, C=O, S) | A170(a4) |
| (thiophene with R¹, O, C=O) | A209(a7) |
| (indole with R³⁷, R¹, C=O, O) | A272(a10) |
| (quinoline with R¹, C=O, O) | A532(a18) |
| (tetrahydronaphthalene with R¹, R³⁸, C=O, O) | A614(a24) | the building blocks of type B are B7, B8, B9 and B-17 as shown in Table 17, below;

TABLE 17

Building Blocks of Type B

| Structure | Label |
|---|---|
| pyrrolidine B7-1 | B7-1 |

TABLE 17-continued

Building Blocks of Type B

| Structure | Label |
|---|---|
| pyrrolidine | B7-2 |
| pyrrolidine | B7-3 |
| pyrrolidine | B7-4 |
| pyrrolidine | B8-1 |
| pyrrolidine | B8-2 |
| pyrrolidine | B8-3 |
| pyrrolidine | B8-4 |
| pyrrolidine | B9-1 |
| pyrrolidine | B9-2 |

TABLE 17-continued

Building Blocks of Type B

[Structure B9-3: pyrrolidine with R¹¹—N(R²⁷) substituent and isopropyl group, N-R³]

[Structure B9-4: pyrrolidine with R¹¹—N(R²⁷) substituent and isopropyl group, N-R³ (different stereochemistry)]

[Structure B17-1: piperazine with R¹¹ on one N, isopropyl group, N-R³]

[Structure B17-2: piperazine with R¹¹ on one N, isopropyl group, N-R³ (different stereochemistry)]

the linkers C are those listed in Table 18, below;

TABLE 18

Embodiments of Linker C

C1: ----N(R⁴)—C(R⁵)(R⁶)—[C(=O)—N(R⁴)—C(R⁷)(R⁸)]₀₋₁—[C(=O)—N(R⁴)—C(R⁹)(R¹⁰)]₀₋₁—U----

C2: ----N(R⁴)—C(R⁵)(R⁶)—[C(=O)—N(R⁴)—C(R⁷)(R⁸)]₀₋₁—C(R³)(H)—Z—C(R⁹)(R¹⁰)—U----

C3: ----N(R⁴)—C(R⁵)(R⁶)—C(R³)(H)—Z—C(R⁷)(R⁸)—C(=O)—N(R⁴)—C(R⁹)(R¹⁰)—U----

C4: ----N(R⁴)—C(R⁵)(R⁶)—[C(=O)—N(R⁴)—C(R⁷)(R⁸)]₀₋₁—C(R¹²)(R¹³)=C(R⁹)(R¹⁰)—U----

C5: ----N(R⁴)—C(R⁵)(R⁶)—C(R¹²)(R¹³)=C(R⁷)(R⁸)—C(=O)—N(R⁴)—C(R⁹)(R¹⁰)—U----

C6: ----N(R⁴)—C(R⁵)(R⁶)—C(R³)(H)—Z—C(R⁷)(R⁸)—C(R³)(H)—Z—C(R⁹)(R¹⁰)—U----

C7: ----N(R⁴)—C(R⁵)(R⁶)—[C(R¹⁴)(R¹⁵)]₀₋₁—[C(=O)—N(R⁴)—C(R⁷)(R⁸)—[C(R¹⁶)(R¹⁷)]ₜ]₀₋₁—U----

C8: ----N(R⁴)—C(R⁵)(R⁶)—[C(R¹⁴)(R¹⁵)]₀₋₁—C(=O)—N(R⁴)—C(R⁷)(R⁸)—[C(R¹⁶)(R¹⁷)]ₜ—U----

C9: ----N(R⁴)—C(R¹⁴)(R¹⁵)—C(R⁵)(R⁶)—[C(=O)—N(R⁴)—C(R⁷)(R⁸)—[C(R¹⁶)(R¹⁷)]ₜ]₀₋₁—U----

C10: ----N(R⁴)—C(R¹⁴)(R¹⁵)—C(R⁵)(R⁶)—C(=O)—N(R⁴)—C(R⁷)(R⁸)—[C(R¹⁶)(R¹⁷)]ᵤ—U----

C11: ----N(R⁴)—C(R⁵)(R⁶)—[C(R¹⁴)(R¹⁵)]₀₋₁—C(R³)(H)—Z—C(R⁷)(R⁸)—[C(R¹⁶)(R¹⁷)]ₜ—U----

C12: ----N(R⁴)—C(R⁵)(R⁶)—C(R¹⁴)(R¹⁵)—C(R³)(H)—Z—C(R⁷)(R⁸)—[C(R¹⁶)(R¹⁷)]ᵤ—U----

C13: ----N(R⁴)—C(R¹⁴)(R¹⁵)—C(R⁵)(R⁶)—C(R³)(H)—Z—[C(R¹⁶)(R¹⁷)]ᵤ—C(R⁷)(R⁸)—U----

C14: ----N(R⁴)—C(R¹⁴)(R¹⁵)—C(R⁵)(R⁶)—C(R³)(H)—Z—C(R⁷)(R⁸)—[C(R¹⁶)(R¹⁷)]ᵤ—U----

C15: ----N(R⁴)—C(R⁵)(R⁶)—[C(R¹⁴)(R¹⁵)]₀₋₁—C(R¹²)(R¹³)=C(R⁷)(R⁸)—[C(R¹⁶)(R¹⁷)]ₜ—U----

TABLE 18-continued

Embodiments of Linker C (Structural diagrams of linker embodiments C16, C17, C18, C19, C20, C21, C25, C26, C27, C28, C29, C30, C34, C35, C36, C37, C38, C39, C43, C44, C45, C46, and C47 are shown.)

TABLE 18-continued

Embodiments of Linker C

TABLE 18-continued

Embodiments of Linker C

C90: Structure with groups $R^4, R^5, [R^{14}, R^{15}]_{1-5}, R^4, O, R^7, [R^{16}, R^{17}]_t, O, R^4, R^9, [R^{10}]_{0-1}$ — U C91: Structure with groups $R^4, [R^{14}, R^{15}]_{1-5}, R^5, R^6, R^4, O, R^7, [R^{16}, R^{17}]_t, R^8, O, R^4, R^9, [R^{10}]_{0-1}$ — U C92: Structure with groups $R^4, [R^{14}, R^{15}]_{1-5}, R^5, R^6, R^4, O, [R^{16}, R^{17}]_t, R^7, R^8, O, R^4, R^9, [R^{10}]_{0-1}$ — U C93: Structure with groups $R^4, R^5, [R^{14}, R^{15}]_{1-5}, R^6, R^4, O, [R^{16}, R^{17}]_t, R^7, R^8, O, R^4, R^9, [R^{10}]_{0-1}$ — U $R^1$ is H; F; Cl; $CF_3$; $OCF_3$; $OCHF_2$; $NO_2$; CN; lower alkyl; lower alkenyl; lower alkynyl; lower cycloalkyl; lower heterocycloalkyl; aryl; heteroaryl; lower arylalkyl; lower heteroarylalkyl;
—$(CR^{18}R^{19})_qOR^{20}$; —$(CR^{18}R^{19})_qNR^4R^{11}$; —$(CR^{18}R^{19})_q NR^4COR^{22}$;
—$(CR^{18}R^{19})_qNR^4CONR^4R^{11}$; —$(CR^{18}R^{19})_q NR^4SO_2R^{23}$; —$(CR^{18}R^{19})_qNR^4SO_2NR^4R^{11}$;
—$(CR^{18}R^{19})_qCOOR^{21}$; —$(CR^{18}R^{19})_qCONR^4R^{11}$; —$(CR^{18}R^{19})_qSO_2NR^4R^{11}$;
—$(CR^{18}R^{19})_qCOR^{22}$; —$(CR^{18}R^{19})_qSO_2R^{23}$; —$(CR^{18}R^{19})_qR^{24}$; —$(CR^{18}R^{19})_qR^{25}$; or —$(CR^{18}R^{19})_q R^{26}$;

$R^2$ is H; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_qOR^{20}$; —$(CR^{18}R^{19})_qNR^4R^{11}$; —$(CR^{18}R^{19})_q NR^4COR^{22}$;
—$(CR^{18}R^{19})_qNR^4CONR^4R^{11}$; —$(CR^{18}R^{19})_q NR^4SO_2R^{23}$; —$(CR^{18}R^{19})_qNR^4SO_2NR^4R^{11}$;
—$(CR^{18}R^{19})_qCOOR^{21}$; —$(CR^{18}R^{19})_qCONR^4R^{11}$; —$(CR^{18}R^{19})_qSO_2NR^4R^{11}$;
—$(CR^{18}R^{19})_qCOR^{22}$; —$(CR^{18}R^{19})_qSO_2R^{23}$; —$(CR^{18}R^{19})_qR^{24}$; —$(CR^{18}R^{19})_qR^{25}$; or —$(CR^{18}R^{19})_q R^{26}$, $R^3$ is as defined in claim 1;

$R^4$ is H; lower alkyl; lower alkenyl;

$R^5$, $R^7$ and $R^9$ are independently defined as H; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_sOR^{20}$; —$(CR^{18}R^{19})_sNR^4R^{11}$; —$(CR^{18}R^{19})_s NR^4COR^{22}$;
—$(CR^{18}R^{19})_sNR^4CONR^4R^{11}$; —$(CR^{18}R^{19})_s NR^4SO_2R^{23}$; —$(CR^{18}R^{19})_qCOOR^{21}$;
—$(CR^{18}R^{19})_qCONR^4R^{11}$; —$(CR^{18}R^{19})_qSO_2NR^4R^{11}$; —$(CR^{18}R^{19})_qCOR^{22}$;
—$(CR^{18}R^{19})_qSO_2R^{23}$; —$(CR^{18}R^{19})_qR^{24}$; —$(CR^{18}R^{19})_qR^{25}$; or —$(CR^{18}R^{19})_q R^{26}$;

$R^6$, $R^8$ and $R^{10}$ are independently defined as H; $CF_3$; or $CH_3$;

$R^{11}$ is H; lower alkyl; lower alkenyl; lower cycloalkyl; lower heterocycloalkyl; aryl; heteroaryl; lower arylalkyl; lower heteroarylalkyl; —$(CR^{18}R^{19})_rOR^{20}$;
—$(CR^{18}R^{19})_rNR^4R^{27}$; —$(CR^{18}R^{19})_rNR^4CONR^4R^{27}$;
—$(CR^{18}R^{19})_rNR^4SO_2R^{23}$; —$(CR^{18}R^{19})_qCOOR^{21}$;
—$(CR^{18}R^{19})_qCONR^4R^{27}$; —$(CR^{18}R^{19})_qCOR^{22}$;
—$(CR^{18}R^{19})_qR^{24}$; —$(CR^{18}R^{19})_sR^{25}$; or —$(CR^{18}R^{19})_q R^{26}$;

$R^{12}$ and $R^{13}$ are independently defined as H; or lower alkyl;

$R^{14}$ and $R^{16}$ are independently defined as H; F; $CF_3$; lower alkyl; lower alkenyl; lower cycloalkyl; lower heterocycloalkyl; aryl; heteroaryl; lower arylalkyl; lower heteroarylalkyl;
—$(CR^{18}R^{19})_sOR^{20}$; —$(CR^{18}R^{19})_sNR^4R^{11}$; —$(CR^{18}R^{19})_s NR^4COR^{22}$;
—$(CR^{18}R^{19})_qCOOR^{21}$; or —$(CR^{18}R^{19})_qCONR^4R^{11}$;

$R^{15}$ and $R^{17}$ are independently defined as H; $CF_3$; or $CH_3$;

$R^{18}$ is H; F; $CF_3$; lower alkyl; lower alkenyl; lower cycloalkyl; lower heterocycloalkyl; aryl; heteroaryl; lower arylalkyl; lower heteroarylalkyl;
—$(CR^{29}R^{30})_sOR^{31}$; —$(CR^{29}R^{30})_sNR^{28}R^{31}$;
—$(CR^{29}R^{30})_sNR^{28}COR^{31}$; —$(CR^{29}R^{30})_s NR^{28}CONR^{28}R^{31}$; —$(CR^{29}R^{30})_sNR^{28}SO_2R^{23}$;
—$(CR^{29}R^{30})_qCOOR^{21}$; —$(CR^{29}R^{30})_qCONR^{28}R^{31}$; —$(CR^{29}R^{30})_qSO_2NR^{28}R^{31}$;
—$(CR^{29}R^{30})_qCOR^{31}$; —$(CR^{29}R^{30})_qSO_2R^{23}$;
—$(CR^{29}R^{30})_qR^{24}$;
—$(CR^{29}R^{30})_qR^{25}$; or —$(CR^{29}R^{30})_qR^{26}$;

$R^{19}$ is H; $CF_3$; or $CH_3$;

$R^{20}$ is H; lower alkyl; lower alkenyl; lower cycloalkyl; lower heterocycloalkyl; aryl; heteroaryl; lower arylalkyl; lower heteroarylalkyl;
—$(CR^{29}R^{30})_rOR^{31}$; —$(CR^{29}R^{30})_rNR^{28}R^{31}$;
—$(CR^{29}R^{30})_rNR^{28}COR^{31}$;
—$(CR^{29}R^{30})_rNR^{28}CONR^{28}R^{31}$; —$(CR^{29}R^{30})_r NR^{28}SO_2R^{23}$; —$(CR^{29}R^{30})_qCOOR^{21}$;
—$(CR^{29}R^{30})_qCONR^{28}R^{31}$; —$(CR^{29}R^{30})_qSO_2NR^{28}R^{31}$; —$(CR^{29}R^{30})_qCOR^{31}$;
—$(CR^{29}R^{30})_qSO_2R^{23}$; —$(CR^{29}R^{30})_qR^{24}$; —$(CR^{29}R^{30})_q R^{25}$; or —$(CR^{29}R^{30})_qR^{26}$;

$R^{21}$ and $R^{23}$ are as defined in claim 1;

$R^{22}$ is lower alkyl; lower alkenyl; lower cycloalkyl; lower heterocycloalkyl; aryl; heteroaryl; lower arylalkyl; lower heteroarylalkyl;
—$(CR^{29}R^{30})_sOR^{31}$; —$(CR^{29}R^{30})_sNR^{28}R^{31}$; —$(CR^{29}R^{30})_sNR^{28}COR^{31}$;
—$(CR^{29}R^{30})_sN^{R28}CONR^{28}R^{31}$; —$(CR^{29}R^{30})_s NR^{28}SO_2R^{23}$; —$(CR^{29}R^{30})_sCOOR^{21}$;
—$(CR^{29}R^{30})_sCONR^{28}R^{31}$; —$(CR^{29}R^{30})_sSO_2NR^{28}R^{31}$; —$(CR^{29}R^{30})_sCOR^{31}$;
—$(CR^{29}R^{30})_sSO_2R^{23}$; —$(CR^{29}R^{30})_sR^{24}$;
—$(CR^{29}R^{30})_sR^{25}$; or —$(CR^{29}R^{30})_sR^{26}$;

$R^{24}$, $R^{25}$, $R^{26}$, $R^{27}$ and $R^{28}$ are as defined in claim 1;

$R^{29}$ is H; F; $CF_3$; lower alkyl; lower alkenyl; lower cycloalkyl; lower heterocycloalkyl; aryl; heteroaryl; lower arylalkyl; lower heteroarylalkyl;
—$(CR^{32}R^{33})_sOR^{31}$; —$(CR^{32}R^{33})_sNR^{28}R^{31}$;
—$(CR^{32}R^{33})_sNR^{28}COR^{31}$; —$(CR^{32}R^{33})_s NR^{28}CONR^{28}R^{31}$; —$(CR^{32}R^{33})_qCOOR^{21}$;
—$(CR^{32}R^{33})_qCONR^{28}R^{31}$; —$(CR^{32}R^{33})_qCOR^{31}$; or —$(CR^{32}R^{33})_qR^{31}$;

$R^{30}$ and $R^{33}$ are H; $CF_3$; or $CH_3$;

$R^{31}$ and $R^{32}$ are as defined in claim 1;

$R^{34}$ and $R^{35}$ are independently defined as H; F; Cl; $CF_3$; $OCF_3$; $OCHF_2$; lower alkyl; lower alkenyl; lower alkynyl; lower cycloalkyl; lower heterocycloalkyl; aryl; heteroaryl; lower arylalkyl; lower heteroarylalkyl; —$(CR^{29}R^{30})_qOR^{31}$; —$(CR^{29}R^{30})_qNR^{28}R^{31}$; —$(CR^{29}R^{30})_qNR^{28}COR^{31}$; —$(CR^{29}R^{30})_q$ $NR^{28}CONR^{28}R^{31}$; —$(CR^{29}R^{30})_qNR^{28}SO_2R^{23}$; —$(CR^{29}R^{30})_qCOOR^{21}$; —$(CR^{29}R^{30})_qCONR^{28}R^{31}$; —$(CR^{29}R^{30})_qSO_2NR^{28}R^{31}$; —$(CR^{29}R^{30})_qCOR^{31}$; —$(CR^{29}R^{30})_qSO_2R^{23}$; or —$(CR^{29}R^{30})_qR^{31}$;

$R^{36}$ is as defined in claim 1;

$R^{37}$ is H; lower alkyl; lower alkenyl; lower cycloalkyl; lower heterocycloalkyl; aryl; heteroaryl; lower arylalkyl; lower heteroarylalkyl; —$(CR^{29}R^{30})_rOR^{31}$; —$(CR^{29}R^{30})_rNR^{28}R^{31}$; —$(CR^{29}R^{30})_rNR^{28}COOR^{21}$; —$(CR^{29}R^{30})_rNR^{28}COR^{31}$; —$(CR^{29}R^{30})_rNR^{28}CONR^{28}R^{31}$; —$(CR^{29}R^{30})_q$ $COOR^{21}$; —$(CR^{29}R^{30})_qCONR^{28}R^{31}$; —$(CR^{29}R^{30})_q$ $COR^{31}$; or —$(CR^{29}R^{30})_qR^{31}$;

$R^{38}$ is H; lower alkyl; lower alkenyl; lower cycloalkyl; lower heterocycloalkyl; aryl; heteroaryl; lower arylalkyl; lower heteroarylalkyl; —$(CR^{29}R^{30})_qOR^{31}$; —$(CR^{29}R^{30})_qNR^{28}R^{31}$; —$(CR^{29}R^{30})_qNR^{28}COR^{31}$; —$(CR^{29}R^{30})_qNR^{28}CONR^{28}R^{31}$; —$(CR^{29}R^{30})_qCOOR^{21}$; —$(CR^{29}R^{30})_9CONR^{28}R^{31}$; —$(CR^{29}R^{30})_qCOR^{31}$; or —$(CR^{29}R^{30})_qR^{31}$;

$R^{39}$; $R^{40}$; $R^{41}$; $R^{42}$; $R^{43}$; $R^{44}$; $R^{45}$; $R^{46}$; $R^{47}$; $R^{48}$; $R^{49}$; and $R^{50}$ are as defined in claim 1;

the variable heteroatom Z and the connector U are defined as:

Z: O; or S(=O);

U: —C(=O)—; —$NR^4$—C(=O)—; or —C(=O)—C(=O)—; and substituents that can be pairwise taken together and form optionally substituted cycloalkyl or heterocycloalkyl moieties;

structural elements that can form one of the groups of formulae H111-H118 as shown in Table 9; and variable heteroatoms Q, T, X and Y;

indices q-u;

are as defined in claim 1.

5. Compounds according to claim 1 wherein readily accessible substances that define possible subunits of the linker C are those listed in Table 19, below;

TABLE 19

| Code | Chemical Name |
|---|---|
| Ala | L-Alanine |
| $^D$Ala | D-Alanine |
| Arg | L-Arginine |
| $^D$Arg | D-Arginine |
| Asn | L-Asparagine |
| $^D$Asn | D-Asparagine |
| Asp | L-Aspartic acid |
| $^D$Asp | D-Aspartic acid |
| Cys | L-Cysteine |
| $^D$Cys | D-Cysteine |
| Glu | L-Glutamic acid |
| $^D$Glu | D-Glutamic acid |
| Gln | L-Glutamine |
| $^D$Gln | D-Glutamine |
| Gly | Glycine |
| His | L-Histidine |
| $^D$His | D-Histidine |
| Ile | L-Isoleucine |
| $^D$Ile | D-Isoleucine |
| Leu | L-Leucine |
| $^D$Leu | D-Leucine |
| Lys | L-Lysine |
| $^D$Lys | D-Lysine |
| Met | L-Methionine |
| $^D$Met | D-Methionine |
| Phe | L-Phenylalanine |
| $^D$Phe | D-Phenylalanine |
| Pro | L-Proline |
| $^D$Pro | D-Proline |
| Ser | L-Serine |
| $^D$Ser | D-Serine |
| Thr | L-Threonine |
| $^D$Thr | D-Threonine |
| Trp | L-Tryptophan |
| $^D$Trp | D-Tryptophan |
| Tyr | L-Tyrosine |
| $^D$Tyr | D-Tyrosine |
| Val | L-Valine |
| $^D$Val | D-Valine |
| Apa | 3-Amino-propanoic acid |
| H-$\beta^3$-HAla-OH | (3S)-3-Amino-butyric acid |
| H-$\beta^3$-HVal-OH | (3R)-3-Amino-4-methyl-valeric acid |
| H-$\beta^3$-HIle-OH | (3R,4S)-3-Amino-4-methyl-hexanoic acid |
| H-$\beta^3$-HLeu-OH | (3S)-3-Amino-5-methyl-hexanoic acid |
| H-$\beta^3$-HMet-OH | (3S)-3-Amino-5-methylthio pentanoic acid |
| H-$\beta^3$-HTyr-OH | (3S)-3-Amino-4-(4'-hydroxyphenyl)-butyric acid |

TABLE 19-continued

| Code | Chemical Name |
|---|---|
| H-β³-HHis-OH | (3S)-3-Amino-4-(imidazole-4'-yl)-butyric acid |
| H-β³-HPhe-OH | (3S)-3-Amino-4-phenyl butyric acid |
| H-β³-HTrp-OH | (3S)-3-Amino-4-(indol-3'-yl)-butyric acid |
| H-β³-HSer-OH | (3R)-3-Amino-4-hydroxy-butyric acid |
| H-β³-HAsp-OH | 3-Amino-pentanedioic acid |
| H-β³-HGlu-OH | (3S)-3-Amino-hexanedioic acid |
| H-β³-HLys-OH | (3S)-3,7-Diamino-heptanoic acid |
| H-β³-HArg-OH | (3S)-3-Amino-6-guanidino-hexanoic-acid |
| H-β³-HCys-OH | (3R)-3-Amino-4-mercapto-butyric acid |
| H-β³-HAsn-OH | (3S)-3-Amino-4-carbamoyl-butyric acid |
| H-β³-HGln-OH | (3S)-3-Amino-5-carbamoyl-pentanoic acid |
| H-β³-HThr-OH | (3R,4R)-3-Amino-4-hydroxy-pentanoic acid |
| Gaba | 4-Amino-butyric acid |
| H-γ⁴-DiHAla-OH | (4S)-4-Amino-pentanoic acid |
| H-γ⁴-DiHVal-OH | (4R)-4-Amino-5-methyl-hexanoic acid |
| H-γ⁴-DiHIle-OH | (4R,5S)-4-Amino-5-methyl-heptanoic acid |
| H-γ⁴-DiHLeu-OH | (4R)-4-Amino-6-methyl-heptanoic acid |
| H-γ⁴-DiHMet-OH | (4R)-4-Amino-6-methylthio-hexanoic acid |
| H-γ⁴-DiHTyr-OH | (4R)-4-Amino-5-(4'-hydroxyphenyl)-pentanoic acid |
| H-γ⁴-DiHHis-OH | (4R)-4-Amino-5-(imidazole-4'-yl)-pentanoic acid |
| H-γ⁴-DiHPhe-OH | (4R)-4-Amino-5-phenyl-pentanoic acid |
| H-γ⁴-DiHTrp-OH | (4R)-4-Amino-5-(indol-3'-yl)-pentanoic acid |
| H-γ⁴-DiHSer-OH | (4R)-4-Amino-5-hydroxy-pentanoic acid |
| H-γ⁴-DiHAsp-OH | (4R)-4-Amino-hexanedioic acid |
| H-γ⁴-DiHGlu-OH | 4-Amino-heptanedioic acid |
| H-γ⁴-DiHLys-OH | (4S)-4,8-Diamino-octanoic acid |
| H-γ⁴-DiHArg-OH | (4S)-4-Amino-7-guanidino-heptanoic-acid |
| H-γ⁴-DiHCys-OH | (4R)-4-Amino-5-mercapto-pentanoic acid |
| H-γ⁴-DiHAsn-OH | (4R)-4-Amino-5-carbamoyl-pentanoic acid |
| H-γ⁴-DiHGln-OH | (3S)-3-Amino-5-carbamoyl-hexanoic acid |
| H-γ⁴-DiHThr-OH | (4R,5R)-4-Amino-5-hydroxy-hexanoic acid |
| Cit | L-Citrulline |
| ᴰCit | D-Citrulline |
| Orn | L-Ornithine |
| ᴰOrn | D-Ornithine |
| tBuA | L-t-Butylalanine |
| ᴰtBuA | D-t-Butylalanine |
| Sar | Sarcosine |
| Pen | L-Penicillamine |
| ᴰPen | D-Penicillamine |
| tBuG | L-tert.-Butylglycine |
| ᴰtBuG | D-tert.-Butylglycine |
| 4AmPhe | L-para-Aminophenylalanine |
| ᴰ4AmPhe | D-para-Aminophenylalanine |
| 3AmPhe | L-meta-Aminophenylalanine |
| ᴰ3AmPne | D-meta-Aminophenylalanine |
| 2AmPhe | L-ortho-Aminophenylalanine |
| ᴰ2AmPhe | D-ortho-Aminophenylalanine |
| Phe(mC(NH₂)=NH) | L-meta-Amidinophenylalanine |
| ᴰPhe(mC(NH₂)=NH) | D-meta-Amidinophenylalanine |
| Phe(pC(NH₂)=NH) | L-para-Amidinophenylalanine |
| ᴰPhe(pC(NH₂)=NH) | D-para-Amidinophenylalanine |
| Phe(mNHC(NH₂)=NH) | L-meta-Guanidinophenylalanine |
| ᴰPhe(mNHC(NH₂)=NH) | D-meta-Guanidinophenylalanine |
| Phe(pNHC(NH₂)=NH) | L-para-Guanidinophenylalanine |
| ᴰPhe(pNHC(NH₂)=NH) | D-para-Guanidinophenylalanine |
| 2Pal | (2S)-2-Amino-3-(pyridine-2'-yl)-propionic acid |
| ᴰ2Pal | (2R)-2-Amino-3-(pyridine-2'-yl)-propionic acid |
| 4Pal | (2S)-2-Amino-3-(pyridine-4'-yl)-propionic acid |
| ᴰ4Pal | (2R)-2-Amino-3-(pyridine-4'-yl)-propionic acid |
| Phg | L-Phenylglycine |
| ᴰPhg | D-Phenylglycine |
| Cha | L-Cyclohexylalanine |
| ᴰCha | D-Cyclohexylalanine |
| C₄al | L-3-Cyclobutylalanine |
| ᴰC₄al | D-3-Cyclobutylalanine |
| C₅al | L-3-Cyclopentylalanine |
| ᴰC₅al | D-3-Cyclopentylalanine |
| Nle | L-Norleucine |
| ᴰNle | D-Norleucine |

TABLE 19-continued

| Code | Chemical Name |
|---|---|
| 2-Nal | L-2-Naphthylalanine |
| <sup>D</sup>2Nal | D-2-Naphthylalanine |
| 1-Nal | L-1-Naphthylalanine |
| <sup>D</sup>1Nal | D-1-Naphthylalanine |
| 4ClPhe | L-4-Chlorophenylalanine |
| <sup>D</sup>4ClPhe | D-4-Chlorophenylalanine |
| 3ClPhe | L-3-Chlorophenylalanine |
| <sup>D</sup>3ClPhe | D-3-Chlorophenylalanine |
| 2ClPhe | L-2-Chlorophenylalanine |
| <sup>D</sup>2ClPhe | D-2-Chlorophenylalanine |
| 3,4Cl$_2$Phe | L-3,4-Dichlorophenylalanine |
| <sup>D</sup>3,4Cl$_2$Phe | D-3,4-Dichlorophenylalanine |
| 4FPhe | L-4-Fluorophenylalanine |
| <sup>D</sup>4FPhe | D-4-Fluorophenylalanine |
| 3FPhe | L-3-Fluorophenylalanine |
| <sup>D</sup>3FPhe | D-3-Fluorophenylalanine |
| 2FPhe | L-2-Fluorophenylalanine |
| <sup>D</sup>2FPhe | D-2-Fluorophenylalanine |
| Thi | L-β-2-Thienylalanine |
| <sup>D</sup>Thi | D-β-2-Thienylalanine |
| Tza | L-2-Thiazolylalanine |
| <sup>D</sup>Tza | D-2-Thiazolylalanine |
| Mso | L-Methionine sulfoxide |
| <sup>D</sup>Mso | D-Methionine sulfoxide |
| AcLys | N-Acetyllysine |
| <sup>D</sup>AcLys | N-Acetyl-D-lysine |
| Dap | 2,3-Diaminopropionic acid |
| <sup>D</sup>Dap | D-2,3-Diaminopropionic acid |
| Dab | 2,4-Diaminobutyric acid |
| <sup>D</sup>Dab | (2R)-2,4-Diaminobutyric acid |
| Dbu | (2S)-2,3-Diamino-butyric acid |
| <sup>D</sup>Dbu | (2R)-2,3-Diamino-butyric acid |
| Abu | γ-Aminobutyric acid (GABA) |
| Aha | ε-Aminohexanoic acid |
| Aib | α-Aminoisobutyric acid |
| Cyp | 1-Amino cyclopentane carboxylic acid |
| Y(Bzl) | L-O-Benzyltyrosine |
| <sup>D</sup>Y(Bzl) | D-O-Benzyltyrosine |
| H(Bzl) | (3S)-2-Amino-3-(1'-benzylimidazole-4'-yl)-propionic acid |
| <sup>D</sup>H(Bzl) | (3R)-2-Amino-3-(1'-benzylimidazole-4'-yl)-propionic acid |
| Bip | L-(4-phenyl)phenylalanine |
| <sup>D</sup>Bip | D-(4-phenyl)phenylalanine |
| S(Bzl) | L-O-Benzylserine |
| <sup>D</sup>S(Bzl) | D-O-Benzylserine |
| T(Bzl) | L-O-Benzylthreonine |
| <sup>D</sup>T(Bzl) | D-O-Benzylthreonine |
| alloT | (2S,3S)-2-Amino-3-hydroxy-butyric acid |
| <sup>D</sup>alloT | (2R,3S)-2-Amino-3-hydroxy-butyric acid |
| Leu3OH | (2S,3R)-2-Amino-3-hydroxy-4-methyl-pentanoic acid |
| <sup>D</sup>Leu3OH | (2R,3R)-2-Amino-3-hydroxy-4-methyl-pentanoic acid |
| hAla | L-Homo-alanine |
| <sup>D</sup>hAla | D-Homo-alanine |
| hArg | L-Homo-arginine |
| <sup>D</sup>hArg | D-Homo-arginine |
| hCys | L-Homo-cysteine |
| <sup>D</sup>hCys | D-Homo-cysteine |
| hGlu | L-Homo-glutamic acid |
| <sup>D</sup>hGlu | D-glutamic acid |
| hGln | L-Homo-glutamine |
| <sup>D</sup>hGln | D-Homo-glutamine |
| hHis | L-Homo-histidine |
| <sup>D</sup>hHis | D-Homo-histidine |
| hIle | L-Homo-isoleucine |
| <sup>D</sup>hIle | D-Homo-isoleucine |
| hLeu | L-Homo-leucine |
| <sup>D</sup>hLeu | D-Homo-leucine |
| hNle | L-Homo-norleucine |
| <sup>D</sup>hNle | D-Homo-norleucine |
| hLys | L-Homo-lysine |
| <sup>D</sup>hLys | D-Homo-lysine |
| hMet | L-Homo-Methionine |
| <sup>D</sup>hMet | D-Homo-Methionine |
| hPhe | L-Homo-phenylalanine |
| <sup>D</sup>hPhe | D-Homo-phenylalanine |

TABLE 19-continued

| Code | Chemical Name |
|---|---|
| hSer | L-Homo-serine |
| $^D$hSer | D-Homo-serine |
| hThr | L-Homo-threonine |
| $^D$hThr | D-Homo-threonine |
| hTrp | L-Homo-tryptophan |
| $^D$hTrp | D-Homo-tryptophan |
| hTyr | L-Homo-tyrosine |
| $^D$hTyr | D-Homo-tyrosine |
| hVal | L-Homo-valine |
| $^D$hVal | D-Homo-valine |
| hCha | L-Homo-cyclohexylalanine |
| $^D$hCha | D-Homo-cyclohexylalanine |
| Bpa | L-4-Benzoylphenylalanine |
| $^D$Bpa | D-4-Benzoylphenylalanine |
| OctG | L-Octylglycine |
| $^D$OctG | D-Octylglycine |
| Tic | (3S)-1,2,3,4-Tetrahydroisoquinoline-3-carboxylic acid |
| $^D$Tic | (3R)-1,2,3,4-Tetrahydroisoquinoline-3-carboxylic acid |
| Tiq | (1S)-1,2,3,4-Tetrahydroisoquinoline-1-carboxylic acid |
| $^D$Tiq | (1R)-1,2,3,4-Tetrahydroisoquinoline-1-carboxylic acid |
| Oic | (2S,3aS,7aS)-1-Octahydro-1H-indole-2-carboxylic acid |
| $^D$Oic | (2R,3aS,7aS)-1-Octahydro-1H-indole-2-carboxylic acid |
| 4AmPyrr1 | (2S,4S)-4-Amino-pyrrolidine-2-carboxylic acid |
| $^D$4AmPyrr1 | (2R,4S)-4-Amino-pyrrolidine-2-carboxylic acid |
| 4AmPyrr2 | (2S,4R)-4-Amino-pyrrolidine-2-carboxylic acid |
| $^D$4AmPyrr2 | (2R,4R)-4-Amino-pyrrolidine-2-carboxylic acid |
| 4PhePyrr1 | (2S,4R)-4-Phenyl-pyrrolidine-2-carboxylic acid |
| $^D$4PhePyrr1 | (2R,4R)-4-Phenyl-pyrrolidine-2-carboxylic acid |
| 4PhePyrr2 | (2S,4S)-4-Phenyl-pyrrolidine-2-carboxylic acid |
| $^D$4PhePyrr2 | (2R,4S)-4-Phenyl-pyrrolidine-2-carboxylic acid |
| 5PhePyrr1 | (2S,5R)-5-Phenyl-pyrrolidine-2-carboxylic acid |
| $^D$5PhePyrr1 | (2R,5R)-5-Phenyl-pyrrolidine-2-carboxylic acid |
| 5PhePyrr2 | (2S,5S)-5-Phenyl-pyrrolidine-2-carboxylic acid |
| $^D$5PhePyrr2 | (2R,5S)-5-Phenyl-pyrrolidine-2-carboxylic acid |
| 4Hyp1 | (4S)-L-Hydroxyproline |
| $^D$4Hyp1 | (4S)-D-Hydroxyproline |
| 4Hyp2 | (4R)-L-Hydroxyproline |
| $^D$4Hyp2 | (4R)-D-Hydroxyproline |
| 4Mp1 | (4S)-L-Mercaptoproline |
| $^D$4Mp1 | (4S)-D-Mercaptoproline |
| 4Mp2 | (4R)-L-Mercaptoproline |
| $^D$4Mp2 | (4R)-D-Mercaptoproline |
| Pip | L-Pipecolic acid |
| $^D$Pip | D-Pipecolic acid |
| H-β$^3$-HCit-OH | (3S)-3-Amino-6-carbamidyl-hexanoic acid |
| H-β$^3$-HOrn-OH | (3S)-3,6-Diamino-hexanoic acid |
| H-β$^3$-HtBuA-OH | (3S)-3-Amino-5,5-dimethyl-hexanoic acid |
| H-β$^3$-HSar-OH | N-Methyl-3-amino-propionic acid |
| H-β$^3$-HPen-OH | (3R)-3-Amino-4-methyl-4-mercapto-pentanoic acid |
| H-β$^3$-HtBuG-OH | (3R)-3-Amino-4,4-dimethyl-pentanoic acid |
| H-β$^3$-H4AmPhe-OH | (3S)-3-Amino-4-(4'-aminophenyl)-butyric acid |
| H-β$^3$-H3AmPhe-OH | (3S)-3-Amino-4-(3'-aminophenyl)-butyric acid |
| H-β$^3$-H2AmPhe-OH | (3S)-3-Amino-4-(2'-aminophenyl)-butyric acid |
| H-β$^3$-HPhe(mC(NH$_2$)=NH)—OH | (3S)-3-Amino-4-(3'-amidinophenyl)-butyric acid |
| H-β$^3$- | (3S)-3-Amino-4-(4'-amidinophenyl)-butyric |

TABLE 19-continued

| Code | Chemical Name |
|---|---|
| HPhe(pC(NH$_2$)=NH)—OH | acid |
| H-β$^3$-HPhe(mNHC(NH$_2$)=NH)—OH | (3S)-3-Amino-4-(3'-guanidinophenyl)-butyric acid |
| H-β$^3$-HPhe(pNHC(NH$_2$)=NH)—OH | (3S)-3-Amino-4-(4'-guanidino-phenyl)-butyric acid |
| H-β$^3$-H2Pal-OH | (3S)-3-Amino-4-(pyridine-2'-yl)-butyric acid |
| H-β$^3$-H4Pal-OH | (3S)-3-Amino-4-(pyridine-4'-yl)-butyric acid |
| H-β$^3$-HPhg-OH | (3R)-3-Amino-3-phenyl-propionic acid |
| H-β$^3$-HCha-OH | (3S)-3-Amino-4-cyclohexyl-butyric acid |
| H-β$^3$-HC$_4$al-OH | (3S)-3-Amino-4-cyclobutyl-butyric acid |
| H-β$^3$-HC$_5$al-OH | (3S)-3-Amino-4-cyclopentyl-butyric acid |
| H-β$^3$-HNle-OH | (3S)-3-Amino-heptanoic acid |
| H-β$^3$-H2Nal-OH | (3S)-3-Amino-4-(2'-naphthyl)-butyric acid |
| H-β$^3$-H1Nal-OH | (3S)-3-Amino-4-(1'-naphthyl)-butyric acid |
| H-β$^3$-H4ClPhe-OH | (3S)-3-Amino-4-(4'-chlorophenyl)-butyric acid |
| H-β$^3$-H3ClPhe-OH | (3S)-3-Amino-4-(3'-chlorophenyl)-butyric acid |
| H-β$^3$-H2ClPhe-OH | (3S)-3-Amino-4-(2'-chlorophenyl)-butyric acid |
| H-β$^3$-H3,4Cl$_2$Phe-OH | (3S)-3-Amino-4-(3',4'-dichlorophenyl)-butyric acid |
| H-β$^3$-H4FPhe-OH | (3S)-3-Amino-4-(4'-fluorophenyl)-butyric acid |
| H-β$^3$-H3FPhe-OH | (3S)-3-Amino-4-(3'-fluorophenyl)-butyric acid |
| H-β$^3$-H2FPhe-OH | (3S)-3-Amino-4-(2'-fluorophenyl)-butyric acid |
| H-β$^3$-HThi-OH | (3R)-3-Amino-4-(2'-thienyl)-butyric acid |
| H-β$^3$-HTza-OH | (3R)-3-Amino-4-(2'-thiazolyl)-butyric acid |
| H-β$^3$-HMso-OH | (3R)-3-Amino-4-methylsulfoxyl-butyric acid |
| Code | Chemical Name |
| H-β$^3$-HAcLys-OH | (3S)-7-Acetylamino-3-amino-heptanoic acid |
| H-β$^3$-HDpr-OH | (3R)-3,4-diamino-butyric acid |
| H-β$^3$-HA$_2$Bu—OH | (3S)-3,5-Diamino-pentanoic acid |
| H-β$^3$-HDbu-OH | (3R)-3,4-Diamino-pentanoic acid |
| H-β$^3$-HAib-OH | Amino-dimethyl acetic acid |
| H-β$^3$-HCyp-OH | 1-Amino-cyclopentane-1-yl-acetic acid |
| H-β$^3$-HY(Bzl)-OH | (3S)-3-Amino-4-(4'-benzyloxyphenyl)-butyric acid |
| H-β$^3$-HH(Bzl)-OH | (3S)-3-Amino-4-(1'-benzylimidazole-4'-yl)-butyric acid |
| H-β$^3$-HBip-OH | (3S)-3-Amino-4-biphenylyl-butyric acid |
| H-β$^3$-HS(Bzl)-OH | (3S)-3-Amino-4-(benzyloxy)-butyric acid |
| H-β$^3$-HT(Bzl)-OH | (3R,4R)-3-Amino-4-benzyloxy-pentanoic acid |
| H-β$^3$-HalloT-OH | (3R,4S)-3-Amino-4-hydroxy-pentanoic acid |
| H-β$^3$-HLeu3OH—OH | (3R,4R)-3-Amino-4-hydroxy-5-methyl-hexanoic acid |
| H-β$^3$-HhAla-OH | (3S)-3-Amino-pentanoic acid |
| H-β$^3$-HhArg-OH | (3S)-3-Amino-7-guanidino-heptanoic acid |
| H-β$^3$-HhCys-OH | (3R)-Amino-5-mercapto-pentanoic acid |
| H-β$^3$-HhGlu-OH | (3S)-3-Amino-heptanedioic acid |
| H-β$^3$-HhGln-OH | (3S)-3-Amino-6-carbamoyl hexanoic acid |
| H-β$^3$-HhHis-OH | (3S)-3-Amino-5-(imidazole-4'-yl)-pentanoic acid |
| H-β$^3$-HhIle-OH | (3S,5S)-3-Amino-5-methyl-heptanoic acid |
| H-β$^3$-HhLeu-OH | (3S)-3-Amino-6-methyl-heptanoic acid |
| H-β$^3$-HhNle-OH | (3S)-3-Amino-octanoic acid |
| H-β$^3$-DiAoc-OH | (3S)-3,8-Diamino-octanoic acid |
| H-β$^3$-HhMet-OH | (3S)-3-Amino-6-methylthio-hexanoic acid |
| H-β$^3$-HhPe-OH | (3S)-3-Amino-5-phenyl-pentanoic acid |
| H-β$^3$-HhSer-OH | (3S)-3-Amino-5-hydroxy-pentanoic acid |
| H-β$^3$-HhThr-OH | (3S,5R)-3-Amino-5-hydroxy-hexanoic acid |
| H-β$^3$-HhTrp-OH | (3S)-3-Amino-5-(indol-3'-yl)-pentanoic acid |
| H-β$^3$-HhThr-OH | (3S)-3-Amino-5-(4'-hydroxyphenyl)-pentanoic acid |
| H-β$^3$-HhCha-OH | (3S)-3-Amino-5-cyclohexyl-pentanoic acid |
| H-β$^3$-HBpa-OH | (3S)-3-Amino-4-(4'-benzoylphenyl)-butyric acid |
| H-β$^3$-HOctG-OH | (3S)-3-Amino-undecanoic acid |
| H-β$^3$-HNle-OH | (3S)-3-Amino-heptanoic acid |

TABLE 19-continued

| Code | Chemical Name |
| --- | --- |
| H-β³-HTic-OH | (3S)-1,2,3,4-Tetrahydroisoquinoline-3-yl-acetic acid |
| H-β³-HTiq-OH | (1S)-1,2,3,4-Tetrahydroisoquinoline-1-acetic acid |
| H-β³-HOic-OH | (2S,3aS,7aS)-1-Octahydro-1H-indole-2-yl-acetic acid |
| H-β³-H4AmPyrr1-OH | (2S,4S)-4-Amino-pyrrolidine-2-acetic acid |
| H-β³-H4AmPyrr2-OH | (2S,4R)-4-Amino-pyrrolidine-2-acetic acid |
| H-β³-H4PhePyrr1-OH | (2S,4R)-4-Phenyl-pyrrolidine-2-acetic acid |
| H-β³-H4PhePyrr2-OH | (2S,4S)-4-Phenyl-pyrrolidine-2-acetic acid |
| H-β³-H5PhePyrr1-OH | (2S,5R)-5-Phenyl-pyrrolidine-2-acetic acid |
| H-β³-H5PhePyrr2-OH | (2S,5S)-5-Phenyl-pyrrolidine-2-acetic acid |
| H-β³-H4Hyp1-OH | (2S,4S)-4-Hydroxy-pyrrolidine-2-acetic acid |
| H-β³-H4Hyp2-OH | (2S,4R)-4-Hydroxy-pyrrolidine-2-acetic acid |
| H-β³-H4Mp1-OH | (2R,4S)-4-Mercapto-pyrrolidine-2-acetic acid |
| H-β³-H4Mp2-OH | (2R,4R)-4-Mercapto-pyrrolidine-2-acetic acid |
| H-β³-HPip-OH | (2S)-piperidine-2-acetic acid |
| H-β³-HPro-OH | (2S)-pyrrolidine-2-acetic acid |
| H-β³-H$^D$Pro-OH | (2R)-pyrrolidine-2-acetic acid |
| Ahb | 4-Amino-2-hydroxy butyric acid |
| H-γ⁴-DiHCit-OH | (4S)-4-Amino-7-carbamidyl-heptanoic acid |
| H-γ⁴-DiHOrn-OH | (4S)-4,7-Diamino-heptanoic acid |
| H-γ⁴-DiHtBuA-OH | (4R)-4-Amino-6,6-dimethyl-heptanoic acid |
| H-γ⁴-DiHSar-OH | N-Methyl-4-amino-butyric acid |
| H-γ⁴-DiHPen-OH | (4R)-4-Amino-5-methyl-5-mercapto-hexanoic acid |
| H-γ⁴-DiHtBuG-OH | (4R)-4-Amino-5,5-dimethyl-hexanoic acid |
| H-γ⁴-DiH4AmPhe-OH | (4R)-4-Amino-5-(4'-aminophenyl)-pentanoic acid |
| H-γ⁴-DiH3AmPhe-OH | (4R)-4-Amino-5-(3'-aminophenyl)-pentanoic acid |
| H-γ⁴-DiH2AmPhe-OH | (4R)-4-Amino-5-(2'-aminophenyl)-pentanoic acid |
| H-γ⁴-DiHPhe(mC(NH₂)=NH)—OH | (4R)-4-Amino-5-(3'-amidinophenyl)-pentanoic acid |
| H-γ⁴-DiHPhe(pC(NH₂)=NH)—OH | (4R)-4-Amino-5-(4'-amidinophenyl)-pentanoic acid |
| H-γ⁴-DiHPhe(mNHC(NH₂)=NH)—OH | (4R)-4-Amino-5-(3'-guanidino-phenyl)-pentanoic acid |
| H-γ⁴-DiHPhe(pNHC(NH₂)=NH)—OH | (4R)-4-Amino-5-(4'-guanidino-phenyl)-pentanoic acid |
| H-γ⁴-DiH2Pal-OH | (4R)-4-Amino-5-(pyridine-4'-yl)-pentanoic acid |
| H-γ⁴-DiH4Pal-OH | (4R)-4-Amino-5-(pyridine-4'-yl)-pentanoic acid |
| H-γ⁴-DiHPhg-OH | (4R)-4-Amino-4-phenyl-butyric acid |
| H-γ⁴-DiHCha-OH | (4R)-4-Amino-5-cyclohexyl-pentanoic acid |
| H-γ⁴-DiHC₄al-OH | (4R)-4-Amino-5-cyclobutyl-pentanoic acid |
| H-γ⁴-DiHC₅al-OH | (4R)-4-Amino-5-cyclopentyl-pentanoic acid |
| H-γ⁴-DiHNle-OH | (4S)-4-Amino-octanoic acid |
| H-γ⁴-DiH2Nal-OH | (4S)-4-Amino-5-(2'-naphthyl)-pentanoic acid |
| H-γ⁴-DiH1Nal-OH | (4S)-4-Amino-5-(1'-naphthyl)-pentanoic acid |
| H-γ⁴-DiH4ClPhe-OH | (4R)-4-Amino-5-(4'-chlorophenyl)-pentanoic acid |
| H-γ⁴-DiH3ClPhe-OH | (4R)-4-Amino-5-(3'-chlorophenyl)-pentanoic acid |
| H-γ⁴-DiH2ClPhe-OH | (4R)-4-Amino-5-(2'-chlorophenyl)-pentanoic acid |
| H-γ⁴-DiH3,4Cl₂Phe-OH | (4R)-4-Amino-5-(3',4'-dichloro-phenyl)-pentanoic acid |
| H-γ⁴-DiH4FPhe-OH | (4R)-4-Amino-5-(4'-fluorophenyl)-pentanoic acid |
| H-γ⁴-DiH3FPhe-OH | (4R)-4-Amino-5-(3'-fluorophenyl)-pentanoic acid |
| H-γ⁴-DiH2FPhe-OH | (4R)-4-Amino-5-(2'-fluorophenyl)-pentanoic acid |

TABLE 19-continued

| Code | Chemical Name |
|---|---|
| H-γ⁴-DiHThi-OH | (4R)-4-Amino-5-(2'-thienyl)-pentanoic acid |
| H-γ⁴-DiHTza-OH | (4R)-4-Amino-5-(2'-thiazolyl)-pentanoic acid |
| H-γ⁴-DiHMso-OH | (4R)-4-Amino-5-methylsulfoxyl-pentanoic acid |
| H-γ⁴-DiHAcLys-OH | (4S)-8-Acetylamino-4-amino-ocatanoic acid |
| H-γ⁴-DiHDpr-OH | (4R)-4,5-diamino-pentanoic acid |
| H-γ⁴-DiHA₂Bu—OH | (4R)-4,5-Diamino-hexanoic acid |
| H-γ⁴-DiHDbu-OH | (4R)-4,5-Diamion-hexanoic acid |
| H-γ⁴-DiHAib-OH | 3-Amino-3,3-dimethyl propionic acid |
| H-γ⁴-DiHCyp-OH | (1'-Amino-cyclopentane-1'-yl)-3-propionic acid |
| H-γ⁴-DiHY(Bzl)-OH | (4R)-4-Amino-5-(4'-benzyloxyphenyl)-pentanoic acid |
| H-γ⁴-DiHH(Bzl)-OH | (4R)-4-Amino-5-(1'-benzylimidazole-4'-yl)-pentanoic acid |
| H-γ⁴-DiHBip-OH | (4R)-4-Amino-5-biphenylyl-pentanoic acid |
| H-γ⁴-DiHS(Bzl)-OH | (4S)-4-Amino-5-(benzyloxy)-pentanoic acid |
| H-γ⁴-DiHT(Bzl)-OH | (4R,5R)-4-Amino-5-benzyloxy-hexanoic acid |
| H-γ⁴-DiHalloT-OH | (4R,5S)-4-Amino-5-hydroxy-hexanoic acid |
| H-γ⁴-DiHLeu3OH—OH | (4R,5R)-4-Amino-5-hydroxy-6-methyl-heptanoic acid |
| H-γ⁴-DiHhAla-OH | (4S)-4-Amino-hexanoic acid |
| H-γ⁴-DiHhArg-OH | (4S)-4-Amino-8-guanidino-octanoic acid |
| H-γ⁴-DiHhCys-OH | (4R)-Amino-6-mercapto-hexanoic acid |
| H-γ⁴-DiHhGlu-OH | (4S)-4-Amino-ocatanedioic acid |
| H-γ⁴-DiHhGln-OH | (4S)-4-Amino-7-carbamoyl-heptanoic acid |
| H-γ⁴-DiHhHis-OH | (4S)-4-Amino-6-(imidazole-4'-yl)-hexanoic acid |
| H-γ⁴-DiHhIle-OH | (4S,6S)-4-Amino-6-methyl-octanoic acid |
| H-γ⁴-DiHhLeu-OH | (4S)-4-Amino-7-methyl-ocatanoic acid |
| H-γ⁴-DiHhNle-OH | (4S)-4-Amino-nonanoic acid |
| H-γ⁴-DiHhLys-OH | (4S)-4,9-Diamino-nonanoic acid |
| H-γ⁴-DiHhMet-OH | (4R)-4-Amino-7-methylthioheptanoic acid |
| H-γ⁴-DiHhPhe-OH | (4S)-4-Amino-6-phenyl-hexanoic acid |
| H-γ⁴-DiHhSer-OH | (4R)-4-Amino-6-hydroxy-hexanoic acid |
| H-γ⁴-DiHhThr-OH | (4R,6R)-4-Amino-6-hydroxy-heptanoic acid |
| H-γ⁴-DiHhTrp-OH | (4S)-4-Amino-6-(indol-3'-yl)-hexanoicacid |
| H-γ⁴-DiHhTyr-OH | (4S)-4-Amino-6-(4'-hydroxyphenyl)-hexanoic acid |
| H-γ⁴-DiHhCha-OH | (4R)-4-Amino-5-cyclohexyl-pentanoic acid |
| H-γ⁴-DihBpa-OH | (4R)-4-Amino-5-(4'-benzoylphenyl)-pentanoic acid |
| H-γ⁴-DiHOctG-OH | (4S)-4-Amino-dodecanoic acid |
| H-γ⁴-DiHNle-OH | (4S)-4-Amino-octanoic acid |
| H-γ⁴-DiHTic-OH | (3R)-1',2',3',4'-Tetrahydroisoquinoline-3'-yl-3-propionic acid |
| H-γ⁴-DiHTiq-OH | (1'R)-1',2',3',4'-Tetrahydroisoquinoline-1'-yl-3-propionic acid |
| H-γ⁴-DiHOic-OH | (2'S,3'aS,7'aS)-1'-Octahydro-1H-indole-2'-yl-3-propionic acid |
| H-γ⁴-DiH4AmPyrr1-OH | (2'R,4'S)-4'-Amino-pyrrolidine-2'-yl-3-propionic acid |
| H-γ⁴-DiH4AmPyrr2-OH | (2'R,4'R)-4'-Amino-pyrrolidine-2'-yl-3-propionic acid |
| H-γ⁴-DiH4PhePyrr1-OH | (2'R,4'R)-4'-Phenyl-pyrrolidine-2'-yl-3-propionic acid |
| H-γ⁴-DiH4PhePyrr2-OH | (2'R,4'S)-4'-Phenyl-pyrrolidine-2'-yl-3-propionic acid |
| H-γ⁴-DiH5PhePyrr1-OH | (2'S,5'R)-5'-Phenyl-pyrrolidine-2'-yl-3-propionic acid |
| H-γ⁴-DiH5PhePyrr2-OH | (2'S,5'S)-5'-Phenyl-pyrrolidine-2'-yl-3-propionic acid |
| H-γ⁴-DiH4Hyp1-OH | (2'R,4'S)-4'-Hydroxy-pyrrolidine-2'-yl-2-propionic acid |
| H-γ⁴-DiH4Hyp2-OH | (2'R,4'R)-4'-Hydroxy-pyrrolidine-2'-yl-3-propionic acid |
| H-γ⁴-DiH4Mp1-OH | (2'R,4'S)-4'-Mercapto-pyrrolidine-2'-yl-3-propionic acid |
| H-γ⁴-DiH4Mp2-OH | (2'R,4'R)-4'-Mercapto-pyrrolidine-2'-yl-3-propionic acid |
| H-γ⁴-DiHPip-OH | (2'S)-Piperidine-2'-yl-3-propionic acid |
| H-γ⁴-DiHPro-OH | (2'S)-Pyrrolidine-2'-yl-3-propionic acid |
| (AEt)G | N-(2-Aminoethyl)glycine |
| (APr)G | N-(3-Amino-n-propyl)glycine |
| (ABu)G | N-(4-Amino-n-butyl)glycine |

TABLE 19-continued

| Code | Chemical Name |
| --- | --- |
| (APe)G | N-(5-Amino-n-pentyl)glycine |
| (GuEt)G | N-(2-Guanidinoethyl)glycine |
| (GuPr)G | N-(3-Guanidino-n-propyl)glycine |
| (GuBu)G | N-(4-Guanidino-n-butyl)glycine |
| (GuPe)G | N-(5-Guanidino-n-pentyl)glycine |
| (PEG$_3$-NH$_2$)G | N—[H$_2$N—(CH$_2$)$_3$—(OCH$_2$—CH$_2$)$_2$—O(CH$_2$)$_3$]glycine |
| (Me)G | N-Methylglycine |
| (Et)G | N-Ethylglycine |
| (Bu)G | N-Butylglycine |
| (Pe)G | N-Pentylglycine |
| (Ip)G | N-Isopropylglycine |
| (2MePr)G | N-(2-Methylpropyl)glycine |
| (3MeBu)G | N-(3-Methylbutyl)glycine |
| (1MePr)G | (1S)-N-(1-Methylpropyl)glycine |
| (2MeBu)G | (2S)-N-(2-Methylbutyl)glycine |
| (MthEt)G | N-(Methylthioethyl)glycine |
| (MthPr)G | N-(Methylthiopropyl)glycine |
| (Ben)G | N-(Benzyl)glycine |
| (PhEt)G | N-(2-Phenylethyl)glycine |
| (HphMe)G | N-([4'-hydroxyphenyl]methyl)glycine |
| (HphEt)G | N-(2-[4'-hydroxyphenyl]ethyl)glycine |
| (ImMe)G | N-(Imidazol-5-yl-methyl)glycine |
| (ImEt)G | N-(2-(Imidazol-5'-yl)ethyl)glycine |
| (InMe)G | N-(Indol-2-yl-methyl)glycine |
| (InEt)G | N-(2-(Indol-2'-yl)ethyl)glycine |
| (CboMe)G | N-(Carboxymethyl)glycine |
| (CboEt)G | N-(2-Carboxyethyl)glycine |
| (CboPr)G | N-(3-Carboxypropyl)glycine |
| (CbaMe)G | N-(Carbamoylmethyl)glycine |
| (CbaEt)G | N-(2-Carbamoylethyl)glycine |
| (CbaPr)G | N-(3-Carbamoylpropyl)glycine |
| (HyEt)G | N-(2-Hydroxyethyl)glycine |
| (HyPr)G | (2R)-N-(2-Hydroxypropyl)glycine |
| (Mcet)G | N-(2-Mercaptoethyl)glycine |
| NMeAla | L-N-Methylalanine |
| NMe$^D$Ala | D-N-Methylalanine |
| NMeVal | L-N-Methylvaline |
| NMe$^D$Val | D-N-Methylvaline |
| NMeIle | L-N-Methylisoleucine |
| NMe$^D$Ile | D-N-Methylisoleucine |
| NMeLeu | L-N-Methylleucine |
| NMe$^D$Leu | D-N-Methylleucine |
| NMeNle | L-N-Methylnorleucine |
| NMe$^D$Nle | D-N-Methylnorleucine |
| NMeMet | L-N-Methylmethionine |
| NMe$^D$Met | D-N-Methylmethionine |
| NMeTyr | L-N-Methyltyrosine |
| NMe$^D$Tyr | D-N-Methyltyrosine |
| NMeHis | L-N-Methylhistidine |
| NMe$^D$His | D-N-Methylhistidine |
| NMePhe | L-N-Methylphenylalanine |
| NMe$^D$Phe | D-N-Methylphenylalanine |
| NMeTrp | L-N-Methyltryptophane |
| NMe$^D$Trp | D-N-Methyltryptophane |
| NMeSer | L-N-Methylserine |
| NMe$^D$Ser | D-N-Methylserine |
| NMeAsp | L-N-Methylaspartic acid |
| NMe$^D$Asp | D-N-Methylaspartic acid |
| NMeGlu | L-N-Methylglutamic acid |
| NMe$^D$Glu | D-N-Methylglutamic acid |
| NMeLys | L-N-Methyllysine |
| NMe$^D$Lys | D-N-Methyllysine |
| NMeArg | L-N-Methylarginine |
| NMe$^D$Arg | D-N-Methylarginine |
| NMeDab | L-N-Methyl-2,4-diamino butyric acid |
| NMe$^D$Dab | D-N-Methyl-2,4-diamino butyric acid |
| NMeCys | L-N-Methylcysteine |
| NMe$^D$Cys | D-N-Methylcysteine |
| NMeAsn | L-N-Methylasparagine |
| NMe$^D$Asn | D-N-Methylasparagine |
| NMeGln | L-N-Methylglutamine |
| NMe$^D$Gln | D-N-Methylglutamine |
| NMeThr | L-N-Methylthreonine |
| NMe$^D$Thr | D-N-Methylthreonine. |

6. Compounds according to claim 1, selected from:
(2S,11S,19aS)-2-(acetylamino)-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide, (2S,11S,19aS)—N-[2-(dimethylamino)ethyl]-15-fluoro-2-{[2-(1H-indol-3-yl)acetyl]amino}-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide; (2S,11S,19aS)-15-fluoro-2-{[2-(1H-indol-3-yl)acetyl]amino}-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide; (2S,11S,19aS)-2-{[2-(dimethylamino)acetyl]amino}-15-fluoro-N-[2-(1H-indol-3-yl)ethyl]-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide; tert-butyl N-[(2S,11S,19aS)-15-fluoro-11-({[2-(1H-indol-3-yl)ethyl]amino}carbonyl)-7,12-dimethyl-5,8,13-trioxo-2,3,6,7,8,9,10,11,12,13,19,19a-dodecahydro-1H,5H-pyrrolo[2,1-c][1,4,7,12]benzoxatriazacyclopentadecin-2-yl]carbamate; (2S,11S,19aS)—N-[2-(dimethylamino)ethyl]-15-fluoro-7,12-dimethyl-2-{[2-(1-naphthyl)acetyl]amino}-5,8,13-trioxo-2,3,6,7,8,9,10,11,12,13,19,19a-dodecahydro-1H,5H-pyrrolo[2,1-c][1,4,7,12]benzoxatriazacyclopentadecine-11-carboxamide; benzyl N-[(4S,6S,10S)-14-methyl-6-{[2-(2-naphthyl)acetyl]amino}-9,15-dioxo-2-oxa-8,14-diazatricyclo[14.3.1.0~4,8~]icosa-1(20),16,18-trien-10-yl]carbamate; benzyl N-[(4S,6S,13S)-6-{[2-(1H-indol-3-yl)acetyl]amino}-11,15-dimethyl-9,12,16-trioxo-2-oxa-8,11,15-triazatricyclo[15.3.1.0~4,8~]henicosa-[(21),17,19-trien-13-yl]carbamat; N-[(4S,6S,13S)-6-{[2-(1H-indol-3-yl)acetyl]amino}-11,15-dimethyl-9,12,16-trioxo-2-oxa-8,11,15-triazatricyclo[15.3.1.0~4,8~]henicosa-[(21),17,19-trien-13-yl]decanamide.

7. A composition having the compound according to any one of claims 2, 3, 5, 6 or 1 in a therapeutically active amount and having agonistic activity on the motilin receptor (MR receptor), on the serotonin receptor of subtype 5-HT$_{2B}$ (5-HT$_{2B}$ receptor), and on the prostaglandin F2α receptor (FP receptor).

8. A pharmaceutical composition containing a compound according to any one of claims 2, 3, 5, 6 or 1 and a therapeutically inert carrier.

9. The composition according to claim 8 having agonistic or antagonistic activity on the motilin receptor (MR receptor), on the serotonin receptor of subtype 5-HT$_{2B}$ (5-HT$_{2B}$ receptor), and on the prostaglandin F2α receptor (FP receptor).

10. The composition according to claim 9 in a form suitable for oral, topical, transdermal, injection, buccal, transmucosal, pulmonary or inhalation administration.

11. The composition according to claim 10 in form of tablet, degree, capsule, solution, liquid, gel, plaster, scream, ointment, syrup, slurry, suspension, spray, nebuliser or suppository.

12. A medicament comprising the compound according to claim 1 having agonistic or antagonistic activity on the motilin receptor (MR receptor), on the serotonin receptor of subtype 5-HT$_{2B}$ (5-HT$_{2B}$ receptor), and on the prostaglandin F2α receptor (FP receptor).

13. A method of treating hypomotility disorders of the gastrointestinal tract selected from the group consisting of diabetic gastroparesis and constipation type irritable bowel syndrome; CNS diseases selected from the group consisting of migraine, schizophrenia, psychosis and depression; ocular hypertension associated with glaucoma or preterm labour; said method comprising:
administering the compound of claim 1 to a patient in need thereof.

* * * * *